(12) United States Patent
Digiandomenico et al.

(10) Patent No.: US 12,428,473 B2
(45) Date of Patent: *Sep. 30, 2025

(54) COMBINATION THERAPIES USING ANTI-PSEUDOMONAS PSL AND PCRV BINDING MOLECULES

(71) Applicant: MEDIMMUNE LIMITED, Cambridge (GB)

(72) Inventors: Antonio Digiandomenico, Gaithersburg, MD (US); Paul Warrener, Gaithersburg, MD (US); Charles Stover, Gaithersburg, MD (US); Bret Sellman, Gaithersburg, MD (US); Ralph Minter, Cambridge (GB); Sandrine Guillard, Cambridge (GB); Steven Rust, Cambridge (GB); Mladen Tomich, Exton, PA (US); Vignesh Venkatraman, Cambridge (GB); Reena Varkey, Gaithersburg, MD (US); Li Peng, Gaithersburg, MD (US); Melissa Damschroder, Gaithersburg, MD (US); Partha S. Chowdhury, Gaithersburg, MD (US); Nazzareno Dimasi, Gaithersburg, MD (US); Ryan Fleming, Gaithersburg, MD (US); Binyam Bezabeh, Gaithersburg, MD (US); Changshou Gao, Gaithersburg, MD (US); Godfrey Rainey, Gaithersburg, MD (US); Cuihua Gao, Gaithersburg, MD (US)

(73) Assignee: MedImmune Limited, Cambridge (GB)

( * ) Notice: Subject to any disclaimer, the term of this patent is extended or adjusted under 35 U.S.C. 154(b) by 968 days.

This patent is subject to a terminal disclaimer.

(21) Appl. No.: 17/454,837

(22) Filed: Nov. 15, 2021

(65) Prior Publication Data
US 2022/0177554 A1 Jun. 9, 2022

Related U.S. Application Data

(62) Division of application No. 16/789,790, filed on Feb. 13, 2020, now Pat. No. 11,203,633, which is a division of application No. 14/356,500, filed as application No. PCT/US2012/063722 on Nov. 6, 2012, now Pat. No. 10,597,439.

(60) Provisional application No. 61/556,645, filed on Nov. 7, 2011, provisional application No. 61/625,299, filed on Apr. 17, 2012, provisional application No. 61/697,585, filed on Sep. 6, 2012.

(51) Int. Cl.
| | | |
|---|---|---|
| C07K 16/00 | (2006.01) | |
| C07K 16/12 | (2006.01) | |
| C07K 16/46 | (2006.01) | |
| A61K 39/00 | (2006.01) | |
| A61P 31/04 | (2006.01) | |

(52) U.S. Cl.
CPC .... *C07K 16/1214* (2013.01); *A61K 2039/505* (2013.01); *A61K 2039/507* (2013.01); *A61P 31/04* (2018.01); *C07K 2317/21* (2013.01); *C07K 2317/31* (2013.01); *C07K 2317/33* (2013.01); *C07K 2317/56* (2013.01); *C07K 2317/565* (2013.01); *C07K 2317/622* (2013.01); *C07K 2317/734* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,444,887 A | 4/1984 | Hoffmann |
| 4,683,195 A | 7/1987 | Mullis et al. |
| 4,716,111 A | 12/1987 | Osband et al. |
| 4,816,397 A | 3/1989 | Boss et al. |
| 4,816,567 A | 3/1989 | Cabilly et al. |
| 4,946,778 A | 8/1990 | Ladner et al. |
| 5,089,262 A | 2/1992 | Sawada et al. |
| 5,122,464 A | 6/1992 | Wilson et al. |
| 5,223,409 A | 6/1993 | Ladner et al. |
| 5,225,539 A | 7/1993 | Winter |
| 5,258,498 A | 11/1993 | Huston et al. |
| 5,403,484 A | 4/1995 | Ladner et al. |
| 5,427,908 A | 6/1995 | Dower et al. |
| 5,516,637 A | 5/1996 | Huang et al. |
| 5,525,491 A | 6/1996 | Huston et al. |
| 5,530,101 A | 6/1996 | Queen et al. |

(Continued)

FOREIGN PATENT DOCUMENTS

| | | |
|---|---|---|
| JP | 2007533295 A | 11/2007 |
| WO | WO-02096948 A2 | 12/2002 |

(Continued)

OTHER PUBLICATIONS

Lynch et al. Polymorphisms in the Pseudomonas aeruginosa Type III secretion protein, PcrV—implications for anti-PcrV Immunotherapy. Microb Pathog. Jun. 2010 ; 48(6): 197-204. (Year: 2010).*

(Continued)

*Primary Examiner* — Maher M Haddad
(74) *Attorney, Agent, or Firm* — Sterne, Kessler, Goldstein & Fox, P.L.L.C.

(57) ABSTRACT

This disclosure relates to combination therapies comprising anti-*Pseudomonas* Psl and PcrV binding molecules and related compositions, for use in prevention and treatment of *Pseudomonas* infection.

Figure 1B:
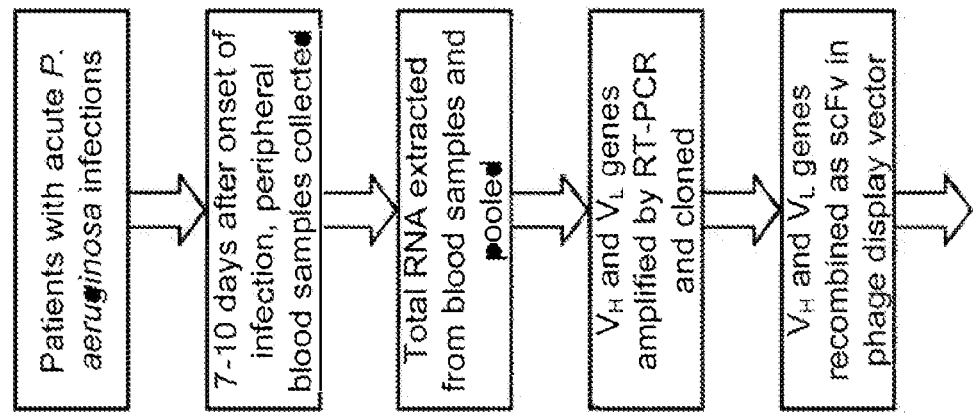

20 Claims, 93 Drawing Sheets
Specification includes a Sequence Listing.

(56) References Cited

U.S. PATENT DOCUMENTS

| | | | |
|---|---|---|---|
| 5,565,332 | A | 10/1996 | Hoogenboom et al. |
| 5,571,698 | A | 11/1996 | Ladner et al. |
| 5,580,717 | A | 12/1996 | Dower et al. |
| 5,585,089 | A | 12/1996 | Queen et al. |
| 5,658,570 | A | 8/1997 | Newman et al. |
| 5,658,727 | A | 8/1997 | Barbas et al. |
| 5,693,761 | A | 12/1997 | Queen et al. |
| 5,693,762 | A | 12/1997 | Queen et al. |
| 5,698,426 | A | 12/1997 | Huse |
| 5,733,743 | A | 3/1998 | Johnson et al. |
| 5,750,753 | A | 5/1998 | Kimae et al. |
| 5,780,225 | A | 7/1998 | Wigler et al. |
| 5,807,715 | A | 9/1998 | Morrison et al. |
| 5,821,047 | A | 10/1998 | Garrard et al. |
| 5,892,019 | A | 4/1999 | Schlom et al. |
| 5,939,598 | A | 8/1999 | Kucherlapati et al. |
| 5,969,108 | A | 10/1999 | McCafferty et al. |
| 6,150,584 | A | 11/2000 | Kucherlapati et al. |
| 6,180,370 | B1 | 1/2001 | Queen et al. |
| 6,190,370 | B1 | 2/2001 | Tsui |
| 6,420,140 | B1 | 7/2002 | Hori et al. |
| 6,458,592 | B1 | 10/2002 | Jakobovits et al. |
| 6,827,935 | B2 | 12/2004 | Frank et al. |
| 7,083,784 | B2 | 8/2006 | Dall'Acqua et al. |
| 7,112,324 | B1 | 9/2006 | Dorken et al. |
| 7,494,653 | B2 | 2/2009 | Frank et al. |
| 7,658,921 | B2 | 2/2010 | Dall'Acqua et al. |
| 8,501,179 | B2 | 8/2013 | Numata et al. |
| 8,642,039 | B2 | 2/2014 | Yarranton |
| 9,403,901 | B2 | 8/2016 | Digiandomenico et al. |
| 9,527,905 | B2 | 12/2016 | Sellman et al. |
| 9,580,509 | B2 | 2/2017 | Dimasi et al. |
| 9,845,348 | B2 | 12/2017 | Sellman et al. |
| 9,879,070 | B2 | 1/2018 | Sellman et al. |
| 10,023,654 | B2 | 7/2018 | Sleeman et al. |
| 10,072,098 | B2 | 9/2018 | De Tavernier et al. |
| 10,370,436 | B2 | 8/2019 | Digiandomenico et al. |
| 10,597,439 | B2 * | 3/2020 | Digiandomenico .... A61P 43/00 |
| 10,759,849 | B2 | 9/2020 | Sellman et al. |
| 10,844,114 | B2 | 11/2020 | DiGiandomenico et al. |
| 10,870,710 | B2 | 12/2020 | DiGandomenico et al. |
| 11,066,461 | B2 | 7/2021 | Jafri et al. |
| 11,203,633 | B2 * | 12/2021 | Digiandomenico .... A61P 43/00 |
| 2002/0123057 | A1 | 9/2002 | Zauderer et al. |
| 2002/0146753 | A1 | 10/2002 | Ditzel et al. |
| 2003/0232387 | A1 | 12/2003 | Lu |
| 2008/0095775 | A1 | 4/2008 | Lewis et al. |
| 2008/0131423 | A1 | 6/2008 | Mori et al. |
| 2009/0191186 | A1 | 7/2009 | Bebbington et al. |
| 2009/0215992 | A1 | 8/2009 | Wu et al. |
| 2010/0150939 | A1 | 6/2010 | Blanchetot et al. |
| 2010/0166768 | A1 | 7/2010 | Sleeman et al. |
| 2010/0172862 | A1 | 7/2010 | Correia et al. |
| 2010/0272736 | A1 | 10/2010 | Baer et al. |
| 2011/0150896 | A1 | 6/2011 | Numata et al. |
| 2014/0227285 | A1 | 8/2014 | Digiandomenico et al. |
| 2014/0302038 | A1 | 10/2014 | Dimasi et al. |
| 2015/0023966 | A1 | 1/2015 | Digiandomenico et al. |
| 2015/0044215 | A1 | 2/2015 | De Tavernier et al. |
| 2015/0239660 | A1 | 8/2015 | Egersdoerfer et al. |
| 2015/0284615 | A1 | 10/2015 | Digiandomenico et al. |
| 2016/0115250 | A1 | 4/2016 | Digiandomenico et al. |
| 2016/0297872 | A1 | 10/2016 | Digiandomenico et al. |
| 2017/0114151 | A1 | 4/2017 | Dimasi et al. |
| 2017/0129943 | A1 | 5/2017 | Sellman et al. |
| 2017/0183397 | A1 | 6/2017 | Digiandomenico et al. |
| 2018/0355026 | A1 | 12/2018 | Jafri et al. |
| 2019/0055322 | A1 | 2/2019 | De Tavernier et al. |
| 2019/0153076 | A1 * | 5/2019 | Weiner ............... C07K 16/468 |
| 2019/0309095 | A1 | 10/2019 | Jafri et al. |
| 2019/0322726 | A1 | 10/2019 | Digiandomenico et al. |
| 2020/0317757 | A1 | 10/2020 | Digiandomenico et al. |
| 2020/0392210 | A1 | 12/2020 | Kyratsous et al. |
| 2021/0130442 | A1 | 5/2021 | Digiandomenico et al. |

FOREIGN PATENT DOCUMENTS

| | | | |
|---|---|---|---|
| WO | WO-2006009525 | A2 | 1/2006 |
| WO | WO-2007024715 | A2 | 3/2007 |
| WO | WO-2008024188 | A2 | 2/2008 |
| WO | WO-2009092011 | A1 | 7/2009 |
| WO | WO-2010107778 | A1 | 9/2010 |
| WO | WO-2010108153 | A2 | 9/2010 |
| WO | WO-2010115606 | A1 | 10/2010 |
| WO | WO-2011005481 | A1 | 1/2011 |
| WO | WO-2012145626 | A1 | 10/2012 |
| WO | WO-2012170807 | A2 | 12/2012 |
| WO | WO-2013070565 | A1 | 5/2013 |
| WO | WO-2013070615 | A1 | 5/2013 |
| WO | WO-2014074470 | A1 | 5/2014 |
| WO | WO-2014074528 | A2 | 5/2014 |
| WO | WO-2014186358 | | 11/2014 |
| WO | WO-2014186358 | A2 | 11/2014 |
| WO | WO-2015171504 | A1 | 11/2015 |
| WO | WO-2017193101 | A1 | 11/2017 |

OTHER PUBLICATIONS

Bendig, Mary M. "Humanization of rodent monoclonal antibodies by CDR grafting," Methods-Companion to Methods in Enzymology 8.2 (1995): 83-93.

Casset, F. et al. "A peptide mimetic of an anti-CD4 monoclonal antibody by rational design," Biochemical and biophysical research communications 307(1): 198-205, Elsevier, Netherlands, (2003).

Colman, P. M. "Effects of amino acid sequence changes on antibody-antigen interactions." Research in Immunology 145(1): 33-36, Elsevier, Netherlands (1994).

"Pseudomonas aeruginosa in Healthcare Settings," CDC, Https://www.cdc.gov/hai/organisms/pseudomonas.html, accessed on Apr. 16, 2018, 2 pages.

Dimasi, N. et al., "The design and characterization of oligospecific anitbodies for simultaneous targeting of multiple disease mediators," J. Mol. Biol. 393(3):672-92 (2009).

Galanos et al., "Galactosamine-induced sensitization to the lethal effects of endotoxin," Proc Natl Acad Sci USA, vol. 76, No. 11, pp. 5939-5943 (1979).

Greenbaum, J. A. et al. "Towards a consensus on datasets and evaluation metrics for developing B-cell epitope prediction tools," Journal of Molecular Recognition: An Interdisciplinary Journal 20(2): 75-82, (2007).

Greenspan, N. S. et al. "Defining epitopes: It's not as easy as it seems." Nature biotechnology 17(10): 936-937, (1999).

Harlow et al., In Antibodies a Laboratory Manual, Cold Spring Harbor Press, 1988, Chapter 3, pp. 23-35.

Höppner, Wolfgang, "Clinical Impact of Molecular Diagnostics in Endocrinology," Hormone Research in Paediatrics 58, Suppl. 3: 7-15, (2002).

Ladner, "Mapping the epitopes of antibodies," Biotechnol. Genet. Eng. Rev., 24:1-30 (2007).

Lodish et al., Mol. Cell Biol., 3rd ed. Scientific American Books, NY, 1995 (Year: 1995).

MacCallum, R. M. et al., "Antibody-antigen interactions: contact analysis and binding site topography," Journal of molecular biology 262(5): 732-745, Elsevier, Netherlands (1996).

Paul, W.E., "Structure and Function of Immunoglobulins," in Fundamental Immunology, Third Edition: pp. 292-295, Raven Press, New York, United States (1993).

Rudikoff, S. et al. "Single amino acid substitution altering antigen-binding specificity." Proceedings of the National Academy of Sciences 79(6): 1979-1983, (1982).

Russian Patent Application No. 2018102606/10, Office Action (English Translation), dated May 20, 2019.

Thaden, J. T. et al. "Pseudomonas aeruginosa bacteremic patients exhibit nonprotective antibody titers against therapeutic antibody targets PcrV and Psl exopolysaccharide." The Journal of infectious diseases 213(4): 640-648, (2016).

Borlee, B.R., et al., "Pseduonomonas aerugioonsa uses a cyclic-di-GMP-regulated adhesion to reinforce the biofilm extracellular matrix," Molecular Microbiology 75(4):827-842, Blackwell Scientific Publications, England (Feb. 2010).

(56) References Cited

OTHER PUBLICATIONS

Byrd, M.S., et al., "The Pseudomonas aeruginosa Exopolysaccharide PSL facilitates surface adherence and NF-kB activation in A549 cells," MBIO 1(3):e00140-10, pp. 1-4 (2010).
Ma, L., et al., "Assembly and Development of the Pseudomonas aeruginosa Biofilm Matrix," PLOS Pathogens 5(3): e31000354, pp. 1-11, PLOS, United States (2009).
Li, H., et al., "Epitope Mapping of Monoclonal Antibodies using Synthetic Oligosacchardies Uncovers Novel Aspects of Immune Recognition of the PSL Exopolysaccharide of Pseudomonas aeruginosa," Chemistry a European Journal 19(51):17425-17431, (2013).
Digiandomenico, A., et al., "Identification of broadly protective human antibodies to Pseudomonas aeruginosa exopolysaccharide PSL by phenotypic screening," Journal of Experimental Medicine 209(7): 1273-1287, Rockefeller University Press, United States (2012).
European Search Report and Search Opinion for EP Application No. EP 17 20 5254, Munich, Germany, mailed on Jul. 6, 2018, 7 pages.
Kobayashi, Y., "A human monoclonal antibody against *Pseudomonas aeruginosa* and the possibility of its clinical use," *Journal of Okayama Medical Association* 102:1267-1273, Okayama Medical Association, Japan (1990).
Pakula, et al., "Genetic analysis of protein stability and function," *Annual Review of Genetics* 23:289-310, Annual Reviews Inc., United States (Dec. 1989).
Franklin, M.J., et al., "Biosynthesis of the *Pseudomonas aeruginosa* extracellular polysaccharides, alginate, Pel and Psl," Frontiers in Microbiology 2(167):1-16, Frontiers Media, Switzerland (Aug. 2011).
Ali, S.O., et al., "Phase 1 Study of MEDI3902, an Investigational Anti-pseudomonas Aeruginosa Pcrv and Psl Bispecific Human Monoclonal Antibody in Healthy Adults," Clinical Microbiology and Infection 25(5):629. e1-629,e6, 6 pages, (May 2019).
Byrd M.S., et al., "Genetic and Biochemical Analyses of the Pseudomonas Aeruginosa Psl Exopolysaccharide Reveal Overlapping Roles for Polysaccharide Synthesis Enzymes in Psi and LPS Production," Molecular Microbiology 73(4):622-638, Blackwell Scientific Publications, England (Aug. 2009).
Casadevall, A and Scharff, M.D., "Serum Therapy Revisited: Animal Models of Infection and Development of Passive Antibody Therapy," Antimicrobial Agents and Chemotherapy 38(8): 1695-1702 (Aug. 1994).
Casadevall, A and Scharff, M.D., "Return to the Past: the Case for Antibody-based Therapies in Infectious Diseases," Clinical Infectious Diseases 21(1):150-161, Clinical Infectious Diseases, United States (Jul. 1995).
Chang, T. T., et al., "Synergistic Effect of 4-Hydroperoxycyclophosphamide and Etoposide on a Human Promyelocytic Leukemia Cell Line (HL-60) Demonstrated by Computer Analysis," Cancer Research 45(6):2434-2439, American Association for Cancer Research, United States (Jun. 1985).
Choi, K. H., et al., "A TN7-based Broad-range Bacterial Cloning and Expression System," Nature Methods 2(6):443-448, Nature Publishing Group, United States (Jun. 2005).
Craven, D. E, and Steger, K.A., "Nosocomial Pneumonia in Mechanically Ventilated Adult Patients: Epidemiology and Prevention in 1996," Seminars in Respiratory Infections 11(1):32-53, W.B. Saunders, United States (Mar. 1996).
Dall'Acqua, W.F., et al., "Properties of Human IgG1s Engineered for Enhanced Binding to the Neonatal Fc Receptor (FcRn)," The Journal of Biological Chemistry 281(33):23514-23524, American Society for Biochemistry and Molecular Biology, United States (Aug. 2006).
Digiandomenico, A., et al., "A Multifunctional Bispecific Antibody Protects Against Pseudomonas Aeruginosa," Science Translational Medicine 6(262):262ra155, pp. 1-13, American Association for the Advancement of Science, United States (Nov. 2014).
Digiandomenico, A., et al., "Intranasal Immunization With Heterologously Expressed Polysaccharide Protects Against Multiple Pseudomonas Aeruginosa Infections," Proceedings of the National Academy of Sciences of the United States of America 104(11):4624-4629, National Academy of Sciences, United States (Mar. 2007).
Digiandomenico, A., et al., "Oral Vaccination of BALB/c Mice with *Salmonella enterica* Serovar Typhimurium Expressing Pseudomonas Aeruginosa O Antigen Promotes Increased Survival in an Acute Fatal Pneumonia Model," Infection and Immunity 72(12):7012-7021, American Society for Microbiology, United States (Dec. 2004).
Dixon, R. A and Chopra I., "Polymyxin B and Polymyxin B Nonapeptide Alter Cytoplasmic Membrane Permeability in *Escherichia coli*," The Journal of Antimicrobial Chemotherapy 18(5):557-563, Oxford University Press, England (Nov. 1986).
Drabick, J. J., et al., "Covalent Polymyxin B Conjugate with Human Immunoglobulin G as an Antiendotoxin Reagent," Antimicrobial Agents and Chemotherapy 42(3):583-588, American Society for Microbiology, United States (Mar. 1998).
Drenkard, E., "Antimicrobial Resistance of Pseudomonas Aeruginosa Biofilms," Microbes and Infection 5(13):1213-1219, Elsevier, France (Nov. 2003).
Extended European Search Report for Application No. EP12796646. 3, mailed on Feb. 2, 2015.
Francois, B., et al., "Safety and Pharmacokinetics of an Anti-PcrV Pegylated Monoclonal Antibody Fragment in Mechanically Ventilated Patients Colonized With Pseudomonas Aeruginosa: a Randomized, Double-Blind, Placebo-controlled Trial," Critical Care Medicine 40(8):2320-2326, Lippincott Williams & Wilkins, United States (Aug. 2012).
Frank, D.W., et al., "Generation and Characterization of a Protective Monoclonal Antibody to Pseudomonas Aeruginosa PcrV," The Journal of Infectious Diseases 186(1):64-73, Oxford University Press, United States (Jul. 2002).
Guidet B., et al., "Endotoxemia and Bacteremia in Patients With Sepsis Syndrome in the Intensive Care Unit," Chest 106(4):1194-1201, Elsevier, United States (Oct. 1994).
Hancock, R.E, and Speert, D.P., "Antibiotic Resistance in Pseudomonas Aeruginosa: Mechanisms and Impact on Treatment," Drug Resist Updates 3(4):247-255, Churchill Livingstone, Scotland (Aug. 2000).
Herbert, W., et al., "Multifunctional Monoclonal Antibody Targeting Pseudomonas aeruginosa Keratitis in Mice," Vaccines 8(4):638, 12 pages, Basel, Switzerland (Nov. 2020).
Hoang, T. T., et al., "A Broad-host-range Flp-FRT Recombination System for Site-specific Excision of Chromosomally-located DNA Sequences: Application for Isolation of Unmarked Pseudomonas Aeruginosa Mutants," Gene 212(1):77-86, Elsevier/North-Holland, Netherlands (May 1998).
Hoppner, W., "Clinical Impact of Molecular Diagnostics in Endocrinology," Hormone Research 58 (Suppl 3):7-15, Basel, Switzerland (2002).
International Preliminary Report on Patentability for International Patent Application No. PCT/US2012/063639, issued May 13, 2014, 5 pages.
International Preliminary Report on Patentability for International Patent Application No. PCT/US2012/063722, issued May 13, 2014, 7 pages.
International Search Report and Written Opinion for International Patent Application No. PCT/US2012/063639, mailed Jan. 22, 2013, 5 pages.
International Search Report and Written Opinion for International Patent Application No. PCT/US2012/063722, mailed Mar. 25, 2013, 11 pages.
Jackson K.D., et al., "Identification of Psl, a Locus Encoding a Potential Exopolysaccharide That is Essential for Pseudomonas Aeruginosa Pao1 Biofilm Formation," Journal of Bacteriology 186(14):4466-4475, American Society for Microbiology, United States (Jul. 2004).
Keller et al., American Journal of Respiratory and Critical Care Medicine, 2017, 195: abstract #A3918. abstract only (Year:2017).
Lyczak, J. B., et al., "Establishment of Pseudomonas Aeruginosa Infection: Lessons From a Versatile Opportunist," Microbes and Infection 2(9):1051-1060, Elsevier, France (Jul. 2000).

(56) References Cited

OTHER PUBLICATIONS

Ma, L., et al., "Pseudomonas Aeruginosa Psl Is a Galactose- and Mannose-Rich Exopolysaccharide, " Journal of Bacteriology 189(22):8353-8356, American Society for Microbiology, United States (Nov. 2007).

Mabry, R and Snavely, M., "Therapeutic Bispecific Antibodies: the Selection of Stable Single-chain Fragments to Overcome Engineering Obstacles," Idrugs : the Investigational Drugs Journal 13(8):543-549, Thomson Reuters (Scientific) Ltd, England (Aug. 2010).

International Preliminary Report on Patentability in International Patent Application No. PCT/US2012/041538, issued Dec. 10, 2013, 8 pages.

International Search Report and Written Opinion for International Patent Application No. PCT/US2012/041538, mailed Jan. 25, 2013, 11 pages.

Moriyama, K., et al., "Protective Effects of Affinity-purified Antibody and Truncated Vaccines Against Pseudomonas Aeruginosa V-antigen in Neutropenic Mice," Microbiology and Immunology 53(11):587-594, Wiley-Blackwell, Australia (Nov. 2009).

Pier, G.B., "Pseudomonas Aeruginosa: A Key Problem in Cystic Fibrosis," ASM News 64(6):339-347 (1998).

Preston, M. J., et al., "Rapid and Sensitive Method for Evaluating Pseudomonas Aeruginosa Virulence Factors During Corneal Infections in Mice," Infection and Immunity 63(9):3497-3501, American Society for Microbiology, United States (Sep. 1995).

Ray, V., et al., "Anti-Psl Targeting of Pseudomonas Aeruginosa Biofilms for Neutrophil-mediated Disruption," Scientific Reports 7(1): 16065, 12 pages, published online (Nov. 2017).

Sawa, T., et al., "Active and Passive Immunization With the Pseudomonas V Antigen Protects Against Type III Intoxication and Lung Injury," Nature Medicine 5(4):392-398, Nature Publishing Company, United States (Apr. 1999).

Schweizer, H. P., "Allelic Exchange in Pseudomonas Aeruginosa Using Novel ColE1-type Vectors and a Family of Cassettes Containing a Portable oriT and the Counter-selectable Bacillus Subtilis Sacb Marker," Molecular Microbiology 6(9):1195-1204, Blackwell Scientific Publications, England (May 1992).

Tabor, D.E., et al., "Pseudomonas aeruginosa PcrV and Psl, the Molecular Targets of Bispecific Antibody MEDI3902, Are Conserved Among Diverse Global Clinical Isolates," Journal of Infectious Diseases 218(12):1983-1994, Oxford University Press, United States (Nov. 2018).

Warrener, P., et al., "A Novel Anti-PcrV Antibody Providing Enhanced Protection Against Pseudomonas Aeruginosa in Multiple Animal Infection Models," Antimicrobial Agents and Chemotherapy 58(8):4384-4391, American Society for Microbiology, United States (May 2014).

Bailat S., et al., "Similarities and Disparities Between Core-specific and O-side-chain-specific Antilipopolysaccharide Monoclonal Antibodies in Models of Endotoxemia and Bacteremia in Mice," Infection and Immunity 65(2):811-814 (Feb. 1997).

Birkenmeier, G., et al., "Polymyxin B-Conjugated a2-Macroglobulin as an Adjunctive Therapy to Sepsis: Modes of Action and Impact on Lethality," The Journal of Pharmacology and Experimental Therapeutics 318(2): 762-771 , American Society for Pharmacology and Experimental Therapeutics, United States (May 2006).

Bucklin, S. E and Morrison D.C., "Differences in Therapeutic Efficacy Among Cell Wall-active Antibiotics in a Mouse Model of Gram-negative Sepsis," The Journal of Infectious Diseases 172(6): 1519-1527, University of Chicago Press, United States (Dec. 1995).

Digiandomenico, A., et al., "Controlling Pseudomonas Aeruginosa Infections Using a Novel Multifunction Antibody Design," American Journal of Respiratory and Critical Care Medicine 189:A5239, Abstract (2014).

Dunn, D. L., et al., "Anticore Endotoxin F(Ab')2 Equine Immunoglobulin Fragments Protect Against Lethal Effects of Gram-negative Bacterial Sepsis," Surgery 96(2):440-446, Mosby, United States (Aug. 1984).

Liu, P. V. and Wang, S., "Three New Major Somatic Antigens of Pseudomonas Aeruginosa," Journal of Clinical Microbiology 28(5):922-925, American Society for Microbiology, United States (May 1990).

Mikkelsen, H., et al., "Key Two-component Regulatory Systems That Control Biofilm Formation in Pseudomonas Aeruginosa," Environmental Microbiology 13(7):1666-1681, Blackwell Science, England (Jul. 2011).

Miyazaki, S., et al., "Role of Exotoxin A in Inducing Severe Pseudomonas Aeruginosa Infections in Mice," Journal of Medical Microbiology 43(3): 169-175, Microbiology Society, England (Sep. 1995).

Morrison, D. C. and Jacobs, D. M., "Binding of Polymyxin B to the Lipid A Portion of Bacterial Lipopolysaccharides," Immunochemistry 13(10):813-818, Pergamon Press, England (Oct. 1976).

Secher, T., et al., "Anti-pseudomonas Aeruginosa Serotype O11 LPS Immunoglobulin M Monoclonal Antibody Panobacumab (KBPA101) Confers Protection in a Murine Model of Acute Lung Infection," The Journal of Antimicrobial Chemotherapy 66(5):1100-1109, Oxford University Press, England (May 2011).

Supplementary European Search Report Corresponding to EP12847479 dated Feb. 2, 2016, 18 pages.

Liu, P.V., et al., "Survey of Heat-Stable, Major Somatic Antigens of Pseudomonas aeruginosa," Int. J. of Syst. and Evol. Microbiology, vol. 33, No. 2, pp. 256-264 (Apr. 1983).

Cao, Y., et al., "Bispecific Antibodies as Novel Bioconjugates," Bioconjugate Chemistry, 9(6): 635-644, American Chemistry Society, United States (1998).

Office action mailed Mar. 4, 2021, in U.S. Appl. No. 16/789,790, inventor Digiandomenico; Antonio, filed Feb. 13, 2020, 6 pages.

\* cited by examiner

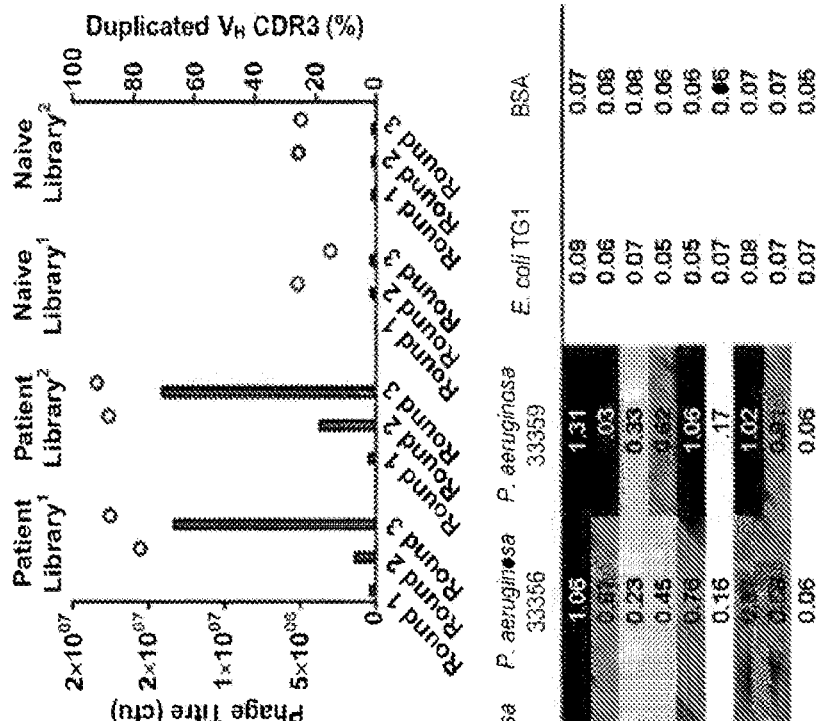
FIG. 1C.
FIG. 1D.
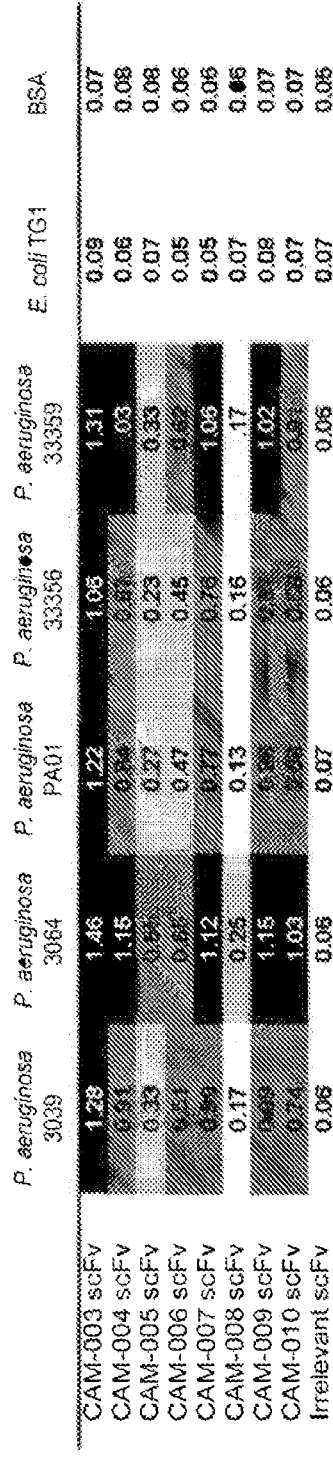
FIG. 1E.

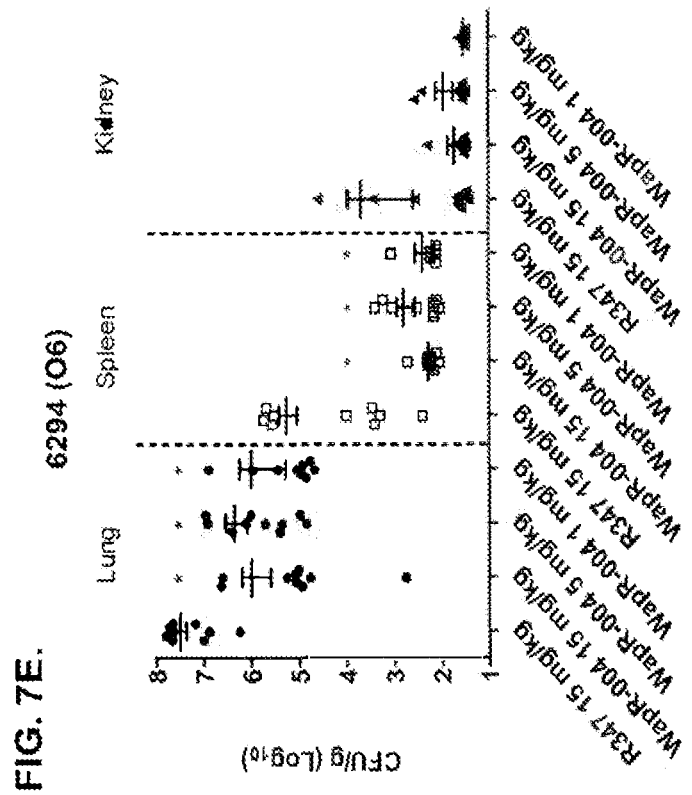
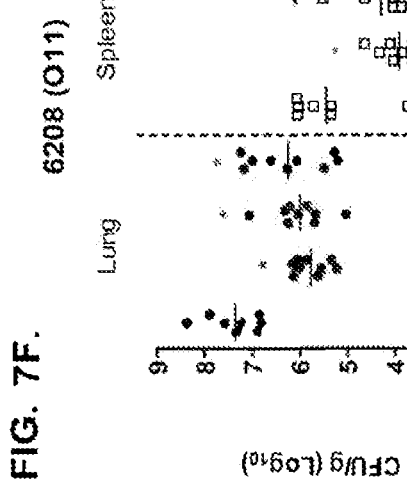
FIG. 7E.
FIG. 7F.

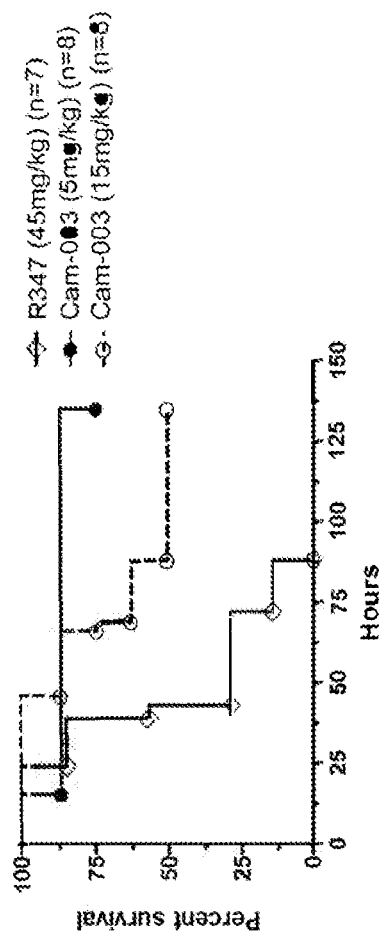
FIG. 8E.
FIG. 8F.
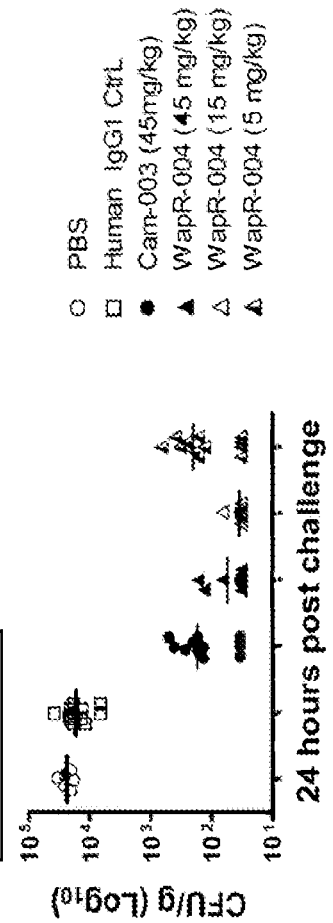
FIG. 8G.
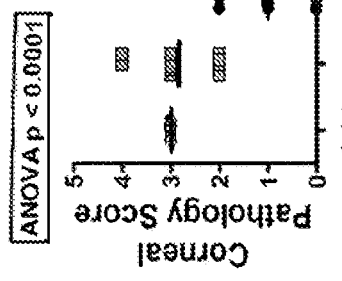

| Epitope | mAb | $K_D$ (nM) | Cell attachment max. inhibition (µg/ml) | OPK EC50 (µg/ml) |
|---|---|---|---|---|
| Class 1 | WapR-004 | 118.00 | 0.3 | 0.0027 |
| | Cam-003 | 144.00 | 1.0 | 0.0220 |
| | Cam-004 | 2100.00 | >30.0 | 0.2771 |
| | Cam-005 | 8400.00 | NA | NA |
| Class 2 | WapR-001 | 0.84 | 30.0 | 0.3100 |
| | WapR-003 | 12.20 | 30.0 | 0.2778 |
| | WapR-002 | 12.60 | ND | 0.3960 |
| Class 3 | WapR-016 | 75.00 | ND | 0.2417 |

FIG. 10A

| scFv-Fc | $k_{off}$ | $k_{on}$ | $K_D$ (nM) | OPK EC50 |
|---|---|---|---|---|
| W4 RAD | 1.30E-02 | 5.39E+04 | 241 | 0.0068 |
| W4-M1 | 8.18E-02 | 1.69E+05 | 483 | 0.0475 |
| W4-M7 | 1.28E-02 | 6.49E+04 | 196 | 0.0060 |
| W4-M8 | 1.90E-02 | 1.54E+05 | 124 | 0.0056 |
| W4-M9 | 1.66E-02 | 1.98E+05 | 84 | 0.0167 |
| W4-M11 | 8.50E-03 | 1.25E+05 | 68 | 0.0045 |
| W4-M12 | 9.10E-03 | 1.26E+05 | 72 | 0.0085 |
| W4-M17 | 1.91E-01 | 9.60E+04 | 1990 | 1.3935 |

FIG. 10B

|  | Exp1 | Exp2 | Exp3 | Exp4 | Average KD (nM) |
|---|---|---|---|---|---|
| W4-RAD | 57.6 | 147.0 | 139.0 | 131.0 | 118.7 |
| W4-RAD(GL) | 24.6 | 57.7 | 44.8 | 35.2 | 40.6 |
| PsI0096 | 29.8 | 11.8 | | | 20.8 |
| PsI00170 | 41.9 | 26.2 | | | 34.1 |
| PsI00225 | 10.7 | 17.5 | | | 14.1 |
| PsI00304 | 60.8 | 57.9 | | | 59.4 |
| PsI00337 | 70.9 | 51.1 | | | 61.0 |
| PsI00348 | 72.9 | 12.6 | | | 42.8 |
| PsI00567 | 74.5 | 31.9 | | | 53.2 |
| PsI00573 | 84.2 | 30.0 | | | 57.1 |
| PsI00574 | 48.1 | 64.0 | | | 56.1 |
| PsI00582 | 48.1 | 54.4 | | | 51.3 |
| PsI00584 | 49.7 | 28.9 | | | 39.3 |
| PsI00585 | 57.8 | 28.8 | | | 43.3 |
| PsI00588 | 46.2 | 25.6 | | | 35.9 |
| PsI00589 | 37.8 | 52.6 | | | 45.2 |

FIG. 10C

FIG. 12A.

| Class 1 | Class 2 | Class 2 | Class 4 | Class 5 | Class 6 |
|---|---|---|---|---|---|
| V2L7 | 1E6 | 29D2 | V2L2 | 21F1 | 3F7 |
| 3G5 | 1F3 | 4A8* | | LE10* | |
| 4C3 | | 2H3* | | SH3* | |
| 11A6 | | | | | | some competition

*In vivo*: ▒ protective ☐ not protective ▓ ND

\* SJL mouse mAbs

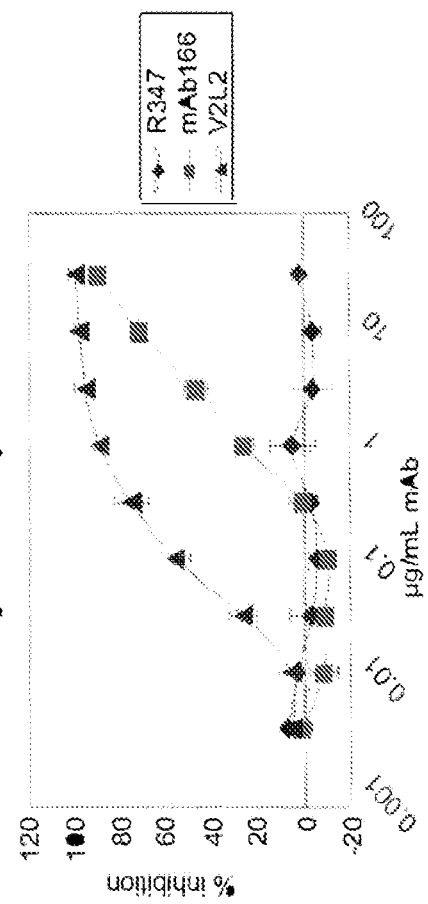
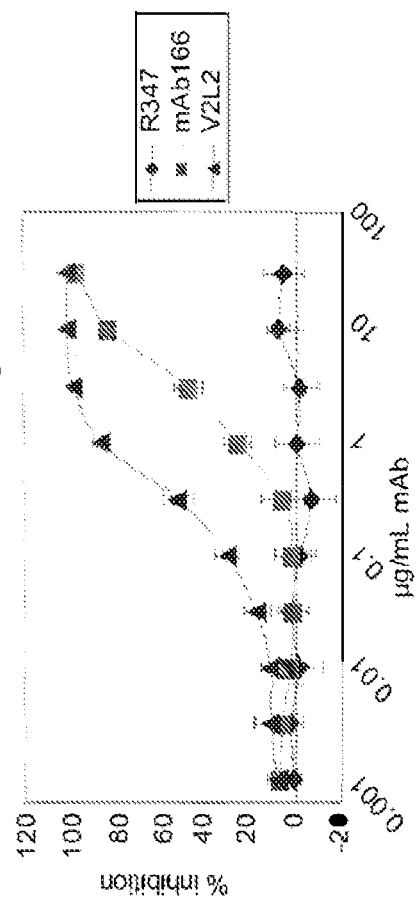
FIG. 12B. A549 Cytotoxicity Inhibition
FIG. 12C. Inhibition of RBC Lysis

*P. aeruginosa* 6077 (O11-cytotoxic) acute pneumonia

Figure 13A:
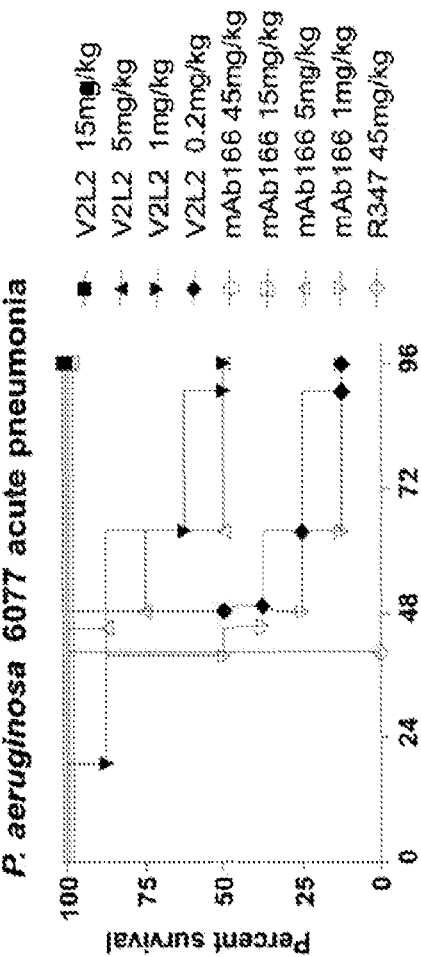
Figure 13B:
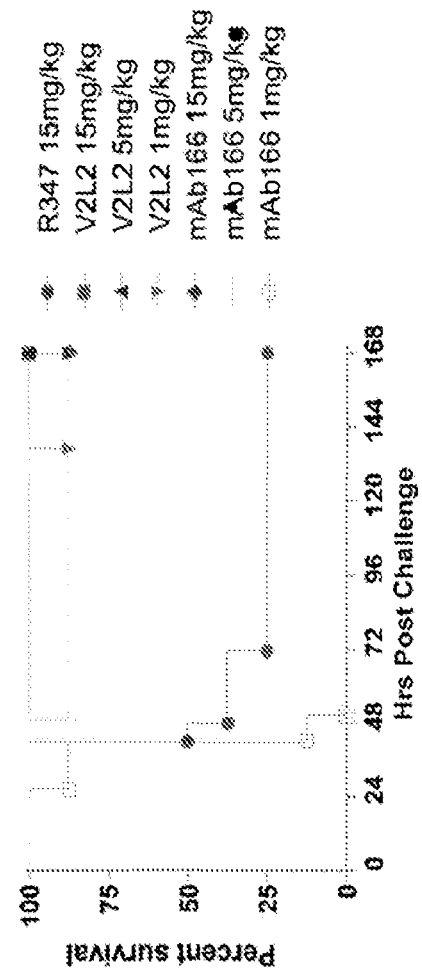
Figure 13C:
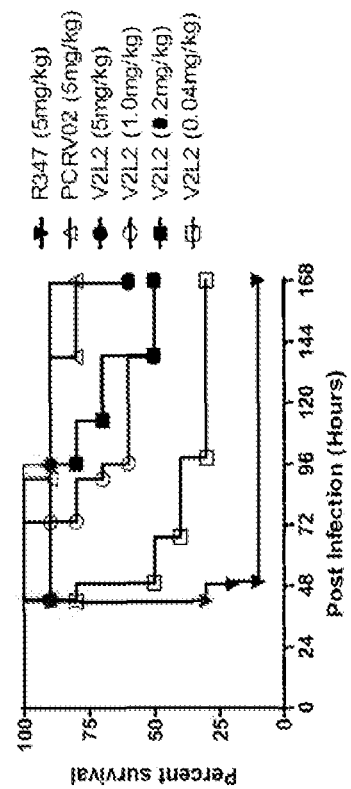
Figure 13D:
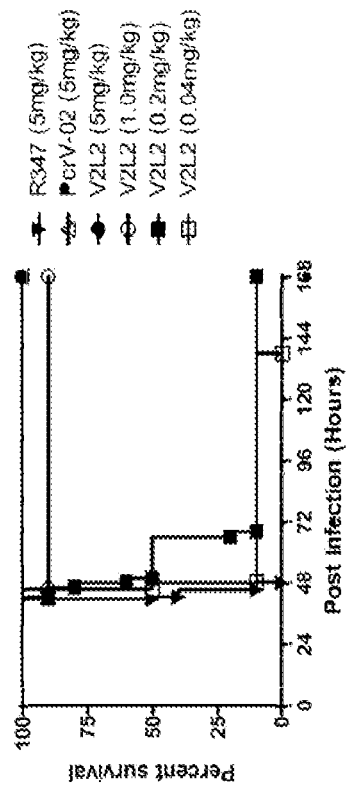
Figure 13E:
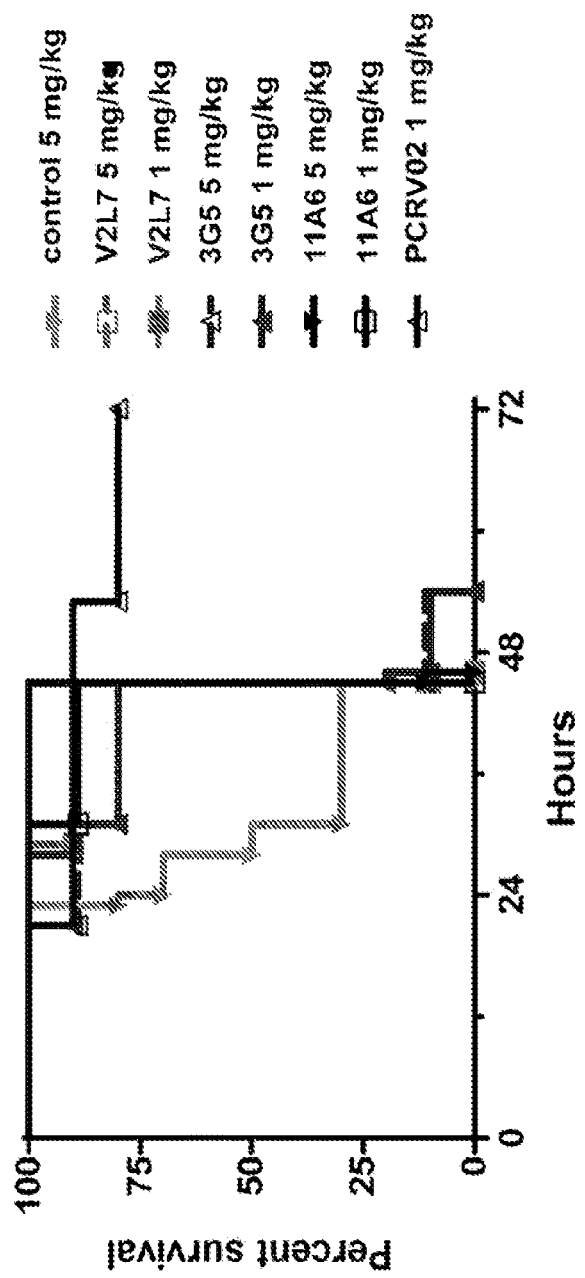
Figure 13G:
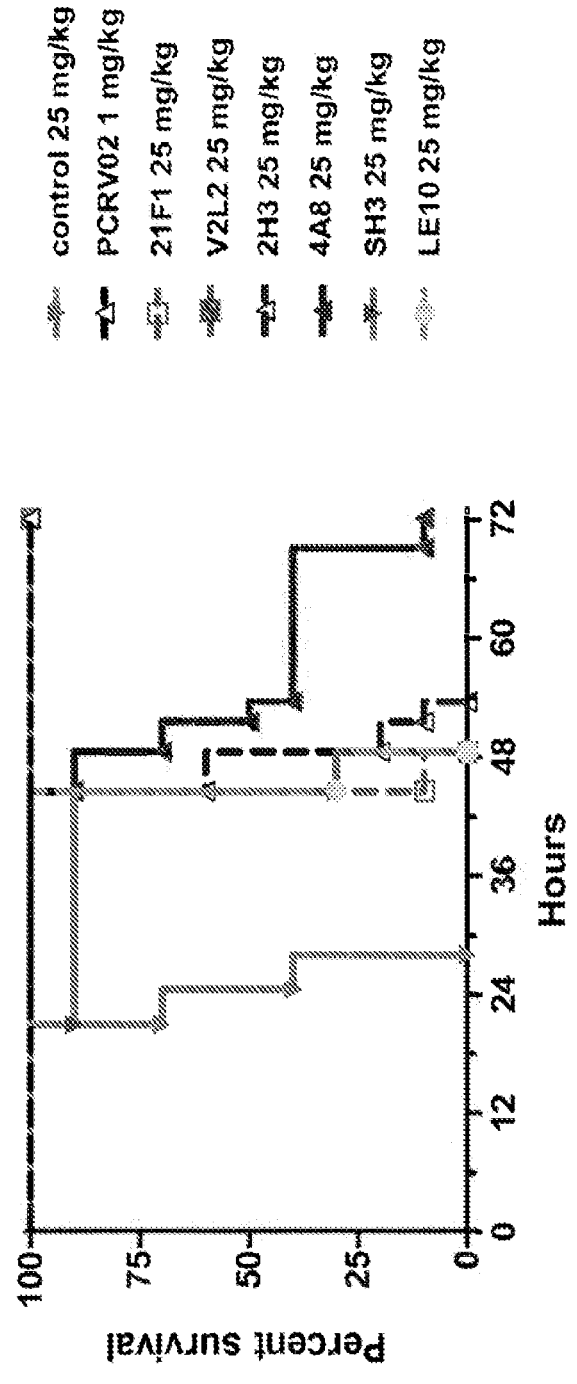
Figure 13H:
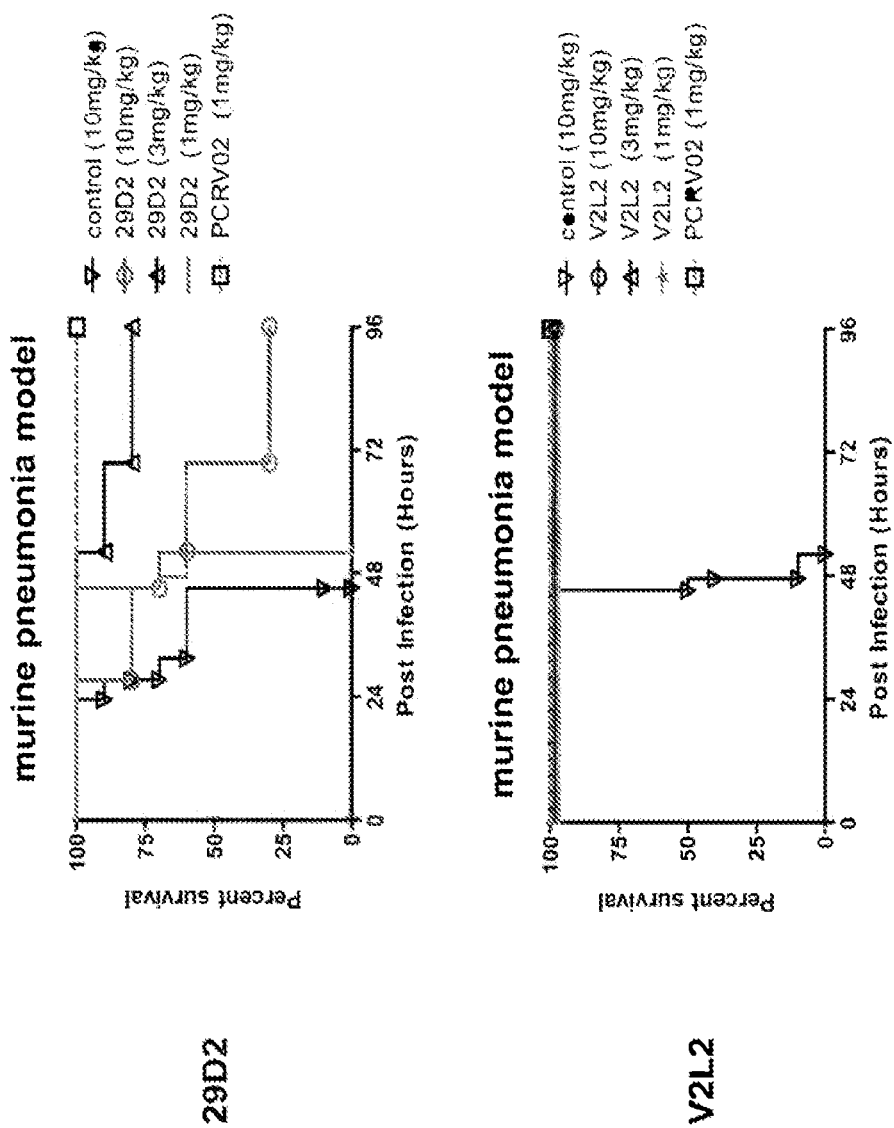
Figure 13I:
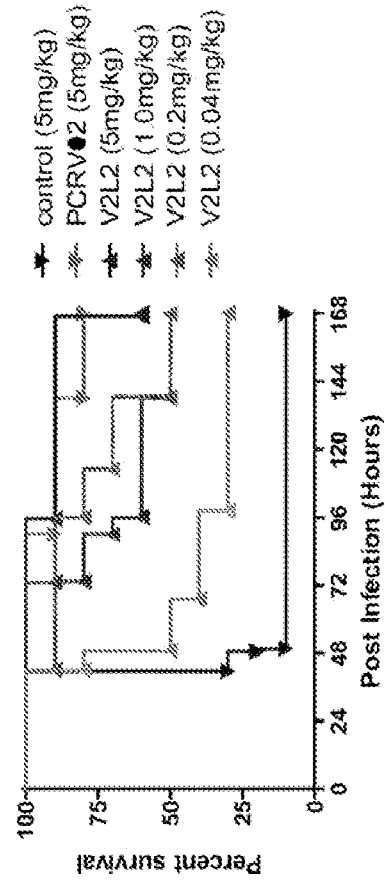
Figure 13I:
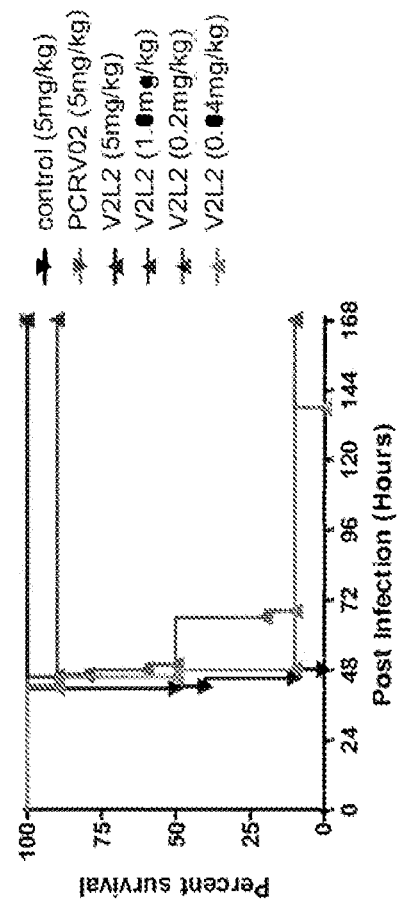

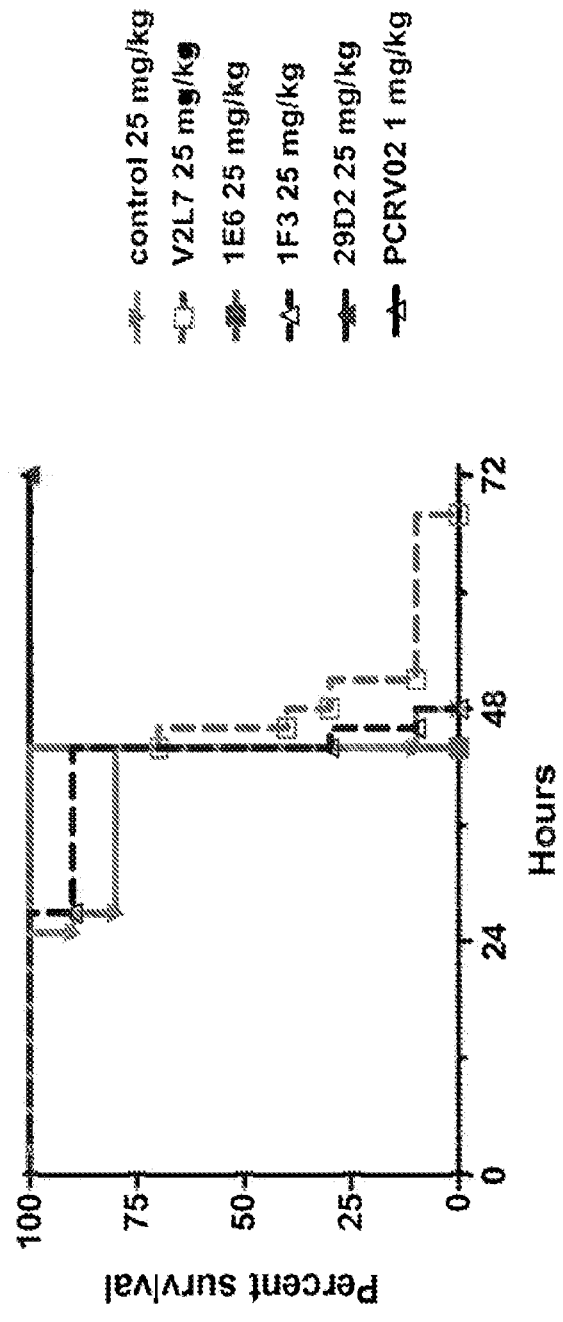
FIG. 13F. *P. aeruginosa* 6077 (O11-cytotoxic) acute pneumonia

*P. aeruginosa* 6077 (O11-cytotoxic) acute pneumonia

Figure 16C:
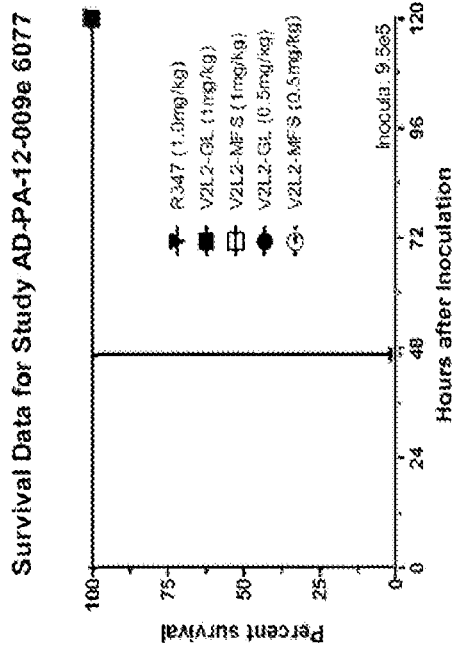
Figure 16D:
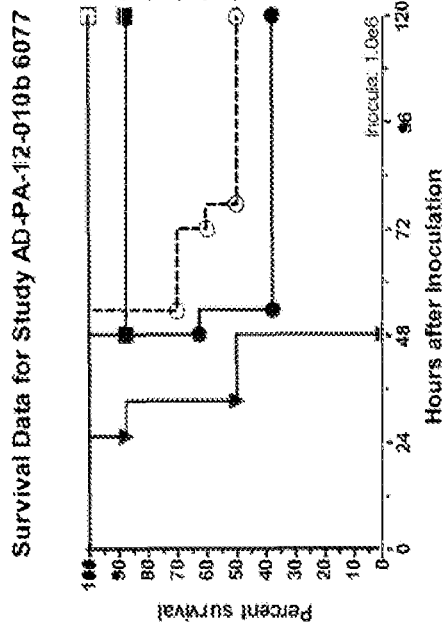
Figure 16E:
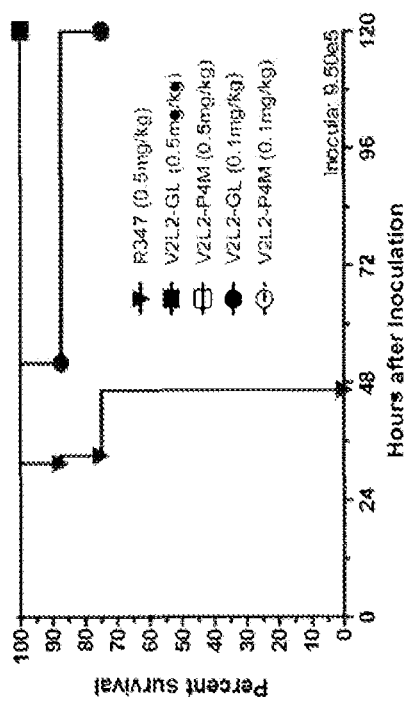
Figure 16F:
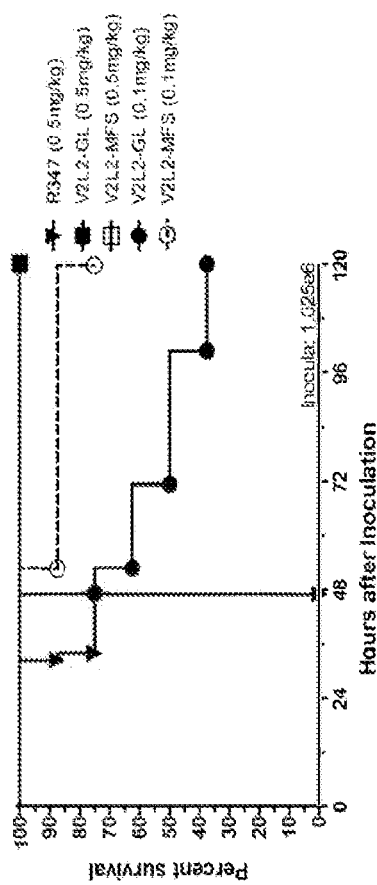
Figure 16G:
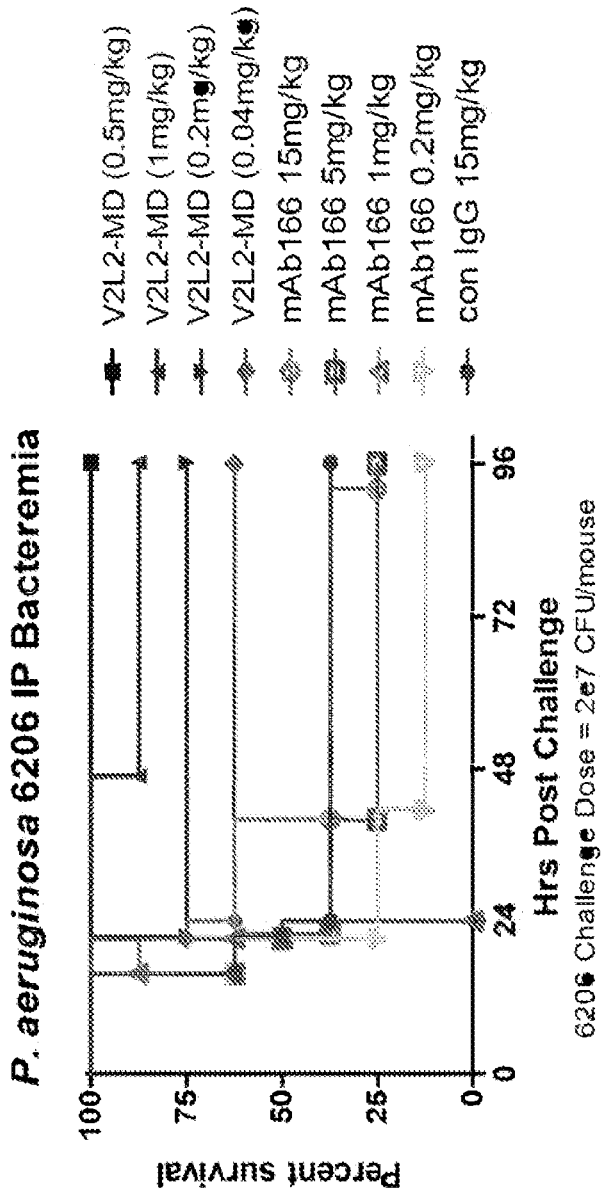

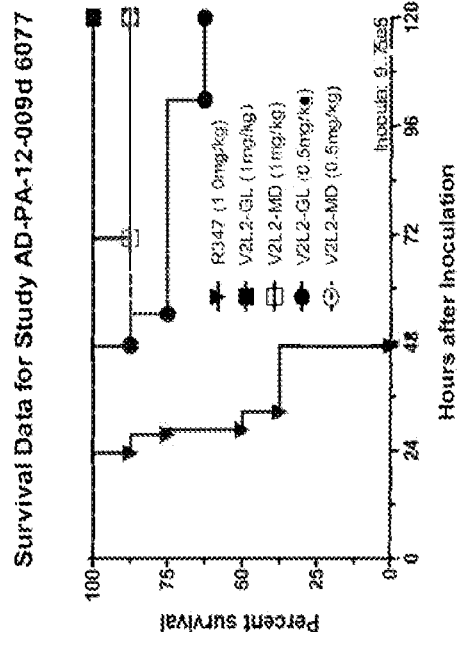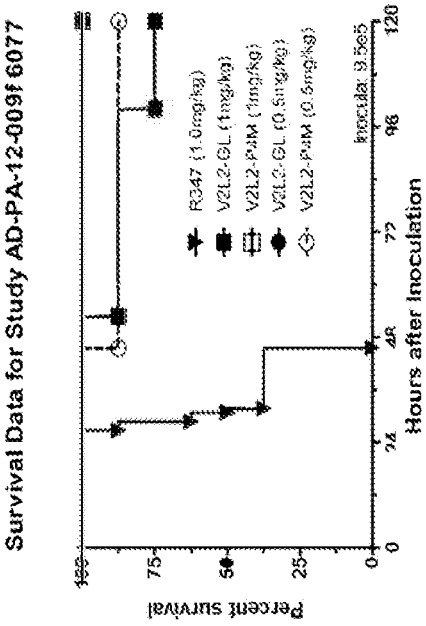
FIG. 16A.
FIG. 16B.

Figure 19C:
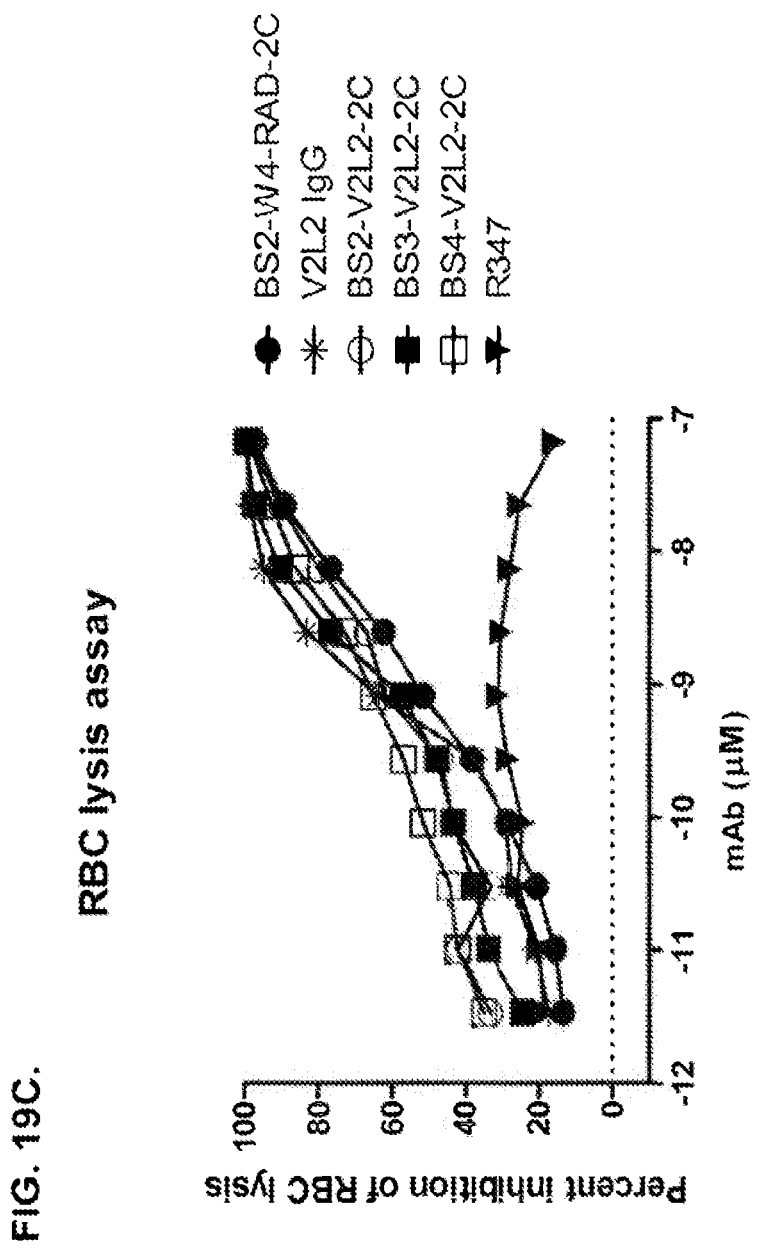

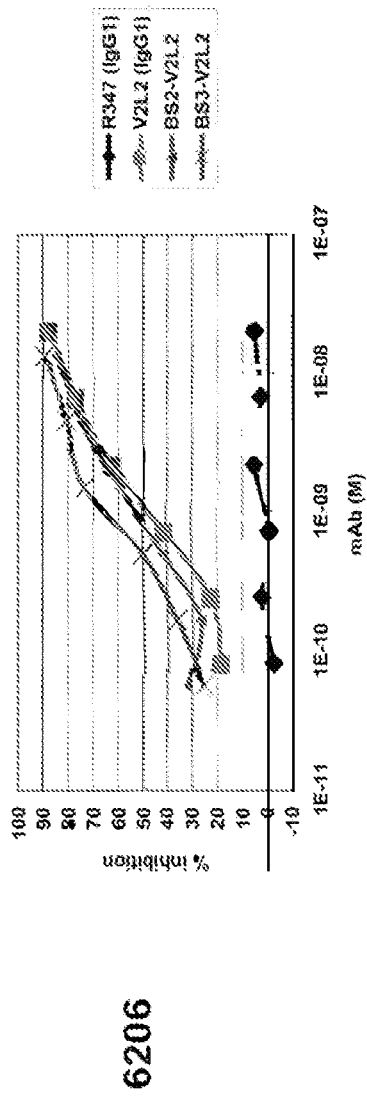
FIG. 19A. 6206
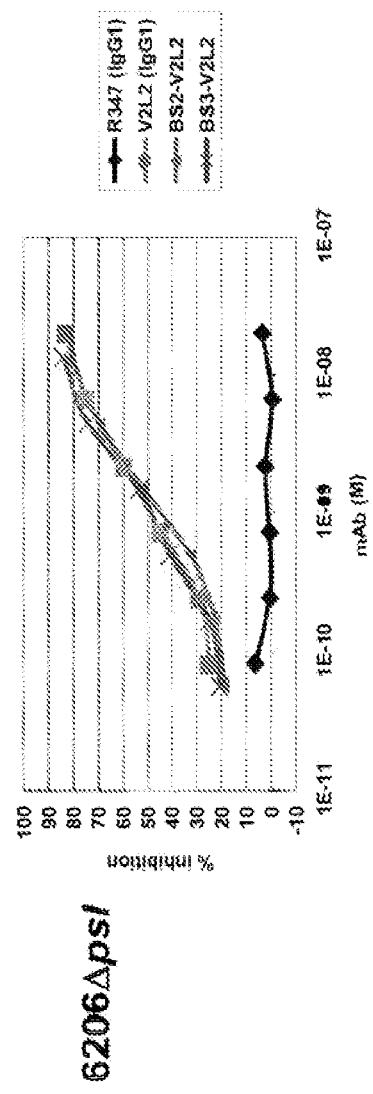
FIG. 19B. 6206Δpsl

FIG. 211.

Percent protection against lethal pneumonia in mice challenged with *P. aeruginosa* strain 6206 (O11-ExoU+)

| Antibody | Antibody concentration (mg/kg) | | | | | | | |
|---|---|---|---|---|---|---|---|---|
| | 15 | 10 | 5 | 2 | 1 | 0.5 | 0.2 | 0.1 |
| BS2-V2L2* | 100 (10) | - | - | - | 67 (30) | 40 (30) | - | - |
| BS2-V2L2-2C | - | - | 90 (20) | - | 25 (20) | 0 (20) | 0 (10) | - |
| BS2-W4-RAD-2C | - | - | 70 (10) | - | 10 (10) | 0 (10) | 0 (10) | - |
| BS3-V2L2-2C | - | 80 (10) | 40 (20) | - | 10 (20) | 0 (20) | 0 (20) | - |
| BS4-V2L2-2C | - | - | 100 (60) | - | 88 (60) | 60 (60) | 60 (60) | - |
| V2L2 | - | - | 80 (10) | - | 20 (10) | 10 (10) | 10 (10) | - |
| W4-RAD | 0 (10) | - | 0 (10) | - | 0 (10) | - | - | - |

| Mixture | Antibody concentration (mg/kg for each mAb) | | | | | |
|---|---|---|---|---|---|---|
| | 5 | 2 | 1 | 0.5 | 0.2 | 0.1 |
| W4-RAD + V2L2 | 100 (10) | 100 (40) | 78 (40) | 15 (40) | - | 3 (40) |

120 hr post-infection (inocula ~1.0e6 CFU/animal)
Parentheses indicate total number of animals
*1mg/kg and 0.5mg/kg includes studies where animals were treated with 1.7 and 0.55mg/kg, respectively

FIG. 28A.

Prophylaxis (T = -24h) – 120 hr post-infection

BS4-GLO Dose (mg/kg)

| Strain/inoculum | 15 | 10 | 5 | 3 | 1 | 0.5 | 0.2 | 0.07 | 0.02 | 0.007 |
|---|---|---|---|---|---|---|---|---|---|---|
| 6206 (1e6) | - | - | 100 (60) | - | 8● (60) | 60 (60) | 10 (60) | - | - | - |
| 6077 (1e6) | - | - | - | - | 100 (10) | 100 (10) | 95.8 (26) | 91.6 (26) | 50 (16) | 12.5 (16) |
| 6294 (2e7) | - | 100 (5) | - | 8● (5) | 60 (5) | 11.1 (18) | 11.1 (18) | - | - | - |
| PA103 (1e6) | 6● (5) | - | 4● (5) | - | 0 (5) | - | - | - | - | - |

FIG. 28B.

Therapy (T = 1h) – 120 hr post-infection

BS4-GLO Dose (mg/kg)

| Strain/inoculum | 45 | 15 | 10 | 5 | 2 | 1 | 0.5 | 0.3 | 0.03 |
|---|---|---|---|---|---|---|---|---|---|
| 6206 (1e6) | 72.2 (18) | 55.6 (18) | - | 33.3 (18) | - | 11.1 (18) | - | - | ●(10) |
| 6077 (1e6) | - | - | - | - | - | 92 (22) | 83.3 (12) | 8● (10) | 3● (10) |
| 6294 (2e7) | - | - | - | 70 (10) | - | 10 (10) | 0 (10) | - | 0 (10) |
| PA103 (1e6) | - | 0 (5) | - | 0 (5) | - | 0 (5) | - | - | - |

Bacteremia model

Thermal injury model

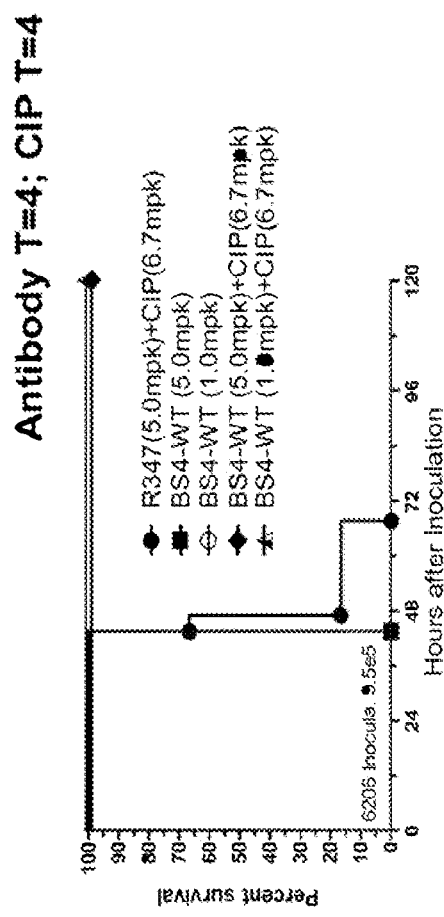
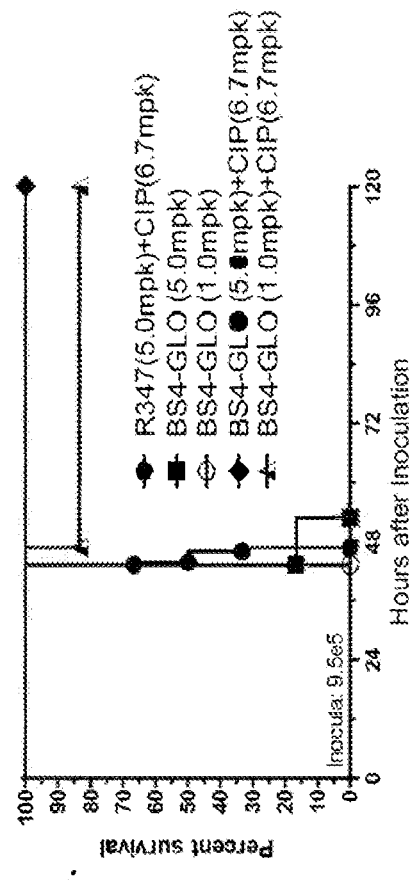
FIG. 32A.
FIG. 32B.

Bs4 T=-24h; Abx T=1h
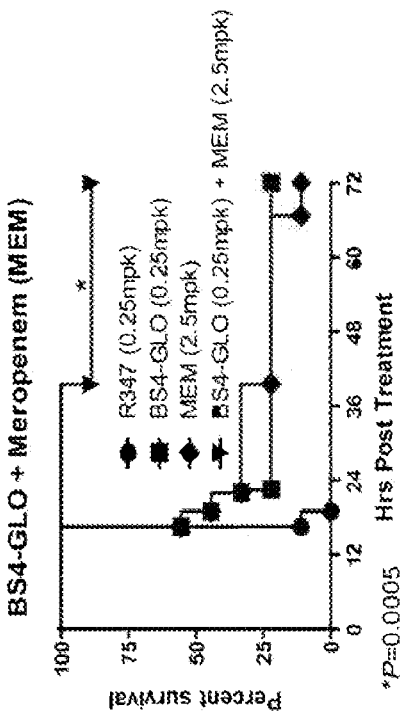
FIG. 34A. BS4-GLO + Ciprofloxacin (CIP)
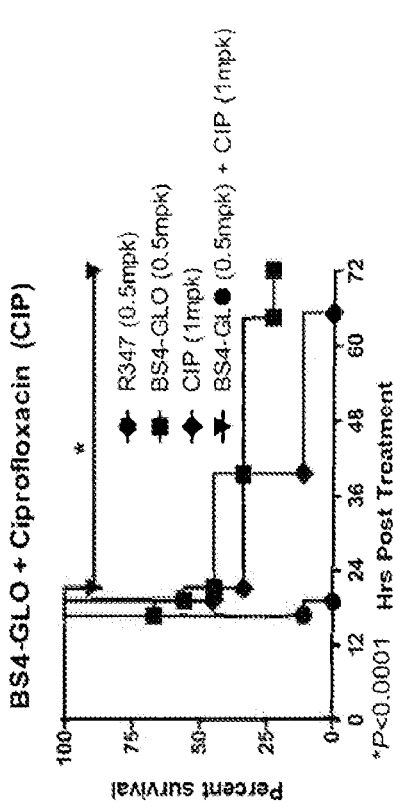
FIG. 34B. BS4-GLO + Meropenem (MEM)
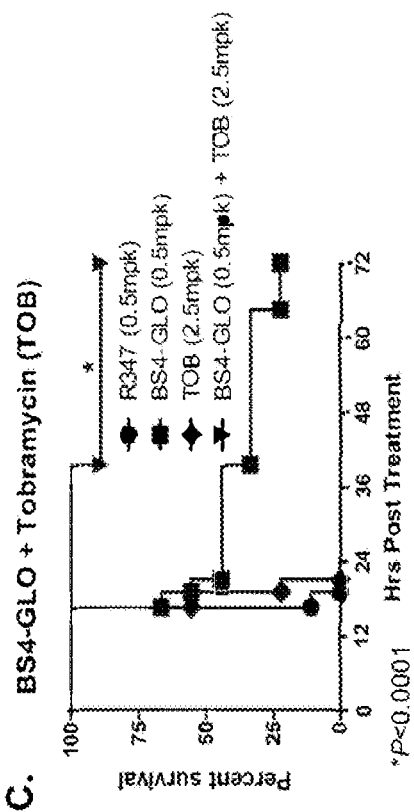
FIG. 34C. BS4-GLO + Tobramycin (TOB)
Strain 6294 (O6)
Bacteremia model

35A.

Bs4 Version I
Light Chain
[Anti – PcrV light chain variable region]-
RTVAAPSVFIFPPSDEQLKSGTASVVCLLNNFYPREAKVQ
WKVDNALQSGNSQESVTEQDSKDSTYSLSSTLTLSKADYEKHKVYACEVTHQGLSSPVTKSFNRGEC
(Kappa light chain constant region represented here – could be a lambda region  SEQ ID NO:332
Heavy Chain
[Anti – PcrV heavy chain variable region]–
ASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVDKRV*EPKSC*GGGGS
G*GGGS*–[anti-PsI scFV]–
*GGGGSGGGGSDKTHTCPPCP*APELLGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKAL
PAPIEKTISKAKGQPREPQVYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK  SEQ ID NO:331

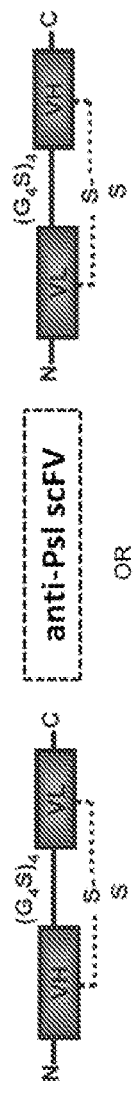

anti-PsI scFV hinge regions are underlined in bolded italics
G4S linkers underlined in italics

FIG. 35

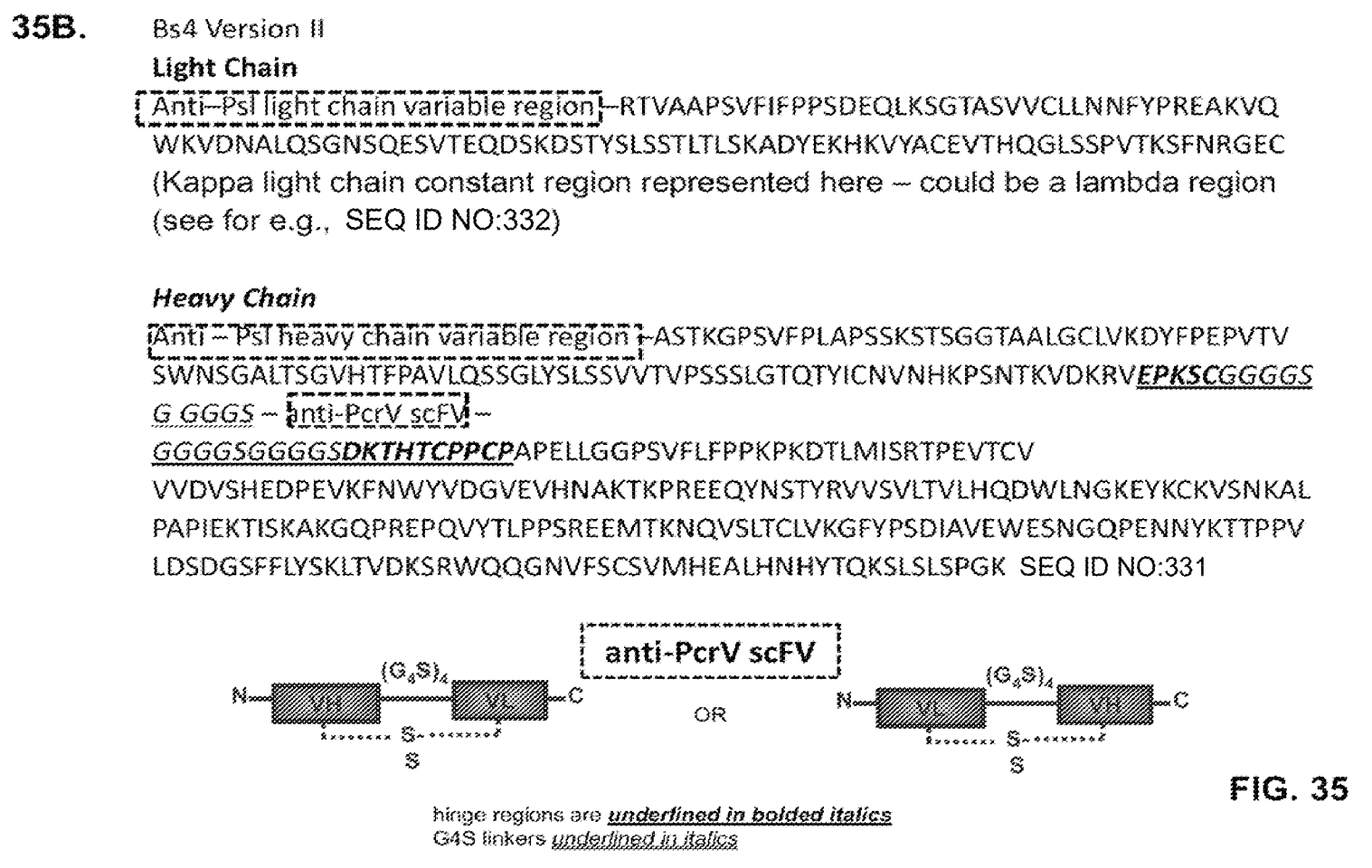

35B. Bs4 Version II

Light Chain

[Anti–PsT light chain variable region]–RTVAAPSVFIFPPSDEQLKSGTASVVCLLNNFYPREAKVQ
WKVDNAL

SEQUENCE LISTING

<160> NUMBER OF SEQ ID NOS: 332

<210> SEQ ID NO 1
<211> LENGTH: 118
<212> TYPE: PRT
<213> ORGANISM: Artificial Sequence
<220> FEATURE:
<223> OTHER INFORMATION: Cam-003 VH

<400> SEQUENCE: 1

Gln Val Arg Leu Gln Gln Ser Gly Pro Gly Leu Val Lys Pro Ser Glu
1               5                   10                  15

Thr Leu Ser Leu Thr Cys Thr Val Ser Gly Gly Ser Thr Ser Pro Tyr

```
                    20                  25                  30

Phe Trp Ser Trp Leu Arg Gln Pro Pro Gly Lys Gly Leu Glu Trp Ile
                35                  40                  45

Gly Tyr Ile His Ser Asn Gly Gly Thr Asn Tyr Asn Pro Ser Leu Lys
            50                  55                  60

Ser Arg Leu Thr Ile Ser Gly Asp Thr Ser Lys Asn Gln Phe Ser Leu
 65                  70                  75                  80

Asn Leu Ser Phe Val Thr Ala Ala Asp Thr Ala Leu Tyr Tyr Cys Ala
                85                  90                  95

Arg Thr Asp Tyr Asp Val Tyr Gly Pro Ala Phe Asp Ile Trp Gly Gln
                100                 105                 110

Gly Thr Met Val Thr Val
                115

<210> SEQ ID NO 2
<211> LENGTH: 108
<212> TYPE: PRT
<213> ORGANISM: Artificial Sequence
<220> FEATURE:
<223> OTHER INFORMATION: Cam-003, Cam-004, and Cam-005 VL

<400> SEQUENCE: 2

Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
                35                  40                  45

Gly Lys Asn Asn Arg Pro Ser Gly Ile Pro Asp Arg Phe Ser Gly Ser
            50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu
                100                 105

<210> SEQ ID NO 3
<211> LENGTH: 118
<212> TYPE: PRT
<213> ORGANISM: Artificial Sequence
<220> FEATURE:
<223> OTHER INFORMATION: Cam-004 VH

<400> SEQUENCE: 3

Gln Val Gln Leu Gln Gln Ser Gly Pro Gly Arg Val Lys Pro Ser Glu
 1               5                  10                  15

Thr Leu Ser Leu Thr Cys Thr Val Ser Gly Tyr Ser Val Ser Ser Gly
                20                  25                  30

Tyr Tyr Trp Gly Trp Ile Arg Gln Ser Pro Gly Thr Gly Leu Glu Trp
                35                  40                  45

Ile Gly Ser Ile Ser His Ser Gly Ser Thr Tyr Tyr Asn Pro Ser Leu
            50                  55                  60

Lys Ser Arg Val Thr Ile Ser Gly Asp Ala Ser Lys Asn Gln Phe Phe
 65                  70                  75                  80

Leu Arg Leu Thr Ser Val Thr Ala Ala Asp Thr Ala Val Tyr Tyr Cys
                85                  90                  95
```

```
Ala Arg Ser Glu Ala Thr Ala Asn Phe Asp Ser Trp Gly Arg Gly Thr
            100                 105                 110

Leu Val Thr Val Ser Ser
        115

<210> SEQ ID NO 4
<211> LENGTH: 119
<212> TYPE: PRT
<213> ORGANISM: Artificial Sequence
<220> FEATURE:
<223> OTHER INFORMATION: Cam-005 VH

<400> SEQUENCE: 4

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Ser Val Ser Ser Ser
            20                  25                  30

Gly Tyr Tyr Trp Thr Trp Ile Arg Gln Pro Pro Gly Lys Gly Leu Glu
        35                  40                  45

Trp Ile Gly Ser Ile Tyr Ser Ser Gly Ser Thr Tyr Tyr Ser Pro Ser
    50                  55                  60

Leu Lys Ser Arg Val Thr Ile Ser Gly Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Leu Asn Trp Gly Thr Val Ser Ala Phe Asp Ile Trp Gly
            100                 105                 110

Arg Gly Thr Leu Val Thr Val
        115

<210> SEQ ID NO 5
<211> LENGTH: 119
<212> TYPE: PRT
<213> ORGANISM: Artificial Sequence
<220> FEATURE:
<223> OTHER INFORMATION: WapR-001 VH

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ser Ala Ser Gly Phe Thr Phe Ser Arg Tyr
            20                  25                  30

Pro Met His Trp Val Arg Gln Ala Pro Gly Lys Gly Leu Glu Tyr Val
        35                  40                  45

Ser Asp Ile Gly Thr Asn Gly Gly Ser Thr Asn Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Ser Ser Leu Arg Ala Glu Asp Thr Ala Val Tyr His Cys
                85                  90                  95

Val Ala Gly Ile Ala Ala Ala Tyr Gly Phe Asp Val Trp Gly Gln Gly
            100                 105                 110

Thr Met Val Thr Val Ser Ser
        115

<210> SEQ ID NO 6
<211> LENGTH: 110
<212> TYPE: PRT
<213> ORGANISM: Artificial Sequence
```

<220> FEATURE:
<223> OTHER INFORMATION: WapR-001 VL

<400> SEQUENCE: 6

```
Gln Ala Gly Leu Thr Gln Pro Ala Ser Val Ser Gly Ser Pro Gly Gln
1               5                   10                  15

Ser Ile Thr Ile Ser Cys Thr Gly Thr Ser Ser Asp Ile Ala Thr Tyr
            20                  25                  30

Asn Tyr Val Ser Trp Tyr Gln Gln His Pro Gly Lys Ala Pro Lys Leu
        35                  40                  45

Met Ile Tyr Glu Gly Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Arg Ser
                85                  90                  95

Tyr Thr Tyr Val Phe Gly Thr Gly Thr Glu Leu Thr Val Leu
            100                 105                 110
```

<210> SEQ ID NO 7
<211> LENGTH: 118
<212> TYPE: PRT
<213> ORGANISM: Artificial Sequence
<220> FEATURE:
<223> OTHER INFORMATION: WapR-002 VH

<400> SEQUENCE: 7

```
Gln Val Gln Leu Val Gln Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Pro Met His Trp Val Arg Gln Ala Pro Gly Lys Gly Leu Asp Tyr Val
        35                  40                  45

Ser Asp Ile Ser Pro Asn Gly Gly Ser Thr Asn Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Ser Ser Leu Arg Ala Glu Asp Thr Ala Val Tyr Tyr Cys
                85                  90                  95

Val Met Gly Leu Val Pro Tyr Gly Phe Asp Ile Trp Gly Gln Gly Thr
            100                 105                 110

Leu Val Thr Val Ser Ser
        115
```

<210> SEQ ID NO 8
<211> LENGTH: 110
<212> TYPE: PRT
<213> ORGANISM: Artificial Sequence
<220> FEATURE:
<223> OTHER INFORMATION: WapR-002 VL

<400> SEQUENCE: 8

```
Gln Thr Val Val Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45
```

```
Met Ile Tyr Glu Val Ser Asn Arg Pro Ser Gly Val Ser Asn His Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Ser
                85                  90                  95

Ser Thr Tyr Val Phe Gly Thr Gly Lys Val Thr Val Leu
            100                 105                 110
```

<210> SEQ ID NO 9
<211> LENGTH: 118
<212> TYPE: PRT
<213> ORGANISM: Artificial Sequence
<220> FEATURE:
<223> OTHER INFORMATION: WapR-003 VH

<400> SEQUENCE: 9

```
Gln Met Gln Leu Val Gln Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Pro Met His Trp Val Arg Gln Ala Pro Gly Lys Gly Leu Asp Tyr Val
            35                  40                  45

Ser Asp Ile Ser Pro Asn Gly Gly Ala Thr Asn Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Ser Ser Leu Arg Ala Glu Asp Thr Ala Val Tyr Tyr Cys
                85                  90                  95

Val Met Gly Leu Val Pro Tyr Gly Phe Asp Asn Trp Gly Gln Gly Thr
            100                 105                 110

Met Val Thr Val Ser Ser
        115
```

<210> SEQ ID NO 10
<211> LENGTH: 110
<212> TYPE: PRT
<213> ORGANISM: Artificial Sequence
<220> FEATURE:
<223> OTHER INFORMATION: WapR-003 VL

<400> SEQUENCE: 10

```
Gln Thr Val Val Thr Gln Pro Ala Ser Val Ser Ala Ser Pro Gly Gln
1               5                   10                  15

Ser Ile Thr Ile Ser Cys Ala Gly Thr Ser Gly Asp Val Gly Asn Tyr
            20                  25                  30

Asn Phe Val Ser Trp Tyr Gln Gln His Pro Gly Lys Ala Pro Lys Leu
            35                  40                  45

Leu Ile Tyr Glu Gly Ser Gln Arg Pro Ser Gly Val Ser Asn Arg Phe
    50                  55                  60

Ser Gly Ser Arg Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Arg Ser
                85                  90                  95

Tyr Thr Tyr Val Phe Gly Thr Gly Thr Lys Leu Thr Val Leu
            100                 105                 110
```

<210> SEQ ID NO 11

-continued

```
<211> LENGTH: 119
<212> TYPE: PRT
<213> ORGANISM: Artificial Sequence
<220> FEATURE:
<223> OTHER INFORMATION: WapR-004 VH

<400> SEQUENCE: 11

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
            100                 105                 110

Thr Leu Val Thr Val Ser Ser
        115

<210> SEQ ID NO 12
<211> LENGTH: 107
<212> TYPE: PRT
<213> ORGANISM: Artificial Sequence
<220> FEATURE:
<223> OTHER INFORMATION: WapR-004 & WarR-004RAD VL

<400> SEQUENCE: 12

Glu Ile Val Leu Thr Gln Ser Pro Ser Ser Leu Ser Thr Ser Val Gly
1               5                   10                  15

Asp Arg Val Thr Ile Thr Cys Arg Ala Ser Gln Ser Ile Arg Ser His
            20                  25                  30

Leu Asn Trp Tyr Gln Gln Lys Pro Gly Lys Ala Pro Lys Leu Leu Ile
        35                  40                  45

Tyr Gly Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Leu
                85                  90                  95

Thr Phe Gly Gly Gly Thr Lys Leu Glu Ile Lys
            100                 105

<210> SEQ ID NO 13
<211> LENGTH: 116
<212> TYPE: PRT
<213> ORGANISM: Artificial Sequence
<220> FEATURE:
<223> OTHER INFORMATION: WapR-007 VH

<400> SEQUENCE: 13

Glu Val Gln Leu Val Gln Ser Gly Ala Asp Val Lys Lys Pro Gly Ala
1               5                   10                  15

Ser Val Arg Val Thr Cys Lys Ala Ser Gly Tyr Thr Phe Thr Gly His
            20                  25                  30
```

Asn Ile His Trp Val Arg Gln Ala Pro Gly Gln Gly Leu Glu Trp Met
         35                  40                  45

Gly Trp Ile Asn Pro Asp Ser Gly Ala Thr Ser Tyr Ala Gln Lys Phe
 50                  55                  60

Gln Gly Arg Val Thr Met Thr Arg Asp Thr Ser Ile Thr Thr Ala Tyr
 65                  70                  75                  80

Met Asp Leu Ser Arg Leu Arg Ser Asp Thr Ala Val Tyr Tyr Cys
                 85                  90                  95

Ala Thr Asp Thr Leu Leu Ser Asn His Trp Gly Gln Gly Thr Leu Val
             100                 105                 110

Thr Val Ser Ser
        115

<210> SEQ ID NO 14
<211> LENGTH: 108
<212> TYPE: PRT
<213> ORGANISM: Artificial Sequence
<220> FEATURE:
<223> OTHER INFORMATION: WapR-007 VL

<400> SEQUENCE: 14

Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Thr
             20                  25                  30

Asn Trp Phe Gln Gln Lys Pro Gly Gln Ala Pro Leu Leu Val Val Tyr
         35                  40                  45

Ala Lys Asn Lys Arg Pro Pro Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys His Ser Arg Asp Ser Ser Gly Asn His
                 85                  90                  95

Val Val Phe Gly Gly Gly Thr Lys Leu Thr Val Leu
             100                 105

<210> SEQ ID NO 15
<211> LENGTH: 123
<212> TYPE: PRT
<213> ORGANISM: Artificial Sequence
<220> FEATURE:
<223> OTHER INFORMATION: WapR-016 VH

<400> SEQUENCE: 15

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Ser Ser Tyr
             20                  25                  30

Ala Thr Ser Trp Val Arg Gln Ala Pro Gly Lys Gly Leu Glu Trp Val
         35                  40                  45

Ala Gly Ile Ser Gly Ser Gly Asp Thr Thr Asp Tyr Val Asp Ser Val
 50                  55                  60

Lys Gly Arg Phe Thr Val Ser Arg Asp Asn Ser Lys Asn Thr Leu Tyr
 65                  70                  75                  80

Leu Gln Met Asn Ser Leu Arg Ala Asp Asp Thr Ala Val Tyr Tyr Cys
                 85                  90                  95

Ala Ser Arg Gly Gly Leu Gly Gly Tyr Tyr Arg Gly Gly Phe Asp Phe
             100                 105                 110

```
Trp Gly Gln Gly Thr Met Val Thr Val Ser Ser
        115                 120

<210> SEQ ID NO 16
<211> LENGTH: 108
<212> TYPE: PRT
<213> ORGANISM: Artificial Sequence
<220> FEATURE:
<223> OTHER INFORMATION: WapR-016 VL

<400> SEQUENCE: 16

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Cys Ser Ser Tyr Ser Ser Gly Thr
                85                  90                  95

Val Val Phe Gly Gly Gly Thr Glu Leu Thr Val Leu
            100                 105

<210> SEQ ID NO 17
<211> LENGTH: 5
<212> TYPE: PRT
<213> ORGANISM: Artificial Sequence
<220> FEATURE:
<223> OTHER INFORMATION: Cam-003 VHCDR1

<400> SEQUENCE: 17

Pro Tyr Phe Trp Ser
1               5

<210> SEQ ID NO 18
<211> LENGTH: 16
<212> TYPE: PRT
<213> ORGANISM: Artificial Sequence
<220> FEATURE:
<223> OTHER INFORMATION: Cam-003 VHCDR2

<400> SEQUENCE: 18

Tyr Ile His Ser Asn Gly Gly Thr Asn Tyr Asn Pro Ser Leu Lys Ser
1               5                   10                  15

<210> SEQ ID NO 19
<211> LENGTH: 12
<212> TYPE: PRT
<213> ORGANISM: Artificial Sequence
<220> FEATURE:
<223> OTHER INFORMATION: Cam-003 VHCDR3

<400> SEQUENCE: 19

Thr Asp Tyr Asp Val Tyr Gly Pro Ala Phe Asp Ile
1               5                   10

<210> SEQ ID NO 20
<211> LENGTH: 11
<212> TYPE: PRT
<213> ORGANISM: Artificial Sequence
```

```
<220> FEATURE:
<223> OTHER INFORMATION: Cam-003, Cam-004, and Cam-005 VLCDR1

<400> SEQUENCE: 20

Gln Gly Asp Ser Leu Arg Ser Tyr Tyr Ala Ser
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Cam-003, Cam-004, and Cam-005 VLCDR2

<400> SEQUENCE: 21

Gly Lys Asn Asn Arg Pro Ser
1               5

<210> SEQ ID NO 22
<211> LENGTH: 11
<212> TYPE: PRT
<213> ORGANISM: Artificial Sequence
<220> FEATURE:
<223> OTHER INFORMATION: Cam-003, Cam-004, and Cam-005 VLCDR3

<400> SEQUENCE: 22

Asn Ser Arg Asp Ser Ser Gly Asn His Val Val
1               5                   10

<210> SEQ ID NO 23
<211> LENGTH: 6
<212> TYPE: PRT
<213> ORGANISM: Artificial Sequence
<220> FEATURE:
<223> OTHER INFORMATION: Cam-004 VHCDR1

<400> SEQUENCE: 23

Ser Gly Tyr Tyr Trp Gly
1               5

<210> SEQ ID NO 24
<211> LENGTH: 16
<212> TYPE: PRT
<213> ORGANISM: Artificial Sequence
<220> FEATURE:
<223> OTHER INFORMATION: Cam-004 VHCDR2

<400> SEQUENCE: 24

Ser Ile Ser His Ser Gly Ser Thr Tyr Tyr Asn Pro Ser Leu Lys Ser
1               5                   10                  15

<210> SEQ ID NO 25
<211> LENGTH: 9
<212> TYPE: PRT
<213> ORGANISM: Artificial Sequence
<220> FEATURE:
<223> OTHER INFORMATION: Cam-004 VHCDR3

<400> SEQUENCE: 25

Ser Glu Ala Thr Ala Asn Phe Asp Ser
1               5

<210> SEQ ID NO 26
<211> LENGTH: 7
<212> TYPE: PRT
<213> ORGANISM: Artificial Sequence
<220> FEATURE:
```

```
<223> OTHER INFORMATION: Cam-005 VHCDR1

<400> SEQUENCE: 26

Ser Ser Gly Tyr Tyr Trp Thr
1               5

<210> SEQ ID NO 27
<211> LENGTH: 16
<212> TYPE: PRT
<213> ORGANISM: Artificial Sequence
<220> FEATURE:
<223> OTHER INFORMATION: Cam-005 VHCDR2

<400> SEQUENCE: 27

Ser Ile Tyr Ser Ser Gly Ser Thr Tyr Tyr Ser Pro Ser Leu Lys Ser
1               5                   10                  15

<210> SEQ ID NO 28
<211> LENGTH: 11
<212> TYPE: PRT
<213> ORGANISM: Artificial Sequence
<220> FEATURE:
<223> OTHER INFORMATION: Cam-005 VHCDR3

<400> SEQUENCE: 28

Leu Asn Trp Gly Thr Val Ser Ala Phe Asp Ile
1               5                   10

<210> SEQ ID NO 29
<211> LENGTH: 5
<212> TYPE: PRT
<213> ORGANISM: Artificial Sequence
<220> FEATURE:
<223> OTHER INFORMATION: WapR-001 VHCDR1

<400> SEQUENCE: 29

Arg Tyr Pro Met His
1               5

<210> SEQ ID NO 30
<211> LENGTH: 17
<212> TYPE: PRT
<213> ORGANISM: Artificial Sequence
<220> FEATURE:
<223> OTHER INFORMATION: WapR-001 VHCDR2

<400> SEQUENCE: 30

Asp Ile Gly Thr Asn Gly Gly Ser Thr Asn Tyr Ala Asp Ser Val Lys
1               5                   10                  15

Gly

<210> SEQ ID NO 31
<211> LENGTH: 10
<212> TYPE: PRT
<213> ORGANISM: Artificial Sequence
<220> FEATURE:
<223> OTHER INFORMATION: WapR-001 VHCDR3

<400> SEQUENCE: 31

Gly Ile Ala Ala Ala Tyr Gly Phe Asp Val
1               5                   10

<210> SEQ ID NO 32
<211> LENGTH: 14
<212> TYPE: PRT
<213> ORGANISM: Artificial Sequence
```

```
<220> FEATURE:
<223> OTHER INFORMATION: WapR-001 VLCDR1

<400> SEQUENCE: 32

Thr Gly Thr Ser Ser Asp Ile Ala Thr Tyr Asn Tyr Val Ser
1               5                   10

<210> SEQ ID NO 33
<211> LENGTH: 7
<212> TYPE: PRT
<213> ORGANISM: Artificial Sequence
<220> FEATURE:
<223> OTHER INFORMATION: WapR-001 VLCDR2

<400> SEQUENCE: 33

Glu Gly Thr Lys Arg Pro Ser
1               5

<210> SEQ ID NO 34
<211> LENGTH: 10
<212> TYPE: PRT
<213> ORGANISM: Artificial Sequence
<220> FEATURE:
<223> OTHER INFORMATION: WapR-001 VLCDR3

<400> SEQUENCE: 34

Ser Ser Tyr Ala Arg Ser Tyr Thr Tyr Val
1               5                   10

<210> SEQ ID NO 35
<211> LENGTH: 5
<212> TYPE: PRT
<213> ORGANISM: Artificial Sequence
<220> FEATURE:
<223> OTHER INFORMATION: WapR-002 VHCDR1

<400> SEQUENCE: 35

Ser Tyr Pro Met His
1               5

<210> SEQ ID NO 36
<211> LENGTH: 17
<212> TYPE: PRT
<213> ORGANISM: Artificial Sequence
<220> FEATURE:
<223> OTHER INFORMATION: WapR-002 VHCDR2

<400> SEQUENCE: 36

Asp Ile Ser Pro Asn Gly Gly Ser Thr Asn Tyr Ala Asp Ser Val Lys
1               5                   10                  15

Gly

<210> SEQ ID NO 37
<211> LENGTH: 9
<212> TYPE: PRT
<213> ORGANISM: Artificial Sequence
<220> FEATURE:
<223> OTHER INFORMATION: WapR-002 VHCDR3

<400> SEQUENCE: 37

Gly Leu Val Pro Tyr Gly Phe Asp Ile
1               5

<210> SEQ ID NO 38
<211> LENGTH: 14
<212> TYPE: PRT
```

```
<213> ORGANISM: Artificial Sequence
<220> FEATURE:
<223> OTHER INFORMATION: WapR-002 VLCDR1

<400> SEQUENCE: 38

Thr Gly Thr Ser Ser Asp Val Gly Gly Tyr Asn Tyr Val Ser
1               5                   10

<210> SEQ ID NO 39
<211> LENGTH: 7
<212> TYPE: PRT
<213> ORGANISM: Artificial Sequence
<220> FEATURE:
<223> OTHER INFORMATION: WapR-002 VLCDR2

<400> SEQUENCE: 39

Glu Val Ser Asn Arg Pro Ser
1               5

<210> SEQ ID NO 40
<211> LENGTH: 10
<212> TYPE: PRT
<213> ORGANISM: Artificial Sequence
<220> FEATURE:
<223> OTHER INFORMATION: WapR-002 VLCDR3

<400> SEQUENCE: 40

Ser Ser Tyr Thr Thr Ser Ser Thr Tyr Val
1               5                   10

<210> SEQ ID NO 41
<211> LENGTH: 5
<212> TYPE: PRT
<213> ORGANISM: Artificial Sequence
<220> FEATURE:
<223> OTHER INFORMATION: WapR-003 VHCDR1

<400> SEQUENCE: 41

Ser Tyr Pro Met His
1               5

<210> SEQ ID NO 42
<211> LENGTH: 17
<212> TYPE: PRT
<213> ORGANISM: Artificial Sequence
<220> FEATURE:
<223> OTHER INFORMATION: WapR-003 VHCDR2

<400> SEQUENCE: 42

Asp Ile Ser Pro Asn Gly Gly Ala Thr Asn Tyr Ala Asp Ser Val Lys
1               5                   10                  15

Gly

<210> SEQ ID NO 43
<211> LENGTH: 9
<212> TYPE: PRT
<213> ORGANISM: Artificial Sequence
<220> FEATURE:
<223> OTHER INFORMATION: WapR-003 VHCDR3

<400> SEQUENCE: 43

Gly Leu Val Pro Tyr Gly Phe Asp Asn
1               5

<210> SEQ ID NO 44
<211> LENGTH: 14
```

```
<212> TYPE: PRT
<213> ORGANISM: Artificial Sequence
<220> FEATURE:
<223> OTHER INFORMATION: WapR-003 VLCDR1

<400> SEQUENCE: 44

Ala Gly Thr Ser Gly Asp Val Gly Asn Tyr Asn Phe Val Ser
1               5                   10

<210> SEQ ID NO 45
<211> LENGTH: 7
<212> TYPE: PRT
<213> ORGANISM: Artificial Sequence
<220> FEATURE:
<223> OTHER INFORMATION: WapR-003 VLCDR2

<400> SEQUENCE: 45

Glu Gly Ser Gln Arg Pro Ser
1               5

<210> SEQ ID NO 46
<211> LENGTH: 10
<212> TYPE: PRT
<213> ORGANISM: Artificial Sequence
<220> FEATURE:
<223> OTHER INFORMATION: WapR-003 VLCDR3

<400> SEQUENCE: 46

Ser Ser Tyr Ala Arg Ser Tyr Thr Tyr Val
1               5                   10

<210> SEQ ID NO 47
<211> LENGTH: 5
<212> TYPE: PRT
<213> ORGANISM: Artificial Sequence
<220> FEATURE:
<223> OTHER INFORMATION: WapR-004 & WapR-004RAD VHCDR1

<400> SEQUENCE: 47

Pro Tyr Tyr Trp Thr
1               5

<210> SEQ ID NO 48
<211> LENGTH: 16
<212> TYPE: PRT
<213> ORGANISM: Artificial Sequence
<220> FEATURE:
<223> OTHER INFORMATION: WapR-004 & WapR-004RAD VHCDR2

<400> SEQUENCE: 48

Tyr Ile His Ser Ser Gly Tyr Thr Asp Tyr Asn Pro Ser Leu Lys Ser
1               5                   10                  15

<210> SEQ ID NO 49
<211> LENGTH: 11
<212> TYPE: PRT
<213> ORGANISM: Artificial Sequence
<220> FEATURE:
<223> OTHER INFORMATION: WapR-004 VHCDR3

<400> SEQUENCE: 49

Gly Asp Trp Asp Leu Leu His Ala Leu Asp Ile
1               5                   10

<210> SEQ ID NO 50
<211> LENGTH: 11
<212> TYPE: PRT
```

```
<213> ORGANISM: Artificial Sequence
<220> FEATURE:
<223> OTHER INFORMATION: WapR-004 & WapR-004RAD VLCDR1

<400> SEQUENCE: 50

Arg Ala Ser Gln Ser Ile Arg Ser His Leu Asn
1               5                   10

<210> SEQ ID NO 51
<211> LENGTH: 7
<212> TYPE: PRT
<213> ORGANISM: Artificial Sequence
<220> FEATURE:
<223> OTHER INFORMATION: WapR-004 & WapR-004RAD VLCDR2

<400> SEQUENCE: 51

Gly Ala Ser Asn Leu Gln Ser
1               5

<210> SEQ ID NO 52
<211> LENGTH: 6
<212> TYPE: PRT
<213> ORGANISM: Artificial Sequence
<220> FEATURE:
<223> OTHER INFORMATION: WapR-004 & WapR-004RAD VLCDR3

<400> SEQUENCE: 52

Tyr Ser Phe Pro Leu Thr
1               5

<210> SEQ ID NO 53
<211> LENGTH: 5
<212> TYPE: PRT
<213> ORGANISM: Artificial Sequence
<220> FEATURE:
<223> OTHER INFORMATION: WapR-007 VHCDR1

<400> SEQUENCE: 53

Gly His Asn Ile His
1               5

<210> SEQ ID NO 54
<211> LENGTH: 17
<212> TYPE: PRT
<213> ORGANISM: Artificial Sequence
<220> FEATURE:
<223> OTHER INFORMATION: WapR-007 VHCDR2

<400> SEQUENCE: 54

Trp Ile Asn Pro Asp Ser Gly Ala Thr Ser Tyr Ala Gln Lys Phe Gln
1               5                   10                  15

Gly

<210> SEQ ID NO 55
<211> LENGTH: 7
<212> TYPE: PRT
<213> ORGANISM: Artificial Sequence
<220> FEATURE:
<223> OTHER INFORMATION: WapR-007 VHCDR3

<400> SEQUENCE: 55

Asp Thr Leu Leu Ser Asn His
1               5

<210> SEQ ID NO 56
<211> LENGTH: 11
```

```
<212> TYPE: PRT
<213> ORGANISM: Artificial Sequence
<220> FEATURE:
<223> OTHER INFORMATION: WapR-007 VLCDR1

<400> SEQUENCE: 56

Gln Gly Asp Ser Leu Arg Ser Tyr Tyr Thr Asn
1               5                   10

<210> SEQ ID NO 57
<211> LENGTH: 7
<212> TYPE: PRT
<213> ORGANISM: Artificial Sequence
<220> FEATURE:
<223> OTHER INFORMATION: WapR-007 VLCDR2

<400> SEQUENCE: 57

Ala Lys Asn Lys Arg Pro Pro
1               5

<210> SEQ ID NO 58
<211> LENGTH: 11
<212> TYPE: PRT
<213> ORGANISM: Artificial Sequence
<220> FEATURE:
<223> OTHER INFORMATION: WapR-007 VLCDR3

<400> SEQUENCE: 58

His Ser Arg Asp Ser Ser Gly Asn His Val Val
1               5                   10

<210> SEQ ID NO 59
<211> LENGTH: 5
<212> TYPE: PRT
<213> ORGANISM: Artificial Sequence
<220> FEATURE:
<223> OTHER INFORMATION: WapR-016 VHCDR1

<400> SEQUENCE: 59

Ser Tyr Ala Thr Ser
1               5

<210> SEQ ID NO 60
<211> LENGTH: 17
<212> TYPE: PRT
<213> ORGANISM: Artificial Sequence
<220> FEATURE:
<223> OTHER INFORMATION: WapR-016 VHCDR2

<400> SEQUENCE: 60

Gly Ile Ser Gly Ser Gly Asp Thr Thr Asp Tyr Val Asp Ser Val Lys
1               5                   10                  15

Gly

<210> SEQ ID NO 61
<211> LENGTH: 14
<212> TYPE: PRT
<213> ORGANISM: Artificial Sequence
<220> FEATURE:
<223> OTHER INFORMATION: WapR-016 VHCDR3

<400> SEQUENCE: 61

Arg Gly Gly Leu Gly Gly Tyr Tyr Arg Gly Gly Phe Asp Phe
1               5                   10

<210> SEQ ID NO 62
```

```
<211> LENGTH: 14
<212> TYPE: PRT
<213> ORGANISM: Artificial Sequence
<220> FEATURE:
<223> OTHER INFORMATION: WapR-016 VLCDR1

<400> SEQUENCE: 62

Thr Gly Thr Ser Ser Asp Val Gly Gly Tyr Asn Tyr Val Ser
1               5                   10

<210> SEQ ID NO 63
<211> LENGTH: 7
<212> TYPE: PRT
<213> ORGANISM: Artificial Sequence
<220> FEATURE:
<223> OTHER INFORMATION: WapR-016 VLCDR2

<400> SEQUENCE: 63

Glu Val Ser Asn Arg Pro Ser
1               5

<210> SEQ ID NO 64
<211> LENGTH: 9
<212> TYPE: PRT
<213> ORGANISM: Artificial Sequence
<220> FEATURE:
<223> OTHER INFORMATION: WapR-016 VLCDR3

<400> SEQUENCE: 64

Ser Ser Tyr Ser Ser Gly Thr Val Val
1               5

<210> SEQ ID NO 65
<211> LENGTH: 753
<212> TYPE: DNA
<213> ORGANISM: Artificial Sequence
<220> FEATURE:
<223> OTHER INFORMATION: Cam-003 scFv

<400> SEQUENCE: 65
cagccggcca tggcccaggt acagctgcag cagtcaggcc caggactggt gaagccttcg      60
gagaccctgt ccctcacctg cactgtctct ggtggctcca ccagtcctta cttctggagc     120
tggctccggc agccccccag gaagggactg gagtggattg gttatatcca ttccaatggg     180
ggcaccaact acaaccccctc cctcaagagt cgactcacca tatcaggaga cacgtccaag     240
aaccaattct ccctgaatct gagttttgtg accgctgcgg acacggccct ctattactgt     300
gcgagaacgg actacgatgt ctacggcccc gcttttgata tctggggcca ggggacaatg     360
gtcaccgtct cgagtggtgg aggcggttca ggcggaggtg gcagcggcgg tggcggatcg     420
tctgagctga ctcaggaccc tgctgtgtct gtggccttgg acagacagt caggatcaca     480 tgccaaggag acagcctcag aagctattat gcaagctggt accagcagaa gccaggacag     540
gcccctgtac ttgtcatcta tggtaaaaac aaccggccct cagggatccc agaccgattc     600
tctggctcca gctcaggaaa cacagcttcc ttgaccatca ctgggctca gcggaagat     660 gaggctgact attactgtaa ctcccgggac agcagtggta accatgtggt attcggcgga     720
gggaccaagc tgaccgtcct aggtgcggcc gca                                  753

<210> SEQ ID NO 66
<211> LENGTH: 747
<212> TYPE: DNA
<213> ORGANISM: Artificial Sequence
<220> FEATURE:
```

<223> OTHER INFORMATION: Cam-004 scFv

<400> SEQUENCE: 66

| | | | | | |
|---|---|---|---|---|---|
| cagccggcca | tggcccaggt | acagctgcag | cagtcaggcc | caggacgggt | gaagccttcg | 60 |
| gagacgctgt | ccctcacctg | cactgtctct | ggttactccg | tcagtagtgg | ttactactgg | 120 |
| ggctggatcc | ggcagtcccc | agggacgggg | ctggagtgga | ttgggagtat | ctctcatagt | 180 |
| gggagcacct | actacaaccc | gtccctcaag | agtcgagtca | ccatatcagg | agacgcatcc | 240 |
| aagaaccagt | ttttcctgag | gctgacttct | gtgaccgccg | cggacacggc | cgtttattac | 300 |
| tgtgcgagat | ctgaggctac | cgccaacttt | gattcttggg | gcaggggcac | cctggtcacc | 360 |
| gtctcttcag | gtggaggcgg | ttcaggcgga | ggtggcagcg | gcggtggcgg | atcgtctgag | 420 |
| ctgactcagg | accctgccgt | gtctgtggcc | ttgggacaga | cagtcaggat | cacatgccaa | 480 |
| ggagacagcc | tcagaagcta | ttatgcaagc | tggtaccagc | agaagccagg | acaggcccct | 540 |
| gtacttgtca | tctatggtaa | aaacaaccgg | ccctcaggga | tcccagaccg | attctctggc | 600 |
| tccagctcag | gaaacacagc | ttccttgacc | atcactgggg | ctcaggcgga | agatgaggct | 660 |
| gactattact | gtaactcccg | ggacagcagt | ggtaaccatg | tggtattcgg | cggagggacc | 720 |
| aagctgaccg | tcctaggtgc | ggccgca | | | | 747 |

<210> SEQ ID NO 67
<211> LENGTH: 756
<212> TYPE: DNA
<213> ORGANISM: Artificial Sequence
<220> FEATURE:
<223> OTHER INFORMATION: Cam-005 scFv

<400> SEQUENCE: 67

| | | | | | |
|---|---|---|---|---|---|
| cagccggcca | tggcccaggt | acagctgcag | cagtcaggcc | caggactggt | gaagccttcg | 60 |
| gagaccctgt | ccctcacctg | cactgtctct | ggtggctccg | tcagcagtag | tggttattac | 120 |
| tggacctgga | tccgccagcc | cccagggaag | ggctggagt | ggattgggag | tatctattct | 180 |
| agtgggagca | catattacag | cccgtccctc | aagagtcgag | tcaccatatc | cggagacacg | 240 |
| tccaagaacc | agttctccct | caagctgagc | tctgtgaccg | ccgcagacac | agccgtgtat | 300 |
| tactgtgcga | gacttaactg | gggcactgtg | tctgcctttg | atatctgggg | cagaggcacc | 360 |
| ctggtcaccg | tctcgagtgg | tggaggcggt | tcaggcggag | gtggcagcgg | cggtggcgga | 420 |
| tcgtctgagc | tgactcagga | ccctgctgtg | tctgtggcct | gggacagac | agtcaggatc | 480 |
| acatgccaag | gagacagcct | cagaagctat | tatgcaagct | ggtaccagca | gaagccagga | 540 |
| caggcccctg | tacttgtcat | ctatggtaaa | aacaaccggc | cctcagggat | cccagaccga | 600 |
| ttctctggct | ccagctcagg | aaacacagct | tccttgacca | tcactggggc | tcaggcggaa | 660 |
| gatgaggctg | actattactg | taactcccgg | gacagcagtg | gtaaccatgt | ggtattcggc | 720 |
| ggagggacca | agctgaccgt | cctaggtgcg | gccgca | | | 756 |

<210> SEQ ID NO 68
<211> LENGTH: 769
<212> TYPE: DNA
<213> ORGANISM: Artificial Sequence
<220> FEATURE:
<223> OTHER INFORMATION: WapR-001 scFv

<400> SEQUENCE: 68

| | | | | | |
|---|---|---|---|---|---|
| tctatgcggc | ccagccggcc | atggccgagg | tgcagctgtt | ggagtctggg | ggaggtttgg | 60 |
| tccagcctgg | ggggtccctg | agactctcct | gttcagcctc | tgggttcacc | ttcagtcggt | 120 |

```
atcctatgca ttgggtccgc caggctccag ggaagggact ggaatatgtt tcagatattg    180
gtactaatgg gggtagtaca aactacgcag actccgtgaa gggcagattc accatctcca    240
gagacaattc caagaacacg gtgtatcttc aaatgagcag tctgagagct gaggacacgg    300
ctgtgtatca ttgtgtggcg ggtatagcag ccgcctatgg ttttgatgtc tggggccaag    360
ggacaatggt caccgtctcg agtggaggcg gcggttcagg cggaggtggc tctggcggtg    420
gcggaagtgc acaggcaggg ctgactcagc ctgcctccgt gtctgggtct cctggacagt    480
cgatcaccat ctcctgcact ggaaccagca gtgacattgc tacttataac tatgtctcct    540
ggtaccaaca gcacccaggc aaagccccca aactcatgat ttatgagggc actaagcggc    600
cctcaggggt ttctaatcgc ttctctggct ccaagtctgg caacacggcc tccctgacaa    660
tctctgggct ccaggctgag gacgaggctg attattactg ttcctcatat gcacgtagtt    720
acacttatgt cttcggaact gggaccgagc tgaccgtcct agcggccgc           769
```

<210> SEQ ID NO 69
<211> LENGTH: 764
<212> TYPE: DNA
<213> ORGANISM: Artificial Sequence
<220> FEATURE:
<223> OTHER INFORMATION: WapR-002 scFv

<400> SEQUENCE: 69

```
ctatgcggcc cagccggcca tgcccaggt gcagctggtg cagtctgggg gaggcttggt     60
ccagcctggg gggtccctga gactctcctg ttcagcctct ggattcacct tcagtagcta    120
tcctatgcac tgggtccgcc aggctccagg aagggactg gattatgttt cagacatcag    180
tccaaatggg ggttccacaa actacgcaga ctccgtgaag gcagattca ccatctccag    240 agacaattcc aagaacacac tgtttcttca aatgagcagt ctgagagctg aggacacggc    300
tgtgtattat tgtgtgatgg ggttagtacc ctatggtttt gatatctggg gccaaggcac    360
cctggtcacc gtctcgagtg gaggcggcgg ttcaggcgga ggtggctctg gcggtggcgg    420
aagtgcacag actgtggtga cccagcctgc ctccgtgtct gggtctcctg gacagtcgat    480
caccatctcc tgcactggaa ccagcagtga cgttggtggt tataactatg tctcctggta    540
ccaacagcac ccaggcaaag cccccaaact catgatttat gaggtcagta atcggccctc    600
aggggtttct aatcacttct ctggctccaa gtctggcaac acggcctccc tgaccatctc    660
tgggctccag gctgaggacg aggctgatta ttactgcagc tcatatacaa ccagcagcac    720
ttatgtcttc ggaactggga ccaaggtcac cgtcctagcg gccg                764
```

<210> SEQ ID NO 70
<211> LENGTH: 761
<212> TYPE: DNA
<213> ORGANISM: Artificial Sequence
<220> FEATURE:
<223> OTHER INFORMATION: WapR-003 scFv

<400> SEQUENCE: 70

```
cggcccagcc ggccatggcc cagatgcagc tggtgcagtc gggggaggc ttggtccagc     60 ctgggggtc cctgagactc tcctgttcag cctctggatt caccttcagt agctatccta    120
tgcactgggt ccgccaggct ccagggaagg gactggatta tgtttcagac atcagtccaa    180 atggggggtgc cacaaactac gcagactccg tgaaggcag attcaccatc tccagagaca    240
attccaagaa cacggtgtat cttcaaatga gcagtctgag agctgaagac acggctgtct    300
```

```
attattgtgt gatggggtta gtgccctatg gttttgataa ctggggccag gggacaatgg      360
tcaccgtctc gagtggaggc ggcggttcag gcggaggtgg ctctggcggt ggcggaagtg      420
cacagactgt ggtgacccag cctgcctccg tgtctgcatc tcctggacag tcgatcacca      480
tctcctgcgc tggaaccagc ggtgatgttg gaattataa ttttgtctcc tggtaccaac      540
aacacccagg caaagccccc aaactcctga tttatgaggg cagtcagcgg ccctcagggg      600
tttctaatcg cttctctggc tccaggtctg caacacggc ctccctgaca atctctgggc      660
tccaggctga ggacgaggct gattattact gttcctcata tgcacgtagt tacacttatg      720
tcttcggaac tgggaccaag ctgaccgtcc tagcggccgc a                          761
```

<210> SEQ ID NO 71
<211> LENGTH: 761
<212> TYPE: DNA
<213> ORGANISM: Artificial Sequence
<220> FEATURE:
<223> OTHER INFORMATION: WapR-004 scFv

<400> SEQUENCE: 71

```
tatgcggccc agccggccat ggccgaggtg cagctgttgg agtcgggccc aggactggtg      60
aagccttcgg agaccctgtc cctcacctgc aatgtcgctg gtggctccat cagtccttac     120
tactggacct ggatccggca gcccccaggg aagggcctgg agttgattgg ttatatccac     180
tccagtgggt acaccgacta caaccctccc ctcaagagtc gagtcaccat atcaggagac     240
acgtccaaga agcagttctc cctgcacgtg agctctgtga ccgctgcgga cacggccgtg     300
tacttctgtg cgagaggcga ttgggacctg cttcatgctc ttgatatctg ggccaaggg     360 accctggtca ccgtctcgag tggaggcggc ggttcaggcg gaggtggctc tggcggtggc     420
ggaagtgcac tcgaaattgt gttgacacag tctccatcct ccctgtctac atctgtagga     480
gacagagtca ccatcacttg ccgggcaagt cagagcatta ggagccattt aaattggtat     540
cagcagaaac cagggaaagc ccctaaactc ctgatctatg gtgcatccaa tttgcaaagt     600
ggggtcccat caaggttcag tggcagtgga tctgggacag atttcactct caccattagt     660
agtctgcaac tgaagatttt gcaacttac tactgtcaac agagttacag tttccccctc      720
actttcggcg gagggaccaa gctggagatc aaagcggccg c                          761
```

<210> SEQ ID NO 72
<211> LENGTH: 747
<212> TYPE: DNA
<213> ORGANISM: Artificial Sequence
<220> FEATURE:
<223> OTHER INFORMATION: WapR-007 scFv

<400> SEQUENCE: 72

```
gcggcccagc cggccatggc cgaagtgcag ctggtgcagt ctggggctga cgtaaagaag      60
cctggggcct cagtgagggt cacctgcaag gcttctggat acaccttcac cggccacaac     120
atacactggg tgcgacaggc ccctggacaa gggcttgaat ggatgggatg gatcaaccct     180
gacagtggtg ccacaagcta tgcacagaag tttcagggca gggtcaccat gaccagggac     240
acgtccatca ccacagccta catggacctg agcaggctga gatctgacga cacggccgta     300
tattactgtg cgaccgatac attactgtct aatcactggg gccaaggaac cctggtcacc     360
gtctcgagtg gtgaggcggc ttcaggcgga ggtggcagcg gcggtggcgg atcgtctgag     420
ctgactcagg accctgctgt gtctgtggcc ttggacagac agtcaggat cacttgccaa     480 ggagacagtc tcagaagcta ttacacaaac tggttccagc agaagccagg acaggcccct     540
```

```
ctacttgtcg tctatgctaa aaataagcgg ccccaggga tcccagaccg attctctggc    600
tccagctcag gaaacacagc ttccttgacc atcactgggg ctcaggcgga agatgaggct    660
gactattact gtcattcccg ggacagcagt ggtaaccatg tggtattcgg cggagggacc    720
aagctgaccg tcctaggtgc ggccgca                                        747
```

<210> SEQ ID NO 73
<211> LENGTH: 771
<212> TYPE: DNA
<213> ORGANISM: Artificial Sequence
<220> FEATURE:
<223> OTHER INFORMATION: WapR-016 scFv

<400> SEQUENCE: 73

```
cagccggcca tggccgaggt gcagctggtg gagtctgggg gaggcttggt acagcctggg     60
gggtccctga gactctcctg tgcagcctct ggatacacct ttagcagcta tgccacgagc    120
tgggtccgcc aggctccagg aaggggctg gagtgggtcg caggtattag tggtagtggt    180
gataccacag actacgtaga ctccgtgaag ggccggttca ccgtctccag agacaattcc    240
aagaacaccc tatatctgca aatgaacagc ctgagaccgg acgacacggc cgtgtattac    300
tgtgcgtcga gaggaggttt aggggttat taccggggcg ctttgactt ctggggccag    360 gggacaatgg tcaccgtctc gagtggaggc ggcggttcag gcggaggtgg ctctggcggt    420
ggcggaagtg cacagtctgt gctgacgcag cctgcctccg tgtctgggtc tcctggacag    480
tcgatcacca tctcctgcac tggaaccagc agtgacgttg gtggttataa ctatgtctcc    540
tggtaccaac agcacccagg caaagccccc aaactcatga tttatgaggt cagtaatcgg    600
ccctcagggg tttctaatcg cttctctggc tccaagtctg gcaacacggc ctccctgacc    660
atctctgggc tccaggctga ggacgaggct gattattact gcagctcata caagcagc    720 ggcactgtgg tattcggcgg agggaccgag ctgaccgtcc tagcggccgc a            771
```

<210> SEQ ID NO 74
<211> LENGTH: 119
<212> TYPE: PRT
<213> ORGANISM: Artificial Sequence
<220> FEATURE:
<223> OTHER INFORMATION: WapR-004RAD VH

<400> SEQUENCE: 74

```
Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser
        115
```

<210> SEQ ID NO 75
<211> LENGTH: 11
<212> TYPE: PRT
<213> ORGANISM: Artificial Sequence
<220> FEATURE:
<223> OTHER INFORMATION: WapR-004RAD VHCDR3

<400> SEQUENCE: 75

Ala Asp Trp Asp Leu Leu His Ala Leu Asp Ile
1               5                   10

<210> SEQ ID NO 76
<211> LENGTH: 351
<212> TYPE: DNA
<213> ORGANISM: Artificial Sequence
<220> FEATURE:
<223> OTHER INFORMATION: WapR-004RAD VH

<400> SEQUENCE: 76
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagg gcctggagtt gattggttat atccactcca gtgggtacac cgactacaac     180
ccctccctca gagtcgagt caccatatca ggagacacgt ccaagaagca gttctccctg      240
cacgtgagct ctgtgaccgc tgcggacacg gccgtgtact tctgtgcgag agccgattgg     300
gacctgcttc atgctcttga tatctggggc aagggaccc tggtcaccgt c                351

<210> SEQ ID NO 77
<211> LENGTH: 321
<212> TYPE: DNA
<213> ORGANISM: Artificial Sequence
<220> FEATURE:
<223> OTHER INFORMATION: WapR-004RAD VL

<400> SEQUENCE: 77
gaaattgtgt tgacacagtc tccatcctcc ctgtctacat ctgtaggaga cagagtcacc      60
atcacttgcc gggcaagtca gagcattagg agccatttaa attggtatca gcagaaacca     120
gggaaagccc ctaaactcct gatctatggt gcatccaatt tgcaaagtgg ggtcccatca     180
aggttcagtg gcagtggatc tgggacagat ttcactctca ccattagtag tctgcaacct     240
gaagattttg caacttacta ctgtcaacag agttacagtt ccccctcac tttcggcgga     300 gggaccaagc tggagatcaa a                                              321

<210> SEQ ID NO 78
<211> LENGTH: 243
<212> TYPE: PRT
<213> ORGANISM: Artificial Sequence
<220> FEATURE:
<223> OTHER INFORMATION: W4-M1 scFv-Fc

<400> SEQUENCE: 78

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

```
Ser Arg Val Thr Ile Ser Gly Asp Thr Ser Lys Lys Gln Phe Ser Leu
 65                  70                  75                  80

His Val Ser Ser Val Thr Ala Ala Asp Thr Ala Val Tyr Phe Cys Ala
                 85                  90                  95

Arg Gly Asp Trp Asp Leu Leu His Ala Leu Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ala Leu Glu Ile Val Leu Thr Gln Ser Pro
130                 135                 140

Ser Ser Leu Ser Ala Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
210                 215                 220

Gln Gln Ser Tyr Ser Thr Pro Gln Thr Phe Gly Gln Gly Thr Lys Leu
225                 230                 235                 240

Glu Ile Lys

<210> SEQ ID NO 79
<211> LENGTH: 245
<212> TYPE: PRT
<213> ORGANISM: Artificial Sequence
<220> FEATURE:
<223> OTHER INFORMATION: W4-M5 scFv-Fc

<400> SEQUENCE: 79

Glu Val Gln Leu Leu Glu Ser Gly Pro Gly Leu Val Lys Pro Ser Glu
 1               5                  10                  15

Thr Leu Ser Leu Thr Cys Asn Val Ala Gly Gly Ser Ile Ser Pro Tyr
                20                  25                  30

Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Pro Ser Leu Lys
        50                  55                  60

Ser Arg Val Thr Ile Ser Gly Asp Thr Ser Lys Lys Gln Phe Ser Leu
 65                  70                  75                  80

His Val Ser Ser Val Thr Ala Ala Asp Thr Ala Val Tyr Phe Cys Ala
                 85                  90                  95

Arg Gly Asp Trp Asp Leu Leu His Ala Leu Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Ser Gly Ser Ala Gln Ser Val Thr Gln Pro Ala Ser
130                 135                 140

Val Ser Gly Ser Leu Gly Gln Ser Ile Thr Ile Ser Cys Thr Gly Thr
145                 150                 155                 160

Ser Ser Asp Ala Gly Ser Tyr Asn Phe Val Ser Trp Tyr Gln Gln His
                165                 170                 175

Pro Gly Lys Ala Pro Lys Leu Ile Ile Tyr Asp Val Asn Asn Arg Pro
```

```
                180                 185                 190
Ser Gly Val Ser Asn Arg Phe Ser Gly Ser Lys Ser Gly Asn Thr Ala
            195                 200                 205

Ser Leu Thr Ile Ser Gly Leu Gln Ala Glu Asp Glu Ala Asp Tyr Tyr
            210                 215                 220

Cys Asn Ser Tyr Gly Ser Ser Thr Trp Leu Phe Gly Gly Gly Thr
225                 230                 235                 240

Lys Leu Thr Val Leu
                245

<210> SEQ ID NO 80
<211> LENGTH: 245
<212> TYPE: PRT
<213> ORGANISM: Artificial Sequence
<220> FEATURE:
<223> OTHER INFORMATION: W4-M6 scFv-Fc

<400> SEQUENCE: 80

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Ala Leu Ser Tyr Glu Leu Met Gln Pro Pro
    130                 135                 140

Ser Val Ser Gly Thr Pro Gly Gln Arg Val Thr Ile Ser Cys Ser Gly
145                 150                 155                 160

Ser Ser Ser Asn Ile Gly Ser Asn Thr Val Asn Trp Tyr Gln Gln Leu
                165                 170                 175

Pro Gly Thr Ala Pro Lys Leu Leu Ile Tyr Ser Asn Asn Gln Arg Pro
            180                 185                 190

Ser Gly Val Pro Asp Arg Phe Ser Gly Ser Lys Ser Gly Thr Ser Ala
        195                 200                 205

Ser Leu Ala Ile Ser Gly Leu Gln Ser Glu Asp Glu Ala Asp Tyr Tyr
    210                 215                 220

Cys Ala Ala Trp Asp Asp Ser Leu Asn Val Val Phe Gly Gly Gly Thr
225                 230                 235                 240

Lys Val Thr Val Leu
                245

<210> SEQ ID NO 81
<211> LENGTH: 245
<212> TYPE: PRT
<213> ORGANISM: Artificial Sequence
<220> FEATURE:
<223> OTHER INFORMATION: W4-M7 scFv-Fc
```

<400> SEQUENCE: 81

```
Glu Val Gln Leu Leu Glu Ser Gly Pro Gly Leu Val Lys Pro Ser Glu
1               5                   10                  15
Thr Leu Ser Leu Thr Cys Asn Val Ala Gly Gly Ser Ile Ser Pro Tyr
            20                  25                  30
Tyr Trp Thr Trp Ile Arg Gln Pro Pro Gly Lys Gly Leu Glu Leu Ile
        35                  40                  45
Gly Tyr Ile His Ser Ser Gly Tyr Thr Asp Tyr Asn Pro Ser Leu Lys
    50                  55                  60
Ser Arg Val Thr Ile Ser Gly Asp Thr Ser Lys Lys Gln Phe Ser Leu
65                  70                  75                  80
His Val Ser Ser Val Thr Ala Ala Asp Thr Ala Val Tyr Phe Cys Ala
                85                  90                  95
Arg Gly Asp Trp Asp Leu Leu His Ala Leu Asp Ile Trp Gly Gln Gly
            100                 105                 110
Thr Leu Val Thr Val Ser Ser Gly Gly Gly Gly Ser Gly Gly Gly Gly
        115                 120                 125
Ser Gly Gly Ser Gly Ser Ala Gln Thr Val Val Thr Gln Pro Ala Ser
    130                 135                 140
Val Ser Gly Ser Pro Gly Gln Ser Ile Thr Ile Ser Cys Thr Gly Thr
145                 150                 155                 160
Ser Ser Asp Ile Gly Gly Tyr Asn Tyr Val Ser Trp Tyr Arg Gln His
                165                 170                 175
Pro Gly Lys Ala Pro Lys Leu Met Ile Tyr Asp Val Ser Asn Arg Pro
            180                 185                 190
Ser Gly Val Ser Asn Arg Phe Ser Gly Ser Lys Ser Gly Asn Thr Ala
        195                 200                 205
Ser Leu Thr Ile Ser Gly Leu Gln Ala Glu Asp Glu Ala Asp Tyr Tyr
    210                 215                 220
Cys Thr Ser Tyr Thr Ser Asp Ser Thr Leu Val Phe Gly Gly Gly Thr
225                 230                 235                 240
Lys Val Thr Val Leu
                245
```

<210> SEQ ID NO 82
<211> LENGTH: 245
<212> TYPE: PRT
<213> ORGANISM: Artificial Sequence
<220> FEATURE:
<223> OTHER INFORMATION: W4-M8 scFv-Fc

<400> SEQUENCE: 82

```
Glu Val Gln Leu Leu Glu Ser Gly Pro Gly Leu Val Lys Pro Ser Glu
1               5                   10                  15
Thr Leu Ser Leu Thr Cys Asn Val Ala Gly Gly Ser Ile Ser Pro Tyr
            20                  25                  30
Tyr Trp Thr Trp Ile Arg Gln Pro Pro Gly Lys Gly Leu Glu Leu Ile
        35                  40                  45
Gly Tyr Ile His Ser Ser Gly Tyr Thr Asp Tyr Asn Pro Ser Leu Lys
    50                  55                  60
Ser Arg Val Thr Ile Ser Gly Asp Thr Ser Lys Lys Gln Phe Ser Leu
65                  70                  75                  80
His Val Ser Ser Val Thr Ala Ala Asp Thr Ala Val Tyr Phe Cys Ala
                85                  90                  95
```

Arg Gly Asp Trp Asp Leu Leu His Ala Leu Asp Ile Trp Gly Gln Gly
                100                 105                 110

Thr Leu Val Thr Val Ser Ser Gly Gly Gly Ser Gly Gly Gly Gly
            115                 120                 125

Ser Gly Gly Gly Gly Ser Ala Gln Ser Val Val Thr Gln Pro Pro Ser
        130                 135                 140

Val Ser Ala Ala Pro Gly Gln Lys Val Thr Ile Ser Cys Thr Gly Thr
145                 150                 155                 160

Ser Ser Asp Val Gly Ser Tyr Asn Phe Val Ser Trp Tyr Gln Gln His
                165                 170                 175

Pro Gly Lys Ala Pro Lys Leu Met Ile Tyr Glu Gly Thr Lys Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Thr Ser Tyr Thr Ser Asp Ser Thr Leu Val Phe Gly Gly Gly Thr
225                 230                 235                 240

Lys Val Thr Val Leu
                245

<210> SEQ ID NO 83
<211> LENGTH: 245
<212> TYPE: PRT
<213> ORGANISM: Artificial Sequence
<220> FEATURE:
<223> OTHER INFORMATION: W4-M9 scFv-Fc

<400> SEQUENCE: 83

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
                100                 105                 110

Thr Leu Val Thr Val Ser Ser Gly Gly Gly Gly Ser Gly Gly Gly Gly
            115                 120                 125

Ser Gly Gly Ser Gly Ser Ala Gln Ser Val Leu Thr Gln Pro Ala Ser
        130                 135                 140

Val Ser Gly Ser Pro Gly Gln Ser Ile Thr Ile Ser Cys Thr Gly Thr
145                 150                 155                 160

Thr Ser Asp Val Gly Ala Phe Gly Phe Val Ser Trp Tyr Gln Gln Lys
                165                 170                 175

Pro Gly Glu Val Pro Lys Leu Met Ile Tyr Asp Val Ser Asp Arg Pro
            180                 185                 190

Ser Gly Val Ser Asp Arg Phe Ser Gly Ser Lys Ser Gly Ser Thr Ala
        195                 200                 205

Ser Leu Thr Ile Ser Gly Leu Gln Ala Glu Asp Glu Ala Asp Tyr Tyr
        210                 215                 220

Cys Gly Ser Tyr Thr Ser Thr Thr Trp Val Phe Gly Gly Gly Thr
225                 230                 235                 240

Lys Leu Thr Val Leu
                245

<210> SEQ ID NO 84
<211> LENGTH: 246
<212> TYPE: PRT
<213> ORGANISM: Artificial Sequence
<220> FEATURE:
<223> OTHER INFORMATION: W4-M11 scFv-Fc

<400> SEQUENCE: 84

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Ala Leu Ser Tyr Glu Leu Met Gln Pro Ala
    130                 135                 140

Ser Val Ser Gly Ser Leu Gly Gln Ser Ile Thr Ile Ser Cys Thr Gly
145                 150                 155                 160

Thr Ser Ser Asp Val Gly Ser Tyr Asn Phe Val Ser Trp Tyr Gln Gln
                165                 170                 175

His Pro Gly Lys Ala Pro Lys Leu Met Ile Tyr Glu Gly Thr Lys Arg
            180                 185                 190

Pro Ser Gly Val Pro Asp Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Ser Ser Tyr Ala Arg Ser Tyr Thr Tyr Val Phe Gly Thr Gly
225                 230                 235                 240

Thr Lys Val Thr Val Leu
                245

<210> SEQ ID NO 85
<211> LENGTH: 245
<212> TYPE: PRT
<213> ORGANISM: Artificial Sequence
<220> FEATURE:
<223> OTHER INFORMATION: W4-M12 scFv-Fc

<400> SEQUENCE: 85

Glu Val Gln Leu Leu Glu Ser Gly Pro Gly Leu Val Lys Pro Ser Glu
1               5                   10                  15

```
Thr Leu Ser Leu Thr Cys Asn Val Ala Gly Gly Ser Ile Ser Pro Tyr
            20                  25                  30

Tyr Trp Thr Trp Ile Arg Gln Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
            115                 120                 125

Ser Gly Gly Gly Gly Ser Ala Gln Thr Val Thr Gln Pro Ala Ser
    130                 135                 140

Val Ser Gly Ser Pro Gly Gln Ser Ile Thr Ile Ser Cys Thr Gly Thr
145                 150                 155                 160

Ser Gly Asp Ile Gly Ala Tyr Asn Phe Val Ser Trp Tyr Gln Gln His
                165                 170                 175

Pro Gly Lys Ala Pro Lys Leu Ile Ile Tyr Asp Val Asn Asn Arg Pro
            180                 185                 190

Ser Gly Val Ser Asn Arg Phe Ser Gly Ser Lys Ser Gly Asn Thr Ala
            195                 200                 205

Ser Leu Thr Ile Ser Gly Leu Gln Ala Glu Asp Glu Ala Asp Tyr Tyr
    210                 215                 220

Cys Ser Ser Tyr Thr Ser Ser Asn Thr Tyr Leu Phe Gly Thr Gly Thr
225                 230                 235                 240

Lys Val Thr Val Leu
            245

<210> SEQ ID NO 86
<211> LENGTH: 245
<212> TYPE: PRT
<213> ORGANISM: Artificial Sequence
<220> FEATURE:
<223> OTHER INFORMATION: W4-M14 scFv-Fc

<400> SEQUENCE: 86

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
            115                 120                 125
```

Ser Gly Gly Ser Gly Ser Ala Gln Ser Val Leu Thr Gln Pro Pro Ser
    130                 135                 140

Ala Phe Gly Thr Pro Gly Gln Ser Leu Thr Ile Ser Cys Ser Gly Ser
145                 150                 155                 160

Asn Ser Asn Ile Gly Arg Asn Thr Val Thr Trp Tyr Gln His Leu Pro
                165                 170                 175

Gly Thr Ala Pro Lys Leu Leu Ile Tyr Ser Ser Asn Gln Arg Pro Ser
            180                 185                 190

Gly Val Pro Asp Arg Phe Ser Gly Ser Lys Ser Gly Thr Ser Ala Ser
        195                 200                 205

Leu Ala Ile Ser Gly Leu Gln Ser Glu Asp Glu Ala His Tyr Tyr Cys
    210                 215                 220

Ala Ala Trp Asp Asp Ser Leu His Gly Met Ile Phe Gly Gly Gly Thr
225                 230                 235                 240

Lys Val Thr Val Leu
                245

<210> SEQ ID NO 87
<211> LENGTH: 245
<212> TYPE: PRT
<213> ORGANISM: Artificial Sequence
<220> FEATURE:
<223> OTHER INFORMATION: W4-M15 scFv-Fc

<400> SEQUENCE: 87

Glu Val Gln Leu Leu Glu Ser Gly Pro Gly Leu Val Lys Pro Ser Glu
1               5                   10                  15

Thr Leu Ser Leu Thr Cys Asn Val Ala Gly Ser Ile Ser Pro Tyr
            20                  25                  30

Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Pro Ser Leu Lys
        50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ala Gln Ser Val Leu Thr Gln Pro Pro Ser
    130                 135                 140

Ala Phe Gly Thr Pro Gly Gln Ser Leu Thr Ile Ser Cys Ser Gly Ser
145                 150                 155                 160

Asn Ser Asn Ile Gly Arg Asn Thr Val Thr Trp Tyr Gln His Leu Pro
                165                 170                 175

Gly Thr Ala Pro Lys Leu Leu Ile Tyr Ser Ser Asn Gln Arg Pro Ser
            180                 185                 190

Gly Val Pro Asp Arg Phe Ser Gly Ser Lys Ser Gly Thr Ser Ala Ser
        195                 200                 205

Leu Ala Ile Ser Gly Leu Gln Ser Glu Asp Glu Ala His Tyr Tyr Cys
    210                 215                 220

Ala Ala Trp Asp Asp Ser Leu His Gly Met Ile Phe Gly Gly Gly Thr
225                 230                 235                 240

Lys Val Thr Val Leu
            245

<210> SEQ ID NO 88
<211> LENGTH: 245
<212> TYPE: PRT
<213> ORGANISM: Artificial Sequence
<220> FEATURE:
<223> OTHER INFORMATION: W4-M16 scFv-Fc

<400> SEQUENCE: 88

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
            100                 105                 110

Thr Leu Val Thr Val Ser Ser Gly Gly Gly Ser Gly Gly Ser Gly
        115                 120                 125

Ser Gly Gly Gly Gly Ser Ala Gln Ser Val Leu Thr Gln Pro Pro Ser
130                 135                 140

Ala Phe Gly Thr Pro Gly Gln Ser Leu Thr Ile Ser Cys Ser Gly Ser
145                 150                 155                 160

Asn Ser Asn Ile Gly Arg Asn Thr Val Thr Trp Tyr Gln His Leu Pro
                165                 170                 175

Gly Thr Ala Pro Lys Leu Leu Ile Tyr Ser Ser Asn Gln Arg Pro Ser
            180                 185                 190

Gly Val Pro Asp Arg Phe Ser Gly Ser Lys Ser Gly Thr Ser Ala Ser
        195                 200                 205

Leu Ala Ile Ser Gly Leu Gln Ser Glu Asp Glu Ala His Tyr Tyr Cys
    210                 215                 220

Ala Ala Trp Asp Asp Ser Leu His Gly Met Ile Phe Gly Gly Gly Thr
225                 230                 235                 240

Lys Val Thr Val Leu
            245

<210> SEQ ID NO 89
<211> LENGTH: 245
<212> TYPE: PRT
<213> ORGANISM: Artificial Sequence
<220> FEATURE:
<223> OTHER INFORMATION: W4-M17 scFv-Fc

<400> SEQUENCE: 89

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile

Gly Tyr Ile His Ser Ser Gly Tyr Thr Asp Tyr Asn Pro Ser Leu Lys
            50                  55                  60

Ser Arg Val Thr Ile Ser Gly Asp Thr Ser Lys Lys Gln Phe Ser Leu
 65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
            115                 120                 125

Ser Gly Gly Ser Gly Ser Ala Gln Thr Val Val Thr Gln Pro Pro Ser
            130                 135                 140

Ala Phe Gly Thr Pro Gly Gln Ser Leu Thr Ile Ser Cys Ser Gly Ser
145                 150                 155                 160

Ser Ser Asn Ile Gly Gly Asn Thr Val Asn Trp Tyr Gln Gln Leu Pro
                165                 170                 175

Gly Thr Ala Pro Arg Leu Leu Ile Tyr Ser Asn Ser Gln Arg Pro Ser
            180                 185                 190

Gly Val Pro Asp Arg Phe Ser Gly Ser Lys Ser Gly Thr Ser Ala Ser
            195                 200                 205

Leu Ala Ile Ser Gly Leu Gln Ser Glu Asp Glu Ala Asp Tyr Tyr Cys
            210                 215                 220

Ala Ala Trp Asp Asp Ser Leu Asn Gly Val Val Phe Gly Gly Gly Thr
225                 230                 235                 240

Lys Leu Thr Val Leu
                245

<210> SEQ ID NO 90
<211> LENGTH: 245
<212> TYPE: PRT
<213> ORGANISM: Artificial Sequence
<220> FEATURE:
<223> OTHER INFORMATION: W4-M19 scFv-Fc

<400> SEQUENCE: 90

Glu Val Gln Leu Leu Glu Ser Gly Pro Gly Leu Val Lys Pro Ser Glu
 1               5                  10                  15

Thr Leu Ser Leu Thr Cys Asn Val Ala Gly Gly Ser Ile Ser Pro Tyr
                20                  25                  30

Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Pro Ser Leu Lys
            50                  55                  60

Ser Arg Val Thr Ile Ser Gly Asp Thr Ser Lys Lys Gln Phe Ser Leu
 65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
            115                 120                 125

Ser Gly Gly Gly Gly Ser Ala Gln Ser Val Leu Thr Gln Pro Ala Ser
            130                 135                 140

Val Ser Gly Ser Pro Gly Gln Ser Ile Thr Ile Ser Cys Thr Gly Thr

```
            145                 150                 155                 160

Ser Ser Asp Val Gly Ala Tyr Asn Tyr Val Ser Trp Phe Gln Gln His
                165                 170                 175

Pro Gly Lys Val Pro Lys Leu Ile Ile Trp Glu Val Ile Asn Arg Pro
                180                 185                 190

Ser Gly Val Ser Asn Arg Phe Ser Gly Ser Lys Ser Gly Asn Thr Ala
                195                 200                 205

Ser Leu Thr Ile Ser Gly Leu Gln Ala Glu Asp Glu Ala Asp Tyr Tyr
                210                 215                 220

Cys Ser Ser Tyr Thr Ser Ser Asn Thr Tyr Val Phe Gly Thr Gly Thr
225                 230                 235                 240

Lys Leu Thr Val Leu
                245

<210> SEQ ID NO 91
<211> LENGTH: 245
<212> TYPE: PRT
<213> ORGANISM: Artificial Sequence
<220> FEATURE:
<223> OTHER INFORMATION: W4-M20 scFv-Fc

<400> SEQUENCE: 91

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
                20                  25                  30

Tyr Trp Thr Trp Ile Arg Gln Pro Pro Gly Lys Gly Leu Glu Leu Ile
                35                  40                  45

Gly Tyr Ile His Ser Ser Gly Tyr Thr Asp Tyr Asn Pro Ser Leu Lys
                50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
                100                 105                 110

Thr Leu Val Thr Val Ser Ser Gly Gly Gly Ser Gly Gly Gly Gly
                115                 120                 125

Ser Gly Gly Ser Gly Ser Ala Gln Ser Ala Leu Thr Gln Pro Pro Ser
                130                 135                 140

Val Ser Ala Ala Pro Gly Gln Lys Val Thr Ile Ser Cys Ser Gly Ser
145                 150                 155                 160

Ser Ser Asn Ile Gly Asn Asn Tyr Val Ser Trp Tyr Leu Gln Leu Pro
                165                 170                 175

Gly Thr Ala Pro Lys Leu Leu Ile Tyr Asp Asn Asn Gly Arg Pro Ser
                180                 185                 190

Gly Ile Pro Asp Arg Phe Ser Gly Ser Lys Ser Gly Thr Ser Ala Thr
                195                 200                 205

Leu Gly Ile Thr Gly Leu Gln Thr Gly Asp Glu Ala Asp Tyr Tyr Cys
                210                 215                 220

Ala Thr Trp Asp Ser Ser Leu Ser Ala Gly Val Phe Gly Gly Gly Thr
225                 230                 235                 240

Lys Val Thr Val Leu
                245
```

<210> SEQ ID NO 92
<211> LENGTH: 244
<212> TYPE: PRT
<213> ORGANISM: Artificial Sequence
<220> FEATURE:
<223> OTHER INFORMATION: W4-M4 scFv-Fc

<400> SEQUENCE: 92

```
Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Ser Gly Ser Ala Leu Ser Tyr Glu Leu Met Gln Asp Pro
    130                 135                 140

Ala Val Ser Val Ala Leu Gly Gln Thr Val Arg Ile Thr Cys Arg Gly
145                 150                 155                 160

Asp Ser Leu Ser Ser Phe Tyr Thr Ser Trp Tyr Gln Gln Lys Pro Gly
                165                 170                 175

Gln Ala Pro Leu Leu Val Ile Tyr Gly Lys Asn Asn Arg Pro Ser Gly
            180                 185                 190

Ile Pro Asp Arg Phe Ser Gly Ser Ser Gly Asn Thr Ala Ser Leu
                195                 200                 205

Thr Ile Thr Gly Ala Gln Ala Glu Asp Glu Ala Asp Tyr Tyr Cys Asn
    210                 215                 220

Ser Arg Asp Ser Ser Asp Asn Tyr Val Leu Phe Gly Gly Gly Thr Lys
225                 230                 235                 240

Leu Thr Val Leu
```

<210> SEQ ID NO 93
<211> LENGTH: 245
<212> TYPE: PRT
<213> ORGANISM: Artificial Sequence
<220> FEATURE:
<223> OTHER INFORMATION: W4-M10 scFv-Fc

<400> SEQUENCE: 93

```
Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
```

| | | | | | | | | | | | |
|---|---|---|---|---|---|---|---|---|---|---|---|
| | | | 65 | | | 70 | | | 75 | | 80 |
| His | Val | Ser | Ser | Val | Thr | Ala | Ala | Asp | Thr | Ala | Val | Tyr | Phe | Cys | Ala |
| | | | | 85 | | | | 90 | | | | 95 | | | |

Arg Gly Asp Trp Asp Leu Leu His Ala Leu Asp Ile Trp Gly Gln Gly
            100                   105                110

Thr Leu Val Thr Val Ser Ser Gly Gly Gly Ser Gly Gly Gly
       115                  120                  125

Ser Gly Gly Gly Ser Ala Gln Ser Val Thr Gln Pro Ala Ser
130                  135                  140

Val Ser Gly Ser Pro Gly Gln Ser Val Thr Ile Ser Cys Thr Gly Thr
145                  150                  155              160

Ser Ser Asp Val Gly Ser Tyr Lys Gly Val Ser Trp Tyr Gln Gln Pro
                  165                  170              175

Pro Gly Thr Ala Pro Lys Leu Leu Ile Tyr Asn Asp Asn Gln Arg Pro
                  180                  185              190

Ser Gly Ile Pro Gly Arg Phe Ser Gly Ser Asn Ser Gly Asn Thr Ala
                  195                  200              205

Ile Leu Thr Ile Ser Gly Thr Gln Ala Met Asp Glu Ala Asp Tyr Tyr
    210                  215                  220

Cys Gln Ala Trp Asp Ser Ser Asn His Val Val Phe Gly Gly Gly Thr
225                  230                  235              240

Lys Leu Thr Val Leu
              245

<210> SEQ ID NO 94
<211> LENGTH: 243
<212> TYPE: PRT
<213> ORGANISM: Artificial Sequence
<220> FEATURE:
<223> OTHER INFORMATION: W4-HC1-LCP

<400> SEQUENCE: 94

Glu Val Gln Leu Leu Glu Ser Gly Pro Gly Leu Val Lys Pro Ser Glu
1                 5                  10                15

Thr Leu Ser Leu Thr Cys Asn Val Ala Gly Gly Ser Ile Ser Pro Tyr
             20                  25                30

Tyr Trp Thr Trp Ile Arg Gln Pro Pro Gly Lys Gly Leu Glu Leu Ile
          35                  40                45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75              80

His Val Ser Ser Val Thr Ala Ala Asp Thr Ala Val Tyr Phe Cys Ala
                  85                  90              95

Arg Ala Asp Trp Asp Leu Leu His Ala Leu Asp Ile Trp Gly Gln Gly
            100                   105                110

Thr Met Val Thr Val Ser Ser Gly Gly Gly Ser Gly Gly Gly Gly
       115                  120                  125

Ser Gly Gly Gly Ser Ala Leu Glu Ile Val Leu Thr Gln Ser Pro
130                  135                  140

Ser Ser Leu Ser Thr Ser Val Gly Asp Arg Val Thr Ile Thr Cys Arg
145                  150                  155              160

Ala Ser Gln Ser Ile Arg Ser His Leu Asn Trp Tyr Gln Gln Lys Pro
                  165                  170              175

Gly Lys Ala Pro Lys Leu Leu Ile Tyr Gly Ala Ser Asn Leu Gln Ser

```
                    180                 185                 190
Gly Val Pro Ser Arg Phe Ser Gly Ser Gly Thr Asp Phe Thr
            195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 95
<211> LENGTH: 245
<212> TYPE: PRT
<213> ORGANISM: Artificial Sequence
<220> FEATURE:
<223> OTHER INFORMATION: W4-HC1-LC7 scFv-Fc

<400> SEQUENCE: 95

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Met Val Thr Val Ser Ser Gly Gly Gly Gly Ser Gly Gly Gly Gly
        115                 120                 125

Ser Gly Gly Ser Gly Ser Ala Gln Thr Val Val Thr Gln Pro Ala Ser
130                 135                 140

Val Ser Gly Ser Pro Gly Gln Ser Ile Thr Ile Ser Cys Thr Gly Thr
145                 150                 155                 160

Ser Ser Asp Ile Gly Gly Tyr Asn Tyr Val Ser Trp Tyr Arg Gln His
                165                 170                 175

Pro Gly Lys Ala Pro Lys Leu Met Ile Tyr Asp Val Ser Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Thr Ser Tyr Thr Ser Asp Ser Thr Leu Val Phe Gly Gly Gly Thr
225                 230                 235                 240

Lys Val Thr Val Leu
                245

<210> SEQ ID NO 96
<211> LENGTH: 245
<212> TYPE: PRT
<213> ORGANISM: Artificial Sequence
<220> FEATURE:
<223> OTHER INFORMATION: W4-HC2-LC7 scFv-Fc
```

<400> SEQUENCE: 96

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Thr Val Thr Val Ser Ser Gly Gly Gly Ser Gly Gly Gly Gly
        115                 120                 125

Ser Gly Gly Ser Gly Ser Ala Gln Thr Val Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Ile Gly Gly Tyr Asn Tyr Val Ser Trp Tyr Arg Gln His
                165                 170                 175

Pro Gly Lys Ala Pro Lys Leu Met Ile Tyr Asp Val Ser Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Thr Ser Tyr Thr Ser Asp Ser Thr Leu Val Phe Gly Gly Gly Thr
225                 230                 235                 240

Lys Val Thr Val Leu
            245

<210> SEQ ID NO 97
<211> LENGTH: 243
<212> TYPE: PRT
<213> ORGANISM: Artificial Sequence
<220> FEATURE:
<223> OTHER INFORMATION: W4-HC3-LCP scFv-Fc

<400> SEQUENCE: 97

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Phe Asp Ile Trp Gly Gln Gly

```
                    100                 105                 110
Thr Met Val Thr Val Ser Ser Gly Gly Gly Ser Gly Gly Gly
            115                 120                 125
Ser Gly Gly Gly Ser Ala Leu Glu Ile Val Leu Thr Gln Ser Pro
        130                 135                 140
Ser Ser Leu Ser Thr Ser Val Gly Asp Arg Val Thr Ile Thr Cys Arg
145                 150                 155                 160
Ala Ser Gln Ser Ile Arg Ser His Leu Asn Trp Tyr Gln Gln Lys Pro
                165                 170                 175
Gly Lys Ala Pro Lys Leu Leu Ile Tyr Gly Ala Ser Asn Leu Gln Ser
            180                 185                 190
Gly Val Pro Ser Arg Phe Ser Gly Ser Gly Ser Gly Thr Asp Phe Thr
        195                 200                 205
Leu Thr Ile Ser Ser Leu Gln Pro Glu Asp Phe Ala Thr Tyr Tyr Cys
    210                 215                 220
Gln Gln Ser Tyr Ser Phe Pro Leu Thr Phe Gly Gly Gly Thr Lys Leu
225                 230                 235                 240
Glu Ile Lys

<210> SEQ ID NO 98
<211> LENGTH: 243
<212> TYPE: PRT
<213> ORGANISM: Artificial Sequence
<220> FEATURE:
<223> OTHER INFORMATION: W4-HC4-LCP scFv-Fc

<400> SEQUENCE: 98

Glu Val Gln Leu Leu Glu Ser Gly Pro Gly Leu Val Lys Pro Ser Glu
1               5                   10                  15
Thr Leu Ser Leu Thr Cys Asn Val Ala Gly Gly Ser Ile Ser Pro Tyr
            20                  25                  30
Tyr Trp Thr Trp Ile Arg Gln Pro Pro Gly Lys Gly Leu Glu Leu Ile
        35                  40                  45
Gly Tyr Ile His Ser Ser Gly Tyr Thr Asp Tyr Asn Pro Ser Leu Lys
    50                  55                  60
Ser Arg Val Thr Ile Ser Gly Asp Thr Ser Lys Lys Gln Phe Ser Leu
65                  70                  75                  80
His Val Ser Ser Val Thr Ala Ala Asp Thr Ala Val Tyr Phe Cys Ala
                85                  90                  95
Arg Ala Asp Trp Asp Leu Leu His Ala Leu Gly Ile Trp Gly Gln Gly
            100                 105                 110
Thr Leu Val Thr Val Ser Ser Gly Gly Gly Ser Gly Gly Gly Gly
            115                 120                 125
Ser Gly Gly Gly Gly Ser Ala Leu Glu Ile Val Leu Thr Gln Ser Pro
        130                 135                 140
Ser Ser Leu Ser Thr Ser Val Gly Asp Arg Val Thr Ile Thr Cys Arg
145                 150                 155                 160
Ala Ser Gln Ser Ile Arg Ser His Leu Asn Trp Tyr Gln Gln Lys Pro
                165                 170                 175
Gly Lys Ala Pro Lys Leu Leu Ile Tyr Gly Ala Ser Asn Leu Gln Ser
            180                 185                 190
Gly Val Pro Ser Arg Phe Ser Gly Ser Gly Ser Gly Thr Asp Phe Thr
        195                 200                 205
Leu Thr Ile Ser Ser Leu Gln Pro Glu Asp Phe Ala Thr Tyr Tyr Cys
    210                 215                 220
```

Gln Gln Ser Tyr Ser Phe Pro Leu Thr Phe Gly Gly Thr Lys Leu
225                 230                 235                 240

Glu Ile Lys

<210> SEQ ID NO 99
<211> LENGTH: 243
<212> TYPE: PRT
<213> ORGANISM: Artificial Sequence
<220> FEATURE:
<223> OTHER INFORMATION: W4-HC5-LCP scFv-Fc

<400> SEQUENCE: 99

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Pro Asp Ile Trp Gly Gln Gly
            100                 105                 110

Thr Leu Val Thr Val Ser Gly Gly Gly Gly Ser Gly Gly Gly Gly
        115                 120                 125

Ser Gly Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Thr Lys Leu
225                 230                 235                 240

Glu Ile Lys

<210> SEQ ID NO 100
<211> LENGTH: 245
<212> TYPE: PRT
<213> ORGANISM: Artificial Sequence
<220> FEATURE:
<223> OTHER INFORMATION: W4-HC5-LC7 scFv-Fc

<400> SEQUENCE: 100

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

```
Tyr Trp Thr Trp Ile Arg Gln Pro Gly Lys Gly Leu Glu Leu Ile
            35                  40                  45

Gly Tyr Ile His Ser Ser Gly Tyr Thr Asp Tyr Asn Pro Ser Leu Lys
 50                  55                  60

Ser Arg Val Thr Ile Ser Gly Asp Thr Ser Lys Lys Gln Phe Ser Leu
 65                  70                  75                  80

His Val Ser Ser Val Thr Ala Ala Asp Thr Ala Val Tyr Phe Cys Ala
                 85                  90                  95

Arg Ala Asp Trp Asp Leu Leu His Ala Pro Asp Ile Trp Gly Gln Gly
            100                 105                 110

Thr Leu Val Thr Val Ser Ser Gly Gly Gly Ser Gly Gly Gly Gly
            115                 120                 125

Ser Gly Gly Ser Gly Ser Ala Gln Thr Val Val Thr Gln Pro Ala Ser
 130                 135                 140

Val Ser Gly Ser Pro Gly Gln Ser Ile Thr Ile Ser Cys Thr Gly Thr
 145                 150                 155                 160

Ser Ser Asp Ile Gly Gly Tyr Asn Tyr Val Ser Trp Tyr Arg Gln His
                 165                 170                 175

Pro Gly Lys Ala Pro Lys Leu Met Ile Tyr Asp Val Ser Asn Arg Pro
            180                 185                 190

Ser Gly Val Ser Asn Arg Phe Ser Gly Ser Lys Ser Gly Asn Thr Ala
            195                 200                 205

Ser Leu Thr Ile Ser Gly Leu Gln Ala Glu Asp Glu Ala Asp Tyr Tyr
 210                 215                 220

Cys Thr Ser Tyr Thr Ser Asp Ser Thr Leu Val Phe Gly Gly Gly Thr
225                 230                 235                 240

Lys Val Thr Val Leu
            245

<210> SEQ ID NO 101
<211> LENGTH: 243
<212> TYPE: PRT
<213> ORGANISM: Artificial Sequence
<220> FEATURE:
<223> OTHER INFORMATION: W4-HC7-LCP scFv-Fc

<400> SEQUENCE: 101

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Gly Lys Gly Leu Glu Leu Ile
            35                  40                  45

Gly Tyr Ile His Ser Ser Gly Tyr Thr Asp Tyr Asn Pro Ser Leu Lys
 50                  55                  60

Ser Arg Val Thr Ile Ser Gly Asp Thr Ser Lys Lys Gln Phe Ser Leu
 65                  70                  75                  80

His Val Ser Ser Val Thr Ala Ala Asp Thr Ala Val Tyr Phe Cys Ala
                 85                  90                  95

Arg Ala Asp Trp Asp Leu Leu His Ala Leu Asp Val Trp Gly Gln Gly
            100                 105                 110

Thr Leu Val Thr Val Ser Ser Gly Gly Gly Ser Gly Gly Gly Gly
            115                 120                 125

Ser Gly Gly Gly Gly Ser Ala Leu Glu Ile Val Leu Thr Gln Ser Pro
 130                 135                 140
```

```
Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 102
<211> LENGTH: 245
<212> TYPE: PRT
<213> ORGANISM: Artificial Sequence
<220> FEATURE:
<223> OTHER INFORMATION: W4-VH1-VL8 scFv-Fc

<400> SEQUENCE: 102

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Met Val Thr Val Ser Ser Gly Gly Gly Ser Gly Gly Gly Gly
        115                 120                 125

Ser Gly Gly Gly Gly Ser Ala Gln Ser Val Val Thr Gln Pro Pro Ser
    130                 135                 140

Val Ser Ala Ala Pro Gly Gln Lys Val Thr Ile Ser Cys Thr Gly Thr
145                 150                 155                 160

Ser Ser Asp Val Gly Ser Tyr Asn Phe Val Ser Trp Tyr Gln Gln His
                165                 170                 175

Pro Gly Lys Ala Pro Lys Leu Met Ile Tyr Glu Gly Thr Lys Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Thr Ser Tyr Thr Ser Asp Ser Thr Leu Val Phe Gly Gly Gly Thr
225                 230                 235                 240

Lys Val Thr Val Leu
                245
```

-continued

```
<210> SEQ ID NO 103
<211> LENGTH: 243
<212> TYPE: PRT
<213> ORGANISM: Artificial Sequence
<220> FEATURE:
<223> OTHER INFORMATION: W4-VH2-VLP scFv-Fc

<400> SEQUENCE: 103

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 104
<211> LENGTH: 245
<212> TYPE: PRT
<213> ORGANISM: Artificial Sequence
<220> FEATURE:
<223> OTHER INFORMATION: W4-VH2-VL8 scFv-Fc

<400> SEQUENCE: 104

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
```

```
                65                  70                  75                  80
His Val Ser Ser Val Thr Ala Ala Asp Thr Ala Val Tyr Phe Cys Ala
                    85                  90                  95

Arg Ala Asp Trp Asp Leu Leu His Ala Leu Asp Ile Trp Gly Gln Gly
                100                 105                 110

Thr Thr Val Thr Val Ser Ser Gly Gly Gly Ser Gly Gly Gly Gly
            115                 120                 125

Ser Gly Gly Gly Gly Ser Ala Gln Ser Val Thr Gln Pro Pro Ser
        130                 135                 140

Val Ser Ala Ala Pro Gly Gln Lys Val Thr Ile Ser Cys Thr Gly Thr
145                 150                 155                 160

Ser Ser Asp Val Gly Ser Tyr Asn Phe Val Ser Trp Tyr Gln Gln His
                165                 170                 175

Pro Gly Lys Ala Pro Lys Leu Met Ile Tyr Glu Gly Thr Lys Arg Pro
            180                 185                 190

Ser Gly Val Ser Asn Arg Phe Ser Gly Ser Lys Ser Gly Asn Thr Ala
                195                 200                 205

Ser Leu Thr Ile Ser Gly Leu Gln Ala Glu Asp Glu Ala Asp Tyr Tyr
        210                 215                 220

Cys Thr Ser Tyr Thr Ser Asp Ser Thr Leu Val Phe Gly Gly Gly Thr
225                 230                 235                 240

Lys Val Thr Val Leu
            245

<210> SEQ ID NO 105
<211> LENGTH: 245
<212> TYPE: PRT
<213> ORGANISM: Artificial Sequence
<220> FEATURE:
<223> OTHER INFORMATION: W4-VH3-VL7 scFv-Fc

<400> SEQUENCE: 105

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
                20                  25                  30

Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Pro Ser Leu Lys
        50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Phe Asp Ile Trp Gly Gln Gly
                100                 105                 110

Thr Met Val Thr Val Ser Ser Gly Gly Gly Gly Ser Gly Gly Gly Gly
            115                 120                 125

Ser Gly Gly Ser Gly Ser Ala Gln Thr Val Thr Gln Pro Ala Ser
        130                 135                 140

Val Ser Gly Ser Pro Gly Gln Ser Ile Thr Ile Ser Cys Thr Gly Thr
145                 150                 155                 160

Ser Ser Asp Ile Gly Gly Tyr Asn Tyr Val Ser Trp Tyr Arg Gln His
                165                 170                 175

Pro Gly Lys Ala Pro Lys Leu Met Ile Tyr Asp Val Ser Asn Arg Pro
```

```
            180                 185                 190
Ser Gly Val Ser Asn Arg Phe Ser Gly Ser Lys Ser Gly Asn Thr Ala
            195                 200                 205

Ser Leu Thr Ile Ser Gly Leu Gln Ala Glu Asp Glu Ala Asp Tyr Tyr
            210                 215                 220

Cys Thr Ser Tyr Thr Ser Asp Ser Thr Leu Val Phe Gly Gly Gly Thr
225                 230                 235                 240

Lys Val Thr Val Leu
            245

<210> SEQ ID NO 106
<211> LENGTH: 245
<212> TYPE: PRT
<213> ORGANISM: Artificial Sequence
<220> FEATURE:
<223> OTHER INFORMATION: W4-VH3-VL8 scFv-Fc

<400> SEQUENCE: 106

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Pro Ser Leu Lys
        50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Phe Asp Ile Trp Gly Gln Gly
            100                 105                 110

Thr Met Val Thr Val Ser Ser Gly Gly Gly Ser Gly Gly Gly Gly
            115                 120                 125

Ser Gly Gly Gly Gly Ser Ala Gln Ser Val Val Thr Gln Pro Pro Ser
            130                 135                 140

Val Ser Ala Ala Pro Gly Gln Lys Val Thr Ile Ser Cys Thr Gly Thr
145                 150                 155                 160

Ser Ser Asp Val Gly Ser Tyr Asn Phe Val Ser Trp Tyr Gln Gln His
                165                 170                 175

Pro Gly Lys Ala Pro Lys Leu Met Ile Tyr Glu Gly Thr Lys Arg Pro
            180                 185                 190

Ser Gly Val Ser Asn Arg Phe Ser Gly Ser Lys Ser Gly Asn Thr Ala
            195                 200                 205

Ser Leu Thr Ile Ser Gly Leu Gln Ala Glu Asp Glu Ala Asp Tyr Tyr
            210                 215                 220

Cys Thr Ser Tyr Thr Ser Asp Ser Thr Leu Val Phe Gly Gly Gly Thr
225                 230                 235                 240

Lys Val Thr Val Leu
            245

<210> SEQ ID NO 107
<211> LENGTH: 245
<212> TYPE: PRT
<213> ORGANISM: Artificial Sequence
<220> FEATURE:
<223> OTHER INFORMATION: W4-VH5-VL8 scFv-Fc
```

<400> SEQUENCE: 107

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Pro Asp Ile Trp Gly Gln Gly
            100                 105                 110

Thr Leu Val Thr Val Ser Gly Gly Gly Ser Gly Gly Gly
            115                 120                 125

Ser Gly Gly Gly Gly Ser Ala Gln Ser Val Val Thr Gln Pro Pro Ser
    130                 135                 140

Val Ser Ala Ala Pro Gly Gln Lys Val Thr Ile Ser Cys Thr Gly Thr
145                 150                 155                 160

Ser Ser Asp Val Gly Ser Tyr Asn Phe Val Ser Trp Tyr Gln Gln His
                165                 170                 175

Pro Gly Lys Ala Pro Lys Leu Met Ile Tyr Glu Gly Thr Lys Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Thr Ser Tyr Thr Ser Asp Ser Thr Leu Val Phe Gly Gly Gly Thr
225                 230                 235                 240

Lys Val Thr Val Leu
                245

<210> SEQ ID NO 108
<211> LENGTH: 245
<212> TYPE: PRT
<213> ORGANISM: Artificial Sequence
<220> FEATURE:
<223> OTHER INFORMATION: W4-VH6-VL7 scFv-Fc

<400> SEQUENCE: 108

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

```
Arg Ala Asp Trp Asp Leu Leu His Ala Leu Asp Met Trp Gly Gln Gly
                100                 105                 110

Thr Leu Val Thr Val Ser Ser Gly Gly Gly Ser Gly Gly Gly Gly
            115                 120                 125

Ser Gly Gly Ser Gly Ser Ala Gln Thr Val Thr Gln Pro Ala Ser
        130                 135                 140

Val Ser Gly Ser Pro Gly Gln Ser Ile Thr Ile Ser Cys Thr Gly Thr
145                 150                 155                 160

Ser Ser Asp Ile Gly Gly Tyr Asn Tyr Val Ser Trp Tyr Arg Gln His
                165                 170                 175

Pro Gly Lys Ala Pro Lys Leu Met Ile Tyr Asp Val Ser Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Thr Ser Tyr Thr Ser Asp Ser Thr Leu Val Phe Gly Gly Gly Thr
225                 230                 235                 240

Lys Val Thr Val Leu
                245

<210> SEQ ID NO 109
<211> LENGTH: 245
<212> TYPE: PRT
<213> ORGANISM: Artificial Sequence
<220> FEATURE:
<223> OTHER INFORMATION: W4-VH6-VL8 scFv-Fc

<400> SEQUENCE: 109

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Met Trp Gly Gln Gly
                100                 105                 110

Thr Leu Val Thr Val Ser Ser Gly Gly Gly Ser Gly Gly Gly Gly
            115                 120                 125

Ser Gly Gly Gly Gly Ser Ala Gln Ser Val Thr Gln Pro Pro Ser
        130                 135                 140

Val Ser Ala Ala Pro Gly Gln Lys Val Thr Ile Ser Cys Thr Gly Thr
145                 150                 155                 160

Ser Ser Asp Val Gly Ser Tyr Asn Phe Val Ser Trp Tyr Gln Gln His
                165                 170                 175

Pro Gly Lys Ala Pro Lys Leu Met Ile Tyr Glu Gly Thr Lys Arg Pro
            180                 185                 190

Ser Gly Val Ser Asn Arg Phe Ser Gly Ser Lys Ser Gly Asn Thr Ala
        195                 200                 205
```

```
Ser Leu Thr Ile Ser Gly Leu Gln Ala Glu Asp Ala Asp Tyr Tyr
    210                 215                 220

Cys Thr Ser Tyr Thr Ser Asp Ser Thr Leu Val Phe Gly Gly Gly Thr
225                 230                 235                 240

Lys Val Thr Val Leu
                245

<210> SEQ ID NO 110
<211> LENGTH: 243
<212> TYPE: PRT
<213> ORGANISM: Artificial Sequence
<220> FEATURE:
<223> OTHER INFORMATION: W4-VH6-VLP scFv-Fc

<400> SEQUENCE: 110

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Met Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 111
<211> LENGTH: 243
<212> TYPE: PRT
<213> ORGANISM: Artificial Sequence
<220> FEATURE:
<223> OTHER INFORMATION: W4-VH7-VLP scFv-Fc

<400> SEQUENCE: 111

Glu Val Gln Leu Leu Glu Ser Gly Pro Gly Leu Val Lys Pro Ser Glu
1               5                   10                  15
```

Thr Leu Ser Leu Thr Cys Asn Val Ala Gly Ser Ile Ser Pro Tyr
                20                  25                  30

Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Pro Ser Leu Lys
        50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Val Trp Gly Gln Gly
                100                 105                 110

Thr Leu Val Thr Val Ser Ser Gly Gly Gly Ser Gly Gly Gly Gly
                115                 120                 125

Ser Gly Gly Gly Gly Ser Ala Leu Glu Ile Val Leu Thr Gln Ser Pro
        130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
        210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 112
<211> LENGTH: 245
<212> TYPE: PRT
<213> ORGANISM: Artificial Sequence
<220> FEATURE:
<223> OTHER INFORMATION: W4-VH7-VL7 scFv-Fc

<400> SEQUENCE: 112

Glu Val Gln Leu Leu Glu Ser Gly Pro Gly Leu Val Lys Pro Ser Glu
1               5                   10                  15

Thr Leu Ser Leu Thr Cys Asn Val Ala Gly Ser Ile Ser Pro Tyr
                20                  25                  30

Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Pro Ser Leu Lys
        50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Val Trp Gly Gln Gly
                100                 105                 110

Thr Leu Val Thr Val Ser Ser Gly Gly Gly Gly Ser Gly Gly Gly Gly
                115                 120                 125

Ser Gly Gly Ser Gly Ser Ala Gln Thr Val Val Thr Gln Pro Ala Ser

```
                130             135             140
Val Ser Gly Ser Pro Gly Gln Ser Ile Thr Ile Ser Cys Thr Gly Thr
145                 150                 155                 160

Ser Ser Asp Ile Gly Gly Tyr Asn Tyr Val Ser Trp Tyr Arg Gln His
                165                 170                 175

Pro Gly Lys Ala Pro Lys Leu Met Ile Tyr Asp Val Ser Asn Arg Pro
                180                 185                 190

Ser Gly Val Ser Asn Arg Phe Ser Gly Ser Lys Ser Gly Asn Thr Ala
                195                 200                 205

Ser Leu Thr Ile Ser Gly Leu Gln Ala Glu Asp Glu Ala Asp Tyr Tyr
                210                 215                 220

Cys Thr Ser Tyr Thr Ser Asp Ser Thr Leu Val Phe Gly Gly Gly Thr
225                 230                 235                 240

Lys Val Thr Val Leu
                245

<210> SEQ ID NO 113
<211> LENGTH: 245
<212> TYPE: PRT
<213> ORGANISM: Artificial Sequence
<220> FEATURE:
<223> OTHER INFORMATION: W4-VH7-VL8 scFv-Fc

<400> SEQUENCE: 113

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
                20                  25                  30

Tyr Trp Thr Trp Ile Arg Gln Pro Pro Gly Lys Gly Leu Glu Leu Ile
                35                  40                  45

Gly Tyr Ile His Ser Ser Gly Tyr Thr Asp Tyr Asn Pro Ser Leu Lys
            50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Val Trp Gly Gln Gly
                100                 105                 110

Thr Leu Val Thr Val Ser Ser Gly Gly Gly Ser Gly Gly Gly Gly
            115                 120                 125

Ser Gly Gly Gly Gly Ser Ala Gln Ser Val Val Thr Gln Pro Pro Ser
            130                 135                 140

Val Ser Ala Ala Pro Gly Gln Lys Val Thr Ile Ser Cys Thr Gly Thr
145                 150                 155                 160

Ser Ser Asp Val Gly Ser Tyr Asn Phe Val Ser Trp Tyr Gln Gln His
                165                 170                 175

Pro Gly Lys Ala Pro Lys Leu Met Ile Tyr Glu Gly Thr Lys Arg Pro
                180                 185                 190

Ser Gly Val Ser Asn Arg Phe Ser Gly Ser Lys Ser Gly Asn Thr Ala
                195                 200                 205

Ser Leu Thr Ile Ser Gly Leu Gln Ala Glu Asp Glu Ala Asp Tyr Tyr
                210                 215                 220

Cys Thr Ser Tyr Thr Ser Asp Ser Thr Leu Val Phe Gly Gly Gly Thr
225                 230                 235                 240

Lys Val Thr Val Leu
```

-continued

245

<210> SEQ ID NO 114
<211> LENGTH: 243
<212> TYPE: PRT
<213> ORGANISM: Artificial Sequence
<220> FEATURE:
<223> OTHER INFORMATION: W4-VH9-VLP scFv-Fc

<400> SEQUENCE: 114

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Val Leu Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 115
<211> LENGTH: 243
<212> TYPE: PRT
<213> ORGANISM: Artificial Sequence
<220> FEATURE:
<223> OTHER INFORMATION: W4-VH10-VLP scFv-Fc

<400> SEQUENCE: 115

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys

```
                50                  55                  60
Ser Arg Val Thr Ile Ser Gly Asp Thr Ser Lys Lys Gln Phe Ser Leu
 65                  70                  75                  80

His Val Ser Ser Val Thr Ala Ala Asp Thr Ala Val Tyr Phe Cys Ala
                 85                  90                  95

Arg Ala Asp Trp Asp Leu Phe His Ala Leu Asp Ile Trp Gly Gln Gly
                100                 105                 110

Thr Leu Val Thr Val Ser Ser Gly Gly Gly Ser Gly Gly Gly Gly
            115                 120                 125

Ser Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
                180                 185                 190

Gly Val Pro Ser Arg Phe Ser Gly Ser Gly Ser Gly Thr Asp Phe Thr
                195                 200                 205

Leu Thr Ile Ser Ser Leu Gln Pro Glu Asp Phe Ala Thr Tyr Tyr Cys
            210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 116
<211> LENGTH: 243
<212> TYPE: PRT
<213> ORGANISM: Artificial Sequence
<220> FEATURE:
<223> OTHER INFORMATION: W4-VH11-VLP scFv-Fc

<400> SEQUENCE: 116

Glu Val Gln Leu Leu Glu Ser Gly Pro Gly Leu Val Lys Pro Ser Glu
 1               5                  10                  15

Thr Leu Ser Leu Thr Cys Asn Val Ala Gly Gly Ser Ile Ser Pro Tyr
                20                  25                  30

Tyr Trp Thr Trp Ile Arg Gln Pro Pro Gly Lys Gly Leu Glu Leu Ile
             35                  40                  45

Gly Tyr Ile His Ser Ser Gly Tyr Thr Asp Tyr Asn Pro Ser Leu Lys
 50                  55                  60

Ser Arg Val Thr Ile Ser Gly Asp Thr Ser Lys Lys Gln Phe Ser Leu
 65                  70                  75                  80

His Val Ser Ser Val Thr Ala Ala Asp Thr Ala Val Tyr Phe Cys Ala
                 85                  90                  95

Arg Ala Asp Trp Asp Leu Pro His Ala Leu Asp Ile Trp Gly Gln Gly
                100                 105                 110

Thr Leu Val Thr Val Ser Ser Gly Gly Gly Ser Gly Gly Gly Gly
            115                 120                 125

Ser Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175
```

```
Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
        210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 117
<211> LENGTH: 243
<212> TYPE: PRT
<213> ORGANISM: Artificial Sequence
<220> FEATURE:
<223> OTHER INFORMATION: W4-VH12-VLP scFv-Fc

<400> SEQUENCE: 117

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu Arg Ala Leu Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
        210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 118
<211> LENGTH: 243
<212> TYPE: PRT
<213> ORGANISM: Artificial Sequence
<220> FEATURE:
<223> OTHER INFORMATION: W4-VH15-VLP scFv-Fc
```

<400> SEQUENCE: 118

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asn Trp Asp Leu Leu His Ala Leu Asp Ile Trp Gly Gln Gly
            100                 105                 110

Thr Leu Val Thr Val Ser Gly Gly Gly Ser Gly Gly Gly
        115                 120                 125

Ser Gly Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
            165                 170                 175

Gly Lys Ala Pro Lys Leu Leu Ile Tyr Gly Ala Ser Asn Leu Gln Ser
        180                 185                 190

Gly Val Pro Ser Arg Phe Ser Gly Ser Gly Ser Gly Thr Asp Phe Thr
    195                 200                 205

Leu Thr Ile Ser Ser Leu Gln Pro Glu Asp Phe Ala Thr Tyr Tyr Cys
210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 119
<211> LENGTH: 243
<212> TYPE: PRT
<213> ORGANISM: Artificial Sequence
<220> FEATURE:
<223> OTHER INFORMATION: W4-VH16-VLP scFv-Fc

<400> SEQUENCE: 119

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asn Leu Leu His Ala Leu Asp Ile Trp Gly Gln Gly

```
                    100                 105                 110
Thr Leu Val Thr Val Ser Ser Gly Gly Gly Ser Gly Gly Gly Gly
            115                 120                 125

Ser Gly Gly Gly Gly Ser Ala Leu Glu Ile Val Leu Thr Gln Ser Pro
        130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 120
<211> LENGTH: 243
<212> TYPE: PRT
<213> ORGANISM: Artificial Sequence
<220> FEATURE:
<223> OTHER INFORMATION: W4-VH20-VLP scFv-Fc

<400> SEQUENCE: 120

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Thr Leu Asp Ile Trp Gly Gln Gly
            100                 105                 110

Thr Leu Val Thr Val Ser Ser Gly Gly Gly Ser Gly Gly Gly Gly
            115                 120                 125

Ser Gly Gly Gly Gly Ser Ala Leu Glu Ile Val Leu Thr Gln Ser Pro
        130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220
```

Gln Gln Ser Tyr Ser Phe Pro Leu Thr Phe Gly Gly Thr Lys Leu
225                 230                 235                 240

Glu Ile Lys

<210> SEQ ID NO 121
<211> LENGTH: 243
<212> TYPE: PRT
<213> ORGANISM: Artificial Sequence
<220> FEATURE:
<223> OTHER INFORMATION: W4-VH31-VLP scFv-Fc

<400> SEQUENCE: 121

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Glu Leu Leu His Ala Leu Asp Ile Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Thr Lys Leu
225                 230                 235                 240

Glu Ile Lys

<210> SEQ ID NO 122
<211> LENGTH: 243
<212> TYPE: PRT
<213> ORGANISM: Artificial Sequence
<220> FEATURE:
<223> OTHER INFORMATION: W4-VH37-VLP scFv-Fc

<400> SEQUENCE: 122

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

```
Tyr Trp Thr Trp Ile Arg Gln Pro Gly Lys Gly Leu Glu Leu Ile
         35                  40                  45

Gly Tyr Ile His Ser Ser Gly Tyr Thr Asp Tyr Asn Pro Ser Leu Lys
 50                  55                  60

Ser Arg Val Thr Ile Ser Gly Asp Thr Ser Lys Lys Gln Phe Ser Leu
65                   70                  75                  80

His Val Ser Ser Val Thr Ala Ala Asp Thr Ala Val Tyr Phe Cys Ala
                 85                  90                  95

Arg Ala Asp Trp Asp Leu Leu His Ala Phe Asp Met Trp Gly Gln Gly
             100                 105                 110

Thr Met Val Thr Val Ser Ser Gly Gly Gly Gly Ser Gly Gly Gly Gly
             115                 120                 125

Ser Gly Gly Gly Gly Ser Ala Leu Glu Ile Val Leu Thr Gln Ser Pro
         130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
             165                 170                 175

Gly Lys Ala Pro Lys Leu Leu Ile Tyr Gly Ala Ser Asn Leu Gln Ser
             180                 185                 190

Gly Val Pro Ser Arg Phe Ser Gly Ser Gly Ser Gly Thr Asp Phe Thr
             195                 200                 205

Leu Thr Ile Ser Ser Leu Gln Pro Glu Asp Phe Ala Thr Tyr Tyr Cys
             210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 123
<211> LENGTH: 243
<212> TYPE: PRT
<213> ORGANISM: Artificial Sequence
<220> FEATURE:
<223> OTHER INFORMATION: W4-VH41-VLP scFv-Fc

<400> SEQUENCE: 123

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
             20                  25                  30

Tyr Trp Thr Trp Ile Arg Gln Pro Pro Gly Lys Gly Leu Glu Leu Ile
         35                  40                  45

Gly Tyr Ile His Ser Ser Gly Tyr Thr Asp Tyr Asn Pro Ser Leu Lys
 50                  55                  60

Ser Arg Val Thr Ile Ser Gly Asp Thr Ser Lys Lys Gln Phe Ser Leu
65                   70                  75                  80

His Val Ser Ser Val Thr Ala Ala Asp Thr Ala Val Tyr Phe Cys Ala
                 85                  90                  95

Arg Ala Asp Trp Ala Leu Leu His Ala Leu Asp Ile Trp Gly Gln Gly
             100                 105                 110

Thr Leu Val Thr Val Ser Ser Gly Gly Gly Gly Ser Gly Gly Gly Gly
             115                 120                 125

Ser Gly Gly Gly Gly Ser Ala Leu Glu Ile Val Leu Thr Gln Ser Pro
         130                 135                 140

Ser Ser Leu Ser Thr Ser Val Gly Asp Arg Val Thr Ile Thr Cys Arg
```

```
                      145                 150                 155                 160
Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
        210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 124
<211> LENGTH: 243
<212> TYPE: PRT
<213> ORGANISM: Artificial Sequence
<220> FEATURE:
<223> OTHER INFORMATION: W4-VH42-VLP scFv-Fc

<400> SEQUENCE: 124

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Arg Asp Leu Leu His Ala Leu Asp Ile Trp Gly Gln Gly
            100                 105                 110

Thr Met Val Thr Val Ser Ser Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 125
<211> LENGTH: 243
```

```
<212> TYPE: PRT
<213> ORGANISM: Artificial Sequence
<220> FEATURE:
<223> OTHER INFORMATION: W4-VH35-VLP scFv-Fc

<400> SEQUENCE: 125

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Thr
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Ser Gly Gly Gly
            115                 120                 125

Ser Gly Gly Gly Gly Ser Ala Leu Glu Ile Val Leu Thr Gln Ser Pro
        130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 126
<211> LENGTH: 243
<212> TYPE: PRT
<213> ORGANISM: Artificial Sequence
<220> FEATURE:
<223> OTHER INFORMATION: W4-VH36-VLP scFv-Fc

<400> SEQUENCE: 126

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80
```

His Val Ser Ser Val Thr Ala Ala Asp Thr Ala Val Tyr Phe Cys Val
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
            115                 120                 125

Ser Gly Gly Gly Gly Ser Ala Leu Glu Ile Val Leu Thr Gln Ser Pro
            130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
            210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 127
<211> LENGTH: 243
<212> TYPE: PRT
<213> ORGANISM: Artificial Sequence
<220> FEATURE:
<223> OTHER INFORMATION: W4-VH52-VLP scFv-Fc

<400> SEQUENCE: 127

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Pro Ser Leu Lys
        50                  55                  60

Gly Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
            115                 120                 125

Ser Gly Gly Gly Gly Ser Ala Leu Glu Ile Val Leu Thr Gln Ser Pro
            130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr

Leu Thr Ile Ser Ser Leu Gln Pro Glu Asp Phe Ala Thr Tyr Tyr Cys
210                 215                 220

Gln Gln Ser Tyr Ser Phe Pro Leu Thr Phe Gly Gly Thr Lys Leu
225                 230                 235                 240

Glu Ile Lys

<210> SEQ ID NO 128
<211> LENGTH: 243
<212> TYPE: PRT
<213> ORGANISM: Artificial Sequence
<220> FEATURE:
<223> OTHER INFORMATION: W4-VH53-VLP scFv-Fc

<400> SEQUENCE: 128

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
                20                  25                  30

Tyr Trp Thr Trp Ile Arg Gln Pro Pro Gly Lys Gly Leu Glu Leu Ile
            35                  40                  45

Gly Tyr Ile His Pro Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Gly Gly Gly Gly Ser Gly Gly Gly Gly
    115                 120                 125

Ser Gly Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
    195                 200                 205

Leu Thr Ile Ser Ser Leu Gln Pro Glu Asp Phe Ala Thr Tyr Tyr Cys
210                 215                 220

Gln Gln Ser Tyr Ser Phe Pro Leu Thr Phe Gly Gly Thr Lys Leu
225                 230                 235                 240

Glu Ile Lys

<210> SEQ ID NO 129
<211> LENGTH: 243
<212> TYPE: PRT
<213> ORGANISM: Artificial Sequence
<220> FEATURE:
<223> OTHER INFORMATION: W4-VH54-VLP scFv-Fc

<400> SEQUENCE: 129

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Asn Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
            115                 120                 125

Ser Gly Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 130
<211> LENGTH: 243
<212> TYPE: PRT
<213> ORGANISM: Artificial Sequence
<220> FEATURE:
<223> OTHER INFORMATION: W4-VH55-VLP scFv-Fc

<400> SEQUENCE: 130

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Thr His Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
            115                 120                 125

Ser Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 131
<211> LENGTH: 243
<212> TYPE: PRT
<213> ORGANISM: Artificial Sequence
<220> FEATURE:
<223> OTHER INFORMATION: W4-VH56-VLP scFv-Fc

<400> SEQUENCE: 131

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Ala Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 132
<211> LENGTH: 243
<212> TYPE: PRT
<213> ORGANISM: Artificial Sequence
<220> FEATURE:
<223> OTHER INFORMATION: W4-VH57-VLP scFv-Fc

<400> SEQUENCE: 132

```
Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Gly Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys
```

<210> SEQ ID NO 133
<211> LENGTH: 243
<212> TYPE: PRT
<213> ORGANISM: Artificial Sequence
<220> FEATURE:
<223> OTHER INFORMATION: W4-VH58-VLP scFv-Fc

<400> SEQUENCE: 133

```
Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60
```

```
Arg Arg Val Thr Ile Ser Gly Asp Thr Ser Lys Lys Gln Phe Ser Leu
 65                  70                  75                  80

His Val Ser Ser Val Thr Ala Ala Asp Thr Ala Val Tyr Phe Cys Ala
                 85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 134
<211> LENGTH: 243
<212> TYPE: PRT
<213> ORGANISM: Artificial Sequence
<220> FEATURE:
<223> OTHER INFORMATION: W4-VH60-VLP scFv-Fc

<400> SEQUENCE: 134

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Ser Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175
```

```
Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Thr Lys Leu
225                 230                 235                 240

Glu Ile Lys

<210> SEQ ID NO 135
<211> LENGTH: 243
<212> TYPE: PRT
<213> ORGANISM: Artificial Sequence
<220> FEATURE:
<223> OTHER INFORMATION: W4-VH61-VLP scFv-Fc

<400> SEQUENCE: 135

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Phe Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Thr Lys Leu
225                 230                 235                 240

Glu Ile Lys

<210> SEQ ID NO 136
<211> LENGTH: 243
<212> TYPE: PRT
<213> ORGANISM: Artificial Sequence
<220> FEATURE:
<223> OTHER INFORMATION: W4-VH62-VLP scFv-Fc
```

```
<400> SEQUENCE: 136

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Arg Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 137
<211> LENGTH: 243
<212> TYPE: PRT
<213> ORGANISM: Artificial Sequence
<220> FEATURE:
<223> OTHER INFORMATION: W4-VH63-VLP scFv-Fc

<400> SEQUENCE: 137

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Gly Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110
```

Thr Leu Val Thr Val Ser Ser Gly Gly Gly Ser Gly Gly Gly
            115                 120                 125

Ser Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145             150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225             230                 235                 240

Glu Ile Lys

<210> SEQ ID NO 138
<211> LENGTH: 243
<212> TYPE: PRT
<213> ORGANISM: Artificial Sequence
<220> FEATURE:
<223> OTHER INFORMATION: W4-VH64-VLP scFv-Fc

<400> SEQUENCE: 138

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile Arg Ser Ser Gly Tyr Thr Asp Tyr Asn Pro Ser Leu Lys
    50                  55                  60

Ser Arg Val Thr Ile Ser Gly Asp Thr Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Ser Gly Gly Gly
            115                 120                 125

Ser Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145             150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Thr Lys Leu
225                 230                 235                 240

Glu Ile Lys

<210> SEQ ID NO 139
<211> LENGTH: 243
<212> TYPE: PRT
<213> ORGANISM: Artificial Sequence
<220> FEATURE:
<223> OTHER INFORMATION: W4-VH65-VLP scFv-Fc

<400> SEQUENCE: 139

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
50                  55                  60

Asn Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Thr Lys Leu
225                 230                 235                 240

Glu Ile Lys

<210> SEQ ID NO 140
<211> LENGTH: 243
<212> TYPE: PRT
<213> ORGANISM: Artificial Sequence
<220> FEATURE:
<223> OTHER INFORMATION: W4-VH66-VLP scFv-Fc

<400> SEQUENCE: 140

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile

-continued

```
            35                  40                  45
Gly Tyr Ile His Ser Ser Gly Tyr Thr Asp His Asn Pro Ser Leu Lys
 50                  55                  60

Ser Arg Val Thr Ile Ser Gly Asp Thr Ser Lys Lys Gln Phe Ser Leu
 65                  70                  75                  80

His Val Ser Ser Val Thr Ala Ala Asp Thr Ala Val Tyr Phe Cys Ala
                 85                  90                  95

Arg Ala Asp Trp Asp Leu Leu His Ala Leu Asp Ile Trp Gly Gln Gly
                100                 105                 110

Thr Leu Val Thr Val Ser Ser Gly Gly Gly Ser Gly Gly Gly Gly
                115                 120                 125

Ser Gly Gly Gly Gly Ser Ala Leu Glu Ile Val Leu Thr Gln Ser Pro
                130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
                180                 185                 190

Gly Val Pro Ser Arg Phe Ser Gly Ser Gly Ser Gly Thr Asp Phe Thr
                195                 200                 205

Leu Thr Ile Ser Ser Leu Gln Pro Glu Asp Phe Ala Thr Tyr Tyr Cys
210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 141
<211> LENGTH: 243
<212> TYPE: PRT
<213> ORGANISM: Artificial Sequence
<220> FEATURE:
<223> OTHER INFORMATION: W4-VH67-VLP scFv-Fc

<400> SEQUENCE: 141

Glu Val Gln Leu Leu Glu Ser Gly Pro Gly Leu Val Lys Pro Ser Glu
 1               5                  10                  15

Thr Leu Ser Leu Thr Cys Asn Val Ala Gly Gly Ser Ile Ser Pro Tyr
                20                  25                  30

Tyr Trp Thr Trp Ile Arg Gln Pro Pro Gly Lys Gly Leu Glu Leu Ile
                35                  40                  45

Gly Tyr Ile His Phe Ser Gly Tyr Thr Asp Tyr Asn Pro Ser Leu Lys
 50                  55                  60

Ser Arg Val Thr Ile Ser Gly Asp Thr Ser Lys Lys Gln Phe Ser Leu
 65                  70                  75                  80

His Val Ser Ser Val Thr Ala Ala Asp Thr Ala Val Tyr Phe Cys Ala
                 85                  90                  95

Arg Ala Asp Trp Asp Leu Leu His Ala Leu Asp Ile Trp Gly Gln Gly
                100                 105                 110

Thr Leu Val Thr Val Ser Ser Gly Gly Gly Gly Ser Gly Gly Gly Gly
                115                 120                 125

Ser Gly Gly Gly Gly Ser Ala Leu Glu Ile Val Leu Thr Gln Ser Pro
                130                 135                 140

Ser Ser Leu Ser Thr Ser Val Gly Asp Arg Val Thr Ile Thr Cys Arg
145                 150                 155                 160
```

Ala Ser Gln Ser Ile Arg Ser His Leu Asn Trp Tyr Gln Lys Pro
            165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
            210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 142
<211> LENGTH: 243
<212> TYPE: PRT
<213> ORGANISM: Artificial Sequence
<220> FEATURE:
<223> OTHER INFORMATION: W4-VH69-VLP scFv-Fc

<400> SEQUENCE: 142

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Ser Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
            115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Lys Pro
            165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
            210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 143
<211> LENGTH: 243
<212> TYPE: PRT

<213> ORGANISM: Artificial Sequence
<220> FEATURE:
<223> OTHER INFORMATION: W4-VH70-VLP scFv-Fc

<400> SEQUENCE: 143

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Arg
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 144
<211> LENGTH: 243
<212> TYPE: PRT
<213> ORGANISM: Artificial Sequence
<220> FEATURE:
<223> OTHER INFORMATION: W4-VH72-VLP scFv-Fc

<400> SEQUENCE: 144

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly His Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala 85                  90                  95
Arg Ala Asp Trp Asp Leu Leu His Ala Leu Asp Ile Trp Gly Gln Gly
                100                 105                 110

Thr Leu Val Thr Val Ser Ser Gly Gly Gly Ser Gly Gly Gly Gly
            115                 120                 125

Ser Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
                180                 185                 190

Gly Val Pro Ser Arg Phe Ser Gly Ser Gly Ser Gly Thr Asp Phe Thr
                195                 200                 205

Leu Thr Ile Ser Ser Leu Gln Pro Glu Asp Phe Ala Thr Tyr Tyr Cys
210                 215                 220

Gln Gln Ser Tyr Ser Phe Pro Leu Thr Phe Gly Gly Thr Lys Leu
225                 230                 235                 240

Glu Ile Lys

<210> SEQ ID NO 145
<211> LENGTH: 243
<212> TYPE: PRT
<213> ORGANISM: Artificial Sequence
<220> FEATURE:
<223> OTHER INFORMATION: W4-VH79-VLP scFv-Fc

<400> SEQUENCE: 145

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
                20                  25                  30

Tyr Trp Thr Trp Ile Arg Gln Pro Pro Gly Lys Gly Leu Glu Leu Ile
            35                  40                  45

Gly Tyr Tyr His Pro Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
                100                 105                 110

Thr Leu Val Thr Val Ser Ser Gly Gly Gly Gly Ser Gly Gly Gly Gly
            115                 120                 125

Ser Gly Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
                180                 185                 190

Gly Val Pro Ser Arg Phe Ser Gly Ser Gly Ser Gly Thr Asp Phe Thr
                195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 146
<211> LENGTH: 243
<212> TYPE: PRT
<213> ORGANISM: Artificial Sequence
<220> FEATURE:
<223> OTHER INFORMATION: W4-VH80-VLP scFv-Fc

<400> SEQUENCE: 146

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Phe Thr Ser Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 147
<211> LENGTH: 729
<212> TYPE: DNA
<213> ORGANISM: Artificial Sequence
<220> FEATURE:
<223> OTHER INFORMATION: W4-M1 scFv-Fc

<400> SEQUENCE: 147
gaggtgcagc tgttggagtc gggcccagga ctggtgaagc cttcggagac cctgtccctc      60
acctgcaatg tcgctggtgg ctccatcagt ccttactact ggacctggat ccggcagccc     120

```
ccagggaagg gcctggagtt gattggttat atccactcca gtgggtacac cgactacaac    180
ccctccctca agagtcgagt caccatatca ggagacacgt ccaagaagca gttctccctg    240
cacgtgagct ctgtgaccgc tgcggacacg gccgtgtact tctgtgcgag aggcgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgctg    420
actcagtctc catcctccct gtctgcatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg ggacagattt cactctcacc atcagcagtc tgcaacctga ggattttgca    660
acttattatt gtcaacagag ttacagtacc cctcagacgt tcggccaagg gaccaagctg    720
gagatcaaa                                                            729

<210> SEQ ID NO 148
<211> LENGTH: 735
<212> TYPE: DNA
<213> ORGANISM: Artificial Sequence
<220> FEATURE:
<223> OTHER INFORMATION: W4-M5 scFv-Fc

<400> SEQUENCE: 148
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180 ccctcccctca agagtcgagt caccatatca ggagacacgt ccaagaagca gttctccctg   240
cacgtgagct ctgtgaccgc tgcggacacg gccgtgtact tctgtgcgag aggcgattgg    300
gacctgcttc atgctcttga tatctggggc caagggaccc tggtcaccgt ctcgagtgga    360
ggcggcggtt caggcggagg tggctctggc ggtagcggaa gtgcacagtc tgtcgtgacg    420
cagcctgcct ccgtgtctgg gtctcttgga cagtcgatca ccatctcctg cactggaacc    480
agcagtgatg ctgggagtta aactttgtc tcctggtacc aacaacaccc aggcaaagcc    540
cccaaactca tcatttatga tgtcaataat cggccctcag gggtttctaa tcgcttctct    600
ggctccaagt ctggcaacac ggcctccctg accatctctg gctccaggc tgaggacgag    660 gctgattatt attgcaactc atacggaggc agcagcactt ggctgttcgg cggagggacc    720
aagctgaccg tccta                                                     735

<210> SEQ ID NO 149
<211> LENGTH: 735
<212> TYPE: DNA
<213> ORGANISM: Artificial Sequence
<220> FEATURE:
<223> OTHER INFORMATION: W4-M6 scFv-Fc

<400> SEQUENCE: 149
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180 ccctcccctca agagtcgagt caccatatca ggagacacgt ccaagaagca gttctccctg   240
cacgtgagct ctgtgaccgc tgcggacacg gccgtgtact tctgtgcgag aggcgattgg    300
```

| | |
|---|---|
| gacctgcttc atgctcttga tatctggggc aagggaccc tggtcaccgt ctcgagtgga | 360 |
| ggcggcggtt caggcggagg tggctctggc ggtggcggaa gtgcactctc ctatgagctg | 420 |
| atgcagccac cctcagtgtc tgggaccccc gggcagaggg tcaccatctc ttgttctgga | 480 |
| agcagctcca acatcggaag taatactgta aactggtacc agcagctccc aggaacggcc | 540 |
| cccaaactcc tcatctatag taataatcag cggccctcag gggtccctga ccgattctct | 600 |
| ggctccaagt ctggcacctc agcctccctg gccatcagtg gctccagtc tgaggatgag | 660 |
| gctgattatt actgtgcagc atgggatgac agcctgaatg tggtattcgg cggagggacc | 720 |
| aaggtcaccg tccta | 735 |

<210> SEQ ID NO 150
<211> LENGTH: 735
<212> TYPE: DNA
<213> ORGANISM: Artificial Sequence
<220> FEATURE:
<223> OTHER INFORMATION: W4-M7 scFv-Fc

<400> SEQUENCE: 150

| | |
|---|---|
| gaggtgcagc tgttggagtc gggcccagga ctggtgaagc cttcggagac cctgtccctc | 60 |
| acctgcaatg tcgctggtgg ctccatcagt ccttactact ggacctggat ccggcagccc | 120 |
| ccagggaagg gcctggagtt gattggttat atccactcca gtgggtacac cgactacaac | 180 |
| ccctccctca gagtcgagt caccatatca ggagacacg ccaagaagca gttctccctg | 240 |
| cacgtgagct ctgtgaccgc tgcggacacg gccgtgtact tctgtgcgag aggcgattgg | 300 |
| gacctgcttc atgctcttga tatctggggc aagggaccc tggtcaccgt ctcgagtgga | 360 |
| ggcggcggtt caggcggagg tggctctggc ggtagcggaa gtgcacagac tgtggtgacc | 420 |
| cagcctgcct ccgtgtctgg gtctcctgga cagtcgatca ccatctcctg cactggaacc | 480 |
| agcagtgaca ttggtggtta taactatgtc tcctggtacc agcagcaccc aggcaaagcc | 540 |
| cccaaactca tgatttatga tgtcagtaat cggccctcag gggtttctaa tcgcttctct | 600 |
| ggctccaagt ctggcaacac ggcctccctg accatctctg gctccaggc tgaggacgag | 660 |
| gctgattatt actgcaccct catataagc gacagcactc tggttttcgg cggaggcacc | 720 |
| aaggtgaccg tcctc | 735 |

<210> SEQ ID NO 151
<211> LENGTH: 735
<212> TYPE: DNA
<213> ORGANISM: Artificial Sequence
<220> FEATURE:
<223> OTHER INFORMATION: W4-M8 scFv-Fc

<400> SEQUENCE: 151

| | |
|---|---|
| gaggtgcagc tgttggagtc gggcccagga ctggtgaagc cttcggagac cctgtccctc | 60 |
| acctgcaatg tcgctggtgg ctccatcagt ccttactact ggacctggat ccggcagccc | 120 |
| ccagggaagg gcctggagtt gattggttat atccactcca gtgggtacac cgactacaac | 180 |
| ccctccctca gagtcgagt caccatatca ggagacacgt ccaagaagca gttctccctg | 240 |
| cacgtgagct ctgtgaccgc tgcggacacg gccgtgtact tctgtgcgag aggcgattgg | 300 |
| gacctgcttc atgctcttga tatctggggc aagggaccc tggtcaccgt ctcgagtgga | 360 |
| ggcggcggtt caggcggagg tggctctggc ggtggcggaa gtgcacagtc tgtcgtgacg | 420 |
| cagccgccct cagtgtctgc ggccccagga cagaaggtca ccatctcctg cactggaacc | 480 |
| agcagtgatg ttgggagtta aactttgtc tcctggtacc aacagcaccc aggcaaagcc | 540 |

```
cccaaaactca tgatttatga gggcactaag cggccctcag gggtttctaa tcgcttctct    600
ggctccaagt ctggcaacac ggcctccctg accatctctg gctccaggc tgaggacgag     660 gctgattatt actgcacctc atatacaagc gacagcactc tggttttcgg cggaggcacc    720
aaggtgaccg tcctc                                                     735
```

<210> SEQ ID NO 152
<211> LENGTH: 735
<212> TYPE: PRT
<213> ORGANISM: Artificial Sequence
<220> FEATURE:
<223> OTHER INFORMATION: W4-M9 scFv-Fc

<400> SEQUENCE: 152

```
Gly Ala Gly Gly Thr Gly Cys Ala Gly Cys Thr Gly Thr Thr Gly Gly
1               5                   10                  15

Ala Gly Thr Cys Gly Gly Cys Cys Cys Ala Gly Gly Ala Cys Thr
            20                  25                  30

Gly Gly Thr Gly Ala Ala Gly Cys Cys Thr Thr Cys Gly Gly Ala Gly
            35                  40                  45

Ala Cys Cys Cys Thr Gly Thr Cys Cys Thr Cys Ala Cys Cys Thr
50                  55                  60

Gly Cys Ala Ala Thr Gly Thr Cys Thr Gly Gly Thr Gly Gly
65                  70                  75                  80

Cys Thr Cys Cys Ala Thr Cys Ala Gly Thr Cys Thr Thr Ala Cys
                85                  90                  95

Thr Ala Cys Thr Gly Gly Ala Cys Thr Gly Gly Ala Thr Cys Cys
                100                 105                 110

Gly Gly Cys Ala Gly Cys Cys Cys Cys Ala Gly Gly Ala Ala
            115                 120                 125

Gly Gly Gly Cys Cys Thr Gly Ala Gly Thr Thr Gly Ala Thr Thr
            130                 135                 140

Gly Gly Thr Thr Ala Thr Ala Thr Cys Thr Ala Thr Thr Ala
145                 150                 155                 160

Gly Thr Gly Gly Thr Ala Cys Thr Ala Cys Cys Gly Ala Cys Thr Ala
                165                 170                 175

Cys Ala Ala Cys Cys Cys Cys Thr Cys Cys Cys Thr Cys Ala Ala Gly
                180                 185                 190

Ala Gly Thr Cys Gly Ala Gly Thr Cys Ala Cys Cys Ala Thr Ala Thr
            195                 200                 205

Cys Ala Gly Thr Ala Gly Ala Cys Ala Cys Gly Thr Cys Cys Ala Ala
            210                 215                 220

Gly Ala Ala Gly Cys Ala Gly Thr Thr Cys Thr Cys Cys Thr Gly
225                 230                 235                 240

Cys Ala Cys Gly Thr Gly Ala Gly Cys Thr Cys Thr Gly Thr Gly Ala
                245                 250                 255

Cys Cys Gly Cys Thr Gly Cys Gly Gly Ala Cys Ala Cys Gly Gly Cys
                260                 265                 270

Cys Gly Thr Gly Thr Ala Cys Thr Thr Cys Thr Gly Thr Gly Cys Gly
            275                 280                 285

Ala Gly Ala Gly Gly Cys Gly Ala Thr Thr Gly Gly Ala Cys Cys
            290                 295                 300

Thr Gly Cys Thr Thr Cys Ala Thr Gly Cys Thr Cys Thr Gly Ala
305                 310                 315                 320
```

```
Thr Ala Thr Cys Thr Gly Gly Gly Gly Cys Ala Gly Gly
                325                 330             335
Ala Cys Cys Cys Thr Gly Gly Thr Cys Ala Cys Gly Thr Cys Thr
            340                 345             350
Cys Gly Ala Gly Thr Gly Gly Ala Gly Cys Gly Gly Cys Gly Gly
                355                 360             365
Thr Thr Cys Ala Gly Gly Cys Gly Ala Gly Gly Thr Gly Gly Cys
    370                 375                 380
Thr Cys Thr Gly Gly Cys Gly Gly Thr Ala Gly Cys Gly Gly Ala Ala
385                 390                 395                 400
Gly Thr Gly Cys Ala Cys Ala Gly Thr Cys Thr Gly Thr Gly Cys Thr
                405                 410                 415
Gly Ala Cys Thr Cys Ala Gly Cys Cys Thr Gly Cys Cys Thr Cys Cys
            420                 425             430
Gly Thr Gly Thr Cys Gly Gly Gly Thr Cys Ala Cys Cys Thr Gly
                435                 440             445
Gly Ala Cys Ala Gly Thr Cys Gly Ala Thr Cys Ala Cys Cys Ala Thr
    450                 455             460
Ala Thr Cys Cys Thr Gly Cys Ala Cys Thr Gly Gly Cys Ala Cys Cys
465             470                 475                 480
Ala Cys Cys Ala Gly Cys Gly Ala Cys Gly Thr Thr Gly Gly Thr Gly
                485                 490                 495
Cys Thr Thr Thr Thr Gly Gly Cys Thr Thr Gly Thr Cys Thr Cys
                500                 505             510
Cys Thr Gly Gly Thr Ala Cys Cys Ala Cys Ala Gly Ala Ala Gly
            515                 520                 525
Cys Cys Ala Gly Gly Cys Gly Ala Ala Gly Thr Cys Cys Cys Ala
            530                 535             540
Ala Ala Cys Thr Cys Ala Thr Gly Ala Thr Thr Thr Ala Thr Gly Ala
545         550                 555                 560
Thr Gly Thr Cys Ala Gly Thr Gly Ala Thr Cys Gly Gly Cys Cys Cys
                565                 570             575
Thr Cys Ala Gly Gly Gly Gly Thr Thr Thr Cys Thr Gly Ala Thr Cys
            580                 585                 590
Gly Cys Thr Thr Cys Thr Cys Thr Gly Gly Cys Thr Cys Cys Ala Ala
                595             600                 605
Gly Thr Cys Thr Gly Gly Cys Ala Gly Cys Ala Cys Gly Gly Cys Cys
        610                 615             620
Thr Cys Cys Cys Thr Gly Ala Cys Cys Ala Thr Cys Thr Cys Thr Gly
625                 630                 635                 640
Gly Gly Cys Thr Cys Cys Ala Gly Gly Cys Thr Gly Ala Gly Gly Ala
                645             650                 655
Cys Gly Ala Gly Gly Cys Thr Gly Ala Thr Thr Ala Thr Thr Ala Cys
            660                 665             670
Thr Gly Cys Gly Gly Cys Thr Cys Ala Thr Ala Cys Ala Ala
        675                 680                 685
Gly Cys Ala Cys Cys Ala Gly Cys Ala Cys Thr Thr Gly Gly Gly Thr
            690                 695             700
Gly Thr Thr Cys Gly Gly Cys Gly Gly Ala Gly Gly Ala Cys Cys
705                 710                 715                 720
Ala Ala Gly Cys Thr Gly Ala Cys Cys Gly Thr Cys Cys Thr Ala
            725                 730                 735
```

<210> SEQ ID NO 153
<211> LENGTH: 738
<212> TYPE: DNA
<213> ORGANISM: Artificial Sequence
<220> FEATURE:
<223> OTHER INFORMATION: W4-M11 scFv-Fc

<400> SEQUENCE: 153

```
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagg gcctggagtt gattggttat atccactcca gtgggtacac cgactacaac     180
ccctccctca gagtcgagt caccatatca ggagacacg ccaagaagca gttctccctg       240
cacgtgagct ctgtgaccgc tgcggacacg gccgtgtact tctgtgcgag aggcgattgg     300
gacctgcttc atgctcttga tatctggggc caagggaccc tggtcaccgt ctcgagtgga     360
ggcggcggtt caggcggagg tggctctggc ggtggcggaa gtgcactctc ctatgagctg     420
atgcagcctg cctccgtgtc tgggtctctt ggacagtcga tcaccatctc ctgcactgga     480
accagcagtg atgttgggag ttataacttt gtctcctggt accaacagca cccaggcaaa     540
gcccccaaac tcatgattta tgagggcact aagcggccct caggggtccc tgaccgattc     600
tctggctcca agtctggcaa cacggcctcc ctgacaatct ctgggctcca ggctgaggac     660
gaggctgatt attactgttc ctcatatgca cgtagttaca cttatgtctt cggaactggc     720
accaaggtga ccgtcctc                                                   738
```

<210> SEQ ID NO 154
<211> LENGTH: 735
<212> TYPE: DNA
<213> ORGANISM: Artificial Sequence
<220> FEATURE:
<223> OTHER INFORMATION: W4-M12 scFv-Fc

<400> SEQUENCE: 154

```
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagg gcctggagtt gattggttat atccactcca gtgggtacac cgactacaac     180
ccctccctca gagtcgagt caccatatca ggagacacgt ccaagaagca gttctccctg      240
cacgtgagct ctgtgaccgc tgcggacacg gccgtgtact tctgtgcgag aggcgattgg     300
gacctgcttc atgctcttga tatctggggc caagggaccc tggtcaccgt ctcgagtgga     360
ggcggcggtt caggcggagg tggctctggc ggtggcggaa gtgcacagac tgtggtgacc     420
cagcctgcct cagtgtctgg gtctcctgga cagtcgatca ccatctcctg cactgggacc     480
agcggtgaca ttggtgctta taactttgtc tcctggtacc aacacaccc aggcaaagcc      540
cccaaactca tcatttatga tgtcaataat cggccctcag gggtttctaa tcgcttctct     600
ggctccaagt ctggcaacac ggcctccctg accatctctg gctccaggc tgaggacgag     660
gctgattatt actgcagctc atatacaagc agcaacactt atctcttcgg aactgggacc     720
aaggtcaccg tccta                                                      735
```

<210> SEQ ID NO 155
<211> LENGTH: 735
<212> TYPE: DNA
<213> ORGANISM: Artificial Sequence
<220> FEATURE:
<223> OTHER INFORMATION: W4-M14 scFv-Fc

<400> SEQUENCE: 155

```
gaggtgcagc tgttggagtc gggcccagga ctggtgaagc cttcggagac cctgtccctc    60
acctgcaatg tcgctggtgg ctccatcagt ccttactact ggacctggat ccggcagccc   120
ccagggaagg gcctggagtt gattggttat atccactcca gtgggtacac cgactacaac   180
ccctccctca agagtcgagt caccatatca ggagacacgt ccaagaagca gttctccctg   240
cacgtgagct ctgtgaccgc tgcggacacg gccgtgtact tctgtgcgag aggcgattgg   300
gacctgcttc atgctcttga tatctggggc caagggaccc tggtcaccgt ctcgagtgga   360
ggcggcggtt caggcggagg tggctctggc ggtagcggaa gtgcacagtc tgtgttgacg   420
cagccaccct cagcgtttgg acccccggga cagagtctca ccatctcttg ttctggaagc   480
aactccaaca tcggacgtaa tactgttact tggtaccagc atctcccagg aacggccccc   540
aaactcctca tctatagttc taatcagcgg ccctcggggg tccctgaccg attctctggc   600
tccaagtctg gcacctcagc ctccctggcc atcagtgggc tccagtctga ggatgaggct   660
cattattact gtgcagcatg ggatgacagc ctgcatggca tgatatttgg cggagggacc   720
aaggtcaccg tccta                                                    735
```

<210> SEQ ID NO 156
<211> LENGTH: 735
<212> TYPE: DNA
<213> ORGANISM: Artificial Sequence
<220> FEATURE:
<223> OTHER INFORMATION: W4-M15 scFv-Fc

<400> SEQUENCE: 156

```
gaggtgcagc tgttggagtc gggcccagga ctggtgaagc cttcggagac cctgtccctc    60
acctgcaatg tcgctggtgg ctccatcagt ccttactact ggacctggat ccggcagccc   120
ccagggaagg gcctggagtt gattggttat atccactcca gtgggtacac cgactacaac   180
ccctccctca agagtcgagt caccatatca ggagacacgt ccaagaagca gttctccctg   240
cacgtgagct ctgtgaccgc tgcggacacg gccgtgtact tctgtgcgag aggcgattgg   300
gacctgcttc atgctcttga tatctggggc caagggaccc tggtcaccgt ctcgagtgga   360
ggcggcggtt caggcggagg tggctctggc ggtggcggaa gtgcacagtc tgtgctgacg   420
cagccaccct cagcgtttgg acccccggga cagagtctca ccatctcttg ttctggaagc   480
aactccaaca tcggacgtaa tactgttact tggtaccagc atctcccagg aacggccccc   540
aaactcctca tctatagttc taatcagcgg ccctcggggg tccctgaccg attctctggc   600
tccaagtctg gcacctcagc ctccctggcc atcagtgggc tccagtctga ggatgaggct   660
cattattact gtgcagcatg ggatgacagc ctgcatggca tgatatttgg cggagggacc   720
aaggtcaccg tccta                                                    735
```

<210> SEQ ID NO 157
<211> LENGTH: 735
<212> TYPE: DNA
<213> ORGANISM: Artificial Sequence
<220> FEATURE:
<223> OTHER INFORMATION: W4-M16 scFv-Fc

<400> SEQUENCE: 157

```
gaggtgcagc tgttggagtc gggcccagga ctggtgaagc cttcggagac cctgtccctc    60
acctgcaatg tcgctggtgg ctccatcagt ccttactact ggacctggat ccggcagccc   120
ccagggaagg gcctggagtt gattggttat atccactcca gtgggtacac cgactacaac   180
```

```
cctcccctca agagtcgagt caccatatca ggagacacgt ccaagaagca gttctccctg    240
cacgtgagct ctgtgaccgc tgcggacacg gccgtgtact tctgtgcgag aggcgattgg    300
gacctgcttc atgctcttga tatctggggc caagggaccc tggtcaccgt ctcgagtgga    360
ggcggcggtt caggcggaag tggctctggc ggtggcggaa gtgcacagtc tgtgttgacg    420
cagccaccct cagcgtttgg accccggga cagagtctca ccatctcttg ttctggaagc    480
aactccaaca tcggacgtaa tactgttact tggtaccagc atctcccagg aacggccccc    540
aaactcctca tctatagttc taatcagcgg ccctcggggg tccctgaccg attctctggc    600
tccaagtctg gcacctcagc ctccctggcc atcagtgggc tccagtctga ggatgaggct    660
cattattact gtgcagcatg ggatgacagc ctgcatgca tgatatttgg cggagggacc    720
aaggtcaccg tccta                                                    735
```

<210> SEQ ID NO 158
<211> LENGTH: 735
<212> TYPE: DNA
<213> ORGANISM: Artificial Sequence
<220> FEATURE:
<223> OTHER INFORMATION: W4-M17 scFv-Fc

<400> SEQUENCE: 158

```
gaggtgcagc tgttggagtc gggcccagga ctggtgaagc cttcggagac cctgtccctc    60
acctgcaatg tcgctggtgg ctccatcagt ccttactact ggacctggat ccggcagccc   120
ccagggaagg gcctggagtt gattggttat atccactcca gtgggtacac cgactacaac   180 ccctcccctca agagtcgagt caccatatca ggagacacgt ccaagaagca gttctccctg   240
cacgtgagct ctgtgaccgc tgcggacacg gccgtgtact tctgtgcgag aggcgattgg    300
gacctgcttc atgctcttga tatctggggc caagggaccc tggtcaccgt ctcgagtgga    360
ggcggcggtt caggcggagg tggctctggc ggtagcggaa gtgcacagac tgtggtgacc   420
cagccaccct cagcgtttgg accccggga cagagtctca ccatctcttg ttctggaagc    480
agctccaaca tcggaggtaa tactgtaaac tggtaccagc agctcccagg aacggccccc    540
agactcctca tctatagtaa tagtcagcgg ccctcagggg tccctgaccg attctctggc    600
tccaagtctg gcacctcagc ctccctggcc atcagtgggc tccagtctga ggatgaggct    660
gactattact gtgcagcatg ggatgacagc ctgaatggtg tggtattcgg cggagggacc    720
aagctgaccg tccta                                                    735
```

<210> SEQ ID NO 159
<211> LENGTH: 735
<212> TYPE: DNA
<213> ORGANISM: Artificial Sequence
<220> FEATURE:
<223> OTHER INFORMATION: W4-M19 scFv-Fc

<400> SEQUENCE: 159

```
gaggtgcagc tgttggagtc gggcccagga ctggtgaagc cttcggagac cctgtccctc    60
acctgcaatg tcgctggtgg ctccatcagt ccttactact ggacctggat ccggcagccc   120
ccagggaagg gcctggagtt gattggttat atccactcca gtgggtacac cgactacaac   180 ccctcccctca agagtcgagt caccatatca ggagacacgt ccaagaagca gttctccctg   240
cacgtgagct ctgtgaccgc tgcggacacg gccgtgtact tctgtgcgag aggcgattgg    300
gacctgcttc atgctcttga tatctggggc caagggaccc tggtcaccgt ctcgagtgga    360
```

```
ggcggcggtt caggcggagg tggctctggc ggtggcggaa gtgcacagtc tgtgctgact      420
cagcctgcct ccgtgtctgg gtctcctgga cagtcgatca ccatctcctg cactggaacc      480
agcagtgacg ttggtgctta aactatgtc tcctggttcc aacaacaccc aggcaaagtc      540
cccaaactca taatttggga ggtcattaat cggccctcag gggtttctaa tcgcttctct      600
ggctccaagt ctggcaacac ggcctccctg accatctctg gctccaggc tgaggacgag      660 gctgattatt actgttcctc atatacaagc agcaacactt atgtcttcgg aactgggacc      720
aagctgaccg tccta                                                      735

<210> SEQ ID NO 160
<211> LENGTH: 735
<212> TYPE: DNA
<213> ORGANISM: Artificial Sequence
<220> FEATURE:
<223> OTHER INFORMATION: W4-M20 scFv-Fc

<400> SEQUENCE: 160
gaggtgcagc tgttggagtc gggcccagga ctggtgaagc cttcggagac cctgtccctc       60
acctgcaatg tcgctggtgg ctccatcagt ccttactact ggacctggat ccggcagccc      120
ccagggaagg gcctggagtt gattggttat atccactcca gtgggtacac cgactacaac      180
ccctccctca agagtcgagt caccatatca ggagacacgt ccaagaagca gttctccctg      240
cacgtgagct ctgtgaccgc tgcggacacg gccgtgtact tctgtgcgag aggcgattgg      300
gacctgcttc atgctcttga tatctggggc caagggaccc tggtcaccgt ctcgagtgga      360
ggcggcggtt caggcggagg tggctctggc ggtagcggaa gtgcacagtc tgccctgact      420
cagccgccct cagtgtctgc ggccccagga cagaaggtca ccatctcctg ctctggaagc      480
agctccaaca ttgggaacaa ttatgtctcc tggtatctgc agctcccagg aacagccccc      540
aaactcctca tttatgacaa taatgggcga ccctcaggga ttcctgaccg attctctggc      600
tccaagtctg gcacgtcagc caccctgggc atcaccggac tccagactgg ggacgaggcc      660
gattattact gcgcaacatg ggatagcagc ctgagtgctg gggtgttcgg cggagggacc      720
aaggtcaccg tccta                                                      735

<210> SEQ ID NO 161
<211> LENGTH: 732
<212> TYPE: DNA
<213> ORGANISM: Artificial Sequence
<220> FEATURE:
<223> OTHER INFORMATION: W4-M4 scFv-Fc

<400> SEQUENCE: 161
gaggtgcagc tgttggagtc gggcccagga ctggtgaagc cttcggagac cctgtccctc       60
acctgcaatg tcgctggtgg ctccatcagt ccttactact ggacctggat ccggcagccc      120
ccagggaagg gcctggagtt gattggttat atccactcca gtgggtacac cgactacaac      180
ccctccctca agagtcgagt caccatatca ggagacacgt ccaagaagca gttctccctg      240
cacgtgagct ctgtgaccgc tgcggacacg gccgtgtact tctgtgcgag aggcgattgg      300
gacctgcttc atgctcttga tatctggggc caagggaccc tggtcaccgt ctcgagtgga      360
ggcggcggtt caggcggagg tggctctggc ggtagcggaa gtgcactctc ctatgagctg      420
atgcaggacc ctgctgtgtc tgtggccttg ggacagacag tcaggatcac atgccgggga      480
gacagcctca gcagctttta tacaagctgg taccagcaga agccaggaca ggcccctcta      540
cttgtcatct atggtaaaaa caaccggccc tcagggatcc agaccggtt ctctggctcc      600
```

| | |
|---|---|
| agctcaggaa acacagcttc cttgaccatc actggggctc aggcggaaga tgaggctgac | 660 |
| tattactgta actcccggga cagcagtgat aactatgtgt tattcggcgg agggaccaag | 720 |
| ctgaccgtcc ta | 732 |

<210> SEQ ID NO 162
<211> LENGTH: 735
<212> TYPE: DNA
<213> ORGANISM: Artificial Sequence
<220> FEATURE:
<223> OTHER INFORMATION: W4-M10 scFv-Fc

<400> SEQUENCE: 162

| | |
|---|---|
| gaggtgcagc tgttggagtc gggcccagga ctggtgaagc cttcggagac cctgtccctc | 60 |
| acctgcaatg tcgctggtgg ctccatcagt ccttactact ggacctggat ccggcagccc | 120 |
| ccagggaagg gcctggagtt gattggttat atccactcca gtgggtacac cgactacaac | 180 |
| ccctccctca agagtcgagt caccatatca ggagacacgt ccaagaagca gttctccctg | 240 |
| cacgtgagct ctgtgaccgc tgcggacacg gccgtgtact tctgtgcgag aggcgattgg | 300 |
| gacctgcttc atgctcttga tatctggggc caagggaccc tggtcaccgt ctcgagtgga | 360 |
| ggcggcggtt caggcggagg tggctctggc ggtggcggaa gtgcacagtc tgtcgtgacg | 420 |
| cagcctgcct ccgtgtctgg gtctcctgga cagtcggtca ccatctcctg cactggaacc | 480 |
| agcagtgacg ttggtagtta aagggtgtc tcctggtacc agcagccccc aggcacagcc | 540 |
| cccaaactcc tcatctataa tgacaatcag cggccctcag ggatccctgg gcgattctct | 600 |
| ggctccaact ctggaaacac agccattctg accatcagcg ggactcaggc tatggatgag | 660 |
| gctgactatt actgtcaggc gtgggacagc agtaatcatg tggttttcgg cggagggacc | 720 |
| aagctgaccg tccta | 735 |

<210> SEQ ID NO 163
<211> LENGTH: 729
<212> TYPE: DNA
<213> ORGANISM: Artificial Sequence
<220> FEATURE:
<223> OTHER INFORMATION: W4-HC1-LCP scFv-Fc

<400> SEQUENCE: 163

| | |
|---|---|
| gaggtgcagc tgttggagtc gggcccagga ctggtgaagc cttcggagac cctgtccctc | 60 |
| acctgcaatg tcgctggtgg ctccatcagt ccttactact ggacctggat ccggcagccc | 120 |
| ccagggaagg gcctggagtt gattggttat atccactcca gtgggtacac cgactacaac | 180 |
| ccctccctca agagtcgagt caccatatca ggagacacgt ccaagaagca gttctccctg | 240 |
| cacgtgagct ctgtgaccgc tgcggacacg gccgtgtact tctgtgcgag agccgattgg | 300 |
| gacctgcttc atgctcttga tatctggggc caagggacca tggtcaccgt ctcgagtgga | 360 |
| ggcggcggtt caggcggagg tggctctggc ggtggcggaa gtgcactcga aattgtgttg | 420 |
| acacagtctc catcctccct gtctacatct gtaggagaca gagtcaccat cacttgccgg | 480 |
| gcaagtcaga gcattaggag ccatttaaat tggtatcagc agaaaccagg gaaagcccct | 540 |
| aaactcctga tctatggtgc atccaatttg caaagtgggg tcccatcaag gttcagtggc | 600 |
| agtggatctg ggacagattt cactctcacc attagtagtc tgcaacctga agattttgca | 660 |
| acttactact gtcaacagag ttacagtttc cccctcactt tcggcggagg gaccaagctg | 720 |
| gagatcaaa | 729 |

<210> SEQ ID NO 164
<211> LENGTH: 735
<212> TYPE: DNA
<213> ORGANISM: Artificial Sequence
<220> FEATURE:
<223> OTHER INFORMATION: W4-HC1-LC7

<400> SEQUENCE: 164

| | | | | |
|---|---|---|---|---|
| gaggtgcagc tgttggagtc gggcccagga ctggtgaagc cttcggagac cctgtccctc | | | | 60 |
| acctgcaatg tcgctggtgg ctccatcagt ccttactact ggacctggat ccggcagccc | | | | 120 |
| ccagggaagg gcctggagtt gattggttat atccactcca gtgggtacac cgactacaac | | | | 180 |
| ccctccctca agagtcgagt caccatatca ggagacacgt ccaagaagca gttctccctg | | | | 240 |
| cacgtgagct ctgtgaccgc tgcggacacg gccgtgtact tctgtgcgag agccgattgg | | | | 300 |
| gacctgcttc atgctcttga tatctggggc caagggacca tggtcaccgt ctcgagtgga | | | | 360 |
| ggcggcggtt caggcggagg tggctctggc ggtagcggaa gtgcacagac tgtggtgacc | | | | 420 |
| cagcctgcct ccgtgtctgg gtctcctgga cagtcgatca ccatctcctg cactggaacc | | | | 480 |
| agcagtgaca ttggtggtta taactatgtc tcctggtacc gacagcaccc aggcaaagcc | | | | 540 |
| cccaaactca tgatttatga tgtcagtaat cggccctcag ggtttctaa tcgcttctct | | | | 600 |
| ggctccaagt ctggcaacac ggcctccctg accatctctg gctccaggc tgaggacgag | | | | 660 |
| gctgattatt actgcacctc atatacaagc gacagcactc tggttttcgg cggaggcacc | | | | 720 |
| aaggtgaccg tcctc | | | | 735 |

<210> SEQ ID NO 165
<211> LENGTH: 735
<212> TYPE: DNA
<213> ORGANISM: Artificial Sequence
<220> FEATURE:
<223> OTHER INFORMATION: W4-HC2-LC7 scFv-Fc

<400> SEQUENCE: 165

| | | | | |
|---|---|---|---|---|
| gaggtgcagc tgttggagtc gggcccagga ctggtgaagc cttcggagac cctgtccctc | | | | 60 |
| acctgcaatg tcgctggtgg ctccatcagt ccttactact ggacctggat ccggcagccc | | | | 120 |
| ccagggaagg gcctggagtt gattggttat atccactcca gtgggtacac cgactacaac | | | | 180 |
| ccctccctca agagtcgagt caccatatca ggagacacgt ccaagaagca gttctccctg | | | | 240 |
| cacgtgagct ctgtgaccgc tgcggacacg gccgtgtact tctgtgcgag agccgattgg | | | | 300 |
| gacctgcttc atgctcttga tatctggggc caagggacca cggtcaccgt ctcgagtgga | | | | 360 |
| ggcggcggtt caggcggagg tggctctggc ggtagcggaa gtgcacagac tgtggtgacc | | | | 420 |
| cagcctgcct ccgtgtctgg gtctcctgga cagtcgatca ccatctcctg cactggaacc | | | | 480 |
| agcagtgaca ttggtggtta taactatgtc tcctggtacc gacagcaccc aggcaaagcc | | | | 540 |
| cccaaactca tgatttatga tgtcagtaat cggccctcag ggtttctaa tcgcttctct | | | | 600 |
| ggctccaagt ctggcaacac ggcctccctg accatctctg gctccaggc tgaggacgag | | | | 660 |
| gctgattatt actgcacctc atatacaagc gacagcactc tggttttcgg cggaggcacc | | | | 720 |
| aaggtgaccg tcctc | | | | 735 |

<210> SEQ ID NO 166
<211> LENGTH: 729
<212> TYPE: DNA
<213> ORGANISM: Artificial Sequence
<220> FEATURE:
<223> OTHER INFORMATION: W4-HC3-LCP scFv-Fc

<400> SEQUENCE: 166

```
gaggtgcagc tgttggagtc gggcccagga ctggtgaagc cttcggagac cctgtccctc    60
acctgcaatg tcgctggtgg ctccatcagt ccttactact ggacctggat ccggcagccc   120
ccagggaagg gcctggagtt gattggttat atccactcca gtgggtacac cgactacaac   180
ccctccctca agagtcgagt caccatatca ggagacacgt ccaagaagca gttctccctg   240
cacgtgagct ctgtgaccgc tgcggacacg gccgtgtact tctgtgcgag agccgattgg   300
gacctgcttc atgcttttga tatctggggc caagggacca tggtcaccgt ctcgagtgga   360
ggcggcggtt caggcggagg tggctctggc ggtggcggaa gtgcactcga aattgtgttg   420
acacagtctc catcctccct gtctacatct gtaggagaca gagtcaccat cacttgccgg   480
gcaagtcaga gcattaggag ccatttaaat tggtatcagc agaaaccagg gaaagcccct   540
aaactcctga tctatggtgc atccaatttg caaagtgggg tcccatcaag gttcagtggc   600
agtggatctg gacagatttc actctcacc attagtagtc tgcaacctga agattttgca   660
acttactact gtcaacagag ttacagtttc cccctcactt tcggcggagg gaccaagctg   720
gagatcaaa                                                           729
```

<210> SEQ ID NO 167
<211> LENGTH: 729
<212> TYPE: DNA
<213> ORGANISM: Artificial Sequence
<220> FEATURE:
<223> OTHER INFORMATION: W4-HC4-LCP scFv-Fc

<400> SEQUENCE: 167

```
gaggtgcagc tgttggagtc gggcccagga ctggtgaagc cttcggagac cctgtccctc    60
acctgcaatg tcgctggtgg ctccatcagt ccttactact ggacctggat ccggcagccc   120
ccagggaagg gcctggagtt gattggttat atccactcca gtgggtacac cgactacaac   180
ccctccctca agagtcgagt caccatatca ggagacacgt ccaagaagca gttctccctg   240
cacgtgagct ctgtgaccgc tgcggacacg gccgtgtact tctgtgcgag agccgattgg   300
gacctgcttc atgctcttgg tatctggggc caagggaccc tggtcaccgt ctcgagtgga   360
ggcggcggtt caggcggagg tggctctggc ggtggcggaa gtgcactcga aattgtgttg   420
acacagtctc catcctccct gtctacatct gtaggagaca gagtcaccat cacttgccgg   480
gcaagtcaga gcattaggag ccatttaaat tggtatcagc agaaaccagg gaaagcccct   540
aaactcctga tctatggtgc atccaatttg caaagtgggg tcccatcaag gttcagtggc   600
agtggatctg gacagatttc actctcacc attagtagtc tgcaacctga agattttgca   660
acttactact gtcaacagag ttacagtttc cccctcactt tcggcggagg gaccaagctg   720
gagatcaaa                                                           729
```

<210> SEQ ID NO 168
<211> LENGTH: 729
<212> TYPE: DNA
<213> ORGANISM: Artificial Sequence
<220> FEATURE:
<223> OTHER INFORMATION: W4-HC5-LCP scFv-Fc

<400> SEQUENCE: 168

```
gaggtgcagc tgttggagtc gggcccagga ctggtgaagc cttcggagac cctgtccctc    60
acctgcaatg tcgctggtgg ctccatcagt ccttactact ggacctggat ccggcagccc   120
```

```
ccagggaagg gcctggagtt gattggttat atccactcca gtgggtacac cgactacaac    180 ccctcccta agagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcctga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc cccctcactt tcggcggagg gaccaagctg    720
gagatcaaa                                                           729

<210> SEQ ID NO 169
<211> LENGTH: 735
<212> TYPE: DNA
<213> ORGANISM: Artificial Sequence
<220> FEATURE:
<223> OTHER INFORMATION: W4-HC5-LC7 scFv-Fc

<400> SEQUENCE: 169
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180 ccctcccta agagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcctga tatctggggc caagggaccc tggtcaccgt ctcgagtgga    360
ggcggcggtt caggcggagg tggctctggc ggtagcggaa gtgcagac tgtggtgacc    420 cagcctgcct ccgtgtctgg gtctcctgga cagtcgatca ccatctcctg cactggaacc    480
agcagtgaca ttggtggtta taactatgtc tcctggtacc acagcaccc aggcaaagcc    540 cccaaactca tgatttatga tgtcagtaat cggccctcag gggtttctaa tcgcttctct    600
ggctccaagt ctggcaacac ggcctccctg accatctctg gctccaggc tgaggacgag    660 gctgattatt actgcacctc atatacaagc gacagcactc tggttttcgg cggaggcacc    720
aaggtgaccg tcctc                                                    735

<210> SEQ ID NO 170
<211> LENGTH: 729
<212> TYPE: DNA
<213> ORGANISM: Artificial Sequence
<220> FEATURE:
<223> OTHER INFORMATION: W4-HC7-LCP scFv-Fc

<400> SEQUENCE: 170
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180 ccctcccta agagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tgtctggggc caagggaccc tggtcaccgt ctcgagtgga    360
```

```
ggcggcggtt caggcggagg tggctctggc ggtggcggaa gtgcactcga aattgtgttg      420
acacagtctc catcctccct gtctacatct gtaggagaca gagtcaccat cacttgccgg      480
gcaagtcaga gcattaggag ccatttaaat tggtatcagc agaaaccagg gaaagcccct      540
aaactcctga tctatggtgc atccaatttg caaagtgggg tcccatcaag gttcagtggc      600
agtggatctg ggacagattt cactctcacc attagtagtc tgcaacctga gattttgca       660 acttactact gtcaacagag ttacagtttc cccctcactt tcggcggagg gaccaagctg      720
gagatcaaa                                                              729
```

<210> SEQ ID NO 171
<211> LENGTH: 735
<212> TYPE: DNA
<213> ORGANISM: Artificial Sequence
<220> FEATURE:
<223> OTHER INFORMATION: W4-VH1-VL8 scFv-Fc

<400> SEQUENCE: 171

```
gaggtgcagc tgttggagtc gggcccagga ctggtgaagc cttcggagac cctgtccctc       60
acctgcaatg tcgctggtgg ctccatcagt ccttactact ggacctggat ccggcagccc      120
ccagggaagg gcctggagtt gattggttat atccactcca gtgggtacac cgactacaac      180 ccctcccteca agagtcgagt caccatatca ggagacacgt ccaagaagca gttctccctg      240
cacgtgagct ctgtgaccgc tgcggacacg gccgtgtact tctgtgcgag agccgattgg      300
gacctgcttc atgctcttga tatctggggc caagggacca tggtcaccgt ctcgagtgga      360
ggcggcggtt caggcggagg tggctctggc ggtggcggaa gtgcacagtc tgtcgtgacg      420
cagccgccct cagtgtctgc ggccccagga cagaaggtca ccatctcctg cactggaacc      480
agcagtgatg ttgggagtta aactttgtc tcctggtacc aacagcaccc aggcaaagcc      540
cccaaactca tgatttatga gggcactaag cggccctcag gggtttctaa tcgcttctct      600
ggctccaagt ctggcaacac ggcctccctg accatctctg gctccaggc tgaggacgag       660 gctgattatt actgcacctc atatacaagc gacagcactc tggttttcgg cggaggcacc      720
aaggtgaccg tcctc                                                       735
```

<210> SEQ ID NO 172
<211> LENGTH: 729
<212> TYPE: DNA
<213> ORGANISM: Artificial Sequence
<220> FEATURE:
<223> OTHER INFORMATION: W4-VH2-VLP scFv-Fc

<400> SEQUENCE: 172

```
gaggtgcagc tgttggagtc gggcccagga ctggtgaagc cttcggagac cctgtccctc       60
acctgcaatg tcgctggtgg ctccatcagt ccttactact ggacctggat ccggcagccc      120
ccagggaagg gcctggagtt gattggttat atccactcca gtgggtacac cgactacaac      180 ccctcccteca agagtcgagt caccatatca ggagacacgt ccaagaagca gttctccctg      240
cacgtgagct ctgtgaccgc tgcggacacg gccgtgtact tctgtgcgag agccgattgg      300
gacctgcttc atgctcttga tatctggggc caagggacca cggtcaccgt ctcgagtgga      360
ggcggcggtt caggcggagg tggctctggc ggtggcggaa gtgcactcga aattgtgttg      420
acacagtctc catcctccct gtctacatct gtaggagaca gagtcaccat cacttgccgg      480
gcaagtcaga gcattaggag ccatttaaat tggtatcagc agaaaccagg gaaagcccct      540
```

| | |
|---|---|
| aaactcctga tctatggtgc atccaatttg caaagtgggg tcccatcaag gttcagtggc | 600 |
| agtggatctg ggacagattt cactctcacc attagtagtc tgcaacctga agattttgca | 660 |
| acttactact gtcaacagag ttacagtttc cccctcactt tcggcggagg gaccaagctg | 720 |
| gagatcaaa | 729 |

<210> SEQ ID NO 173
<211> LENGTH: 735
<212> TYPE: DNA
<213> ORGANISM: Artificial Sequence
<220> FEATURE:
<223> OTHER INFORMATION: W4-VH2-VL8 scFv-Fc

<400> SEQUENCE: 173

| | |
|---|---|
| gaggtgcagc tgttggagtc gggcccagga ctggtgaagc cttcggagac cctgtccctc | 60 |
| acctgcaatg tcgctggtgg ctccatcagt ccttactact ggacctggat ccggcagccc | 120 |
| ccagggaagg gcctggagtt gattggttat atccactcca gtgggtacac cgactacaac | 180 |
| ccctccctca gagtcgagt caccatatca ggagacacg ccaagaagca gttctccctg | 240 |
| cacgtgagct ctgtgaccgc tgcggacacg gccgtgtact tctgtgcgag agccgattgg | 300 |
| gacctgcttc atgctcttga tatctggggc caagggacca cggtcaccgt ctcgagtgga | 360 |
| ggcggcggtt caggcggagg tggctctggc ggtggcggaa gtgcacagtc tgtcgtgacg | 420 |
| cagccgccct cagtgtctgc ggccccagga cagaaggtca ccatctcctg cactggaacc | 480 |
| agcagtgatg ttgggagtta aactttgtc tcctggtacc aacagcaccc aggcaaagcc | 540 |
| cccaaactca tgattatga gggcactaag cggccctcag gggtttctaa tcgcttctct | 600 |
| ggctccaagt ctggcaacac ggcctccctg accatctctg gctccaggc tgaggacgag | 660 |
| gctgattatt actgcacctc atatacaagc gacagcactc tggttttcgg cggaggcacc | 720 |
| aaggtgaccg tcctc | 735 |

<210> SEQ ID NO 174
<211> LENGTH: 735
<212> TYPE: DNA
<213> ORGANISM: Artificial Sequence
<220> FEATURE:
<223> OTHER INFORMATION: W4-VH3-VL7 scFv-Fc

<400> SEQUENCE: 174

| | |
|---|---|
| gaggtgcagc tgttggagtc gggcccagga ctggtgaagc cttcggagac cctgtccctc | 60 |
| acctgcaatg tcgctggtgg ctccatcagt ccttactact ggacctggat ccggcagccc | 120 |
| ccagggaagg gcctggagtt gattggttat atccactcca gtgggtacac cgactacaac | 180 |
| ccctccctca gagtcgagt caccatatca ggagacacgt ccaagaagca gttctccctg | 240 |
| cacgtgagct ctgtgaccgc tgcggacacg gccgtgtact tctgtgcgag agccgattgg | 300 |
| gacctgcttc atgcttttga tatctggggc caagggacca tggtcaccgt ctcgagtgga | 360 |
| ggcggcggtt caggcggagg tggctctggc ggtagcggaa gtgcacagac tgtggtgacc | 420 |
| cagcctgcct ccgtgtctgg gtctcctgga cagtcgatca ccatctcctg cactggaacc | 480 |
| agcagtgaca ttggtggtta taactatgtc tcctggtacc gacagcaccc aggcaaagcc | 540 |
| cccaaactca tgatttatga tgtcagtaat cggccctcag gggtttctaa tcgcttctct | 600 |
| ggctccaagt ctggcaacac ggcctccctg accatctctg gctccaggc tgaggacgag | 660 |
| gctgattatt actgcacctc atatacaagc gacagcactc tggttttcgg cggaggcacc | 720 |
| aaggtgaccg tcctc | 735 |

<210> SEQ ID NO 175
<211> LENGTH: 735
<212> TYPE: DNA
<213> ORGANISM: Artificial Sequence
<220> FEATURE:
<223> OTHER INFORMATION: W4-VH3-VL8 scFv-Fc

<400> SEQUENCE: 175

```
gaggtgcagc tgttggagtc gggcccagga ctggtgaagc cttcggagac cctgtccctc    60
acctgcaatg tcgctggtgg ctccatcagt ccttactact ggacctggat ccggcagccc   120
ccagggaagg gcctggagtt gattggttat atccactcca gtgggtacac cgactacaac   180
ccctccctca gagtcgagt caccatatca ggagacacgt ccaagaagca gttctccctg    240
cacgtgagct ctgtgaccgc tgcggacacg gccgtgtact tctgtgcgag agccgattgg   300
gacctgcttc atgcttttga tatctggggc caagggacca tggtcaccgt ctcgagtgga   360
ggcggcggtt caggcggagg tggctctggc ggtggcggaa gtgcacagtc tgtcgtgacg   420
cagccgccct cagtgtctgc ggccccagga cagaaggtca ccatctcctg cactggaacc   480
agcagtgatg ttgggagtta aactttgtc tcctggtacc aacagcaccc aggcaaagcc    540
cccaaactca tgatttatga gggcactaag cggccctcag gggtttctaa tcgcttctct   600
ggctccaagt ctggcaacac ggcctccctg accatctctg gctccaggc tgaggacgag    660
gctgattatt actgcacctc atatacaagc gacagcactc tggttttcgg cggaggcacc   720
aaggtgaccg tcctc                                                    735
```

<210> SEQ ID NO 176
<211> LENGTH: 735
<212> TYPE: DNA
<213> ORGANISM: Artificial Sequence
<220> FEATURE:
<223> OTHER INFORMATION: W4-VH5-VL8 scFv-Fc

<400> SEQUENCE: 176

```
gaggtgcagc tgttggagtc gggcccagga ctggtgaagc cttcggagac cctgtccctc    60
acctgcaatg tcgctggtgg ctccatcagt ccttactact ggacctggat ccggcagccc   120
ccagggaagg gcctggagtt gattggttat atccactcca gtgggtacac cgactacaac   180
ccctccctca gagtcgagt caccatatca ggagacacgt ccaagaagca gttctccctg    240
cacgtgagct ctgtgaccgc tgcggacacg gccgtgtact tctgtgcgag agccgattgg   300
gacctgcttc atgctcctga tatctggggc caagggaccc tggtcaccgt ctcgagtgga   360
ggcggcggtt caggcggagg tggctctggc ggtggcggaa gtgcacagtc tgtcgtgacg   420
cagccgccct cagtgtctgc ggccccagga cagaaggtca ccatctcctg cactggaacc   480
agcagtgatg ttgggagtta aactttgtc tcctggtacc aacagcaccc aggcaaagcc    540
cccaaactca tgatttatga gggcactaag cggccctcag gggtttctaa tcgcttctct   600
ggctccaagt ctggcaacac ggcctccctg accatctctg gctccaggc tgaggacgag    660
gctgattatt actgcacctc atatacaagc gacagcactc tggttttcgg cggaggcacc   720
aaggtgaccg tcctc                                                    735
```

<210> SEQ ID NO 177
<211> LENGTH: 735
<212> TYPE: DNA
<213> ORGANISM: Artificial Sequence
<220> FEATURE:

<223> OTHER INFORMATION: W4-VH6-VL7 scFv-Fc

<400> SEQUENCE: 177

```
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagg gcctggagtt gattggttat atccactcca gtgggtacac cgactacaac     180
ccctccctca agagtcgagt caccatatca ggagacacgt ccaagaagca gttctccctg     240
cacgtgagct ctgtgaccgc tgcggacacg gccgtgtact tctgtgcgag agccgattgg     300
gacctgcttc atgctcttga tatgtggggc caagggaccc tggtcaccgt ctcgagtgga     360
ggcggcggtt caggcggagg tggctctggc ggtagcggaa gtgcacagac tgtggtgacc     420
cagcctgcct ccgtgtctgg gtctcctgga cagtcgatca ccatctcctg cactggaacc     480
agcagtgaca ttggtggtta aactatgtc tcctggtacc gacagcaccc aggcaaagcc     540
cccaaactca tgatttatga tgtcagtaat cggccctcag gggtttctaa tcgcttctct     600
ggctccaagt ctggcaacac ggcctccctg accatctctg gctccaggc tgaggacgag     660
gctgattatt actgcaccct catatacaagc gacagcactc tggttttcgg cggaggcacc     720
aaggtgaccg tcctc                                                      735
```

<210> SEQ ID NO 178
<211> LENGTH: 735
<212> TYPE: DNA
<213> ORGANISM: Artificial Sequence
<220> FEATURE:
<223> OTHER INFORMATION: W4-VH6-VL8 scFv-Fc

<400> SEQUENCE: 178

```
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagg gcctggagtt gattggttat atccactcca gtgggtacac cgactacaac     180
ccctccctca agagtcgagt caccatatca ggagacacgt ccaagaagca gttctccctg     240
cacgtgagct ctgtgaccgc tgcggacacg gccgtgtact tctgtgcgag agccgattgg     300
gacctgcttc atgctcttga tatgtggggc caagggaccc tggtcaccgt ctcgagtgga     360
ggcggcggtt caggcggagg tggctctggc ggtggcggaa gtgcacagtc tgtcgtgacg     420
cagccgccct cagtgtctgc ggcccaggga cagaaggtca ccatctcctg cactggaacc     480
agcagtgatg ttgggagtta aactttgtc tcctggtacc aacagcaccc aggcaaagcc     540
cccaaactca tgatttatga gggcactaag cggccctcag gggtttctaa tcgcttctct     600
ggctccaagt ctggcaacac ggcctccctg accatctctg gctccaggc tgaggacgag     660
gctgattatt actgcaccct catatacaagc gacagcactc tggttttcgg cggaggcacc     720
aaggtgaccg tcctc                                                      735
```

<210> SEQ ID NO 179
<211> LENGTH: 729
<212> TYPE: DNA
<213> ORGANISM: Artificial Sequence
<220> FEATURE:
<223> OTHER INFORMATION: W4-VH6-VLP scFv-Fc

<400> SEQUENCE: 179

```
gaggtgcagc tgttggagtc gggcccagga ctggtgaagc cttcggagac cctgtccctc      60
acctgcaatg tcgctggtgg ctccatcagt ccttactact ggacctggat ccggcagccc     120
```

```
ccagggaagg gcctggagtt gattggttat atccactcca gtgggtacac cgactacaac    180
ccctccctca agagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tatgtggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc cccctcactt tcggcggagg gaccaagctg    720
gagatcaaa                                                            729

<210> SEQ ID NO 180
<211> LENGTH: 729
<212> TYPE: DNA
<213> ORGANISM: Artificial Sequence
<220> FEATURE:
<223> OTHER INFORMATION: W4-VH7-VLP scFv-Fc

<400> SEQUENCE: 180
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180
ccctccctca agagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tgtctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc cccctcactt tcggcggagg gaccaagctg    720
gagatcaaa                                                            729

<210> SEQ ID NO 181
<211> LENGTH: 735
<212> TYPE: DNA
<213> ORGANISM: Artificial Sequence
<220> FEATURE:
<223> OTHER INFORMATION: W4-VH7-VL7 scFv-Fc

<400> SEQUENCE: 181
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180
ccctccctca agagtcgagt caccatatca ggagacacgt ccaagaagca gttctccctg    240
cacgtgagct ctgtgaccgc tgcggacacg gccgtgtact tctgtgcgag agccgattgg    300
```

```
gacctgcttc atgctcttga tgtctggggc aagggaccc tggtcaccgt ctcgagtgga    360
ggcggcggtt caggcggagg tggctctggc ggtagcggaa gtgcacagac tgtggtgacc    420
cagcctgcct ccgtgtctgg gtctcctgga cagtcgatca ccatctcctg cactggaacc    480
agcagtgaca ttgtggggta taactatgtc tcctggtacc gacagcaccc aggcaaagcc    540
cccaaactca tgatttatga tgtcagtaat cggccctcag gggtttctaa tcgcttctct    600
ggctccaagt ctggcaacac ggcctccctg accatctctg gctccaggc tgaggacgag    660
gctgattatt actgcacctc atatacaagc gacagcactc tggttttcgg cggaggcacc    720
aaggtgaccg tcctc                                                     735

<210> SEQ ID NO 182
<211> LENGTH: 735
<212> TYPE: DNA
<213> ORGANISM: Artificial Sequence
<220> FEATURE:
<223> OTHER INFORMATION: W4-VH7-VL8 scFc-Fv

<400> SEQUENCE: 182
gaggtgcagc tgttggagtc gggcccagga ctggtgaagc cttcggagac cctgtccctc    60
acctgcaatg tcgctggtgg ctccatcagt ccttactact ggacctggat ccggcagccc    120
ccagggaagg gcctggagtt gattggttat atccactcca gtgggtacac cgactacaac    180
ccctccctca gagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tgtctggggc aagggaccc tggtcaccgt ctcgagtgga    360
ggcggcggtt caggcggagg tggctctggc ggtggcggaa gtgcacagtc tgtcgtgacg    420
cagccgccct cagtgtctgc ggccccagga cagaaggtca ccatctcctg cactggaacc    480
agcagtgatg ttgggagtta aactttgtc tcctggtacc aacagcaccc aggcaaagcc    540
cccaaactca tgatttatga gggcactaag cggccctcag gggtttctaa tcgcttctct    600
ggctccaagt ctggcaacac ggcctccctg accatctctg gctccaggc tgaggacgag    660
gctgattatt actgcacctc atatacaagc gacagcactc tggttttcgg cggaggcacc    720
aaggtgaccg tcctc                                                     735

<210> SEQ ID NO 183
<211> LENGTH: 729
<212> TYPE: DNA
<213> ORGANISM: Artificial Sequence
<220> FEATURE:
<223> OTHER INFORMATION: W4-VH9-VLP scFv-Fc

<400> SEQUENCE: 183
gaggtgcagc tgttggagtc gggcccagga ctggtgaagc cttcggagac cctgtccctc    60
acctgcaatg tcgctggtgg ctccatcagt ccttactact ggacctggat ccggcagccc    120
ccagggaagg gcctggagtt gattggttat atccactcca gtgggtacac cgactacaac    180
ccctccctca gagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgttcttga tatctggggc aagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
```

```
aaactcctga tctatggtgc atccaatttg caaagtgggg tcccatcaag gttcagtggc        600
agtggatctg ggacagattt cactctcacc attagtagtc tgcaacctga agattttgca        660
acttactact gtcaacagag ttacagtttc cccctcactt tcggcggagg gaccaagctg        720
gagatcaaa                                                                729
```

<210> SEQ ID NO 184
<211> LENGTH: 729
<212> TYPE: DNA
<213> ORGANISM: Artificial Sequence
<220> FEATURE:
<223> OTHER INFORMATION: W4-VH10-VLP scFv-Fc

<400> SEQUENCE: 184

```
gaggtgcagc tgttggagtc gggcccagga ctggtgaagc cttcggagac cctgtccctc         60
acctgcaatg tcgctggtgg ctccatcagt ccttactact ggacctggat ccggcagccc        120
ccagggaagg gcctggagtt gattggttat atccactcca gtgggtacac cgactacaac        180
ccctccctca gagtcgagt caccatatca ggagacacgt ccaagaagca gttctccctg        240
cacgtgagct ctgtgaccgc tgcggacacg gccgtgtact tctgtgcgag agccgattgg        300
gacctgtttc atgctcttga tatctggggc caagggaccc tggtcaccgt ctcgagtgga        360
ggcggcggtt caggcggagg tggctctggc ggtggcggaa gtgcactcga aattgtgttg        420
acacagtctc catcctccct gtctacatct gtaggagaca gagtcaccat cacttgccgg        480
gcaagtcaga gcattaggag ccatttaaat tggtatcagc agaaaccagg gaaagcccct        540
aaactcctga tctatggtgc atccaatttg caaagtgggg tcccatcaag gttcagtggc        600
agtggatctg ggacagattt cactctcacc attagtagtc tgcaacctga agattttgca        660
acttactact gtcaacagag ttacagtttc cccctcactt tcggcggagg gaccaagctg        720
gagatcaaa                                                                729
```

<210> SEQ ID NO 185
<211> LENGTH: 729
<212> TYPE: DNA
<213> ORGANISM: Artificial Sequence
<220> FEATURE:
<223> OTHER INFORMATION: W4-VH11-VLP scFv-Fc

<400> SEQUENCE: 185

```
gaggtgcagc tgttggagtc gggcccagga ctggtgaagc cttcggagac cctgtccctc         60
acctgcaatg tcgctggtgg ctccatcagt ccttactact ggacctggat ccggcagccc        120
ccagggaagg gcctggagtt gattggttat atccactcca gtgggtacac cgactacaac        180
ccctccctca gagtcgagt caccatatca ggagacacgt ccaagaagca gttctccctg        240
cacgtgagct ctgtgaccgc tgcggacacg gccgtgtact tctgtgcgag agccgattgg        300
gacctgcctc atgctcttga tatctggggc caagggaccc tggtcaccgt ctcgagtgga        360
ggcggcggtt caggcggagg tggctctggc ggtggcggaa gtgcactcga aattgtgttg        420
acacagtctc catcctccct gtctacatct gtaggagaca gagtcaccat cacttgccgg        480
gcaagtcaga gcattaggag ccatttaaat tggtatcagc agaaaccagg gaaagcccct        540
aaactcctga tctatggtgc atccaatttg caaagtgggg tcccatcaag gttcagtggc        600
agtggatctg ggacagattt cactctcacc attagtagtc tgcaacctga agattttgca        660
acttactact gtcaacagag ttacagtttc cccctcactt tcggcggagg gaccaagctg        720
```

```
gagatcaaa                                                               729

<210> SEQ ID NO 186
<211> LENGTH: 729
<212> TYPE: DNA
<213> ORGANISM: Artificial Sequence
<220> FEATURE:
<223> OTHER INFORMATION: W4-VH12-VLP scFv-Fc

<400> SEQUENCE: 186
gaggtgcagc tgttggagtc gggcccagga ctggtgaagc cttcggagac cctgtccctc        60
acctgcaatg tcgctggtgg ctccatcagt ccttactact ggacctggat ccggcagccc       120
ccagggaagg gcctggagtt gattggttat atccactcca gtgggtacac cgactacaac       180
ccctccctca agagtcgagt caccatatca ggagacacgt ccaagaagca gttctccctg       240
cacgtgagct ctgtgaccgc tgcggacacg gccgtgtact tctgtgcgag agccgattgg       300
gacctgcttc gtgctcttga tatctggggc caagggaccc tggtcaccgt ctcgagtgga       360
ggcggcggtt caggcggagg tggctctggc ggtggcggaa gtgcactcga aattgtgttg       420
acacagtctc catcctccct gtctacatct gtaggagaca gagtcaccat cacttgccgg       480
gcaagtcaga gcattaggag ccatttaaat tggtatcagc agaaaccagg gaaagcccct       540
aaactcctga tctatggtgc atccaatttg caaagtgggg tcccatcaag gttcagtggc       600
agtggatctg ggacagattt cactctcacc attagtagtc tgcaacctga agattttgca       660
acttactact gtcaacagag ttacagtttc cccctcactt tcggcggagg gaccaagctg       720
gagatcaaa                                                              729

<210> SEQ ID NO 187
<211> LENGTH: 729
<212> TYPE: DNA
<213> ORGANISM: Artificial Sequence
<220> FEATURE:
<223> OTHER INFORMATION: W4-VH15-VLP scFv-Fc

<400> SEQUENCE: 187
gaggtgcagc tgttggagtc gggcccagga ctggtgaagc cttcggagac cctgtccctc        60
acctgcaatg tcgctggtgg ctccatcagt ccttactact ggacctggat ccggcagccc       120
ccagggaagg gcctggagtt gattggttat atccactcca gtgggtacac cgactacaac       180
ccctccctca agagtcgagt caccatatca ggagacacgt ccaagaagca gttctccctg       240
cacgtgagct ctgtgaccgc tgcggacacg gccgtgtact tctgtgcgag aggcaattgg       300
gacctgcttc atgctcttga tatctggggc caagggaccc tggtcaccgt ctcgagtgga       360
ggcggcggtt caggcggagg tggctctggc ggtggcggaa gtgcactcga aattgtgttg       420
acacagtctc catcctccct gtctacatct gtaggagaca gagtcaccat cacttgccgg       480
gcaagtcaga gcattaggag ccatttaaat tggtatcagc agaaaccagg gaaagcccct       540
aaactcctga tctatggtgc atccaatttg caaagtgggg tcccatcaag gttcagtggc       600
agtggatctg ggacagattt cactctcacc attagtagtc tgcaacctga agattttgca       660
acttactact gtcaacagag ttacagtttc cccctcactt tcggcggagg gaccaagctg       720
gagatcaaa                                                              729

<210> SEQ ID NO 188
<211> LENGTH: 729
<212> TYPE: DNA
<213> ORGANISM: Artificial Sequence
```

<220> FEATURE:
<223> OTHER INFORMATION: W4-VH16-VLP scFv-Fc

<400> SEQUENCE: 188

```
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagg gcctggagtt gattggttat atccactcca gtgggtacac cgactacaac     180
ccctccctca agagtcgagt caccatatca ggagacacgt ccaagaagca gttctccctg     240
cacgtgagct ctgtgaccgc tgcggacacg gccgtgtact tctgtgcgag agccgattgg     300
aacctgcttc atgctcttga tatctggggc caagggaccc tggtcaccgt ctcgagtgga     360
ggcggcggtt caggcggagg tggctctggc ggtggcggaa gtgcactcga aattgtgttg     420
acacagtctc catcctccct gtctacatct gtaggagaca gagtcaccat cacttgccgg     480
gcaagtcaga gcattaggag ccatttaaat tggtatcagc agaaaccagg gaaagcccct     540
aaactcctga tctatggtgc atccaatttg caaagtgggg tcccatcaag gttcagtggc     600
agtggatctg ggacagattt cactctcacc attagtagtc tgcaacctga agattttgca     660
acttactact gtcaacagag ttacagtttc cccctcactt tcggcggagg gaccaagctg     720
gagatcaaa                                                             729
```

<210> SEQ ID NO 189
<211> LENGTH: 729
<212> TYPE: DNA
<213> ORGANISM: Artificial Sequence
<220> FEATURE:
<223> OTHER INFORMATION: W4-VH20-VLP scFv-Fc

<400> SEQUENCE: 189

```
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagg gcctggagtt gattggttat atccactcca gtgggtacac cgactacaac     180
ccctccctca agagtcgagt caccatatca ggagacacgt ccaagaagca gttctccctg     240
cacgtgagct ctgtgaccgc tgcggacacg gccgtgtact tctgtgcgag agccgattgg     300
gacctgcttc atactcttga tatctggggc caagggaccc tggtcaccgt ctcgagtgga     360
ggcggcggtt caggcggagg tggctctggc ggtggcggaa gtgcactcga aattgtgttg     420
acacagtctc catcctccct gtctacatct gtaggagaca gagtcaccat cacttgccgg     480
gcaagtcaga gcattaggag ccatttaaat tggtatcagc agaaaccagg gaaagcccct     540
aaactcctga tctatggtgc atccaatttg caaagtgggg tcccatcaag gttcagtggc     600
agtggatctg ggacagattt cactctcacc attagtagtc tgcaacctga agattttgca     660
acttactact gtcaacagag ttacagtttc cccctcactt tcggcggagg gaccaagctg     720
gagatcaaa                                                             729
```

<210> SEQ ID NO 190
<211> LENGTH: 729
<212> TYPE: DNA
<213> ORGANISM: Artificial Sequence
<220> FEATURE:
<223> OTHER INFORMATION: W4-VH31-VLP scFv-Fc

<400> SEQUENCE: 190

```
gaggtgcagc tgttggagtc gggcccagga ctggtgaagc cttcggagac cctgtccctc      60
```

| | |
|---|---|
| acctgcaatg tcgctggtgg ctccatcagt ccttactact ggacctggat ccggcagccc | 120 |
| ccagggaagg gcctggagtt gattggttat atccactcca gtgggtacac cgactacaac | 180 |
| ccctccctca agagtcgagt caccatatca ggagacacgt ccaagaagca gttctccctg | 240 |
| cacgtgagct ctgtgaccgc tgcggacacg gccgtgtact tctgtgcgag agccgattgg | 300 |
| gagctgcttc atgctcttga tatctggggc caagggaccc tggtcaccgt ctcgagtgga | 360 |
| ggcggcggtt caggcggagg tggctctggc ggtggcggaa gtgcactcga aattgtgttg | 420 |
| acacagtctc catcctccct gtctacatct gtaggagaca gagtcaccat cacttgccgg | 480 |
| gcaagtcaga gcattaggag ccatttaaat tggtatcagc agaaaccagg gaaagcccct | 540 |
| aaactcctga tctatggtgc atccaatttg caaagtgggg tcccatcaag gttcagtggc | 600 |
| agtggatctg ggacagattt cactctcacc attagtagtc tgcaacctga agattttgca | 660 |
| acttactact gtcaacagag ttacagtttc cccctcactt tcggcggagg gaccaagctg | 720 |
| gagatcaaa | 729 |

<210> SEQ ID NO 191
<211> LENGTH: 729
<212> TYPE: DNA
<213> ORGANISM: Artificial Sequence
<220> FEATURE:
<223> OTHER INFORMATION: W4-VH37-VLP scFv-Fc

<400> SEQUENCE: 191

| | |
|---|---|
| gaggtgcagc tgttggagtc gggcccagga ctggtgaagc cttcggagac cctgtccctc | 60 |
| acctgcaatg tcgctggtgg ctccatcagt ccttactact ggacctggat ccggcagccc | 120 |
| ccagggaagg gcctggagtt gattggttat atccactcca gtgggtacac cgactacaac | 180 |
| ccctccctca agagtcgagt caccatatca ggagacacgt ccaagaagca gttctccctg | 240 |
| cacgtgagct ctgtgaccgc tgcggacacg gccgtgtact tctgtgcgag agccgattgg | 300 |
| gacctgcttc atgcttttga tatgggggc caagggacca tggtcaccgt ctcgagtgga | 360 |
| ggcggcggtt caggcggagg tggctctggc ggtggcggaa gtgcactcga aattgtgttg | 420 |
| acacagtctc catcctccct gtctacatct gtaggagaca gagtcaccat cacttgccgg | 480 |
| gcaagtcaga gcattaggag ccatttaaat tggtatcagc agaaaccagg gaaagcccct | 540 |
| aaactcctga tctatggtgc atccaatttg caaagtgggg tcccatcaag gttcagtggc | 600 |
| agtggatctg ggacagattt cactctcacc attagtagtc tgcaacctga agattttgca | 660 |
| acttactact gtcaacagag ttacagtttc cccctcactt tcggcggagg gaccaagctg | 720 |
| gagatcaaa | 729 |

<210> SEQ ID NO 192
<211> LENGTH: 729
<212> TYPE: DNA
<213> ORGANISM: Artificial Sequence
<220> FEATURE:
<223> OTHER INFORMATION: W4-VH41-VLP scFv-Fc

<400> SEQUENCE: 192

| | |
|---|---|
| gaggtgcagc tgttggagtc gggcccagga ctggtgaagc cttcggagac cctgtccctc | 60 |
| acctgcaatg tcgctggtgg ctccatcagt ccttactact ggacctggat ccggcagccc | 120 |
| ccagggaagg gcctggagtt gattggttat atccactcca gtgggtacac cgactacaac | 180 |
| ccctccctca agagtcgagt caccatatca ggagacacgt ccaagaagca gttctccctg | 240 |
| cacgtgagct ctgtgaccgc tgcggacacg gccgtgtact tctgtgcgag agccgattgg | 300 |

```
gccctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg aaagcccct     540 aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc ccctcactt tcggcggagg gaccaagctg     720
gagatcaaa                                                            729
```

```
<210> SEQ ID NO 193
<211> LENGTH: 729
<212> TYPE: DNA
<213> ORGANISM: Artificial Sequence
<220> FEATURE:
<223> OTHER INFORMATION: W4-VH42-VLP scFv-Fc

<400> SEQUENCE: 193
gaggtgcagc tgttggagtc gggcccagga ctggtgaagc cttcggagac cctgtccctc    60
acctgcaatg tcgctggtgg ctccatcagt ccttactact ggacctggat ccggcagccc    120
ccagggaagg gcctggagtt gattggttat atccactcca gtgggtacac cgactacaac    180
ccctccctca gagtcgagt caccatatca ggagacacgt ccaagaagca gttctccctg     240
cacgtgagct ctgtgaccgc tgcggacacg gccgtgtact tctgtgcgag agccgatcgg    300
gacctgcttc atgctcttga tatctggggc caagggacca tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg aaagcccct     540 aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc ccctcactt tcggcggagg gaccaagctg     720
gagatcaaa                                                            729
```

```
<210> SEQ ID NO 194
<211> LENGTH: 729
<212> TYPE: DNA
<213> ORGANISM: Artificial Sequence
<220> FEATURE:
<223> OTHER INFORMATION: W4-VH35-VLP scFv-Fc

<400> SEQUENCE: 194
gaggtgcagc tgttggagtc gggcccagga ctggtgaagc cttcggagac cctgtccctc    60
acctgcaatg tcgctggtgg ctccatcagt ccttactact ggacctggat ccggcagccc    120
ccagggaagg gcctggagtt gattggttat atccactcca gtgggtacac cgactacaac    180
ccctccctca gagtcgagt caccatatca ggagacacgt ccaagaagca gttctccctg     240
cacgtgagct ctgtgaccgc tgcggacacg gccgtgtact tctgtacgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
```

```
gcaagtcaga gcattaggag ccatttaaat tggtatcagc agaaaccagg gaaagcccct      540
aaactcctga tctatggtgc atccaatttg caaagtgggg tcccatcaag gttcagtggc      600
agtggatctg ggacagattt cactctcacc attagtagtc tgcaacctga agattttgca      660
acttactact gtcaacagag ttacagtttc cccctcactt tcggcggagg gaccaagctg      720
gagatcaaa                                                              729
```

<210> SEQ ID NO 195
<211> LENGTH: 729
<212> TYPE: DNA
<213> ORGANISM: Artificial Sequence
<220> FEATURE:
<223> OTHER INFORMATION: W4-VH36-VLP scFv-Fc

<400> SEQUENCE: 195

```
gaggtgcagc tgttggagtc gggcccagga ctggtgaagc cttcggagac cctgtccctc       60
acctgcaatg tcgctggtgg ctccatcagt ccttactact ggacctggat ccggcagccc      120
ccagggaagg gcctggagtt gattggttat atccactcca gtgggtacac cgactacaac      180
ccctccctca gagtcgagt caccatatca ggagacacgt ccaagaagca gttctccctg      240
cacgtgagct ctgtgaccgc tgcggacacg gccgtgtact tctgtgtgag agccgattgg      300
gacctgcttc atgctcttga tatctggggc caagggaccc tggtcaccgt ctcgagtgga      360
ggcggcggtt caggcggagg tggctctggc ggtggcggaa gtgcactcga aattgtgttg      420
acacagtctc catcctccct gtctacatct gtaggagaca gagtcaccat cacttgccgg      480
gcaagtcaga gcattaggag ccatttaaat tggtatcagc agaaaccagg gaaagcccct      540
aaactcctga tctatggtgc atccaatttg caaagtgggg tcccatcaag gttcagtggc      600
agtggatctg ggacagattt cactctcacc attagtagtc tgcaacctga agattttgca      660
acttactact gtcaacagag ttacagtttc cccctcactt tcggcggagg gaccaagctg      720
gagatcaaa                                                              729
```

<210> SEQ ID NO 196
<211> LENGTH: 729
<212> TYPE: DNA
<213> ORGANISM: Artificial Sequence
<220> FEATURE:
<223> OTHER INFORMATION: W4-VH52-VLP scFv-Fc

<400> SEQUENCE: 196

```
gaggtgcagc tgttggagtc gggcccagga ctggtgaagc cttcggagac cctgtccctc       60
acctgcaatg tcgctggtgg ctccatcagt ccttactact ggacctggat ccggcagccc      120
ccagggaagg gcctggagtt gattggttat atccactcca gtgggtacac cgactacaac      180
ccctccctca agggtcgagt caccatatca ggagacacgt ccaagaagca gttctccctg      240
cacgtgagct ctgtgaccgc tgcggacacg gccgtgtact tctgtgcgag agccgattgg      300
gacctgcttc atgctcttga tatctggggc caagggaccc tggtcaccgt ctcgagtgga      360
ggcggcggtt caggcggagg tggctctggc ggtggcggaa gtgcactcga aattgtgttg      420
acacagtctc catcctccct gtctacatct gtaggagaca gagtcaccat cacttgccgg      480
gcaagtcaga gcattaggag ccatttaaat tggtatcagc agaaaccagg gaaagcccct      540
aaactcctga tctatggtgc atccaatttg caaagtgggg tcccatcaag gttcagtggc      600
agtggatctg ggacagattt cactctcacc attagtagtc tgcaacctga agattttgca      660
acttactact gtcaacagag ttacagtttc cccctcactt tcggcggagg gaccaagctg      720
```

```
gagatcaaa                                                            729

<210> SEQ ID NO 197
<211> LENGTH: 729
<212> TYPE: DNA
<213> ORGANISM: Artificial Sequence
<220> FEATURE:
<223> OTHER INFORMATION: W4-VH53-VLP scFv-Fc

<400> SEQUENCE: 197
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccacccca gtgggtacac cgactacaac    180
ccctccctca agagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg gacagatttc cactctcacc attagtagtc tgcaacctga agattttgca    660
acttactact gtcaacagag ttacagtttc ccctcactt tcggcggagg gaccaagctg    720
gagatcaaa                                                            729

<210> SEQ ID NO 198
<211> LENGTH: 729
<212> TYPE: DNA
<213> ORGANISM: Artificial Sequence
<220> FEATURE:
<223> OTHER INFORMATION: W4-VH54-VLP scFv-Fc

<400> SEQUENCE: 198
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca atgggtacac cgactacaac    180
ccctccctca agagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg gacagatttc cactctcacc attagtagtc tgcaacctga agattttgca    660
acttactact gtcaacagag ttacagtttc ccctcactt tcggcggagg gaccaagctg    720
gagatcaaa                                                            729

<210> SEQ ID NO 199
<211> LENGTH: 729
<212> TYPE: DNA
```

<213> ORGANISM: Artificial Sequence
<220> FEATURE:
<223> OTHER INFORMATION: W4-VH55-VLP scFv-Fc

<400> SEQUENCE: 199

```
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagg gcctggagtt gattggttat acccactcca gtgggtacac cgactacaac     180
ccctccctca agagtcgagt caccatatca ggagacacgt ccaagaagca gttctccctg     240
cacgtgagct ctgtgaccgc tgcggacacg gccgtgtact tctgtgcgag agccgattgg     300
gacctgcttc atgctcttga tatctggggc caagggaccc tggtcaccgt ctcgagtgga     360
ggcggcggtt caggcggagg tggctctggc ggtggcggaa gtgcactcga aattgtgttg     420
acacagtctc catcctccct gtctacatct gtaggagaca gagtcaccat cacttgccgg     480
gcaagtcaga gcattaggag ccatttaaat tggtatcagc agaaaccagg gaaagcccct     540
aaactcctga tctatggtgc atccaatttg caaagtgggg tcccatcaag gttcagtggc     600
agtggatctg ggacagattt cactctcacc attagtagtc tgcaacctga agattttgca     660
acttactact gtcaacagag ttacagtttc cccctcactt tcggcggagg gaccaagctg     720
gagatcaaa                                                             729
```

<210> SEQ ID NO 200
<211> LENGTH: 729
<212> TYPE: DNA
<213> ORGANISM: Artificial Sequence
<220> FEATURE:
<223> OTHER INFORMATION: W4-VH56-VLP scFv-Fc

<400> SEQUENCE: 200

```
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagg gcctggagtt gattggttat atccactcca gtgggtacgc cgactacaac     180
ccctccctca agagtcgagt caccatatca ggagacacgt ccaagaagca gttctccctg     240
cacgtgagct ctgtgaccgc tgcggacacg gccgtgtact tctgtgcgag agccgattgg     300
gacctgcttc atgctcttga tatctggggc caagggaccc tggtcaccgt ctcgagtgga     360
ggcggcggtt caggcggagg tggctctggc ggtggcggaa gtgcactcga aattgtgttg     420
acacagtctc catcctccct gtctacatct gtaggagaca gagtcaccat cacttgccgg     480
gcaagtcaga gcattaggag ccatttaaat tggtatcagc agaaaccagg gaaagcccct     540
aaactcctga tctatggtgc atccaatttg caaagtgggg tcccatcaag gttcagtggc     600
agtggatctg ggacagattt cactctcacc attagtagtc tgcaacctga agattttgca     660
acttactact gtcaacagag ttacagtttc cccctcactt tcggcggagg gaccaagctg     720
gagatcaaa                                                             729
```

<210> SEQ ID NO 201
<211> LENGTH: 729
<212> TYPE: DNA
<213> ORGANISM: Artificial Sequence
<220> FEATURE:
<223> OTHER INFORMATION: W4-VH57-VLP scFv-Fc

<400> SEQUENCE: 201

```
gaggtgcagc tgttggagtc gggcccagga ctggtgaagc cttcggagac cctgtccctc      60
```

```
acctgcaatg tcgctggtgg ctccatcagt ccttactact ggacctggat ccggcagccc    120
ccagggaagg gcctggagtt gattggttat atccactccg gtgggtacac cgactacaac    180 ccctcccctca agagtcgagt caccatatca ggagacacgt ccaagaagca gttctccctg   240
cacgtgagct ctgtgaccgc tgcggacacg gccgtgtact tctgtgcgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg aaagcccct    540 aaactcctga tctatggtgc atccaatttg caaagtgggg tcccatcaag gttcagtggc    600
agtggatctg ggacagattt cactctcacc attagtagtc tgcaacctga gattttgca    660 acttactact gtcaacagag ttacagtttc ccctcactt tcggcggagg gaccaagctg    720
gagatcaaa                                                            729

<210> SEQ ID NO 202
<211> LENGTH: 729
<212> TYPE: DNA
<213> ORGANISM: Artificial Sequence
<220> FEATURE:
<223> OTHER INFORMATION: W4-VH58-VLP scFv-Fc

<400> SEQUENCE: 202
gaggtgcagc tgtttggagtc gggcccagga ctggtgaagc cttcggagac cctgtccctc    60
acctgcaatg tcgctggtgg ctccatcagt ccttactact ggacctggat ccggcagccc   120
ccagggaagg gcctggagtt gattggttat atccactcca gtgggtacac cgactacaac   180 ccctcccctca agcgtcgagt caccatatca ggagacacgt ccaagaagca gttctccctg  240
cacgtgagct ctgtgaccgc tgcggacacg gccgtgtact tctgtgcgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg aaagcccct    540 aaactcctga tctatggtgc atccaatttg caaagtgggg tcccatcaag gttcagtggc    600
agtggatctg ggacagattt cactctcacc attagtagtc tgcaacctga gattttgca    660 acttactact gtcaacagag ttacagtttc ccctcactt tcggcggagg gaccaagctg    720
gagatcaaa                                                            729

<210> SEQ ID NO 203
<211> LENGTH: 729
<212> TYPE: DNA
<213> ORGANISM: Artificial Sequence
<220> FEATURE:
<223> OTHER INFORMATION: W4-VH60-VLP scFv-Fc

<400> SEQUENCE: 203
gaggtgcagc tgtttggagtc gggcccagga ctggtgaagc cttcggagac cctgtccctc    60
acctgcaatg tcgctggtgg ctccatcagt ccttactact ggacctggat ccggcagccc   120
ccagggaagg gcctggagtt gattggttat atccactcca gtgggtacac cgactacagc   180 ccctcccctca agagtcgagt caccatatca ggagacacgt ccaagaagca gttctccctg  240
```

```
cacgtgagct ctgtgaccgc tgcggacacg gccgtgtact tctgtgcgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg aaagcccct    540 aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc cccctcactt tcggcggagg gaccaagctg    720
gagatcaaa                                                            729
```

<210> SEQ ID NO 204
<211> LENGTH: 729
<212> TYPE: DNA
<213> ORGANISM: Artificial Sequence
<220> FEATURE:
<223> OTHER INFORMATION: W4-VH61-VLP scFv-Fc

<400> SEQUENCE: 204

```
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180
cccttcctca gagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg aaagcccct    540 aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc cccctcactt tcggcggagg gaccaagctg    720
gagatcaaa                                                            729
```

<210> SEQ ID NO 205
<211> LENGTH: 729
<212> TYPE: DNA
<213> ORGANISM: Artificial Sequence
<220> FEATURE:
<223> OTHER INFORMATION: W4-VH62-VLP scFv-Fc

<400> SEQUENCE: 205

```
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtcggtacac cgactacaac    180
cccttcctca gagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
```

```
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc cccctcactt tcggcggagg gaccaagctg    720
gagatcaaa                                                            729
```

<210> SEQ ID NO 206
<211> LENGTH: 729
<212> TYPE: DNA
<213> ORGANISM: Artificial Sequence
<220> FEATURE:
<223> OTHER INFORMATION: W4-VH63-VLP scFv-Fc

<400> SEQUENCE: 206

```
gaggtgcagc tgttggagtc gggcccagga ctggtgaagc cttcggagac cctgtccctc    60
acctgcaatg tcgctggtgg ctccatcagt ccttactact ggacctggat ccggcagccc    120
ccagggaagg gcctggagtt gattggttat atccactcca gtgggtacac cggctacaac    180
ccctccctca agagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc cccctcactt tcggcggagg gaccaagctg    720
gagatcaaa                                                            729
```

<210> SEQ ID NO 207
<211> LENGTH: 729
<212> TYPE: DNA
<213> ORGANISM: Artificial Sequence
<220> FEATURE:
<223> OTHER INFORMATION: W4-VH64-VLP scFv-Fc

<400> SEQUENCE: 207

```
gaggtgcagc tgttggagtc gggcccagga ctggtgaagc cttcggagac cctgtccctc    60
acctgcaatg tcgctggtgg ctccatcagt ccttactact ggacctggat ccggcagccc    120
ccagggaagg gcctggagtt gattggttat atccgctcca gtgggtacac cgactacaac    180
ccctccctca agagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg ggacagattt cactctcacc attagtagtc tgcaacctga agattttgca    660
```

```
acttactact gtcaacagag ttacagtttc ccoctcactt tcggcggagg gaccaagctg    720
gagatcaaa                                                            729
```

<210> SEQ ID NO 208
<211> LENGTH: 729
<212> TYPE: DNA
<213> ORGANISM: Artificial Sequence
<220> FEATURE:
<223> OTHER INFORMATION: W4-VH65-VLP scFv-Fc

<400> SEQUENCE: 208

```
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180
ccctccctca gaatcgagt caccatatca ggagacacgt ccaagaagca gttctccctg     240
cacgtgagct ctgtgaccgc tgcggacacg gccgtgtact tctgtgcgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc cccctcactt tcggcggagg gaccaagctg    720
gagatcaaa                                                            729
```

<210> SEQ ID NO 209
<211> LENGTH: 729
<212> TYPE: DNA
<213> ORGANISM: Artificial Sequence
<220> FEATURE:
<223> OTHER INFORMATION: W4-VH66-VLP scFv-Fc

<400> SEQUENCE: 209

```
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgaccacaac    180
ccctccctca gagtcgagt caccatatca ggagacacgt ccaagaagca gttctccctg     240
cacgtgagct ctgtgaccgc tgcggacacg gccgtgtact tctgtgcgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc cccctcactt tcggcggagg gaccaagctg    720
gagatcaaa                                                            729
```

<210> SEQ ID NO 210
<211> LENGTH: 729

```
<212> TYPE: DNA
<213> ORGANISM: Artificial Sequence
<220> FEATURE:
<223> OTHER INFORMATION: W4-VH67-VLP scFv-Fc

<400> SEQUENCE: 210
gaggtgcagc tgttggagtc gggcccagga ctggtgaagc cttcggagac cctgtccctc    60
acctgcaatg tcgctggtgg ctccatcagt ccttactact ggacctggat ccggcagccc   120
ccagggaagg gcctggagtt gattggttat atccacttca gtgggtacac cgactacaac   180
ccctccctca gagtcgagt caccatatca ggagacacgt ccaagaagca gttctccctg   240
cacgtgagct ctgtgaccgc tgcggacacg gccgtgtact tctgtgcgag agccgattgg   300
gacctgcttc atgctcttga tatctggggc caagggaccc tggtcaccgt ctcgagtgga   360
ggcggcggtt caggcggagg tggctctggc ggtggcggaa gtgcactcga aattgtgttg   420
acacagtctc catcctccct gtctacatct gtaggagaca gagtcaccat cacttgccgg   480
gcaagtcaga gcattaggag ccatttaaat tggtatcagc agaaaccagg gaaagcccct   540
aaactcctga tctatggtgc atccaatttg caaagtgggg tcccatcaag gttcagtggc   600
agtggatctg ggacagattt cactctcacc attagtagtc tgcaacctga agattttgca   660
acttactact gtcaacagag ttacagtttc cccctcactt tcggcggagg gaccaagctg   720
gagatcaaa                                                            729

<210> SEQ ID NO 211
<211> LENGTH: 729
<212> TYPE: DNA
<213> ORGANISM: Artificial Sequence
<220> FEATURE:
<223> OTHER INFORMATION: W4-VH69-VLP scFv-Fc

<400> SEQUENCE: 211
gaggtgcagc tgttggagtc gggcccagga ctggtgaagc cttcggagac cctgtccctc    60
acctgcaatg tcgctggtgg ctccatcagt ccttactact ggacctggat ccggcagccc   120
ccagggaagg gcctggagtt gattggttat atccactcca gtgggtacac cgactacaac   180
tcctccctca gagtcgagt caccatatca ggagacacgt ccaagaagca gttctccctg   240
cacgtgagct ctgtgaccgc tgcggacacg gccgtgtact tctgtgcgag agccgattgg   300
gacctgcttc atgctcttga tatctggggc caagggaccc tggtcaccgt ctcgagtgga   360
ggcggcggtt caggcggagg tggctctggc ggtggcggaa gtgcactcga aattgtgttg   420
acacagtctc catcctccct gtctacatct gtaggagaca gagtcaccat cacttgccgg   480
gcaagtcaga gcattaggag ccatttaaat tggtatcagc agaaaccagg gaaagcccct   540
aaactcctga tctatggtgc atccaatttg caaagtgggg tcccatcaag gttcagtggc   600
agtggatctg ggacagattt cactctcacc attagtagtc tgcaacctga agattttgca   660
acttactact gtcaacagag ttacagtttc cccctcactt tcggcggagg gaccaagctg   720
gagatcaaa                                                            729

<210> SEQ ID NO 212
<211> LENGTH: 729
<212> TYPE: DNA
<213> ORGANISM: Artificial Sequence
<220> FEATURE:
<223> OTHER INFORMATION: W4-VH70-VLP scFv-Fc

<400> SEQUENCE: 212
```

```
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagg gcctggagtt gattggttat atccactcca gtgggtacac cgactacaac     180
ccctccctca ggagtcgagt caccatatca ggagacacgt ccaagaagca gttctccctg     240
cacgtgagct ctgtgaccgc tgcggacacg gccgtgtact tctgtgcgag agccgattgg     300
gacctgcttc atgctcttga tatctggggc caagggaccc tggtcaccgt ctcgagtgga     360
ggcggcggtt caggcggagg tggctctggc ggtggcggaa gtgcactcga aattgtgttg     420
acacagtctc catcctccct gtctacatct gtaggagaca gagtcaccat cacttgccgg     480
gcaagtcaga gcattaggag ccatttaaat tggtatcagc agaaaccagg gaaagcccct     540
aaactcctga tctatggtgc atccaatttg caaagtgggg tcccatcaag gttcagtggc     600
agtggatctg ggacagattt cactctcacc attagtagtc tgcaacctga agattttgca     660
acttactact gtcaacagag ttacagtttc ccctcacttt cggcggaggg accaagctg     720 gagatcaaa                                                              729

<210> SEQ ID NO 213
<211> LENGTH: 729
<212> TYPE: DNA
<213> ORGANISM: Artificial Sequence
<220> FEATURE:
<223> OTHER INFORMATION: W4-VH72-VLP scFv-Fc

<400> SEQUENCE: 213
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagg gcctggagtt gattggttat atccactcca gtgggcacac cgactacaac     180
ccctccctca agagtcgagt caccatatca ggagacacgt ccaagaagca gttctccctg     240
cacgtgagct ctgtgaccgc tgcggacacg gccgtgtact tctgtgcgag agccgattgg     300
gacctgcttc atgctcttga tatctggggc caagggaccc tggtcaccgt ctcgagtgga     360
ggcggcggtt caggcggagg tggctctggc ggtggcggaa gtgcactcga aattgtgttg     420
acacagtctc catcctccct gtctacatct gtaggagaca gagtcaccat cacttgccgg     480
gcaagtcaga gcattaggag ccatttaaat tggtatcagc agaaaccagg gaaagcccct     540
aaactcctga tctatggtgc atccaatttg caaagtgggg tcccatcaag gttcagtggc     600
agtggatctg ggacagattt cactctcacc attagtagtc tgcaacctga agattttgca     660
acttactact gtcaacagag ttacagtttc ccctcacttt cggcggaggg accaagctg     720 gagatcaaa                                                              729

<210> SEQ ID NO 214
<211> LENGTH: 729
<212> TYPE: DNA
<213> ORGANISM: Artificial Sequence
<220> FEATURE:
<223> OTHER INFORMATION: W4-VH79-VLP scFv-Fc

<400> SEQUENCE: 214
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagg gcctggagtt gattggttat taccacccca gtgggtacac cgactacaac     180
ccctccctca agagtcgagt caccatatca ggagacacgt ccaagaagca gttctccctg     240
```

-continued

```
cacgtgagct ctgtgaccgc tgcggacacg gccgtgtact tctgtgcgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg aaagcccct    540 aaactcctga tctatggtgc atccaatttg caaagtgggg tcccatcaag gttcagtggc    600
agtggatctg gacagattt cactctcacc attagtagtc tgcaacctga agattttgca    660
acttactact gtcaacagag ttacagtttc cccctcactt tcggcggagg gaccaagctg    720
gagatcaaa                                                            729
```

<210> SEQ ID NO 215
<211> LENGTH: 729
<212> TYPE: DNA
<213> ORGANISM: Artificial Sequence
<220> FEATURE:
<223> OTHER INFORMATION: W4-VH80-VLP scFv-Fc

<400> SEQUENCE: 215

```
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggttcac cagctacaac    180
ccctccctca gagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg aaagcccct    540 aaactcctga tctatggtgc atccaatttg caaagtgggg tcccatcaag gttcagtggc    600
agtggatctg gacagattt cactctcacc attagtagtc tgcaacctga agattttgca    660
acttactact gtcaacagag ttacagtttc cccctcactt tcggcggagg gaccaagctg    720
gagatcaaa                                                            729
```

<210> SEQ ID NO 216
<211> LENGTH: 124
<212> TYPE: PRT
<213> ORGANISM: Artificial Sequence
<220> FEATURE:
<223> OTHER INFORMATION: V2L2 VH

<400> SEQUENCE: 216

```
Glu Met Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Glu Gly Leu Glu Trp Val
        35                  40                  45

Ser Ala Ile Thr Ile Ser Gly Ile Thr Ala Tyr Tyr Thr Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Gly Asp Thr Ala Val Tyr Tyr Cys
                85                  90                  95

Ala Lys Glu Glu Phe Leu Pro Gly Thr His Tyr Tyr Gly Met Asp
            100                 105                 110

Val Trp Gly Gln Gly Thr Thr Val Thr Val Ser Ser
        115                 120

<210> SEQ ID NO 217
<211> LENGTH: 107
<212> TYPE: PRT
<213> ORGANISM: Artificial Sequence
<220> FEATURE:
<223> OTHER INFORMATION: V2L2 VL

<400> SEQUENCE: 217

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Val Ile
        35                  40                  45

Tyr Ser Ala Ser Thr Leu Gln Ser Gly Val Pro Ser Arg Phe Ser Gly
    50                  55                  60

Ser Gly Ser Gly Thr Asp Phe Thr Leu Ser Ile Ser Ser Leu Gln Pro
65                  70                  75                  80

Asp Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys
            100                 105

<210> SEQ ID NO 218
<211> LENGTH: 5
<212> TYPE: PRT
<213> ORGANISM: Artificial Sequence
<220> FEATURE:
<223> OTHER INFORMATION: V2L2  VHCDR1

<400> SEQUENCE: 218

Ser Tyr Ala Met Asn
1               5

<210> SEQ ID NO 219
<211> LENGTH: 17
<212> TYPE: PRT
<213> ORGANISM: Artificial Sequence
<220> FEATURE:
<223> OTHER INFORMATION: V2L2  VHCDR2

<400> SEQUENCE: 219

Ala Ile Thr Ile Ser Gly Ile Thr Ala Tyr Tyr Thr Asp Ser Val Lys
1               5                   10                  15

Gly

<210> SEQ ID NO 220
<211> LENGTH: 15
<212> TYPE: PRT
<213> ORGANISM: Artificial Sequence
<220> FEATURE:
<223> OTHER INFORMATION: V2L2  VHCDR3

<400> SEQUENCE: 220
```

```
Glu Glu Phe Leu Pro Gly Thr His Tyr Tyr Tyr Gly Met Asp Val
1               5                   10                  15
```

<210> SEQ ID NO 221
<211> LENGTH: 11
<212> TYPE: PRT
<213> ORGANISM: Artificial Sequence
<220> FEATURE:
<223> OTHER INFORMATION: V2L2 VLCDR1

<400> SEQUENCE: 221

```
Arg Ala Ser Gln Gly Ile Arg Asn Asp Leu Gly
1               5                   10
```

<210> SEQ ID NO 222
<211> LENGTH: 7
<212> TYPE: PRT
<213> ORGANISM: Artificial Sequence
<220> FEATURE:
<223> OTHER INFORMATION: V2LC VLCDR2

<400> SEQUENCE: 222

```
Ser Ala Ser Thr Leu Gln Ser
1               5
```

<210> SEQ ID NO 223
<211> LENGTH: 9
<212> TYPE: PRT
<213> ORGANISM: Artificial Sequence
<220> FEATURE:
<223> OTHER INFORMATION: V2L2 VLCDR3

<400> SEQUENCE: 223

```
Leu Gln Asp Tyr Asn Tyr Pro Trp Thr
1               5
```

<210> SEQ ID NO 224
<211> LENGTH: 57
<212> TYPE: PRT
<213> ORGANISM: Artificial Sequence
<220> FEATURE:
<223> OTHER INFORMATION: W4-RAD VH forward primer

<400> SEQUENCE: 224

```
Gly Thr Ala Ala Ala Gly Gly Cys Gly Ala Gly Gly Gly Gly
1               5                   10                  15

Ala Thr Cys Cys Gly Gly Cys Gly Ala Gly Gly Gly Gly Cys
                20                  25                  30

Thr Cys Thr Gly Ala Gly Gly Thr Gly Cys Ala Gly Cys Thr Gly Thr
                35                  40                  45

Thr Gly Gly Ala Gly Thr Cys Gly Gly
    50                  55
```

<210> SEQ ID NO 225
<211> LENGTH: 66
<212> TYPE: PRT
<213> ORGANISM: Artificial Sequence
<220> FEATURE:
<223> OTHER INFORMATION: W4-RAD VH reverse primer

<400> SEQUENCE: 225

```
Gly Ala Thr Cys Cys Thr Cys Cys Gly Cys Cys Gly Cys Cys Gly Cys
1               5                   10                  15

Thr Gly Cys Cys Cys Cys Cys Thr Cys Cys Cys Cys Ala Gly Ala
                20                  25                  30
```

```
Gly Cys Cys Cys Cys Cys Thr Cys Cys Gly Cys Cys Ala Cys Thr Cys
        35                  40                  45

Gly Ala Gly Ala Cys Gly Gly Thr Gly Ala Cys Cys Ala Gly Gly Gly
    50                  55                  60

Thr Cys
65

<210> SEQ ID NO 226
<211> LENGTH: 62
<212> TYPE: PRT
<213> ORGANISM: Artificial Sequence
<220> FEATURE:
<223> OTHER INFORMATION: W4-RAD VL forward primer

<400> SEQUENCE: 226

Ala Gly Gly Gly Gly Cys Ala Gly Cys Gly Gly Cys Gly Gly Cys
1               5                   10                  15

Gly Gly Ala Gly Gly Ala Thr Cys Thr Gly Gly Gly Gly Ala Gly
            20                  25                  30

Gly Gly Gly Gly Cys Ala Gly Cys Gly Ala Ala Thr Thr Gly Thr
        35                  40                  45

Gly Thr Thr Gly Ala Cys Ala Cys Ala Gly Thr Cys Thr Cys
    50                  55                  60

<210> SEQ ID NO 227
<211> LENGTH: 44
<212> TYPE: PRT
<213> ORGANISM: Artificial Sequence
<220> FEATURE:
<223> OTHER INFORMATION: W4-RAD VL reverse primer

<400> SEQUENCE: 227

Cys Ala Ala Thr Gly Ala Ala Thr Thr Cys Gly Cys Gly Gly Cys Cys
1               5                   10                  15

Gly Cys Thr Cys Ala Thr Thr Thr Gly Ala Thr Cys Thr Cys Cys Ala
            20                  25                  30

Gly Cys Thr Thr Gly Gly Thr Cys Cys Cys Ala Cys
        35                  40

<210> SEQ ID NO 228
<211> LENGTH: 256
<212> TYPE: PRT
<213> ORGANISM: Artificial Sequence
<220> FEATURE:
<223> OTHER INFORMATION: W4-RAD scFv sequence in BS3 vector

<400> SEQUENCE: 228

Gly Gly Gly Gly Ser Gly Gly Gly Ser Glu Val Gln Leu Leu Glu
1               5                   10                  15

Ser Gly Pro Gly Leu Val Lys Pro Ser Glu Thr Leu Ser Leu Thr Cys
            20                  25                  30

Asn Val Ala Gly Gly Ser Ile Ser Pro Tyr Tyr Trp Thr Trp Ile Arg
        35                  40                  45

Gln Pro Pro Gly Lys Cys Leu Glu Leu Ile Gly Tyr Ile His Ser Ser
    50                  55                  60

Gly Tyr Thr Asp Tyr Asn Pro Ser Leu Lys Ser Arg Val Thr Ile Ser
65                  70                  75                  80

Gly Asp Thr Ser Lys Lys Gln Phe Ser Leu His Val Ser Ser Val Thr
                85                  90                  95
```

```
Ala Ala Asp Thr Ala Val Tyr Phe Cys Ala Arg Ala Asp Trp Asp Leu
            100                 105                 110

Leu His Ala Leu Asp Ile Trp Gly Gln Gly Thr Leu Val Thr Val Ser
        115                 120                 125

Ser Gly Gly Gly Gly Ser Gly Gly Gly Gly Ser Gly Gly Gly Gly Ser
    130                 135                 140

Gly Gly Gly Gly Ser Glu Ile Val Leu Thr Gln Ser Pro Ser Ser Leu
145                 150                 155                 160

Ser Thr Ser Val Gly Asp Arg Val Thr Ile Thr Cys Arg Ala Ser Gln
                165                 170                 175

Ser Ile Arg Ser His Leu Asn Trp Tyr Gln Gln Lys Pro Gly Lys Ala
        180                 185                 190

Pro Lys Leu Leu Ile Tyr Gly Ala Ser Asn Leu Gln Ser Gly Val Pro
    195                 200                 205

Ser Arg Phe Ser Gly Ser Gly Ser Gly Thr Asp Phe Thr Leu Thr Ile
    210                 215                 220

Ser Ser Leu Gln Pro Glu Asp Phe Ala Thr Tyr Tyr Cys Gln Gln Ser
225                 230                 235                 240

Tyr Ser Phe Pro Leu Thr Phe Gly Cys Gly Thr Lys Leu Glu Ile Lys
                245                 250                 255

<210> SEQ ID NO 229
<211> LENGTH: 380
<212> TYPE: PRT
<213> ORGANISM: Artificial Sequence
<220> FEATURE:
<223> OTHER INFORMATION: W4-RAD scFv-V2L2 VH sequences in Bs2 vector

<400> SEQUENCE: 229

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Cys Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Glu Ile Val Leu Thr
    130                 135                 140

Gln Ser Pro Ser Ser Leu Ser Thr Ser Val Gly Asp Arg Val Thr Ile
145                 150                 155                 160

Thr Cys Arg Ala Ser Gln Ser Ile Arg Ser His Leu Asn Trp Tyr Gln
                165                 170                 175

Gln Lys Pro Gly Lys Ala Pro Lys Leu Leu Ile Tyr Gly Ala Ser Asn
            180                 185                 190

Leu Gln Ser Gly Val Pro Ser Arg Phe Ser Gly Ser Gly Ser Gly Thr
        195                 200                 205
```

Asp Phe Thr Leu Thr Ile Ser Ser Leu Gln Pro Glu Asp Phe Ala Thr
210                 215                 220

Tyr Tyr Cys Gln Gln Ser Tyr Ser Phe Pro Leu Thr Phe Gly Cys Gly
225                 230                 235                 240

Thr Lys Leu Glu Ile Lys Gly Gly Gly Ser Gly Gly Gly Ser
            245                 250                 255

Glu Met Gln Leu Leu Glu Ser Gly Gly Leu Val Gln Pro Gly Gly
            260                 265                 270

Ser Leu Arg Leu Ser Cys Ala Ala Ser Gly Phe Thr Phe Ser Ser Tyr
        275                 280                 285

Ala Met Asn Trp Val Arg Gln Ala Pro Gly Lys Gly Leu Glu Trp Val
290                 295                 300

Ser Ala Ile Thr Ile Ser Gly Ile Thr Ala Tyr Tyr Thr Asp Ser Val
305                 310                 315                 320

Lys Gly Arg Phe Thr Ile Ser Arg Asp Asn Ser Lys Asn Thr Leu Tyr
            325                 330                 335

Leu Gln Met Asn Ser Leu Arg Ala Gly Asp Thr Ala Val Tyr Tyr Cys
            340                 345                 350

Ala Lys Glu Glu Phe Leu Pro Gly Thr His Tyr Tyr Tyr Gly Met Asp
        355                 360                 365

Val Trp Gly Gln Gly Thr Thr Val Thr Val Ser Ser
370                 375                 380

<210> SEQ ID NO 230
<211> LENGTH: 45
<212> TYPE: DNA
<213> ORGANISM: Artificial Sequence
<220> FEATURE:
<223> OTHER INFORMATION: W4-RAD VH forward primer for Bs2 vector

<400> SEQUENCE: 230
ttctctccac aggtgtacac tccgaggtgc agctgttgga gtcgg          45

<210> SEQ ID NO 231
<211> LENGTH: 58
<212> TYPE: DNA
<213> ORGANISM: Artificial Sequence
<220> FEATURE:
<223> OTHER INFORMATION: W4-RAD VL reverse primer for Bs2 vector

<400> SEQUENCE: 231 cccctccgc cggatccccc tccgcctttg atctccagct tggtcccaca gccgaaag          58

<210> SEQ ID NO 232
<211> LENGTH: 53
<212> TYPE: DNA
<213> ORGANISM: Artificial Sequence
<220> FEATURE:
<223> OTHER INFORMATION: V2L2 VH forward primer

<400> SEQUENCE: 232
ggcggagggg gatccggcgg aggggctct gagatgcagc tgttggagtc tgg          53

<210> SEQ ID NO 233
<211> LENGTH: 41
<212> TYPE: DNA
<213> ORGANISM: Artificial Sequence
<220> FEATURE:
<223> OTHER INFORMATION: V2L2 VH reverse primer

<400> SEQUENCE: 233

```
atgggccctt ggtcgacgct gaggagacgg tgaccgtggt c                          41
```

<210> SEQ ID NO 234
<211> LENGTH: 36
<212> TYPE: PRT
<213> ORGANISM: Artificial Sequence
<220> FEATURE:
<223> OTHER INFORMATION: hinge region of BiMab-V2L2-W4-RAD

<400> SEQUENCE: 234

```
Lys Val Asp Lys Arg Val Glu Pro Lys Ser Cys Gly Gly Gly Ser
1               5                   10                  15

Gly Gly Gly Gly Ser Asp Lys Thr His Thr Cys Pro Pro Cys Pro Ala
            20                  25                  30

Pro Glu Leu Leu
        35
```

<210> SEQ ID NO 235
<211> LENGTH: 281
<212> TYPE: PRT
<213> ORGANISM: Artificial Sequence
<220> FEATURE:
<223> OTHER INFORMATION: W4-RAD scFv sequences in BiMab vector

<400> SEQUENCE: 235

```
Glu Pro Lys Ser Cys Gly Gly Gly Ser Gly Gly Gly Gly Ser Glu
1               5                   10                  15

Val Gln Leu Leu Glu Ser Gly Pro Gly Leu Val Lys Pro Ser Glu Thr
            20                  25                  30

Leu Ser Leu Thr Cys Asn Val Ala Gly Gly Ser Ile Ser Pro Tyr Tyr
        35                  40                  45

Trp Thr Trp Ile Arg Gln Pro Pro Gly Lys Cys Leu Glu Leu Ile Gly
    50                  55                  60

Tyr Ile His Ser Ser Gly Tyr Thr Asp Tyr Asn Pro Ser Leu Lys Ser
65                  70                  75                  80

Arg Val Thr Ile Ser Gly Asp Thr Ser Lys Lys Gln Phe Ser Leu His
                85                  90                  95

Val Ser Ser Val Thr Ala Ala Asp Thr Ala Val Tyr Phe Cys Ala Arg
            100                 105                 110

Ala Asp Trp Asp Leu Leu His Ala Leu Asp Ile Trp Gly Gln Gly Thr
        115                 120                 125

Leu Val Thr Val Ser Ser Gly Gly Gly Ser Gly Gly Gly Gly Ser
    130                 135                 140

Gly Gly Gly Gly Ser Gly Gly Gly Ser Glu Ile Val Leu Thr Gln
145                 150                 155                 160

Ser Pro Ser Ser Leu Ser Thr Ser Val Gly Asp Arg Val Thr Ile Thr
                165                 170                 175

Cys Arg Ala Ser Gln Ser Ile Arg Ser His Leu Asn Trp Tyr Gln Gln
            180                 185                 190

Lys Pro Gly Lys Ala Pro Lys Leu Leu Ile Tyr Gly Ala Ser Asn Leu
        195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln Ser Tyr Ser Phe Pro Leu Thr Phe Gly Cys Gly Thr
                245                 250                 255
```

Lys Leu Glu Ile Lys Gly Gly Gly Gly Ser Gly Gly Gly Gly Ser Asp
            260                 265                 270

Lys Thr His Thr Cys Pro Pro Cys Pro
        275                 280

<210> SEQ ID NO 236
<211> LENGTH: 24
<212> TYPE: DNA
<213> ORGANISM: Artificial Sequence
<220> FEATURE:
<223> OTHER INFORMATION: W4-RAD VH forward primer for BiMab vector

<400> SEQUENCE: 236
gaggtgcagc tgttggagtc gggc                                        24

<210> SEQ ID NO 237
<211> LENGTH: 65
<212> TYPE: DNA
<213> ORGANISM: Artificial Sequence
<220> FEATURE:
<223> OTHER INFORMATION: W4-RAD VL reverse primer for BiMab vector

<400> SEQUENCE: 237
gtgtgagttt tgtcggatcc ccctccgcca gagccacctc cgcctttgat ctccagcttg    60
gtccc                                                                65

<210> SEQ ID NO 238
<211> LENGTH: 372
<212> TYPE: DNA
<213> ORGANISM: Artificial Sequence
<220> FEATURE:
<223> OTHER INFORMATION: V2L2 VH

<400> SEQUENCE: 238
gagatgcagc tgttggagtc tgggggaggc ttggtacagc ctgggggtc cctgagactc      60 tcctgtgcag cctctggatt cacctttagc agctatgcca tgaactgggt ccgccaggct   120
ccaggggagg gctggagtg gtctcagct attactatta gtggtattac cgcatactac    180
accgactccg tgaagggccg gttcaccatc tccagagaca attccaagaa cacgctatat   240
ctgcaaatga acagcctgag gccgggac acggccgtat attactgtgc aaggaagaa    300 ttttacctg gaacgcacta ctactacggt atggacgtct ggggccaagg gaccacggtc   360
accgtctcct ca                                                      372

<210> SEQ ID NO 239
<211> LENGTH: 321
<212> TYPE: DNA
<213> ORGANISM: Artificial Sequence
<220> FEATURE:
<223> OTHER INFORMATION: V2L2 VL

<400> SEQUENCE: 239
gccatccaga tgacccagtc tccatcctcc ctgtctgcat ctgtaggaga cagagtcacc      60
atcacttgcc gggcaagtca gggcattaga aatgatttag ctggtatca acagaagcca    120 gggaaagccc ctaaactcgt gatctattct gcatccactt tacaaagtgg gtcccatca    180 aggttcagcg gcagtggatc tggcacagat ttcactctct ccatcagcag cctgcagcct   240
gacgattttg caacttatta ctgtctacaa gattacaatt accgtggac gttcggccaa   300 gggaccaagg ttgaaatcaa a                                              321

<210> SEQ ID NO 240
<211> LENGTH: 243
<212> TYPE: PRT
<213> ORGANISM: Artificial Sequence
<220> FEATURE:
<223> OTHER INFORMATION: Psl0096-Germline scFv

<400> SEQUENCE: 240

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

Lys Leu Ser Ser Val Thr Ala Ala Asp Thr Ala Val Tyr Tyr Cys Ala
                85                  90                  95

Arg Ala Asp Trp Asp Arg Leu Arg Ala Leu Asp Ile Trp Gly Gln Gly
            100                 105                 110

Thr Met Val Thr Val Ser Ser Gly Gly Gly Ser Gly Gly Gly Gly
        115                 120                 125

Ser Gly Gly Gly Gly Ser Ala Leu Asp Ile Gln Leu Thr Gln Ser Pro
    130                 135                 140

Ser Ser Leu Ser Ala Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Thr Gly Ala Trp Asn Trp Phe Gly Gly Gly Thr Lys Val
225                 230                 235                 240

Glu Ile Lys
```

<210> SEQ ID NO 241
<211> LENGTH: 243
<212> TYPE: PRT
<213> ORGANISM: Artificial Sequence
<220> FEATURE:
<223> OTHER INFORMATION: Psl0225-Germline scFv

<400> SEQUENCE: 241

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
```

```
                65                  70                  75                  80
Lys Leu Ser Ser Val Thr Ala Ala Asp Thr Ala Val Tyr Tyr Cys Ala
                    85                  90                  95

Arg Ala Met Asp Ile Glu Pro His Ala Leu Asp Ile Trp Gly Gln Gly
                100                 105                 110

Thr Met Val Thr Val Ser Ser Gly Gly Gly Ser Gly Gly Gly Gly
            115                 120                 125

Ser Gly Gly Gly Ser Ala Leu Asp Ile Gln Leu Thr Gln Ser Pro
        130                 135                 140

Ser Ser Leu Ser Ala Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Asp Asp Gly Phe Pro Asn Phe Gly Gly Thr Lys Val
225                 230                 235                 240

Glu Ile Lys

<210> SEQ ID NO 242
<211> LENGTH: 243
<212> TYPE: PRT
<213> ORGANISM: Artificial Sequence
<220> FEATURE:
<223> OTHER INFORMATION: Psl0337-Germline scFv

<400> SEQUENCE: 242

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

Lys Leu Ser Ser Val Thr Ala Ala Asp Thr Ala Val Tyr Tyr Cys Ala
                85                  90                  95

Arg Ala Asp Trp Asp His Lys His Ala Leu Asp Ile Trp Gly Gln Gly
            100                 105                 110

Thr Met Val Thr Val Ser Ser Gly Gly Gly Gly Ser Gly Gly Gly Gly
        115                 120                 125

Ser Gly Gly Gly Gly Ser Ala Leu Asp Ile Gln Leu Thr Gln Ser Pro
    130                 135                 140

Ser Ser Leu Ser Ala Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190
```

Gly Val Pro Ser Arg Phe Ser Gly Ser Gly Thr Asp Phe Thr
            195                 200                 205

Leu Thr Ile Ser Ser Leu Gln Pro Glu Asp Phe Ala Thr Tyr Tyr Cys
        210                 215                 220

Gln Asp Ser Ser Ser Trp Pro Leu Thr Phe Gly Gly Gly Thr Lys Val
225                 230                 235                 240

Glu Ile Lys

<210> SEQ ID NO 243
<211> LENGTH: 243
<212> TYPE: PRT
<213> ORGANISM: Artificial Sequence
<220> FEATURE:
<223> OTHER INFORMATION: Psl0567-Germline scFv

<400> SEQUENCE: 243

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

Lys Leu Ser Ser Val Thr Ala Ala Asp Thr Ala Val Tyr Tyr Cys Ala
                85                  90                  95

Arg Ala Asp Trp Asn Glu Gly Arg Lys Leu Asp Ile Trp Gly Gln Gly
            100                 105                 110

Thr Met Val Thr Val Ser Ser Gly Gly Gly Gly Ser Gly Gly Gly Gly
        115                 120                 125

Ser Gly Gly Gly Gly Ser Ala Leu Asp Ile Gln Leu Thr Gln Ser Pro
    130                 135                 140

Ser Ser Leu Ser Ala Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Val
225                 230                 235                 240

Glu Ile Lys

<210> SEQ ID NO 244
<211> LENGTH: 243
<212> TYPE: PRT
<213> ORGANISM: Artificial Sequence
<220> FEATURE:
<223> OTHER INFORMATION: Psl0588-Germline

<400> SEQUENCE: 244

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Pro Tyr
            20                  25                  30

Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Pro Ser Leu Lys
        50                  55                  60

Ser Arg Val Thr Ile Ser Gly Asp Thr Ser Lys Lys Gln Phe Ser Leu
65                  70                  75                  80

Lys Leu Ser Ser Val Thr Ala Ala Asp Thr Ala Val Tyr Tyr Cys Ala
                85                  90                  95

Arg Ala Asp Asp Pro Phe Pro Gly Tyr Leu Asp Ile Trp Gly Gln Gly
                100                 105                 110

Thr Met Val Thr Val Ser Ser Gly Gly Gly Ser Gly Gly Gly Gly
            115                 120                 125

Ser Gly Gly Gly Ser Ala Leu Asp Ile Gln Leu Thr Gln Ser Pro
        130                 135                 140

Ser Ser Leu Ser Ala Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
                180                 185                 190

Gly Val Pro Ser Arg Phe Ser Gly Ser Gly Ser Gly Thr Asp Phe Thr
                195                 200                 205

Leu Thr Ile Ser Ser Leu Gln Pro Glu Asp Phe Ala Thr Tyr Tyr Cys
        210                 215                 220

Gln Gln Ser Asp Thr Phe Pro Leu Lys Phe Gly Gly Thr Lys Val
225                 230                 235                 240

Glu Ile Lys

<210> SEQ ID NO 245
<211> LENGTH: 243
<212> TYPE: PRT
<213> ORGANISM: Artificial Sequence
<220> FEATURE:
<223> OTHER INFORMATION: Psl0170 scFv

<400> SEQUENCE: 245

Glu Val Gln Leu Leu Glu Ser Gly Pro Gly Leu Val Lys Pro Ser Glu
1               5                   10                  15

Thr Leu Ser Leu Thr Cys Asn Val Ala Gly Ser Ile Ser Pro Tyr
            20                  25                  30

Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Pro Ser Leu Lys
        50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Thr Asp Glu Ala Asp His Ala Leu Asp Ile Trp Gly Gln Gly
                100                 105                 110

Thr Leu Val Thr Val Ser Ser Gly Gly Gly Gly Ser Gly Gly Gly Gly

```
                115             120             125
Ser Gly Gly Gly Gly Ser Ala Leu Glu Ile Val Leu Thr Gln Ser Pro
            130             135             140

Ser Ser Leu Ser Thr Ser Val Gly Asp Arg Val Thr Ile Thr Cys Arg
145             150             155             160

Ala Ser Gln Ser Ile Arg Ser His Leu Asn Trp Tyr Gln Gln Lys Pro
                165             170             175

Gly Lys Ala Pro Lys Leu Leu Ile Tyr Gly Ala Ser Asn Leu Gln Ser
            180             185             190

Gly Val Pro Ser Arg Phe Ser Gly Ser Gly Ser Gly Thr Asp Phe Thr
                195             200             205

Leu Thr Ile Ser Ser Leu Gln Pro Glu Asp Phe Ala Thr Tyr Tyr Cys
            210             215             220

Ser Gln Ser Asp Thr Phe Pro Leu Thr Phe Gly Gly Gly Thr Lys Leu
225             230             235             240

Glu Ile Lys

<210> SEQ ID NO 246
<211> LENGTH: 243
<212> TYPE: PRT
<213> ORGANISM: Artificial Sequence
<220> FEATURE:
<223> OTHER INFORMATION: Psl0304 scFv

<400> SEQUENCE: 246

Glu Val Gln Leu Leu Glu Ser Gly Pro Gly Leu Val Lys Pro Ser Glu
1               5               10              15

Thr Leu Ser Leu Thr Cys Asn Val Ala Gly Gly Ser Ile Ser Pro Tyr
            20              25              30

Tyr Trp Thr Trp Ile Arg Gln Pro Pro Gly Lys Gly Leu Glu Leu Ile
        35              40              45

Gly Tyr Ile His Ser Ser Gly Tyr Thr Asp Tyr Asn Pro Ser Leu Lys
    50              55              60

Ser Arg Val Thr Ile Ser Gly Asp Thr Ser Lys Lys Gln Phe Ser Leu
65              70              75              80

His Val Ser Ser Val Thr Ala Ala Asp Thr Ala Val Tyr Phe Cys Ala
            85              90              95

Arg Ala Asp Trp Ser Gly Thr Arg Ala Leu Asp Ile Trp Gly Gln Gly
            100             105             110

Thr Leu Val Thr Val Ser Ser Gly Gly Gly Gly Ser Gly Gly Gly Gly
            115             120             125

Ser Gly Gly Gly Gly Ser Ala Leu Glu Ile Val Leu Thr Gln Ser Pro
            130             135             140

Ser Ser Leu Ser Thr Ser Val Gly Asp Arg Val Thr Ile Thr Cys Trp
145             150             155             160

Ala Ser Gln Ser Ile Arg Ser His Leu Asn Trp Tyr Gln Gln Lys Pro
                165             170             175

Gly Lys Ala Pro Lys Leu Leu Ile Tyr Gly Ala Ser Asn Leu Gln Ser
            180             185             190

Gly Val Pro Ser Arg Phe Ser Gly Ser Gly Ser Gly Thr Asp Phe Thr
                195             200             205

Leu Thr Ile Ser Ser Leu Gln Pro Glu Asp Phe Ala Thr Tyr Tyr Cys
            210             215             220

Gly Gln Ser Asp Ala Phe Pro Leu Thr Phe Gly Gly Gly Thr Lys Leu
225             230             235             240
```

<210> SEQ ID NO 247
<211> LENGTH: 243
<212> TYPE: PRT
<213> ORGANISM: Artificial Sequence
<220> FEATURE:
<223> OTHER INFORMATION: Psl0348 scFv

<400> SEQUENCE: 247

```
Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Leu Pro Glu Lys Pro His Ala Leu Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Leu Gln Gly Asp Leu Trp Pro Leu Thr Phe Gly Gly Thr Lys Leu
225                 230                 235                 240

Glu Ile Lys
```

<210> SEQ ID NO 248
<211> LENGTH: 243
<212> TYPE: PRT
<213> ORGANISM: Artificial Sequence
<220> FEATURE:
<223> OTHER INFORMATION: Psl0573 scFv

<400> SEQUENCE: 248

```
Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45
```

Gly Tyr Ile His Ser Ser Gly Tyr Thr Asp Tyr Asn Pro Ser Leu Lys
            50                  55                  60

Ser Arg Val Thr Ile Ser Gly Asp Thr Ser Lys Lys Gln Phe Ser Leu
 65                  70                  75                  80

His Val Ser Ser Val Thr Ala Ala Asp Thr Ala Val Tyr Phe Cys Ala
                 85                  90                  95

Arg Ser Leu Phe Thr Asp Asp His Ala Leu Asp Ile Trp Gly Gln Gly
                100                 105                 110

Thr Leu Val Thr Val Ser Ser Gly Gly Gly Gly Ser Gly Gly Gly Gly
            115                 120                 125

Ser Gly Gly Gly Gly Ser Ala Leu Glu Ile Val Leu Thr Gln Ser Pro
            130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
            210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 249
<211> LENGTH: 243
<212> TYPE: PRT
<213> ORGANISM: Artificial Sequence
<220> FEATURE:
<223> OTHER INFORMATION: Psl0574 scFv

<400> SEQUENCE: 249

Glu Val Gln Leu Leu Glu Ser Gly Pro Gly Leu Val Lys Pro Ser Glu
 1               5                  10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
                35                  40                  45

Gly Tyr Ile His Ser Ser Gly Tyr Thr Asp Tyr Asn Pro Ser Leu Lys
            50                  55                  60

Ser Arg Val Thr Ile Ser Gly Asp Thr Ser Lys Lys Gln Phe Ser Leu
 65                  70                  75                  80

His Val Ser Ser Val Thr Ala Ala Asp Thr Ala Val Tyr Phe Cys Ala
                 85                  90                  95

Arg Ala Ser Pro Gly Val Val His Ala Leu Asp Ile Trp Gly Gln Gly
                100                 105                 110

Thr Leu Val Thr Val Ser Ser Gly Gly Gly Gly Ser Gly Gly Gly Gly
            115                 120                 125

Ser Gly Gly Gly Gly Ser Ala Leu Glu Ile Val Leu Thr Gln Ser Pro
            130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro 165                 170                 175
Gly Lys Ala Pro Lys Leu Leu Ile Tyr Gly Ala Ser Asn Leu Gln Ser
                180                 185                 190

Gly Val Pro Ser Arg Phe Ser Gly Ser Gly Ser Gly Thr Asp Phe Thr
                195                 200                 205

Leu Thr Ile Ser Ser Leu Gln Pro Glu Asp Phe Ala Thr Tyr Tyr Cys
        210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 250
<211> LENGTH: 243
<212> TYPE: PRT
<213> ORGANISM: Artificial Sequence
<220> FEATURE:
<223> OTHER INFORMATION: Psl0582 scFv

<400> SEQUENCE: 250

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
                20                  25                  30

Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Pro Ser Leu Lys
        50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala His Ile Glu Ser His His Ala Leu Asp Ile Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 251
<211> LENGTH: 243
<212> TYPE: PRT
<213> ORGANISM: Artificial Sequence
<220> FEATURE:

<223> OTHER INFORMATION: Psl0584 scFv

<400> SEQUENCE: 251

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Thr Gln Ala Pro Ala His Ala Leu Asp Ile Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 252
<211> LENGTH: 243
<212> TYPE: PRT
<213> ORGANISM: Artificial Sequence
<220> FEATURE:
<223> OTHER INFORMATION: Psl0585 scFv

<400> SEQUENCE: 252

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ser Gln His Asp Leu Glu His Ala Leu Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 253
<211> LENGTH: 243
<212> TYPE: PRT
<213> ORGANISM: Artificial Sequence
<220> FEATURE:
<223> OTHER INFORMATION: Psl0589 scFv

<400> SEQUENCE: 253

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Met Pro Asp Met Pro His Ala Leu Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys

```
                210                 215                 220
Gln Gln Ser Leu Glu Phe Pro Leu Thr Phe Gly Gly Thr Lys Leu
225                 230                 235                 240

Glu Ile Lys

<210> SEQ ID NO 254
<211> LENGTH: 243
<212> TYPE: PRT
<213> ORGANISM: Artificial Sequence
<220> FEATURE:
<223> OTHER INFORMATION: WapR0004-Germline scFv

<400> SEQUENCE: 254

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Pro Tyr
                20                  25                  30

Tyr Trp Thr Trp Ile Arg Gln Pro Pro Gly Lys Gly Leu Glu Leu Ile
            35                  40                  45

Gly Tyr Ile His Ser Gly Tyr Thr Asp Tyr Asn Pro Ser Leu Lys
        50                  55                  60

Ser Arg Val Thr Ile Ser Gly Asp Thr Ser Lys Lys Gln Phe Ser Leu
65                  70                  75                  80

Lys Leu Ser Ser Val Thr Ala Ala Asp Thr Ala Val Tyr Tyr Cys Ala
                85                  90                  95

Arg Ala Asp Trp Asp Leu Leu His Ala Leu Asp Ile Trp Gly Gln Gly
            100                 105                 110

Thr Met Val Thr Val Ser Ser Gly Gly Gly Ser Gly Gly Gly Gly
        115                 120                 125

Ser Gly Gly Gly Gly Ser Ala Leu Asp Ile Gln Leu Thr Gln Ser Pro
        130                 135                 140

Ser Ser Leu Ser Ala Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
        210                 215                 220

Gln Gln Ser Tyr Ser Phe Pro Leu Thr Phe Gly Gly Gly Thr Lys Val
225                 230                 235                 240

Glu Ile Lys

<210> SEQ ID NO 255
<211> LENGTH: 124
<212> TYPE: PRT
<213> ORGANISM: Artificial Sequence
<220> FEATURE:
<223> OTHER INFORMATION: V2L2-MD VH

<400> SEQUENCE: 255

Glu Met Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30
```

```
Ala Met Asn Trp Val Arg Gln Ala Pro Gly Glu Gly Leu Glu Trp Val
            35                  40                  45

Ser Ala Ile Thr Ile Ser Gly Ile Thr Ala Tyr Tyr Thr Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Gly Asp Thr Ala Val Tyr Tyr Cys
                 85                  90                  95

Ala Lys Glu Glu Phe Leu Pro Gly Thr His Tyr Tyr Tyr Gly Met Asp
                100                 105                 110

Val Trp Gly Gln Gly Thr Thr Val Thr Val Ser Ser
            115                 120
```

<210> SEQ ID NO 256
<211> LENGTH: 107
<212> TYPE: PRT
<213> ORGANISM: Artificial Sequence
<220> FEATURE:
<223> OTHER INFORMATION: V2L2-MD and V2L2-GL VL

<400> SEQUENCE: 256

```
Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Val Ile
            35                  40                  45

Tyr Ser Ala Ser Thr Leu Gln Ser Gly Val Pro Ser Arg Phe Ser Gly
 50                  55                  60

Ser Gly Ser Gly Thr Asp Phe Thr Leu Ser Ile Ser Ser Leu Gln Pro
 65                  70                  75                  80

Asp Asp Phe Ala Thr Tyr Tyr Cys Leu Gln Asp Tyr Asn Tyr Pro Trp
                 85                  90                  95

Thr Phe Gly Gln Gly Thr Lys Val Glu Ile Lys
                100                 105
```

<210> SEQ ID NO 257
<211> LENGTH: 124
<212> TYPE: PRT
<213> ORGANISM: Artificial Sequence
<220> FEATURE:
<223> OTHER INFORMATION: V2L2-GL VH

<400> SEQUENCE: 257

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Ala Ile Thr Ile Ser Gly Ile Thr Ala Tyr Tyr Thr Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Glu Phe Leu Pro Gly Thr His Tyr Tyr Tyr Gly Met Asp
```

```
              100                 105                 110
Val Trp Gly Gln Gly Thr Thr Val Thr Val Ser Ser
        115                 120
```

<210> SEQ ID NO 258
<211> LENGTH: 11
<212> TYPE: PRT
<213> ORGANISM: Artificial Sequence
<220> FEATURE:
<223> OTHER INFORMATION: Psl0096-Germline VHCDR3

<400> SEQUENCE: 258

```
Ala Asp Trp Asp Arg Leu Arg Ala Leu Asp Ile
1               5                   10
```

<210> SEQ ID NO 259
<211> LENGTH: 372
<212> TYPE: DNA
<213> ORGANISM: Artificial Sequence
<220> FEATURE:
<223> OTHER INFORMATION: V2L2-MD VH

<400> SEQUENCE: 259

| | | | | | |
|---|---|---|---|---|---|
| gaggtgcagc | tgttggagtc | tgggggaggc | ttggtacagc | ctgggggtc | cctgagactc | 60 |
| tcctgtgcag | cctctggatt | cacctttagc | agctatgcca | tgaactgggt | ccgccaggct | 120 |
| ccagggaagg | gcctggagtg | ggtctcagct | attactatga | gtggtattac | cgcatactac | 180 |
| accgacgacg | tgaagggccg | gttcaccatc | tccagagaca | attccaagaa | cacgctatat | 240 |
| ctgcaaatga | acagcctgag | ggccgaggac | acggccgtat | attactgtgc | gaaggaagaa | 300 |
| tttttacctg | gaacgcacta | ctactacggt | atggacgtct | ggggccaagg | gaccacggtc | 360 |
| accgtctcct | ca | | | | | 372 |

<210> SEQ ID NO 260
<211> LENGTH: 321
<212> TYPE: DNA
<213> ORGANISM: Artificial Sequence
<220> FEATURE:
<223> OTHER INFORMATION: V2L2-MD and V2L2-GL VL

<400> SEQUENCE: 260

| | | | | | |
|---|---|---|---|---|---|
| gccatccaga | tgacccagtc | tccatcctcc | ctgtctgcat | ctgtaggaga | cagagtcacc | 60 |
| atcacttgcc | gggcaagtca | gggcattaga | aatgatttag | gctggtatca | acagaaacca | 120 |
| gggaaagccc | ctaaactcct | gatctattct | gcatccactt | tacaaagtgg | ggtcccatca | 180 |
| aggttcagcg | gcagtggatc | tggcacagat | ttcactctca | ccatcagcag | cctgcagcct | 240 |
| gaggattttg | caacttatta | ctgtctacaa | gattacaatt | acccgtggac | gttcggccaa | 300 |
| gggaccaagg | ttgaaatcaa | a | | | | 321 |

<210> SEQ ID NO 261
<211> LENGTH: 372
<212> TYPE: DNA
<213> ORGANISM: Artificial Sequence
<220> FEATURE:
<223> OTHER INFORMATION: V2L2-GL VH

<400> SEQUENCE: 261

| | | | | | |
|---|---|---|---|---|---|
| gaggtgcagc | tgttggagtc | tgggggaggc | ttggtacagc | ctgggggtc | cctgagactc | 60 |
| tcctgtgcag | cctctggatt | cacctttagc | agctatgcca | tgaactgggt | ccgccaggct | 120 |
| ccagggaagg | gcctggagtg | ggtctcagct | attactatta | gtggtattac | cgcatactac | 180 |

```
accgactccg tgaagggccg gttcaccatc tccagagaca attccaagaa cacgctatat    240
ctgcaaatga acagcctgag ggccgaggac acggccgtat attactgtgc gaaggaagaa    300 ttttacctg aacgcacta ctactacggt atggacgtct ggggccaagg gaccacggtc    360
accgtctcct ca                                                      372
```

<210> SEQ ID NO 262
<211> LENGTH: 246
<212> TYPE: PRT
<213> ORGANISM: Artificial Sequence
<220> FEATURE:
<223> OTHER INFORMATION: Psl0096(5-G4s)

<400> SEQUENCE: 262

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Pro Tyr
            20                  25                  30

Tyr Trp Thr Trp Ile Arg Gln Pro Pro Gly Lys Cys Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

Lys Leu Ser Ser Val Thr Ala Ala Asp Thr Ala Val Tyr Tyr Cys Ala
                85                  90                  95

Arg Ala Asp Trp Asp Arg Leu Arg Ala Leu Asp Ile Trp Gly Gln Gly
            100                 105                 110

Thr Met Val Thr Val Ser Ser Gly Gly Gly Gly Ser Gly Gly Gly Gly
        115                 120                 125

Ser Gly Gly Gly Gly Ser Gly Gly Gly Gly Ser Asp Ile Gln Leu Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Ser Ile Arg Ser His Leu Asn Trp Tyr Gln
                165                 170                 175

Gln Lys Pro Gly Lys Ala Pro Lys Leu Leu Ile Tyr Gly Ala Ser Asn
            180                 185                 190

Leu Gln Ser Gly Val Pro Ser Arg Phe Ser Gly Ser Gly Ser Gly Thr
        195                 200                 205

Asp Phe Thr Leu Thr Ile Ser Ser Leu Gln Pro Glu Asp Phe Ala Thr
    210                 215                 220

Tyr Tyr Cys Gln Gln Ser Thr Gly Ala Trp Asn Trp Phe Gly Cys Gly
225                 230                 235                 240

Thr Lys Val Glu Ile Lys
                245
```

<210> SEQ ID NO 263
<211> LENGTH: 214
<212> TYPE: PRT
<213> ORGANISM: Artificial Sequence
<220> FEATURE:
<223> OTHER INFORMATION: Bs4-GLO LC

<400> SEQUENCE: 263

```
Ala Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ser Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 264
<211> LENGTH: 720
<212> TYPE: PRT
<213> ORGANISM: Artificial Sequence
<220> FEATURE:
<223> OTHER INFORMATION: Bs4-GLO HC

<400> SEQUENCE: 264

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Thr Met Ser Gly Ile Thr Ala Tyr Tyr Thr Asp Asp Val
50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Glu Phe Leu Pro Gly Thr His Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160
```

-continued

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Arg Val Glu Pro
            210                 215                 220

Lys Ser Cys Gly Gly Gly Gly Ser Gly Gly Gly Gly Ser Gln Val Gln
225                 230                 235                 240

Leu Gln Glu Ser Gly Pro Gly Leu Val Lys Pro Ser Glu Thr Leu Ser
            245                 250                 255

Leu Thr Cys Thr Val Ser Gly Gly Ser Ile Ser Pro Tyr Tyr Trp Thr
            260                 265                 270

Trp Ile Arg Gln Pro Pro Gly Lys Cys Leu Glu Leu Ile Gly Tyr Ile
            275                 280                 285

His Ser Ser Gly Tyr Thr Asp Tyr Asn Pro Ser Leu Lys Ser Arg Val
            290                 295                 300

Thr Ile Ser Gly Asp Thr Ser Lys Lys Gln Phe Ser Leu Lys Leu Ser
305                 310                 315                 320

Ser Val Thr Ala Ala Asp Thr Ala Val Tyr Tyr Cys Ala Arg Ala Asp
            325                 330                 335

Trp Asp Arg Leu Arg Ala Leu Asp Ile Trp Gly Gln Gly Thr Met Val
            340                 345                 350

Thr Val Ser Ser Gly Gly Gly Gly Ser Gly Gly Gly Gly Ser Gly Gly
            355                 360                 365

Gly Gly Ser Gly Gly Gly Gly Ser Asp Ile Gln Leu Thr Gln Ser Pro
            370                 375                 380

Ser Ser Leu Ser Ala Ser Val Gly Asp Arg Val Thr Ile Thr Cys Arg
385                 390                 395                 400

Ala Ser Gln Ser Ile Arg Ser His Leu Asn Trp Tyr Gln Gln Lys Pro
            405                 410                 415

Gly Lys Ala Pro Lys Leu Leu Ile Tyr Gly Ala Ser Asn Leu Gln Ser
            420                 425                 430

Gly Val Pro Ser Arg Phe Ser Gly Ser Gly Ser Gly Thr Asp Phe Thr
            435                 440                 445

Leu Thr Ile Ser Ser Leu Gln Pro Glu Asp Phe Ala Thr Tyr Tyr Cys
            450                 455                 460

Gln Gln Ser Thr Gly Ala Trp Asn Trp Phe Gly Cys Gly Thr Lys Val
465                 470                 475                 480

Glu Ile Lys Gly Gly Gly Gly Ser Gly Gly Gly Gly Ser Asp Lys Thr
            485                 490                 495

His Thr Cys Pro Pro Cys Pro Ala Pro Glu Leu Leu Gly Gly Pro Ser
            500                 505                 510

Val Phe Leu Phe Pro Pro Lys Pro Lys Asp Thr Leu Met Ile Ser Arg
            515                 520                 525

Thr Pro Glu Val Thr Cys Val Val Val Asp Val Ser His Glu Asp Pro
530                 535                 540

Glu Val Lys Phe Asn Trp Tyr Val Asp Gly Val Glu Val His Asn Ala
545                 550                 555                 560

Lys Thr Lys Pro Arg Glu Glu Gln Tyr Asn Ser Thr Tyr Arg Val Val
            565                 570                 575

```
Ser Val Leu Thr Val Leu His Gln Asp Trp Leu Asn Gly Lys Glu Tyr
            580                 585                 590
Lys Cys Lys Val Ser Asn Lys Ala Leu Pro Ala Pro Ile Glu Lys Thr
        595                 600                 605
Ile Ser Lys Ala Lys Gly Gln Pro Arg Glu Pro Gln Val Tyr Thr Leu
    610                 615                 620
Pro Pro Ser Arg Glu Glu Met Thr Lys Asn Gln Val Ser Leu Thr Cys
625                 630                 635                 640
Leu Val Lys Gly Phe Tyr Pro Ser Asp Ile Ala Val Glu Trp Glu Ser
                645                 650                 655
Asn Gly Gln Pro Glu Asn Asn Tyr Lys Thr Thr Pro Pro Val Leu Asp
            660                 665                 670
Ser Asp Gly Ser Phe Phe Leu Tyr Ser Lys Leu Thr Val Asp Lys Ser
        675                 680                 685
Arg Trp Gln Gln Gly Asn Val Phe Ser Cys Ser Val Met His Glu Ala
    690                 695                 700
Leu His Asn His Tyr Thr Gln Lys Ser Leu Ser Leu Ser Pro Gly Lys
705                 710                 715                 720

<210> SEQ ID NO 265
<211> LENGTH: 642
<212> TYPE: DNA
<213> ORGANISM: Artificial Sequence
<220> FEATURE:
<223> OTHER INFORMATION: Bs4-GLO LC

<400> SEQUENCE: 265
gccatccaga tgacccagtc tccatcctcc ctgtctgcat ctgtaggaga cagagtcacc      60
atcacttgcc gggcaagtca gggcattaga aatgatttag ctggtatcaa cagaagcca     120
gggaaagccc ctaaactcct gatctattct gcatccactt tacaaagtgg ggtcccatca    180
aggttcagcg gcagtggatc tggcacagat ttcactctca ccatcagcag cctgcagcct    240
gaggattttg caacttatta ctgtctacaa gattacaatt cccgtggac gttcggccaa     300
gggaccaagg ttgaaatcaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642

<210> SEQ ID NO 266
<211> LENGTH: 2160
<212> TYPE: DNA
<213> ORGANISM: Artificial Sequence
<220> FEATURE:
<223> OTHER INFORMATION: Bs4-GLO HC

<400> SEQUENCE: 266
gaggtgcagc tgttggagtc tgggggaggc ttggtacagc ctgggggtc cctgagactc      60
tcctgtgcag cctctggatt cacctttagc agctatgcca tgaactgggt ccgccaggct    120
ccagggaagg ggctggagtg ggtctcagct attactatga gtggtattac cgcatactac    180
accgacgacg tgaagggccg gttcaccatc tccagagaca attccaagaa cacgctatat    240
ctgcaaatga acagcctgag ggccgaggac acggccgtat attactgtgc gaaggaagaa    300
```

```
tttttacctg aacgcacta ctactacggt atggacgtct ggggccaagg gaccacggtc      360
accgtctcct cagcgtcgac caagggccca tccgtcttcc ccctggcacc ctcctccaag      420
agcacctctg ggggcacagc ggccctgggc tgcctggtca aggactactt ccccgaaccg      480
gtgacggtgt cctggaactc aggcgctctg accagcggcg tgcacacctt ccggctgtc       540
ctacagtcct caggactcta ctccctcagc agcgtggtga ccgtgccctc agcagcttg       600
ggcacccaga cctacatctg caacgtgaat cacaagccca gcaacaccaa ggtggacaag      660
agagttgagc ccaaatcttg tggcggaggg ggctctggcg agggggatc ccaggtgcag       720
ctgcaggaat ctggccctgg cctcgtgaag ccctccgaga cactgtctct gacctgcacc      780
gtgtccggcg gctccatctc cccttactac tggacctgga tcagacagcc ccctggcaag     840
tgcctggaac tgatcggcta catccactcc tccggctaca ccgactacaa ccccagcctg     900
aagtccagag tgaccatctc cggcgacacc tccaagaagc agttctccct gaagctgtcc     960
tccgtgaccg ccgctgatac cgccgtgtac tactgcgcca gagccgactg ggacagactg    1020
agagccctgg acatctgggg ccagggcaca atggtcaccg tgtctagcgg aggcggagga    1080
tctggtggtg gtggatctgg cggcggagga agtggtggcg gaggctctga tatccagctg    1140
acccagtccc cctccagcct gtctgcttct gtgggcgacc gcgtgaccat cacctgtaga    1200
gcctcccagt ccatccggtc ccacctgaac tggtatcagc agaagcccgg caaggccccc    1260
aagctgctga tctacggcgc ctccaatctg cagtccggcg tgccctctag attctccgga    1320
tctggctccg gcaccgactt taccctgacc atcagctccc tgcagcccga ggacttcgcc    1380
acctactact gccagcagtc taccggcgcc tggaattggt tcggctgcgg caccaaggtg    1440
gaaatcaagg gcggaggtgg ctctggcgga ggggatccg acaaaactca cacatgccca    1500
ccgtgcccag cacctgaact cctgggggga ccgtcagtct tcctcttccc cccaaaaccc     1560
aaggacaccc tcatgatctc ccggaccccct gaggtcacat gcgtggtggt ggacgtgagc    1620
cacgaagacc ctgaggtcaa gttcaactgg tacgtggacg gcgtggaggt gcataatgcc    1680
aagacaaagc cgcgggagga gcagtacaac agcacgtacc gtgtggtcag cgtcctcacc    1740
gtcctgcacc aggactggct gaatggcaag gagtacaagt gcaaggtctc caacaaagcc    1800
ctcccagccc ccatcgagaa aaccatctcc aaagccaaag gcagccccg agaaccacag    1860
gtctacaccc tgccccccatc ccgggaggag atgaccaaga accaggtcag cctgacctgc    1920
ctggtcaaag gcttctatcc cagcgacatc gccgtggagt gggagagcaa tgggcagccg    1980
gagaacaact acaagaccac gcctcccgtg ctggactccg acggctcctt cttcctctat    2040
agcaagctca ccgtggacaa gagcaggtgg cagcagggga acgtcttctc atgctccgtg    2100
atgcatgagg ctctgcacaa ccactacacg cagaagagct taagcctgtc tccgggtaaa    2160
```

<210> SEQ ID NO 267
<211> LENGTH: 11
<212> TYPE: PRT
<213> ORGANISM: Artificial Sequence
<220> FEATURE:
<223> OTHER INFORMATION: Psl0225-Germline VHCDR3

<400> SEQUENCE: 267

Ala Met Asp Ile Glu Pro His Ala Leu Asp Ile
1               5                   10

<210> SEQ ID NO 268
<211> LENGTH: 11
<212> TYPE: PRT

```
<213> ORGANISM: Artificial Sequence
<220> FEATURE:
<223> OTHER INFORMATION: Psl0588-Germline VHCDR3

<400> SEQUENCE: 268

Ala Asp Asp Pro Phe Pro Gly Tyr Leu Asp Ile
1               5                   10

<210> SEQ ID NO 269
<211> LENGTH: 11
<212> TYPE: PRT
<213> ORGANISM: Artificial Sequence
<220> FEATURE:
<223> OTHER INFORMATION: Psl0567-Germline VHCDR3

<400> SEQUENCE: 269

Ala Asp Trp Asn Glu Gly Arg Lys Leu Asp Ile
1               5                   10

<210> SEQ ID NO 270
<211> LENGTH: 11
<212> TYPE: PRT
<213> ORGANISM: Artificial Sequence
<220> FEATURE:
<223> OTHER INFORMATION: Psl0337-Germline VHCDR3

<400> SEQUENCE: 270

Ala Asp Trp Asp His Lys His Ala Leu Asp Ile
1               5                   10

<210> SEQ ID NO 271
<211> LENGTH: 11
<212> TYPE: PRT
<213> ORGANISM: Artificial Sequence
<220> FEATURE:
<223> OTHER INFORMATION: Psl0170 VHCDR3

<400> SEQUENCE: 271

Ala Thr Asp Glu Ala Asp His Ala Leu Asp Ile
1               5                   10

<210> SEQ ID NO 272
<211> LENGTH: 11
<212> TYPE: PRT
<213> ORGANISM: Artificial Sequence
<220> FEATURE:
<223> OTHER INFORMATION: Psl0304 VHCDR3

<400> SEQUENCE: 272

Ala Asp Trp Ser Gly Thr Arg Ala Leu Asp Ile
1               5                   10

<210> SEQ ID NO 273
<211> LENGTH: 11
<212> TYPE: PRT
<213> ORGANISM: Artificial Sequence
<220> FEATURE:
<223> OTHER INFORMATION: Psl0348 VHCDR3

<400> SEQUENCE: 273

Gly Leu Pro Glu Lys Pro His Ala Leu Asp Ile
1               5                   10

<210> SEQ ID NO 274
<211> LENGTH: 11
<212> TYPE: PRT
<213> ORGANISM: Artificial Sequence
```

```
<220> FEATURE:
<223> OTHER INFORMATION: Ps10573 VHCDR3

<400> SEQUENCE: 274

Ser Leu Phe Thr Asp Asp His Ala Leu Asp Ile
1               5                   10

<210> SEQ ID NO 275
<211> LENGTH: 11
<212> TYPE: PRT
<213> ORGANISM: Artificial Sequence
<220> FEATURE:
<223> OTHER INFORMATION: Ps10574 VHCDR3

<400> SEQUENCE: 275

Ala Ser Pro Gly Val Val His Ala Leu Asp Ile
1               5                   10

<210> SEQ ID NO 276
<211> LENGTH: 11
<212> TYPE: PRT
<213> ORGANISM: Artificial Sequence
<220> FEATURE:
<223> OTHER INFORMATION: Ps10582 VHCDR3

<400> SEQUENCE: 276

Ala His Ile Glu Ser His His Ala Leu Asp Ile
1               5                   10

<210> SEQ ID NO 277
<211> LENGTH: 11
<212> TYPE: PRT
<213> ORGANISM: Artificial Sequence
<220> FEATURE:
<223> OTHER INFORMATION: Ps10584 VHCDR3

<400> SEQUENCE: 277

Ala Thr Gln Ala Pro Ala His Ala Leu Asp Ile
1               5                   10

<210> SEQ ID NO 278
<211> LENGTH: 11
<212> TYPE: PRT
<213> ORGANISM: Artificial Sequence
<220> FEATURE:
<223> OTHER INFORMATION: Ps10585 VHCDR3

<400> SEQUENCE: 278

Ser Gln His Asp Leu Glu His Ala Leu Asp Ile
1               5                   10

<210> SEQ ID NO 279
<211> LENGTH: 11
<212> TYPE: PRT
<213> ORGANISM: Artificial Sequence
<220> FEATURE:
<223> OTHER INFORMATION: Ps10589 VHCDR3

<400> SEQUENCE: 279

Ala Met Pro Asp Met Pro His Ala Leu Asp Ile
1               5                   10

<210> SEQ ID NO 280
<211> LENGTH: 9
<212> TYPE: PRT
<213> ORGANISM: Artificial Sequence
<220> FEATURE:
```

<223> OTHER INFORMATION: Psl0096-Germline VLCDR3

<400> SEQUENCE: 280

Gln Gln Ser Thr Gly Ala Trp Asn Trp
1               5

<210> SEQ ID NO 281
<211> LENGTH: 9
<212> TYPE: PRT
<213> ORGANISM: Artificial Sequence
<220> FEATURE:
<223> OTHER INFORMATION: Psl0225 VLCDR3

<400> SEQUENCE: 281

Gln Gln Asp Phe Phe His Gly Pro Asn
1               5

<210> SEQ ID NO 282
<211> LENGTH: 9
<212> TYPE: PRT
<213> ORGANISM: Artificial Sequence
<220> FEATURE:
<223> OTHER INFORMATION: Psl0588 VLCDR3

<400> SEQUENCE: 282

Gln Gln Ser Asp Thr Phe Pro Leu Lys
1               5

<210> SEQ ID NO 283
<211> LENGTH: 9
<212> TYPE: PRT
<213> ORGANISM: Artificial Sequence
<220> FEATURE:
<223> OTHER INFORMATION: Psl0337 VLCDR3

<400> SEQUENCE: 283

Gln Asp Ser Ser Ser Trp Pro Leu Thr
1               5

<210> SEQ ID NO 284
<211> LENGTH: 9
<212> TYPE: PRT
<213> ORGANISM: Artificial Sequence
<220> FEATURE:
<223> OTHER INFORMATION: Psl0170 VLCDR3

<400> SEQUENCE: 284

Ser Gln Ser Asp Thr Phe Pro Leu Thr
1               5

<210> SEQ ID NO 285
<211> LENGTH: 9
<212> TYPE: PRT
<213> ORGANISM: Artificial Sequence
<220> FEATURE:
<223> OTHER INFORMATION: Psl0304 VLCDR3

<400> SEQUENCE: 285

Gly Gln Ser Asp Ala Phe Pro Leu Thr
1               5

<210> SEQ ID NO 286
<211> LENGTH: 9
<212> TYPE: PRT
<213> ORGANISM: Artificial Sequence
<220> FEATURE:
<223> OTHER INFORMATION: Psl0348 VLCDR3

```
<400> SEQUENCE: 286

Leu Gln Gly Asp Leu Trp Pro Leu Thr
1               5

<210> SEQ ID NO 287
<211> LENGTH: 9
<212> TYPE: PRT
<213> ORGANISM: Artificial Sequence
<220> FEATURE:
<223> OTHER INFORMATION: Psl0589 VLCDR3

<400> SEQUENCE: 287

Gln Gln Ser Leu Glu Phe Pro Leu Thr
1               5

<210> SEQ ID NO 288
<211> LENGTH: 119
<212> TYPE: PRT
<213> ORGANISM: Artificial Sequence
<220> FEATURE:
<223> OTHER INFORMATION: Psl0096-Germline VH
<220> FEATURE:
<221> NAME/KEY: misc_feature
<222> LOCATION: (44)..(44)
<223> OTHER INFORMATION: Xaa is Gly or Cys

<400> SEQUENCE: 288

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Pro Tyr
            20                  25                  30

Tyr Trp Thr Trp Ile Arg Gln Pro Pro Gly Lys Xaa Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

Lys Leu Ser Ser Val Thr Ala Ala Asp Thr Ala Val Tyr Tyr Cys Ala
                85                  90                  95

Arg Ala Asp Trp Asp Arg Leu Arg Ala Leu Asp Ile Trp Gly Gln Gly
            100                 105                 110

Thr Met Val Thr Val Ser Ser
        115

<210> SEQ ID NO 289
<211> LENGTH: 107
<212> TYPE: PRT
<213> ORGANISM: Artificial Sequence
<220> FEATURE:
<223> OTHER INFORMATION: Psl0096-Germline VL
<220> FEATURE:
<221> NAME/KEY: misc_feature
<222> LOCATION: (100)..(100)
<223> OTHER INFORMATION: Xaa can be Gly or Cys

<400> SEQUENCE: 289

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Arg Ser His
            20                  25                  30

Leu Asn Trp Tyr Gln Gln Lys Pro Gly Lys Ala Pro Lys Leu Leu Ile
        35                  40                  45
```

```
Tyr Gly Ala Ser Asn Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Thr Gly Ala Trp Asn
                 85                  90                  95

Trp Phe Gly Xaa Gly Thr Lys Val Glu Ile Lys
            100                 105
```

<210> SEQ ID NO 290
<211> LENGTH: 119
<212> TYPE: PRT
<213> ORGANISM: Artificial Sequence
<220> FEATURE:
<223> OTHER INFORMATION: Psl0225-Germline VH

<400> SEQUENCE: 290

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Pro Tyr
             20                  25                  30

Tyr Trp Thr Trp Ile Arg Gln Pro Pro Gly Lys Gly Leu Glu Leu Ile
         35                  40                  45

Gly Tyr Ile His Ser Ser Gly Tyr Thr Asp Tyr Asn Pro Ser Leu Lys
     50                  55                  60

Ser Arg Val Thr Ile Ser Gly Asp Thr Ser Lys Lys Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Met Asp Ile Glu Pro His Ala Leu Asp Ile Trp Gly Gln Gly
            100                 105                 110

Thr Met Val Thr Val Ser Ser
        115
```

<210> SEQ ID NO 291
<211> LENGTH: 107
<212> TYPE: PRT
<213> ORGANISM: Artificial Sequence
<220> FEATURE:
<223> OTHER INFORMATION: Psl0225-Germline VL

<400> SEQUENCE: 291

```
Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Ser Ile Arg Ser His
             20                  25                  30

Leu Asn Trp Tyr Gln Gln Lys Pro Gly Lys Ala Pro Lys Leu Leu Ile
         35                  40                  45

Tyr Gly Ala Ser Asn Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asp Asp Gly Phe Pro
                 85                  90                  95

Asn Phe Gly Gly Gly Thr Lys Val Glu Ile Lys
            100                 105
```

```
<210> SEQ ID NO 292
<211> LENGTH: 119
<212> TYPE: PRT
<213> ORGANISM: Artificial Sequence
<220> FEATURE:
<223> OTHER INFORMATION: Psl0588-Germline VH

<400> SEQUENCE: 292
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

Lys Leu Ser Ser Val Thr Ala Ala Asp Thr Ala Val Tyr Tyr Cys Ala
                85                  90                  95

Arg Ala Asp Asp Pro Phe Pro Gly Tyr Leu Asp Ile Trp Gly Gln Gly
            100                 105                 110

Thr Met Val Thr Val Ser Ser
        115

```
<210> SEQ ID NO 293
<211> LENGTH: 107
<212> TYPE: PRT
<213> ORGANISM: Artificial Sequence
<220> FEATURE:
<223> OTHER INFORMATION: Psl0588-Germline VH

<400> SEQUENCE: 293
```

Asp Ile Gln Leu Thr Gln Ser Pro Ser Leu Ser Ala Ser Val Gly
1               5                   10                  15

Asp Arg Val Thr Ile Thr Cys Arg Ala Ser Gln Ser Ile Arg Ser His
            20                  25                  30

Leu Asn Trp Tyr Gln Gln Lys Pro Gly Lys Ala Pro Lys Leu Leu Ile
        35                  40                  45

Tyr Gly Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Thr Phe Pro Leu
                85                  90                  95

Lys Phe Gly Gly Gly Thr Lys Val Glu Ile Lys
            100                 105

```
<210> SEQ ID NO 294
<211> LENGTH: 119
<212> TYPE: PRT
<213> ORGANISM: Artificial Sequence
<220> FEATURE:
<223> OTHER INFORMATION: Psl0567-Germline VL

<400> SEQUENCE: 294
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Pro Tyr
            20                  25                  30

```
Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

Lys Leu Ser Ser Val Thr Ala Ala Asp Thr Ala Val Tyr Tyr Cys Ala
                85                  90                  95

Arg Ala Asp Trp Asn Glu Gly Arg Lys Leu Asp Ile Trp Gly Gln Gly
            100                 105                 110

Thr Met Val Thr Val Ser Ser
        115

<210> SEQ ID NO 295
<211> LENGTH: 119
<212> TYPE: PRT
<213> ORGANISM: Artificial Sequence
<220> FEATURE:
<223> OTHER INFORMATION: Psl0337-Germline VH

<400> SEQUENCE: 295

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

Lys Leu Ser Ser Val Thr Ala Ala Asp Thr Ala Val Tyr Tyr Cys Ala
                85                  90                  95

Arg Ala Asp Trp Asp His Lys His Ala Leu Asp Ile Trp Gly Gln Gly
            100                 105                 110

Thr Met Val Thr Val Ser Ser
        115

<210> SEQ ID NO 296
<211> LENGTH: 107
<212> TYPE: PRT
<213> ORGANISM: Artificial Sequence
<220> FEATURE:
<223> OTHER INFORMATION: Psl0337-Germline VL

<400> SEQUENCE: 296

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Arg Ser His
            20                  25                  30

Leu Asn Trp Tyr Gln Gln Lys Pro Gly Lys Ala Pro Lys Leu Leu Ile
        35                  40                  45

Tyr Gly Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asp Ser Ser Ser Trp Pro Leu
```

```
                    85                  90                  95

Thr Phe Gly Gly Gly Thr Lys Val Glu Ile Lys
                100                 105

<210> SEQ ID NO 297
<211> LENGTH: 119
<212> TYPE: PRT
<213> ORGANISM: Artificial Sequence
<220> FEATURE:
<223> OTHER INFORMATION: Psl0170- VH

<400> SEQUENCE: 297

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Thr Asp Glu Ala Asp His Ala Leu Asp Ile Trp Gly Gln Gly
            100                 105                 110

Thr Leu Val Thr Val Ser Ser
        115

<210> SEQ ID NO 298
<211> LENGTH: 107
<212> TYPE: PRT
<213> ORGANISM: Artificial Sequence
<220> FEATURE:
<223> OTHER INFORMATION: Psl0170- VL

<400> SEQUENCE: 298

Glu Ile Val Leu Thr Gln Ser Pro Ser Ser Leu Ser Thr Ser Val Gly
1               5                   10                  15

Asp Arg Val Thr Ile Thr Cys Arg Ala Ser Gln Ser Ile Arg Ser His
            20                  25                  30

Leu Asn Trp Tyr Gln Gln Lys Pro Gly Lys Ala Pro Lys Leu Leu Ile
        35                  40                  45

Tyr Gly Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ser Gln Ser Asp Thr Phe Pro Leu
                85                  90                  95

Thr Phe Gly Gly Gly Thr Lys Leu Glu Ile Lys
            100                 105

<210> SEQ ID NO 299
<211> LENGTH: 119
<212> TYPE: PRT
<213> ORGANISM: Artificial Sequence
<220> FEATURE:
<223> OTHER INFORMATION: Psl10304- VH

<400> SEQUENCE: 299
```

```
Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65              70                  75                  80

His Val Ser Ser Val Thr Ala Ala Asp Thr Ala Val Tyr Phe Cys Ala
            85                  90                  95

Arg Ala Asp Trp Ser Gly Thr Arg Ala Leu Asp Ile Trp Gly Gln Gly
            100                 105                 110

Thr Leu Val Thr Val Ser Ser
            115

<210> SEQ ID NO 300
<211> LENGTH: 107
<212> TYPE: PRT
<213> ORGANISM: Artificial Sequence
<220> FEATURE:
<223> OTHER INFORMATION: Psl0304- VL

<400> SEQUENCE: 300

Glu Ile Val Leu Thr Gln Ser Pro Ser Ser Leu Ser Thr Ser Val Gly
1               5                   10                  15

Asp Arg Val Thr Ile Thr Cys Trp Ala Ser Gln Ser Ile Arg Ser His
            20                  25                  30

Leu Asn Trp Tyr Gln Gln Lys Pro Gly Lys Ala Pro Lys Leu Leu Ile
        35                  40                  45

Tyr Gly Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gly Gln Ser Asp Ala Phe Pro Leu
            85                  90                  95

Thr Phe Gly Gly Gly Thr Lys Leu Glu Ile Lys
            100                 105

<210> SEQ ID NO 301
<211> LENGTH: 119
<212> TYPE: PRT
<213> ORGANISM: Artificial Sequence
<220> FEATURE:
<223> OTHER INFORMATION: Psl0348- VL

<400> SEQUENCE: 301

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
```

```
                65                  70                  75                  80
His Val Ser Ser Val Thr Ala Ala Asp Thr Ala Val Tyr Phe Cys Ala
                    85                  90                  95

Arg Gly Leu Pro Glu Lys Pro His Ala Leu Asp Ile Trp Gly Gln Gly
                100                 105                 110

Thr Leu Val Thr Val Ser Ser
            115

<210> SEQ ID NO 302
<211> LENGTH: 107
<212> TYPE: PRT
<213> ORGANISM: Artificial Sequence
<220> FEATURE:
<223> OTHER INFORMATION: Psl0348- VL

<400> SEQUENCE: 302

Glu Ile Val Leu Thr Gln Ser Pro Ser Ser Leu Ser Thr Ser Val Gly
1               5                   10                  15

Asp Arg Val Thr Ile Thr Cys Arg Ala Ser Gln Ser Ile Arg Ser His
                20                  25                  30

Leu Asn Trp Tyr Gln Gln Lys Pro Gly Lys Ala Pro Lys Leu Leu Ile
            35                  40                  45

Tyr Gly Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Gly Asp Leu Trp Pro Leu
                85                  90                  95

Thr Phe Gly Gly Gly Thr Lys Leu Glu Ile Lys
                100                 105

<210> SEQ ID NO 303
<211> LENGTH: 119
<212> TYPE: PRT
<213> ORGANISM: Artificial Sequence
<220> FEATURE:
<223> OTHER INFORMATION: Psl0573- VH

<400> SEQUENCE: 303

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
                20                  25                  30

Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Pro Ser Leu Lys
        50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ser Leu Phe Thr Asp Asp His Ala Leu Asp Ile Trp Gly Gln Gly
                100                 105                 110

Thr Leu Val Thr Val Ser Ser
            115

<210> SEQ ID NO 304
<211> LENGTH: 119
```

```
<212> TYPE: PRT
<213> ORGANISM: Artificial Sequence
<220> FEATURE:
<223> OTHER INFORMATION: Ps10574- VH

<400> SEQUENCE: 304

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Ser Pro Gly Val Val His Ala Leu Asp Ile Trp Gly Gln Gly
            100                 105                 110

Thr Leu Val Thr Val Ser Ser
        115

<210> SEQ ID NO 305
<211> LENGTH: 119
<212> TYPE: PRT
<213> ORGANISM: Artificial Sequence
<220> FEATURE:
<223> OTHER INFORMATION: Ps10582- VH

<400> SEQUENCE: 305

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala His Ile Glu Ser His His Ala Leu Asp Ile Trp Gly Gln Gly
            100                 105                 110

Thr Leu Val Thr Val Ser Ser
        115

<210> SEQ ID NO 306
<211> LENGTH: 119
<212> TYPE: PRT
<213> ORGANISM: Artificial Sequence
<220> FEATURE:
<223> OTHER INFORMATION: Ps10584- VH

<400> SEQUENCE: 306

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30
```

```
            20                  25                  30
Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Pro Ser Leu Lys
        50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Thr Gln Ala Pro Ala His Ala Leu Asp Ile Trp Gly Gln Gly
            100                 105                 110

Thr Leu Val Thr Val Ser Ser
        115

<210> SEQ ID NO 307
<211> LENGTH: 119
<212> TYPE: PRT
<213> ORGANISM: Artificial Sequence
<220> FEATURE:
<223> OTHER INFORMATION: Psl0585- VH

<400> SEQUENCE: 307

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Pro Ser Leu Lys
        50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ser Gln His Asp Leu Glu His Ala Leu Asp Ile Trp Gly Gln Gly
            100                 105                 110

Thr Leu Val Thr Val Ser Ser
        115

<210> SEQ ID NO 308
<211> LENGTH: 119
<212> TYPE: PRT
<213> ORGANISM: Artificial Sequence
<220> FEATURE:
<223> OTHER INFORMATION: Psl0589- VH

<400> SEQUENCE: 308

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Pro Ser Leu Lys
        50                  55                  60

Ser Arg Val Thr Ile Ser Gly Asp Thr Ser Lys Lys Gln Phe Ser Leu
65                  70                  75                  80
```

-continued

His Val Ser Ser Val Thr Ala Ala Asp Thr Ala Val Tyr Phe Cys Ala
                85                  90                  95

Arg Ala Met Pro Asp Met Pro His Ala Leu Asp Ile Trp Gly Gln Gly
            100                 105                 110

Thr Leu Val Thr Val Ser Ser
        115

<210> SEQ ID NO 309
<211> LENGTH: 119
<212> TYPE: PRT
<213> ORGANISM: Artificial Sequence
<220> FEATURE:
<223> OTHER INFORMATION: WapR-004 Germline VH

<400> SEQUENCE: 309

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65              70                  75                  80

Lys Leu Ser Ser Val Thr Ala Ala Asp Thr Ala Val Tyr Tyr Cys Ala
                85                  90                  95

Arg Ala Asp Trp Asp Leu Leu His Ala Leu Asp Ile Trp Gly Gln Gly
            100                 105                 110

Thr Met Val Thr Val Ser Ser
        115

<210> SEQ ID NO 310
<211> LENGTH: 107
<212> TYPE: PRT
<213> ORGANISM: Artificial Sequence
<220> FEATURE:
<223> OTHER INFORMATION: WapR-004 Germline VL

<400> SEQUENCE: 310

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Arg Ser His
            20                  25                  30

Leu Asn Trp Tyr Gln Gln Lys Pro Gly Lys Ala Pro Lys Leu Leu Ile
        35                  40                  45

Tyr Gly Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Ser Tyr Ser Phe Pro Leu
                85                  90                  95

Thr Phe Gly Gly Gly Thr Lys Val Glu Ile Lys
            100                 105

<210> SEQ ID NO 311
<211> LENGTH: 5
<212> TYPE: PRT
<213> ORGANISM: Artificial Sequence

```
<220> FEATURE:
<223> OTHER INFORMATION: 29D2 VHCDR1

<400> SEQUENCE: 311

Ser Tyr Ala Met Ser
1               5

<210> SEQ ID NO 312
<211> LENGTH: 17
<212> TYPE: PRT
<213> ORGANISM: Artificial Sequence
<220> FEATURE:
<223> OTHER INFORMATION: 29D2 VHCDR2

<400> SEQUENCE: 312

Ala Ile Ser Gly Ser Gly Tyr Ser Thr Tyr Tyr Ala Asp Ser Val Lys
1               5                   10                  15

Gly

<210> SEQ ID NO 313
<211> LENGTH: 14
<212> TYPE: PRT
<213> ORGANISM: Artificial Sequence
<220> FEATURE:
<223> OTHER INFORMATION: 29D2 VHCDR3

<400> SEQUENCE: 313

Glu Tyr Ser Ile Ser Ser Asn Tyr Tyr Tyr Gly Met Asp Val
1               5                   10

<210> SEQ ID NO 314
<211> LENGTH: 11
<212> TYPE: PRT
<213> ORGANISM: Artificial Sequence
<220> FEATURE:
<223> OTHER INFORMATION: 29D2 VLCDR1

<400> SEQUENCE: 314

Trp Ala Ser Gln Gly Ile Ser Ser Tyr Leu Ala
1               5                   10

<210> SEQ ID NO 315
<211> LENGTH: 8
<212> TYPE: PRT
<213> ORGANISM: Artificial Sequence
<220> FEATURE:
<223> OTHER INFORMATION: 29D2 VLCDR2

<400> SEQUENCE: 315

Ala Ala Ser Thr Leu Gln Ser Ala
1               5

<210> SEQ ID NO 316
<211> LENGTH: 9
<212> TYPE: PRT
<213> ORGANISM: Artificial Sequence
<220> FEATURE:
<223> OTHER INFORMATION: 29D2 VLCDR3

<400> SEQUENCE: 316

Gln Gln Leu Asn Ser Ser Pro Leu Thr
1               5

<210> SEQ ID NO 317
<211> LENGTH: 123
<212> TYPE: PRT
```

<213> ORGANISM: Artificial Sequence
<220> FEATURE:
<223> OTHER INFORMATION: 29D2 VH

<400> SEQUENCE: 317

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Tyr Ser Thr Tyr Tyr Ala Asp Ser Val
    50                  55                  60

Lys Gly Arg Phe Thr Met Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Glu Tyr Ser Ile Ser Ser Asn Tyr Tyr Tyr Gly Met Asp Val
            100                 105                 110

Trp Gly Gln Gly Thr Thr Val Thr Val Ser Ser
        115                 120

<210> SEQ ID NO 318
<211> LENGTH: 107
<212> TYPE: PRT
<213> ORGANISM: Artificial Sequence
<220> FEATURE:
<223> OTHER INFORMATION: 29D2 VL

<400> SEQUENCE: 318

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Ser Pro Leu
                85                  90                  95

Thr Phe Gly Gly Gly Thr Lys Val Glu Ile Lys
            100                 105

<210> SEQ ID NO 319
<211> LENGTH: 98
<212> TYPE: PRT
<213> ORGANISM: Artificial Sequence
<220> FEATURE:
<223> OTHER INFORMATION: Bs4-GLO CH1 region

<400> SEQUENCE: 319

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

```
Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val

<210> SEQ ID NO 320
<211> LENGTH: 5
<212> TYPE: PRT
<213> ORGANISM: Artificial Sequence
<220> FEATURE:
<223> OTHER INFORMATION: Bs4-GLO H1 region

<400> SEQUENCE: 320

Glu Pro Lys Ser Cys
1               5

<210> SEQ ID NO 321
<211> LENGTH: 10
<212> TYPE: PRT
<213> ORGANISM: Artificial Sequence
<220> FEATURE:
<223> OTHER INFORMATION: Bs4-GLO H2 region

<400> SEQUENCE: 321

Asp Lys Thr His Thr Cys Pro Pro Cys Pro
1               5                   10

<210> SEQ ID NO 322
<211> LENGTH: 217
<212> TYPE: PRT
<213> ORGANISM: Artificial Sequence
<220> FEATURE:
<223> OTHER INFORMATION: Bs4-GLO CH2CH3 region
<220> FEATURE:
<221> NAME/KEY: misc_feature
<222> LOCATION: (22)..(22)
<223> OTHER INFORMATION: Xaa is Met or Tyr
<220> FEATURE:
<221> NAME/KEY: misc_feature
<222> LOCATION: (24)..(24)
<223> OTHER INFORMATION: Xaa is Ser or Thr
<220> FEATURE:
<221> NAME/KEY: misc_feature
<222> LOCATION: (26)..(26)
<223> OTHER INFORMATION: Xaa is Thr or Glu

<400> SEQUENCE: 322

Ala Pro Glu Leu Leu Gly Gly Pro Ser Val Phe Leu Phe Pro Pro Lys
1               5                   10                  15

Pro Lys Asp Thr Leu Xaa Ile Xaa Arg Xaa Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
         50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
```

```
               100                 105                 110
Pro Arg Glu Pro Gln Val Tyr Thr Leu Pro Pro Ser Arg Glu Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Ser Leu Asp Ser Asp Gly Ser Phe Phe Leu
            165                 170                 175

Tyr Ser Lys Leu Thr Val Asp Lys Ser Arg Trp Gln Gln Gly Asn Val
        180                 185                 190

Phe Ser Cys Ser Val Met His Glu Ala Leu His Asn His Tyr Thr Gln
            195                 200                 205

Lys Ser Leu Ser Leu Ser Pro Gly Lys
        210                 215

<210> SEQ ID NO 323
<211> LENGTH: 107
<212> TYPE: PRT
<213> ORGANISM: Artificial Sequence
<220> FEATURE:
<223> OTHER INFORMATION: Kappa LC

<400> SEQUENCE: 323

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
        100                 105

<210> SEQ ID NO 324
<211> LENGTH: 292
<212> TYPE: PRT
<213> ORGANISM: Artificial Sequence
<220> FEATURE:
<223> OTHER INFORMATION: W4-RAD scFv in Bs4 vector

<400> SEQUENCE: 324

Lys Val Asp Lys Arg Val Glu Pro Lys Ser Cys Gly Gly Gly Gly Ser
1               5                   10                  15

Gly Gly Gly Gly Ser Glu Val Gln Leu Glu Ser Gly Pro Gly Leu
            20                  25                  30

Val Lys Pro Ser Glu Thr Leu Ser Leu Thr Cys Asn Val Ala Gly Gly
        35                  40                  45

Ser Ile Ser Pro Tyr Tyr Trp Thr Trp Ile Arg Gln Pro Pro Gly Lys
50                  55                  60

Cys Leu Glu Leu Ile Gly Tyr Ile His Ser Ser Gly Tyr Thr Asp Tyr
65                  70                  75                  80
```

```
Asn Pro Ser Leu Lys Ser Arg Val Thr Ile Ser Gly Asp Thr Ser Lys
                 85                  90                  95

Lys Gln Phe Ser Leu His Val Ser Ser Val Thr Ala Ala Asp Thr Ala
            100                 105                 110

Val Tyr Phe Cys Ala Arg Ala Asp Trp Asp Leu Leu His Ala Leu Asp
            115                 120                 125

Ile Trp Gly Gln Gly Thr Leu Val Thr Val Ser Ser Gly Gly Gly Gly
130                 135                 140

Ser Gly Gly Gly Gly Ser Gly Gly Gly Ser Gly Gly Gly Gly Gly Ser
145                 150                 155                 160

Glu Ile Val Leu Thr Gln Ser Pro Ser Ser Leu Ser Thr Ser Val Gly
                165                 170                 175

Asp Arg Val Thr Ile Thr Cys Arg Ala Ser Gln Ser Ile Arg Ser His
                180                 185                 190

Leu Asn Trp Tyr Gln Gln Lys Pro Gly Lys Ala Pro Lys Leu Leu Ile
            195                 200                 205

Tyr Gly Ala Ser Asn Leu Gln Ser Gly Val Pro Ser Arg Phe Ser Gly
210                 215                 220

Ser Gly Ser Gly Thr Asp Phe Thr Leu Thr Ile Ser Ser Leu Gln Pro
225                 230                 235                 240

Glu Asp Phe Ala Thr Tyr Tyr Cys Gln Gln Ser Tyr Ser Phe Pro Leu
                245                 250                 255

Thr Phe Gly Cys Gly Thr Lys Leu Glu Ile Lys Gly Gly Gly Gly Ser
            260                 265                 270

Gly Gly Gly Gly Ser Asp Lys Thr His Thr Cys Pro Pro Cys Pro Ala
            275                 280                 285

Pro Glu Leu Leu
    290

<210> SEQ ID NO 325
<211> LENGTH: 107
<212> TYPE: PRT
<213> ORGANISM: Artificial Sequence
<220> FEATURE:
<223> OTHER INFORMATION: Ps10589 VL

<400> SEQUENCE: 325

Glu Ile Val Leu Thr Gln Ser Pro Ser Ser Leu Ser Thr Ser Val Gly
1               5                   10                  15

Asp Arg Val Thr Ile Thr Cys Arg Ala Ser Gln Ser Ile Arg Ser His
            20                  25                  30

Leu Asn Trp Tyr Gln Gln Lys Pro Gly Lys Ala Pro Lys Leu Leu Ile
        35                  40                  45

Tyr Gly Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Glu Phe Pro Leu
                85                  90                  95

Thr Phe Gly Gly Gly Thr Lys Leu Glu Ile Lys
            100                 105

<210> SEQ ID NO 326
<211> LENGTH: 25
<212> TYPE: PRT
<213> ORGANISM: Artificial Sequence
<220> FEATURE:
```

<223> OTHER INFORMATION: Linker

<400> SEQUENCE: 326

Gly Gly Gly Gly Ser Gly Gly Gly Ser Gly Gly Gly Ser Gly
1               5                   10                  15

Gly Gly Gly Ser Gly Gly Gly Gly Ser
            20                  25

<210> SEQ ID NO 327
<211> LENGTH: 214
<212> TYPE: PRT
<213> ORGANISM: Artificial Sequence
<220> FEATURE:
<223> OTHER INFORMATION: Bs4-V2L2-C2 VL

<400> SEQUENCE: 327

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Val Ile
        35                  40                  45

Tyr Ser Ala Ser Thr Leu Gln Ser Gly Val Pro Ser Arg Phe Ser Gly
    50                  55                  60

Ser Gly Ser Gly Thr Asp Phe Thr Leu Ser Ile Ser Ser Leu Gln Pro
65                  70                  75                  80

Asp Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 328
<211> LENGTH: 720
<212> TYPE: PRT
<213> ORGANISM: Artificial Sequence
<220> FEATURE:
<223> OTHER INFORMATION: Bs4-V2L2-C2 VL

<400> SEQUENCE: 328

Glu Met Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Glu Gly Leu Glu Trp Val

-continued

```
                35                  40                  45
Ser Ala Ile Thr Ile Ser Gly Ile Thr Ala Tyr Tyr Thr Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Gly Asp Thr Ala Val Tyr Tyr Cys
                 85                  90                  95

Ala Lys Glu Glu Phe Leu Pro Gly Thr His Tyr Tyr Tyr Gly Met Asp
                100                 105                 110

Val Trp Gly Gln Gly Thr Thr Val Thr Val Ser Ser Ala Ser Thr Lys
                115                 120                 125

Gly Pro Ser Val Phe Pro Leu Ala Pro Ser Ser Lys Ser Thr Ser Gly
            130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Arg Val Glu Pro
210                 215                 220

Lys Ser Cys Gly Gly Gly Ser Gly Gly Gly Ser Glu Val Gln
225                 230                 235                 240

Leu Leu Glu Ser Gly Pro Gly Leu Val Lys Pro Ser Glu Thr Leu Ser
            245                 250                 255

Leu Thr Cys Asn Val Ala Gly Gly Ser Ile Ser Pro Tyr Tyr Trp Thr
            260                 265                 270

Trp Ile Arg Gln Pro Pro Gly Lys Cys Leu Glu Leu Ile Gly Tyr Ile
            275                 280                 285

His Ser Ser Gly Tyr Thr Asp Tyr Asn Pro Ser Leu Lys Ser Arg Val
            290                 295                 300

Thr Ile Ser Gly Asp Thr Ser Lys Lys Gln Phe Ser Leu His Val Ser
305                 310                 315                 320

Ser Val Thr Ala Ala Asp Thr Ala Val Tyr Phe Cys Ala Arg Ala Asp
                325                 330                 335

Trp Asp Leu Leu His Ala Leu Asp Ile Trp Gly Gln Gly Thr Leu Val
            340                 345                 350

Thr Val Ser Ser Gly Gly Gly Ser Gly Gly Gly Ser Gly Gly
            355                 360                 365

Gly Gly Ser Gly Gly Gly Ser Glu Ile Val Leu Thr Gln Ser Pro
            370                 375                 380

Ser Ser Leu Ser Thr Ser Val Gly Asp Arg Val Thr Ile Thr Cys Arg
385                 390                 395                 400

Ala Ser Gln Ser Ile Arg Ser His Leu Asn Trp Tyr Gln Gln Lys Pro
                405                 410                 415

Gly Lys Ala Pro Lys Leu Leu Ile Tyr Gly Ala Ser Asn Leu Gln Ser
            420                 425                 430

Gly Val Pro Ser Arg Phe Ser Gly Ser Gly Ser Gly Thr Asp Phe Thr
            435                 440                 445

Leu Thr Ile Ser Ser Leu Gln Pro Glu Asp Phe Ala Thr Tyr Tyr Cys
450                 455                 460
```

Gln Gln Ser Tyr Ser Phe Pro Leu Thr Phe Gly Cys Gly Thr Lys Leu
465                 470                 475                 480

Glu Ile Lys Gly Gly Gly Ser Gly Gly Gly Ser Asp Lys Thr
            485                 490                 495

His Thr Cys Pro Pro Cys Pro Ala Pro Glu Leu Leu Gly Gly Pro Ser
            500                 505                 510

Val Phe Leu Phe Pro Pro Lys Pro Lys Asp Thr Leu Met Ile Ser Arg
        515                 520                 525

Thr Pro Glu Val Thr Cys Val Val Val Asp Val Ser His Glu Asp Pro
    530                 535                 540

Glu Val Lys Phe Asn Trp Tyr Val Asp Gly Val Glu Val His Asn Ala
545                 550                 555                 560

Lys Thr Lys Pro Arg Glu Glu Gln Tyr Asn Ser Thr Tyr Arg Val Val
                565                 570                 575

Ser Val Leu Thr Val Leu His Gln Asp Trp Leu Asn Gly Lys Glu Tyr
            580                 585                 590

Lys Cys Lys Val Ser Asn Lys Ala Leu Pro Ala Pro Ile Glu Lys Thr
        595                 600                 605

Ile Ser Lys Ala Lys Gly Gln Pro Arg Glu Pro Gln Val Tyr Thr Leu
    610                 615                 620

Pro Pro Ser Arg Glu Glu Met Thr Lys Asn Gln Val Ser Leu Thr Cys
625                 630                 635                 640

Leu Val Lys Gly Phe Tyr Pro Ser Asp Ile Ala Val Glu Trp Glu Ser
                645                 650                 655

Asn Gly Gln Pro Glu Asn Asn Tyr Lys Thr Thr Pro Pro Val Leu Asp
            660                 665                 670

Ser Asp Gly Ser Phe Phe Leu Tyr Ser Lys Leu Thr Val Asp Lys Ser
        675                 680                 685

Arg Trp Gln Gln Gly Asn Val Phe Ser Cys Ser Val Met His Glu Ala
    690                 695                 700

Leu His Asn His Tyr Thr Gln Lys Ser Leu Ser Leu Ser Pro Gly Lys
705                 710                 715                 720

<210> SEQ ID NO 329
<211> LENGTH: 21
<212> TYPE: PRT
<213> ORGANISM: Artificial Sequence
<220> FEATURE:
<223> OTHER INFORMATION: Bs4-V2L2-C2 CH1-hinge-linker

<400> SEQUENCE: 329

Lys Val Asp Lys Arg Val Glu Pro Lys Ser Cys Gly Gly Gly Gly Ser
1               5                   10                  15

Gly Gly Gly Gly Ser
            20

<210> SEQ ID NO 330
<211> LENGTH: 25
<212> TYPE: PRT
<213> ORGANISM: Artificial Sequence
<220> FEATURE:
<223> OTHER INFORMATION: Bs4-V2L2-C2 linker-hinge-CH2

<400> SEQUENCE: 330

Gly Gly Gly Gly Ser Gly Gly Gly Gly Ser Asp Lys Thr His Thr Cys
1               5                   10                  15

Pro Pro Cys Pro Ala Pro Glu Leu Leu

-continued

```
<210> SEQ ID NO 331
<211> LENGTH: 352
<212> TYPE: PRT
<213> ORGANISM: Artificial sequence
<220> FEATURE:
<223> OTHER INFORMATION: Bs4 Heavy Chain
<220> FEATURE:
<221> NAME/KEY: SITE
<222> LOCATION: (1)..(1)
<223> OTHER INFORMATION: Anti-PcrV heavy chain variable region or
      Anti-Psl heavy chain variable region
<220> FEATURE:
<221> NAME/KEY: SITE
<222> LOCATION: (2)..(99)
<223> OTHER INFORMATION: Bs4-GLO CH1 region
<220> FEATURE:
<221> NAME/KEY: SITE
<222> LOCATION: (100)..(104)
<223> OTHER INFORMATION: Bs4-GLO H1 region
<220> FEATURE:
<221> NAME/KEY: SITE
<222> LOCATION: (105)..(114)
<223> OTHER INFORMATION: G4S linkers
<220> FEATURE:
<221> NAME/KEY: SITE
<222> LOCATION: (115)..(115)
<223> OTHER INFORMATION: anti-Psl scFV or anti-PcrV scFV
<220> FEATURE:
<221> NAME/KEY: SITE
<222> LOCATION: (116)..(125)
<223> OTHER INFORMATION: G4S linkers
<220> FEATURE:
<221> NAME/KEY: SITE
<222> LOCATION: (126)..(135)
<223> OTHER INFORMATION: Bs4-GLO H2 region
<220> FEATURE:
<221> NAME/KEY: SITE
<222> LOCATION: (136)..(352)
<223> OTHER INFORMATION: Bs4-GLO CH2CH3 region

<400> SEQUENCE: 331

Xaa Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Arg Val Glu Pro Lys Ser Cys Gly Gly Gly Gly Ser Gly Gly Gly
            100                 105                 110

Gly Ser Xaa Gly Gly Gly Gly Ser Gly Gly Gly Gly Ser Asp Lys Thr
        115                 120                 125

His Thr Cys Pro Pro Cys Pro Ala Pro Glu Leu Leu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
```

```
            180              185              190
Lys Thr Lys Pro Arg Glu Glu Gln Tyr Asn Ser Thr Tyr Arg Val Val
        195              200              205

Ser Val Leu Thr Val Leu His Gln Asp Trp Leu Asn Gly Lys Glu Tyr
        210              215              220

Lys Cys Lys Val Ser Asn Lys Ala Leu Pro Ala Pro Ile Glu Lys Thr
225              230              235              240

Ile Ser Lys Ala Lys Gly Gln Pro Arg Glu Pro Gln Val Tyr Thr Leu
                245              250              255

Pro Pro Ser Arg Glu Glu Met Thr Lys Asn Gln Val Ser Leu Thr Cys
            260              265              270

Leu Val Lys Gly Phe Tyr Pro Ser Asp Ile Ala Val Glu Trp Glu Ser
        275              280              285

Asn Gly Gln Pro Glu Asn Asn Tyr Lys Thr Thr Pro Pro Val Leu Asp
    290              295              300

Ser Asp Gly Ser Phe Phe Leu Tyr Ser Lys Leu Thr Val Asp Lys Ser
305              310              315              320

Arg Trp Gln Gln Gly Asn Val Phe Ser Cys Ser Val Met His Glu Ala
                325              330              335

Leu His Asn His Tyr Thr Gln Lys Ser Leu Ser Leu Ser Pro Gly Lys
                340              345              350

<210> SEQ ID NO 332
<211> LENGTH: 108
<212> TYPE: PRT
<213> ORGANISM: Artificial Sequence
<220> FEATURE:
<223> OTHER INFORMATION: Bs4 Light Chain
<220> FEATURE:
<221> NAME/KEY: SITE
<222> LOCATION: (1)..(1)
<223> OTHER INFORMATION: Anti-PcrV light chain variable region or
      Anti-Psl light chain variable region

<400> SEQUENCE: 332

Xaa Arg Thr Val Ala Ala Pro Ser Val Phe Ile Phe Pro Pro Ser Asp
1               5               10              15

Glu Gln Leu Lys Ser Gly Thr Ala Ser Val Val Cys Leu Leu Asn Asn
            20              25              30

Phe Tyr Pro Arg Glu Ala Lys Val Gln Trp Lys Val Asp Asn Ala Leu
        35              40              45

Gln Ser Gly Asn Ser Gln Glu Ser Val Thr Glu Gln Asp Ser Lys Asp
    50              55              60

Ser Thr Tyr Ser Leu Ser Ser Thr Leu Thr Leu Ser Lys Ala Asp Tyr
65              70              75              80

Glu Lys His Lys Val Tyr Ala Cys Glu Val Thr His Gln Gly Leu Ser
                85              90              95

Ser Pro Val Thr Lys Ser Phe Asn Arg Gly Glu Cys
            100             105
```

COMBINATION THERAPIES USING ANTI-PSEUDOMONAS PSL AND PCRV BINDING MOLECULES

CROSS REFERENCE TO RELATED APPLICATIONS

This application is a divisional of U.S. application Ser. No. 16/789,790, filed Feb. 13, 2020, now U.S. Pat. No. 11,203,633, which is a divisional of U.S. application Ser. No. 14/356,500, 371 (c) date May 6, 2014, now U.S. Pat. No. 10,597,439, which is a 35 U.S.C. § 371 National Phase Application of International Application No. PCT/US2012/063722, filed Nov. 6, 2012, which claims the priority benefit of U.S. Provisional Application Nos. 61/697,585, filed Sep. 6, 2012, 61/625,299, filed Apr. 17, 2012, and 61/556,645, filed Nov. 7, 2011, each of which is hereby incorporated by reference herein in its entirety.

REFERENCE TO SEQUENCE LISTING SUBMITTED ELECTRONICALLY

The content of the electronically submitted sequence listing in ASCII text file entitled 2943_1130005_SequenceListing_ST25.txt created on Jan. 23, 2025 and having a size of 399,369 bytes filed with the application is incorporated herein by reference in its entirety.

BACKGROUND

Field of the Disclosure

This disclosure relates to combination therapies using anti-*Pseudomonas* Psl and PcrV binding domains for use in the prevention and treatment of *Pseudomonas* infection. Furthermore, the disclosure provides compositions useful in such therapies.

Background of the Disclosure

*Pseudomonas aeruginosa* (*P. aeruginosa*) is a gram-negative opportunistic pathogen that causes both acute and chronic infections in compromised individuals (Ma et al., *Journal of Bacteriology* 189 (22): 8353-8356 (2007)). This is partly due to the high innate resistance of the bacterium to clinically used antibiotics, and partly due to the formation of highly antibiotic-resistant biofilms (Drenkard E., *Microbes Infect* 5:1213-1219 (2003); Hancokc & Speert, *Drug Resist Update* 3:247-255 (2000)).

*P. aeruginosa* is a common cause of hospital-acquired infections in the Western world. It is a frequent causative agent of bacteremia in burn victims and immune compromised individuals (Lyczak et al., *Microbes Infect* 2:1051-1060 (2000)). It is also the most common cause of nosocomial gram-negative pneumonia (Craven et al., *Semin Respir Infect* 11:32-53 (1996)), especially in mechanically ventilated patients, and is the most prevalent pathogen in the lungs of individuals with cystic fibrosis (Pier et al., *ASM News* 6:339-347 (1998)).

*Pseudomonas* Psl exopolysaccharide is reported to be anchored to the surface of *P. aeruginosa* and is thought to be important in facilitating colonization of host tissues and in establishing/maintaining biofilm formation (Jackson, K. D., et al., *J Bacteriol* 186, 4466-4475 (2004)). Its structure comprises mannose-rich repeating pentasaccharide (Byrd, M. S., et al., *Mol Microbiol* 73, 622-638 (2009)).

PcrV is a relatively conserved component of the type III secretion system. PcrV appears to be an integral component of the translocation apparatus of the type III secretion system mediating the delivery of the type III secretory toxins into target eukaryotic cells (Sawa T., et al. *Nat. Med.* 5, 392-398 (1999)). Active and passive immunization against PcrV improved acute lung injury and mortality of mice infected with cytotoxic *P. aeruginosa* (Sawa et al. 2009). The major effect of immunization against PcrV was due to the blockade of translocation of the type III secretory toxins into eukaryotic cells.

Due to increasing multidrug resistance, there remains a need in the art for the development of novel strategies for the identification of new *Pseudomonas*-specific prophylactic and therapeutic agents.

BRIEF SUMMARY

The disclosure provides a binding molecule or antigen binding fragment thereof that specifically binds *Pseudomonas* PcrV, which comprises: (a) a heavy chain CDR1 comprising SYAMN (SEQ ID NO:218), or a variant thereof comprising 1, 2, 3, or 4 conservative amino acid substitutions; a heavy chain CDR2 comprising AITISGITAYYTDSVKG (SEQ ID NO: 219), or a variant thereof comprising 1, 2, 3, or 4 conservative amino acid substitutions; and a heavy chain CDR3 comprising EEFLPGTHYYYGMDV (SEQ ID NO: 220), or a variant thereof comprising 1, 2, 3, or 4 conservative amino acid substitutions; (b) a light chain CDR1 comprising RASQGIRNDLG (SEQ ID NO: 221), or a variant thereof comprising 1, 2, 3, or 4 conservative amino acid substitutions; a light chain CDR2 comprising SASTLQS (SEQ ID NO: 222), or a variant thereof comprising 1, 2, 3, or 4 conservative amino acid substitutions; and a light chain CDR3 comprising LQDYNYPWT (SEQ ID NO: 223), or a variant thereof comprising 1, 2, 3, or 4 conservative amino acid substitutions; or combinations of (a) and (b). In one embodiment, the binding molecule or antigen binding fragment thereof specifically binds *Pseudomonas* PcrV, and comprises: (a) a heavy chain CDR1 comprising SYAMN (SEQ ID NO: 218), a heavy chain CDR2 comprising AITISGITAYYTDSVKG (SEQ ID NO: 219), and a heavy chain CDR3 comprising EEFLPGTHYYYGMDV (SEQ ID NO: 220); and (b) a light chain CDR1 comprising RASQGIRNDLG (SEQ ID NO: 221), a light chain CDR2 comprising SASTLQS (SEQ ID NO: 222), and a light chain CDR3 comprising LQDYNYPWT (SEQ ID NO: 223). In one embodiment, the isolated binding molecule or antigen binding fragment thereof specifically binds *Pseudomonas* PcrV and comprises (a) a heavy chain variable region having at least 90% sequence identity to SEQ ID NO: 216; (b) a light chain variable region having at least 90% sequence identity to SEQ ID NO: 217; or combinations of (a) and (b). In another embodiment, the binding molecule or fragment thereof comprises: (a) a heavy chain variable region having at least 95% sequence identity to SEQ ID NO: 216; (b) a light chain variable region having at least 95% sequence identity to SEQ ID NO: 217; or combinations of (a) and (b). In another embodiment, the binding molecule or fragment thereof is V2L2 and comprises: (a) a heavy chain variable region comprising SEQ ID NO: 216; and (b) a light chain variable region comprising SEQ ID NO: 217.

In one embodiment, the disclosure provides an isolated binding molecule or antigen binding fragment thereof that specifically binds to the same *Pseudomonas* PcrV epitope as an antibody or antigen-binding fragment thereof comprising the VH and VL region of V2L2. In another embodiment, the disclosure provides an isolated binding molecule or antigen binding fragment thereof that specifically binds to *Pseudomonas* PcrV, and competitively inhibits *Pseudomonas* PcrV binding by an antibody or antigen-binding fragment thereof comprising the VH and VL of V2L2. In one embodiment, the binding molecule or fragment thereof is a recombinant antibody. In one embodiment, the binding molecule or fragment thereof is a monoclonal antibody. In one embodiment, the binding molecule or fragment thereof is a chimeric antibody. In one embodiment, the binding molecule or fragment thereof is a humanized antibody. In one embodiment, the binding molecule or fragment thereof is a human antibody. In one embodiment, the binding molecule or fragment thereof is a bispecific antibody.

In one embodiment, the binding molecule or fragment thereof inhibits delivery of type III secretory toxins into target cells.

In one embodiment, the disclosure provides a bispecific antibody comprising a binding domain that binds to *Pseudomonas* Psl and a binding domain that binds to *Pseudomonas* PcrV. In one embodiment, the Psl binding domain comprises a scFv fragment and the PcrV binding domain comprises an intact immunoglobulin. In one embodiment, the Psl binding domain comprises an intact immunoglobulin and said PcrV binding domain comprises a scFv fragment. In one embodiment, the scFv is fused to the amino-terminus of the VH region of the intact immunoglobulin. In one embodiment, the scFv is fused to the carboxy-terminus of the CH3 region of the intact immunoglobulin. In one embodiment, the scFv is inserted in the hinge region of the intact immunoglobulin.

In one embodiment, the anti-Psl binding domain specifically binds to the same *Pseudomonas* Psl epitope as an antibody or antigen-binding fragment thereof comprising the heavy chain variable region (VH) and light chain variable region (VL) region at least 90% identical to the corresponding region of WapR-004. In one embodiment, the anti-Psl binding domain specifically binds to *Pseudomonas* Psl, and competitively inhibits *Pseudomonas* Psl binding by an antibody or antigen-binding fragment thereof comprising a VH and VL region at least 90% identical to the corresponding region of WapR-004. In one embodiment, the VH and VL of WapR-004 comprise SEQ ID NO:11 and SEQ ID NO: 12, respectively. In one embodiment, the WapR-004 sequence is selected from the group consisting of: SEQ ID NO:228, SEQ ID NO:229, and SEQ ID NO:235. In one embodiment, the anti-PcrV binding domain specifically binds to the same *Pseudomonas* PcrV epitope as an antibody or antigen-binding fragment thereof comprising the VH and VL region of V2L2. In one embodiment, the anti-PcrV binding domain specifically binds to *Pseudomonas* PcrV, and competitively inhibits *Pseudomonas* PcrV binding by an antibody or antigen-binding fragment thereof comprising the VH and VL of V2L2. In another embodiment, the anti-PcrV binding domain specifically binds to the same *Pseudomonas* PcrV epitope as an antibody or antigen-binding fragment thereof comprising a VH and VL region at least 90% identical to the corresponding region of V2L2. In one embodiment, the VH and VL of V2L2 comprise SEQ ID NO:216 and SEQ ID NO:217, respectively. In one embodiment, the VH and VL of WapR-004 (SEQ ID NOs: 11 and 12, respectively) and the VH and VL of V2L2 (SEQ ID NOs: 216 and 217, respectively). In one embodiment, the bispecific antibody comprises an amino acid sequence selected from the group consisting of: SEQ ID NO:228, SEQ ID NO:229, and SEQ ID NO:235.

In one embodiment, the disclosure provides a polypeptide comprising an amino acid sequence of SEQ ID NO:216 or SEQ ID NO:217. In one embodiment, the polypeptide is an antibody.

In one embodiment, the disclosure provides a cell comprising or producing the binding molecule or polypeptide disclosed herein.

In one embodiment, the disclosure provides an isolated polynucleotide molecule comprising a polynucleotide that encodes a binding molecule or polypeptide described herein. In one embodiment, the polynucleotide molecule comprises a polynucleotide sequence selected from the group consisting of: SEQ ID NO:238 and SEQ ID NO:239. In another embodiment, the disclosure provides a vector comprising a polynucleotide described herein. In another embodiment, the disclosure provides a cell comprising a polynucleotide or vector.

In one embodiment, the disclosure provides a composition comprising a binding molecule, bispecific antibody, or polypeptide described herein and a pharmaceutically acceptable carrier.

In one embodiment, the disclosure provides a composition comprising a binding domain that binds to *Pseudomonas* Psl and a binding domain that binds to *Pseudomonas* PcrV. In one embodiment, the anti-Psl binding domain specifically binds to the same *Pseudomonas* Psl epitope as an antibody or antigen-binding fragment thereof comprising the heavy chain variable region (VH) and light chain variable region (VL) region at least 90% identical to the corresponding region of WapR-004, Cam-003, Cam-004, Cam-005, WapR-001, WapR-002, WapR-003, or WapR-016. In one embodiment, the anti-Psl binding domain specifically binds to *Pseudomonas* Psl, and competitively inhibits *Pseudomonas* Psl binding by an antibody or antigen-binding fragment thereof comprising a VH and VL region at least 90% identical to the corresponding region of WapR-004, Cam-003, Cam-004, Cam-005, WapR-001, WapR-002, WapR-003, or WapR-016. In one embodiment, the VH and VL of WapR-004 comprise SEQ ID NO:11 and SEQ ID NO:12, respectively, the VH and VL of Cam-003 comprise SEQ ID NO: 1 and SEQ ID NO:2, respectively, the VH and VL of Cam-004 comprise SEQ ID NO:3 and SEQ ID NO:2, respectively, the VH and VL of Cam-005 comprise SEQ ID NO:4 and SEQ ID NO:2, respectively, the VH and VL of WapR-001 comprise SEQ ID NO:5 and SEQ ID NO:6, respectively, the VH and VL of WapR-002 comprise SEQ ID NO:7 and SEQ ID NO:8, respectively, the VH and VL of WapR-003 comprise SEQ ID NO:9 and SEQ ID NO:10, respectively, and the VH and VL of WapR-016 comprise SEQ ID NO: 15 and SEQ ID NO:16, respectively. In one embodiment, the anti-PcrV binding domain specifically binds to the same *Pseudomonas* PcrV epitope as an antibody or antigen-binding fragment thereof comprising the VH and VL region of V2L2. In one embodiment, the anti-PcrV binding domain specifically binds to *Pseudomonas* PcrV, and competitively inhibits *Pseudomonas* PcrV binding by an antibody or antigen-binding fragment thereof comprising the VH and VL of V2L2. In one embodiment, the anti-PcrV binding domain specifically binds to the same *Pseudomonas* PcrV epitope as an antibody or antigen-binding fragment thereof comprising a VH and VL region at least 90% identical to the corresponding region of V2L2. In one embodiment, the VH and VL of V2L2 comprise SEQ ID NO:216 and SEQ ID NO:217, respectively. In one embodiment, the anti-Psl binding domain comprises the VH and VL region of WapR-004, and said anti-PcrV binding domain comprises the VH and VL region of V2L2, or antigen-binding fragments thereof.

In one embodiment, the composition comprises a first binding molecule comprising said anti Psl-binding domain, and a second binding molecule comprising a PcrV-binding domain. In one embodiment, the first binding molecule is an antibody or antigen binding fragment thereof, and said second binding molecule is an antibody or antigen binding fragment thereof. In one embodiment, the antibodies or antigen binding fragments are independently selected from the group consisting of: monoclonal, humanized, chimeric, human, Fab fragment, Fab' fragment, F (ab) 2 fragment, and scFv fragment. In one embodiment, the binding domains, binding molecules or fragments thereof, bind to two or more, three or more, four or more, or five or more different *P. aeruginosa* serotypes. In one embodiment, the binding domains, binding molecules or fragments thereof, bind to at least 80%, at least 85%, at least 90% or at least 95% of *P. aeruginosa* strains isolated from infected patients. In one embodiment, the *P. aeruginosa* strains are isolated from one or more of lung, sputum, eye, pus, feces, urine, sinus, a wound, skin, blood, bone, or knee fluid. In one embodiment, the antibody or antigen binding fragment thereof is conjugated to an agent selected from the group consisting of antimicrobial agent, a therapeutic agent, a prodrug, a peptide, a protein, an enzyme, a lipid, a biological response modifier, pharmaceutical agent, a lymphokine, a heterologous antibody or fragment thereof, a detectable label, polyethylene glycol (PEG), and a combination of two or more of any said agents. In one embodiment, the detectable label is selected from the group consisting of an enzyme, a fluorescent label, a chemiluminescent label, a bioluminescent label, a radioactive label, or a combination of two or more of any said detectable labels.

In one embodiment, the disclosure provides a method of preventing or treating a *Pseudomonas* infection in a subject in need thereof, comprising administering to the subject an effective amount of a composition described herein, wherein said administration provides a synergistic therapeutic effect in the prevention or treatment of the *Pseudomonas* infection in said subject, and wherein said synergistic effect is greater than the sum of the individual effects of administration of equal molar quantities of the individual binding domains. In one embodiment, the synergistic therapeutic effect results in greater percent survival than the additive percent survival of subjects to which only one of the binding domains has been administered. In one embodiment, the composition is administered for two or more prevention/treatment cycles. In one embodiment, the binding domains or binding molecules are administered simultaneously. In one embodiment, the binding domains or binding molecules are administered sequentially. In one embodiment, the *Pseudomonas* infection is a *P. aeruginosa* infection. In one embodiment, the subject is a human. In one embodiment, the infection is an ocular infection, a lung infection, a burn infection, a wound infection, a skin infection, a blood infection, a bone infection, or a combination of two or more of said infections. In one embodiment, the subject has acute pneumonia, burn injury, corneal infection, cystic fibrosis, or a combination thereof.

In one embodiment, the disclosure provides a method of preventing or treating a *Pseudomonas* infection in a subject in need thereof, comprising administering to the subject an effective amount of the binding molecule or fragment thereof, a bispecific antibody, a polypeptide, or a composition described herein.

In one embodiment, the disclosure provides a kit comprising a composition described herein.

BRIEF DESCRIPTION OF THE DRAWINGS/FIGURES

FIG. 1(A-F): Phenotypic whole cell screening with human antibody phage libraries identified *P. aeruginosa* functionally active specific antibodies. (A) Overview of complete antibody selection strategy. (B) Flow diagram describing the process to isolate antibody variable region genes from patients recently exposed to *P. aeruginosa*. (C) Characteristics of the scFv phage display libraries, indicating the size and diversity of the cloned antibody repertoire. (D) Comparison of the phage display selection efficiency using either the patient antibody library or a naïve antibody library, when selected on *P. aeruginosa* 3064 Δ WapR ($^1$) or *P. aeruginosa* PAO1 MexAB OprM Δ WapR ($^2$) in suspension. Bars indicate the output titers (in CFU) at each round of selection, and circles indicate the proportion of duplicated VH CDR3 sequences, an indication of clonal enrichment. (E) ELISA screen of scFv from phage display to test binding to multiple strains of *P. aeruginosa*. ELISA data (absorbance at 450 nm) are shown for eight individual phage-scFvs from selections and one irrelevant phage-scFv. (F) FACS binding of *P. aeruginosa* specific antibodies with representative strains from unique *P. aeruginosa* serotypes. For each antibody tested a human IgG negative control antibody is shown as a shaded peak.

FIG. 2(A-B): Evaluation of mAbs promoting OPK of *P. aeruginosa* (A) Opsonophagocytosis assay with luminescent *P. aeruginosa* serogroup O5 strain (PAO1.lux), with dilutions of purified monoclonal antibodies derived from phage panning. (B) Opsonophagocytosis assay with luminescent *P. aeruginosa* serogroup O11 strain (9882-80.lux), with dilutions of purified WapR-004 and Cam-003 monoclonal antibodies derived from phage panning. In both A and B, R347, an isotype matched human monoclonal antibody that does not bind *P. aeruginosa* antigens, was used as a negative control.

FIG. 3(A-I): Identification of the *P. aeruginosa* Psl exopolysaccharide target of antibodies derived from phenotypic screening. Reactivity of antibodies was determined by indirect ELISA on plates coated with indicated *P. aeruginosa* strains: (A) wild type PAO1, PAO1ΔwbpL, PAO1ΔrmlC and PAO1ΔgalU. (B) PAO1ΔpslA. The Genway antibody is specific to a *P. aeruginosa* outer membrane protein and was used as a positive control. (C) FACS binding analysis of Cam-003 to PAO1 and PAO1ΔpslA. Cam-003 is indicated by a solid black line and clear peak; an isotype matched non-*P. aeruginosa*-specific human IgG1 antibody was used as a negative control and is indicated by a gray line and shaded peak. (D) LPS purified from PAO1 and PAO1ΔpslA was resolved by SDS-PAGE and immunobloted with antisera derived from mice vaccinated with PAO1ΔwapRΔalgD, a mutant strain deficient in O-antigen transport to the outer membrane and alginate production. (E) Cam-003 ELISA binding data with isogenic mutants of PAO1. Cam-003 is only capable of binding to strains expressing Psl. pPW145 is a pUCP expression vector containing pslA. (F and G) Opsonophagocytosis assays indicating that Cam-003 only mediates killing of strains capable of producing Psl (wild type PAO1 and PAO1ΔpslA complemented in trans with the pslA gene). (H and I) ELISA data indicating reactivity of anti-Psl antibodies WapR-001, WapR-004, and WapR-016 with PAO1 ΔwbpLΔalgD and PAO1 ΔwbpLΔalgDΔpslA. R347 was used as a negative control in all experiments.

Figure 4:
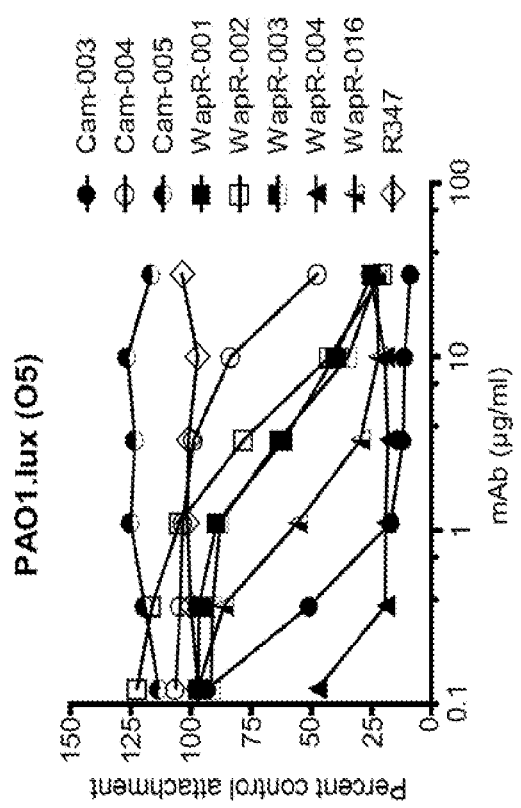

FIG. 4: Anti-Psl mAbs inhibit cell attachment of luminescent *P. aeruginosa* strain PAO1.lux to A549 cells. Log-phase PAO1.lux were added to a confluent monolayer of A549 cells at an MOI of 10 followed by analysis of RLU after repeated washing to remove unbound *P. aeruginosa*. Results are representative of three independent experiments performed in duplicate for each antibody concentration.

Figure 5:
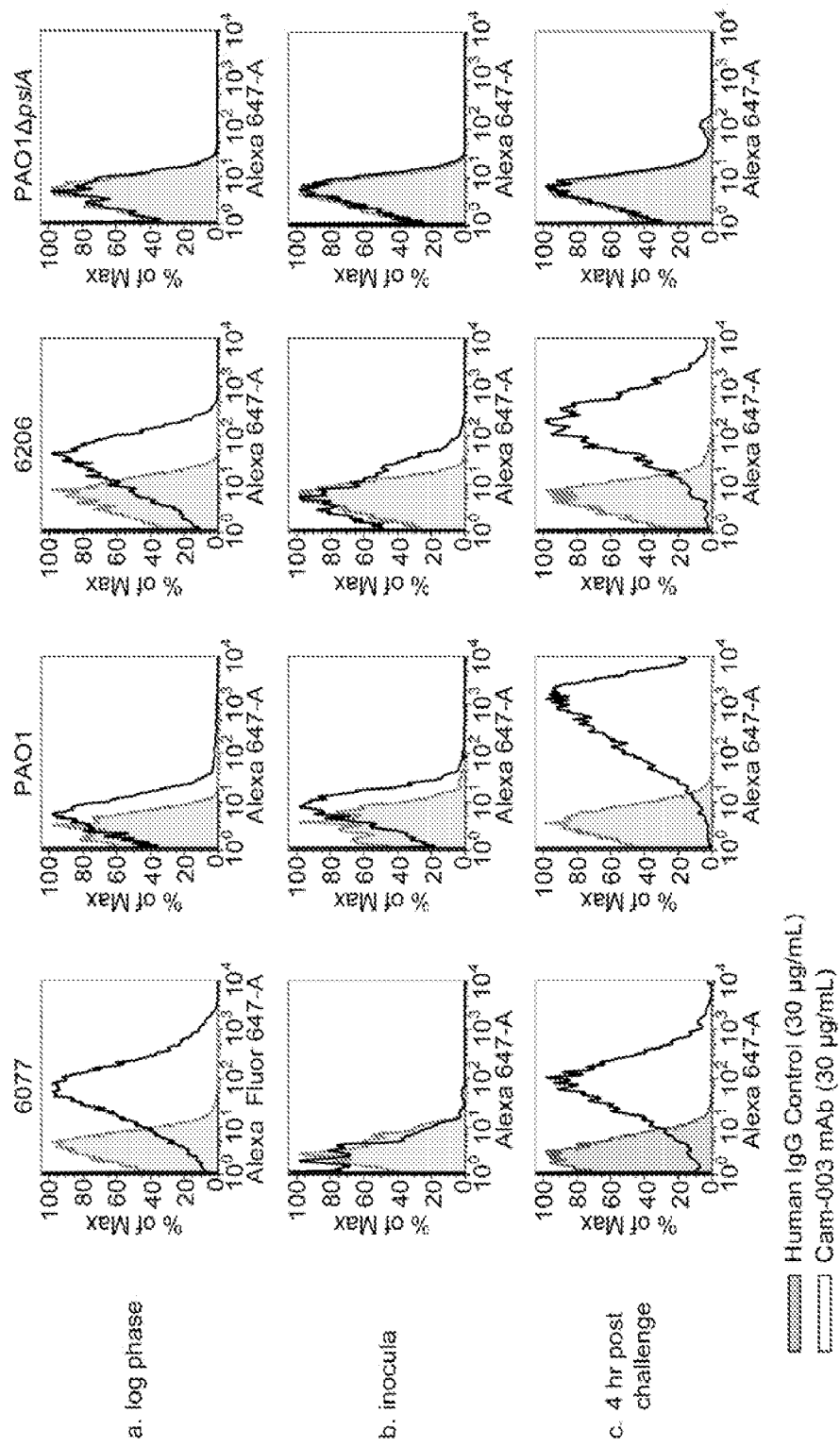

FIG. 5(A-C): In vivo passaged *P. aeruginosa* strains maintain/increase expression of Psl. The Cam-003 antibody is shown by a solid black line and a clear peak; the human IgG negative control antibody is shown as a gray line and a shaded peak. (A) For the positive control, Cam-003 was assayed for binding to strains grown to log phase from an overnight culture ($\sim 5 \times 10^8$/ml). (B) The inocula for each strain were prepared to $5 \times 10^8$ CFU/ml from an overnight TSA plate grown to lawn and tested for reactivity to Cam-003 by flow cytometry. (C) Four hours post intraperitoneal challenge, bacteria was harvested from mice by peritoneal lavage and assayed for the presence of Psl with Cam-003 by flow cytometry.

FIG. 6(A-F): Survival rates for animals treated with anti-Psl monoclonal antibodies Cam-003 or WapR-004 in a *P. aeruginosa* acute pneumonia model. (A-D) Animals were treated with Cam-003 at 45, 15, and 5 mg/kg and R347 at 45 mg/kg or PBS 24 hours prior to intranasal infection with (A) PAO1 ($1.6 \times 10^7$ CFU), (B) 33356 ($3 \times 10^7$ CFU), (C) 6294 ($7 \times 10^6$ CFU), (D) 6077 ($1 \times 10^6$ CFU). (E-F) Animals were treated with WapR-004 at 5 and 1 mg/kg as indicated followed by infection with 6077 at (E) ($8 \times 10^5$ CFU), or (F) ($6 \times 10^5$ CFU). Animals were carefully monitored for survival up to 72 hours (A-D) or for 120 hours (E-F). In all experiments, PBS and R347 served as negative controls. Results are represented as Kaplan-Meier survival curves; differences in survival were calculated by the Log-rank test for Cam-003 vs. R347. (A) Cam-003 (45 mg/kg—P<0.0001; 15 mg/kg—P=0.0003; 5 mg/kg—P=0.0033). (B) Cam-003 (45 mg/kg—P=0.0012; 15 mg/kg—P=0.0012; 5 mg/kg—P=0.0373). (C) Cam-003 (45 mg/kg—P=0.0007; 15 mg/kg—P=0.0019; 5 mg/kg—P=0.0212). (D) Cam-003 (45 mg/kg—P<0.0001; 15 mg/kg—P<0.0001; 5 mg/kg—P=0.0001). Results are representative of at least two independent experiments. (E) [Cam-003 (5 mg/kg) vs. R347 (5 mg/kg): P=0.02; Cam-003 (1 mg/kg) vs. R347 (5 mg/kg): P=0.4848; WapR-004 (5 mg/kg) vs. R347 (5 mg/kg): P<0.0001; WapR-004 (1 mg/kg) vs. R347 (5 mg/kg): P=0.0886; WapR-004 (5 mg/kg) vs. Cam-003 (5 mg/kg): P=0.0017; WapR-004 (1 mg/kg) vs. Cam-003 (1 mg/kg): P=0.2468; R347 (5 mg/kg) vs. PBS: P=0.6676] (F) [Cam-003 (5 mg/kg) vs. R347 (5 mg/kg): P=0.0004; Cam-003 (1 mg/kg) vs. R347 (5 mg/kg): P<0.0001; WapR-004 (5 mg/kg) vs. R347 (5 mg/kg): P<0.0001; WapR-004 (1 mg/kg) vs. R347 (5 mg/kg): P<0.0001; WapR-004 (5 mg/kg) vs. Cam-003 (5 mg/kg): P=0.0002; WapR-004 (1 mg/kg) vs. Cam-003 (1 mg/kg): P=0.2628; R347 (5 mg/kg) vs. PBS: P=0.6676]. Results are representative of five independent experiments.

FIG. 7(A-F): Anti-Psl monoclonal antibodies, Cam-003 and WapR-004, reduce organ burden after induction of acute pneumonia. Mice were treated with Cam-003 antibody 24 hours prior to infection with (A) PAO1 ($1.1 \times 10^7$ CFU), (B) 33356 ($1 \times 10^7$ CFU), (C) 6294 ($6.25 \times 10^6$ CFU) (D) 6077 ($1 \times 10^6$ CFU), and WapR-004 antibody 24 hours prior to infection with (E) 6294 ($\sim 1 \times 10^7$ CFU), and (F) 6206 ($\sim 1 \times 10^6$ CFU). 24 hours post-infection, animals were euthanized followed by harvesting or organs for identification of viable CFU. Differences in viable CFU were determined by the Mann-Whitney U-test for Cam-003 or WapR-004 vs. R347. (A) Lung: Cam-003 (45 mg/kg—P=0.0015; 15 mg/kg—P=0.0021; 5 mg/kg—P=0.0015); Spleen: Cam-003 (45 mg/kg—P=0.0120; 15 mg/kg—P=0.0367); Kidneys: Cam-003 (45 mg/kg—P=0.0092; 15 mg/kg—P=0.0056); (B) Lung: Cam-003 (45 mg/kg—P=0.0010; 15 mg/kg—P<0.0001; 5 mg/kg—P=0.0045); (C) Lung: Cam-003 (45 mg/kg—P=0.0003; 15 mg/kg—P=0.0039; 5 mg/kg—P=0.0068); Spleen: Cam-003 (45 mg/kg—P=0.0057; 15 mg/kg—P=0.0230; 5 mg/kg—P=0.0012); (D) Lung: Cam-003 (45 mg/kg—P=0.0005; 15 mg/kg—P=0.0003; 5 mg/kg—P=0.0007); Spleen: Cam-003 (45 mg/kg—P=0.0015; 15 mg/kg—P=0.0089; 5 mg/kg—P=0.0089); Kidneys: Cam-003 (45 mg/kg—P=0.0191; 15 mg/kg—P=0.0355; 5 mg/kg—P=0.0021). (E) Lung: WapR-004 (15 mg/kg—P=0.0011; 5 mg/kg—P=0.0004; 1 mg/kg—P=0.0002); Spleen: WapR-004 (15 mg/kg—P<0.0001; 5 mg/kg—P=0.0014; 1 mg/kg—P<0.0001); F) Lung: WapR-004 (15 mg/kg—P<0.0001; 5 mg/kg—P=0.0006; 1 mg/kg—P=0.0079); Spleen: WapR-004 (15 mg/kg—P=0.0059; 5 mg/kg—P=0.0261; 1 mg/kg—P=0.0047); Kidney: WapR-004 (15 mg/kg—P=0.0208; 5 mg/kg—P=0.0268.

FIG. 8(A-H): Anti-Psl monoclonal antibodies Cam-003 and WapR-004 are active in a *P. aeruginosa* keratitis model and thermal injury model. Mice were treated with a control IgG1 antibody or Cam-003 at 45 mg/kg (A, B) or 15 mg/kg (C, D) or PBS or a control IgG1 antibody or Cam-003 at 45 mg/kg or WapR-004 at 45 mg/kg or 15 mg/kg or 5 mg/kg (F, G) 24 hours prior to infection with 6077 (O11-cytotoxic—$2 \times 10^6$ CFU). Immediately before infection, three 1 mm scratches were made on the left cornea of each animal followed by topical application of *P. aeruginosa* in a 5 µl inoculum. 24 hours after infection, the corneal pathology scores were calculated followed by removal of the eye for determination of viable CFU. Differences in pathology scores and viable CFU were determined by the Mann-Whitney U-test. (A) P=0.0001, (B) P<0.0001, (C) P=0.0003, (D) P=0.0015. (F) and (G) Cam-003 (45 mg/kg) vs. WapR-004 (45 mg/kg): P=0.018; Cam-003 (45 mg/kg) vs. WapR-004 (15 mg/kg): P=0.0025; WapR-004 (45 mg/kg) vs. WapR-004 (15 mg/kg): P=0.1331; WapR-004 (5 mg/kg) vs. Ctrl: P<0.0001. Results are representative of five independent experiments. (E) Survival analysis from Cam-003 and R347 treated CF-1 mice in a *P. aeruginosa* thermal injury model after 6077 infection ($2 \times 10^5$ CFU) (log-rank: R347 vs. Cam-003 15 mg/kg, P=0.0094; R347 vs. Cam-003 5 mg/kg, P=0.0017). Results are representative of at least three independent experiments. (n) refers to number of animals in each group. FIG. 8(H): Anti-Psl and anti-PcrV monoclonal antibodies are active in a *P. aeruginosa* mouse ocular keratitis model. Mice were injected intraperitoneally (IP) with PBS or a control IgG1 antibody (R347) at 45 mg/kg or WapR-004 (a-Psl) at 5 mg/kg or V2L2 (a-PcrV) at 5 mg/kg, 16 hours prior to infection with 6077 (O11-cytotoxic—$1 \times 10^6$ CFU). Immediately before infection, mice were anesthetized followed by initiation of three 1 mm scratches on the cornea and superficial stroma of one eye of each mouse using a 27-gauge needle under a dissection microscope, followed by topical application of *P. aeruginosa* 6077 strain in a 5 µl inoculum.

FIG. 9(A-C): A Cam-003 Fc mutant antibody, Cam-003-TM, has diminished OPK and in vivo efficacy but maintains anti-cell attachment activity. (A) PAO1.lux OPK assay with Cam-003 and Cam-003-TM, which harbors mutations in the Fc domain that prevents Fc interactions with Fcγ receptors (Oganesyan, V., et al., *Acta Crystallogr D Biol Crystallogr* 64, 700-704 (2008)). R347 was used as a negative control.

(B) PAO1 cell attachment assay with Cam-003 and Cam-003-TM. (C) Acute pneumonia model comparing efficacy of Cam-003 vs. Cam-003-TM.

FIG. 10(A-C): A: Epitope mapping and identification of the relative binding affinity for anti-Psl monoclonal antibodies. Epitope mapping was performed by competition ELISA and confirmed using an OCTET® flow system with Psl derived from the supernatant of an overnight culture of *P. aeruginosa* strain PAO1. Relative binding affinities were measured on a FORTEBIO® OCTET® 384 instrument. Also shown are antibody concentrations where cell attachment was maximally inhibited and OPK EC50 values for each antibody. B, C. Relative binding affinities of various WapR-004 mutants as measured on a FORTEBIO® OCTET® 384 instrument. Also shown are OPK EC50 values for the various mutants.

FIG. 11(A-Q): Evaluation of WapR-004 (W4) mutants clones in the *P. aeruginosa* opsonophagocytic killing (OPK) assay (A-M) OPK assay with luminescent *P. aeruginosa* serogroup O5 strain (PAO1.lux), with dilutions of different W4 mutant clones in scFv-Fc format. In some instances, W4 IgG1 was included in the assay and is indicated as W4-IgG1. W4-RAD-Cam and W4-RAD-GB represent the same WapR-004RAD sequence described herein. "W4-RAD" is a shorthand name for WapR-004RAD, and W4-RAD-Cam and W4-RAD-GB designations in panels D through M represent two different preparations of WapR-004RAD. (N-Q): Evaluation of the optimized anti-Psl mAbs derived from lead (WapR-004) optimization in the *P. aeruginosa* OPK assay. (N-O) OPK assay with luminescent PAO1.lux using dilutions of purified lead optimized monoclonal antibodies. (P-Q) Repeat OPK assay with PAO1.lux with dilutions of purified mAbs to confirm results. (N-Q): W4-RAD was used as a comparative positive control. In all experiments, R347, a human IgG1 monoclonal antibody that does not bind *P. aeruginosa* antigens, was used as a negative control.

FIG. 12(A-H): (A) The PcrV epitope diversity. (B) Percent inhibition of cytotoxicity analysis for the parental V2L2 mAb, mAb166 (positive control) and R347 (negative control). (C) Evaluation of the V2L2 mAb, mAb166 (positive control) and R347 (negative control) ability to prevent lysis of RBCs. (D) Evaluation of the V2L2-germlined mAb (V2L2-GL) and optimized V2L2-GL mAbs (V2L2-P4M, V2L2-MFS, V2L2-MD and V2L2-MR) to prevent lysis of RBCs. (E) Evaluation of mAbs 1E6, 1F3, 11A6, 29D2, PCRV02 and V2L7 to prevent lysis of RBCs (F) Evaluation of mAbs V2L2 and 29D2 to prevent lysis of RBCs. (G-H) Relative binding affinities of V2L2-GL and V2L2-MD antibodies.

FIG. 13(A-I): In vivo survival study of anti-PcrV antibody treated mice. (A) Mice were treated 24 hours prior to infection with: $1.03 \times 10^6$ CFU 6077 (exoU$^+$) with 45 mg/kg R347 (negative control), 45 mg/kg, 15.0 mg/kg, 5.0 mg/kg, or 1.0 mg/kg mAb166 (positive control), or 15 mg/kg, 5.0 mg/kg, 1.0 mg/kg, or 0.2 mg/kg V2L2. Survival was monitored for 96 hours. (B) Mice were treated 24 hours prior to infection with: $2.1 \times 10^7$ CFU 6294 (exoS$^+$) with 15 mg/kg R347 (negative control), 15.0 mg/kg, 5.0 mg/kg, or 1.0 mg/kg mAb166 (positive control), or 15 mg/kg, 5.0 mg/kg, or 1.0 mg/kg V2L2. Survival was monitored for 168 hours. Mice were treated 24 hours prior to infection with: (C) 6294 (O6) or (D) PA103A with R347 (negative control), 5 mg/kg of the PcrV antibody PcrV-02, or 5 mg/kg, 1.0 mg/kg, 0.2 mg/kg, or 0.04 mg/kg V2L2. Mice were treated 24 hours prior to infection with strain 6077 with R347 (negative control), 5 mg/kg of the PcrV antibody PcrV-02, V2L7 (5 mg/kg or 1 mg/kg), 3G5 (5 mg/kg or 1 mg/kg), or 11A6 (5 mg/kg or 1 mg/kg) (E), or 25 mg/kg of the V2L7, 1E6, 1F3, 29D2, R347 or 1 mg/kg of the PcrV antibody PcrV-01 (F), or 25 mg/kg of the 21F1, V2L2, 2H3, 4A8, SH3, LE10, R347 or 1 mg/kg of the PcrV-02 (G), or the 29D2 (1 mg/kg, 3 mg/kg or 10 mg/kg), the V2L2 (1 mg/kg, 3 mg/kg or 10 mg/kg) R347 or 1 mg/kg of the PcrV-02 (H). Mice were treated 24 hours prior to infection with: 6294 (O6) or PA103A with the V2L2 (0.04 mg/kg, 0.2 mg/kg, 1 mg/kg or 5 mg/kg), R347 or 5 mg/kg of the PcrV-02. Percent survival was assayed in an acute pneumonia model.

FIG. 14(A-B): Organ burden analysis of V2L2 treated mice. Mice were treated 24 hours prior to infection with 6206 with (A) R347 (negative control), 1 mg/kg, 0.2 mg/kg, or 0.07 mg/kg V2L2 and (B) 15 mg/kg R347 (negative control); 15.0 mg/kg, 5.0 mg/kg, or 1.0 mg/kg mAb166 (positive control); or 5.0 mg/kg, 1.0 mg/kg, or 0.2 mg/kg V2L2. Colony forming units were identified per gram of tissue in lung, spleen, and kidney.

Figure 15:
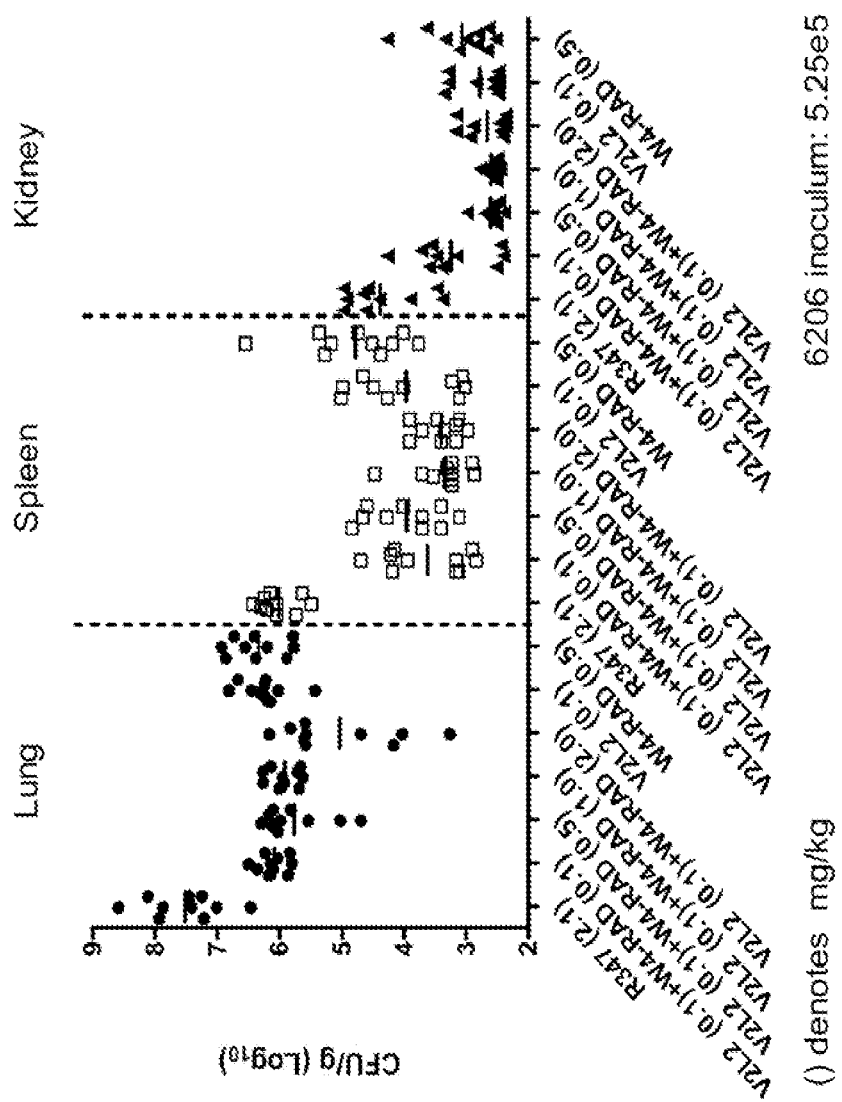

FIG. 15: Organ burden analysis of V2L2 and WapR-004 (W4) treated mice. Mice were treated 24 hours prior to infection with 6206 (O11-ExoU+) with R347 (negative control), V2L2 alone, or V2L2 (0.1 mg/kg) in combination with increasing concentrations of W4 (0.1, 0.5, 1.0, or 2.0 mg/kg). Colony forming units were identified per gram of tissue in lung, spleen, and kidney.

FIG. 16(A-G): Survival rates for animals treated with anti-PcrV monoclonal antibody V2L2 in a *P. aeruginosa* acute pneumonia model. V2L2-GL, V2L2-MD, V2L2-PM4, V2L2-A and V2L2-MFS designations in panels A through G represent different preparations of V2L2. (A-C) Animals were treated with V2L2 at 1 mg/kg, 0.5 mg/kg or R347 at 0.5 mg/kg prior to intranasal infection with (A) 6077 ($9.75 \times 10^5$ CFU), (B, C) 6077 ($9.5 \times 10^5$ CFU). (D-F) Animals were treated with V2L2 at 0.5 mg/kg, 0.1 mg/kg or R347 at 0.5 mg/kg followed by infection with 6077 (D) ($1 \times 10^6$ CFU), (E) ($9.5 \times 10^5$ CFU) or F ($1.026 \times 10^6$ CFU). (G) Animals were treated with V2L2-MD at (0.04 mg/kg, 0.2 mg/kg, 1 mg/kg or 5 mg/kg), mAb166 (positive control) at (0.2 mg/kg, 1 mg/kg, 5 mg/kg or 15 mg/kg), or R347 at 0.5 mg/kg followed by infection with 6206 ($2 \times 10^{7+}$ CFU).

Figure 17A:
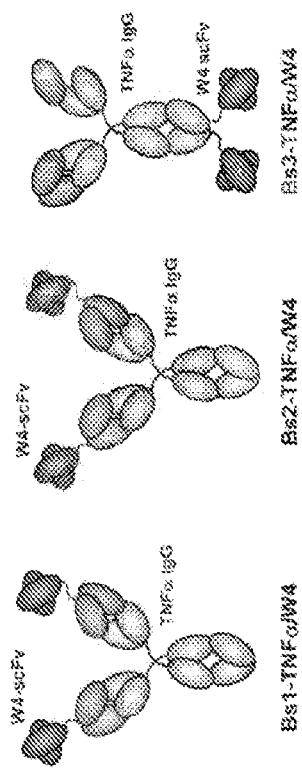
Figure 17B:
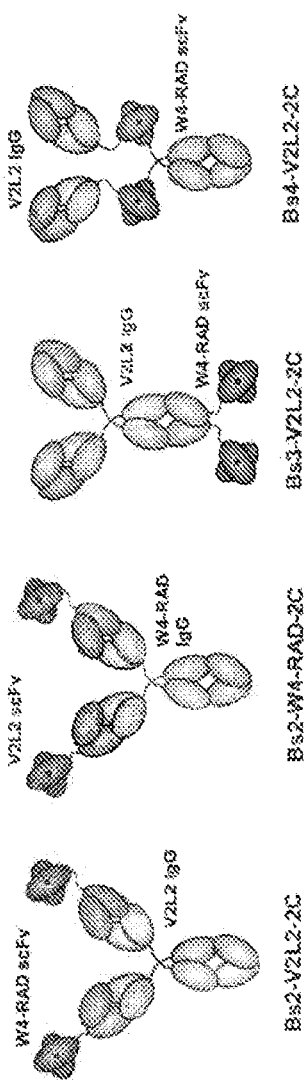
Figure 17B:

FIG. 17(A-B): Schematic representation of (A) Bs1-TNFα/W4, Bs2-TNFα/W4, Bs3-TNFα/W4 and (B) Bs2-V2L2/W4-RAD, Bs3-V2L2/W4-RAD, and Bs4-V2L2-W4-RAD Psl/PcrV bispecific antibodies. (A) For Bs1-TNFα/W4, the W4 scFv is fused to the amino-terminus of TNFα VL through a (G4S) 2 linker. For Bs2-TNFα/W4, the W4 scFv is fused to the amino-terminus of TNF& VH through a (G4S) 2 linker. For Bs3-TNFα/W4, the W4 scFv is fused to the carboxy-terminus of CH3 through a (G4S) 2 linker. (B) For Bs2-V2L2-2C, the W4-RAD scFv is fused to the amino-terminus of V2L2 VH through a (G4S) 2 linker. For Bs2-W4-RAD-2C, the V2L2 scFv is fused to the amino-terminus of W4-RAD VH through a (G4S) 2 linker. For Bs3-V2L2-2C, the W4-RAD scFv is fused to the carboxy-terminus of CH3 through a (G4S) 2 linker. For Bs4-V2L2-2C, the W4-RAD scFv is inserted in the hinge region, linked by (G4S) 2 linker on the N-terminal and C-terminal of the scFv.

Figure 18:
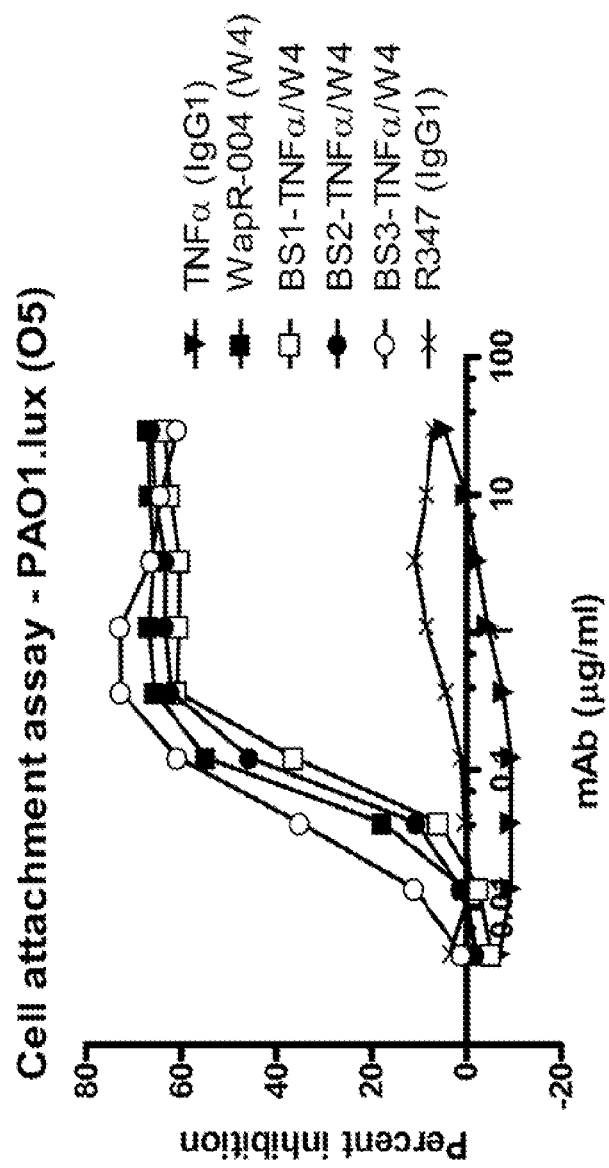

FIG. 18: Evaluation of WapR-004 (W4) scFv activity in a bispecific constructs depicted in FIG. 17A. The W4 scFv was ligated onto two different bispecific constructs (in alternating N- or C-terminal orientations) having a TNFα binding arm. Each W4-TNFα bispecific construct (Bs1-TNFα/W4, Bs2-TNFα/W4 and Bs3-TNFα/W4) retained the ability to inhibit cell attachment similarly as W4 using the PAO1.lux (O5) assay indicating that the W4 scFv retains its activity in a bispecific format. R347 was used as a negative control.

FIG. 19(A-C): Anti-Psl and anti-PcrV binding domains were combined in the bispecific format by replacing the TNFα antibody of FIG. 17B with V2L2. These constructs are identical to those depicted in FIG. 17B with the exception of using the non-stabilized W4-scFv in place of the stabilized W4-RAD scFv. Both W4 and W4-RAD target identical epitopes and have identical functional activities. Percent inhibition of cytotoxicity was analysed for both BS2-V2L2 and BS3-V2L2 using both (A) 6206 and (B) 6206ΔpslA treated A549 cells. (C) BS2-V2L2, BS3-V2L2, and BS4-V2L2 were evaluated for their ability to prevent lysis of RBCs compared to the parental control. All bispecific constructs retained anti-cytotoxicity activity similar to the parental V2L2 antibody using 6206 and 6206ΔpslA infected cells and prevented lysis of RBCs similar to the parental control (V2L2). R347 was used as a negative control in all experiments.

FIG. 20(A-C): Evaluation of anti-Psl/anti-PcrV bispecific constructs for promoting OPK of *P. aeruginosa*. Opsonophagocytosis assay is shown with luminescent *P. aeruginosa* serogroup O5 strain (PAO1.lux), with dilutions of purified Psl/TNFα bispecific antibodies (Bs2-TNFα and Bs3-TNFα); the W4-RAD or V2L2-IgG1 parental antibodies; the Psl/PcrV bispecific antibodies Bs2-V2L2 or Bs3-V2L2, or the Bs2-V2L2-2C, Bs3-V2L2-2C, Bs4-V2L2-2C or the Bs4-V2L2-2C antibody harboring a YTE mutation (Bs4-V2L2-2C-YTE). (A) While the Bs2-V2L2 antibody showed similar killing compared to the parental W4-RAD antibody, the killing for the Bs3-V2L2 antibody was decreased. (B) While the Bs2-V2L2-2C and Bs4-V2L2-2C antibodies showed similar killing compared to the parental W4-RAD antibody, the killing for the Bs3-V2L2-2C antibody was decreased. (C) W4-RAD and W4-RAD-YTE designations represent different preparations of W4-RAD. Bs4-V2L2-2C (old lot) and Bs4-V2L2-2C (new lot), designations represent different preparations of Bs4-V2L2-2C. The YTE modification in Bs4-V2L2-2C-YTE is a modification made to antibodies that increases the half-life of antibodies. Different preparations of Bs4 antibodies (old lot vs. new lot) showed similar killing compared to the parental W4-RAD antibody, however the Bs4-V2L2-2C-YTE antibodies had a 3-fold drop in OPK activity when compared to Bs4-V2L2-2C (See EC50 table). R347 was used as a negative control in all experiments.

FIG. 21(A-I): In vivo survival study of anti-Psl/anti-PcrV bispecific antibodies Bs2-V2L2, Bs3-V2L2, Bs4-V2L2-2C and Bs4-V2L2-2C-YTE-treated mice in a 6206 acute pneumonia model system. Mice (n=10) were treated with (A): R347 (negative control, 0.2 mg/kg), Bs2-V2L2 (0.28 mg/kg), Bs3-V2L2 (0.28 mg/kg), V2L2 (0.2 mg/kg) or W4-RAD (0.2 mg/kg); (B-C): R347 (negative control, 1 mg/kg), Bs2-V2L2 (0.5 mg/kg or 1 mg/kg), or Bs4-V2L2-2C (0.5 mg/kg or 1 mg/kg); (D): R347 (negative control, 1 mg/kg), Bs3-V2L2 (0.5 mg/kg or 1 mg/kg), or Bs4-V2L2-2C (0.5 mg/kg or 1 mg/kg); (E): R347 (negative control, 2 mg/kg), a combination of the individual W4 and V2L2 antibodies (0.5 mg/kg or 1 mg/kg each) or Bs4-V2L2-2C (1 mg/kg or 2 mg/kg); (F): R347 (negative control, 1 mg/kg), a mixture of the individual W4 and V2L2 antibodies (0.5 mg/kg or 1 mg/kg each) or Bs4-V2L2-2C (1 mg/kg or 0.5 mg/kg). Twenty-four hours post-treatment, all mice were infected with ~ ($6.25 \times 10^5$-$1 \times 10^6$ CFU/animal) 6206 (O11-ExoU+). All mice were monitored for 120 hours. (A): All of the control mice succumbed to infection by approximately 30 hours post-infection. All of the Bs3-V2L2 animals survived, along with those which received the V2L2 control. Approximately 90% of the W4-RAD immunized animals survived. In contrast, approximately 50% of the Bs2-V2L2 animals succumbed to infection by 120 hours. (B-F): All of the control mice succumbed to infection by approximately 48 hours post-infection. (B): Bs4-V2L2-2C had greater activity in comparison to Bs2-V2L2 at both 1.0 and 0.5 mg/kg. (C): Bs4-V2L2-2C appeared to have greater activity in comparison to Bs2-V2L2 at 1.0 mg/kg (results are not statistically significant). (D): Bs4-V2L2-2C had greater activity in comparison to Bs3-V2L2 at 0.5 mg/kg. (E): Bs4-V2L2-2C at both 2 mg/kg and 1 mg/kg had greater activity in comparison to the antibody mixture at both 1.0 and 0.5 mg/kg. (F): Bs4-V2L2 (1 mg/kg) has similar activity at both 1.0 and 0.5 mg/kg. (G-H): Both Bs4-V2L2-2C and Bs4-V2L2-2C-YTE had similar activity at both 1.0 and 0.5 mg/kg. Results are represented as Kaplan-Meier survival curves; differences in survival were calculated by the Log-rank test for (B) Bs4-V2L2-2C vs. Bs2-V2L2 (1 mg/kg—P=0.034; 0.5 mg/kg—P=0.0002); (D) Bs4-V2L2-2C vs. Bs3-V2L2 (0.5 mg/kg—P<0.0001); (E): Bs4-V2L2-2C (2 mg/kg) vs. antibody mixture (1 mg/kg each)-P=0.0012; Bs4-V2L2-2C (1 mg/kg) vs. antibody mixture (0.5 mg/kg each)-P=0.0002. (G-H): Mice (n=8) were treated with: R347 (negative control, 1 mg/kg), Bs4-V2L2-2C (1 and 0.5 mg/kg), and Bs4-V2L2-2C-YTE (1 and 0.5 mg/kg) and 6206 (9e5 CFU). No difference in survival between Bs4-V2L2-2C and Bs4-V2L2-2C-YTE at either dose were observed by Log-Rank. (I): To analyze the efficacy of each antibody construct, mice were treated with 0.1 mg/kg, 0.2 mg/kg, 0.5 mg/kg, 1 mg/kg, 2 mg/kg, 5 mg/kg, 10 mg/kg or 15 mg/kg and analyzed for survival in a 6206 lethal pneumonia model. The percent survival is indicated in the table with the number of animals for each comparison indicated in parentheses.

Figure 22:
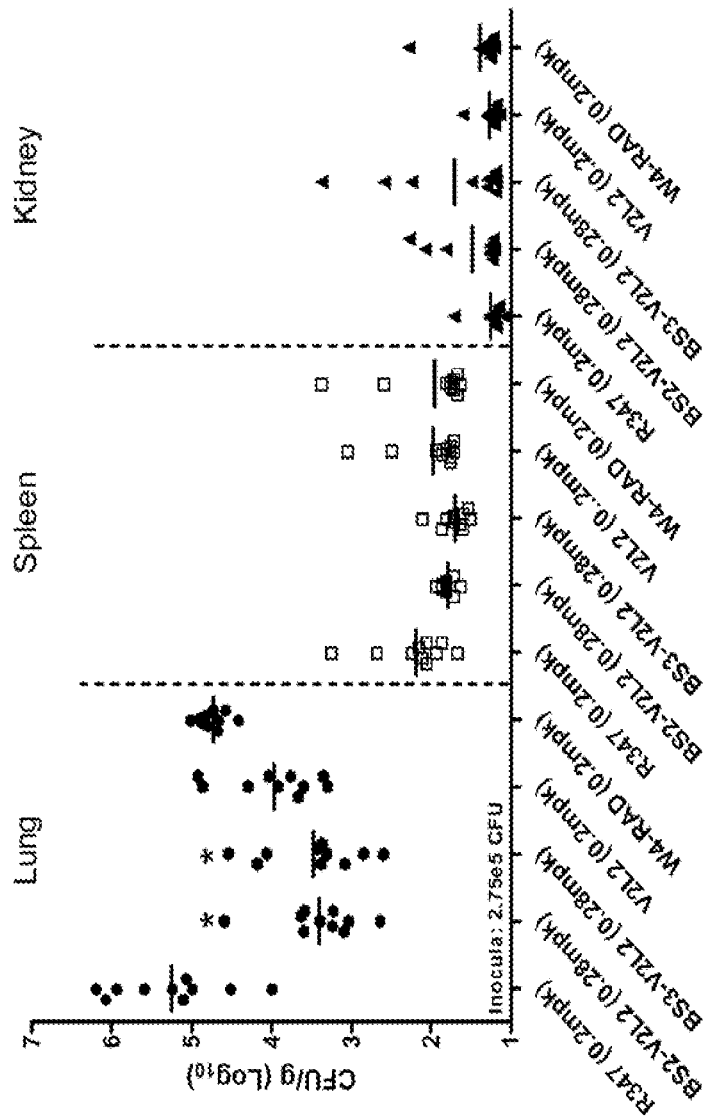

FIG. 22: Organ burden analysis of anti-Psl/PcrV bispecific antibody-treated animals using the 6206 acute pneumonia model. Mice were treated 24 hours prior to infection with 6206 (O11-ExoU+) with R347 (negative control), V2L2 or W4-RAD alone (0.2 mg/kg), Bs2-V2L2 (0.28 mg/kg), or BS3-V2L2 (0.28 mg/kg). Colony forming units were identified per gram of tissue in lung, spleen, and kidney. At the concentration tested, both Bs2-V2L2 and Bs3-V2L2 significantly decreased organ burden in lung. However, neither of the bispecific constructs was able to significantly affect organ burden in spleen or kidney compared to the parental antibodies.

FIG. 23(A-B): Organ burden analysis of anti-Psl/PcrV bispecific antibody-treated animals using a 6294 model system. Mice were treated 24 hours prior to infection with 6294 with R347 (negative control), V2L2 or W4-RAD alone (0.5 mg/kg), Bs2-V2L2 (0.7 mg/kg), or Bs3-V2L2 (0.7 mg/kg) (A), or V2L2 or W4-RAD alone (0.2 mg/kg), Bs2-V2L2 (0.2 mg/kg), Bs3-V2L2 (0.2 mg/kg) or a combination of the individual W4-RAD and V2L2 antibodies (0.1 mg/kg each) (B). Twenty-four hours post-administration of antibody, all mice were infected with an inoculum containing $2.5 \times 10^7$ CFU 6294 (A) or $1.72 \times 10^7$ CFU 6294 (B). Colony forming units were identified per gram of tissue in lung, spleen, and kidney. Using the 6294 model system, (A) both the BS2-V2L2 and BS3-V2L2 significantly decreased organ burden in all of the tissues to a level comparable to that of the V2L2 parental antibody. The W4-RAD parental antibody had no effect on decreasing organ burden. (B) Bs2-V2L2, Bs3-V2L2, and W4-RAD+

V2L2 combination significantly decreased organ burden in all of the tissues to a level comparable to that of the V2L2 parental antibody.

Figure 24:
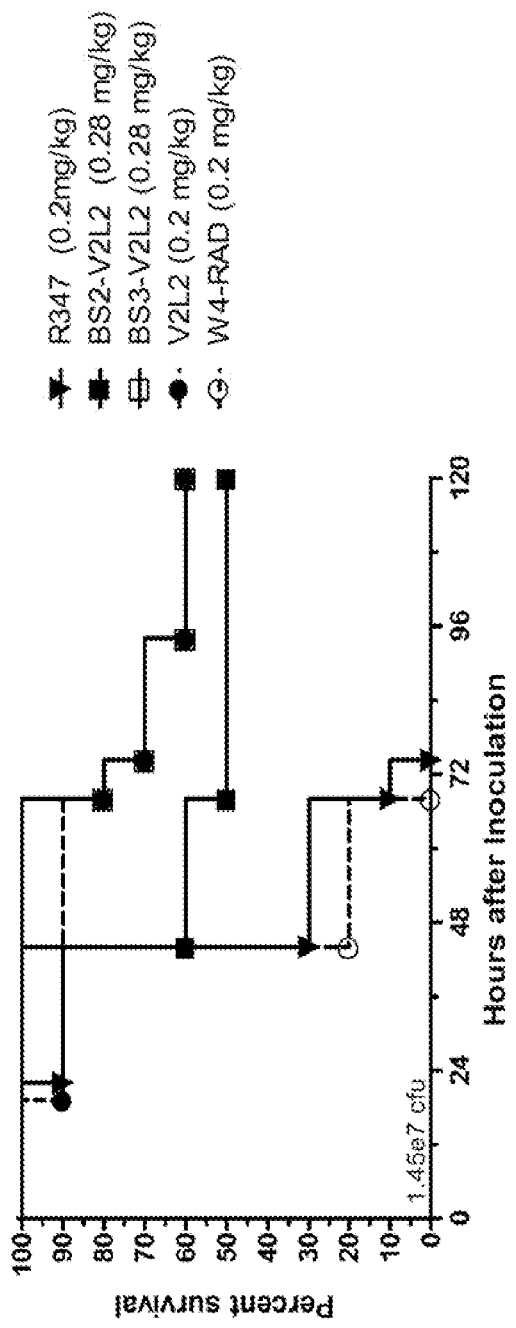

FIG. 24: In vivo survival study of Bs2-W4/V2L2 and Bs3-W4/V2L2-treated mice in a 6294 model system. Mice were treated with R347 (negative control, 0.2 mg/kg), Bs2-V2L2 (0.28 mg/kg), Bs3-V2L2 (0.28 mg/kg), V2L2 (0.2 mg/kg) or W4-RAD (0.2 mg/kg). Twenty-four hours post-treatment, all mice were infected with 6294. All mice were monitored for 120 hours. All of the control mice succumbed to infection by approximately 75 hours post-infection. Sixty percent of the Bs3-V2L2 and 50% of the Bs2-V2L2 animals survived after 120 hours post-inoculation. As was seen in the organ burden studies, W4-RAD immunization did not affect survival with all mice succumbing to infection at approximately the same time as the controls.

FIG. 25(A-D): Organ burden analysis of anti-Psl/PcrV bispecific antibody or W4+V2L2 combination therapy in the 6206 model system. Suboptimal concentrations of antibody were used (A-C) to enable the ability to decipher antibody activity. (D) High concentrations of Bs4 were used. Mice were treated 24 hours prior to infection with 6206 with R347 (negative control), V2L2 or W4-RAD alone (0.2 mg/kg), Bs2-V2L2 (0.2 mg/kg), Bs3-V2L2 (0.2 mg/kg), Bs4 (15.0, 5.0 and 1.0 mg/kg) or a combination of the individual W4 and V2L2 antibodies (0.1 mg/kg each). Twenty-four hours post-administration of antibody, all mice were infected with an inoculum containing (A), (B) $4.75 \times 10^5$ CFU 6206 (O11-ExoU+), or (C) $7.75 \times 10^5$ CFU 6206 (O11-ExoU+) or (D) $9.5 \times 10^5$ CFU 6206 (O11-ExoU+). Colony forming units were identified per gram of tissue in lung, spleen, and kidney. Using the 6206 model system, both the BS2-V2L2 and BS3-V2L2 decreased organ burden in the lung, spleen and kidneys to a level comparable to that of the W4+V2L2 combination. In the lung, the combination significantly reduced bacterial CFUs Bs2- and Bs3-V2L2 and V2L2 using the Kruskal-Wallis with Dunn's post test. Significant differences in bacterial burden in the spleen and kidney were not observed, although a trend towards reduction was noted. (D) When optimal concentrations of Bs4-V2L2-2C were used (15.0, 5.0, and 1.0), rapid and efficient bacterial clearance was observed from the lung. In addition, bacterial dissemination to the spleen and kidneys were also ablated. Asterisks indicate statistical significance when compared to the R347 control using the Kruskal-Wallis with Dunn's post test.

FIG. 26(A-J): Therapeutic adjunctive therapy: Bs4-V2L2-2C+ antibiotic. (A)-(B) Mice were treated 24 hours prior to infection with $1 \times 10^6$ CFU 6206 with 0.5 mg/kg R347 (negative control) or Bs4-V2L2-2C (0.2 mg/kg or 0.5 mg/kg) or Ciprofloxacin (CIP) (20 mg/kg or 6.7 mg/kg) 1 hour post infection, or a combination of the Bs4-V2L2-2C 24 hours prior to infection and CIP 1 hour post infection (0.5 mg/kg+20 mg/kg or 0.5 mg/kg+6.7 mg/kg or 0.2 mg/kg+20 mg/kg or 0.2 mg/kg+6.7 mg/kg, respectively). (C) Mice were treated 1 hour post infection with $9.5 \times 10^5$ CFU 6206 with 5 mg/kg R347 or CIP (20 mg/kg or 6.7 mg/kg) or Bs4-V2L2-2C (1 mg/kg or 5 mg/kg), or a combination of the Bs4-V2L2-2C and CIP (5 mg/kg+20 mg/kg or 5 mg/kg+6.7 mg/kg or 1 mg/kg+20 mg/kg or 1 mg/kg+6.7 mg/kg, respectively). (D) Mice were treated 2 hours post infection with $9.5 \times 10^5$ CFU 6206 with 5 mg/kg R347 or CIP (20 mg/kg or 6.7 mg/kg) or Bs4-V2L2-2C (1 mg/kg or 5 mg/kg), or a combination of the Bs4-V2L2-2C and Cipro (5 mg/kg+20 mg/kg or 5 mg/kg+6.7 mg/kg or 1 mg/kg+20 mg/kg or 1 mg/kg+6.7 mg/kg, respectively). (E) Mice were treated 2 hours post infection with $9.75 \times 10^5$ CFU 6206 with 5 mg/kg R347 or Bs4-V2L2-2C (1 mg/kg or 5 mg/kg) or CIP (20 mg/kg or 6.7 mg/kg) 1 hour post infection, or a combination of the Bs4-V2L2-2C 2 hours post infection and CIP 1 hour post infection (5 mg/kg+20 mg/kg or 5 mg/kg+6.7 mg/kg or 1 mg/kg+20 mg/kg or 1 mg/kg+6.7 mg/kg, respectively). (F) Mice were treated 1 hour post infection with $9.5 \times 10^5$ CFU 6206 with 5 mg/kg R347 or Meropenem (MEM) (0.75 mg/kg or 2.3 mg/kg) or Bs4-V2L2-2C (1 mg/kg or 5 mg/kg), or a combination of the Bs4-V2L2-2C and MEM (5 mg/kg+2.3 mg/kg or 5 mg/kg+0.75 mg/kg or 1 mg/kg+2.3 mg/kg or 1 mg/kg+0.75 mg/kg, respectively). (G) Mice were treated 2 hours post infection with $9.75 \times 10^5$ CFU 6206 with 5 mg/kg R347 or Bs4-V2L2-2C (1 mg/kg or 5 mg/kg) or MEM (0.75 mg/kg or 2.3 mg/kg) 1 hour post infection, or a combination of the Bs4-V2L2-2C 2 hours post infection and MEM 1 hour post infection (5 mg/kg+2.3 mg/kg or 5 mg/kg+0.75 mg/kg or 1 mg/kg+2.3 mg/kg or 1 mg/kg+0.75 mg/kg, respectively). (H) Mice were treated 2 hours post infection with $1 \times 10^6$ CFU 6206 with 5 mg/kg R347 or Bs4-V2L2-2C (1 mg/kg or 5 mg/kg) or MEM (0.75 mg/kg or 2.3 mg/kg), or a combination of the Bs4-V2L2-2C 2 and MEM (5 mg/kg+2.3 mg/kg or 5 mg/kg+0.75 mg/kg or 1 mg/kg+2.3 mg/kg or 1 mg/kg+0.75 mg/kg, respectively). (I) Mice were treated 4 hour post infection with $9.25 \times 10^5$ CFU 6206 with 5 mg/kg R347 or CIP (6.7 mg/kg) or Bs4-V2L2-2C (1 mg/kg or 5 mg/kg) or a combination of the Bs4-V2L2-2C and CIP (5 mg/kg+6.7 mg/kg or 1 mg/kg+6.7 mg/kg, respectively), (J) Mice were treated 4 hour post infection with $1.2 \times 10^6$ CFU 6206 with 5 mg/kg R347+CIP (6.7 mg/kg), CIP (6.7 mg/kg), or Bs4-V2L2-2C (1 mg/kg or 5 mg/kg) or a combination of the Bs4-V2L2-2C and CIP (5 mg/kg+6.7 mg/kg or 1 mg/kg+6.7 mg/kg, respectively). (A-J) Bs4 antibody combined with either CIP or MEM increases efficacy of antibiotic therapy, indicating synergistic protection when the molecules are combined. In addition, although antibiotic delivered by itself or in combination with a P. aeruginosa non-specific antibody can reduce or control bacterial CFU in the lung, antibiotic alone does not protect mice from lethality in this setting. Optimal protection in this setting requires including Bs4-V2L2-2C in combination with antibiotic.

Figure 27A:
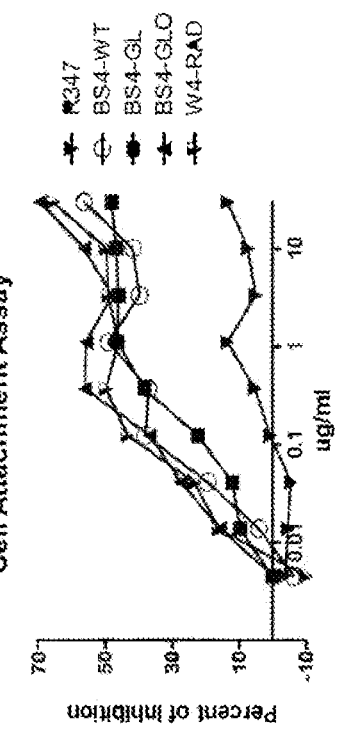
Figure 27B:
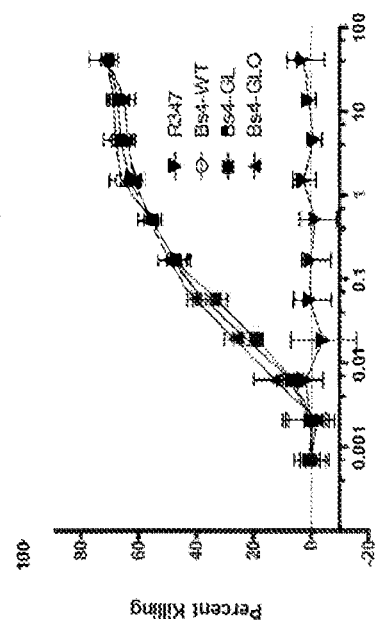
Figure 27C:
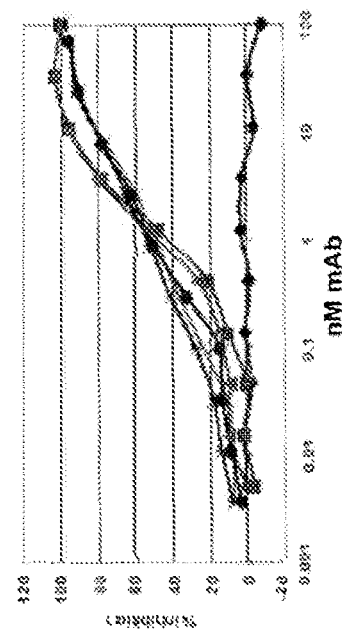

FIG. 27(A-C): Difference in functional activity of bi-specific antibodies BS4-WT, BS4-GL and BS4-GLO: opsonophagocytic killing assay (A), anti-cell attachment assay (B), and a RBC lysis anti-cytotoxicity assay (C).

FIG. 28(A-B): Percent protection against lethal pneumonia in mice challenged in prophylactic (A) or therapeutic (B) settings with P. aeruginosa strains. The percent survival is indicated in the table with the number of animals for each comparison indicated in parentheses. The dashes indicate not tested.

Figure 29B:
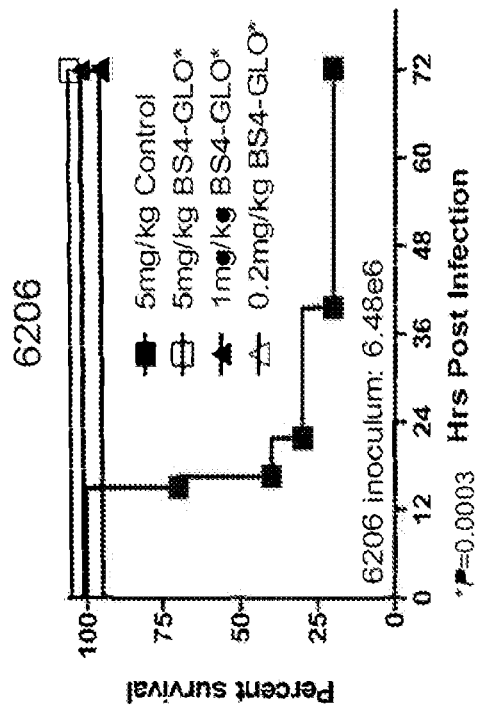
Figure 29A:
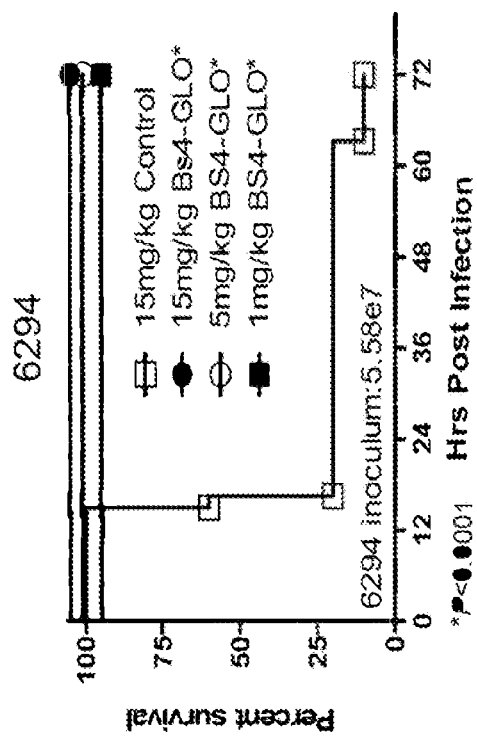

FIG. 29(A-B): Survival rates for animals treated with bispecific antibody Bs4-GLO in a P. aeruginosa lethal bacteremia model. (A) Animals were treated with Bs4-GLO at 15 mg/kg, 5 mg/kg, 1 mg/kg or R347 at 15 mg/kg 24 hours prior to intraperitoneal infection with 6294 (O6) ($5.58 \times 10^7$ CFU). (B) Animals were treated with Bs4-GLO at 5 mg/kg, 1 mg/kg, 0.2 mg/kg or R347 at 5 mg/kg 24 hours prior to intraperitoneal infection with 6206 (O11-ExoU+) ($6.48 \times 10^6$ CFU). Results are represented as Kaplan-Meier survival curves; differences in survival were calculated by the Log-rank test for BS4-GLO at each concentration vs. R347. (A) Bs4-GLO at all concentrations vs. R347 P<0.0001. (B) Bs4-GLO at all concentrations vs. R347 P=0.0003. Results are representative of three independent experiments.

Figure 30A:
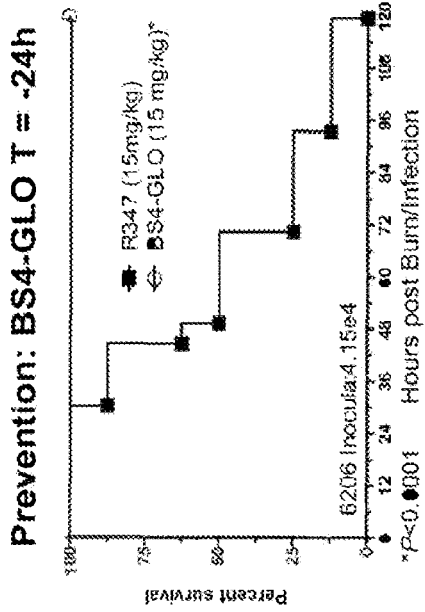
Figure 30B:
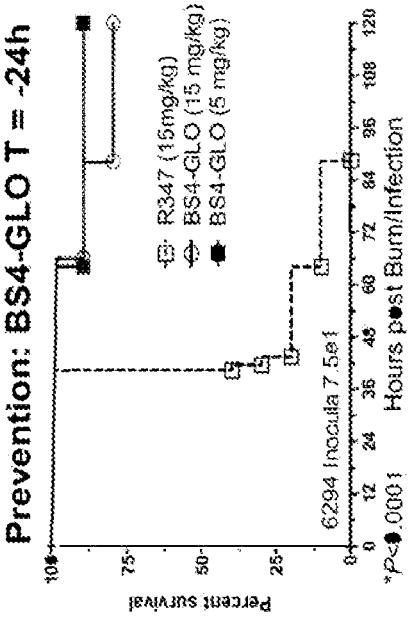
Figure 30C:
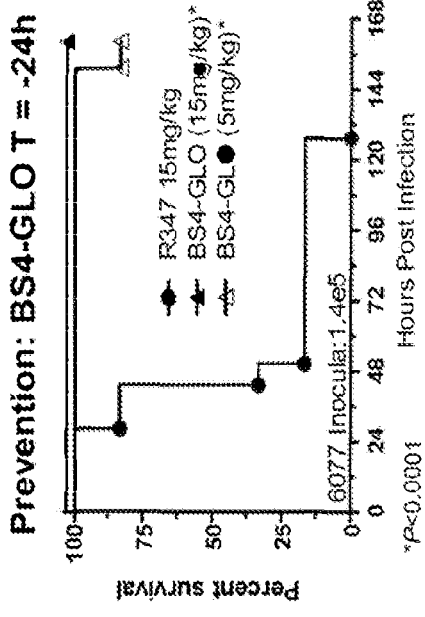

FIG. 30(A-C): Survival rates for animals prophylactically treated (prevention) with Bs4-GLO in a P. aeruginosa thermal injury model. (A) Animals were treated with Bs4-GLO at 15 mg/kg, 5 mg/kg or R347 at 15 mg/kg 24 hours prior to induction of thermal injury and subcutaneous infection with *P. aeruginosa* strain 6077 (O11-ExoU$^+$) with $1.4\times10^5$ CFU directly under the wound. (B) Animals were treated with Bs4-GLO at 15 mg/kg or R347 at 15 mg/kg 24 hours prior to induction of thermal injury and subcutaneous infection with *P. aeruginosa* strain 6206 (O11-ExoU$^+$) with $4.15\times10^4$ CFU directly under the wound. (C) Animals were treated with Bs4-GLO at 15 mg/kg, 5 mg/kg or R347 at 15 mg/kg 24 hours prior to induction of thermal injury and subcutaneous infection with *P. aeruginosa* strain 6294 (O6) with $7.5\times10^1$ CFU directly under the wound. Results are represented as Kaplan-Meier survival curves; differences in survival were calculated by the Log-rank test for Bs4-GLO at each concentration vs. R347. (A-C) Bs4-GLO at all concentrations vs. R347-P<0.0001. Results are representative of two independent experiments for each *P. aeruginosa* strain.

Figure 31A:
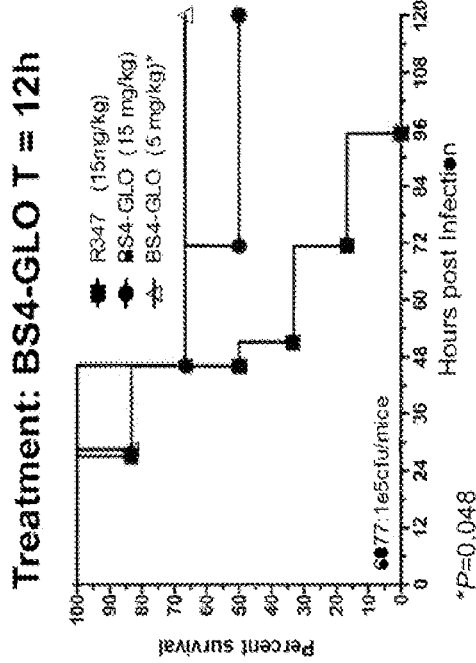
Figure 31B:
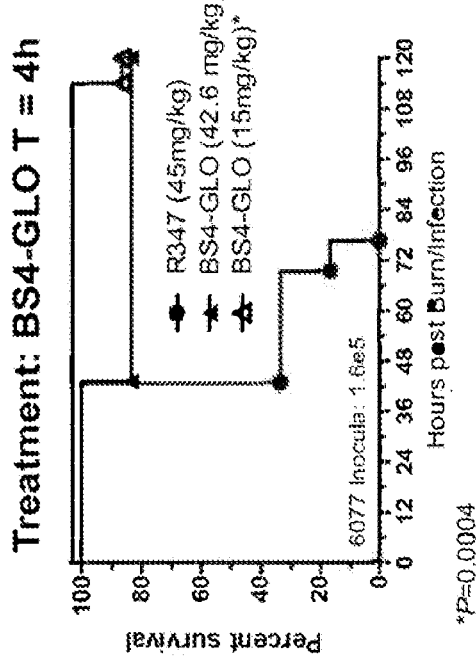

FIG. 31(A-B): Survival rates for animals therapeutically treated (treatment)) with Bs4-GLO in a *P. aeruginosa* thermal injury model. (A) Animals were treated with Bs4-GLO at 42.6 mg/kg, 15 mg/kg or R347 at 45 mg/kg 4h hours after induction of thermal injury and subcutaneous infection with *P. aeruginosa* strain 6077 (O11-ExoU$^+$) with $1.6\times10^5$ CFU directly under the wound. (B) Animals were treated with Bs4-GLO at 15 mg/kg, 5 mg/kg or R347 at 15 mg/kg 12h hours after induction of thermal injury and subcutaneous infection with *P. aeruginosa* strain 6077 (O11-ExoU+) with $1.0\times10^5$ CFU directly under the wound. Results are represented as Kaplan-Meier survival curves; differences in survival were calculated by the Log-rank test for BS4-GLO at each concentration vs. R347. (A) Bs4-GLO at both concentrations vs. R347-P=0.0004. (B) Bs4-GLO at 5 mg/kg vs. R347-P=0.048. Results are representative of two independent experiments.

FIG. 32(A-B): Therapeutic adjunctive therapy: Bs4GLO+ciprofloxacin (CIP): (A) Mice were treated 4 hour post infection with $9.5\times10^5$ CFU 6206 with 5 mg/kg R347+CIP (6.7 mg/kg) or Bs4-WT (1 mg/kg or 5 mg/kg) or a combination of the Bs4-WT and CIP (5 mg/kg+6.7 mg/kg or 1 mg/kg+6.7 mg/kg, respectively). (B) Mice were treated 4 hour post infection with $9.5\times10^5$ CFU 6206 with 5 mg/kg R347+CIP (6.7 mg/kg) or Bs4-GLO (1 mg/kg or 5 mg/kg) or a combination of the Bs4-GLO and CIP (5 mg/kg+6.7 mg/kg or 1 mg/kg+6.7 mg/kg, respectively FIG. 33(A-B): Therapeutic adjunctive therapy: Bs4-GLO+meropenem (MEM): (A) Mice were treated 4 hour post infection with $9.5\times10^5$ CFU 6206 with 5 mg/kg R347+MEM (0.75 mg/kg) or Bs4-WT (1 mg/kg or 5 mg/kg) or a combination of the Bs4-WT and MEM (5 mg/kg+0.75 mg/kg or 1 mg/kg+0.75 mg/kg, respectively). (B) Mice were treated 4 hour post infection with $9.5\times10^5$ CFU 6206 with 5 mg/kg R347+MEM (0.75 mg/kg) or Bs4-GLO (1 mg/kg or 5 mg/kg) or a combination of the Bs4-GLO and MEM (5 mg/kg+0.75 mg/kg or 1 mg/kg+0.75 mg/kg, respectively).

FIG. 34(A-C): Therapeutic adjunctive therapy: Bs4-GLO+antibiotic in a lethal bacteremia model. Mice were treated 24 hours prior to intraperitoneal infection with *P. aeruginosa* strain 6294 (O6) $9.3\times10^7$ with Bs4-GLO at (0.25 mg/kg or 0.5 mg/kg) or R347 (negative control). One hour post infection, mice were treated subcutaneously with (A) 1 mg/kg CIP, (B) 2.5 mg/kg MEM or (C) 2.5 mg/kg TOB. Results are represented as Kaplan-Meier survival curves; differences in survival were calculated by the Log-rank test for Bs4-GLO at each concentration vs. R347.

FIG. 35(A-B) Schematic representation of alternative formats for Bs4 constructs (A) anti-PcrV variable regions are present separately on the heavy and light chains while the anti-Psl variable regions are present as an scFv within the hinge region of the heavy chain and (B) anti-Psl variable regions are present separately on the heavy and light chains while the anti-PcrV variable regions are present as an scFv within the hinge region of the heavy chain.

DETAILED DESCRIPTION

I. Definitions

It is to be noted that the term "a" or "an" entity refers to one or more of that entity; for example, "a binding molecule which specifically binds to *Pseudomonas* Psl and/or PcrV," is understood to represent one or more binding molecules which specifically bind to *Pseudomonas* Psl and/or PcrV. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced by recombinant technology, but is not necessarily translated from a designated nucleic acid sequence. It can be generated in any manner, including by chemical synthesis.

A polypeptide as disclosed herein can be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides can have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are native or recombinant polypeptides which have been separated, fractionated, or partially or substantially purified by any suitable technique.

Other polypeptides disclosed herein are fragments, derivatives, analogs, or variants of the foregoing polypeptides, and any combination thereof. The terms "fragment," "variant," "derivative" and "analog" when referring to a binding molecule such as an antibody which specifically binds to *Pseudomonas* Psl and/or PcrV as disclosed herein include any polypeptides which retain at least some of the antigen-binding properties of the corresponding native antibody or polypeptide. Fragments of polypeptides include, for example, proteolytic fragments, as well as deletion fragments, in addition to specific antibody fragments discussed elsewhere herein. Variants of a binding molecule, e.g., an antibody which specifically binds to *Pseudomonas* Psl and/or PcrV as disclosed herein include fragments as described above, and also polypeptides with altered amino acid sequences due to amino acid substitutions, deletions, or insertions. Variants can occur naturally or be non-naturally occurring. Non-naturally occurring variants can be produced using art-known mutagenesis techniques. Variant polypeptides can comprise conservative or non-conservative amino acid substitutions, deletions or additions. Derivatives of a binding molecule, e.g., an antibody which specifically binds to *Pseudomonas* Psl and/or PcrV as disclosed herein are polypeptides which have been altered so as to exhibit additional features not found on the native polypeptide. Examples include fusion proteins. Variant polypeptides can also be referred to herein as "polypeptide analogs." As used herein a "derivative" of a binding molecule, e.g., an antibody which specifically binds to *Pseudomonas* Psl and/or PcrV refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide can comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a binding molecule, e.g., an antibody which specifically binds to *Pseudomonas* Psl and/or PcrV contained in a vector is considered isolated as disclosed herein. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides. Isolated polynucleotides or nucleic acids further include such molecules produced synthetically. In addition, polynucleotide or a nucleic acid can be or can include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode an immunoglobulin heavy chain variable region and an immunoglobulin light chain variable region. In addition, a vector, polynucleotide, or nucleic acid can encode heterologous coding regions, either fused or unfused to a nucleic acid encoding an a binding molecule which specifically binds to *Pseudomonas* Psl and/or PcrV, e.g., an antibody, or antigen-binding fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally can include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide can be RNA, for example, in the form of messenger RNA (mRNA).

Polynucleotide and nucleic acid coding regions can be associated with additional coding regions which encode secretory or signal peptides, which direct the secretion of a polypeptide encoded by a polynucleotide as disclosed herein, e.g., a polynucleotide encoding a binding molecule which specifically binds to *Pseudomonas* Psl and/or PcrV, e.g., an antibody, or antigen-binding fragment, variant, or derivative thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse β-glucuronidase.

Disclosed herein are certain binding molecules, or antigen-binding fragments, variants, or derivatives thereof. Unless specifically referring to full-sized antibodies such as naturally-occurring antibodies, the term "binding molecule" encompasses full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

As used herein, the term "binding molecule" refers in its broadest sense to a molecule that specifically binds an antigenic determinant. As described further herein, a binding molecule can comprise one or more of the binding domains described herein. As used herein, a "binding domain" includes a site that specifically binds the antigenic determinant. A non-limiting example of an antigen binding molecule is an antibody or fragment thereof that retains antigen-specific binding.

The terms "antibody" and "immunoglobulin" can be used interchangeably herein. An antibody (or a fragment, variant, or derivative thereof as disclosed herein comprises at least the variable domain of a heavy chain and at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, etc. are well characterized and are known to confer functional specialization. Modified versions of each of these classes and isotypes are readily discernible to the skilled artisan in view of the instant disclosure and, accordingly, are within the scope of this disclosure.

Light chains are classified as either kappa or lambda (κ, λ). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the binding molecule to selectively recognize and specifically bind epitopes on antigens. That is, the VL domain and VH domain, or subset of the complementarity determining regions (CDRs), of a binding molecule, e.g., an antibody combine to form the variable region that defines a three dimensional antigen binding site. This quaternary binding molecule structure forms the antigen binding site present at the end of each arm of the Y. More specifically, the antigen binding site is defined by three CDRs on each of the VH and VL chains.

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops which connect, and in some cases form part of, the B-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, *J. Mol. Biol.*, 196:901-917 (1987), which are incorporated herein by reference in their entireties).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table I as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

| | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in a binding molecule which specifically binds to *Pseudomonas* Psl and/or PcrV, e.g, an antibody, or antigen-binding fragment, variant, or derivative thereof as disclosed herein are according to the Kabat numbering system.

Binding molecules, e.g., antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VL or VH domain, fragments produced by a Fab expression library. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

By "specifically binds," it is generally meant that a binding molecule, e.g., an antibody or fragment, variant, or derivative thereof binds to an epitope via its antigen binding domain, and that the binding entails some complementarity between the antigen binding domain and the epitope. According to this definition, a binding molecule is said to "specifically bind" to an epitope when it binds to that epitope, via its antigen binding domain more readily than it would bind to a random, unrelated epitope. The term "specificity" is used herein to qualify the relative affinity by which a certain binding molecule binds to a certain epitope. For example, binding molecule "A" may be deemed to have a higher specificity for a given epitope than binding molecule "B," or binding molecule "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody can cross-react with the related epitope.

By way of non-limiting example, a binding molecule, e.g., an antibody can be considered to bind a first epitope preferentially if it binds said first epitope with a dissociation constant ($K_D$) that is less than the antibody's $K_D$ for the second epitope. In another non-limiting example, a binding molecule such as an antibody can be considered to bind a first antigen preferentially if it binds the first epitope with an affinity that is at least one order of magnitudeless than the antibody's $K_D$ for the second epitope. In another non-limiting example, a binding molecule can be considered to bind a first epitope preferentially if it binds the first epitope with an affinity that is at least two orders of magnitude less than the antibody's $K_D$ for the second epitope.

In another non-limiting example, a binding molecule, e.g., an antibody or fragment, variant, or derivative thereof can be considered to bind a first epitope preferentially if it binds the first epitope with an off rate (k(off)) that is less than the antibody's k(off) for the second epitope. In another non-limiting example, a binding molecule can be considered to bind a first epitope preferentially if it binds the first epitope with an affinity that is at least one order of magnitude less than the antibody's k(off) for the second epitope. In another non-limiting example, a binding molecule can be considered to bind a first epitope preferentially if it binds the first epitope with an affinity that is at least two orders of magnitude less than the antibody's k(off) for the second epitope.

A binding molecule, e.g., an antibody or fragment, variant, or derivative thereof disclosed herein can be said to bind a target antigen, e.g., a polysaccharide disclosed herein or a fragment or variant thereof with an off rate (k(off)) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. A binding molecule as disclosed herein can be said to bind a target antigen, e.g., a polysaccharide with an off rate (k(off)) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$ $5 \times 10^{-6}$ sec$^{-1}$, $10^{-6}$ sec$^{-1}$, $5 \times 10^{-7}$ sec$^{-1}$ or $10^{-7}$ sec$^{-1}$.

A binding molecule, e.g., an antibody or antigen-binding fragment, variant, or derivative disclosed herein can be said to bind a target antigen, e.g., a polysaccharide with an on rate (k(on)) of greater than or equal to $10^3$ M$^{-1}$ sec$^{-1}$, $5 \times 10^3$ M$^{-1}$ $sec^{-1}$, $10^4 M^{-1} sec^{-1}$ or $5 \times 10^4 M^{-1} sec^{-1}$. A binding molecule as disclosed herein can be said to bind a target antigen, e.g., a polysaccharide with an on rate (k(on)) greater than or equal to $10^5 M^{-1} sec^{-1}$, $5 \times 10^5 M^{-1} sec^{-1}$, $10^6 M^{-1} sec^{-1}$, or $5 \times 10^6 M^{-1} sec^{-1}$ or $10^7 M^{-1} sec^{-1}$.

A binding molecule, e.g., an antibody or fragment, variant, or derivative thereof is said to competitively inhibit binding of a reference antibody or antigen binding fragment to a given epitope if it preferentially binds to that epitope to the extent that it blocks, to some degree, binding of the reference antibody or antigen binding fragment to the epitope. Competitive inhibition can be determined by any method known in the art, for example, competition ELISA assays. A binding molecule can be said to competitively inhibit binding of the reference antibody or antigen binding fragment to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Binding molecules or antigen-binding fragments, variants or derivatives thereof as disclosed herein can also be described or specified in terms of their cross-reactivity. As used herein, the term "cross-reactivity" refers to the ability of a binding molecule, e.g., an antibody or fragment, variant, or derivative thereof, specific for one antigen, to react with a second antigen; a measure of relatedness between two different antigenic substances. Thus, a binding molecule is cross reactive if it binds to an epitope other than the one that induced its formation. The cross reactive epitope generally contains many of the same complementary structural features as the inducing epitope, and in some cases, can actually fit better than the original.

A binding molecule, e.g., an antibody or fragment, variant, or derivative thereof can also be described or specified in terms of their binding affinity to an antigen. For example, a binding molecule can bind to an antigen with a dissociation constant or $K_D$ no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

Antibody fragments including single-chain antibodies can comprise the variable region(s) alone or in combination with the entirety or a portion of the following: hinge region, CH1, CH2, and CH3 domains. Also included are antigen-binding fragments also comprising any combination of variable region(s) with a hinge region, CH1, CH2, and CH3 domains. Binding molecules, e.g., antibodies, or antigen-binding fragments thereof disclosed herein can be from any animal origin including birds and mammals. The antibodies can be human, murine, donkey, rabbit, goat, guinea pig, camel, llama, horse, or chicken antibodies. In another embodiment, the variable region can be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al.

As used herein, the term "heavy chain portion" includes amino acid sequences derived from an immunoglobulin heavy chain. a binding molecule, e.g., an antibody comprising a heavy chain portion comprises at least one of: a CH1 domain, a hinge (e.g., upper, middle, and/or lower hinge region) domain, a CH2 domain, a CH3 domain, or a variant or fragment thereof. For example, a binding molecule, e.g., an antibody or fragment, variant, or derivative thereof can comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a binding molecule, e.g., an antibody or fragment, variant, or derivative thereof comprises a polypeptide chain comprising a CH3 domain. Further, a binding molecule for use in the disclosure can lack at least a portion of a CH2 domain (e.g., all or part of a CH2 domain). As set forth above, it will be understood by one of ordinary skill in the art that these domains (e.g., the heavy chain portions) can be modified such that they vary in amino acid sequence from the naturally occurring immunoglobulin molecule.

The heavy chain portions of a binding molecule, e.g., an antibody as disclosed herein can be derived from different immunoglobulin molecules. For example, a heavy chain portion of a polypeptide can comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. The light chain portion comprises at least one of a VL or CL domain.

Binding molecules, e.g., antibodies or antigen-binding fragments, variants, or derivatives thereof disclosed herein can be described or specified in terms of the epitope(s) or portion(s) of an antigen, e.g., a target polysaccharide that they recognize or specifically bind. The portion of a target polysaccharide which specifically interacts with the antigen binding domain of an antibody is an "epitope," or an "antigenic determinant." A target antigen, e.g., a polysaccharide can comprise a single epitope, but typically comprises at least two epitopes, and can include any number of epitopes, depending on the size, conformation, and type of antigen.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CHI domain" includes the first (most amino terminal)

constant region domain of an immunoglobulin heavy chain. The CHI domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit. The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CHI domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., J. Immunol. 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CHI and CL regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which can be intact, partial or modified) is obtained from a second species. In some embodiments the target binding region or site will be from a non-human source (e.g. mouse or primate) and the constant region is human.

The term "bispecific antibody" as used herein refers to an antibody that has binding sites for two different antigens within a single antibody molecule. It will be appreciated that other molecules in addition to the canonical antibody structure can be constructed with two binding specificities. It will further be appreciated that antigen binding by bispecific antibodies can be simultaneous or sequential. Triomas and hybrid hybridomas are two examples of cell lines that can secrete bispecific antibodies. Bispecific antibodies can also be constructed by recombinant means. (Ströhlein and Heiss, *Future Oncol.* 6:1387-94 (2010); Mabry and Snavely, *IDrugs.* 13:543-9 (2010)).

As used herein, the term "engineered antibody" refers to an antibody in which the variable domain in either the heavy and light chain or both is altered by at least partial replacement of one or more CDRs from an antibody of known specificity and, if necessary, by partial framework region replacement and sequence changing. Although the CDRs can be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable region to transfer the antigen binding capacity of one variable domain to another. Rather, it may only be necessary to transfer those residues that are necessary to maintain the activity of the target binding site. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein the term "properly folded polypeptide" includes polypeptides (e.g., anti-*Pseudomonas* Psl and PcrV antibodies) in which all of the functional domains comprising the polypeptide are distinctly active. As used herein, the term "improperly folded polypeptide" includes polypeptides in which at least one of the functional domains of the polypeptide is not active. In one embodiment, a properly folded polypeptide comprises polypeptide chains linked by at least one disulfide bond and, conversely, an improperly folded polypeptide comprises polypeptide chains not linked by at least one disulfide bond.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

As used herein, the terms "linked," "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature.) Although the reading frame is thus made continuous throughout the fused segments, the segments can be physically or spatially separated by, for example, in-frame linker sequence. For example, polynucleotides encoding the CDRs of an immunoglobulin variable region can be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the terms "treat" or "treatment" refer to both therapeutic treatment and prophylactic or preventative measures, wherein the object is to prevent or slow down (lessen) an undesired physiological change, infection, or disorder. Beneficial or desired clinical results include, but are not limited to, alleviation of symptoms, diminishment of extent of disease, stabilized (i.e., not worsening) state of disease, clearance or reduction of an infectious agent such as *P. aeruginosa* in a subject, a delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the infection, condition, or disorder as well as those prone to have the condition or disorder or those in which the condition or disorder is to be prevented, e.g., in burn patients or immunosuppressed patients susceptible to *P. aeruginosa* infection.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, bears, and so on.

As used herein, phrases such as "a subject that would benefit from administration of anti-*Pseudomonas* Psl and PcrV binding domains or binding molecules" and "an animal in need of treatment" includes subjects, such as mammalian subjects, that would benefit from administration of anti-*Pseudomonas* Psl and PcrV binding domains or a binding molecule, such as an antibody, comprising one or more of the binding domains. Such binding domains, or binding molecules can be used, e.g., for detection of *Pseudomonas* Psl or PcrV (e.g., for a diagnostic procedure) and/or for treatment, i.e., palliation or prevention of a disease, with anti-*Pseudomonas* Psl and PcrV binding molecules. As described in more detail herein, the anti-*Pseudomonas* Psl and PcrV binding molecules can be used in unconjugated form or can be conjugated, e.g., to a drug, prodrug, or an isotope.

The term "synergistic effect", as used herein, refers to a greater-than-additive therapeutic effect produced by a combination of compounds wherein the therapeutic effect obtained with the combination exceeds the additive effects that would otherwise result from individual administration the compounds alone. Certain embodiments include methods of producing a synergistic effect in the treatment of *Pseudomonas* infections, wherein said effect is at least 5%, at least 10%, at least 20%, at least 30%, at least 40%, at least 50%, at least 60%, at least 70%, at least 80%, at least 90%, at least 100%, at least 200%, at least 500%, or at least 1000% greater than the corresponding additive effect.

"Co-administration" refers to the administration of different compounds, such as an anti-Psl and an anti-PcrV binding domain, or binding molecule comprising one or both an anti-Psl and anti-PcrV binding domain, such that the compounds elicit a synergistic effect on anti-*Pseudomonas* immunity. The compounds can be administered in the same or different compositions which if separate are administered proximate to one another, generally within 24 hours of each other and more typically within about 1-8 hours of one another, and even more typically within 1-4 hours of each other or close to simultaneous administration. The relative amounts are dosages that achieve the desired synergism.

II. Binding Domains and Binding Molecules

Antibodies that bind Psl and formats for using these antibodies have been described in the art. See, for example, International Application Nos. PCT/US2012/041538, filed Jun. 8, 2012, and PCT/US2012/63639, filed Nov. 6, 2012, entitled "MULTISPECIFIC AND MULTIVALENT BINDING PROTEINS AND USES THEREOF"), which are herein incorporated in their entireties by reference.

One embodiment is directed to binding domains that specifically bind to *Pseudomonas* PcrV, wherein binding can disrupt the activity of the type III toxin secretion system. In certain embodiments, the binding domains have the same *Pseudomonas* binding specificity as the antibody V2L2.

Another embodiment is directed to binding domains that specifically bind to *Pseudomonas* Psl or PcrV, wherein administration of both binding domains results in synergistic effects against *Pseudomonas* infections by (a) inhibiting attachment of *Pseudomonas aeruginosa* to epithelial cells, (b) promoting, mediating, or enhancing opsonophagocytic killing (OPK) of *P. aeruginosa*, (c) inhibiting attachment of *P. aeruginosa* to epithelial cells, or (d) disrupting the activity of the type III toxin secretion system. In certain embodiments, the binding domains have the same *Pseudomonas* binding specificity as the antibodies Cam-003, WapR-004, V2L2, or 29D2.

Other embodiments are directed to an isolated binding molecule(s) comprising one or both binding domains that specifically bind to *Pseudomonas* Psl and/or PcrV, wherein administration of the binding molecule results in synergistic effects against *Pseudomonas* infections. In certain embodiments, the binding molecule can comprise a binding domain from the antibodies or fragments thereof that include, but are not limited to Cam-003, WapR-004, V2L2, or 29D22.

As used herein, the terms "binding domain" or "antigen binding domain" includes a site that specifically binds an epitope on an antigen (e.g., an epitope of *Pseudomonas* Psl or PcrV). The antigen binding domain of an antibody typically includes at least a portion of an immunoglobulin heavy chain variable region and at least a portion of an immunoglobulin light chain variable region. The binding site formed by these variable regions determines the specificity of the antibody.

The disclosure is more specifically directed to a composition comprising at least two anti-*Pseudomonas* binding domains, wherein one binding domain specifically binds Psl and the other binding domain specifically binds PcrV. In one embodiment, the composition comprises one binding domain that specifically binds to the same *Pseudomonas* Psl epitope as an antibody or antigen-binding fragment thereof comprising the heavy chain variable region (VH) and light chain variable region (VL) region of WapR-004, Cam-003, Cam-004, Cam-005, WapR-001, WapR-002, WapR-003, or WapR-016. In certain embodiments, the second binding domain specifically binds to the same *Pseudomonas* PcrV epitope as an antibody or antigen binding fragment thereof comprising the heavy chain variable region (VH) and light chain variable region (VL) of V2L2 or 29D2.

In one embodiment, the composition comprises one binding domain that specifically binds to *Pseudomonas* Psl and/or competitively inhibits *Pseudomonas* Psl binding by an antibody or antigen-binding fragment thereof comprising the VH and VL of WapR-004, Cam-003, Cam-004, Cam-005, WapR-001, WapR-002, WapR-003, or WapR-016. In certain embodiments, the second binding domain specifically binds to the same *Pseudomonas* PcrV epitope and/or competitively inhibits *Pseudomonas* PcrV binding by an antibody or antigen binding fragment thereof comprising the heavy chain variable region (VH) and light chain variable region (VL) of V2L2 or 29D2.

Another embodiment is directed to an isolated binding molecule, e.g., an antibody or antigen-binding fragment thereof which specifically binds to the same *Pseudomonas* PcrV epitope as an antibody or antigen-binding fragment thereof comprising the VH and VL region of V2L2 or 29D2.

Also included is an isolated binding molecule, e.g., an antibody or fragment thereof which specifically binds to *Pseudomonas* PcrV and competitively inhibits *Pseudomonas* PcrV binding by an antibody or antigen-binding fragment thereof comprising the VH and VL of V2L2 or 29D2.

One embodiment is directed to an isolated binding molecule, e.g., an antibody or antigen-binding fragment thereof which specifically binds to the same *Pseudomonas* Psl epitope as an antibody or antigen-binding fragment thereof comprising the VH and VL region of WapR-001, WapR-002, or WapR-003.

Also included is an isolated binding molecule, e.g., an antibody or fragment thereof which specifically binds to *Pseudomonas* Psl and competitively inhibits *Pseudomonas* Psl binding by an antibody or antigen-binding fragment thereof comprising the VH and VL of WapR-001, WapR-002, or WapR-003.

Further included is an isolated binding molecule, e.g., an antibody or fragment thereof which specifically binds to the same *Pseudomonas* Psl epitope as an antibody or antigen-binding fragment thereof comprising the VH and VL of WapR-016.

Also included is an isolated binding molecule, e.g., an antibody or fragment thereof which specifically binds to *Pseudomonas* Psl and competitively inhibits *Pseudomonas* Psl binding by an antibody or antigen-binding fragment thereof comprising the VH and VL of WapR-016.

Methods of making antibodies are well known in the art and described herein. Once antibodies to various fragments of, or to the full-length *Pseudomonas* Psl or PcrV without the signal sequence, have been produced, determining which amino acids, or epitope, of *Pseudomonas* Psl or PcrV to which the antibody or antigen binding fragment binds can be determined by epitope mapping protocols as described herein as well as methods known in the art (e.g. double antibody-sandwich ELISA as described in "Chapter 11-Immunology," Current Protocols in Molecular Biology, Ed. Ausubel et al., v.2, John Wiley & Sons, Inc. (1996)). Additional epitope mapping protocols can be found in Morris, G. *Epitope Mapping Protocols*, New Jersey: Humana Press (1996), which are both incorporated herein by reference in their entireties. Epitope mapping can also be performed by commercially available means (i.e. Proto-PROBE, Inc. (Milwaukee, Wisconsin)).

In certain aspects, the disclosure is directed to a binding molecule, e.g., an antibody or fragment, variant, or derivative thereof which specifically binds to *Pseudomonas* Psl and/or PcrV with an affinity characterized by a dissociation constant ($K_D$) which is less than the $K_D$ for said reference monoclonal antibody.

In certain embodiments an anti-*Pseudomonas* Psl and/or PcrV binding molecule, e.g., an antibody or antigen-binding fragment, variant or derivative thereof as disclosed herein binds specifically to at least one epitope of Psl or PcrV, i.e., binds to such an epitope more readily than it would bind to an unrelated, or random epitope; binds preferentially to at least one epitope of Psl or PcrV, i.e., binds to such an epitope more readily than it would bind to a related, similar, homologous, or analogous epitope; competitively inhibits binding of a reference antibody which itself binds specifically or preferentially to a certain epitope of Psl or PcrV; or binds to at least one epitope of Psl or PcrV with an affinity characterized by a dissociation constant $K_D$ of less than about $5 \times 10^{-2}$ M, about $10^{-2}$ M, about $5 \times 10^{-3}$ M, about $10^{-3}$ M, about $5 \times 10^{-4}$ M, about $10^{-4}$ M, about $5 \times 10^{-5}$ M, about $10^{-5}$ M, about $5 \times 10^{-6}$ M, about $10^{-6}$ M, about $5 \times 10^{-7}$ M, about $10^{-7}$ M, about $5 \times 10^{-8}$ M, about $10^{-8}$ M, about $5 \times 10^{-9}$ M, about $10^{-9}$ M, about $5 \times 10^{-10}$ M, about $10^{-10}$ M, about $5 \times 10^{-11}$ M, about $10^{-11}$ M, about $5 \times 10^{-12}$ M, about $10^{-12}$ M, about $5 \times 10^{-13}$ M, about $10^{-13}$ M, about $5 \times 10^{-14}$ M, about $10^{-14}$ M, about $5 \times 10^{-15}$ M, or about $10^{-15}$ M.

As used in the context of binding dissociation constants, the term "about" allows for the degree of variation inherent in the methods utilized for measuring antibody affinity. For example, depending on the level of precision of the instrumentation used, standard error based on the number of samples measured, and rounding error, the term "about $10^{-2}$ M" might include, for example, from 0.05 M to 0.005 M.

In specific embodiments a binding molecule, e.g., an antibody, or antigen-binding fragment, variant, or derivative thereof binds *Pseudomonas* Psl and/or PcrV with an off rate (k(off)) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. Alternatively, an antibody, or antigen-binding fragment, variant, or derivative thereof binds *Pseudomonas* Psl and/or PcrV with an off rate (k(off)) of less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$ $5 \times 10^{-6}$ sec$^{-1}$, $10^{-6}$ sec$^{-1}$, $5 \times 10^{-7}$ sec$^{-1}$ or $10^{-7}$ sec$^{-1}$.

In other embodiments, a binding molecule, e.g., an antibody, or antigen-binding fragment, variant, or derivative thereof as disclosed herein binds *Pseudomonas* Psl and/or PcrV with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$ or $5 \times 10^4$ M$^{-1}$ sec$^{-1}$. Alternatively, a binding molecule, e.g., an antibody, or antigen-binding fragment, variant, or derivative thereof as disclosed herein binds *Pseudomonas* Psl and/or PcrV with an on rate (k(on)) greater than or equal to $10^5$ M$^{-1}$ sec$^{-1}$, $5 \times 10^5$ M$^{-1}$ sec$^{-1}$, $10^6$ M$^{-1}$ sec$^{-1}$, or $5 \times 10^6$ M$^{-1}$ sec$^{-1}$ or $10^7$ M$^{-1}$ sec$^{-1}$.

In various embodiments, an anti-*Pseudomonas* Psl and/or PcrV binding molecule, e.g., an antibody, or antigen-binding fragment, variant, or derivative thereof as described herein promotes opsonophagocytic killing of *Pseudomonas*, or inhibits *Pseudomonas* binding to epithelial cells. In certain embodiments described herein, the *Pseudomonas* Psl or PcrV target is *Pseudomonas aeruginosa* Psl or PcrV. In other embodiments, certain binding molecules described herein can bind to structurally related polysaccharide molecules regardless of their source. Such Psl-like molecules would be expected to be identical to or have sufficient structural relatedness to *P. aeruginosa* Psl to permit specific recognition by one or more of the binding molecules disclosed. In other embodiments, certain binding molecules described herein can bind to structurally related polypeptide molecules regardless of their source. Such PcrV-like molecules would be expected to be identical to or have sufficient structural relatedness to *P. aeruginosa* PcrV to permit specific recognition by one or more of the binding molecules disclosed. Therefore, for example, certain binding molecules described herein can bind to Psl-like and/or PcrV-like molecules produced by other bacterial species, for example, Psl-like or PcrV-like molecules produced by other *Pseudomonas* species, e.g., *Pseudomonas fluorescens, Pseudomonas putida*, or *Pseudomonas alcaligenes*. Alternatively, certain binding molecules as described herein can bind to Psl-like and/or PcrV-like molecules produced synthetically or by host cells genetically modified to produce Psl-like or PcrV-like molecules.

Unless it is specifically noted, as used herein a "fragment thereof" in reference to a binding molecule, e.g., an antibody refers to an antigen-binding fragment, i.e., a portion of the antibody which specifically binds to the antigen.

Anti-*Pseudomonas* Psl and/or PcrV binding molecules, e.g., antibodies or antigen-binding fragments, variants, or derivatives thereof can comprise a constant region which mediates one or more effector functions. For example, binding of the C1 component of complement to an antibody constant region can activate the complement system. Activation of complement is important in the opsonization and lysis of pathogens. The activation of complement also stimulates the inflammatory response and can also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

Accordingly, certain embodiments disclosed herein include an anti-*Pseudomonas* Psl and/or PcrV binding molecule, e.g., an antibody, or antigen-binding fragment, variant, or derivative thereof, in which at least a fraction of one or more of the constant region domains has been deleted or otherwise altered so as to provide desired biochemical characteristics such as reduced effector functions, the ability to non-covalently dimerize, increased ability to localize at the site of a tumor, reduced serum half-life, or increased serum half-life when compared with a whole, unaltered antibody of approximately the same immunogenicity. For example, certain binding molecules described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted.

Modified forms of anti-*Pseudomonas* Psl and/or PcrV binding molecules, e.g., antibodies or antigen-binding fragments, variants, or derivatives thereof can be made from whole precursor or parent antibodies using techniques known in the art. Exemplary techniques are discussed elsewhere herein.

In certain embodiments both the variable and constant regions of anti-*Pseudomonas* Psl and/or PcrV binding molecules, e.g., antibodies or antigen-binding fragments are fully human. Fully human antibodies can be made using techniques that are known in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140. Other techniques are known in the art. Fully human anti bodies can likewise be produced by various display technologies, e.g., phage display or other viral display systems, as described in more detail elsewhere herein.

Anti-*Pseudomonas* Psl and/or PcrV binding molecules, e.g., antibodies or antigen-binding fragments, variants, or derivatives thereof as disclosed herein can be made or manufactured using techniques that are known in the art. In certain embodiments, binding molecules or fragments thereof are "recombinantly produced," i.e., are produced using recombinant DNA technology. Exemplary techniques for making antibody molecules or fragments thereof are discussed in more detail elsewhere herein.

In certain anti-*Pseudomonas* Psl and/or PcrV binding molecules, e.g., antibodies or antigen-binding fragments, variants, or derivatives thereof described herein, the Fc portion can be mutated to decrease effector function using techniques known in the art. For example, the deletion or inactivation (through point mutations or other means) of a constant region domain can reduce Fc receptor binding of the circulating modified antibody thereby increasing tumor localization. In other cases it can be that constant region modifications moderate complement binding and thus reduce the serum half-life and nonspecific association of a conjugated cytotoxin. Yet other modifications of the constant region can be used to modify disulfide linkages or oligosaccharide moieties that allow for enhanced localization due to increased antigen specificity or antibody flexibility. The resulting physiological profile, bioavailability and other biochemical effects of the modifications, such as localization, biodistribution and serum half-life, can easily be measured and quantified using well known immunological techniques without undue experimentation.

In certain embodiments, anti-*Pseudomonas* Psl and/or PcrV binding molecules, e.g., antibodies or antigen-binding fragments, variants, or derivatives thereof will not elicit a deleterious immune response in the animal to be treated, e.g., in a human. In one embodiment, anti-*Pseudomonas* Psl and/or PcrV binding molecules, e.g., antibodies or antigen-binding fragments, variants, or derivatives thereof are modified to reduce their immunogenicity using art-recognized techniques. For example, antibodies can be humanized, de-immunized, or chimeric antibodies can be made. These types of antibodies are derived from a non-human antibody, typically a murine or primate antibody, that retains or substantially retains the antigen-binding properties of the parent antibody, but which is less immunogenic in humans. This can be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci.* 81:6851-6855 (1984); Morrison et al., *Adv. Immunol.* 44:65-92 (1988); Verhoeyen et al., *Science* 239:1534-1536 (1988); Padlan, *Molec. Immun.* 28:489-498 (1991); Padlan, *Molec. Immun.* 31:169-217 (1994), and U.S. Pat. Nos.

5,585,089, 5,693,761, 5,693,762, and 6,190,370, all of which are hereby incorporated by reference in their entirety.

De-immunization can also be used to decrease the immunogenicity of an antibody. As used herein, the term "de-immunization" includes alteration of an antibody to modify T cell epitopes (see, e.g., WO9852976A1, WO0034317A2). For example, VH and VL sequences from the starting antibody are analyzed and a human T cell epitope "map" from each V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of binding polypeptides, e.g., *Pseudomonas* Psl- and/or PcrV-specific antibodies or antigen-binding fragments thereof disclosed herein, which are then tested for function. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Anti-*Pseudomonas* Psl and/or PcrV binding molecules, e.g., antibodies or antigen-binding fragments, variants, or derivatives thereof can be generated by any suitable method known in the art. Polyclonal antibodies to an antigen of interest can be produced by various procedures well known in the art. For example, an anti-*Pseudomonas* Psl and/or PcrV antibody or antigen-binding fragment thereof can be administered to various host animals including, but not limited to, rabbits, mice, rats, chickens, hamsters, goats, donkeys, etc., to induce the production of sera containing polyclonal antibodies specific for the antigen. Various adjuvants can be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: *A Laboratory Manual*, Cold Spring Harbor Laboratory Press, 2nd ed. (1988)

DNA encoding antibodies or antibody fragments (e.g., antigen binding sites) can also be derived from antibody libraries, such as phage display libraries. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with scFv, Fab, Fv OE DAB (individual Fv region from light or heavy chains) or disulfide stabilized Fv antibody domains recombinantly fused to either the phage gene III or gene VIII protein. Exemplary methods are set forth, for example, in EP 368 684 B1; U.S. Pat. No. 5,969,108, Hoogenboom, H. R. and Chames, *Immunol. Today* 21:371 (2000); Nagy et al. Nat. Med. 8:801 (2002); Huie et al., *Proc. Natl. Acad. Sci. USA* 98:2682 (2001); Lui et al., *J. Mol. Biol.* 315:1063 (2002), each of which is incorporated herein by reference. Several publications (e.g., Marks et al., *Bio/Technology* 10:779-783 (1992)) have described the production of high affinity human antibodies by chain shuffling, as well as combinatorial infection and in vivo recombination as a strategy for constructing large phage libraries. In another embodiment, Ribosomal display can be used to replace bacteriophage as the display platform (see, e.g., Hanes et al., *Nat. Biotechnol.* 18:1287 (2000); Wilson et al., *Proc. Natl. Acad. Sci. USA* 98:3750 (2001); or Irving et al., *J. Immunol. Methods* 248:31 (2001)). In yet another embodiment, cell surface libraries can be screened for antibodies (Boder et al., *Proc. Natl. Acad. Sci. USA* 97:10701 (2000); Daugherty et al., *J. Immunol. Methods* 243:211 (2000)). Such procedures provide alternatives to traditional hybridoma techniques for the isolation and subsequent cloning of monoclonal antibodies.

In phage display methods, functional antibody domains are displayed on the surface of phage particles which carry the polynucleotide sequences encoding them. For example, DNA sequences encoding VH and VL regions are amplified from animal cDNA libraries (e.g., human or murine cDNA libraries of lymphoid tissues) or synthetic cDNA libraries. In certain embodiments, the DNA encoding the VH and VL regions are joined together by an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the VH or VL regions are usually recombinantly fused to either the phage gene III or gene VIII. Phage expressing an antigen binding domain that binds to an antigen of interest (i.e., *Pseudomonas* Psl or PcrV) can be selected or identified with antigen, e.g., using labeled antigen or antigen bound or captured to a solid surface or bead.

Additional examples of phage display methods that can be used to make the antibodies include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187:9-18 (1997); Burton et al., *Advances in Immunology* 57:191-280 (1994); PCT Application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references and in the examples below, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria. For example, techniques to recombinantly produce Fab, Fab' and F(ab')$_2$ fragments can also be employed using methods known in the art such as those disclosed in PCT publication WO 92/22324; Mullinax et al., *BioTechniques* 12 (6): 864-869 (1992); and Sawai et al.,

*AJRI* 34:26-34 (1995); and Better et al., *Science* 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988). In certain embodiments such as therapeutic administration, chimeric, humanized, or human antibodies can be used. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, *Science* 229:1202 (1985); Oi et al., *BioTechniques* 4:214 (1986); Gillies et al., *J. Immunol. Methods* 125:191-202 (1989); U.S. Pat. Nos. 5,807,715; 4,816,567; and 4,816397, which are incorporated herein by reference in their entireties. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, *Molecular Immunology* 28 (4/5): 489-498 (1991); Studnicka et al., *Protein Engineering* 7 (6): 805-814 (1994); Roguska. et al., *PNAS* 91:969-973 (1994)), and chain shuffling (U.S. Pat. No. 5,565,332).

Fully human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes can be introduced randomly or by homologous recombination into mouse embryonic stem cells. In addition, various companies can be engaged to provide human antibodies produced in transgenic mice directed against a selected antigen using technology similar to that described above.

Fully human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/Technology* 12:899-903 (1988). See also, U.S. Pat. No. 5,565,332.)

In another embodiment, DNA encoding desired monoclonal antibodies can be readily isolated and sequenced using conventional procedures (e.g., by using oligonucleotide probes that are capable of binding specifically to genes encoding the heavy and light chains of murine antibodies). Isolated and subcloned hybridoma cells or isolated phage, for example, can serve as a source of such DNA. Once isolated, the DNA can be placed into expression vectors, which are then transfected into prokaryotic or eukaryotic host cells such as *E. coli* cells, simian COS cells, Chinese Hamster Ovary (CHO) cells or myeloma cells that do not otherwise produce immunoglobulins. More particularly, the isolated DNA (which can be synthetic as described herein) can be used to clone constant and variable region sequences for the manufacture antibodies as described in Newman et al., U.S. Pat. No. 5,658,570, filed Jan. 25, 1995, which is incorporated by reference herein. Transformed cells expressing the desired antibody can be grown up in relatively large quantities to provide clinical and commercial supplies of the immunoglobulin.

In one embodiment, an isolated binding molecule, e.g., an antibody comprises at least one heavy or light chain CDR of an antibody molecule. In another embodiment, an isolated binding molecule comprises at least two CDRs from one or more antibody molecules. In another embodiment, an isolated binding molecule comprises at least three CDRs from one or more antibody molecules. In another embodiment, an isolated binding molecule comprises at least four CDRs from one or more antibody molecules. In another embodiment, an isolated binding molecule comprises at least five CDRs from one or more antibody molecules. In another embodiment, an isolated binding molecule of the description comprises at least six CDRs from one or more antibody molecules.

In a specific embodiment, the amino acid sequence of the heavy and/or light chain variable domains can be inspected to identify the sequences of the complementarity determining regions (CDRs) by methods that are well-known in the art, e.g., by comparison to known amino acid sequences of other heavy and light chain variable regions to determine the regions of sequence hypervariability. Using routine recombinant DNA techniques, one or more of the CDRs can be inserted within framework regions, e.g., into human framework regions to humanize a non-human antibody. The framework regions can be naturally occurring or consensus framework regions, and preferably human framework regions (see, e.g., Chothia et al., *J. Mol. Biol.* 278:457-479 (1998) for a listing of human framework regions). The polynucleotide generated by the combination of the framework regions and CDRs encodes an antibody that specifically binds to at least one epitope of a desired antigen, e.g., Psl or PcrV. One or more amino acid substitutions can be made within the framework regions, and, the amino acid substitutions improve binding of the antibody to its antigen. Additionally, such methods can be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present disclosure and are within the capabilities of a person of skill of the art.

Also provided are binding molecules that comprise, consist essentially of, or consist of, variants (including derivatives) of antibody molecules (e.g., the VH regions and/or VL regions) described herein, which binding molecules or fragments thereof specifically bind to *Pseudomonas* Psl or PcrV. Standard techniques known to those of skill in the art can be used to introduce mutations in the nucleotide sequence encoding a binding molecule or fragment thereof which specifically binds to *Pseudomonas* Psl and/or PcrV, including, but not limited to, site-directed mutagenesis and PCR-mediated mutagenesis which result in amino acid substitutions. The variants (including derivatives) encode polypeptides comprising less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VHCDR1, VHCDR2, VHCDR3, VL region, VLCDR1, VLCDR2, or VLCDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind an *Pseudomonas* Psl or PcrV).

For example, it is possible to introduce mutations only in framework regions or only in CDR regions of an antibody molecule. Introduced mutations can be silent or neutral missense mutations, i.e., have no, or little, effect on an antibody's ability to bind antigen. These types of mutations can be useful to optimize codon usage, or improve a hybridoma's antibody production. Alternatively, non-neutral missense mutations can alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein can routinely be expressed and the functional and/or biological activity of the encoded protein, (e.g., ability to bind at least one epitope of *Pseudomonas* Psl or PcrV) can be determined using techniques described herein or by routinely modifying techniques known in the art.

One embodiment provides a bispecific antibody comprising an anti-*Pseudomonas* Psl and PcrV binding domain disclosed herein. In certain embodiments, the bispecific antibody contains a first Psl binding domain, and the second PcrV binding domain. Bispecific antibodies with more than two valencies are contemplated. For example, trispecific antibodies can also be prepared using the methods described herein. (Tutt et al., J. Immunol., 147:60 (1991)).

One embodiment provides a method of producing a bispecific antibody, that utilizes a single light chain that can pair with both heavy chain variable domains present in the bispecific molecule. To identify this light chain, various strategies can be employed. In one embodiment, a series of monoclonal antibodies are identified to each antigen that can be targeted with the bispecific antibody, followed by a determination of which of the light chains utilized in these antibodies is able to function when paired with the heavy chain of any of the antibodies identified to the second target. In this manner a light chain that can function with two heavy chains to enable binding to both antigens can be identified. In another embodiment, display techniques, such as phage display, can enable the identification of a light chain that can function with two or more heavy chains. In one embodiment, a phage library is constructed which comprises a diverse repertoire of heavy chain variable domains and a single light chain variable domain. This library can further be utilized to identify antibodies that bind to various antigens of interest. Thus, in certain embodiments, the antibodies identified will share a common light chain.

In certain embodiments, the bispecific antibody comprises at least one single chain Fv (scFv). In certain embodiments the bispecific antibody comprises two scFvs. For example, a scFv can be fused to one or both of a CH3 domain-containing polypeptide contained within an antibody. Some methods comprise producing a bispecific molecule wherein one or both of the heavy chain constant regions comprising at least a CH3 domain is utilized in conjunction with a single chain Fv domain to provide antigen binding.

III. Antibody Polypeptides

The disclosure is further directed to isolated polypeptides which make up binding molecules, e.g., antibodies or antigen-binding fragments thereof, which specifically bind to *Pseudomonas* Psl and/or PcrV and polynucleotides encoding such polypeptides. Binding molecules, e.g., antibodies or fragments thereof as disclosed herein, comprise polypeptides, e.g., amino acid sequences encoding, for example, Psl-specific and/or PcrV-specific antigen binding regions derived from immunoglobulin molecules. A polypeptide or amino acid sequence "derived from" a designated protein refers to the origin of the polypeptide. In certain cases, the polypeptide or amino acid sequence which is derived from a particular starting polypeptide or amino acid sequence has an amino acid sequence that is essentially identical to that of the starting sequence, or a portion thereof, wherein the portion consists of at least 10-20 amino acids, at least 20-30 amino acids, at least 30-50 amino acids, or which is otherwise identifiable to one of ordinary skill in the art as having its origin in the starting sequence.

Also disclosed is an isolated binding molecule, e.g., an antibody or antigen-binding fragment thereof which specifically binds to *Pseudomonas* Psl comprising an immunoglobulin heavy chain variable region (VH) amino acid sequence at least 80%, 85%, 90% 95% or 100% identical to one or more of: SEQ ID NO: 1, SEQ ID NO: 3, SEQ ID NO: 4, SEQ ID NO: 5, SEQ ID NO: 7, SEQ ID NO: 9, SEQ ID NO: 11, SEQ ID NO: 13, SEQ ID NO: 15, or SEQ ID NO: 74 as shown in Table 2.

Further disclosed is an isolated binding molecule, e.g., an antibody or antigen-binding fragment thereof which specifically binds to *Pseudomonas* Psl comprising a VH amino acid sequence identical to, or identical except for one, two, three, four, five, or more amino acid substitutions to one or more of: SEQ ID NO: 1, SEQ ID NO: 3, SEQ ID NO: 4, SEQ ID NO: 5, SEQ ID NO: 7, SEQ ID NO: 9, SEQ ID NO: 11, SEQ ID NO: 13, SEQ ID NO: 15, or SEQ ID NO: 74 as shown in Table 2.

Some embodiments include an isolated binding molecule, e.g., an antibody or antigen-binding fragment thereof which specifically binds to *Pseudomonas* Psl comprising a VH, where one or more of the VHCDR1, VHCDR2 or VHCDR3 regions of the VH are at least 80%, 85%, 90%, 95% or 100% identical to one or more reference heavy chain VHCDR1, VHCDR2 or VHCDR3 amino acid sequences of one or more of: SEQ ID NO: 1, SEQ ID NO: 3, SEQ ID NO: 4, SEQ ID NO: 5, SEQ ID NO: 7, SEQ ID NO: 9, SEQ ID NO: 11, SEQ ID NO: 13, SEQ ID NO: 15, or SEQ ID NO: 74 as shown in Table 2.

Further disclosed is an isolated binding molecule, e.g., an antibody or antigen-binding fragment thereof which specifically binds to *Pseudomonas* Psl comprising a VH, where one or more of the VHCDR1, VHCDR2 or VHCDR3 regions of the VH are identical to, or identical except for four, three, two, or one amino acid substitutions, to one or more reference heavy chain VHCDR1, VHCDR2 and/or VHCDR3 amino acid sequences of one or more of: SEQ ID NO: 1, SEQ ID NO: 3, SEQ ID NO: 4, SEQ ID NO: 5, SEQ ID NO: 7, SEQ ID NO: 9, SEQ ID NO: 11, SEQ ID NO: 13, SEQ ID NO: 15, or SEQ ID NO: 74 as shown in Table 2. Thus, according to this embodiment the VH comprises one or more of a VHCDR1, VHCDR2, or VHCDR3 identical to or identical except for four, three, two, or one amino acid substitutions, to one or more of the VHCDR1, VHCDR2, or VHCDR3 amino acid sequences shown in Table 3.

Also disclosed is an isolated binding molecule, e.g., an antibody or antigen-binding fragment thereof which specifically binds to *Pseudomonas* Psl comprising an immunoglobulin light chain variable region (VL) amino acid sequence at least 80%, 85%, 90% 95% or 100% identical to one or more of SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16 as shown in Table 2.

Some embodiments disclose an isolated binding molecule, e.g., an antibody or antigen-binding fragment thereof which specifically binds to *Pseudomonas* Psl comprising a VL amino acid sequence identical to, or identical except for one, two, three, four, five, or more amino acid substitutions, to one or more of SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16 as shown in Table 2.

Also provided is an isolated binding molecule, e.g., an antibody or antigen-binding fragment thereof which specifically binds to *Pseudomonas* Psl comprising a VL, where one or more of the VLCDR1, VLCDR2 or VLCDR3 regions of the VL are at least 80%, 85%, 90%, 95% or 100% identical to one or more reference light chain VLCDR1, VLCDR2 or VLCDR3 amino acid sequences of one or more of: SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16 as shown in Table 2.

Further provided is an isolated binding molecule, e.g., an antibody or antigen-binding fragment thereof which specifically binds to *Pseudomonas* Psl comprising a VL, where one or more of the VLCDR1, VLCDR2 or VLCDR3 regions of the VL are identical to, or identical except for four, three, two, or one amino acid substitutions, to one or more reference heavy chain VLCDR1, VLCDR2 and/or VLCDR3 amino acid sequences of one or more of: SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16 as shown in Table 2. Thus, according to this embodiment the VL comprises one or more of a VLCDR1, VLCDR2, or VLCDR3 identical to or identical except for four, three, two, or one amino acid substitutions, to one or more of the VLCDR1, VLCDR2, or VLCDR3 amino acid sequences shown in Table 3.

In other embodiments, an isolated antibody or antigen-binding fragment thereof which specifically binds to *Pseudomonas* Psl, comprises, consists essentially of, or consists of VH and VL amino acid sequences at least 80%, 85%, 90% 95% or 100% identical to:

(a) SEQ ID NO: 1 and SEQ ID NO: 2, respectively, (b) SEQ ID NO: 3 and SEQ ID NO: 2, respectively, (c) SEQ ID NO: 4 and SEQ ID NO: 2, respectively, (d) SEQ ID NO: 5 and SEQ ID NO: 6, respectively, (e) SEQ ID NO: 7 and SEQ ID NO: 8, respectively, (f) SEQ ID NO: 9 and SEQ ID NO: 10, respectively, (g) SEQ ID NO: 11 and SEQ ID NO: 12, respectively, (h) SEQ ID NO: 13 and SEQ ID NO: 14, respectively; (i) SEQ ID NO: 15 and SEQ ID NO: 16, respectively; or (j) SEQ ID NO: 74 and SEQ ID NO: 12, respectively. In certain embodiments, the above-described antibody or antigen-binding fragment thereof comprises a VH with the amino acid sequence SEQ ID NO: 11 and a VL with the amino acid sequence of SEQ ID NO: 12. In some embodiments, the above-described antibody or antigen-binding fragment thereof comprises a VH with the amino acid sequence SEQ ID NO: 1 and a VL with the amino acid sequence of SEQ ID NO: 2. In other embodiments, the above-described antibody or antigen-binding fragment thereof comprises a VH with the amino acid sequence SEQ ID NO: 11 and a VL with the amino acid sequence of SEQ ID NO: 12.

Certain embodiments provide an isolated binding molecule, e.g, an antibody, or antigen-binding fragment thereof which specifically binds to *Pseudomonas* Psl, comprising an immunoglobulin VH and an immunoglobulin VL, each comprising a complementarity determining region 1 (CDR1), CDR2, and CDR3, wherein the VH CDR1 is PYYWT (SEQ ID NO: 47), the VH CDR2 is YIHSSGYTDYNPSLKS (SEQ ID NO: 48), the VH CDR3 is selected from the group consisting of ADWDRLRALDI (Psl0096, SEQ ID NO:258), AMDIEPHALDI (Psl0225, SEQ ID NO:267), ADDPFPGYLDI (Psl0588, SEQ ID NO: 268), ADWNEGRKLDI (Psl0567, SEQ ID NO:269), ADWDHKHALDI (Psl0337, SEQ ID NO:270), ATDEADHALDI (Psl0170, SEQ ID NO:271), ADWSGTRALDI (Psl0304, SEQ ID NO:272), GLPEKPHALDI (Psl0348, SEQ ID NO:273), SLFTDDHALDI (Psl0573, SEQ ID NO:274), ASPGVVHALDI (Psl0574, SEQ ID NO: 275), AHIESHHALDI (Psl0582, SEQ ID NO:276), ATQAPAHALDI (Psl0584, SEQ ID NO: 277), SQHDLEHALDI (Psl0585, SEQ ID NO:278), and AMPDMPHALDI (Psl0589, SEQ ID NO:279), the VL CDR1 is RASQSIRSHLN (SEQ ID NO:50), the VL CDR2 is GASNLQS (SEQ ID NO:51), and the VL CDR3 is selected from the group consisting of QQSTGAWNW (Psl0096, SEQ ID NO:280), QQDFFHGPN (Psl0225, SEQ ID NO: 281), QQSDTFPLK (Psl0588, SEQ ID NO:282), QQSYSFPLT (WapR0004, Psl0567, Psl0573, Psl00574, Psl0582, Psl0584, Psl0585, SEQ ID NO:52), QDSSSWPLT (Psl0337, SEQ ID NO:283), SQSDTFPLT (Psl0170, SEQ ID NO:284), GQSDAFPLT (Psl0304, SEQ ID NO:285), LQGDLWPLT (Psl0348, SEQ ID NO:286), and QQSLEFPLT (Psl0589, SEQ ID NO:287), wherein the VH and VL CDRs are according to the Kabat numbering system.

Certain embodiments provide an isolated binding molecule, e.g., an antibody, or antigen-binding fragment thereof which specifically binds to *Pseudomonas* Psl, comprising an immunoglobulin VH and an immunoglobulin VL, each comprising a complementarity determining region 1 (CDR1), CDR2, and CDR3, wherein the VH CDR1 is PYYWT (SEQ ID NO: 47), the VH CDR2 is YIHSSGYT-DYNPSLKS (SEQ ID NO: 48), the VL CDR1 is RASQ-SIRSHLN (SEQ ID NO:50), the VL CDR2 is GASNLQS (SEQ ID NO:51), and the VH CDR3 and the VL CDR3 comprise, respectively, ADWDRLRALDI (Psl0096, SEQ ID NO: 258) and QQSTGAWNW (Psl0096, SEQ ID NO:280); AMDIEPHALDI (Psl0225, SEQ ID NO:267) and QQDFFHGPN (Psl0225, SEQ ID NO:281); ADDPFPGYLDI (Psl0588, SEQ ID NO:268) and QQSDTFPLK (Psl0588, SEQ ID NO:282); ADWNE-GRKLDI (Psl0567, SEQ ID NO:269) and the VL CDR3 is QQSYSFPLT (WapR0004, Psl0567, Psl0573, Psl00574, Psl0582, Psl0584, Psl0585, SEQ ID NO:52); ADWDHKHALDI (Psl0337, SEQ ID NO:270) and QDSSSWPLT (Psl0337, SEQ ID NO: 283); ATDEAD-HALDI (Psl0170, SEQ ID NO: 271) and SQSDTFPLT (Psl0170, SEQ ID NO: 284); ADWSGTRALDI (Psl0304, SEQ ID NO:272) and GQSDAFPLT (Psl0304, SEQ ID NO:285); GLPEKPHALDI (Psl0348, SEQ ID NO:273) and (Psl0348, SEQ ID NO: 286); SLFTDDHALDI (Psl0573, SEQ ID NO:274) and SEQ ID NO:52; ASPGVVHALDI (Psl0574, SEQ ID NO:275) and SEQ ID NO:52; AHIESHHALDI (Psl0582, SEQ ID NO:276) and SEQ ID NO:52; ATQAPAHALDI (Psl0584, SEQ ID NO: 277) and SEQ ID NO:52; SQHDLEHALDI (Psl0585, SEQ ID NO:278) and SEQ ID NO: 52; or AMPDMPHALDI (Psl0589, SEQ ID NO:279) and QQSLEFPLT (Psl0589, SEQ ID NO:287).

Certain embodiments provide an isolated binding molecule, e.g., an antibody or antigen-binding fragment thereof which specifically binds to *Pseudomonas* Psl, comprising an immunoglobulin VH and an immunoglobulin VL, wherein the VH comprises QVQLQESGPGLVKPSETLSLTCT-VSGGSISPYYWTWIRQPPGKX1LELIGYIHSSGY TDYNPSLKSRVTISGDTSKKQFSLKLSSVTAAD-TAVYYCARADWDRLRALDIWG QGTMVTVSS, wherein X1 is G or C (Psl0096, SEQ ID NO:288), and the VL comprises DIQLTQSPSSLSASVGDRVTITCRASQ-SIRSHLNWYQQKPGKAPKLLIYGASNLQS GVPSRFSGSGSGTDFTLTISSLQPEDFATYYCQQST-GAWNWFGX2GTKVEIK, wherein X2 is G or C (Psl0096, SEQ ID NO:289); wherein the VH comprises QVQLQESGPGLVKPSETLSLTCTVSGGSISPYYW-TWIRQPPGKGLELIGYIHSSGY TDYNPSLKSRVTIS-GDTSKKQFSLKLSSVTAADTAVYYCARAMDIEPHA-LDIWG GTMVTVSS (Psl0225, ID SEQ NO: 290), and the VL comprises DIQLTQSPSSLSASVGDRVTIT-CRASQSIRSHLNWYQQKPGKAPKLLIYGASNLQS GVPSRFSGSGSGTDFTLTISSLQPEDFATYYCQQ-SDDGFPNFGGGTKVEIK (Psl0225, SEQ ID wherein the VH comprises NO: 291); QVQLQESGPGLVKP-SETLSLTCTVSGGSISPYYWTWIRQPPGKGLELI-GYIHSSGY TDYNPSLKSRVTISGDTSKKQFSLKL-SSVTAADTAVYYCARADDPFPGYLDIWG GTMV-TVSS (Psl0588, SEQ ID NO: 292), and the VL comprises DIQLTQSPSSLSASVGDRVTITCRASQSIRSHLNW-YQQKPGKAPKLLIYGASNLQS GVPSRFSGSGSG-TDFTLTISSLQPEDFATYYCQQSDTFPLKFG-GGTKVEIK (Psl0588, SEQ ID NO:293); wherein the VH comprises QVQLQESGPGLVKPSETLSLTCTVSGGSIS-PYYWTWIRQPPGKGLELIGYIHSSGY TDYNPSLKS-RVTISGDTSKKQFSLKLSSVTAADTAVYYCAR-ADWNEGRKLDIWG QGTMVTVSS (Psl0567, SEQ ID NO:294), and the VL comprises SEQ ID NO:11; herein the VH comprises QVQLQESGPGLVKPSETLSLTCTVSGG-SISPYYWTWIRQPPGKGLELIGYIHSSGY TDYNPS-LKSRVTISGDTSKKQFSLKLSSVTAADTAVYYCAR-ADWDHKHALDIWG QGTMVTVSS (Psl0337, SEQ ID NO:295), and the VL comprises DIQLTQSPSSL-SASVGDRVTITCRASQSIRSHLNWYQQKPGKAP-KLLIYGASNLQS GVPSRFSGSGSGTDFTLTISSLQPE-DFATYYCQDSSSWPLTFGGGTKVEIK (Psl0337, SEQ ID NO:296); wherein the VH comprises EVQLLESGPGLVKPSETLSLTCNVAGGSISPYYWTWI-RQPPGKGLELIGYIHSSGY TDYNPSLKSRVTIS-GDTSKKQFSLHVSSVTAADTAVYFCARATDEAD-HALDIWG QGTLVTVSS (Psl0170, SEQ ID NO:297), and the VL comprises EIVLTQSPSSLSTSVGDRVTITCRASQ-SIRSHLNWYQQKPGKAPKLLIYGASNLQS GVPSRFS-GSGSGTDFTLTISSLQPEDFATYYCSQSDTFPLTF-GGGTKLEIK (Psl0170, SEQ ID NO:298); wherein the VH comprises EVQLLESGPGLVKPSETLSLTCNVAGGSIS-PYYWTWIRQPPGKGLELIGYIHSSGY TDYNPSLKS-RVTISGDTSKKQFSLHVSSVTAADTAVYFCAR-ADWSGTRALDIWG QGTLVTVSS (Psl0304, SEQ ID NO: 299), and the VL comprises EIVLTQSPSSLS-TSVGDRVTITCWASQSIRSHLNWYQQKPGKAPKLLI-YGASNLQS GVPSRFSGSGSGTDFTLTISSLQPEDFA-TYYCGQSDAFPLTFGGGTKLEIK (Psl0304, SEQ ID NO:300); wherein the VH comprises EVQLLESGPGLVKPSETLSLTCNVAGGSISPYYWTWI-RQPPGKGLELIGYIHSSGY TDYNPSLKSRVTIS-GDTSKKQFSLHVSSVTAADTAVYFCARGLPEKPHA-LDIWGQ GTLVTVSS (Psl0348, SEQ ID NO:301), and the VL comprises EIVLTQSPSSLSTSVGDRVTITCRASQ-SIRSHLNWYQQKPGKAPKLLIYGASNLQS GVPSRFS-GSGSGTDFTLTISSLQPEDFATYYCLQGDLWPLT-FGGGTKLEIK (Psl0348, SEQ ID NO:302); wherein the VH comprises EVQLLESGPGLVKPSETLSLTCNVAGG-SISPYYWTWIRQPPGKGLELIGYIHSSGY TDYNPS-LKSRVTISGDTSKKQFSLHVSSVTAADTAVYFCA-RSLFTDDHALDIWG QGTLVTVSS (Psl0573, SEQ ID NO:303), and the VL comprises SEQ ID NO:11; wherein the VH comprises EVQLLESGPGLVKPSETLSLTCNVAGG-SISPYYWTWIRQPPGKGLELIGYIHSSGY TDYNPSL-KSRVTISGDTSKKQFSLHVSSVTAADTAVYFCAR-ASPGVVHALDIWGQ GTLVTVSS (Psl0574, SEQ ID NO:304), and the VL comprises SEQ ID NO:11; wherein the VH comprises EVQLLESGPGLVKPSETLSLTCNVAGG-SISPYYWTWIRQPPGKGLELIGYIHSSGY TDYNPSLK-SRVTISGDTSKKQFSLHVSSVTAADTAVYFCARA-HIESHHALDIWGQ GTLVTVSS (Psl0582, SEQ ID NO:305), and the VL comprises SEQ ID NO:11; wherein the VH comprises EVQLLESGPGLVKPSETLSLTCNVAGG-SISPYYWTWIRQPPGKGLELIGYIHSSGY TDYNPSLK-SRVTISGDTSKKQFSLHVSSVTAADTAVYFCAR-ATQAPAHALDIWG QGTLVTVSS (Psl0584, SEQ ID NO:306), and the VL comprises SEQ ID NO:11; wherein the VH comprises EVQLLESGPGLVKPSETLSLTCNVAGG-SISPYYWTWIRQPPGKGLELIGYIHSSGY TDYNPSLKSRVTISGDTSKKQFSLHVSSVTAAD-TAVYFCARSQHDLEHALDIWGQ GTLVTVSS (Psl0585, SEQ ID NO:307), and the VL comprises SEQ ID NO:11; or wherein the VH comprises EVQLLESGPGLVKP-SETLSLTCNVAGGSISPYYWTWIRQPPGKGLELI- GYIHSSGY TDYNPSLKSRVTISGDTSKKQFSLH-VSSVTAADTAVYFCARAMPDMPHALDIWG QGTLVTVSS (Psl0589, SEQ ID NO:308), and the VL comprises EIVLTQSPSSLSTSVGDRVTITCRASQSIR-SHLNWYQQKPGKAPKLLIYGASNLQS GVPSRFSGS-GSGTDFTLTISSLQPEDFATYYCQQSLEFPLTF-GGGTKLEIK (Psl0589, SEQ ID NO:325).

Also disclosed is an isolated antibody single chain Fv (ScFv) fragment which specifically binds to *Pseudomonas* Psl (an "anti-Psl ScFv"), comprising the formula VH-L-VL or alternatively VL-L-VH, where L is a linker sequence. In certain aspects the linker can comprise (a) [GGGGS]n, wherein n is 0, 1, 2, 3, 4, or 5, (b) [GGGG]n, wherein n is 0, 1, 2, 3, 4, or 5, or a combination of (a) and (b). For example, an exemplary linker comprises: GGGGSGGGGSGGGGSGGGGSGGGGS (SEQ ID NO:326). In certain embodiments the linker further comprises the amino acids ala-leu at the C-terminus of the linker. In certain embodiments the anti-Psl ScFv comprises the amino acid sequence of SEQ ID NO:240, SEQ ID NO:241, SEQ ID NO:242, SEQ ID NO:243, SEQ ID NO:244, SEQ ID NO:245, SEQ ID NO:246, SEQ ID NO:247, SEQ ID NO:248, SEQ ID NO:249, SEQ ID NO:250, SEQ ID NO:251, SEQ ID NO:252, SEQ ID NO:253, SEQ ID NO:254, or SEQ ID NO:262.

Also disclosed is an isolated antibody single chain Fv (ScFv) fragment which specifically binds to *Pseudomonas* PcrV (an "anti-PcrV ScFv"), comprising the formula VH-L-VL or alternatively VL-L-VH, where L is a linker sequence. In certain aspects the linker can comprise (a) [GGGGS]n, wherein n is 0, 1, 2, 3, 4, or 5, (b) [GGGG]n, wherein n is 0, 1, 2, 3, 4, or 5, or a combination of (a) and (b). For example, an exemplary linker comprises: GGGGSGGGGSGGGGSGGGGSGGGGS (SEQ ID NO:326). In certain embodiments the linker further comprises the amino acids ala-leu at the C-terminus of the linker.

Also disclosed is an isolated binding molecule, e.g., an antibody or antigen-binding fragment thereof which specifically binds to *Pseudomonas* PcrV comprising an immunoglobulin heavy chain variable region (VH) and/or light chain variable region (VL) amino acid sequence at least 80%, 85%, 90% 95% or 100% identical to SEQ ID NO: 216 or SEQ ID NO: 217.

Further disclosed is an isolated binding molecule, e.g., an antibody or antigen-binding fragment thereof which specifically binds to *Pseudomonas* PcrV comprising a VH, where one or more of the VHCDR1, VHCDR2 or VHCDR3 regions of the VH are identical to, or identical except for four, three, two, or one amino acid substitutions, to one or more reference heavy chain VHCDR1, VHCDR2 and/or VHCDR3 amino acid sequences of one or more of: SEQ ID NOs: 218-220 as shown in Table 3. Thus, according to this embodiment the VH comprises one or more of a VHCDR1, VHCDR2, or VHCDR3 identical to or identical except for four, three, two, or one amino acid substitutions, to one or more of the VHCDR1, VHCDR2, or VHCDR3 amino acid sequences shown in Table 3.

Further provided is an isolated binding molecule, e.g., an antibody or antigen-binding fragment thereof which specifically binds to *Pseudomonas* PcrV comprising a VL, where one or more of the VLCDR1, VLCDR2 or VLCDR3 regions of the VL are identical to, or identical except for four, three, two, or one amino acid substitutions, to one or more reference heavy chain VLCDR1, VLCDR2 and/or VLCDR3 amino acid sequences of one or more of: SEQ ID NOs: 221-223 as shown in Table 3. Thus, according to this embodiment the VL comprises one or more of a VLCDR1, VLCDR2, or VLCDR3 identical to or identical except for four, three, two, or one amino acid substitutions, to one or more of the VLCDR1, VLCDR2, or VLCDR3 amino acid sequences shown in Table 3.

Also provided is an isolated binding molecule, e.g., an antibody or antigen-binding fragment thereof which specifically binds to *Pseudomonas* PcrV comprising a VH and a VL, wherein the VH comprises an amino acid sequence selected from the group consisting of SEQ ID NO:255 and SEQ ID NO:257, and wherein the VL comprises the amino acid sequence of SEQ ID NO:256.

Further provided is an isolated binding molecule, e.g., an antibody or antigen-binding fragment thereof which specifically binds to *Pseudomonas* PcrV comprising a VH and a VL, each comprising a CDR1, CDR2, and CDR3, wherein the VH CDR1 is (a) SYAMS (SEQ ID NO:311), or a variant thereof comprising 1, 2, 3, or 4 conservative amino acid substitutions, the VH CDR2 is AISGSGYSTYYADSVKG (SEQ ID NO: 312), or a variant thereof comprising 1, 2, 3, or 4 conservative amino acid substitutions, and the VHCDR3 is EYSISSNYYYGMDV (SEQ ID NO: 313), or a variant thereof comprising 1, 2, 3, or 4 conservative amino acid substitutions; or (b) wherein the VL CDR1 is WASQ-GISSYLA (SEQ ID NO:314), or a variant thereof comprising 1, 2, 3, or 4 conservative amino acid substitutions, the VL CDR2 is AASTLQS (SEQ ID NO:315), or a variant thereof comprising 1, 2, 3, or 4 conservative amino acid substitutions, and the VL CDR3 is QQLNSSPLT (SEQ ID NO:316), or a variant thereof comprising 1, 2, 3, or 4 conservative amino acid substitutions; or (c) a combination of (a) and (b); wherein the VH and VL CDRs are according to the Kabat numbering system. In certain aspects of this embodiment, (a) the VH comprises an amino acid sequence at least 80%, 85%, 90%, 95%, 96%, 97%, 98% 99%, or 100% identical to SEQ ID NO:317, (b) the VL comprises an amino acid sequence at least 80%, 85%, 90%, 95%, 96%, 97%, 98% 99%, or 100% identical to SEQ ID NO:318; or (c) a combination of (a) and (b).

Also disclosed is an isolated bispecific binding molecule, e.g., a bispecific antibody or antigen-binding fragment thereof which specifically binds to both *Pseudomonas* Psl and *Pseudomonas* PcrV comprising an immunoglobulin heavy chain variable region (VH) and/or light chain variable region (VL) amino acid sequence at least 80%, 85%, 90% 95% or 100% identical to SEQ ID NO: 228, SEQ ID NO:229, or SEQ ID NO: 235.

In certain embodiments, a bispecific antibody as disclosed herein has the structure of BS1, BS2, BS3, or BS4, all as shown in FIG. 17. In certain bispecific antibodies disclosed herein the binding domain which specifically binds to *Pseudomonas* Psl comprises an anti-Psl ScFv molecule. In other aspects the binding domain which specifically binds to *Pseudomonas* Psl comprises a conventional heavy chain and light chain. Similarly in certain bispecific antibodies disclosed herein the binding domain which specifically binds to *Pseudomonas* PcrV comprises an anti-PcrV ScFv molecule. In other aspects the binding domain which specifically binds to *Pseudomonas* PcrV comprises a conventional heavy chain and light chain.

In certain aspects a bispecific antibody as disclosed herein had the BS4 structure, disclosed in detail in U.S. Provisional Appl. No. 61/624,651 filed on Apr. 16, 2012 and International Application No: PCT/US2012/63639, filed Nov. 6, 2012, entitled "MULTISPECIFIC AND MULTIVALENT BINDING PROTEINS AND USES THEREOF"), which is incorporated herein by reference in its entirety. For example, this disclosure provides a bispecific antibody in which an anti-Psl ScFv molecule is inserted into the hinge region of each heavy chain of an anti-PcrV antibody or fragment thereof.

This disclosure provides an isolated binding molecule, e.g., a bispecfic antibody comprising an antibody heavy chain and an antibody light chain, where the antibody heavy chain comprises the formula VH-CH1-H1-L1-S-L2-H2-CH2-CH3, wherein CHI is a heavy chain constant region domain-1, Hl is a first heavy chain hinge region fragment, L1 is a first linker, S is an anti-PcrV ScFv molecule, L2 is a second linker, H2 is a second heavy chain hinge region fragment, CH2 is a heavy chain constant region domain-2, and CH3 is a heavy chain constant region domain-3. In certain aspects the VH comprises the amino acid sequence of SEQ ID NO:255, SEQ ID NO:257, or SEQ ID NO:317. In certain aspects L1 and L2 are the same or different, and independently comprise (a) [GGGGS]n, wherein n is 0, 1, 2, 3, 4, or 5, (b) [GGGG]n, wherein n is 0, 1, 2, 3, 4, or 5, or a combination of (a) and (b). In certain embodiments H1 comprises EPKSC (SEQ ID NO:320), and H2 comprises DKTHTCPPCP (SEQ ID NO:321).

In certain aspects, S comprises an anti-Psl ScFv molecule having the amino acid sequence of SEQ ID NO:240, SEQ ID NO:241, SEQ ID NO:242, SEQ ID NO:243, SEQ ID NO:244, SEQ ID NO:245, SEQ ID NO:246, SEQ ID NO:247, SEQ ID NO:248, SEQ ID NO:249, SEQ ID NO:250, SEQ ID NO:251, SEQ ID NO:252, SEQ ID NO:253, SEQ ID NO:254, or SEQ ID NO:262, or any combination of two or more of these amino acid sequences.

In further aspects, CH2-CH3 comprises (SEQ ID NO:322), wherein X1 is M or Y, X2 is S or T, and X3 is T or E. In further aspects the antibody light chain comprises VL-CL, wherein CL is an antibody light chain kappa constant region or am an antibody light chain lambda constant region. In further aspects VL comprises the amino acid sequence of SEQ ID NO: 256 or SEQ ID NO:318. CL can comprise, e.g., the amino acid sequence of SEQ ID NO: 323.

Further provided is an isolated binding molecule, e.g., a bispecific antibody which specifically binds to both *Pseudomonas* Psl and *Pseudomonas* PcrV comprising a VH comprising the amino acid sequence SEQ ID NO:264, and a VL comprising the amino acid sequence SEQ ID NO:263.

In some embodiments, the bispecific antibodies of the invention can be a tandem single chain (sc) Fv fragment, which contain two different scFv fragments (i.e., V2L2 and W4) covalently tethered together by a linker (e.g., a polypeptide linker). (Ren-Heidenreich et al. *Cancer* 100:1095-1103 (2004); Korn et al. *J Gene Med* 6:642-651 (2004)). In some embodiments, the linker can contain, or be, all or part of a heavy chain polypeptide constant region such as a CH1 domain. In some embodiments, the two antibody fragments can be covalently tethered together by way of a polyglycine-serine or polyserine-glycine linker as described in, e.g., U.S. Pat. Nos. 7,112,324 and 5,525,491, respectively. Methods for generating bispecific tandem scFv antibodies are described in, e.g., Maletz et al. *Int J Cancer* 93:409-416 (2001); and Honemann et al. *Leukemia* 18:636-644 (2004). Alternatively, the antibodies can be "linear antibodies" as described in, e.g., Zapata et al. *Protein Eng.* 8:1057-1062 (1995). Briefly, these antibodies comprise a pair of tandem Fd segments (VH-CH1-VH-CH1) that form a pair of antigen binding regions.

The disclosure also embraces variant forms of bispecific antibodies such as the tetravalent dual variable domain immunoglobulin (DVD-Ig) molecules described in Wu et al. (2007) *Nat Biotechnol* 25 (11): 1290-1297. The DVD-Ig molecules are designed such that two different light chain variable domains (VL) from two different parent antibodies are linked in tandem directly or via a short linker by recombinant DNA techniques, followed by the light chain constant domain. For example, the DVD-Ig light chain polypeptide can contain in tandem: (a) the VL from V2L2; and (b) the VL from WapR-004. Similarly, the heavy chain comprises the two different heavy chain variable domains (VH) linked in tandem, followed by the constant domain CHI and Fc region. For example, the DVD-Ig heavy chain polypeptide can contain in tandem: (a) the VH from V2L2; and (b) the VH from WapR-004. In this case, expression of the two chains in a cell results in a heterotetramer containing four antigen combining sites, two that specifically bind to V2L2 and two that specifically bind to Psl. Methods for generating DVD-Ig molecules from two parent antibodies are further described in, e.g., PCT Publication Nos. WO 2008/024188 and WO 2007/024715.

In certain embodiments, an isolated binding molecule, e.g., an antibody or antigen-binding fragment thereof as described herein specifically binds to *Pseudomonas* Psl and/or PcrV with an affinity characterized by a dissociation constant ($K_D$) no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

In specific embodiments, an isolated binding molecule, e.g., an antibody or antigen-binding fragment thereof as described herein specifically binds to *Pseudomonas* Psl and/or PcrV, with an affinity characterized by a dissociation constant ($K_D$) in a range of about $1\times10^{-10}$ to about $1\times10^{-6}$ M. In one embodiment, an isolated binding molecule, e.g., an antibody or antigen-binding fragment thereof as described herein specifically binds to *Pseudomonas* Psl and/or PcrV, with an affinity characterized by a $K_D$ of about $1.18\times10^{-7}$ M, as determined by the OCTET® binding assay described herein. In another embodiment, an isolated binding molecule, e.g., an antibody or antigen-binding fragment thereof as described herein specifically binds to *Pseudomonas* Psl and/or PcrV, with an affinity characterized by a $K_D$ of about $1.44\times10^{-7}$ M, as determined by the OCTET® binding assay described herein.

Some embodiments include the isolated binding molecules e.g., an antibody or fragment thereof as described above, which (a) can inhibit attachment of *Pseudomonas aeruginosa* to epithelial cells, (b) can promote OPK of *P. aeruginosa*, or (c) can inhibit attachment of *P. aeruginosa* to epithelial cells and can promote OPK of *P. aeruginosa*.

In some embodiments the isolated binding molecule e.g., an antibody or fragment thereof as described above, where maximum inhibition of *P. aeruginosa* attachment to epithelial cells is achieved at an antibody concentration of about 50 µg/ml or less, 5.0 µg/ml or less, or about 0.5 µg/ml or less, or at an antibody concentration ranging from about 30 µg/ml to about 0.3 µg/ml, or at an antibody concentration of about 1 µg/ml, or at an antibody concentration of about 0.3 µg/ml.

Certain embodiments include the isolated binding molecule e.g., an antibody or fragment thereof as described above, where the OPK EC50 is less than about 0.5 µg/ml, less than about 0.05 µg/ml, or less than about 0.005 g/ml, or where the OPK EC50 ranges from about 0.001 µg/ml to about 0.5 µg/ml, or where the OPK EC50 ranges from about 0.02 µg/ml to about 0.08 µg/ml, or where the OPK EC50 ranges from about 0.002 µg/ml to about 0.01 µg/ml or where the OPK EC50 is less than about 0.2 µg/ml, or wherein the OPK EC50 is less than about 0.02 µg/ml. In certain embodiments, an anti-*Pseudomonas* Psl binding molecule, e.g., antibody or fragment, variant or derivative thereof described herein specifically binds to the same Psl epitope as monoclonal antibody WapR-004, WapR-004RAD, Cam-003, Cam-004, or Cam-005, or will competitively inhibit such a monoclonal antibody from binding to *Pseudomonas* Psl. WapR-004RAD is identical to WapR-004 except for an amino acid substitution G98A of the VH amino acid sequence of SEQ ID NO:11.

Some embodiments include WapR-004 (W4) mutants comprising an scFv-Fc molecule amino acid sequence identical to, or identical except for one, two, three, four, five, or more amino acid substitutions to one or more of: SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145; or SEQ ID NO: 146.

Other embodiments include WapR-004 (W4) mutants comprising an scFv-Fc molecule amino acid sequence at least 80%, 85%, 90% 95% or 100% identical to one or more of: SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145; or SEQ ID NO: 146.

In some embodiments, an anti-*Pseudomonas* Psl binding molecule, e.g., antibody or fragment, variant or derivative thereof described herein specifically binds to the same epitope as monoclonal antibody WapR-001, WapR-002, or WapR-003, or will competitively inhibit such a monoclonal antibody from binding to *Pseudomonas* Psl.

In certain embodiments, an anti-*Pseudomonas* Psl binding molecule, e.g., antibody or fragment, variant or derivative thereof described herein specifically binds to the same epitope as monoclonal antibody WapR-016, or will competitively inhibit such a monoclonal antibody from binding to *Pseudomonas* Psl.

TABLE 2

| Reference VH and VL amino acid sequences* | | |
|---|---|---|
| Antibody Name | VH | VL |
| Cam-003 | QVRLQQSGPGLVKPSET LSLTCTVSGGSTSPYFW SWLRQPGKGLEWIGYI HSNGGTNYNPSLKSRL TISGDTSKNQFSLNLSF VTAADTALYYCARTDY DVYGPAFDIWGQGTM VTV SEQ ID NO: 1 | SSELTQDPAVSVALGQTVRITCQGDS LRSYYASWYQQKPGQAPVLVIYGKN NRPSGIPDRFSGSSSGNTASLTITGAQ AEDEADYYCNSRDSSGNHVVFGGGT KLTVL SEQ ID NO: 2 |
| Cam-004 | QVQLQQSGPGRVKPSE TLSLTCTVSGYSVSSGY YWGWIRQSPGTGLEWI GSISHSGSTYYNPSLKS RVTISGDASKNQFFLRL TSVTAADTAVYYCARS EATANFDSWGRGTLVT VSS SEQ ID NO: 3 | SSELTQDPAVSVALGQTVRITCQGDS LRSYYASWYQQKPGQAPVLVIYGKN NRPSGIPDRFSGSSSGNTASLTITGAQ AEDEADYYCNSRDSSGNHVVFGGGT KLTVL SEQ ID NO: 2 |
| Cam-005 | QVQLQQSGPGLVKPSET LSLTCTVSGGSVSSGY YWTWIRQPPGKGLEWI GSIYSSGSTYYSPSLKS RVTISGDTSKNQFSLKL SSVTAADTAVYYCARL NWGTVSAFDIWGRGTL VTV SEQ ID NO: 4 | SSELTQDPAVSVALGQTVRITCQGDS LRSYYASWYQQKPGQAPVLVIYGKN NRPSGIPDRFSGSSSGNTASLTITGAQ AEDEADYYCNSRDSSGNHVVFGGGT KLTVL SEQ ID NO: 2 |

TABLE 2-continued

Reference VH and VL amino acid sequences*

| Antibody Name | VH | VL |
|---|---|---|
| WapR-001 | EVQLLESGGGLVQPGG SLRLSCSASGFTFSRYP MHWVRQAPGKGLEYV SDIGTNGGSTNYADSV KGRFTISRDNSKNTVYL QMSSLRAEDTAVYHCV AGIAAAYGFDVWGQG TMVTVSS SEQ ID NO: 5 | QAGLTQPASVSGSPGQSITISCTGTSS DIATYNYVSWYQQHPGKAPKLMIYE GTKRPSGVSNRFSGSKSGNTASLTIS GLQAEDEADYYCSSYARSYTYVFGT GTELTVL SEQ ID NO: 6 |
| WapR-002 | QVQLVQSGGGLVQPGG SLRLSCSASGFTFSSYP MHWVRQAPGKGLDYV SDISPNGGSTNYADSV KGRFTISRDNSKNTLFL QMSSLRAEDTAVYYCV MGLVPYGFDIWGQGTL VTVSS SEQ ID NO: 7 | QTVVTQPASVSGSPGQSITISCTGTSS DVGGYNYVSWYQQHPGKAPKLMIY EVSNRPSGVSNHFSGSKSGNTASLTIS GLQAEDEADYYCSSYTTSSTYVFGT GTKVTVL SEQ ID NO: 8 |
| WapR-003 | QMQLVQSGGGLVQPGG SLRLSCSASGFTFSSYP MHWVRQAPGKGLDYV SDISPNGGATNYADSV KGRFTISRDNSKNTVYL QMSSLRAEDTAVYYCV MGLVPYGFDNWGQGT MVTVSS SEQ ID NO: 9 | QTVVTQPASVSASPGQSITISCAGTSG DVGNYNFVSWYQQHPGKAPKLLIYE GSQRPSGVSNRFSGSRSGNTASLTIS GLQAEDEADYYCSSYARSYTYV FGTGTKLTVL SEQ ID NO: 10 |
| WapR-004 | EVQLLESGPGLVKPSET LSLTCNVAGGSISPYYW TWIRQPPGKGLELIGYI HSSGYTDYNPSLKSRV TISGDTSKKQFSLHVSS VTAADTAVYFCARGD WDLLHALDIWGQGTL VTVSS SEQ ID NO: 11 | EIVLTQSPSSLSTSVGDRVTITCRASQ SIRSHLNWYQQKPGKAPKLLIYGAS NLQSGVPSRFSGSGSGTDFTLTISSLQ PEDFATYYCQQSYSFPLTFGGGTKLE IK SEQ ID NO: 12 |
| WapR-007 | EVQLVQSGADVKKPGA SVRVTCKASGYTFTGH NIHWVRQAPGQGLEW MGWINPDSGATSYAQ KFQGRVTMTRDTSITT AYMDLSRLRSDDTAVY YCATDTLLSNHWGQGT LVTVSS SEQ ID NO: 13 | SSELTQDPAVSVALGQTVRITCQGDS LRSYYTNWFQQKPGQAPLLVVYAK NKRPPGIPDRFSGSSSGNTASLTITGA QAEDEADYYCHSRDSSGNHVVFGG GTKLTVL SEQ ID NO: 14 |
| WapR-016 | EVQLVESGGGLVQPGGSL RLSCAASGYTFSSYATSWV RQAPGKGLEWVAGISGSG DTTDYVDSVKGRFTVSRD NSKNTLYLQMNSLRADDT AVYYCASRGGLGGYYRG GFDFWGQGTMVTVSS SEQ ID NO: 15 | QSVLTQPASVSGSPGQSITISCTGTSSDVG GYNYVSWYQQHPGKAPKLMIYEVSNRPS GVSNRFSGSKSGNTASLTISGLQAEDEAD YCSSYSSGTVVFGGGTELTVL SEQ ID NO: 16 |
| WapR-004RAD | EVQLLESGPGLVKPSET LSLTCNVAGGSISPYYW TWIRQPPGKGLELIGYI HSSGYTDYNPSLKSRV TISGDTSKKQFSLHVSS VTAADTAVYFCARAD WDLLHALDIWGQGTL VTVSS SEQ ID NO: 74 | EIVLTQSPSSLSTSVGDRVTITCRASQ SIRSHLNWYQQKPGKAPKLLIYGAS NLQSGVPSRFSGSGSGTDFTLTISSLQ PEDFATYYCQQSYSFPLTFGGGTKLE IK SEQ ID NO: 12 |

TABLE 2-continued

Reference VH and VL amino acid sequences*

| Antibody Name | VH | VL |
|---|---|---|
| V2L2 | EMQLLESGGGLVQPGG SLRLSCAASGFTFSSYA MNWVRQAPGEGLEWV SAITISGITAYYTDSVK GRFTISRDNSKNTLYLQ MNSLRAGDTAVYYCA KEEFLPGTHYYYGMD VWGQGTTVTVSS SEQ ID NO: 216 | AIQMTQSPSSLSASVGDRVTITCRAS QGIRNDLGWYQQKPGKAPKLVIYSA STLQSGVPSRFSGSGSGTDFTLSISSL QPDDFATYYCLQDYNYPWTFGQGT KVEIK SEQ ID NO: 217 |

*VH and VL CDR1, CDR2, and CDR3 amino acid sequences are underlined

TABLE 3

Reference VH and VL CDR1, CDR2, and CDR3 amino acid sequences

| Antibody Name | VHCDR1 | VHCDR2 | VHCDR3 | VLCDR1 | VLCDR2 | VLCDR3 |
|---|---|---|---|---|---|---|
| Cam-003 | PYFWS SEQ ID NO: 17 | YIHSNGG TNYNPSL KS SEQ ID NO: 18 | TDYDVY GPAFDI SEQ ID NO: 19 | QGDSLRSY YAS SEQ ID NO: 20 | GKNNRPS SEQ ID NO: 21 | NSRDSSGNH VV SEQ ID NO: 22 |
| Cam-004 | SGYYW G SEQ ID NO: 23 | SISHSGST YYNPSLK S SEQ ID NO: 24 | SEATAN FDS SEQ ID NO: 25 | QGDSLRSY YAS SEQ ID NO: 20 | GKNNRPS SEQ ID NO: 21 | NSRDSSGNH VV SEQ ID NO: 22 |
| Cam-005 | SSGYYW T SEQ ID NO: 26 | SIYSSGST YYSPSLKS SEQ ID NO: 27 | LNWGTV SAFDI SEQ ID NO: 28 | QGDSLRSY YAS SEQ ID NO: 20 | GKNNRPS SEQ ID NO: 21 | NSRDSSGNH VV SEQ ID NO:22 |
| WapR-001 | RYPMH SEQ ID NO: 29 | DIGTNG GSTNYA DSVKG SEQ ID NO: 30 | GIAAAY GFDV SEQ ID NO: 31 | TGTSSDIAT YNYVS SEQ ID NO: 32 | EGTKRPS SEQ ID NO: 33 | SSYARSYT YV SEQ ID NO: 34 |
| WapR-002 | SYPMH SEQ ID NO:35 | DISPNGG STNYAD SVKG SEQ ID NO: 36 | GLVPY GFDI SEQ ID NO: 37 | TGTSSDV GGYNYVS SEQ ID NO: 38 | EVSNRPS SEQ ID NO: 39 | SSYTTSSTY V SEQ ID NO: 40 |
| WapR-003 | SYPMH SEQ ID NO: 41 | DISPNGG ATNYAD SVKG SEQ ID NO: 42 | GLVPY GFDN SEQ ID NO: 43 | AGTSGDV GNYNFVS SEQ ID NO: 44 | EGSQRPS SEQ ID NO: 45 | SSYARSYT YV SEQ ID NO: 46 |
| WapR-004 | PYYWT SEQ ID NO: 47 | YIHSSGY TDYNPSL KS SEQ ID NO: 48 | GDWDL LHALDI SEQ ID NO: 49 | RASQSIRS HLN SEQ ID NO: 50 | GASNLQS SEQ ID NO: 51 | QQSYSFPLT SEQ ID NO: 52 |
| WapR-007 | GHNIH SEQ ID NO: 53 | WINPDS GATSYA QKFQG SEQ ID NO: 54 | DTLLSN H SEQ ID NO: 55 | QGDSLRS YYTN SEQ ID NO: 56 | AKNKRPP SEQ ID NO: 57 | HSRDSSGN HVV SEQ ID NO: 58 |
| WapR-016 | SYATS SEQ ID NO: 59 | GISGSGDT TDYVDSV KG SEQ ID NO: 60 | RGGLGG YYRGGF DF SEQ ID NO: 61 | TGTSSDVG GYNYVS SEQ ID NO: 62 | EVSNRPS SEQ ID NO: 63 | SSYSSGTVV SEQ ID NO: 64 |

TABLE 3-continued

Reference VH and VL CDR1, CDR2, and CDR3 amino acid sequences

| Antibody Name | VHCDR1 | VHCDR2 | VHCDR3 | VLCDR1 | VLCDR2 | VLCDR3 |
|---|---|---|---|---|---|---|
| WapR-004RAD | PYYWT SEQ ID NO: 47 | YIHSSGY TDYNPSL KS SEQ ID NO: 48 | ADWDL LHALDI SEQ ID NO: 75 | RASQSIRS HLN SEQ ID NO: 50 | GASNLQS SEQ ID NO: 51 | QQSYSFPLT SEQ ID NO: 52 |
| V2L2 | SYAMN SEQ ID NO: 218 | AITISGIT AYYTDS VKG SEQ ID NO: 219 | EEFLPG THYYY GMDV SEQ ID NO: 220 | RASQGIRN DLG SEQ ID NO: 221 | SASTLQS SEQ ID NO: 222 | LQDYNYPWT SEQ ID NO: 223 |

In certain embodiments, an anti-*Pseudomonas* PcrV binding molecule, e.g., antibody or fragment, variant or derivative thereof described herein specifically binds to the same PerV epitope as monoclonal antibody V2L2, and/or will competitively inhibit such a monoclonal antibody from binding to *Pseudomonas* PcrV.

For example, in certain aspects the anti-*Pseudomonas* PcrV binding molecule, e.g., antibody or fragment, variant or derivative thereof comprises V2L2-GL and/or V2L2-MD.

In certain embodiments, an anti-*Pseudomonas* PcrV binding molecule, e.g., antibody or fragment, variant or derivative thereof described herein specifically binds to the same PerV epitope as monoclonal antibody 29D2, and/or will competitively inhibit such a monoclonal antibody from binding to *Pseudomonas* PcrV.

Any anti-*Pseudomonas* Psl and/or PcrV binding molecules, e.g., antibodies or fragments, variants or derivatives thereof described herein can further include additional polypeptides, e.g., a signal peptide to direct secretion of the encoded polypeptide, antibody constant regions as described herein, or other heterologous polypeptides as described herein. Additionally, binding molecules or fragments thereof of the description include polypeptide fragments as described elsewhere. Additionally anti-*Pseudomonas* Psl and/or PcrV binding molecules, e.g., antibodies or fragments, variants or derivatives thereof described herein can be fusion polypeptides, Fab fragments, scFvs, or other derivatives, as described herein.

Also, as described in more detail elsewhere herein, the disclosure includes compositions comprising anti-*Pseudomonas* Psl and/or PcrV binding molecules, e.g., antibodies or fragments, variants or derivatives thereof described herein.

It will also be understood by one of ordinary skill in the art that anti-*Pseudomonas* Psl and/or PcrV binding molecules, e.g., antibodies or fragments, variants or derivatives thereof described herein can be modified such that they vary in amino acid sequence from the naturally occurring binding polypeptide from which they were derived. For example, a polypeptide or amino acid sequence derived from a designated protein can be similar, e.g., have a certain percent identity to the starting sequence, e.g., it can be 60%, 70%, 75%, 80%, 85%, 90%, or 95% identical to the starting sequence.

As known in the art, "sequence identity" between two polypeptides is determined by comparing the amino acid sequence of one polypeptide to the sequence of a second polypeptide. When discussed herein, whether any particular polypeptide is at least about 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, WI 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence, the parameters are set, of course, such that the percentage of identity is calculated over the full length of the reference polypeptide sequence and that gaps in homology of up to 5% of the total number of amino acids in the reference sequence are allowed.

Percentage of "sequence identity" can also be determined by comparing two optimally aligned sequences over a comparison window. In order to optimally align sequences for comparison, the portion of a polynucleotide or polypeptide sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which was available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (*Proc. Natl. Acad. Sci. USA* 90 (12): 5873-5877, 1993). When utilizing "BLAST 2 Sequences," parameters that were default parameters as of Sep. 1, 2004, can be used for word size (3), open gap penalty (11), extension gap penalty (1), gap drop-off (50), expect value (10) and any other required parameter including but not limited to matrix option.

Furthermore, nucleotide or amino acid substitutions, deletions, or insertions leading to conservative substitutions or changes at "non-essential" amino acid regions can be made. For example, a polypeptide or amino acid sequence derived from a designated protein can be identical to the starting sequence except for one or more individual amino acid substitutions, insertions, or deletions, e.g., one, two, three, four, five, six, seven, eight, nine, ten, fifteen, twenty or more individual amino acid substitutions, insertions, or deletions.

In certain embodiments, a polypeptide or amino acid sequence derived from a designated protein has one to five, one to ten, one to fifteen, or one to twenty individual amino acid substitutions, insertions, or deletions relative to the starting sequence.

An anti-*Pseudomonas* Psl and/or PcrV binding molecule, e.g., an antibody or fragment, variant or derivative thereof described herein can comprise, consist essentially of, or consist of a fusion protein. Fusion proteins are chimeric molecules which comprise, for example, an immunoglobulin antigen-binding domain with at least one target binding site, and at least one heterologous portion, i.e., a portion with which it is not naturally linked in nature. The amino acid sequences can normally exist in separate proteins that are brought together in the fusion polypeptide or they can normally exist in the same protein but are placed in a new arrangement in the fusion polypeptide. Fusion proteins can be created, for example, by chemical synthesis, or by creating and translating a polynucleotide in which the peptide regions are encoded in the desired relationship.

The term "heterologous" as applied to a polynucleotide, polypeptide, or other moiety means that the polynucleotide, polypeptide, or other moiety is derived from a distinct entity from that of the rest of the entity to which it is being compared. In a non-limiting example, a "heterologous polypeptide" to be fused to a binding molecule, e.g., an antibody or an antigen-binding fragment, variant, or derivative thereof is derived from a non-immunoglobulin polypeptide of the same species, or an immunoglobulin or non-immunoglobulin polypeptide of a different species.

IV. Fusion Proteins and Antibody Conjugates

In some embodiments, the anti-*Pseudomonas* Psl and/or PcrV binding molecules, e.g., antibodies or fragments, variants or derivatives thereof can be administered multiple times in conjugated form. In still another embodiment, the anti-*Pseudomonas* Psl and/or PcrV binding molecules, e.g., antibodies or fragments, variants or derivatives thereof can be administered in unconjugated form, then in conjugated form, or vice versa.

In specific embodiments, the anti-*Pseudomonas* Psl and/ or PcrV binding molecules, e.g., antibodies or fragments, variants or derivatives thereof can be conjugated to one or more antimicrobial agents, for example, Polymyxin B (PMB). PMB is a small lipopeptide antibiotic approved for treatment of multidrug-resistant Gram-negative infections. In addition to its bactericidal activity, PMB binds lipopolysaccharide (LPS) and neutralizes its proinflammatory effects. (Dixon, R. A. & Chopra, I. *J Antimicrob Chemother* 18, 557-563 (1986)). LPS is thought to significantly contribute to inflammation and the onset of Gram-negative sepsis. (Guidet, B., et al., *Chest* 106, 1194-1201 (1994)). Conjugates of PMB to carrier molecules have been shown to neutralize LPS and mediate protection in animal models of endotoxemia and infection. (Drabick, J. J., et al. *Antimicrob Agents Chemother* 42, 583-588 (1998)). Also disclosed is a method for attaching one or more PMB molecules to cysteine residues introduced into the Fc region of monoclonal antibodies (mAb) of the disclosure. For example, the Cam-003-PMB conjugates retained specific, mAb-mediated binding to *P. aeruginosa* and also retained OPK activity. Furthermore, mAb-PMB conjugates bound and neutralized LPS in vitro. In specific embodiments, the anti-*Pseudomonas* Psl and/or PcrV binding molecules, e.g., antibodies or fragments, variants or derivatives thereof can be combined with antibiotics (e.g., Ciprofloxacin, Meropenem, Tobramycin, Aztreonam).

In certain embodiments, an anti-*Pseudomonas* Psl and/or PcrV binding molecule, e.g., an antibody or fragment, variant or derivative thereof described herein can comprise a heterologous amino acid sequence or one or more other moieties not normally associated with an antibody (e.g., an antimicrobial agent, a therapeutic agent, a prodrug, a peptide, a protein, an enzyme, a lipid, a biological response modifier, pharmaceutical agent, a lymphokine, a heterologous antibody or fragment thereof, a detectable label, polyethylene glycol (PEG), and a combination of two or more of any said agents). In further embodiments, an anti-*Pseudomonas* Psl and/or PcrV binding molecule, e.g., an antibody or fragment, variant or derivative thereof can comprise a detectable label selected from the group consisting of an enzyme, a fluorescent label, a chemiluminescent label, a bioluminescent label, a radioactive label, or a combination of two or more of any said detectable labels.

V. Polynucleotides Encoding Binding Molecules

Also provided herein are nucleic acid molecules encoding the anti-*Pseudomonas* Psl and/or PcrV binding molecules, e.g., antibodies or fragments, variants or derivatives thereof described herein.

One embodiment provides an isolated polynucleotide comprising, consisting essentially of, or consisting of a nucleic acid encoding an immunoglobulin heavy chain variable region (VH) amino acid sequence at least 80%, 85%, 90% 95% or 100% identical to one or more of: SEQ ID NO: 1, SEQ ID NO: 3, SEQ ID NO: 4, SEQ ID NO: 5, SEQ ID NO: 7, SEQ ID NO: 9, SEQ ID NO: 11, SEQ ID NO: 13, SEQ ID NO: 15, SEQ IS NO: 74, or SEQ ID NO: 216 as shown in Table 2.

One embodiment provides an isolated polynucleotide comprising, consisting essentially of, or consisting of a nucleic acid encoding an immunoglobulin heavy chain variable region (VH) amino acid sequence of SEQ ID NO:257 or SEQ ID NO:259. For example the nucleic acid sequences of SEQ ID NO:261, and SEQ ID NO: 259, respectively.

Another embodiment provides an isolated polynucleotide comprising, consisting essentially of, or consisting of a nucleic acid encoding a VH amino acid sequence identical to, or identical except for one, two, three, four, five, or more amino acid substitutions to one or more of: SEQ ID NO: 1, SEQ ID NO: 3, SEQ ID NO: 4, SEQ ID NO: 5, SEQ ID NO: 7, SEQ ID NO: 9, SEQ ID NO: 11, SEQ ID NO: 13, SEQ ID NO: 15, SEQ ID NO: 74, or SEQ ID NO:216 as shown in Table 2.

Further embodiment provides an isolated polynucleotide comprising, consisting essentially of, or consisting of a nucleic acid encoding a VH, where one or more of the VHCDR1, VHCDR2 or VHCDR3 regions of the VH are identical to, or identical except for four, three, two, or one amino acid substitutions, to one or more reference heavy chain VHCDR1, VHCDR2 and/or VHCDR3 amino acid sequences of one or more of: SEQ ID NO: 1, SEQ ID NO: 3, SEQ ID NO: 4, SEQ ID NO: 5, SEQ ID NO: 7, SEQ ID NO: 9, SEQ ID NO: 11, SEQ ID NO: 13, SEQ ID NO: 15, SEQ ID NO: 74, or SEQ ID NO:216 as shown in Table 2.

Another embodiment provides an isolated polynucleotide comprising, consisting essentially of, or consisting of a nucleic acid encoding an isolated binding molecule, e.g., an antibody or antigen-binding fragment thereof which specifically binds to *Pseudomonas* Psl comprising a VH, where one or more of the VHCDR1, VHCDR2 or VHCDR3 regions of the VH are identical to, or identical except for four, three, two, or one amino acid substitutions, to one or more reference heavy chain VHCDR1, VHCDR2 and/or VHCDR3 amino acid sequences of one or more of: SEQ ID NO: 1, SEQ ID NO: 3, SEQ ID NO: 4, SEQ ID NO: 5, SEQ ID NO: 7, SEQ ID NO: 9, SEQ ID NO: 11, SEQ ID NO: 13, SEQ ID NO: 15, or SEQ ID NO: 74 as shown in Table 2.

A further embodiment provides an isolated binding molecule e.g., an antibody or antigen-binding fragment comprising the VH encoded by the polynucleotide specifically or preferentially binds to *Pseudomonas* Psl and/or PcrV.

Another embodiment provides an isolated polynucleotide comprising, consisting essentially of, or consisting of a nucleic acid encoding an immunoglobulin light chain variable region (VL) amino acid sequence at least 80%, 85%, 90% 95% or 100% identical to one or more of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO:217 as shown in Table 2.

Another embodiment provides an isolated polynucleotide comprising, consisting essentially of, or consisting of a nucleic acid encoding the immunoglobulin light chain variable region (VL) amino acid sequence of SEQ ID NO:256, e.g., the nucleic acid sequence SEQ ID NO:260.

A further embodiment provides an isolated polynucleotide comprising, consisting essentially of, or consisting of a nucleic acid encoding a VL amino acid sequence identical to, or identical except for one, two, three, four, five, or more amino acid substitutions to one or more of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO:217 as shown in Table 2.

Another embodiment provides an isolated polynucleotide comprising, consisting essentially of, or consisting of a nucleic acid encoding a VL, where one or more of the VLCDR1, VLCDR2 or VLCDR3 regions of the VL are at least 80%, 85%, 90%, 95% or 100% identical to one or more reference light chain VLCDR1, VLCDR2 or VLCDR3 amino acid sequences of one or more of: SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16, or SEQ ID NO:217 as shown in Table 2.

A further embodiment provides an isolated polynucleotide comprising, consisting essentially of, or consisting of a nucleic acid encoding an isolated binding molecule, e.g., an antibody or antigen-binding fragment thereof which specifically binds to *Pseudomonas* Psl comprising an VL, where one or more of the VLCDR1, VLCDR2 or VLCDR3 regions of the VL are identical to, or identical except for four, three, two, or one amino acid substitutions, to one or more reference heavy chain VLCDR1, VLCDR2 and/or VLCDR3 amino acid sequences of one or more of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO:217 as shown in Table 2.

In another embodiment, isolated binding molecules e.g., an antibody or antigen-binding fragment comprising the VL encoded by the polynucleotide specifically or preferentially bind to *Pseudomonas* Psl and/or PcrV.

One embodiment provides an isolated polynucleotide comprising, consisting essentially of, or consisting of a nucleic acid which encodes an scFv molecule including a VH and a VL, where the scFv is at least 80%, 85%, 90% 95% or 100% identical to one or more of SEQ ID NO: 65, SEQ ID NO:66, SEQ ID NO:67, SEQ ID NO:68, SEQ ID NO:69, or SEQ ID NO: 70 as shown in Table 4.

TABLE 4

Reference scFv nucleic acid sequences

| Antibody Name | scFv nucleotide sequences |
|---|---|
| Cam-003 | CAGCCGGCCATGGCCCAGGTACAGCTGCAGCAGTCAGGCCCAGG<br>ACTGGTGAAGCCTTCGGAGACCCTGTCCCTCACCTGCACTGTCTCT<br>GGTGGCTCCACCAGTCCTTACTTCTGGAGCTGGCTCCGGCAGCCC<br>CCAGGGAAGGGACTGGAGTGGATTGGTTATATCCATTCCAATGGG<br>GGCACCAACTACAACCCCTCCCTCAAGAGTCGACTCACCATATCA<br>GGAGACACGTCCAAGAACCAATTCTCCCTGAATCTGAGTTTTGTG<br>ACCGCTGCGGACACGGCCCTCTATTACTGTGCGAGAACGGACTAC<br>GATGTCTACGGCCCCGCTTTTGATATCTGGGGCCAGGGGACAATG<br>GTCACCGTCTCGAGTGGTGGAGGCGGTTCAGGCGGAGGTGGCAG<br>CGGCGGTGGCGGATCGTCTGAGCTGACTCAGGACCCTGCTGTGTC<br>TGTGGCCTTGGGACAGACAGTCAGGATCACATGCCAAGGAGACA<br>GCCTCAGAAGCTATTATGCAAGCTGGTACCAGCAGAAGCCAGGA<br>CAGGCCCCTGTACTTGTCATCTATGGTAAAAACAACCGGCCCTCA<br>GGGATCCCAGACCGATTCTCTGGCTCCAGCTCAGGAAACACAGCT<br>TCCTTGACCATCACTGGGGCTCAGGCGGAAGATGAGGCTGACTAT<br>TACTGTAACTCCCGGGACAGCAGTGGTAACCATGTGGTATTCGGC<br>GGAGGGACCAAGCTGACCGTCCTAGGTGCGGCCGCA<br>SEQ ID NO: 65 |
| Cam-004 | CAGCCGGCCATGGCCCAGGTACAGCTGCAGCAGTCAGGCCCAGG<br>ACGGGTGAAGCCTTCGGAGAGCGCTGTCCCTCACCTGCACTGTCTC<br>TGGTTACTCCGTCAGTAGTGGTTACTACTGGGGCTGGATCCGGCA<br>GTCCCCAGGGACGGGGCTGGAGTGGATTGGGAGTATCTCTCATAG<br>TGGGAGCACCTACTACAACCCGTCCCTCAAGAGTCGAGTCACCAT<br>ATCAGGAGACGCATCCAAGAACCAGTTTTTCCTGAGGCTGACTTC<br>TGTGACCGCCGCGGACACGGCCGTTTATTACTGTGCGAGATCTGA<br>GGCTACCGCCAACTTTGATTCTTGGGGCAGGGGCACCCTGGTCAC<br>CGTCTCTTCAGGTGGAGGCGGTTCAGGCGGAGGTGGCAGCGGCG<br>GTGGCGGATCGTCTGAGCTGACTCAGGACCCTGCCGTGTCTGTGG<br>CCTTGGGACAGACAGTCAGGATCACATGCCAAGGAGACAGCCTC<br>AGAAGCTATTATGCAAGCTGGTACCAGCAGAAGCCAGGACAGGC<br>CCCTGTACTTGTCATCTATGGTAAAAACAACCGGCCCTCAGGGAT<br>CCCAGACCGATTCTCTGGCTCCAGCTCAGGAAACACAGCTTCCTT |

TABLE 4-continued

Reference scFv nucleic acid sequences

| Antibody Name | scFv nucleotide sequences |
|---|---|
| | GACCATCACTGGGGCTCAGGCGGAAGATGAGGCTGACTATTACTG
TAACTCCCGGGACAGCAGTGGTAACCATGTGGTATTCGGCGGAGG
GACCAAGCTGACCGTCCTAGGTGCGGCCGCA
SEQ ID NO: 66 |
| Cam-005 | CAGCCGGCCATGGCCCAGGTACAGCTGCAGCAGTCAGGCCCAGG
ACTGGTGAAGCCTTCGGAGACCCTGTCCCTCACCTGCACTGTCTCT
GGTGGCTCCGTCAGCAGTAGTGGTTATTACTGGACCTGGATCCGC
CAGCCCCCAGGGAAGGGGCTGGAGTGGATTGGGAGTATCTATTCT
AGTGGGAGCACATATTACAGCCCGTCCCTCAAGAGTCGAGTCACC
ATATCCGGAGACACGTCCAAGAACCAGTTCTCCCTCAAGCTGAGC
TCTGTGACCGCCGCAGACACAGCCGTGTATTACTGTGCGAGACTT
AACTGGGGCACTGTGTCTGCCTTTGATATCTGGGGCAGAGGCACC
CTGGTCACCGTCTCGAGTGGTGGAGGCGGTTCAGGCGGAGGTGGC
AGCGGCGGTGGCGGATCGTCTGAGCTGACTCAGGACCCTGCTGTG
TCTGTGGCCTTGGGACAGACAGTCAGGATCACATGCCAAGGAGAC
AGCCTCAGAAGCTATTATGCAAGCTGGTACCAGCAGAAGCCAGG
ACAGGCCCCTGTACTTGTCATCTATGGTAAAAACAACCGGCCCTC
AGGGATCCCAGACCGATTCTCTGGCTCCAGCTCAGGAAACACAGC
TTCCTTGACCATCACTGGGGCTCAGGCGGAAGATGAGGCTGACTA
TTACTGTAACTCCCGGGACAGCAGTGGTAACCATGTGGTATTCGG
CGGAGGGACCAAGCTGACCGTCCTAGGTGCGGCCGCA
SEQ ID NO: 67 |
| WapR-001 | TCTATGCGGCCCAGCCGGCCATGGCCGAGGTGCAGCTGTTGGAGT
CTGGGGGAGGTTTGGTCCAGCCTGGGGGGTCCCTGAGACTCTCCT
GTTCAGCCTCTGGGTTCACCTTCAGTCGGTATCCTATGCATTGGGT
CCGCCAGGCTCCAGGGAAGGGACTGGAATATGTTTCAGATATTGG
TACTAATGGGGGTAGTACAAACTACGCAGACTCCGTGAAGGGCA
GATTCACCATCTCCAGAGACAATTCCAAGAACACGGTGTATCTTC
AAATGAGCAGTCTGAGAGCTGAGGACACGGCTGTGTATCATTGTG
TGGCGGGTATAGCAGCCGCCTATGGTTTTGATGTCTGGGGCCAAG
GGACAATGGTCACCGTCTCGAGTGGAGGCGGCGGTTCAGGCGGA
GGTGGCTCTGGCGGTGGCGGAAGTGCACAGGCAGGGCTGACTCA
GCCTGCCTCCGTGTCTGGGTCTCCTGGACAGTCGATCACCATCTCC
TGCACTGGAACCAGCAGTGACATTGCTACTTATAACTATGTCTCCT
GGTACCAACAGCACCCAGGCAAAGCCCCCAAACTCATGATTTATG
AGGGCACTAAGCGGCCCTCAGGGGTTTCTAATCGCTTCTCTGGCT
CCAAGTCTGGCAACACGGCCTCCCTGACAATCTCTGGGCTCCAGG
CTGAGGACGAGGCTGATTATTACTGTTCCTCATATGCACGTAGTT
ACACTTATGTCTTCGGAACTGGGACCGAGCTGACCGTCCTAGCGG
CCGC
SEQ ID NO: 68 |
| WapR-002 | CTATGCGGCCCAGCCGGCCATGGCCCAGGTGCAGCTGGTGCAGTC
TGGGGGAGGCTTGGTCCAGCCTGGGGGGTCCCTGAGACTCTCCTG
TTCAGCCTCTGGATTCACCTTCAGTAGCTATCCTATGCACTGGGTC
CGCCAGGCTCCAGGGAAGGGACTGGATTATGTTTCAGACATCAGT
CCAAATGGGGGTTCCACAAACTACGCAGACTCCGTGAAGGGCAG
ATTCACCATCTCCAGAGACAATTCCAAGAACACACTGTTTCTTCA
AATGAGCAGTCTGAGAGCTGAGGACACGGCTGTGTATTATTGTGT
GATGGGGTTAGTACCCTATGGTTTTGATATCTGGGGCCAAGGCAC
CCTGGTCACCGTCTCGAGTGGAGGCGGCGGTTCAGGCGGAGGTGG
CTCTGGCGGTGGCGGAAGTGCACAGACTGTGGTGACCCAGCCTGC
CTCCGTGTCTGGGTCTCCTGGACAGTCGATCACCATCTCCTGCACT
GGAACCAGCAGTGACGTTGGTGGTTATAACTATGTCTCCTGGTAC
CAACAGCACCCAGGCAAAGCCCCCAAACTCATGATTTATGAGGTC
AGTAATCGGCCCTCAGGGGTTTCTAATCACTTCTCTGGCTCCAAGT
CTGGCAACACGGCCTCCCTGACCATCTCTGGGCTCCAGGCTGAGG
ACGAGGCTGATTATTACTGCAGCTCATATACAACCAGCAGCACTT
ATGTCTTCGGAACTGGGACCAAGGTCACCGTCCTAGCGGCCG
SEQ ID NO: 69 |
| WapR-003 | CGGCCCAGCCGGCCATGGCCCAGATGCAGCTGGTGCAGTCGGGG
GGAGGCTTGGTCCAGCCTGGGGGGTCCCTGAGACTCTCCTGTTCA
GCCTCTGGATTCACCTTCAGTAGCTATCCTATGCACTGGGTCCGCC
AGGCTCCAGGGAAGGGACTGGATTATGTTTCAGACATCAGTCCAA
ATGGGGGTGCCACAAACTACGCAGACTCCGTGAAGGGCAGATTC
ACCATCTCCAGAGACAATTCCAAGAACACGGTGTATCTTCAAATG
AGCAGTCTGAGAGCTGAAGACACGGCTGTCTATTATTGTGTGATG
GGGTTAGTGCCCTATGGTTTTGATAACTGGGGCCAGGGGACAATG
GTCACCGTCTCGAGTGGAGGCGGCGGTTCAGGCGGAGGTGGCTCT
GGCGGTGGCGGAAGTGCACAGACTGTGGTGACCCAGCCTGCCTCC
GTGTCTGCATCCTGGACAGTCGATCACCATCTCCTGCGCTGGA
ACCAGCGGTGATGTTGGGAATTATAATTTTGTCTCCTGGTACCAA
CAACACCCAGGCAAAGCCCCCAAACTCCTGATTTATGAGGGCAGT |

TABLE 4-continued

Reference scFv nucleic acid sequences

| Antibody Name | scFv nucleotide sequences |
|---|---|
| | CAGCGGCCCTCAGGGGTTTCTAATCGCTTCTCTGGCTCCAGGTCTG<br>GCAACACGGCCTCCCTGACAATCTCTGGGCTCCAGGCTGAGGACG<br>AGGCTGATTATTACTGTTCCTCATATGCACGTAGTTACACTTATGT<br>CTTCGGAACTGGGACCAAGCTGACCGTCCTAGCGGCCGCA<br>SEQ ID NO: 70 |
| WapR-004 | TATGCGGCCCAGCCGGCCATGGCCGAGGTGCAGCTGTTGGAGTCG<br>GGCCCAGGACTGGTGAAGCCTTCGGAGACCCTGTCCCTCACCTGC<br>AATGTCGCTGGTGGCTCCATCAGTCCTTACTACTGGACCTGGATCC<br>GGCAGCCCCAGGGAAGGGCCTGGAGTTGATTGGTTATATCCACT<br>CCAGTGGGTACACCGACTACAACCCCTCCCTCAAGAGTCGAGTCA<br>CCATATCAGGAGACACGTCCAAGAAGCAGTTCTCCCTGCACGTGA<br>GCTCTGTGACCGCTGCGGACACGGCCGTGTACTTCTGTGCGAGAG<br>GCGATTGGGACCTGCTTCATGCTCTTGATATCTGGGGCCAAGGGA<br>CCCTGGTCACCGTCTCGAGTGGAGGCGGCGGTTCAGGCGGAGGTG<br>GCTCTGGCGGTGGCGGAAGTGCACTCGAAATTGTGTTGACACAGT<br>CTCCATCCTCCCTGTCTACATCTGTAGGAGACAGAGTCACCATCA<br>CTTGCCGGGCAAGTCAGAGCATTAGGAGCCATTTAAATTGGTATC<br>AGCAGAAACCAGGGAAAGCCCCTAAACTCCTGATCTATGGTGCAT<br>CCAATTTGCAAAGTGGGGTCCCATCAAGGTTCAGTGGCAGTGGAT<br>CTGGGACAGATTTCACTCTCACCATTAGTAGTCTGCAACCTGAAG<br>ATTTTGCAACTTACTACTGTCAACAGAGTTACAGTTTCCCCCTCAC<br>TTTCGGCGGAGGGACCAAGCTGGAGATCAAAGCGGCCGC<br>SEQ ID NO: 71 |
| WapR-007 | GCGGCCCAGCCGGCCATGGCCGAAGTGCAGCTGGTGCAGTCTGG<br>GGCTGACGTAAAGAAGCCTGGGGCCTCAGTGAGGGTCACCTGCA<br>AGGCTTCTGGATACACCTTCACCGGCCACAACATACACTGGGTGC<br>GACAGGCCCCTGGACAAGGGCTTGAATGGATGGGATGGATCAAC<br>CCTGACAGTGGTGCCACAAGCTATGCACAGAAGTTTCAGGGCAGG<br>GTCACCATGACCAGGGACACGTCCATCACCACAGCCTACATGGAC<br>CTGAGCAGGCTGAGATCTGACGACACGGCCGTATATTACTGTGCG<br>ACCGATACATTACTGTCTAATCACTGGGGCCAAGGAACCCTGGTC<br>ACCGTCTCGAGTGGTGGAGGCGGTTCAGGCGGAGGTGGCAGCGG<br>CGGTGGCGGATCGTCTGAGCTGACTCAGGACCCTGCTGTGTCTGT<br>GGCCTTGGGACAGACAGTCAGGATCACTTGCCAAGGAGACAGTCT<br>CAGAAGCTATTACACAAACTGGTTCCAGCAGAAGCCAGGACAGG<br>CCCCTCTACTTGTCGTCTATGCTAAAAATAAGCGGCCCCCAGGGA<br>TCCCAGACCGATTCTCTGGCTCCAGCTCAGGAAACACAGCTTCCT<br>TGACCATCACTGGGGCTCAGGCGGAAGATGAGGCTGACTATTACT<br>GTCATTCCCGGGACAGCAGTGGTAACCATGTGGTATTCGGCGGAG<br>GGACCAAGCTGACCGTCCTAGGTGCGGCCGCA<br>SEQ ID NO: 72 |
| WapR-016 | CAGCCGGCCATGGCCGAGGTGCAGCTGGTGGAGTCTGGGGGAGG<br>CTTGGTACAGCCTGGGGGGTCCCTGAGACTCTCCTG<br>TGCAGCCTCTGGATACACCTTTAGCAGCTATGCCACGAGCTGGGT<br>CCGCCAGGCTCCAGGGAAGGGGCTGGAGTGGGTCG<br>CAGGTATTAGTGGTAGTGGTGATACCACAGACTACGTAGACTCCG<br>TGAAGGGCCGGTTCACCGTCTCCAGAGACAATTCC<br>AAGAACACCCTATATCTGCAAATGAACAGCCTGAGAGCCGACGA<br>CACGGCCGTGTATTACTGTGCGTCGAGAGGAGGTTT<br>AGGGGGTTATTACCGGGCGGCTTTGACTTCTGGGGCCAGGGGAC<br>AATGGTCACCGTCTCGAGTGGAGGCGGCGGTTCAG<br>GCGGAGGTGGCTCTGGCGGTGGCGGAAGTGCACAGTCTGTGCTGA<br>CGCAGCCTGCCTCCGTGTCTGGGTCTCCTGGACAG<br>TCGATCACCATCTCCTGCACTGGAACCAGCAGTGACGTTGGTGGT<br>TATAACTATGTCTCCTGGTACCAACAGCACCCAGG<br>CAAAGCCCCCAAACTCATGATTTATGAGGTCAGTAATCGGCCCTC<br>AGGGGTTTCTAATCGCTTCTCTGGCTCCAAGTCTG<br>GCAACACGGCCTCCCTGACCATCTCTGGGCTCCAGGCTGAGGACG<br>AGGCTGATTATTACTGCAGCTCATATACAAGCAGC<br>GGCACTGTGGTATTCGGCGGAGGGACCGAGCTGACCGTCCTAGCG<br>GCCGCA<br>SEQ ID NO: 73 |
| V2L2-VH | GAGATGCAGCTGTTGGAGTCTGGGGGAGGCTTGGTACAGCCTGGG<br>GGGTCCCTGAGACTCTCCTGTGCAGCCTCTGGATTCACCTTTAGCA<br>GCTATGCCATGAACTGGGTCCGCCAGGCTCCAGGGGAGGGGCTGG<br>AGTGGGTCTCAGCTATTACTATTAGTGGTATTACCGCATACTACAC<br>CGACTCCGTGAAGGGCCGGTTCACCATCTCCAGAGACAATTCCAA<br>GAACACGGCTATATCTGCAAATGAACAGCCTGAGGGCCGGGGACAC<br>GGCCGTATATTACTGTGCGAAGGAAGAATTTTTACCTGGAACGCA<br>CTACTACACGGTATGGACGTCTGGGGCCAAGGGACCACGGTCAC<br>CGTCTCCTCA<br>SEQ ID NO: 238 |

TABLE 4-continued

Reference scFv nucleic acid sequences

| Antibody Name | scFv nucleotide sequences |
|---|---|
| V2L2-VL | GCCATCCAGATGACCCAGTCTCCATCCTCCCTGTCTGCATCTGTAG<br>GAGACAGAGTCACCATCACTTGCCGGGCAAGTCAGGGCATTAGAA<br>ATGATTTAGGCTGGTATCAACAGAAGCCAGGGAAAGCCCCTAAAC<br>TCGTGATCTATTCTGCATCCACTTTACAAAGTGGGGTCCCATCAAG<br>GTTCAGCGGCAGTGGATCTGGCACAGATTTCACTCTCTCCATCAGC<br>AGCCTGCAGCCTGACGATTTTGCAACTTATTACTGTCTACAAGATT<br>ACAATTACCCGTGGACGTTCGGCCAAGGGACCAAGGTTGAAATCA<br>AA<br>SEQ ID NO: 239 |

In some embodiments, an isolated antibody or antigen-binding fragment thereof encoded by one or more of the polynucleotides described above, which specifically binds to *Pseudomonas* Psl and/or PcrV, comprises, consists essentially of, or consists of VH and VL amino acid sequences at least 80%, 85%, 90%, 95% or 100% identical to:

(a) SEQ ID NO: 1 and SEQ ID NO: 2, respectively, (b) SEQ ID NO: 3 and SEQ ID NO: 2, respectively, (c) SEQ ID NO: 4 and SEQ ID NO: 2, respectively, (d) SEQ ID NO: 5 and SEQ ID NO: 6, respectively, (e) SEQ ID NO: 7 and SEQ ID NO: 8, respectively, (f) SEQ ID NO: 9 and SEQ ID NO: 10, respectively, (g) SEQ ID NO: 11 and SEQ ID NO: 12, respectively, (h) SEQ ID NO: 13 and SEQ ID NO: 14, respectively; (i) SEQ ID NO: 15 and SEQ ID NO: 16, respectively; or (j) SEQ ID NO: 74 and SEQ ID NO: 12, respectively.

In certain embodiments, an isolated binding molecule, e.g., an antibody or antigen-binding fragment thereof encoded by one or more of the polynucleotides described above, specifically binds to *Pseudomonas* Psl and/or PcrV with an affinity characterized by a dissociation constant ($K_D$) no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

In specific embodiments, an isolated binding molecule, e.g., an antibody or antigen-binding fragment thereof encoded by one or more of the polynucleotides described above, specifically binds to *Pseudomonas* Psl and/or PcrV, with an affinity characterized by a dissociation constant ($K_D$) in a range of about $1\times10^{-10}$ to about $1\times10^{-6}$ M. In one embodiment, an isolated binding molecule, e.g., an antibody or antigen-binding fragment thereof encoded by one or more of the polynucleotides described above, specifically binds to *Pseudomonas* Psl and/or PcrV, with an affinity characterized by a $K_D$ of about $1.18\times10^{-7}$ M, as determined by the OCTET® binding assay described herein. In another embodiment, an isolated binding molecule, e.g., an antibody or antigen-binding fragment thereof encoded by one or more of the polynucleotides described above, specifically binds to *Pseudomonas* Psl and/or PcrV, with an affinity characterized by a $K_D$ of about $1.44\times10^{-7}$ M, as determined by the OCTET® binding assay described herein.

In certain embodiments, an anti-*Pseudomonas* Psl and/or PcrV binding molecule, e.g., antibody or fragment, variant or derivative thereof encoded by one or more of the polynucleotides described above, specifically binds to the same Psl epitope as monoclonal antibody WapR-004, WapR-004RAD, Cam-003, Cam-004, or Cam-005, or will competitively inhibit such a monoclonal antibody from binding to *Pseudomonas* Psl; and/or specifically binds to the same PcrV epitope as monoclonal antibody V2L2, or will competitively inhibit such a monoclonal antibody from binding to *Pseudomonas* PcrV. WapR-004RAD is identical to WapR-004 except for a nucleic acid substitution G293C of the VH nucleic acid sequence encoding the VH amino acid sequence of SEQ ID NO:11 (a substitution of the nucleotide in the VH-encoding portion of SEQ ID NO:71 at position 317). The nucleic acid sequence encoding the WapR-004RAD VH is presented as SEQ ID NO 76.

Some embodiments provide an isolated polynucleotide comprising, consisting essentially of, or consisting of a nucleic acid encoding a W4 mutant scFv-Fc molecule amino acid sequence identical to, or identical except for one, two, three, four, five, or more amino acid substitutions to one or more of: SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145; or SEQ ID NO: 146.

Other embodiments provide an isolated polynucleotide comprising, consisting essentially of, or consisting of a nucleic acid encoding a W4 mutant scFv-Fc molecule amino acid sequence at least 80%, 85%, 90% 95% or 100% identical to one or more of: SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145; or SEQ ID NO: 146.

One embodiment provides an isolated polynucleotide comprising, consisting essentially of, or consisting of a nucleic acid which encodes a W4 mutant scFv-Fc molecule, where the nucleic acid is at least 80%, 85%, 90% 95% or 100% identical to one or more of SEQ ID NO: 147, SEQ ID NO: 148, SEQ ID NO: 149, SEQ ID NO: 150, SEQ ID NO: 151, or SEQ ID NO: 152, SEQ IS NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214; or SEQ ID NO: 215.

One embodiment provides an isolated polynucleotide comprising, consisting essentially of, or consisting of a nucleic acid which encodes a V2L2 polypeptide, where the nucleic acid is at least 80%, 85%, 90% 95% or 100% identical to one or more of SEQ ID NO: 238 or SEQ ID NO: 239.

In other embodiments, an anti-*Pseudomonas* Psl and/or PcrV binding molecule, e.g., antibody or fragment, variant or derivative thereof encoded by one or more of the polynucleotides described above, specifically binds to the same epitope as monoclonal antibody WapR-001, WapR-002, or WapR-003, or will competitively inhibit such a monoclonal antibody from binding to *Pseudomonas* Psl.

In certain embodiments, an anti-*Pseudomonas* Psl and/or PcrV binding molecule, e.g., antibody or fragment, variant or derivative thereof encoded by one or more of the polynucleotides described above, specifically binds to the same epitope as monoclonal antibody WapR-016, or will competitively inhibit such a monoclonal antibody from binding to *Pseudomonas* Psl.

The disclosure also includes fragments of the polynucleotides as described elsewhere herein. Additionally polynucleotides which encode fusion polynucleotides, Fab fragments, and other derivatives, as described herein, are also provided.

The polynucleotides can be produced or manufactured by any method known in the art. For example, if the nucleotide sequence of the antibody is known, a polynucleotide encoding the antibody can be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an anti-*Pseudomonas* Psl and/or PcrV binding molecule, e.g., antibody or fragment, variant or derivative thereof can be generated from nucleic acid from a suitable source. If a clone containing a nucleic acid encoding a particular antibody is not available, but the sequence of the antibody molecule is known, a nucleic acid encoding the antibody can be chemically synthesized or obtained from a suitable source (e.g., an antibody cDNA library, or a cDNA library generated from, or nucleic acid, preferably poly A+RNA, isolated from, any tissue or cells expressing the antibody or such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

Once the nucleotide sequence and corresponding amino acid sequence of an anti-*Pseudomonas* Psl and/or PcrV binding molecule, e.g., antibody or fragment, variant or derivative thereof is determined, its nucleotide sequence can be manipulated using methods well known in the art for the manipulation of nucleotide sequences, e.g., recombinant DNA techniques, site directed mutagenesis, PCR, etc. (see, for example, the techniques described in Sambrook et al., Molecular Cloning, A Laboratory Manual, 2d Ed., Cold Spring Harbor Laboratory, Cold Spring Harbor, N.Y. (1990) and Ausubel et al., eds., Current Protocols in Molecular Biology, John Wiley & Sons, NY (1998), which are both incorporated by reference herein in their entireties), to generate antibodies having a different amino acid sequence, for example to create amino acid substitutions, deletions, and/or insertions.

A polynucleotide encoding an anti-*Pseudomonas* Psl and/or PcrV binding molecule, e.g., antibody or fragment, variant or derivative thereof can be composed of any polyribonucleotide or polydeoxribonucleotide, which can be unmodified RNA or DNA or modified RNA or DNA. For example, a polynucleotide encoding an anti-*Pseudomonas* Psl and/or PcrV binding molecule, e.g., antibody or fragment, variant or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, a polynucleotide encoding an anti-*Pseudomonas* Psl and/or PcrV binding molecule, e.g., antibody or fragment, variant or derivative thereof can be composed of triple-stranded regions comprising RNA or DNA or both RNA and DNA. A polynucleotide encoding an anti-*Pseudomonas* Psl and/or PcrV binding molecule, e.g., antibody or fragment, variant or derivative thereof can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations can be introduced by standard techniques, such as site-directed mutagenesis and PCR-mediated mutagenesis. Conservative amino acid substitutions are made at one or more non-essential amino acid residues.

VI. Expression of Antibody Polypeptides

As is well known, RNA can be isolated from the original hybridoma cells or from other transformed cells by standard techniques, such as guanidinium isothiocyanate extraction and precipitation followed by centrifugation or chromatography. Where desirable, mRNA can be isolated from total RNA by standard techniques such as chromatography on oligo dT cellulose. Suitable techniques are familiar in the art.

In one embodiment, cDNAs that encode the light and the heavy chains of the anti-*Pseudomonas* Psl and/or PcrV binding molecule, e.g., antibody or fragment, variant or derivative thereof can be made, either simultaneously or separately, using reverse transcriptase and DNA polymerase in accordance with well-known methods. PCR can be initiated by consensus constant region primers or by more specific primers based on the published heavy and light chain DNA and amino acid sequences. As discussed above, PCR also can be used to isolate DNA clones encoding the antibody light and heavy chains. In this case the libraries can be screened by consensus primers or larger homologous probes, such as mouse constant region probes.

DNA, typically plasmid DNA, can be isolated from the cells using techniques known in the art, restriction mapped and sequenced in accordance with standard, well known techniques set forth in detail, e.g., in the foregoing references relating to recombinant DNA techniques. Of course, the DNA can be synthetic according to the present disclosure at any point during the isolation process or subsequent analysis.

Following manipulation of the isolated genetic material to provide an anti-*Pseudomonas* Psl and/or PcrV binding molecule, e.g., antibody or fragment, variant or derivative thereof of the disclosure, the polynucleotides encoding anti-*Pseudomonas* Psl and/or PcrV binding molecules, are typically inserted in an expression vector for introduction into host cells that can be used to produce the desired quantity of anti-*Pseudomonas* Psl and/or PcrV binding molecules.

Recombinant expression of an antibody, or fragment, derivative or analog thereof, e.g., a heavy or light chain of an antibody which binds to a target molecule described herein, e.g., Psl and/or PcrV, requires construction of an expression vector containing a polynucleotide that encodes the antibody. Once a polynucleotide encoding an antibody molecule or a heavy or light chain of an antibody, or portion thereof (containing the heavy or light chain variable domain), of the disclosure has been obtained, the vector for the production of the antibody molecule can be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The disclosure, thus, provides replicable vectors comprising a nucleotide sequence encoding an antibody molecule of the disclosure, or a heavy or light chain thereof, or a heavy or light chain variable domain, operably linked to a promoter. Such vectors can include the nucleotide sequence encoding the constant region of the antibody molecule (see, e.g., PCT Publication WO 86/05807; PCT Publication WO 89/01036; and U.S. Pat. No. 5,122,464) and the variable domain of the antibody can be cloned into such a vector for expression of the entire heavy or light chain.

The term "vector" or "expression vector" is used herein to mean vectors used in accordance with the present disclosure as a vehicle for introducing into and expressing a desired gene in a host cell. As known to those skilled in the art, such vectors can easily be selected from the group consisting of plasmids, phages, viruses and retroviruses. In general, vectors compatible with the instant disclosure will comprise a selection marker, appropriate restriction sites to facilitate cloning of the desired gene and the ability to enter and/or replicate in eukaryotic or prokaryotic cells.

For the purposes of this disclosure, numerous expression vector systems can be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes can be selected by introducing one or more markers which allow selection of transfected host cells. The marker can provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements can also be needed for optimal synthesis of mRNA. These elements can include signal sequences, splice signals, as well as transcriptional promoters, enhancers, and termination signals.

In some embodiments the cloned variable region genes are inserted into an expression vector along with the heavy and light chain constant region genes (e.g., human) synthetic as discussed above. Of course, any expression vector which is capable of eliciting expression in eukaryotic cells can be used in the present disclosure. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, PUB6/V5-His, pVAX1, and pZeoSV2 (available from Invitrogen, San Diego, CA), and plasmid pCI (available from Promega, Madison, WI). In general, screening large numbers of transformed cells for those which express suitably high levels if immunoglobulin heavy and light chains is routine experimentation which can be carried out, for example, by robotic systems.

More generally, once the vector or DNA sequence encoding a monomeric subunit of the anti-*Pseudomonas* Psl and/or PcrV binding molecule, e.g., antibody or fragment, variant or derivative thereof of the disclosure has been prepared, the expression vector can be introduced into an appropriate host cell. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Vectors, Rodriguez and Denhardt, Eds., Butterworths, Boston, Mass., Chapter 24.2, pp. 470-472 (1988). Typically, plasmid introduction into the host is via electroporation. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques and the transfected cells are then cultured by conventional techniques to produce an antibody for use in the methods described herein. Thus, the disclosure includes host cells containing a polynucleotide encoding an anti-*Pseudomonas* Psl and/or PcrV binding molecule, e.g., antibody or fragment, variant or derivative thereof, or a heavy or light chain thereof, operably linked to a heterologous promoter. In some embodiments for the expression of double-chained antibodies, vectors encoding both the heavy and light chains can be co-expressed in the host cell for expression of the entire immunoglobulin molecule, as detailed below.

Certain embodiments include an isolated polynucleotide comprising a nucleic acid which encodes the above-described VH and VL, wherein a binding molecule or antigen-binding fragment thereof expressed by the polynucleotide specifically binds *Pseudomonas* Psl and/or PcrV. In some embodiments the polynucleotide as described encodes an scFv molecule including VH and VL, at least 80%, 85%, 90% 95% or 100% identical to one or more of SEQ ID NO: 65, SEQ ID NO: 66, SEQ ID NO: 67, SEQ ID NO: 68, SEQ ID NO: 69, or SEQ ID NO: 70 as shown in Table 4.

Some embodiments include vectors comprising the above-described polynucleotides. In further embodiments, the polynucleotides are operably associated with a promoter. In additional embodiments, the disclosure provides host cells comprising such vectors. In further embodiments, the disclosure provides vectors where the polynucleotide is operably associated with a promoter, wherein vectors can express a binding molecule which specifically binds *Pseudomonas* Psl and/or PcrV in a suitable host cell.

Also provided is a method of producing a binding molecule or fragment thereof which specifically binds *Pseudomonas* Psl and/or PcrV, comprising culturing a host cell containing a vector comprising the above-described polynucleotides, and recovering said antibody, or fragment thereof. In further embodiments, the disclosure provides an isolated binding molecule or fragment thereof produced by the above-described method.

As used herein, "host cells" refers to cells which harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" can mean either from spun down whole cells, or from the cell culture containing both the medium and the suspended cells.

A variety of host-expression vector systems can be utilized to express antibody molecules for use in the methods described herein. Such host-expression systems represent vehicles by which the coding sequences of interest can be produced and subsequently purified, but also represent cells which can, when transformed or transfected with the appropriate nucleotide coding sequences, express an antibody molecule of the disclosure in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Bacterial cells such as *Escherichia coli*, or eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

The host cell line used for protein expression is often of mammalian origin; those skilled in the art are credited with ability to determine particular host cell lines which are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, 293, WI38, R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature.

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used.

For long-term, high-yield production of recombinant proteins, stable expression is preferred. For example, cell lines which stably express the antibody molecule can be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which stably express the antibody molecule.

A number of selection systems can be used, including but not limited to the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:202 (1992)), and adenine phosphoribosyltransferase (Lowy et al., *Cell* 22:817 1980) genes can be employed in tk-, hgprt- or aprt-cells, respectively. Also, antimetabolite resistance can be used as the basis of selection for the following genes: dhfr, which confers resistance to methotrexate (Wigler et al., *Natl. Acad. Sci. USA* 77:357 (1980); O'Hare et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 Clinical Pharmacy 12:488-505; Wu and Wu, *Biotherapy* 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); *TIB TECH* 11 (5): 155-215 (May 1993); and hygro, which confers resistance to hygromycin (Santerre et al., *Gene* 30:147 (1984). Methods commonly known in the art of recombinant DNA technology which can be used are described in Ausubel et al. (eds.), *Current Protocols in Molecular Biology*, John Wiley & Sons, NY (1993); Kriegler, Gene Transfer and Expression, *A Laboratory Manual*, Stockton Press, NY (1990); and in Chapters 12 and 13, Dracopoli et al. (eds), *Current Protocols in Human Genetics*, John Wiley & Sons, NY (1994); Colberre-Garapin et al., *J. Mol. Biol.* 150:1 (1981), which are incorporated by reference herein in their entireties.

The expression levels of an antibody molecule can be increased by vector amplification (for a review, see Bebbington and Hentschel, *The use of vectors based on gene amplification for the expression of cloned genes in mammalian cells in DNA cloning*, Academic Press, New York, Vol. 3. (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-) affinity chromatography, e.g., after preferential biosynthesis of a synthetic hinge region polypeptide or prior to or subsequent to the HIC chromatography step described herein.

Constructs encoding anti-*Pseudomonas* Psl and/or PcrV binding molecules, e.g., antibodies or fragments, variants or derivatives thereof, as disclosed herein can also be expressed non-mammalian cells such as bacteria or yeast or plant cells. Bacteria which readily take up nucleic acids include members of the enterobacteriaceae, such as strains of *Escherichia coli* or *Salmonella*; Bacillaceae, such as *Bacillus subtilis*; Pneumococcus; *Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies (WO02/096948A2).

In bacterial systems, a number of expression vectors can be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified can be desirable. Such vectors include, but are not limited, to the *E. coli* expression vector pUR278 (Ruther et al., *EMBO J.* 2:1791 (1983)), in which the antibody coding sequence can be ligated individually into the vector in frame with the lacZ coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)); and the like. pGEX vectors can also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes can also be used. *Saccharomyces cerevisiae*, or common baker's yeast, is the most commonly used among eukaryotic microorganisms although a number of other strains are commonly available, e.g., *Pichia pastoris*.

For expression in *Saccharomyces*, the plasmid YRp7, for example, (Stinchcomb et al., Nature 282:39 (1979); Kingsman et al., *Gene* 7:141 (1979); Tschemper et al., *Gene* 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, *Genetics* 85:12 (1977)). The presence of the trpl lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

Once the anti-*Pseudomonas* Psl and/or PcrV binding molecule, e.g., antibody or fragment, variant or derivative thereof, as disclosed herein has been recombinantly expressed, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Another method for increasing the affinity of antibodies of the disclosure is disclosed in US 2002 0123057 A1.

VII. Identification of Serotype-Indifferent Binding Molecules

The disclosure encompasses a target indifferent whole-cell approach to identify serotype independent therapeutic binding molecules e.g., antibodies or fragments thereof with superior or desired therapeutic activities. The method can be utilized to identify binding molecules which can antagonize, neutralize, clear, or block an undesired activity of an infectious agent, e.g., a bacterial pathogen. As is known in the art, many infectious agents exhibit significant variation in their dominant surface antigens, allowing them to evade immune surveillance. The identification method described herein can identify binding molecules which target antigens which are shared among many different *Pseudomonas* species or other Gram-negative pathogens, thus providing a therapeutic agent which can target multiple pathogens from multiple species. For example, the method was utilized to identify a series of binding molecules which bind to the surface of *P. aeruginosa* in a serotype-independent manner, and when bound to bacterial pathogens, mediate, promote, or enhance opsonophagocytic (OPK) activity against bacterial cells such as bacterial pathogens, e.g. opportunistic *Pseudomonas* species (e.g., *Pseudomonas aeruginosa*, *Pseudomonas fluorescens*, *Pseudomonas putida*, and *Pseudomonas alcaligenes*) and/or inhibit the attachment of such bacterial cells to epithelial cells.

Certain embodiments disclose a method of identifying serotype-indifferent binding molecules comprising: (a) preparing naïve and/or convalescent antibody libraries in phage, (b) removing serotype-specific antibodies from the library by depletion panning, (c) screening the library for antibodies that specifically bind to whole cells independent of serotype, and (d) screening of the resulting antibodies for desired functional properties.

Certain embodiments provide a whole-cell phenotypic screening approach as disclosed herein with antibody phage libraries derived from either naive or *P. aeruginosa* infected convalescing patients. Using a panning strategy that initially selected against serotype-specific reactivity, different clones that bound *P. aeruginosa* whole cells were isolated. Selected clones were converted to human IgG1 antibodies and were confirmed to react with *P. aeruginosa* clinical isolates regardless of serotype classification or site of tissue isolation (See Examples). Functional activity screens described herein indicated that the antibodies were effective in preventing *P. aeruginosa* attachment to mammalian cells and mediated opsonophagocytic (OPK) killing in a concentration-dependent and serotype-independent manner.

In further embodiments, the above-described binding molecules or fragments thereof, antibodies or fragments thereof, or compositions, bind to two or more, three or more, four or more, or five or more different *P. aeruginosa* serotypes, or to at least 80%, at least 85%, at least 90% or at least 95% of *P. aeruginosa* strains isolated from infected patients. In further embodiments, the *P. aeruginosa* strains are isolated from one or more of lung, sputum, eye, pus, feces, urine, sinus, a wound, skin, blood, bone, or knee fluid.

VIII. Pharmaceutical Compositions Comprising Anti-*Pseudomonas* Psl and/or PCRV Binding Molecules The pharmaceutical compositions used in this disclosure comprise pharmaceutically acceptable carriers well known to those of ordinary skill in the art. Preparations for parenteral administration include sterile aqueous or non-aqueous solutions, suspensions, and emulsions. Certain pharmaceutical compositions as disclosed herein can be orally administered in an acceptable dosage form including, e.g., capsules, tablets, aqueous suspensions or solutions. Certain pharmaceutical compositions also can be administered by nasal aerosol or inhalation. Preservatives and other additives can also be present such as for example, antimicrobials, antioxidants, chelating agents, and inert gases and the like. Suitable formulations for use in the therapeutic methods disclosed herein are described in Remington's Pharmaceutical Sciences, Mack Publishing Co., 16th ed. (1980).

The amount of an anti-*Pseudomonas* Psl and/or PcrV binding molecule, e.g., antibody or fragment, variant or derivative thereof, that can be combined with the carrier materials to produce a single dosage form will vary depending upon the host treated and the particular mode of administration. Dosage regimens also can be adjusted to provide the optimum desired response (e.g., a therapeutic or prophylactic response). The compositions can also comprise the anti-*Pseudomonas* Psl and/or PcrV binding molecules, e.g., antibodies or fragments, variants or derivatives thereof dispersed in a biocompatible carrier material that functions as a suitable delivery or support system for the compounds.

IX. Treatment Methods Using Therapeutic Binding Molecules

Methods of preparing and administering anti-*Pseudomonas* Psl and/or PcrV binding molecules, e.g., an antibody or fragment, variant or derivative thereof, as disclosed herein to a subject in need thereof are well known to or are readily determined by those skilled in the art. The route of administration of the anti-*Pseudomonas* Psl and/or PcrV binding molecules, e.g., antibody or fragment, variant or derivative thereof, can be, for example, oral, parenteral, by inhalation or topical. The term parenteral as used herein includes, e.g., intravenous, intraarterial, intraperitoneal, intramuscular, or subcutaneous administration. A suitable form for administration would be a solution for injection, in particular for intravenous or intraarterial injection or drip. However, in other methods compatible with the teachings herein, an anti-*Pseudomonas* Psl and/or PcrV binding molecules, e.g., antibody or fragment, variant or derivative thereof, as disclosed herein can be delivered directly to the site of the adverse cellular population e.g., infection thereby increasing the exposure of the diseased tissue to the therapeutic agent. For example, an anti-*Pseudomonas* Psl and/or PcrV binding molecule can be directly administered to ocular tissue, burn injury, or lung tissue.

Anti-*Pseudomonas* Psl and/or PcrV binding molecules, e.g., antibodies or fragments, variants or derivatives thereof, as disclosed herein can be administered in a pharmaceutically effective amount for the in vivo treatment of *Pseudomonas* infection. In this regard, it will be appreciated that the disclosed binding molecules will be formulated so as to facilitate administration and promote stability of the active agent. For the purposes of the instant application, a pharmaceutically effective amount shall be held to mean an amount sufficient to achieve effective binding to a target and to achieve a benefit, e.g., treat, ameliorate, lessen, clear, or prevent *Pseudomonas* infection.

Some embodiments are directed to a method of preventing or treating a *Pseudomonas* infection in a subject in need thereof, comprising administering to the subject an effective amount of the binding molecule or fragment thereof, the antibody or fragment thereof, the composition, the polynucleotide, the vector, or the host cell described herein. In further embodiments, the *Pseudomonas* infection is a *P. aeruginosa* infection. In some embodiments, the subject is a human. In certain embodiments, the infection is an ocular infection, a lung infection, a burn infection, a wound infection, a skin infection, a blood infection, a bone infection, or a combination of two or more of said infections. In further embodiments, the subject suffers from acute pneumonia, burn injury, corneal infection, cystic fibrosis, or a combination thereof.

Certain embodiments are directed to a method of blocking or preventing attachment of *P. aeruginosa* to epithelial cells comprising contacting a mixture of epithelial cells and *P. aeruginosa* with the binding molecule or fragment thereof, the antibody or fragment thereof, the composition, the polynucleotide, the vector, or the host cell described herein.

Also disclosed is a method of enhancing OPK of *P. aeruginosa* comprising contacting a mixture of phagocytic cells and *P. aeruginosa* with the binding molecule or fragment thereof, the antibody or fragment thereof, the composition, the polynucleotide, the vector, or the host cell described herein. In further embodiments, the phagocytic cells are differentiated HL-60 cells or human polymorphonuclear leukocytes (PMNs).

In keeping with the scope of the disclosure, anti-*Pseudomonas* Psl and/or PcrV binding molecules, e.g., antibodies or fragments, variants or derivatives thereof, can be administered to a human or other animal in accordance with the aforementioned methods of treatment in an amount sufficient to produce a therapeutic effect. The anti-*Pseudomonas* Psl and/or PcrV binding molecules, e.g., antibodies or fragments, variants or derivatives thereof, disclosed herein can be administered to such human or other animal in a conventional dosage form prepared by combining the antibody of the disclosure with a conventional pharmaceutically acceptable carrier or diluent according to known techniques.

Effective doses of the compositions of the present disclosure, for treatment of *Pseudomonas* infection vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages can be titrated using routine methods known to those of skill in the art to optimize safety and efficacy.

Anti-*Pseudomonas* Psl and/or PcrV binding molecules, e.g., antibodies or fragments, variants or derivatives thereof can be administered multiple occasions at various frequencies depending on various factors known to those of skill in the art. Alternatively, anti-*Pseudomonas* Psl and/or PcrV binding molecules, e.g., antibodies or fragments, variants or derivatives thereof can be administered as a sustained release formulation, in which case less frequent administration is required. Dosage and frequency vary depending on the half-life of the antibody in the patient.

The compositions of the disclosure can be administered by any suitable method, e.g., parenterally, intraventricularly, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

X. Synergy

Chou and Talalay (Adv. Enzyme Regul., 22:27-55 (1984)) developed a mathematical method to describe the experimental findings of combined drug effects in a qualitative and quantitative manner. For mutually exclusive drugs, they showed that the generalized isobol equation applies for any degree of effect (see page 52 in Chou and Talalay). An isobol or isobologram is the graphic representation of all dose combinations of two drugs that have the same degree of effect. In isobolograms, a straight line indicates additive effects, a concave curve (curve below the straight line) represents synergistic effects, and a convex curve (curve above the straight line) represents antagonistic effects. These curves also show that a combination of two mutually exclusive drugs will show the same type of effect over the whole concentration range, either the combination is additive, synergistic, or antagonistic. Most drug combinations show an additive effect. In some instances however, the combinations show less or more than an additive effect. These combinations are called antagonistic or synergistic, respectively. A combination manifests therapeutic synergy if it is therapeutically superior to one or other of the constituents used at its optimum dose. See, T. H. Corbett et al., Cancer Treatment Reports, 66, 1187 (1982). Tallarida R J (J Pharmacol Exp Ther. 2001 September; 298 (3): 865-72) also notes "Two drugs that produce overtly similar effects will sometimes produce exaggerated or diminished effects when used concurrently. A quantitative assessment is necessary to distinguish these cases from simply additive action."

A synergistic effect can be measured using the combination index (CI) method of Chou and Talalay (see Chang et al., Cancer Res. 45:2434-2439, (1985)) which is based on the median-effect principle. This method calculates the degree of synergy, additivity, or antagonism between two drugs at various levels of cytotoxicity. Where the CI value is less than 1, there is synergy between the two drugs. Where the CI value is 1, there is an additive effect, but no synergistic effect. CI values greater than 1 indicate antagonism. The smaller the CI value, the greater the synergistic effect. In another embodiment, a synergistic effect is determined by using the fractional inhibitory concentration (FIC). This fractional value is determined by expressing the IC50 of a drug acting in combination, as a function of the IC50 of the drug acting alone. For two interacting drugs, the sum of the FIC value for each drug represents the measure of synergistic interaction. Where the FIC is less than 1, there is synergy between the two drugs. An FIC value of 1 indicates an additive effect. The smaller the FIC value, the greater the synergistic interaction.

In some embodiments, a synergistic effect is obtained in *Pseudomonas* treatment wherein one or more of the binding agents are administered in a "low dose" (i.e., using a dose or doses which would be considered non-therapeutic if administered alone), wherein the administration of the low dose binding agent in combination with other binding agents (administered at either a low or therapeutic dose) results in a synergistic effect which exceeds the additive effects that would otherwise result from individual administration of the binding agent alone. In some embodiments, the synergistic effect is achieved via administration of one or more of the binding agents administered in a "low dose" wherein the low dose is provided to reduce or avoid toxicity or other undesirable side effects.

XI. Immunoassays

Anti-*Pseudomonas* Psl and/or PcrV binding molecules, e.g., antibodies or fragments, variants or derivatives thereof can be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, *Current Protocols in Molecular Biology*, John Wiley & Sons, Inc., New York, Vol. 1 (1994), which is incorporated by reference herein in its entirety). Exemplary immunoassays are described briefly below (but are not intended by way of limitation).

There are a variety of methods available for measuring the affinity of an antibody-antigen interaction, but relatively few for determining rate constants. Most of the methods rely on either labeling antibody or antigen, which inevitably complicates routine measurements and introduces uncertainties in the measured quantities. Antibody affinity can be measured by a number of methods, including OCTET®, BIACORE®, ELISA, and FACS.

The OCTET® system uses biosensors in a 96-well plate format to report kinetic analysis. Protein binding and dissociation events can be monitored by measuring the binding of one protein in solution to a second protein immobilized on the FortéBio biosensor. In the case of measuring binding of anti-Psl or PcrV antibodies to Psl or PcrV, the Psl or PcrV is immobilized onto OCTET® tips followed by analysis of binding of the antibody, which is in solution. Association and disassociation of antibody to immobilized Psl or PcrV is then detected by the instrument sensor. The data is then collected and exported to GraphPad Prism for affinity curve fitting.

Surface plasmon resonance (SPR) as performed on BIACORE® offers a number of advantages over conventional methods of measuring the affinity of antibody-antigen interactions: (i) no requirement to label either antibody or antigen; (ii) antibodies do not need to be purified in advance, cell culture supernatant can be used directly; (iii) real-time measurements, allowing rapid semi-quantitative comparison of different monoclonal antibody interactions, are enabled and are sufficient for many evaluation purposes; (iv) biospecific surface can be regenerated so that a series of different monoclonal antibodies can easily be compared under identical conditions; (v) analytical procedures are fully automated, and extensive series of measurements can be performed without user intervention. BIAapplications Handbook, version AB (reprinted 1998), BIACORE® code No. BR-1001-86; BIAtechnology Handbook, version AB (reprinted 1998), BIACORE® code No. BR-1001-84.

SPR based binding studies require that one member of a binding pair be immobilized on a sensor surface. The binding partner immobilized is referred to as the ligand. The binding partner in solution is referred to as the analyte. In some cases, the ligand is attached indirectly to the surface through binding to another immobilized molecule, which is referred as the capturing molecule. SPR response reflects a change in mass concentration at the detector surface as analytes bind or dissociate.

Based on SPR, real-time BIACORE® measurements monitor interactions directly as they happen. The technique is well suited to determination of kinetic parameters. Comparative affinity ranking is extremely simple to perform, and both kinetic and affinity constants can be derived from the sensorgram data.

When analyte is injected in a discrete pulse across a ligand surface, the resulting sensorgram can be divided into three essential phases: (i) Association of analyte with ligand during sample injection; (ii) Equilibrium or steady state during sample injection, where the rate of analyte binding is balanced by dissociation from the complex; (iii) Dissociation of analyte from the surface during buffer flow.

The association and dissociation phases provide information on the kinetics of analyte-ligand interaction ($k_a$ and $k_d$, the rates of complex formation and dissociation, $k_d/k_a=K_D$). The equilibrium phase provides information on the affinity of the analyte-ligand interaction ($K_D$).

BIAevaluation software provides comprehensive facilities for curve fitting using both numerical integration and global fitting algorithms. With suitable analysis of the data, separate rate and affinity constants for interaction can be obtained from simple BIACORE® investigations. The range of affinities measurable by this technique is very broad ranging from mM to pM.

Epitope specificity is an important characteristic of a monoclonal antibody. Epitope mapping with BIACORE®, in contrast to conventional techniques using radioimmunoassay, ELISA or other surface adsorption methods, does not require labeling or purified antibodies, and allows multi-site specificity tests using a sequence of several monoclonal antibodies. Additionally, large numbers of analyses can be processed automatically.

Pair-wise binding experiments test the ability of two MAbs to bind simultaneously to the same antigen. MAbs directed against separate epitopes will bind independently, whereas MAbs directed against identical or closely related epitopes will interfere with each other's binding. These binding experiments with BIACORE® are straightforward to carry out.

For example, one can use a capture molecule to bind the first Mab, followed by addition of antigen and second MAb sequentially. The sensorgrams will reveal: 1. how much of the antigen binds to first Mab, 2. to what extent the second MAb binds to the surface-attached antigen, 3. if the second MAb does not bind, whether reversing the order of the pair-wise test alters the results.

Peptide inhibition is another technique used for epitope mapping. This method can complement pair-wise antibody binding studies, and can relate functional epitopes to structural features when the primary sequence of the antigen is known. Peptides or antigen fragments are tested for inhibition of binding of different MAbs to immobilized antigen. Peptides which interfere with binding of a given MAb are assumed to be structurally related to the epitope defined by that MAb.

XII. Administration

A composition comprising either an anti-Psl binding domain or anti-PcrV binding domain, or a composition comprising both an anti-Psl and anti-PcrV binding domain are administered in such a way that they provide a synergistic effect in the treatment of *Pseudomonas* in a patient. Administration can be by any suitable means provided that the administration provides the desired therapeutic effect, i.e., synergism. In certain embodiments, the antibodies are administered during the same cycle of therapy, e.g., during one cycle of therapy during a prescribed time period, both of the antibodies are administered to the subject. In some embodiments, administration of the antibodies can be during sequential administration in separate therapy cycles, e.g., the first therapy cycle involving administration of an anti-Psl antibody and the second therapy cycle involving administration of an anti-PcrV antibody. The dosage of the binding domains administered to a patient will also depend on frequency of administration and can be readily determined by one of ordinary skill in the art.

In other embodiments the binding domains are administered more than once during a treatment cycle. For example, in some embodiments, the binding domains are administered weekly for three consecutive weeks in a three or four week treatment cycle.

Administration of the composition comprising one or more of the binding domains can be on the same or different days provided that administration provides the desired therapeutic effect.

It will be readily apparent to those skilled in the art that other doses or frequencies of administration that provide the desired therapeutic effect are suitable for use in the present invention.

XII. Kits

In yet other embodiments, the present invention provides kits that can be used to perform the methods described herein. In certain embodiments, a kit comprises a binding molecule disclosed herein in one or more containers. One skilled in the art will readily recognize that the disclosed binding domains, polypeptides and antibodies of the present invention can be readily incorporated into one of the established kit formats which are well known in the art.

The practice of the disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); *Molecular Cloning: A Laboratory Manual*, Sambrook et al., ed., Cold Springs Harbor Laboratory, New York (1992), *DNA Cloning*, D. N. Glover ed., Volumes I and II (1985); *Oligonucleotide Synthesis, M. J. Gait ed.*, (1984); Mullis et al. U.S. Pat. No. 4,683,195; *Nucleic Acid Hybridization*, B. D. Hames & S. J. Higgins eds. (1984); *Transcription And Translation*, B. D. Hames & S. J. Higgins eds. (1984); *Culture Of Animal Cells*, R. I. Freshney, Alan R. Liss, Inc., (1987); *Immobilized Cells And Enzymes*, IRL Press, (1986); B. Perbal, *A Practical Guide To Molecular Cloning* (1984); the treatise, *Methods In Enzymology*, Academic Press, Inc., N.Y.; *Gene Transfer Vectors For Mammalian Cells*, J. H. Miller and M. P. Calos eds., Cold Spring Harbor Laboratory (1987); *Methods In Enzymology*, Vols. 154 and 155 (Wu et al. eds.); *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds., (1986); *Manipulating the Mouse Embryo*, Cold Spring Harbor Laboratory Press, Cold Spring Harbor, N.Y., (1986); and in Ausubel et al., *Current Protocols in Molecular Biology*, John Wiley and Sons, Baltimore, Maryland (1989).

General principles of antibody engineering are set forth in Antibody Engineering, 2nd edition, C. A. K. Borrebaeck, Ed., Oxford Univ. Press (1995). General principles of protein engineering are set forth in *Protein Engineering, A Practical Approach*, Rickwood, D., et al., Eds., IRL Press at Oxford Univ. Press, Oxford, Eng. (1995). General principles of antibodies and antibody-hapten binding are set forth in: Nisonoff, A., *Molecular Immunology*, 2nd ed., Sinauer Associates, Sunderland, MA (1984); and Steward, M. W., *Antibodies, Their Structure and Function*, Chapman and Hall, New York, NY (1984). Additionally, standard methods in immunology known in the art and not specifically described are generally followed as in Current Protocols in Immunology, John Wiley & Sons, New York; Stites et al. (eds), *Basic and Clinical-Immunology* (8th ed.), Appleton & Lange, Norwalk, CT (1994) and Mishell and Shiigi (eds), *Selected Methods in Cellular Immunology*, W. H. Freeman and Co., New York (1980).

Standard reference works setting forth general principles of immunology include *Current Protocols in Immunology*, John Wiley & Sons, New York; Klein, J., Immunology: *The Science of Self-Nonself Discrimination*, John Wiley & Sons, New York (1982); Kennett, R., et al., eds., *Monoclonal Antibodies, Hybridoma: A New Dimension in Biological Analyses*, Plenum Press, New York (1980); Campbell, A., "Monoclonal Antibody Technology" in Burden, R., et al., eds., *Laboratory Techniques in Biochemistry and Molecular Biology*, Vol. 13, Elsevere, Amsterdam (1984), *Kuby Immunnology* $4^{th}$ ed. Ed. Richard A. Goldsby, *Thomas J. Kindt and Barbara A. Osborne, H. Freemand & Co*. (2000); Roitt, I., Brostoff, J. and Male D., *Immunology* $6^{th}$ ed. London: Mosby (2001); Abbas A., Abul, A. and Lichtman, A., *Cellular and Molecular Immunology* Ed. 5, Elsevier Health Sciences Division (2005); Kontermann and Dubel, *Antibody Engineering*, Springer Verlan (2001); Sambrook and Russell, *Molecular Cloning: A Laboratory Manual*. Cold Spring Harbor Press (2001); Lewin, *Genes VIII*, Prentice Hall (2003); Harlow and Lane, *Antibodies: A Laboratory Manual*, Cold Spring Harbor Press (1988); Dieffenbach and Dveksler, *PCR Primer* Cold Spring Harbor Press (2003).

EXAMPLES

Example 1: Construction and Screening of Human Antibody Phage Display Libraries This example describes a target indifferent whole cell panning approach with human antibody phage libraries derived from both naive and *P. aeruginosa* infected convalescing patients to identify novel protective antigens against *Pseudomonas* infection (FIG. 1A). Assays included in the in vitro functional screens included opsonophagocytosis (OPK) killing assays and cell attachment assays using the epithelial cell line A549. The lead candidates, based on superior in vitro activity, were tested in *P. aeruginosa* acute pneumonia, keratitis, and burn infection models.

Figure 1A:
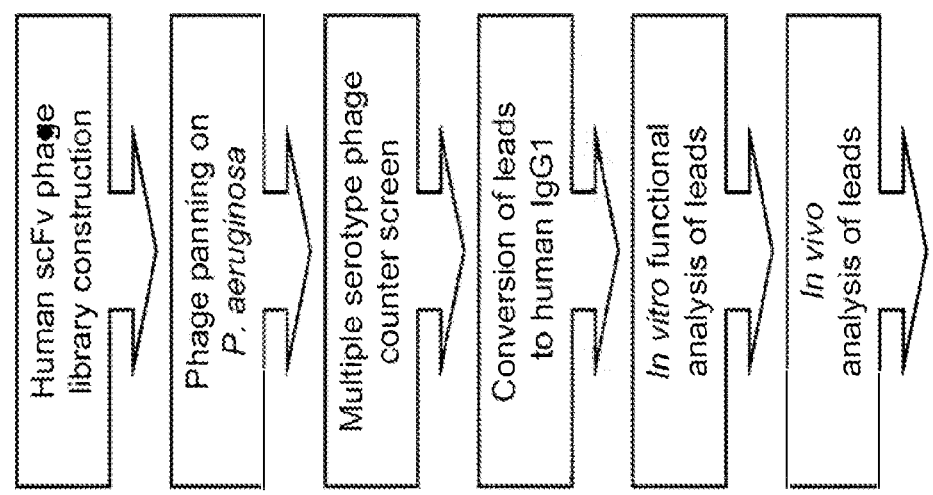
Figure 1F:
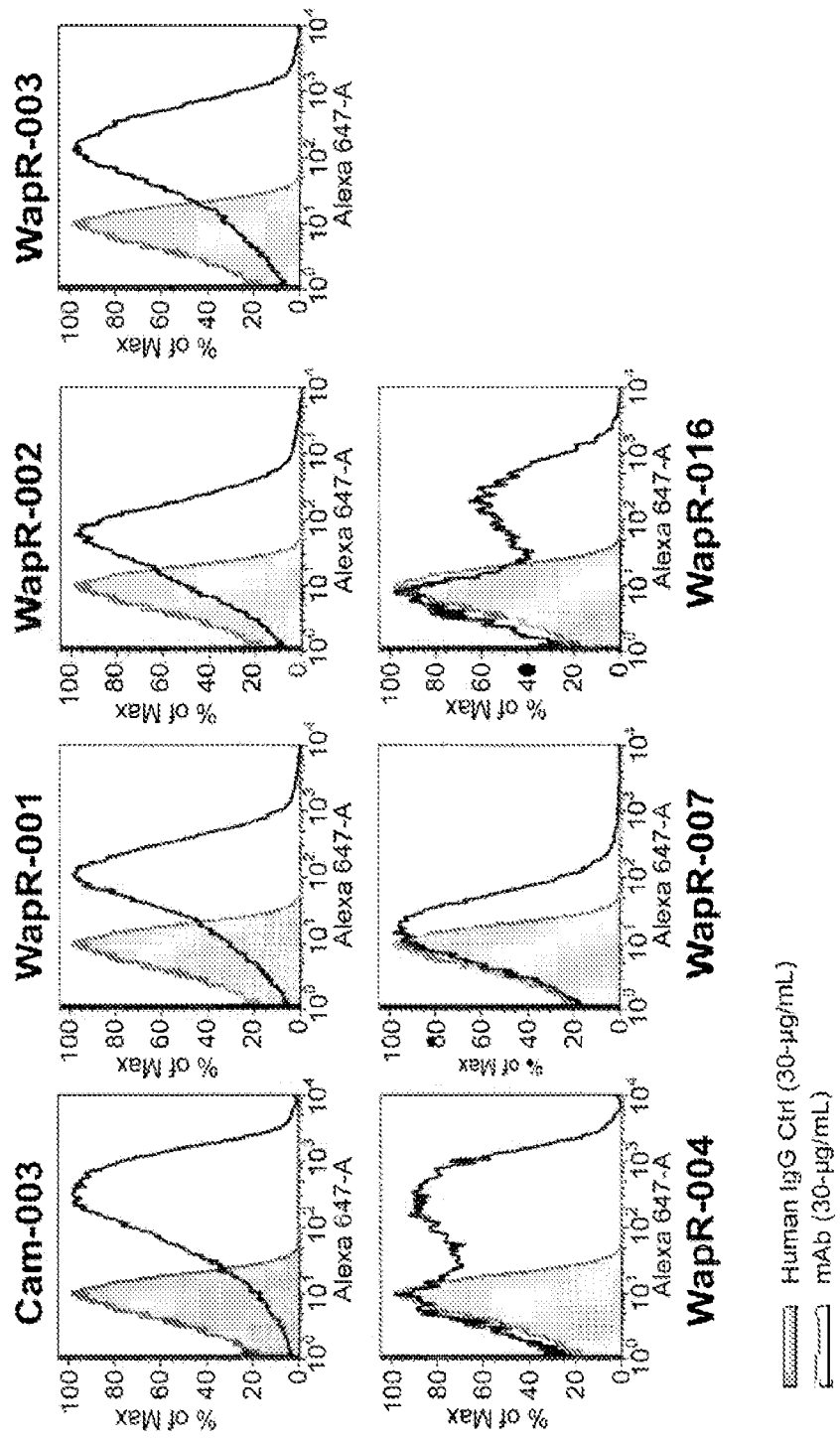

FIG. 1B shows construction of patient antibody phage display library. Whole blood was pooled from 6 recovering patients 7-10 days post diagnosis followed by RNA extraction and phage library construction as previously described (Vaughan, T. J., et al., *Nat Biotechnol* 14, 309-314 (1996); Wrammert, J., et al., *Nature* 453, 667-671 (2008)). FIG. 1C shows that the final cloned scFv library contained $5.4 \times 10^8$ transformants and sequencing revealed that 79% of scFv genes were full-length and in frame. The VH CDR3 loops, often important for determining epitope specificity, were 84% diverse at the amino acid level prior to library selection.

In addition to the patient library, a naïve human scFv phage display library containing up to $1 \times 10^{11}$ binding members (Lloyd, C., et al., *Protein Eng Des Sel* 22, 159-168 (2009)) was used for antibody isolation (Vaughan, T. J., et al., *Nat Biotechnol* 14, 309-314 (1996)). Heat killed *P. aeruginosa* ($1 \times 10^9$) was immobilized in IMMUNO™ Tubes (Nunc; MAXISORP™) followed for phage display selections as described (Vaughan, T. J., et al., *Nat Biotechnol* 14, 309-314 (1996)) with the exception of triethanolamine (100 nM) being used as the elution buffer. For selection on *P. aeruginosa* in suspension, heat killed cells were blocked followed by addition of blocked phage to cells. After washing, eluted phage was used to infect *E. coli* cells as described (Vaughan, 1996). Rescue of phage from *E. coli* and binding to heat-killed *P. aeruginosa* by ELISA was performed as described (Vaughan, 1996).

Following development and validation of the whole-cell affinity selection methodology, both the new convalescing patient library and a previously constructed naive library (Vaughan, T. J., et al., *Nat Biotechnol* 14, 309-314 (1996)) underwent affinity selection on suspensions of *P. aeruginosa* strain 3064 possessing a complete O-antigen as well as an isogenic wapR mutant strain which lacked surface expression of O-antigen. FIG. 1D shows that output titers from successive patient library selections were found to increase at a greater rate for the patient library than for the naïve library ($1 \times 10^7$ vs $3 \times 10^5$ at round 3, respectively). In addition, duplication of VH CDR3 loop sequences in the libraries (a measure of clonal enrichment during selection), was also found to be higher in the patient library, reaching 88-92%, compared to 15-25% in the naïve library at round 3 (FIG. 1D). Individual scFv phage from affinity selections were next screened by ELISA for reactivity to *P. aeruginosa* heterologous serotype strains (FIG. 1E). ELISA plates (Nunc; MAXISORP™) were coated with *P. aeruginosa* strains from overnight cultures as described (DiGiandomenico, A., et al., *Infect Immun* 72, 7012-7021 (2004)). Diluted antibodies were added to blocked plates for 1 hour, washed, and treated with HRP-conjugated anti-human secondary antibodies for 1 hour followed by development and analysis as described (Ulbrandt, N. D., et al., *J Virol* 80, 7799-7806 (2006)). The dominant species of phage obtained from whole cell selections with both libraries yielded serotype specific reactivity (data not shown). Clones exhibiting serotype independent binding in the absence of nonspecific binding to *E. coli* or bovine serum albumin were selected for further evaluation.

For IgG expression, the VH and VL chains of selected antibodies were cloned into human IgG1 expression vectors, co-expressed in HEK293 cells, and purified by protein A affinity chromatography as described (Persic, L., et al., *Gene* 187, 9-18 (1997)). Human IgG1 antibodies made with the variable regions from these selected serotype independent phage were confirmed for *P. aeruginosa* specificity and prioritized for subsequent analysis by whole cell binding to dominant clinically relevant serotypes by FACS analysis (FIG. 1F), since this method is more stringent than ELISA. For the flow cytometry based binding assays mid-log phase *P. aeruginosa* strains were concentrated in PBS to an $OD_{650}$ of 2.0. After incubation of antibody (10 μg/mL) and bacteria ($\sim 1 \times 10^7$ cells) for 1 hr at 4° C. with shaking, washed cells were incubated with an ALEXA FLUOR 647® goat anti-human IgG antibody (Invitrogen, Carlsbad, CA) for 0.5 hr at 4° C. Washed cells were stained with BACLIGHT™ green bacterial stain as recommended (Invitrogen, Carlsbad, CA). Samples were run on a LSR II flow cytometer (BD Biosciences) and analyzed using BD FacsDiva (v. 6.1.3) and FlowJo (v. 9.2; TreeStar). Antibodies exhibiting binding by FACS were further prioritized for functional activity testing in an opsonophagocytosis killing (OPK) assay.

Example 2: Evaluation of mAbs Promoting OPK of *P. aeruginosa*

Figure 2B:
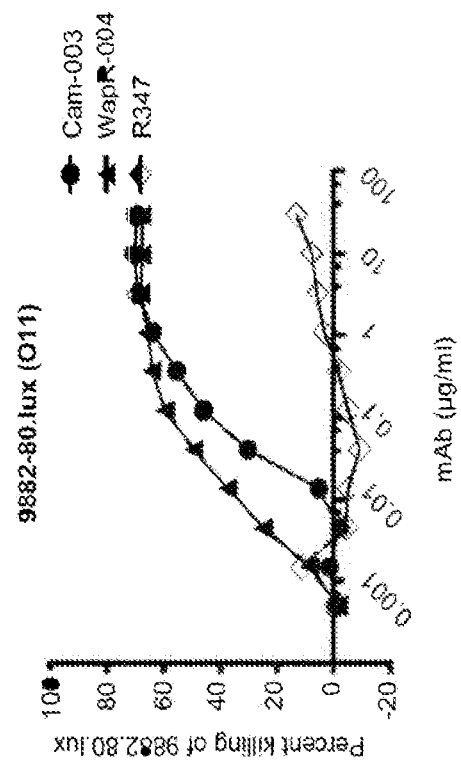
Figure 2A:
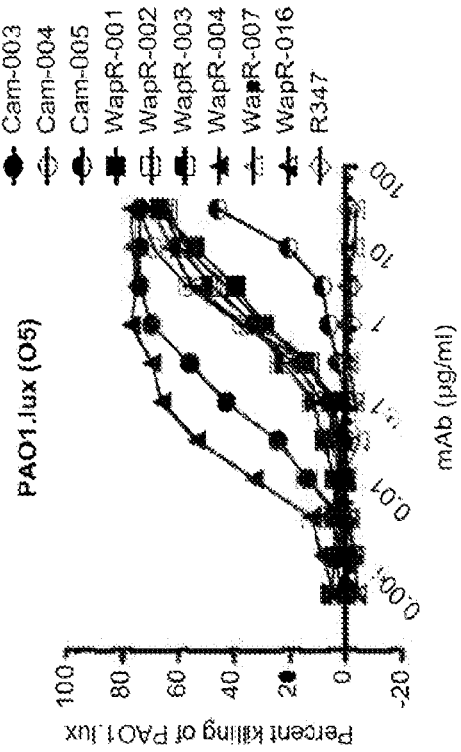

This example describes the evaluation of prioritized human IgG1 antibodies to promote OPK of *P. aeruginosa*. FIG. 2A shows that with the exception of WapR-007 and the negative control antibody R347, all antibodies mediated concentration dependent killing of luminescent *P. aeruginosa* serogroup O5 strain (PAO1.lux). WapR-004 and Cam-003 exhibited superior OPK activity. OPK assays were performed as described in (DiGiandomenico, A., et al., *Infect Immun* 72, 7012-7021 (2004)), with modifications. Briefly, assays were performed in 96-well plates using 0.025 ml of each OPK component; *P. aeruginosa* strains; diluted baby rabbit serum; differentiated HL-60 cells; and monoclonal antibody. In some OPK assays, luminescent *P. aeruginosa* strains, which were constructed as described (Choi, K. H., et al., *Nat Methods* 2, 443-448 (2005))., were used. Luminescent OPK assays were performed as described above but with determination of relative luciferase units (RLUs) using a Perkin Elmer ENVISION Multilabel plate reader (Perkin Elmer).

The ability of the WapR-004 and Cam-003 antibodies to mediate OPK activity against another clinically relevant O-antigen serotype strain, 9882-80.lux, was evaluated. FIG. 2B shows that enhanced WapR-004 and Cam-003 OPK activity extends to strain 9882-80 (O11).

In addition, this example describes the evaluation of WapR-004 (W4) mutants in scFv-Fc format to promote OPK of *P. aeruginosa*. One mutant, Wap-004RAD (W4-RAD), was specifically created through site-directed mutagenesis to remove an RGD motif in VH. Other W4 mutants were prepared as follows. Nested PCR was performed as described (Roux, K. H., *PCR Methods Appl* 4, S185-194 (1995)), to amplify W4 variants (derived from somatic hypermutation) from the scFv library derived from the convalescing *P. aeruginosa* infected patients, for analysis. This is the library from which WapR-004 was derived. W4 variant fragments were subcloned and sequenced using standard procedures known in the art. W4 mutant light chains (LC) were recombined with the WapR-004 heavy chain (HC) to produce W4 mutants in scFv-Fc format. In addition WapR-004 RAD heavy chain (HC) mutants were recombined with parent LCs of M7 and M8 in the scFv-Fc format. Constructs were prepared using standard procedures known in the art. FIGS. 11(A-M) show that with the exception of the negative control antibody R347, all WapR-004 (W4) mutants mediated concentration dependent killing of luminescent *P. aeruginosa* serogroup O5 strain (PAO1.lux).

The WapR-004-RAD variable region was germ-lined to reduce potential immunogenicity, producing WapR-004-germline ("WapR-004-GL"), and was lead optimized via site-directed mutagenesis. Clones with improved affinity for Psl were selected in competition-based screens. Top clones were ranked by affinity improvement and analyzed in an in vitro functional assay. The 14 lead optimized clones are: Psl0096, Psl0170, Psl0225, Psl0304, Psl0337, Ps1348, Psl0567, Psl0573, Psl0574, Psl0582, Psl0584, Psl0585, Psl0588 and Psl0589.

Figure 3A:
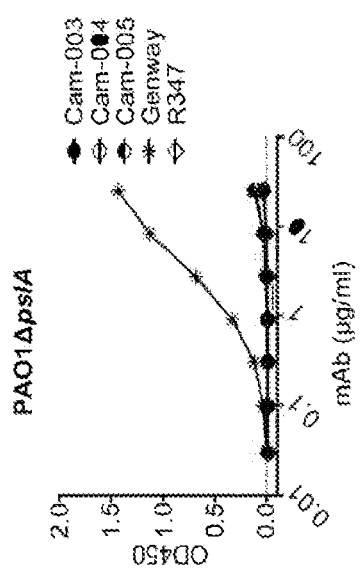
Figure 3B:
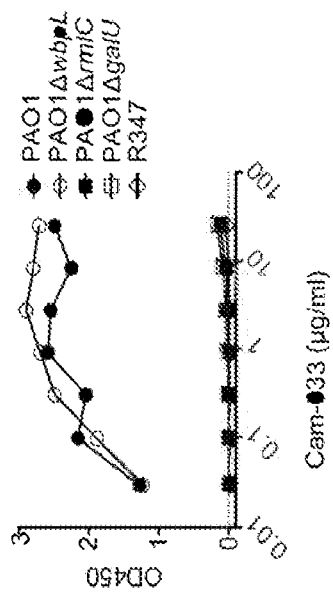
Figure 3C:
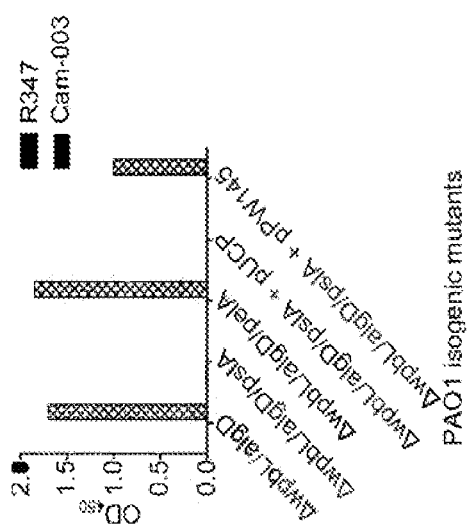
Figure 3D:
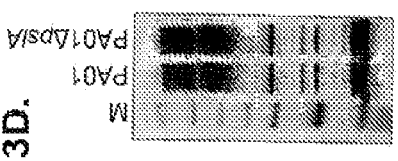
Figure 3E:
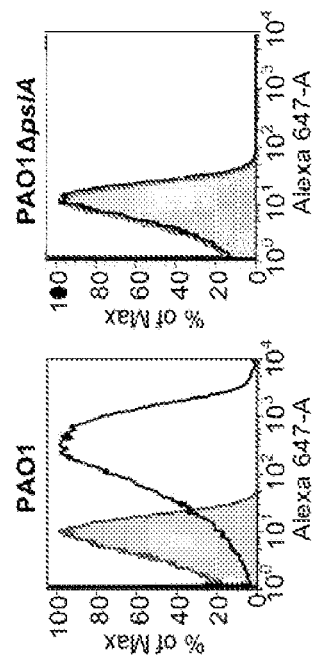
Figure 3F:
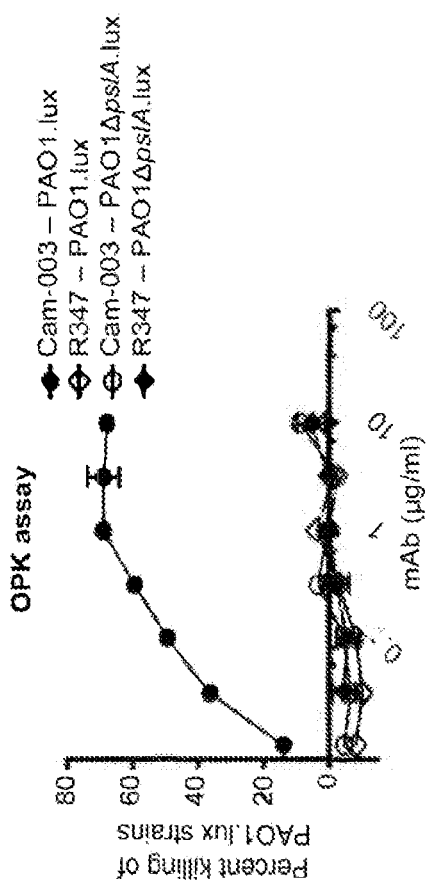
Figure 3G:
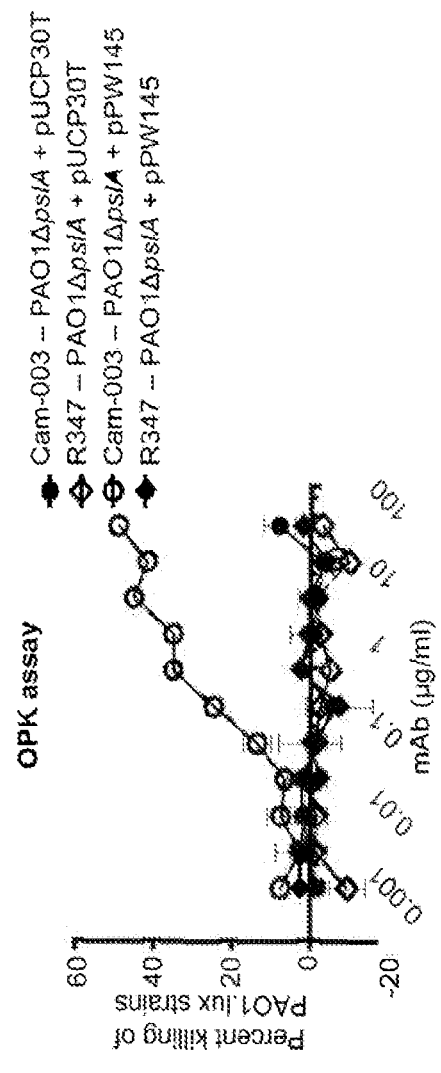
Figure 3I:
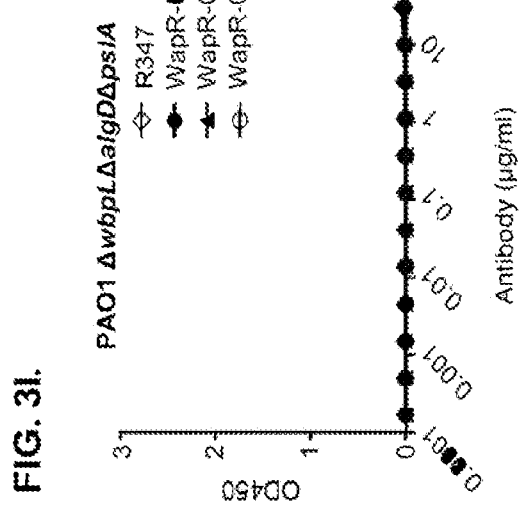
Figure 3H:
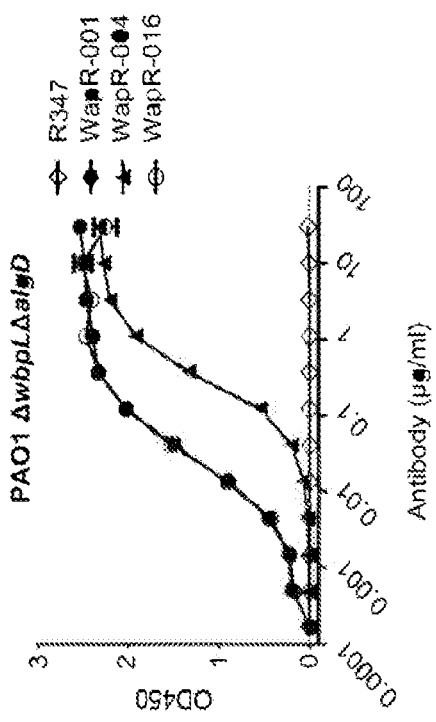

Example 3: Serotype Independent Anti-*P. aeruginosa* Antibodies Target the Psl Exopolysaccharide This example describes identification of the target of anti-*P. aeruginosa* antibodies derived from phenotypic screening. Target analysis was performed to test whether the serotype independent antibodies targeted protein or carbohydrate antigens. No loss of binding was observed in ELISA to PAO1 whole cell extracts exhaustively digested with proteinase K, suggesting that reactivity targeted surface accessible carbohydrate residues (data not shown). Isogenic mutants were constructed in genes responsible for O-antigen, alginate, and LPS core biosynthesis; wbpL (O-antigen-deficient); wbpL/algD (O-antigen and alginate deficient); rmlC (O-antigen-deficient and truncated outer core); and galU (O-antigen-deficient and truncated inner core). *P. aeruginosa* mutants were constructed based on the allele replacement strategy described by Schweizer (Schweizer, H. P., *Mol Microbiol* 6, 1195-1204 (1992); Schweizer, H. D., *Biotechniques* 15, 831-834 (1993)). Vectors were mobilized from *E. coli* strain S17.1 into *P. aeruginosa* strain PAO1; recombinants were isolated as described (Hoang, T. T., et al., *Gene* 212, 77-86 (1998)). Gene deletion was confirmed by PCR. *P. aeruginosa* mutants were complemented with pUCP30T-based constructs harboring wild type genes. Reactivity of antibodies was determined by indirect ELISA on plates coated with above indicated *P. aeruginosa* strains: FIG. 3A shows that Cam-003 binding to the wbpL or the wbpL/algD double mutant was unaffected, however binding to the rmlC and galU mutants were abolished. While these results were consistent with binding to LPS core, reactivity to LPS purified from PAO1 was not observed. The rmlC and galU genes were recently shown to be required for biosynthesis of the Psl exopolysaccharide, a repeating pentasaccharide polymer consisting of D-mannose, L-rhamnose, and D-glucose. Cam-003 binding to an isogenic pslA knockout PAO1ΔpslA, was tested, as pslA is required for Psl biosynthesis (Byrd, M. S., et al., *Mol Microbiol* 73, 622-638 (2009)). Binding of Cam-003 to PAO1ΔpslA was abolished when tested by ELISA (FIG. 3B) and FACS (FIG. 3C), while the LPS molecule in this mutant was unaffected (FIG. 3D). Binding of Cam-003 was restored in a PAO1ΔwbpL/algD/pslA triple mutant complemented with pslA (FIG. 3E) as was the ability of Cam-003 to mediate opsonic killing to complemented PAO1ΔpslA in contrast to the mutant (FIGS. 3F and 3G). Binding of Cam-003 antibody to a Pel exopolysaccharide mutant was also unaffected further confirming Psl as our antibody target (FIG. 3E). Binding assays confirmed that the remaining antibodies also bound Psl (FIGS. 3H and 3I).

Example 4: Anti-Psl mAbs Block Attachment of *P. aeruginosa* to Cultured Epithelial Cells This example shows that anti-Psl antibodies blocked *P. aeruginosa* association with epithelial cells. Anti-Psl antibodies were added to a confluent monolayer of A549 cells (an adenocarcinoma human alveolar basal epithelial cell line) grown in opaque 96-well plates (Nunc Nunclon Delta). Log-phase luminescent *P. aeruginosa* PAO1 strain (PAO1.lux) was added at an MOI of 10. After incubation of PAO1.lux with A549 cells at 37° C. for 1 hour, the A549 cells were washed, followed by addition of LB+0.5% glucose. Bacteria were quantified following a brief incubation at 37° C. as performed in the OPK assay described in Example 2. Measurements from wells without A549 cells were used to correct for non-specific binding. FIG. 4 shows that with the exception of Cam-005 and WapR-007, all antibodies reduced association of PAO1.lux to A549 cells in a dose-dependent manner. The mAbs which performed best in OPK assays, WapR-004 and Cam-003 (see FIGS. 2A-B, and Example 2), were also most active at inhibiting *P. aeruginosa* cell attachment to A549 lung epithelial cells, providing up to ~80% reduction compared to the negative control. WapR-016 was the third most active antibody, showing similar inhibitory activity as WapR-004 and Cam-003 but at 10-fold higher antibody concentration.

Example 5: In Vivo Passaged *P. aeruginosa* Strains Maintain/Increase Expression of Psl To test if Psl expression in vivo is maintained, mice were injected intraperitoneally with *P. aeruginosa* isolates followed by harvesting of bacteria by peritoneal lavage four hours post-infection. The presence of Psl was analyzed with a control antibody and Cam-003 by flow cytometry as conditions for antibody binding are more stringent and allow for quantification of cells that are positive or negative for Psl expression. For ex vivo binding, bacterial inocula (0.1 ml) was prepared from an overnight TSA plate and delivered intraperitoneally to BALB/c mice. At 4 hr. following challenge, bacteria were harvested, RBCs lysed, sonicated and resuspended in PBS supplemented with 0.1% Tween-20 and 1% BSA. Samples were stained and analyzed as previously described in Example 1. FIG. 5 shows that bacteria harvested after peritoneal lavage with three wild type *P. aeruginosa* strains showed strong Cam-003 staining, which was comparable to log phase cultured bacteria (compare FIGS. 5A and 5C). In vivo passaged wild type bacteria exhibited enhanced staining when compared to the inoculum (compare FIGS. 5B and 5C). Within the inocula, Psl was not detected for strain 6077 and was minimally detected for strains PAO1 (O5) and 6206 (O11-cytotoxic). The binding of Cam-003 to bacteria increased in relation to the inocula indicating that Psl expression is maintained or increased in vivo. Wild type strains 6077, PAO1, and 6206 express Psl after in vivo passage, however strain PAO1 harboring a deletion of pslA (PAO1ΔpslA) is unable to react with Cam-003. These results further emphasize Psl as the target of the monoclonal antibodies.

Example 6: Survival Rates for Animals Treated with Anti-Psl Monoclonal Antibodies Cam-003 and WapR-004 in a *P. aeruginosa* Acute Pneumonia Model Antibodies or PBS were administered 24 hours before infection in each model. *P. aeruginosa* acute pneumonia, keratitis, and thermal injury infection models were performed as described (DiGiandomenico, A., et al., *Proc Natl Acad Sci USA* 104, 4624-4629 (2007)), with modifications. In the acute pneumonia model, BALB/c mice (The Jackson Laboratory) were infected with *P. aeruginosa* strains suspended in a 0.05 ml inoculum. In the thermal injury model, CF-1 mice (Charles River) received a 10% total body surface area burn with a metal brand heated to 92° C. for 10 seconds. Animals were infected subcutaneously with *P. aeruginosa* strain 6077 at the indicated dose. For organ burden experiments, acute pneumonia was induced in mice followed by harvesting of lungs, spleens, and kidneys 24 hours post-infection for determination of CFU.

Figure 6A:
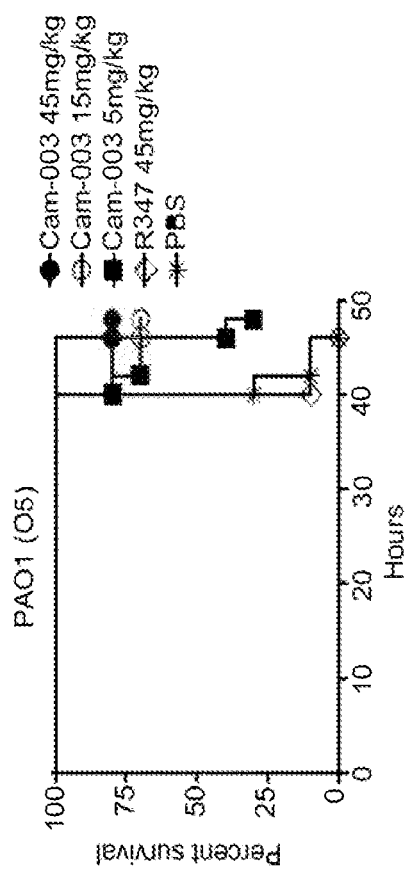
Figure 6B:
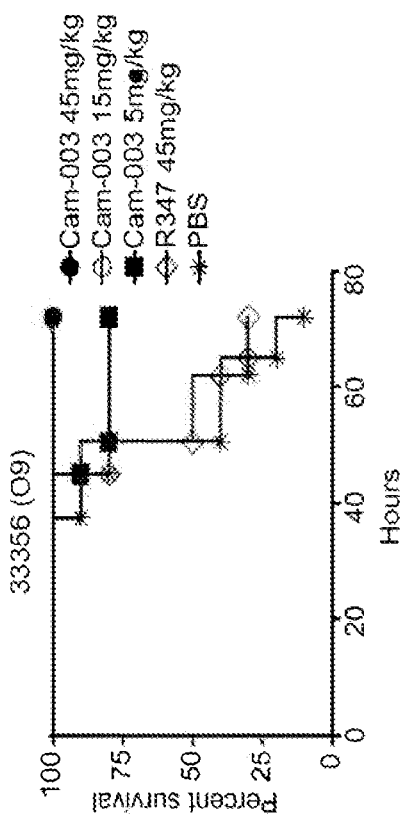
Figure 6C:
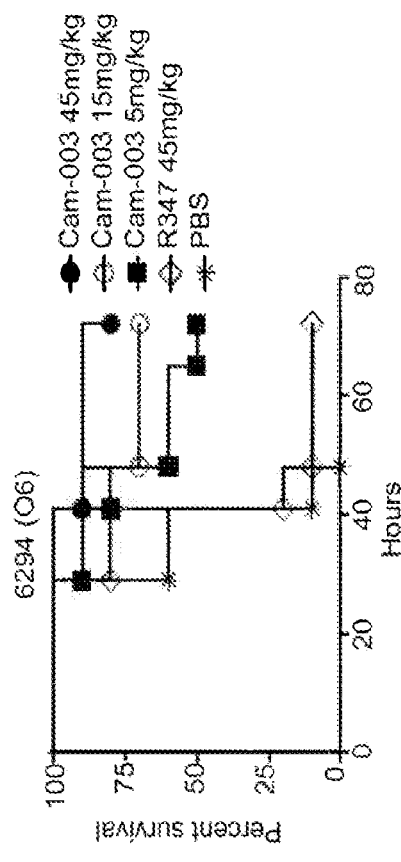
Figure 6D:
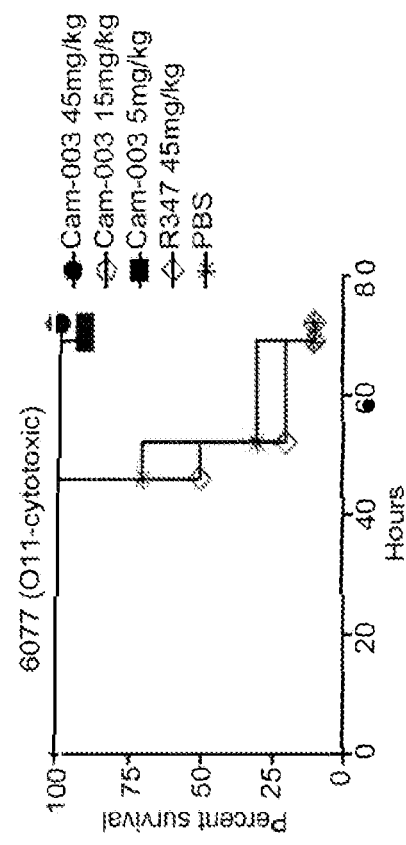
Figure 6E:
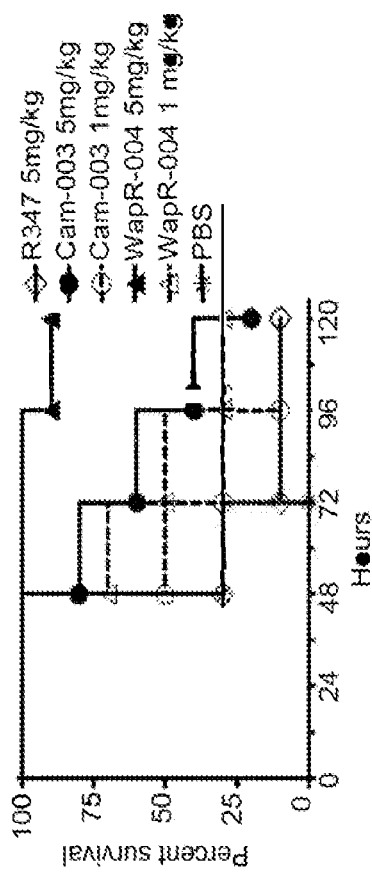
Figure 6F:
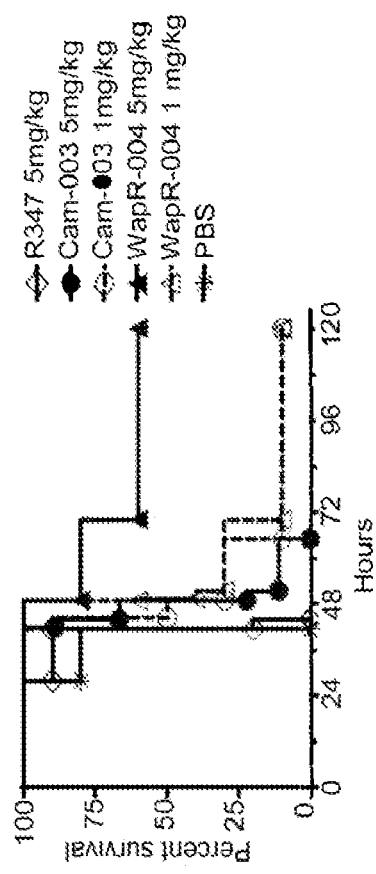

Monoclonal antibodies Cam-003 and WapR-004 were evaluated in an acute lethal pneumonia model against *P. aeruginosa* strains representing the most frequent serotypes associated with clinical disease. FIGS. 6A and 6C show significant concentration-dependent survival in Cam-003-treated mice infected with strains PAO1 and 6294 when compared to controls. FIGS. 6B and 6D show that complete protection from challenge with 33356 and cytotoxic strain 6077 was afforded by Cam-003 at 45 and 15 mg/kg while 80 and 90% survival was observed at 5 mg/kg for 33356 and 6077, respectively. FIGS. 6E and 6F show significant concentration-dependent survival in WapR-004-treated mice in the acute pneumonia model with strain 6077 (O11) ($8 \times 10^5$ CFU) (FIG. 6E), or 6077 (O11) ($6 \times 10^5$ CFU) (FIG. 6F).

Figure 7B:
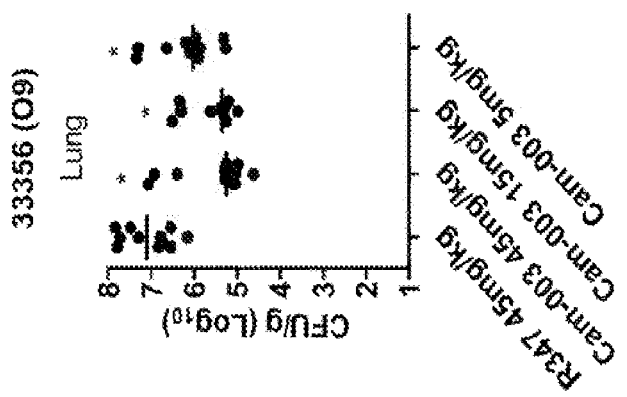
Figure 7A:
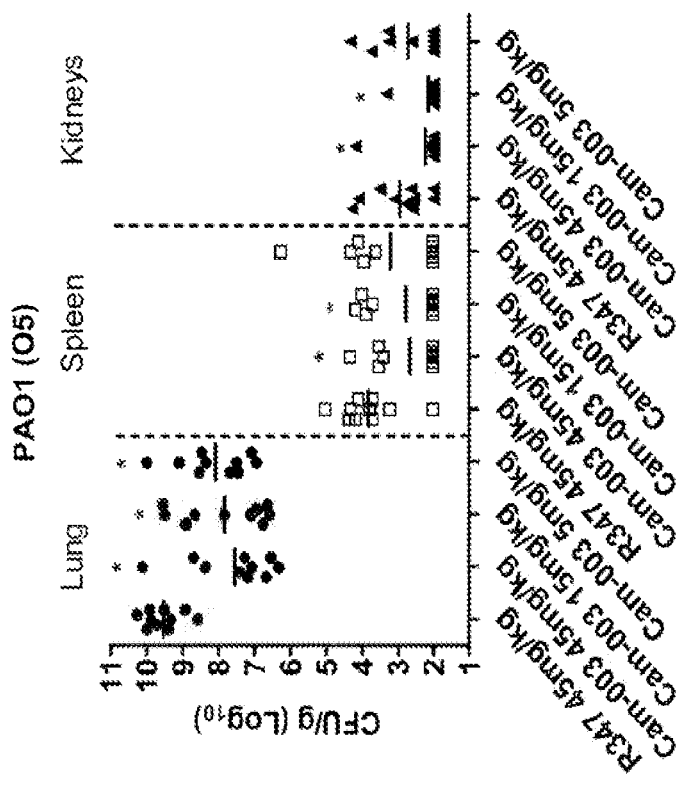
Figure 7D:
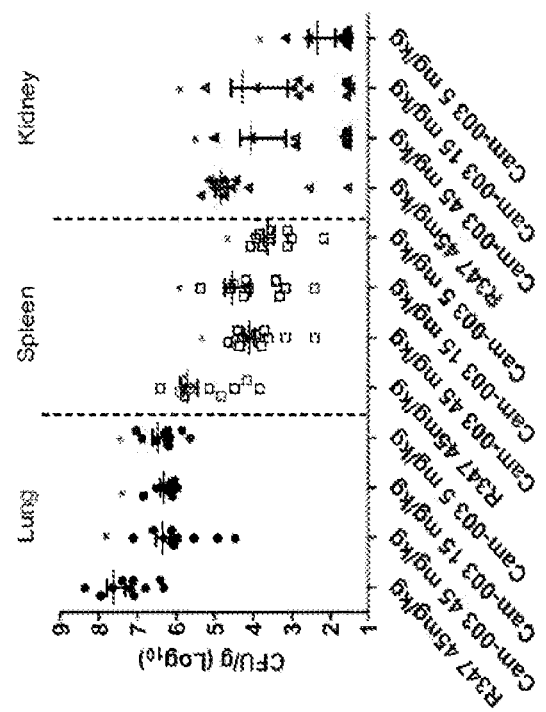
Figure 7C:
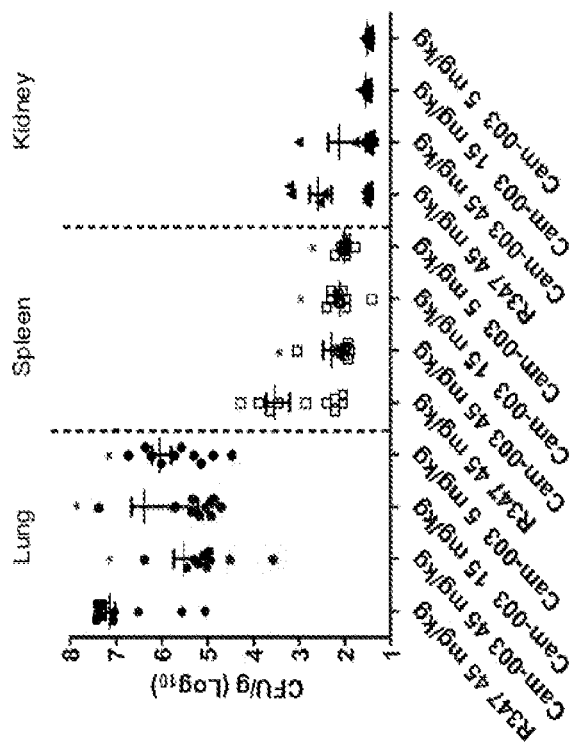

Cam-003 and WapR-004 were next examined for their ability to reduce *P. aeruginosa* organ burden in the lung and spread to distal organs, and later the animals were treated with various concentrations of WapR-004, Cam-003, or control antibodies at several different concentrations. Cam-003 was effective at reducing *P. aeruginosa* lung burden against all four strains tested. Cam-003 was most effective against the highly pathogenic cytotoxic strain, 6077, where the low dose was as effective as the higher dose (FIG. 7D). Cam-003 also had a marked effect in reducing dissemination to the spleen and kidneys in mice infected with PAO1 (FIG. 7A), 6294 (FIG. 7C), and 6077 (FIG. 7D), while dissemination to these organs was not observed in 33356 infected mice (FIG. 7B). FIGS. 7E and 7F show that similarly, WapR-004 reduced organ burden after induction of acute pneumonia with 6294 (O6) and 6206 (O11). Specifically, WapR-004 was effective at reducing *P. aeruginosa* dissemination to the spleen and kidneys in mice infected.

Example 7: Construction of Anti-PcrV Monoclonal Antibody V2L2

VelocImmune® mice (Regeneron Pharmaceuticals) were immunized by Ultra-Short immunization method with r-PcrV and serum titers were followed for binding to PcrV and neutralizing the hemolytic activity of live *P. aeruginosa*. Mice showing anti-hemolytic activity in the serum were sacrificed and the spleen and lymph nodes (axial, inguinal and popliteal) were harvested. The cell populations from these organs were panned with biotinylated r-Pcrv to select for anti-PcrV specific B-cells. The selected cells were then fused with mouse myeloma partner P3X63-Ag8 and seeded at 25K cells/well in hybridoma selection medium. After 10 days the medium from the hybridoma wells were completely changed with fresh medium and after another 3-4 days the hybridoma supernatants were assayed for anti-hemolytic activity. Colonies showing anti-hemolytic activity were limited dilution cloned at 0.2 cells/well of 96-well plates and the anti-hemolytic activity assay was repeated. Clones showing anti-hemolytic activity were adapted to Ultra-low IgG containing hybridoma culture medium. The IgG from the conditioned media were purified and assayed for in vitro anti-hemolytic activity and in vivo for protection against infection by *P. aeruginosa*. The antibodies were also categorized by competition assay into different groups. The variable (V) domains from the antibodies of interest were subcloned from the cDNA derived from their different respective clones. The subcloned V-segments were fused in frame with the cDNA for the corresponding constant domain in a mammalian expression plasmid. Recombinant IgG were expressed and purified from HEK293 cells. In instances where more than one cDNA V-sequence was obtained from a particular clone, all combinations of variable heavy and light chains were expressed and characterized to identify the functional IgG.

Figure 8D:
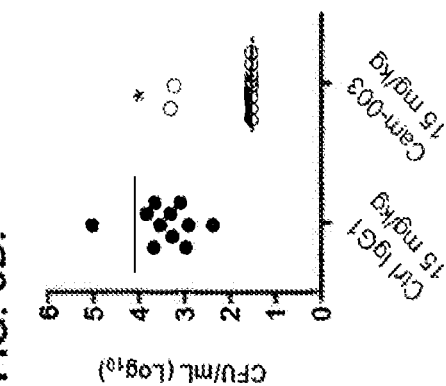
Figure 8C:
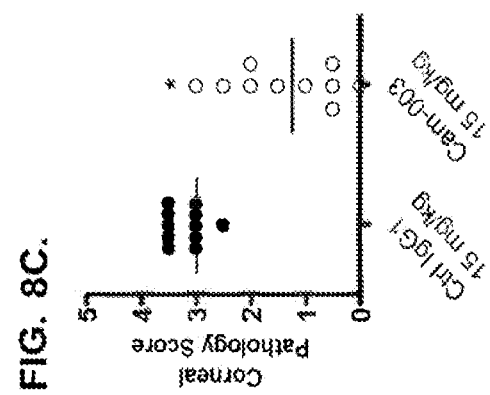
Figure 8B:
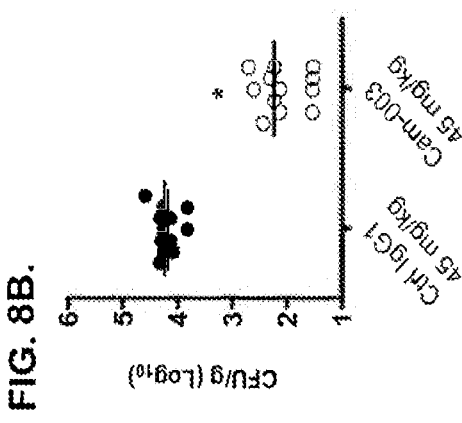
Figure 8A:
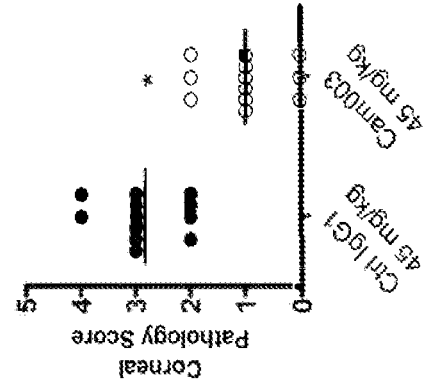
Figure 8H:
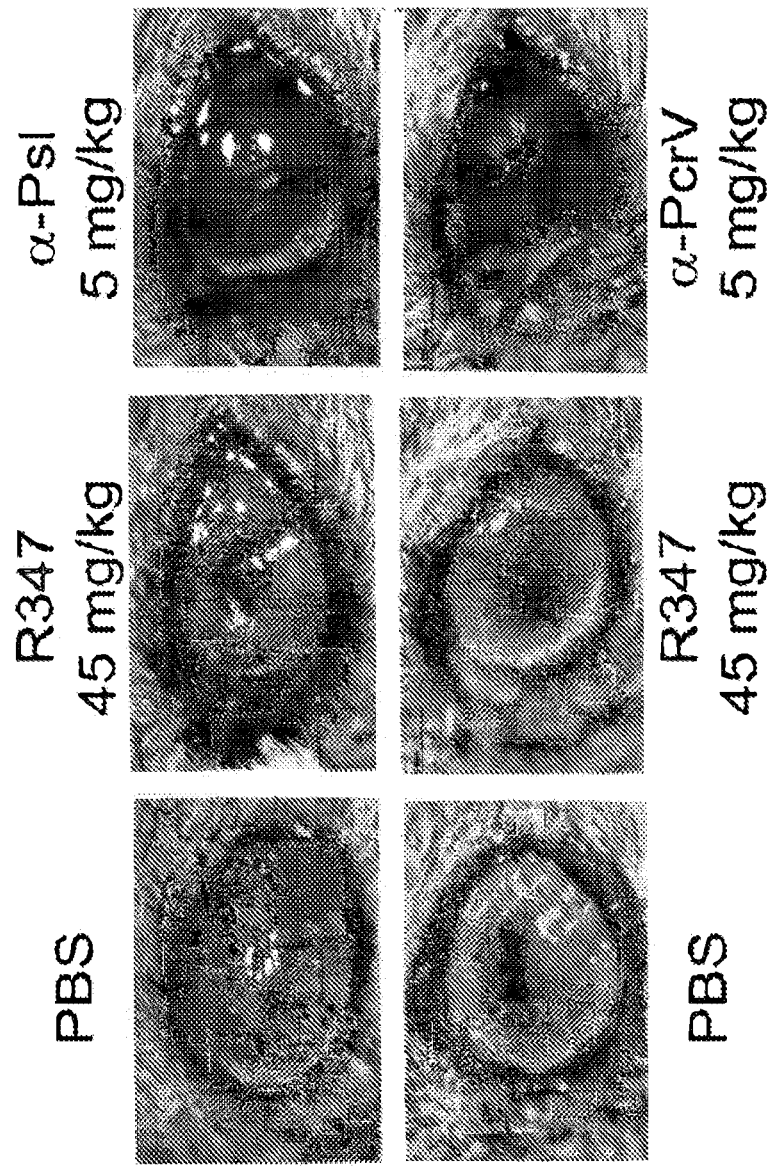

Example 8: Survival Rates for Animals Treated with Anti-Psl Monoclonal Antibodies Cam-003, WapR-004 and Anti-PcrV Monoclonal Antibody V2L2 in a *P. aeruginosa* Corneal Infection Model Cam-003 and WapR-004 efficacy was next evaluated in a *P. aeruginosa* corneal infection model which emphasizes the pathogens ability to attach and colonize damaged tissue. FIGS. 8A-D and 8F-G show that mice receiving Cam-003 and WapR-004 had significantly less pathology and reduced bacterial counts in total eye homogenates than was observed in negative control-treated animals. FIG. 8E shows that Cam-003 was also effective when tested in a thermal injury model, providing significant protection at 15 and 5 mg/kg when compared to the antibody-treated control. FIG. 8(H): The activity of anti-Psl and anti-PcrV monoclonal antibodies V2L2 was tested in a *P. aeruginosa* mouse ocular keratitis model. C3H/HeN mice were injected intraperitoneally (IP) with PBS or a control IgG1 antibody (R347) at 45 mg/kg or WapR-004 (a-Psl) at 5 mg/kg or V2L2 (a-PcrV) at 5 mg/kg, 16 hours prior to infection with 6077 (O11-cytotoxic—$1 \times 10^6$ CFU). Immediately before infection, mice were anesthetized followed by initiation of three 1 mm scratches on the cornea and superficial stroma of one eye of each mouse using a 27-gauge needle under a dissection microscope, followed by topical application of *P. aeruginosa* 6077 strain in a 5 µl inoculum. Eyes were photographed at 48 hours post infection followed by corneal grading by visualization of eyes under a dissection microscope. Grading of corneal infection was performed as previously described by Preston et al. (Preston, M J., 1995, Infect. Immun. 63:3497). Briefly, infected eyes were graded 48 h after infection with strain 6077 by an investigator who was unaware of the animal treatments. The following grading scheme was used: grade 0, eye macroscopically identical to an uninfected eye; grade 1, faint opacity partially covering the pupil; grade 2, dense opacity covering the pupil; grade 3, dense opacity covering the entire pupil; grade 4, perforation of the cornea (shrinkage of the eyeball). Mice receiving systemically dosed (IP) Cam-003 or WapR-004RAD showed significantly less pathology and reduced bacterial colony forming units (CFU) in total eye homogenates than was observed in the R347 control mAb-treated animals. Similar results were observed in V2L2-treated animals when compared to R347-treated controls.

Figure 9B:
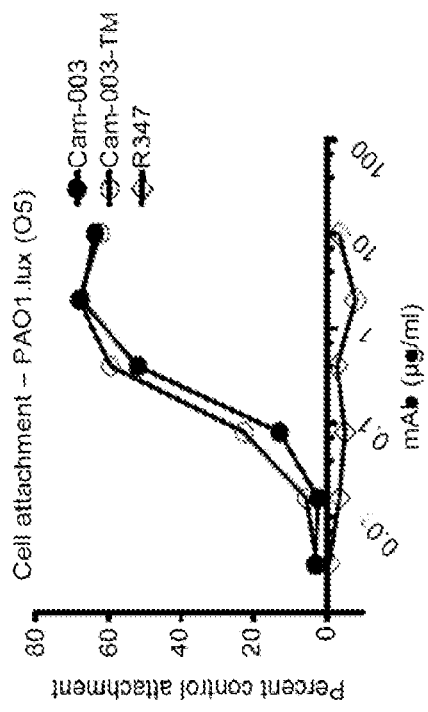
Figure 9A:
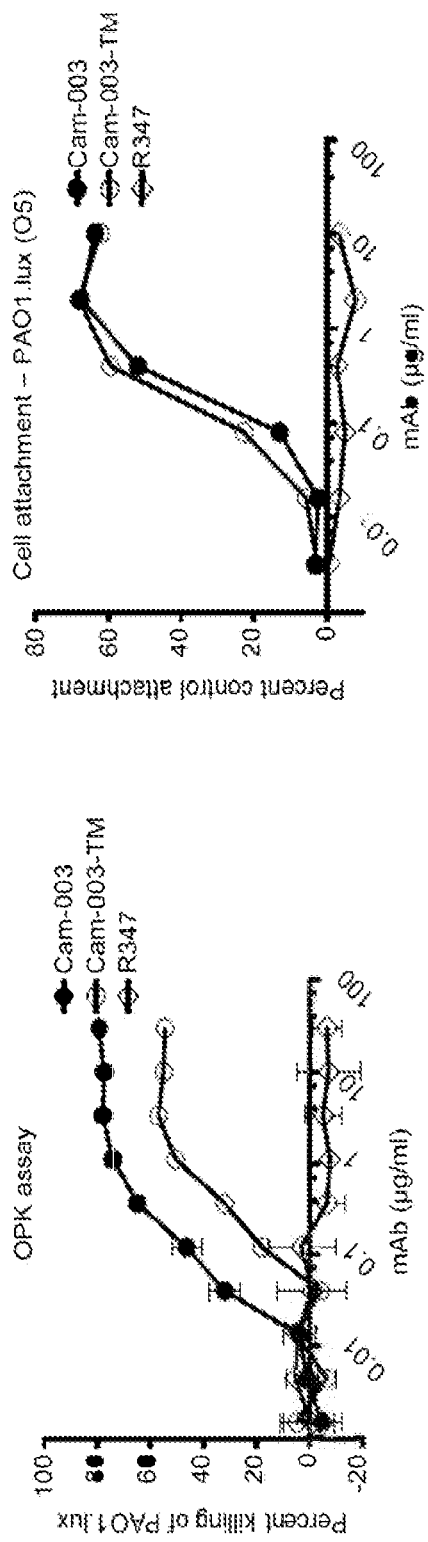
Figure 9C:
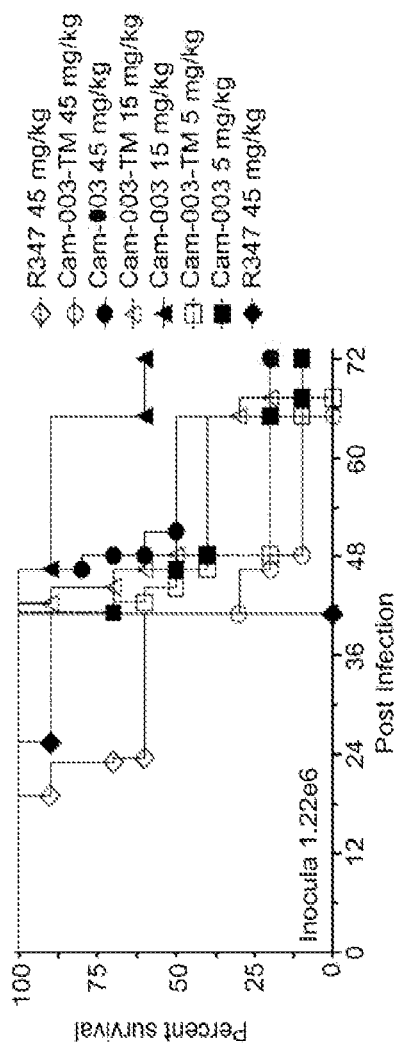

Example 9: A Cam-003 Fc Mutant Antibody, Cam-003-TM, has Diminished OPK and In Vivo Efficacy but Maintains Anti-Cell Attachment Activity Given the potential for dual mechanisms of action, a Cam-003 Fc mutant, Cam-003-TM, was created which harbors mutations in the Fc domain that reduces its interaction with Fcγ receptors (Oganesyan, V., et al., *Acta Crystallogr D Biol Crystallogr* 64, 700-704 (2008)), to identify if protection was more correlative to anti-cell attachment or OPK activity. *P. aeruginosa* mutants were constructed based on the allele replacement strategy described by Schweizer (Schweizer, H. P., *Mol Microbiol* 6, 1195-1204 (1992); Schweizer, H. D., *Biotechniques* 15, 831-834 (1993)). Vectors were mobilized from *E. coli* strain S17.1 into *P. aerugi-* nosa strain PAO1; recombinants were isolated as described (Hoang, T. T., et al., *Gene* 212, 77-86 (1998)). Gene deletion was confirmed by PCR. *P. aeruginosa* mutants were complemented with pUCP30T-based constructs harboring wild type genes. FIG. 9A shows that Cam-003-TM exhibited a 4-fold drop in OPK activity compared to Cam-003 ($EC_{50}$ of 0.24 and 0.06, respectively) but was as effective in the cell attachment assay (FIG. 9B). FIG. 9C shows that Cam-003-TM was also less effective against pneumonia suggesting that optimal OPK activity is necessary for optimal protection. OPK and cell attachment assays were performed as previously described in Examples 2 and 4, respectively.

Example 10: Epitope Mapping and Relative Affinity for Anti-Psl Antibodies

Epitope mapping was performed by competition ELISA and confirmed using an OCTET® flow system with Psl derived from the supernatant of an overnight culture of *P. aeruginosa* strain PAO1. For competition ELISA, antibodies were biotinylated using the EZ-Link Sulfo-NHS-Biotin and Biotinylation Kit (Thermo Scientific). Antigen coated plates were treated with the EC50 of biotinylated antibodies coincubated with unlabeled antibodies. After incubation with HRP-conjugated streptavidin (Thermo Scientific), plates were developed as described above. Competition experiments between anti-Psl mAbs determined that antibodies targeted at least three unique epitopes, referred to as class 1, 2, and 3 antibodies (FIG. 10A). Class 1 and 2 antibodies do not compete for binding, however the class 3 antibody, WapR-016, partially inhibits binding of the Class 1 and 2 antibodies.

Antibody affinity was determined by the OCTET® binding assays using Psl derived from the supernatant of overnight PAO1 cultures. Antibody $K_D$ was determined by averaging the binding kinetics of seven concentrations for each antibody. Affinity measurements were taken with a FORTEBIO® OCTET® 384 instrument using 384 slanted well plates. The supernatant from overnight PAO1 cultures±the pslA gene were used as the Psl source. Samples were loaded onto OCTET® AminoPropylSilane (hydrated in PBS) sensors and blocked, followed by measurement of anti-Psl mAb binding at several concentrations, and disassociation into PBS+1% BSA. All procedures were performed as described (Wang, X., et al., *J Immunol Methods* 362, 151-160). Association and disassociation raw ΔnM data were curve-fitted with GraphPad Prism. FIG. 10A shows the relative binding affinities of anti-Psl antibodies characterized above. Class 2 antibodies had the highest affinities of all the anti-Psl antibodies. FIG. 10A also shows a summary of cell attachment and OPK data experiments. FIG. 10B shows the relative binding affinities and OPK EC50 values of the Wap-004RAD (W4RAD) mutant as well as other W4 mutants lead optimized via site-directed mutagenesis as described in Example 2. FIG. 10C shows the relative binding affinities of the Wap-004RAD (W4RAD), Wap-004RAD-Germline (W4RAD-GL) as well as lead optimized anti-Psl monoclonal antibodies (Psl0096, Psl0170, Psl0225, Psl0304, Psl0337, Ps1348, Psl0567, Psl0573, Psl0574, Psl0582, Psl0584, Psl0585, Psl0588 and Psl0589). Highlighted clones Psl0096, Psl0225, Psl0337, Psl0567 and Psl0588 were selected based on their enhanced OPK activity, as shown in Example 10 below.

Figure 11B:
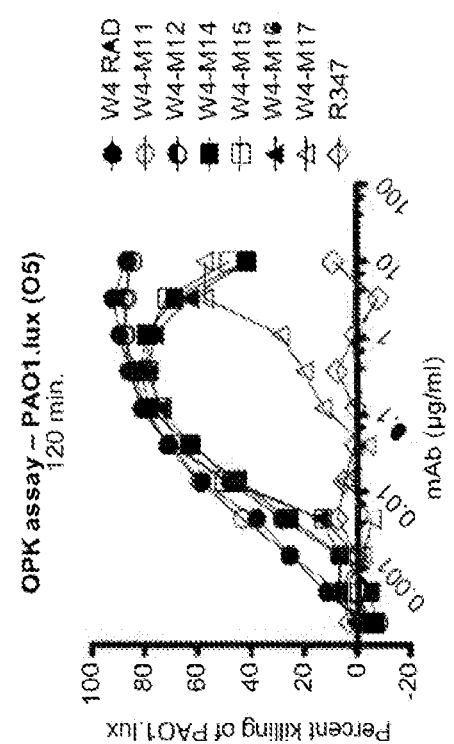
Figure 11A:
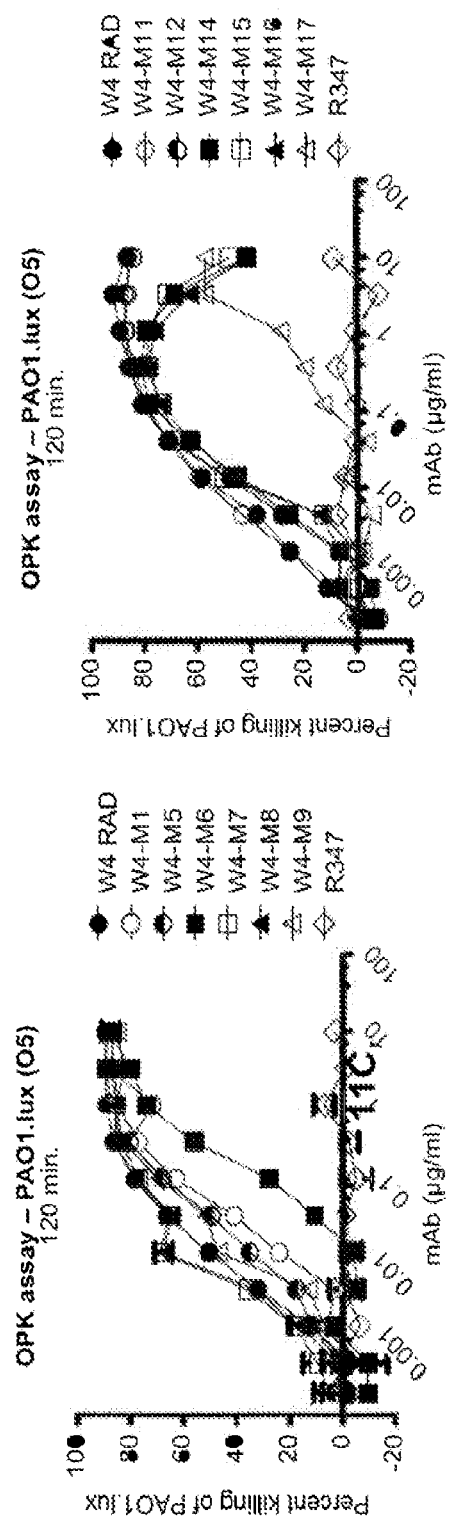
Figure 11C:
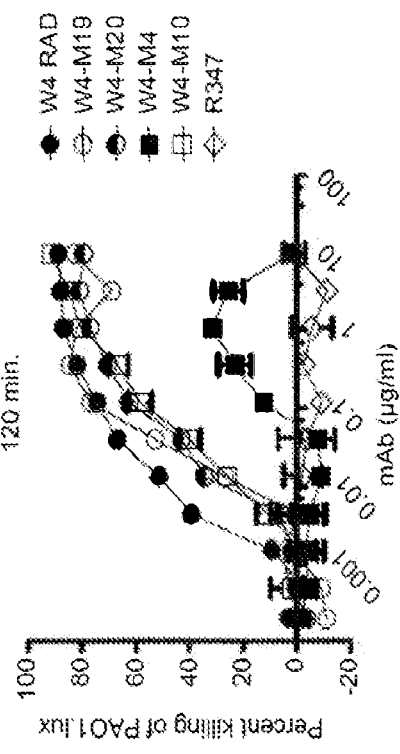
Figure 11D:
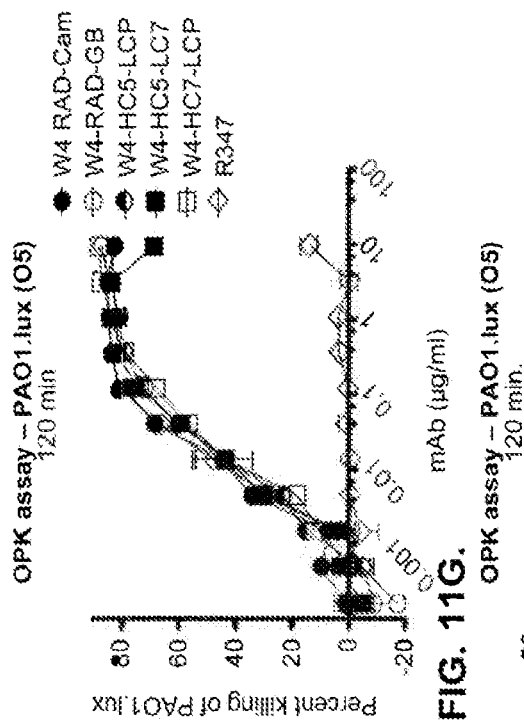
Figure 11E:
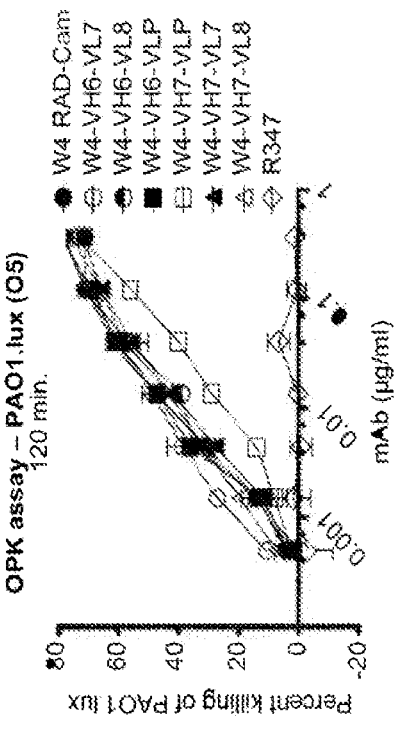
Figure 11F:
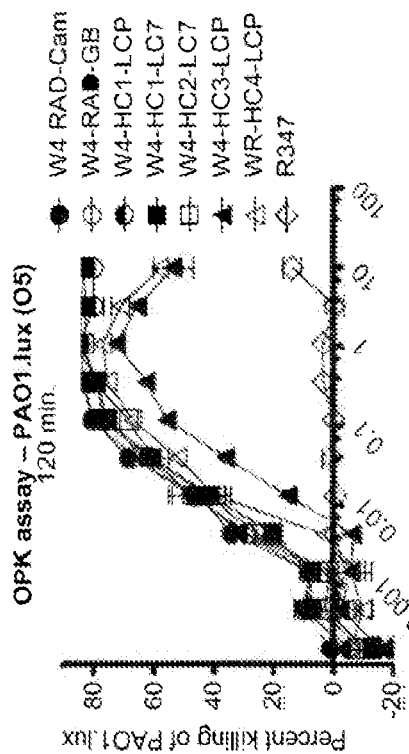
Figure 11G:
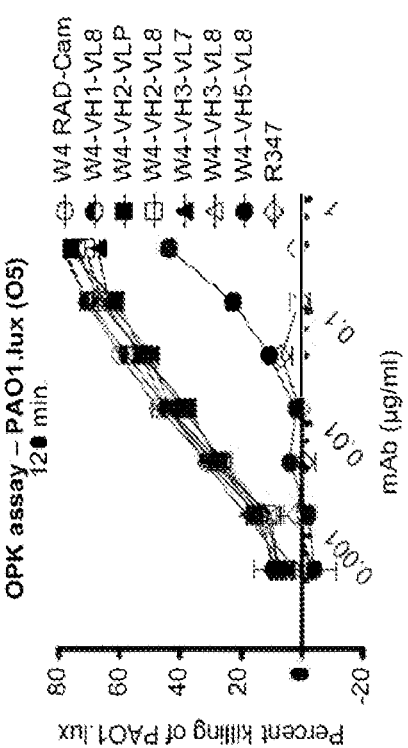
Figure 11H:
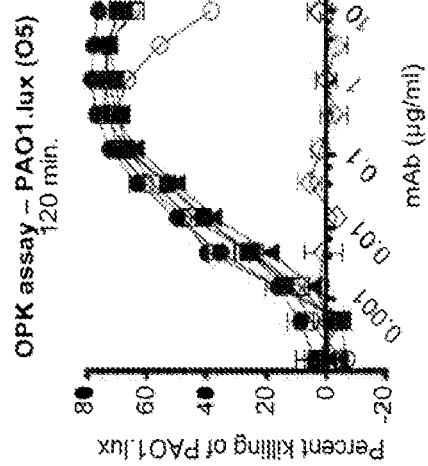
Figure 11I:
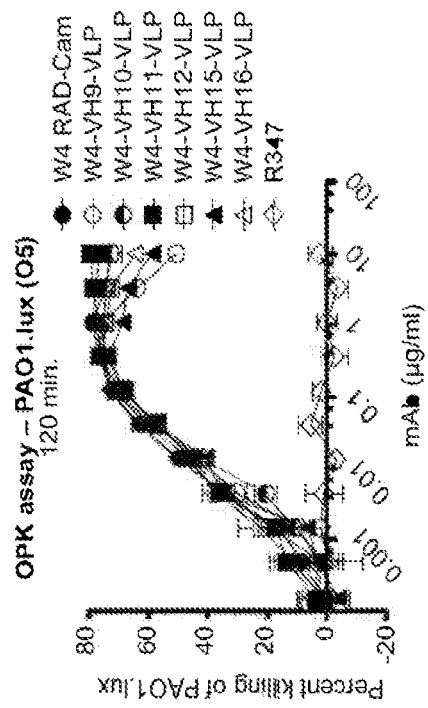
Figure 11K:
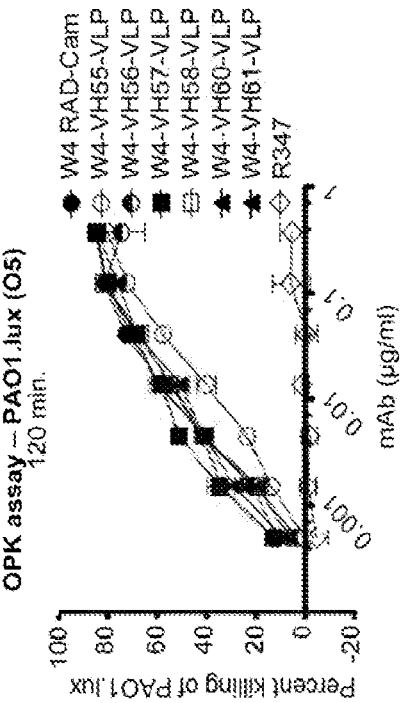
Figure 11J:
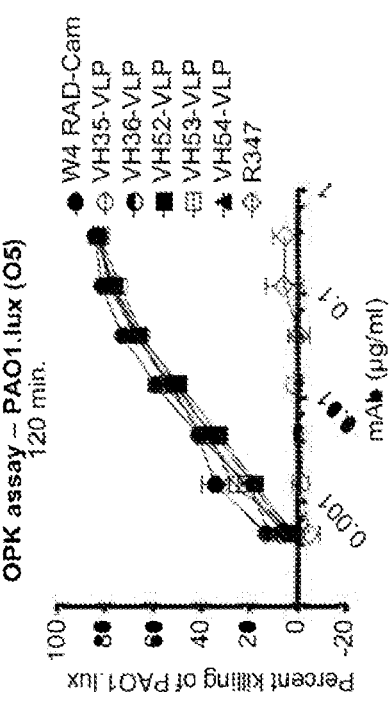
Figures 11L, 11M:
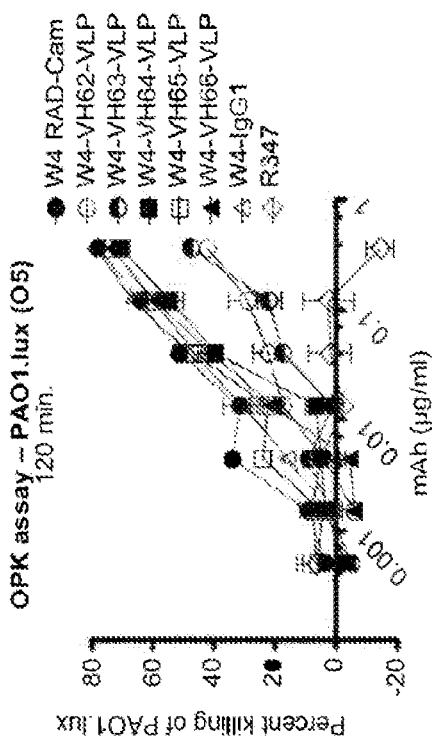
Figure 11N:
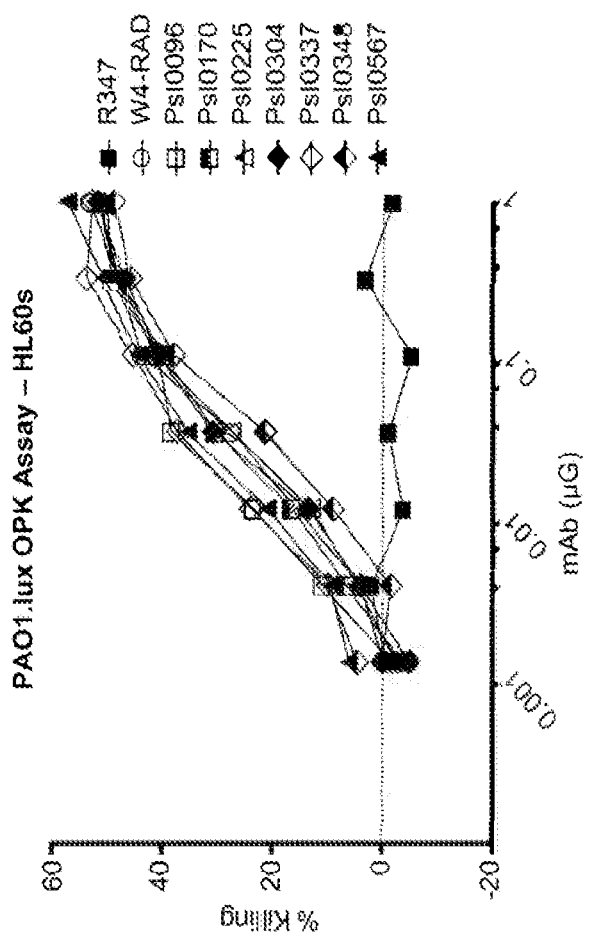
Figure 11O:
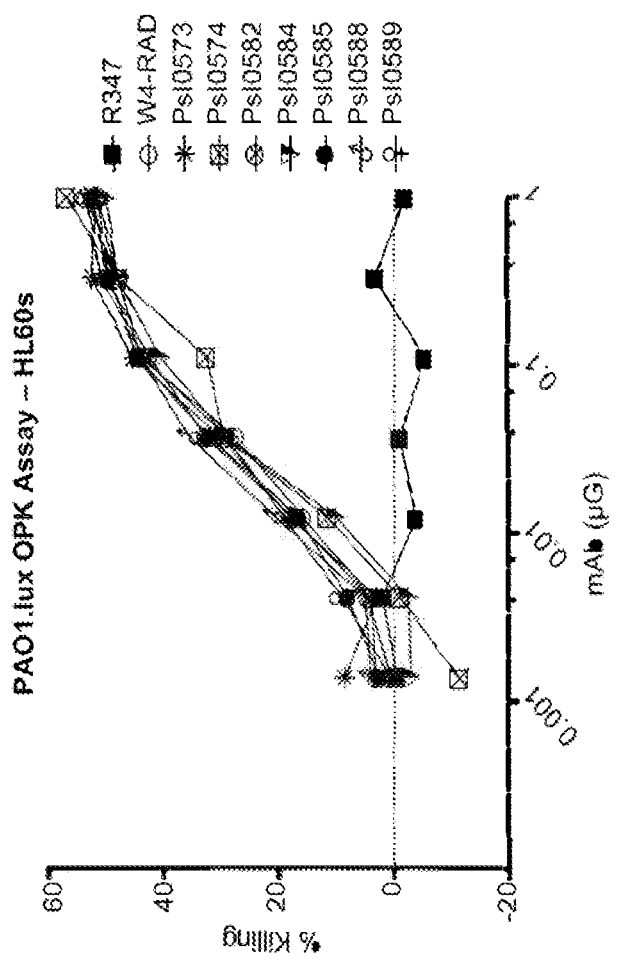
Figure 11P:
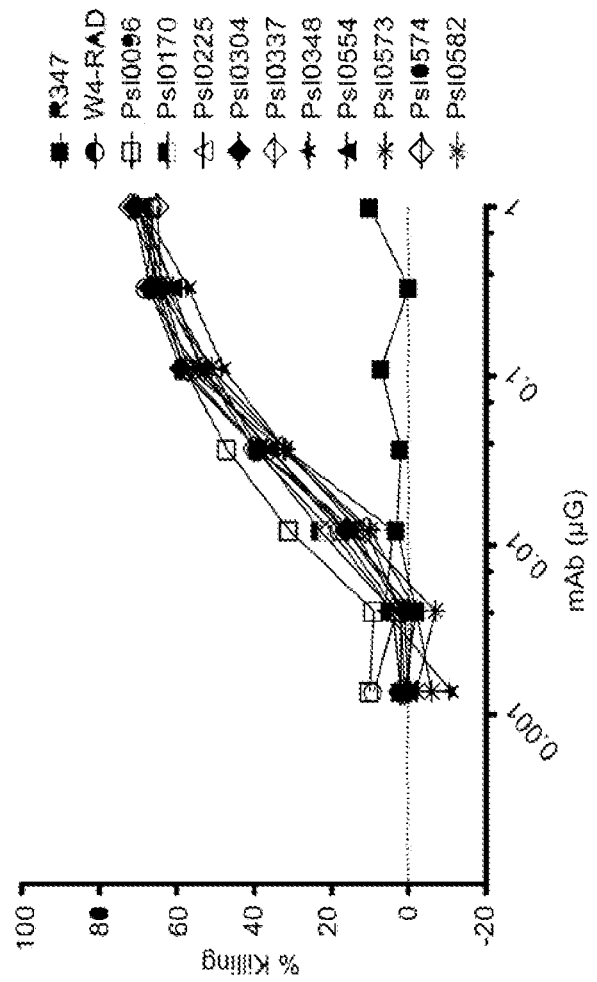
Figure 11Q:
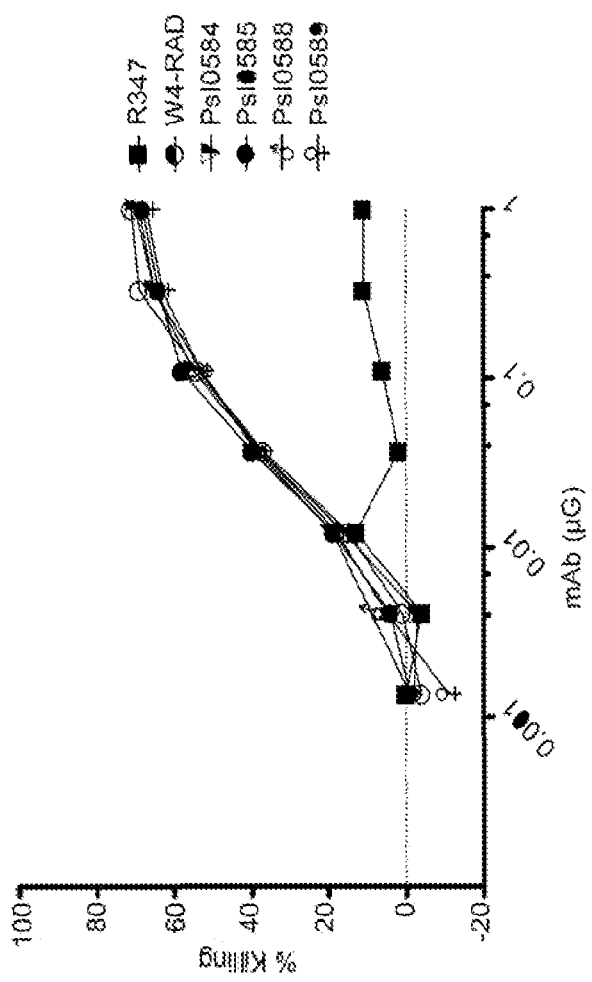

Example 11: Evaluation of Lead Optimized WapR-004 (W4) Mutant Clones and Lead Optimized Anti-Psl Monoclonal Antibodies in the *P. aeruginosa* Opsonophagocytic Killing (OPK) Assay This example describes the evaluation of lead optimized WapR-004 (W4) mutant clones and lead optimized anti-Psl monoclonal antibodies to promote OPK of *P. aeruginosa* using the method described in Example 2. FIGS. 11A-Q show that with the exception of the negative control antibody R347, all antibodies mediated concentration dependent killing of luminescent *P. aeruginosa* serogroup O5 strain (PAO1.lux).

Example 12: Anti-Pcrv Monoclonal Antibody V2L2 Reduces Lethality from Acute Pneumonia from Multiple Strains The PcrV epitope diversity was analyzed using three approaches: bead based flow cytometry method, competition ELISA and western blotting of fragmented rPcrV. Competition experiments between anti-PcrV mAbs determined that antibodies targeted at least six unique epitopes, referred to as class 1, 2, 3, 4, 5 and 6 antibodies (FIG. 12A). Class 2 and 3 antibodies partially compete for binding. mAbs representing additional epitope classes: class 1 (V2L7, 3G5, 4C3 and 11A6), class 2 (1E6 and 1F3), class 3 (29D2, 4A8 and 2H3), class 4 (V2L2) and class 5 (21F1, LE10 and SH3) were tested for in vivo protection as below described.

Novel anti-PcrV mAbs were isolated using hybridoma technology and the most potent T3SS inhibitors were selected using a rabbit red blood cell lysis inhibition assay. Percent inhibition of cytotoxicity analysis was analysed for the parental V2L2 mAb, mAb166 (positive control) and R347 (negative control), where the antibodies were administered to cultured broncho-epithelial cell line A549 combined with log-phase *P. aeruginosa* strain 6077 (exoU+) at a MOI of approximately 10. A549 lysis was assayed by measuring released lactate dehydrogenase (LDH) activity and lysis in the presence of mAbs was compared to wells without mAb to determine percent inhibition. The V2L2 mAb, mAb166 (positive control) and R347 (negative control) were evaluated for their ability to prevent lysis of RBCs, where the antibodies were mixed with log-phase *P. aeruginosa* 6077 (exoU+) and washed rabbit red blood cells (RBCs) and incubated for 2 hours at 37°. Intact RBCs were pelleted and the extent of lysis determined by measuring the $OD_{405}$ of the cell-free supernatant. Lysis in the presence of anti-PcrV mAbs was compared to wells without mAb to determine percent inhibition. The positive control antibody, mAb166, is a previously characterized anti-PcrV antibody (*J Infect Dis.* 186:64-73 (2002), *Crit Care Med.* 40:2320-2326 (2012)). (B) The parental V2L2 mAb demonstrated inhibition of cytotoxicity with an IC50 of 0.10 µg/ml and exhibited an IC50 concentration 28-fold lower than mAb166 (IC50 of 2.8 µg/ml). (C) V2L2 also demonstrated prevention of RBC lysis with an IC50 of 0.37 µg/ml and exhibited an IC50 concentration 10-fold lower than mAb166 (IC50 of 3.7 µg/ml).

Figure 12D:
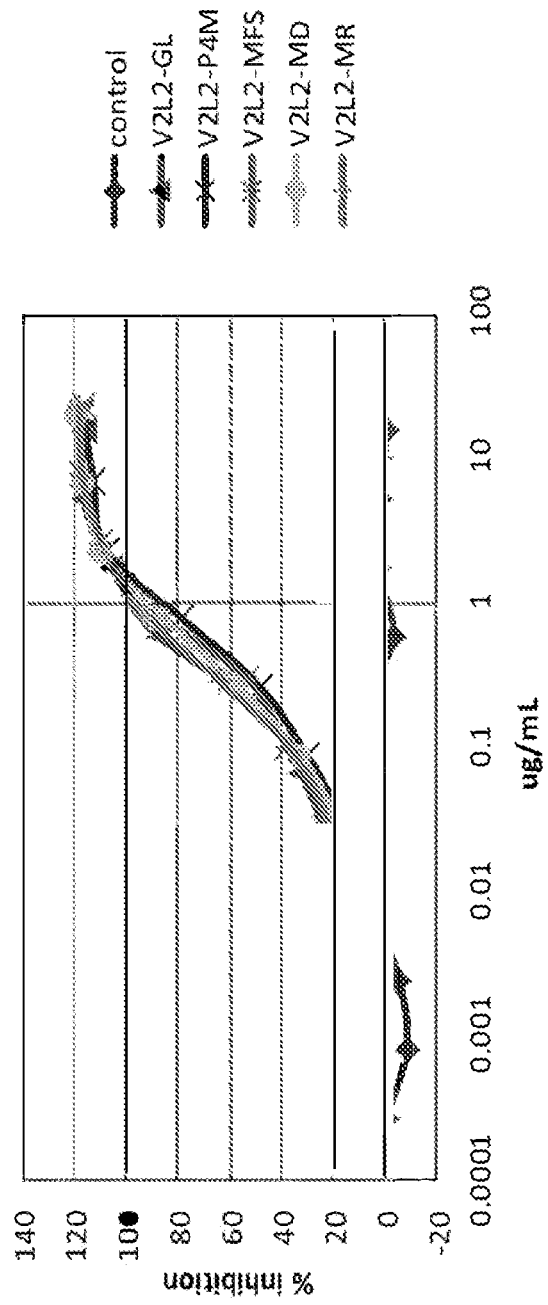
Figure 12E:
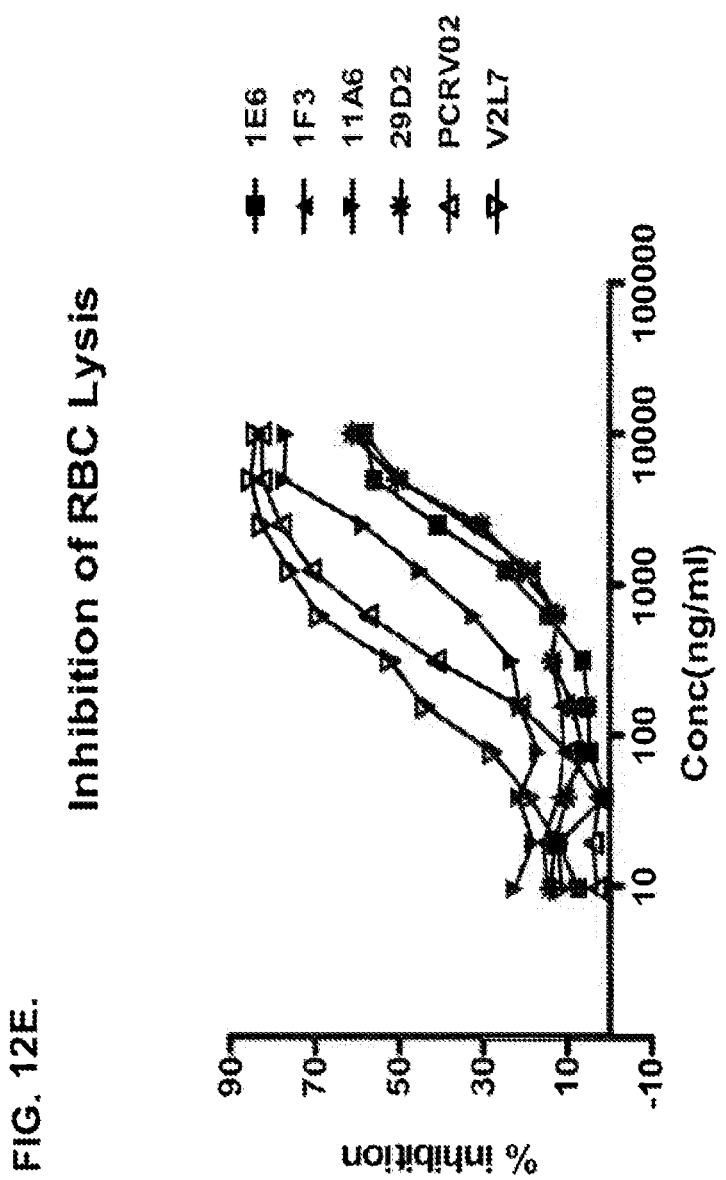
Figure 12F:
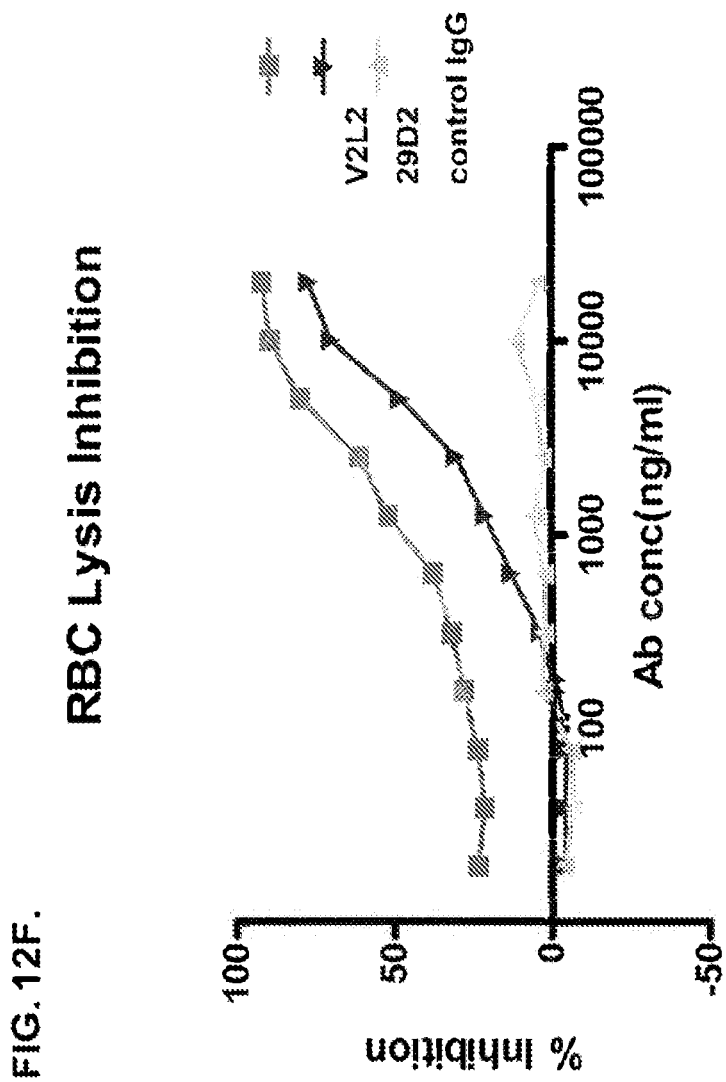
Figure 12G:
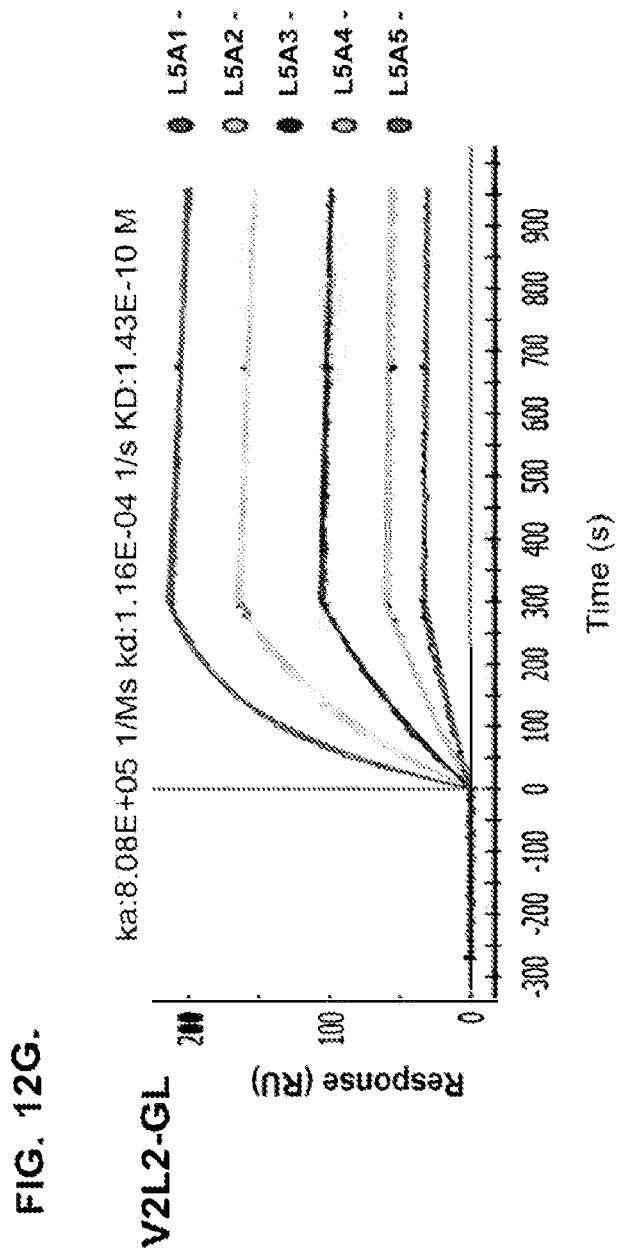
Figure 12H:
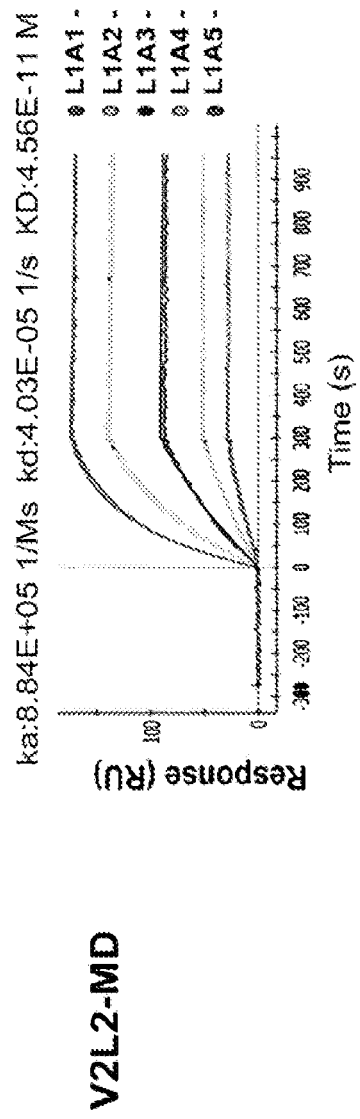

The V2L2 variable region was fully germlined to reduce potential immunogenicity. V2L2 was affinity matured using the parsimonious mutagenesis approach to randomize each position with 20 amino acids for all six CDRs, identifying affinity-improved single mutations. A combinatorial library was then used, encoding all possible combinations of affinity-improved single mutations. Clones with improved affinity to PcrV were selected using binding ELISA in IgG format. Top clones were ranked by affinity improvement and analyzed in an in vitro functional assay. V2L2 CDRs were systematically mutagenized and clones with improved affinity to PcrV were selected in competition-based screens. Clones were ranked by increases in affinity and analyzed in a functional assay. As shown in FIG. 12D, RBC lysis was analyzed for V2L2-germlined MAb (V2L2-GL), V2L2-GL optimized mAbs (V2L2-P4M, V2L2-MFS, V2L2-MD and V2L2-MR), and a negative control antibody R347 using Pseudomonas strain 6077 infected A549 cells. V2L2-GL, V2L2-P4M, V2L2-MFS, V2L2-MD and V2L2-MR demonstrated prevention of RBC lysis. As shown in FIG. 12E, mAbs 1E6, 1F3, 11A6, 29D2, PCRV02 and V2L7 demonstrated prevention of RBC lysis. As shown in FIG. 12F, V2L2 was more potent in prevention of RBC lysis than the 29D2.

Binding kinetics of V2L2-GL and V2L2-MD were measured using a Bio-Rad ProteOn™ XPR36 instrument. Antibodies were captured on a GLC bisensor chip using anti-human IgG reagents. rPcrV protein was injected at multiple concentrations and the dissociation phase followed for 600 seconds. Data was captured and analyzed using ProteOn Manager software. FIG. 12(G-H) shows the relative binding affinities of (G) V2L2-GL and (H) V2L2-MD antibodies. The clone V2L2-MD had increased Kd by 2-3 folds over V2L2-GL.

The in vivo effect of administration of an anti-PcrV antibodies was studied in mice using an acute pneumonia model. Groups of mice were treated with either increasing concentrations of the V2L2 antibody, a positive control anti-PcrV antibody (mAb166), or a negative control (R347), as shown in FIG. 13(A-B). Groups of mice were also treated with either increasing concentrations of the V2L2 antibody, the PcrV antibody PcrV-02, or a negative control (R347), as shown in FIG. 13(C-D). Twenty-four hours after treatment, all mice were infected with $5\times10^7$ CFU (C) Pseudomonas aeruginosa 6294 (O6) or (D) PA103A (O11). As shown in FIG. 13, nearly all control treated animals succumbed to infection by 48 hours post infection. However, V2L2 showed a dose-dependent effect on improved survival even out to 168 hours post-infection. Further, V2L2 provided significantly more potent protection than mAb166 at similar doses (P=0.025, 5 mg/kg for strain 6077; P<0.0001, 1 mg/kg for strain 6294).

Groups of mice were treated with either increasing concentrations of the 11A6, 3G5 or V2L7, the same concentrations of 29D2, 1F3, 1E6, V2L2, LE10, SH3, 4A8, 2H3, or 21F1, increasing concentrations of the 29D2, increasing concentrations of the V2L2, the PcrV antibody PcrV-02, or a negative control (R347), as shown in FIG. 13(E-H). Mice were injected intraperitoneally (IP) with mAbs 24 hours prior to to intranasal infection with Pseudomonas strain 6077 ($1\times10^6$ CFU/animal). As shown in FIG. 13E mAbs 11A6, 3G5 and V2L7 did not provide protection in vivo. As shown in FIG. 13F, mAb 29D2 provides protection in vivo. As shown in FIG. 13G, mAb V2L2 also provides protection in vivo. FIG. 13H shows in vivo comparison of 29D2 and V2L2. FIG. 13I shows that mAb V2L2 protects against additional Pseudomonas strains (i.e., 6294 and PA103A).

Figure 14A:
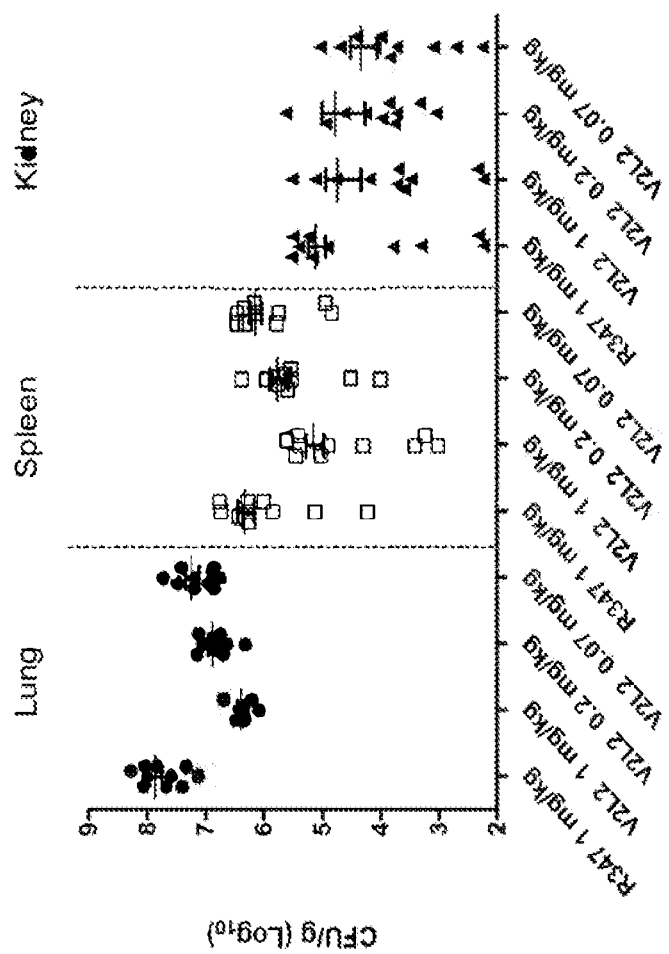
Figure 14B:
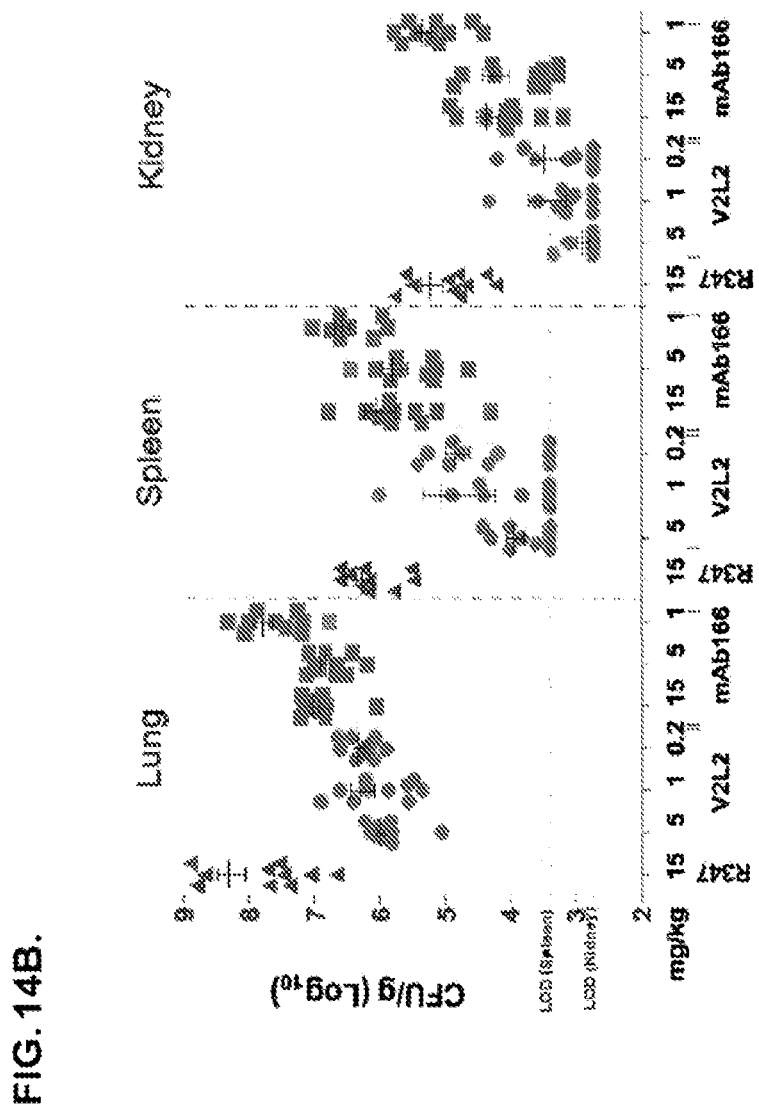

Organ burden of Pseudomonas-infected mice was also studied in response to administration of V2L2. FIG. 14(A) Mice were treated with either 1 mg/kg R347 (control), or 1 mg/kg, 0.2 mg/kg, or 0.07 mg/kg of V2L2 and then were infected intranasally with $1.2\times10^6$ cfu of Pseudomonas 6206. FIG. 14(B) Mice were also treated with either 15 mg/kg R347 (negative control); 15.0 mg/kg, 5.0 mg/kg, or 1.0 mg/kg mAb 166 (positive control); or 5.0 mg/kg, 1.0 mg/kg, or 0.2 mg/kg V2L2 and then were infected intranasally with $5.5\times10^6$ cfu of Pseudomonas 6206. As shown in FIG. 14(A-B), while V2L2 had little effect on clearance in the kidney, it greatly reduced dissemination to both the lung and spleen in a dose-dependent manner. In addition, V2L2 provided significantly greater reduction in organ CFU than mAb166 at similar doses (P<0.0001, 1 mg/kg, lung).

Example 13: In Vivo Activity of Combination Therapy Using WapR-004 (Anti-Psl) and V2L2 (Anti-PcrV) Antibodies The in vivo effect of combination administration of anti-Psl and anti-PcrV binding domains was further studied in mice using the antibodies V2L2 and WapR-004 (RAD). Groups of mice were treated with R347 (2.1 mg/kg-negative control), V2L2 (0.1 mg/kg), W4-RAD (0.5 mg/kg), or V2L2/W4 combination (either 0.1, 0.5, 1.0 or 2.0 mg/kg each). Twenty-four hours post-administration of antibody, all mice were infected with an inoculum containing $5.25\times10^5$ cfu 6206 (O11-ExoU+). Twenty-four hours post infection, lungs, spleens, and kidneys were harvested, homogenized, and plated for colony forming unit (CFU) identification per gram of tissue. As shown in FIG. 15, at the concentrations tested, both V2L2 and W4 were effective in lowering organ burden, the V2L2/W4 combination showed an additive effect in tissue clearance. Histological examination of lung tissue revealed less hemorrhaging, less edema, and less inflammatory infiltrate compared to mice receiving V2L2 or WapR-004 alone (Table 5).

Similarly immunized animals were also assessed for survival from acute pneumonia infections.

TABLE 5

| Group (n) | Treatment | Overall Impression (Involved Lung Surface Area) | Hemorrhage | Edema | Inflammatory Infiltrate | Gram Stain |
|---|---|---|---|---|---|---|
| 1(2) | R347 (2.1 mg/kg) | Broncho interstitial pneumonia (75%) fibrinoid necrosis and marked congestion | 3+ | 3+ | PMN 3+ | |
| 6(3) | V2L2 (0.1 mg/kg) | Broncho interstitial pneumonia (55%) broncho epithelial injury and marked congestion | 3+ | 3+ | PMN 3+ | |
| 7(3) | WapR-004 (0.5 mg/kg) | Broncho interstitial pneumonia (50%) broncho epithelial injury and marked congestion | 2-3+ | 3+ | PMN 2-3+ | |
| 2(3) | V2L2 + WapR-004 (0.1 mg/kg + 0.1 mg/kg) | Broncho interstitial pneumonia (15%) Mild broncho epithelial injury | 1+ | 3+ | PMN 1+ | |
| 3(3) | V2L2 + WapR-004 (0.1 mg/kg + 0.5 mg/kg) | Broncho interstitial pneumonia (40%), Moderate congestion | 2+ | 3+ | PMN 2+ | |

TABLE 5-continued

| Group (n) | Treatment | Overall Impression (Involved Lung Surface Area) | Hemorrhage | Edema | Inflammatory Infiltrate | Gram Stain |
|---|---|---|---|---|---|---|
| 4(3) | V2L2 + WapR-004 (0.1 mg/kg + 1.0 mg/kg) | Primarily Broncho pneumonia; Broncho interstitial pneumonia (20%) | 1-3+ | 3+ | PMN 1-2+ | |
| 5(3) | V2L2 + WapR-004 (0.1 mg/kg + 2.0 mg/kg) | Mild Broncho pneumonia (20%) | 1+ | 3+ | PMN 1-2+ | |

Example 14: Survival Rates for Animals Treated with Anti-PcrV Monoclonal Antibody V2L2 in a *P. aeruginosa* Acute Pneumonia Model Monoclonal antibodies V2L2-GL, V2L2-MD, V2L2-A, V2L2-C, V2L2-PM4 and V2L2-MFS were evaluated in an acute lethal pneumonia model against *P. aeruginosa* 6077 strain as previously described in Example 11. FIGS. 16(A-F) show survival in all V2L2 treated mice infected with strain 6077 when compared to control. However, no significant difference in survival is observed between V2L2 antibodies at either dose: 0.5 mg/kg and 1 mg/kg (A-C) or 0.5 mg/kg and 0.1 mg/kg (D-F). FIGS. 16(G-I) show survival in all V2L2 treated mice infected with strain 6077 when compared to control. No significant difference in survival is observed between V2L2 antibodies at either dose: 0.5 mg/kg and 1 mg/kg (G-I). (A-H)

All of the control mice succumbed to infection by approximately 48 hours post-infection.

Example 15: Construction of WapR-004/V2L2 Bispecific Antibodies

FIG. 17A shows TNFα bispecific model constructs. For Bs1-TNFα/W4, the W4 scFv is fused to the amino-terminus of TNFα VL through a (G4S) 2 linker. For Bs2-TNFα/W4, the W4 scFv is fused to the amino-terminus of TNF& VH through a (G4S) 2 linker. For Bs3-TNFα/W4, the W4 scFv is fused to the carboxy-terminus of CH3 through a (G4S) 2 linker.

Since the combination of WapR-004+V2L2 provide protection against *Pseudomonas* challenge, bispecific constructs were generated comprising a WapR-004 scFv (W4-RAD) and V2L2 IgG (FIG. 17B). To generate Bs2-V2L2-2C, the W4-RAD scFv is fused to N-terminal of V2L2 VH through (G4S) 2 linker. To generate Bs3-V2L2-2C, W4-RAD scFv was fused to C-terminal of CH3 through (G4S) 2 linker. To generate Bs4-V2L2-2C, the W4-RAD scFv was inserted in hinge region, linked by (G4S) 2 linker on N-terminal and C-terminal of scFv. To generate Bs2-W4-RAD-2C, the V2L2 scFv was fused to the amino-terminus of W4-RAD VH through a (G4S) 2 linker.

To generate the W4-RAD scFv for the Bs3 construct, the W4-RAD VH and VL were amplified by PCR. The primers used to amplify the W4-RAD VH were: W4-RAD VH forward primer: includes (G4S) 2 linker and 22 bp of VH N-terminal sequence (GTAAAGGCGGAGGGG-GATCCGGCGGAGGGGGCTCTGAGGTGCAGCTG-TTGG AGTCGG (SEQ ID NO:224)); and W4-RAD VH reverse primer: includes part of (G4S) 4 linker C-terminal and 22 bp of VH sequence (GATCCTCCGCCG-CCGCTGCCCCCTCCCCCAGAGCCCCCTCCGC-CACTCGAGA CGGTGACCAGGGTC (SEQ ID NO:225). Similarly, the W4-RAD VL was amplified by PCR using the primers: W4-RAD VL forward primer: includes part of (G4S) 2 linker and 22 bp of VL N-terminal sequence (AGGGGGCAGCGGCGGCGGAGGATCTGGGG- GAGGGGGCAGCGAAATTGTGTT GACACAGTCTC (SEQ ID NO:226)); and W4-RAD VL reverse primer: includes part of vector sequence and 22 of bp VL C-terminal sequence (CAATGAATTCGCGGCCGCTCATTT-GATCTCCAGCTTGGTCCCAC SEQ ID NO: 227)). The overlapping fragments were then fused together to form the W4-RAD scFv.

W4-RAD scFv sequence in Bs3 vector: underlined sequences are G4S linker
(SEQ ID NO: 228)
GGGGSGGGGSEVQLLESGPGLVKPSETLSLTCNVAGGSISPYYWTWIRQP

PGKCLELIGYIHSSGYTDYNPSLKSRVTISGDTSKKQFSLHVSSVTAADT

AVYFCARADWDLLHALDIWGQGTLVTVSSGGGGSGGGGSGGGGSGGGGSE

IVLTQSPSSLSTSVGDRVTITCRASQSIRSHLNWYQQKPGKAPKLLIYGA

SNLQSGVPSRFSGSGSGTDFTLTISSLQPEDFATYYCQQSYSFPLTFGCG

TKLEIK

After the W4-RAD scFv fragment was amplified, it was then gel purified and ligated into the Bs3 vector which had been digested with BamHI/NotI. The ligation was done using the In-Fusion system, followed by transformation in Stellar competent cells. Colonies were sequenced to confirm the correct W4-RAD scFv insert.

To generate the Bs3-V2L2-2C, the IgG portion in the Bs3 vector was replaced with V2L2 IgG. Briefly, the Bs3 vector which contains W4-RAD scFv was digested with BssHII/SalI and the resultant vector band was gel purified. Similarly, the vector containing V2L2 vector was digested with BssHII/SalI and the V2L2 insert was gel purified. The V2L2 insert was then ligated with the Bs3-W4-RAD scFv vector and colonies were sequenced to confirm the correct V2L2 IgG insert.

A similar approach was used to generate Bs2-V2L2-2C.

W4-RAD scFv-V2L2 VH sequences in Bs2 vector: underlined sequences are G4S linker
(SEQ ID NO: 229)
EVQLLESGPGLVKPSETLSLTCNVAGGSISPYYWTWIRQPPGKCLELIGY

IHSSGYTDYNPSLKSRVTISGDTSKKQFSLHVSSVTAADTAVYFCARADW

DLLHALDIWGQGTLVTVSSGGGGSGGGGSGGGGSGGGGSEIVLTQSPSSL

STSVGDRVTITCRASQSIRSHLNWYQQKPGKAPKLLIYGASNLQSGVPSR

FSGSGSGTDFTLTISSLQPEDFATYYCQQSYSFPLTFGCGTKLEIKGGGG

SGGGGSEMQLLESGGGLVQPGGSLRLSCAASGFTFSSYAMNWVRQAPGEG

LEWVSAITISGITAYYTDSVKGRFTISRDNSKNTLYLQMNSLRAGDTAVY

YCAKEEFLPGTHYYYGMDVWGQGTTVTSS

The following primers were used to amplify W4-RAD scFv. VH (forward primer) and VL (reverse primer): W4-RAD VH forward primer for Bs2 vector which includes some intron, 3' signal peptide and 22 bp of W4-RAD VH N-terminal sequence (TTCTCTCCACAGGTGTA-CACTCCGAGGTGCAGCTGTTGGAGTCGG (SEQ ID NO: 230)) and W4-RAD VL reverse primer for Bs2 vector: include (G4S) 2 linker and 32 bp of VL C-terminal sequence (CCCCCTCCGCCGGATCCCCCTCCGCCTTTGATCTC-CAGCTTGGTCCCACAGCC GAAAG (SEQ ID NO:231))

To amplify the V2L2 VH region the following primers were used: V2L2 VH forward primer: includes (G4S) 2 linker and 22 bp of V2L2 VH N-terminal sequence (GGCG-GAGGGGGATCCGGCGGAGGGGGCTCTGAGATG-CAGCTGTTGGAGTCT GG (SEQ ID NO:232)), and V2L2 VH reverse primer: includes some of CHI N-terminal sequence and 22 bp of V2L2 VH C-terminal sequence (ATGGGCCCTTGGTCGACGCTGAGGAGACGGTG-ACCGTGGTC (SEQ ID NO: 233)).

These primers were then used to amplify V2L2 VH, which was then joined by overlap with W4-RAD scFv and V2L2 VH to get W4-RAD scFv-V2L2-VH. The W4-RAD scFv-V2L2 VH was then ligated into Bs2 vector by gel purifying W4-RAD scFv-V2L2 VH (from overlap PCR); digesting Bs2 vector with BsrGI/SalI, and gel purifying vector band. The W4-RAD scFv-V2L2-VH was then ligated with Bs2 vector by In-Fusion system and transformed into Stellar competent cells and the colonies were confirmed for the correct W4-RAD scFv-V2L2 VH insert. To replace VL in Bs2 vector with V2L2 VL, the Bs2 vector which contains W4-RAD scFv-V2L2-VH was digested with BssHII/BsiWI and the vector band was gel purified. The pOE-V2L2 vector was then digested with BssHII/BsiWI and the V2L2 VL insert was gel purified. The V2L2 VL insert was then ligated with Bs2-W4-RAD scFv-V2L2-VH vector and the colonies were sequenced for correct V2L2 IgG insert.

Finally, a similar PCR-based approach was used to generate the Bs4-V2L2-2C construct. The hinge region with linker sequence is shown below:

```
Hinge region with linker sequence:
KVDKRVEPKSCGGGGSGGGGS - N-terminus of scFv (SEQ ID NO: 329)
 CH1    hinge    linker C-terminus of scFv - GGGGSGGGGSDKTHTCPPCPAPELL (SEQ ID NO: 330)
                       linker      hinge    CH2

W4-RAD scFv sequences in BS4 vector: W4-RAD scFv is in bolded italics with the G4S
linkers underlined in bolded italics; hinge regions are doubled underlined
```

(SEQ ID NO: 324)

KVDKRV]EPKSC*GGGGSGGGGSEVQLLESGPGLVKPSETLSLTCNVAGGSISPYYWTWIR*

*QPPGKCLELIGYIHSSGYTDYNPSLKSRVTISGDTSKKQFSLHVSSVTAADTAVYFCARAD*

*WDLLHALDIWGQGTLVTVSSGGGGSGGGGSGGGGSGGGGSEIVLTQSPSSLSTSVGDRV*

*TITCRASQSIRSHLNWYQQKPGKAPKLLIYGASNLQSGVPSRFSGSGSGTDFTLTISSLQP*

*EDFATYYCQQSYSFPLTFGCGTKLEIKGGGGSGGGGSDKTHTCPPCP*APELL

W4-RAD scFv is presented in *bolded italics* with the G4S linkers *underlined in bolded italics*

*EVQLLESGPGLVKPSETLSLTCNVAGGSISPYYWTWIRQPPGKCLELIGYIHSSGYTDYNP*

*SLKSRVTISGDTSKKQFSLHVSSVTAADTAVYFCARADWDLLHALDIWGQGTLVTVSSGG*

*GGSGGGGSGGGGSGGGGSEIVLTQSPSSLSTSVGDRVTITCRASQSIRSHLNWYQQKPGK*

*APKLLIYGASNLQSGVPSRFSGSGSGTDFTLTISSLQPEDFATYYCQQSYSFPLTFGCGTK*

*LEIK*

W4-RAD scFv was generated using PCR and the following primers: W4-RAD VH forward primer for Bs4 vector: includes some of linker sequences and 24 bp of W4-RAD VH N-terminal sequence (GAGGTGCAGCTGTTG-GAGTCGGGC (SEQ ID NO:236)); and W4-RAD VL reverse primer for Bs4 vector: includes some hinge sequence, linker and 21 bp of W4-RAD VL C-terminal sequence (GTGTGAGTTTTGTCggatccCCCTCCGC-CAGAGCCACCTCCGCCTTTGATCTCCA GCTTGG-TCCC (SEQ ID NO: 237)).

W4-RAD scFv was then ligated into Bs4 vector to get Bs4-V2L2-2C by gel purifying W4-RAD scFv (from PCR); the Bs4-V2L2 vector was digested with BamHI and the vector band was gel purified. The W4-RAD scFv was ligated with Bs4 vector by In-Fusion system and the vector transform Stellar competent cells. Colonies were sequenced for the correct W4-RAD scFv insert.

The sequences for the light chain and heavy chain of the Bs4-V2L2-2C construct are provided in SEQ ID NOS: 327 and 328, respectively.

Example 16: A Psl/PcrV Bispecific Antibody Promotes Survival in Pneumonia Models As an initial matter, the Bs2 and Bs3 bispecific antibodies were tested to examine whether they retained their W4 or V2L2 activity in a bispecific format. For the parental W4 scFv, a bispecific antibody was generated having W4 and a TNF-alpha binding arm. A cell attachment assay was performed as described above using the luminescent *P. aeruginosa* strain PAO1.lux. As shown in FIG. 18, all bispecific constructs performed similarly to the parent W4-IgG1 construct.

As shown in FIG. 19(A-C), percent inhibition of cytotoxicity was analyzed for both Bs2-V2L2 and Bs3-V2L2 using both (A) 6206 and (B) 6206ΔpslA infected cells, and (C) percent inhibition of RBC lysis was analyzed for Bs2-V2L2-2C, Bs3-V2L2-2C and Bs4-V2L2-2C using 6206 infected cells. As shown in FIG. 19(A-C), all bispecific antibodies retained anti-cytotoxicity activity and inhibited RBC lysis at levels similar to the parental V2L2 antibody using 6206 and 6206ΔpslA infected cells.

Figure 20A:
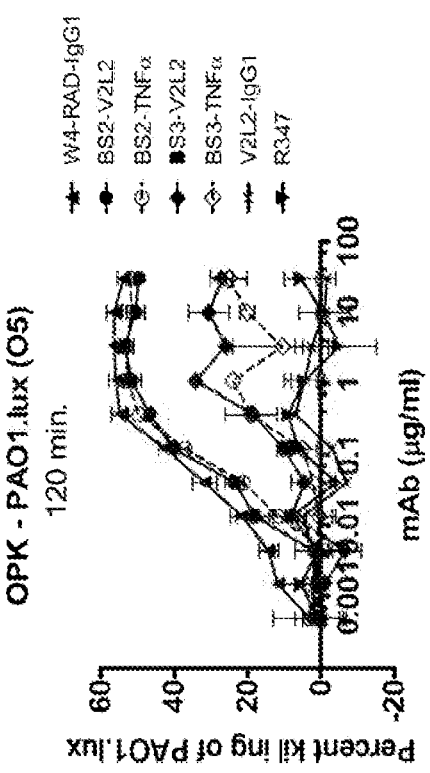
Figure 20B:
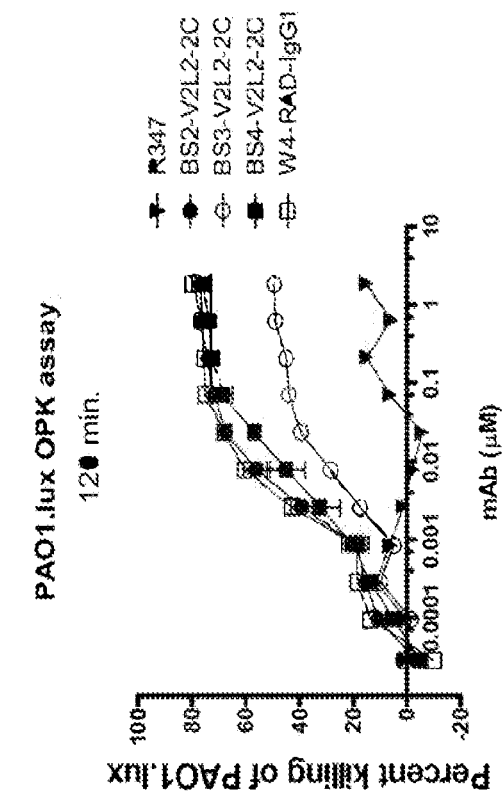
Figure 20C:
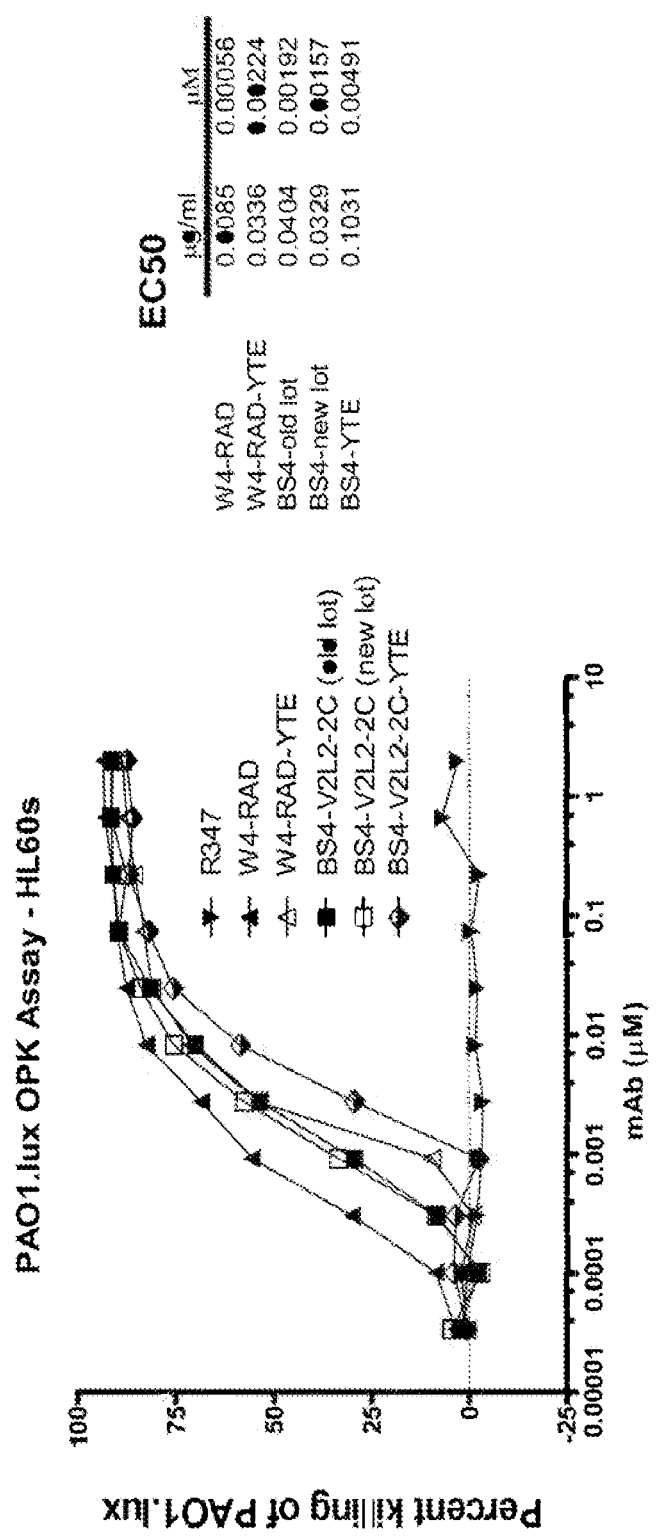

The ability of the Bs2 and Bs3 bispecific antibodies to mediate OPK of *P. aeruginosa* was assessed using the method described in Example 2. While the Bs2-V2L2 antibody showed similar killing compared to the parental W4-RAD antibody, the killing for the Bs3-V2L2 antibody was decreased (FIG. 20A). While the Bs2-V2L2-2C and Bs4-V2L2-2C antibodies showed similar killing compared to the parental W4-RAD antibody, the killing for the Bs3-V2L2-2C antibody was decreased (FIG. 20B). FIG. 20C shows that different preparations of Bs4 antibodies (old lot vs. new lot) showed similar killing compared to the parental W4-RAD antibody, however the Bs4-V2L2-2C-YTE antibodies had a 3-fold drop in OPK activity when compared to Bs4-V2L2-2C. A YTE mutant comprises a combination of three "YTE mutations": M252Y, S254T, and T256E, wherein the numbering is according to the EU index as set forth in Kabat, introduced into the heavy chain of an IgG. See U.S. Pat. No. 7,658,921, which is incorporated by reference herein. The YTE mutant has been shown to increase the serum half-life of antibodies approximately four-times as compared to wild-type versions of the same antibody. See, e.g., Dall'Acqua et al., J. Biol. Chem. 281: 23514-24 (2006) and U.S. Pat. No. 7,083,784, which are hereby incorporated by reference in their entireties.

Figure 21A:
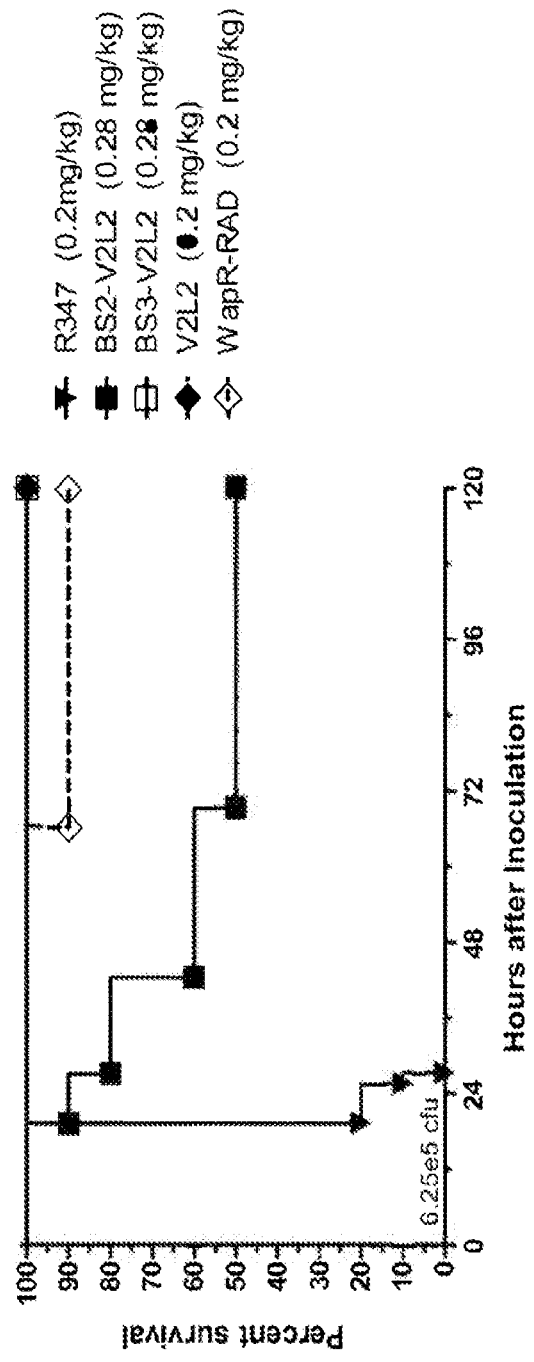
Figure 21B:
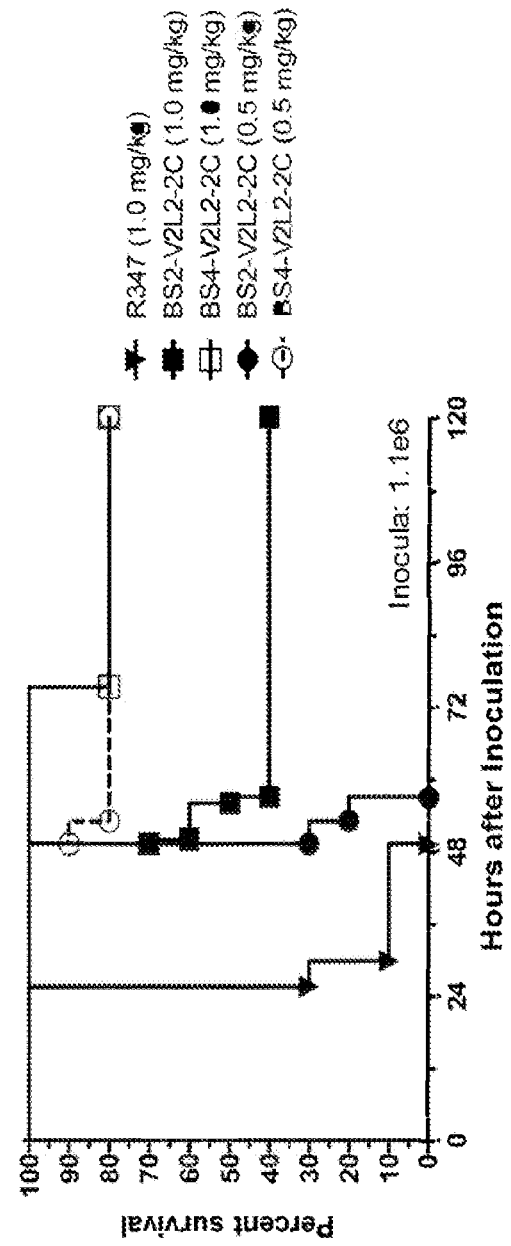
Figure 21C:
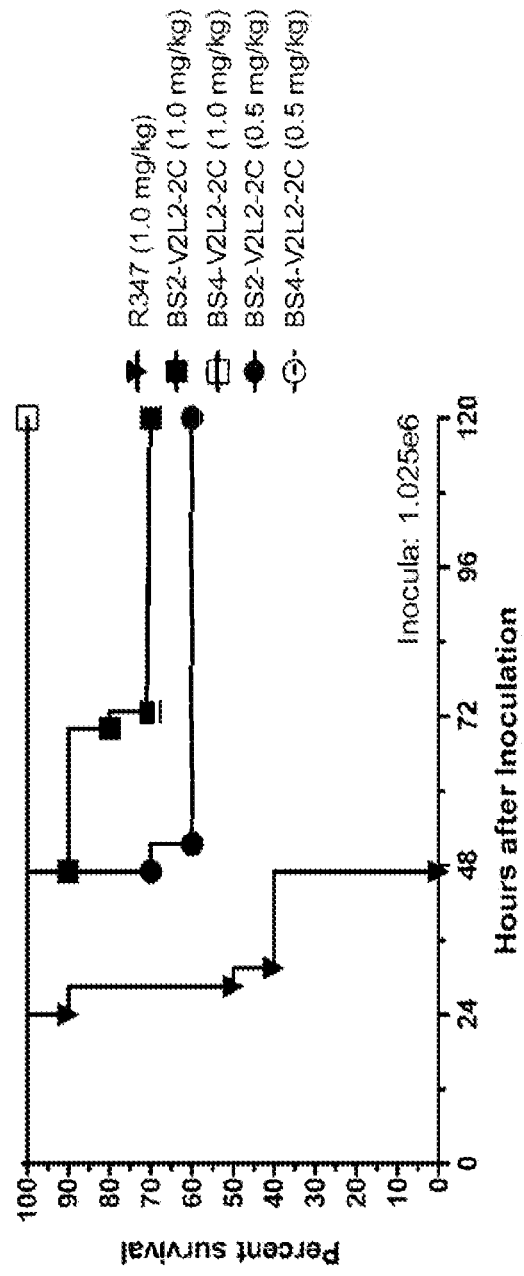
Figure 21D:
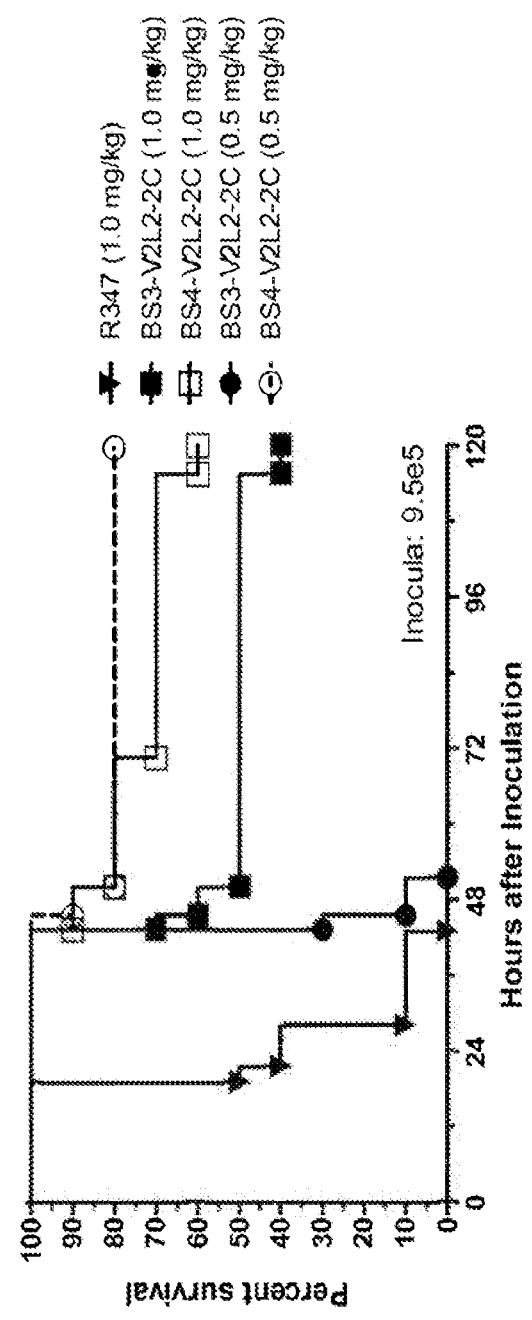
Figure 21E:
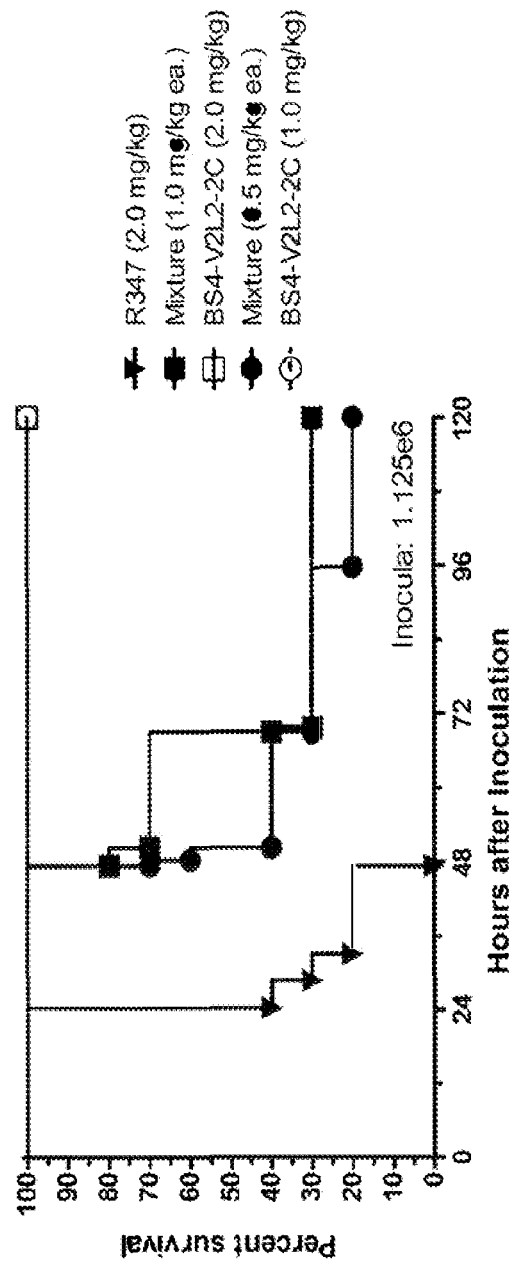
Figure 21F:
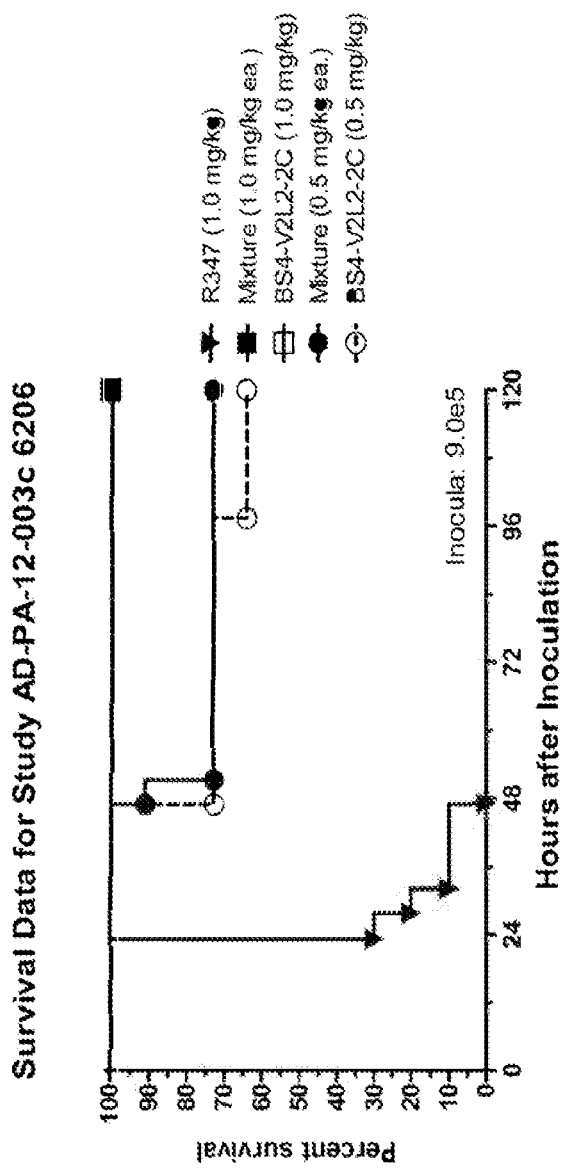
Figure 21G:
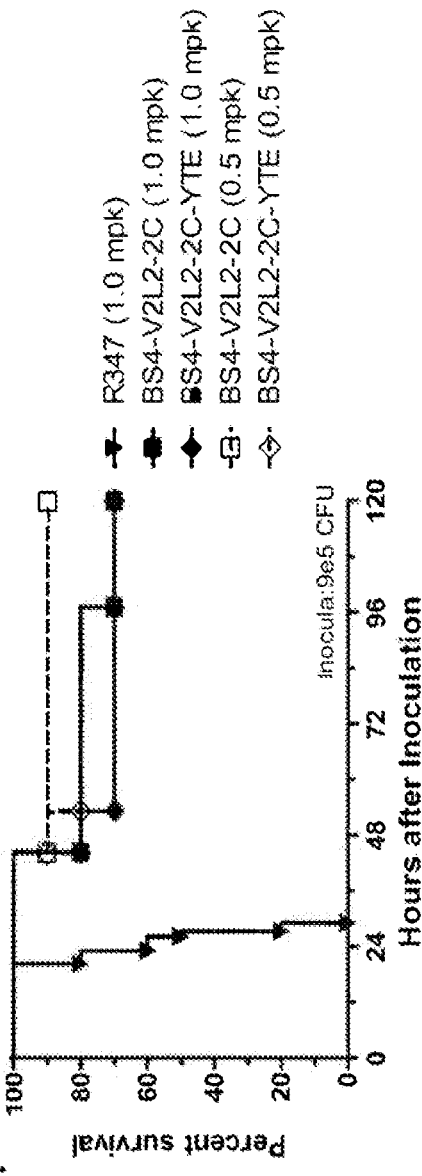
Figure 21H:
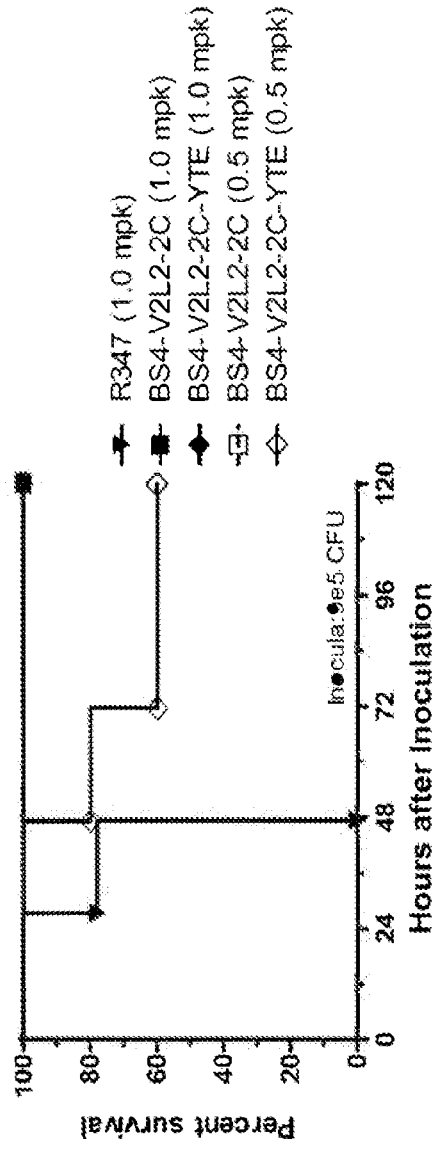

Following confirmation that both W4 and V2L2 retained activity in a bispecific format, the Bs2-V2L2, Bs3-V2L2 and Bs4-V2L2 constructs were assessed for survival from acute pneumonia infections. As shown in FIG. 21A, all of the control mice succumbed to infection by approximately 30 hours post-infection. All of the Bs3-V2L2 animals survived, along with those which received the V2L2 control. Approximately 90% of the W4-RAD immunized animals survived. In contrast, Figures B-F show that approximately 50% of the Bs2-V2L2 animals succumbed to infection by 120 hours. All of the control mice succumbed to infection by approximately 48 hours post-infection. Figures G-H do not show difference in survival between Bs4-V2L2-2C and Bs4-V2L2-2C-YTE treated mice at either dose. These results suggest that both antibodies function equivalently in the 6206 acute pneumonia model. FIG. 21I shows that Bs2-V2L2, Bs4-V2L2-2C, and W4-RAD+V2L2 antibody mixture are the most effective in protection against lethal pneumonia in mice challenged with *P. aeruginosa* strain 6206 (ExoU+).

Organ burden was also assessed for similar immunized mice as described above. Following immunization as above, mice were challenged with $2.75 \times 10^5$ CFU 6206. As shown in FIG. 22, at the concentration tested, both Bs2-V2L2 and Bs3-V2L2 significantly decreased organ burden in lung. However, neither of the bispecific constructs was able to significantly affect organ burden in spleen or kidney compared to the parental antibodies due to the use of suboptimal concentrations of the bispecific constructs. Suboptimal concentrations were used to enable the ability to decipher antibody activity.

Figure 23A:
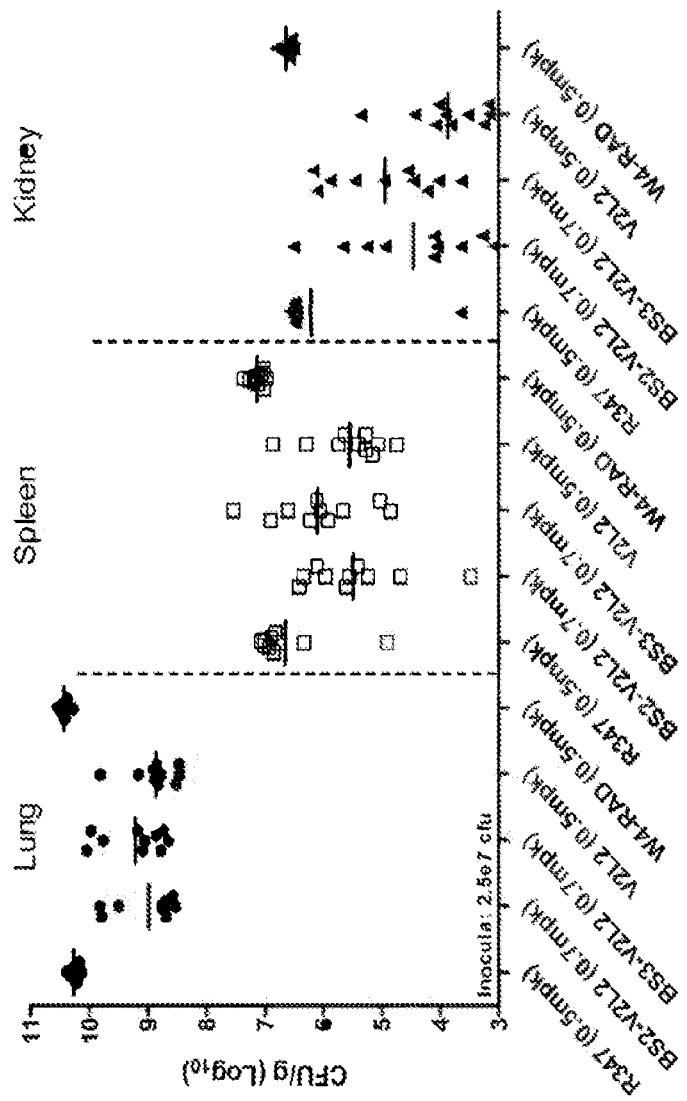
Figure 23B:
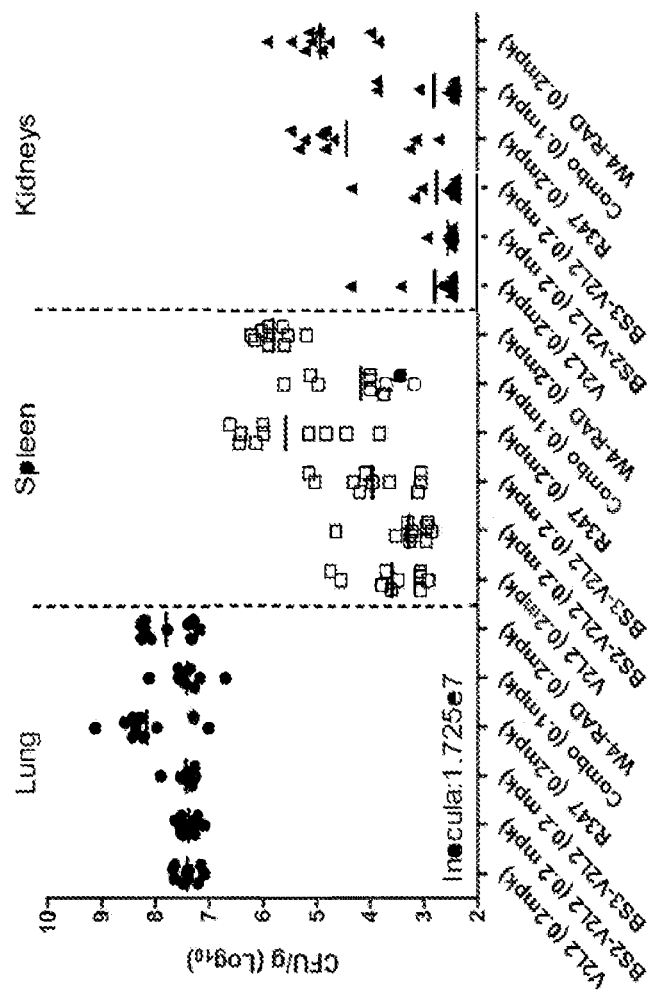

Survival and organ burden effects of the bispecific antibodies were also addressed using the 6294 strain. Using the 6294 model system, both the BS2-V2L2 and BS3-V2L2 significantly decreased organ burden in all of the tissues to a level comparable to that of the V2L2 parental antibody. The W4-RAD parental antibody had no effect on decreasing organ burden (FIG. 23A). As shown in FIG. 23B, Bs2-V2L2, Bs3-V2L2, and W4-RAD+V2L2 combination significantly decreased organ burden in all of the tissues to a level comparable to that of the V2L2 parental antibody.

The survival data for immunized mice was similar in the 6294 challenged mice as before. As shown in FIG. 24, BS3-V2L2 showed similar survival activity to V2L2 alone-treated mice, while BS2-V2L2 treated mice showed a slightly lower level of protection from challenge.

Figure 25A:
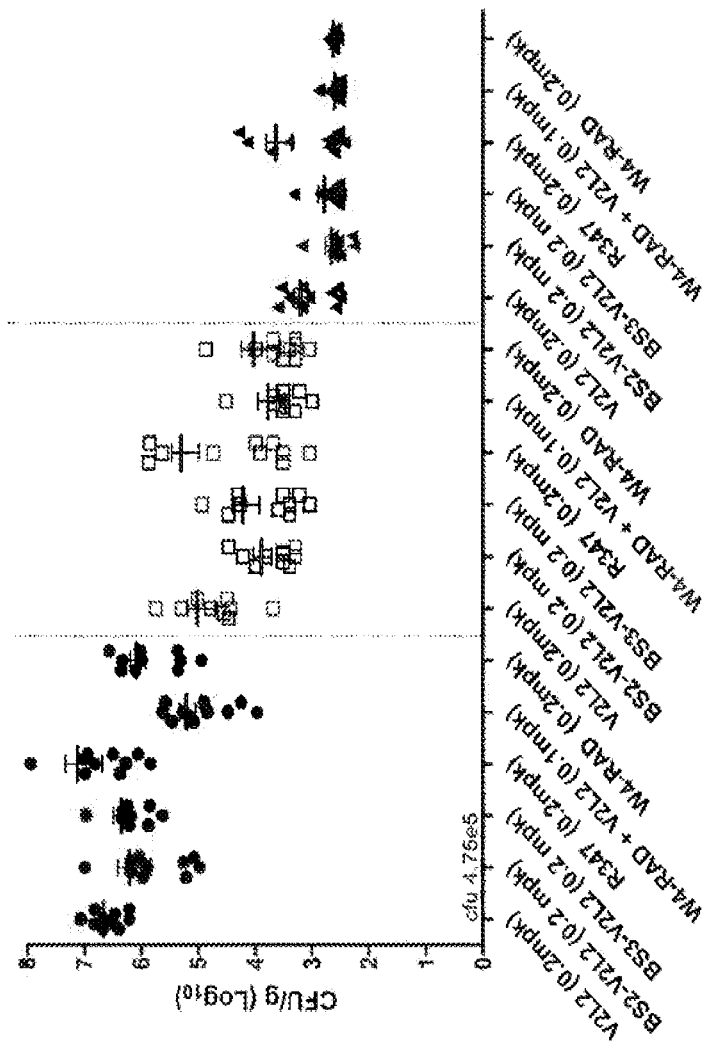
Figure 25B:
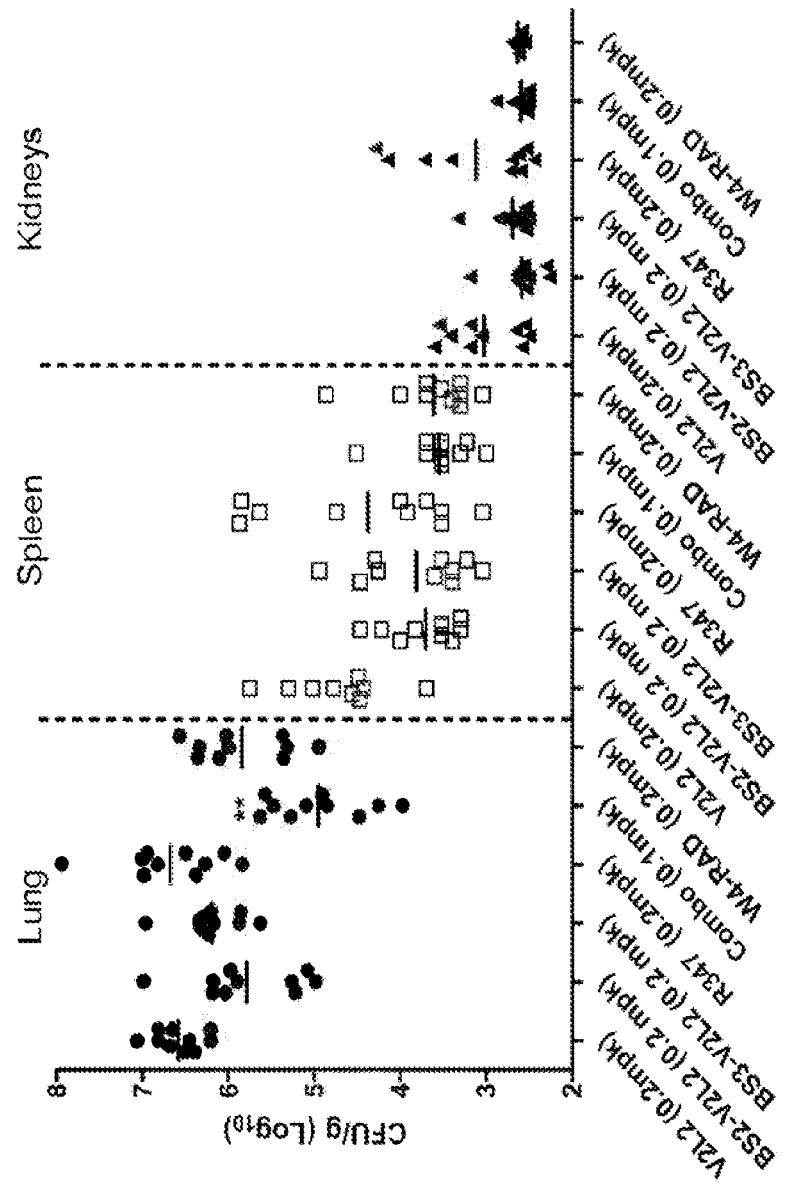
Figure 25C:
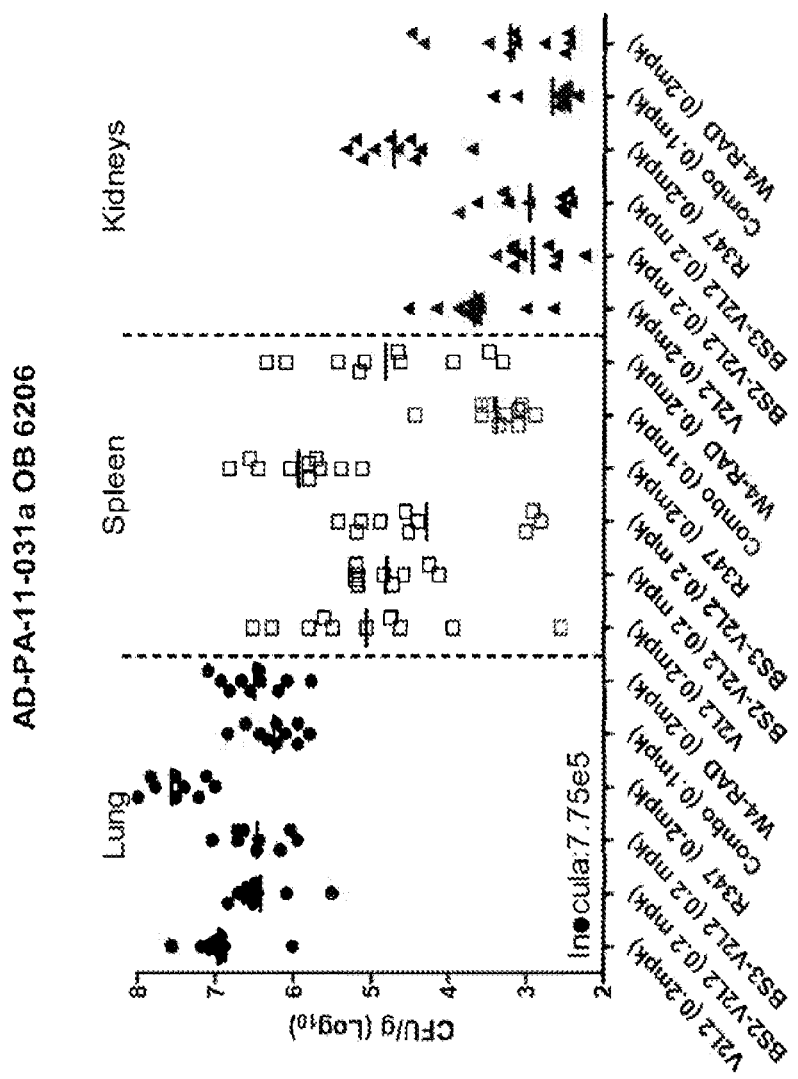
Figure 25D:
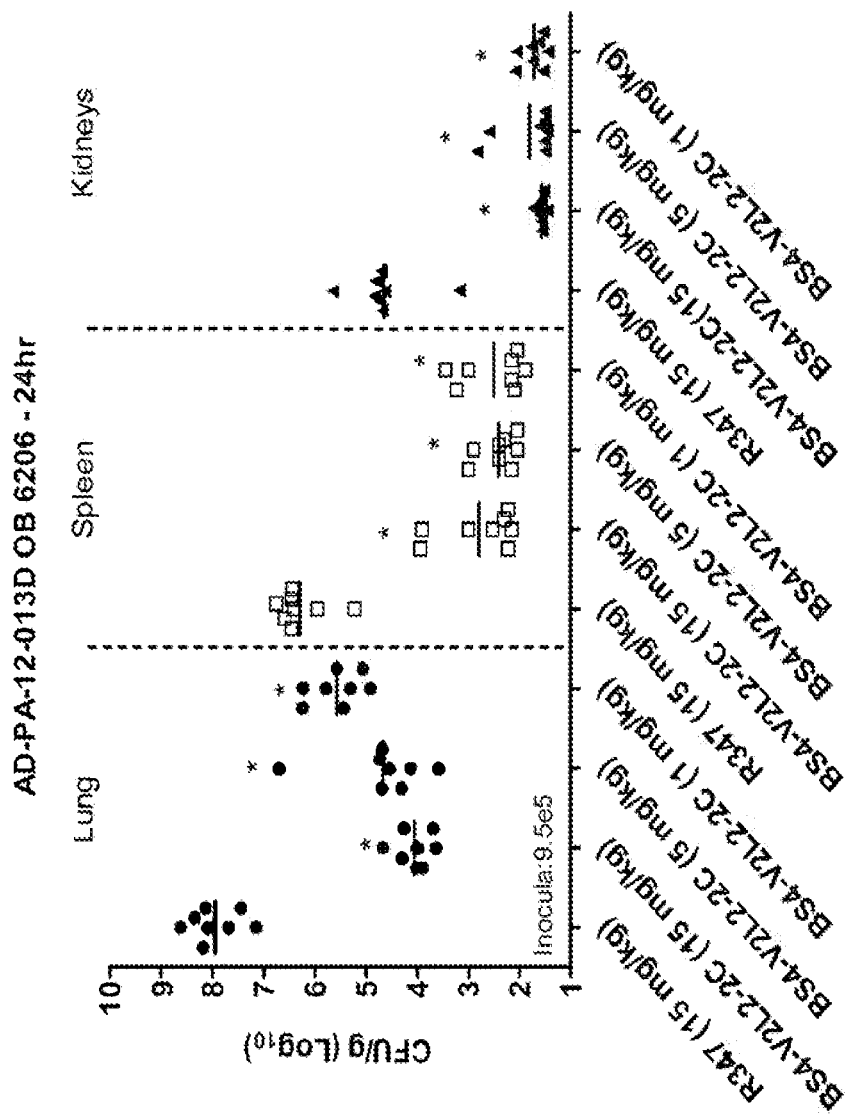
Figure 26A:
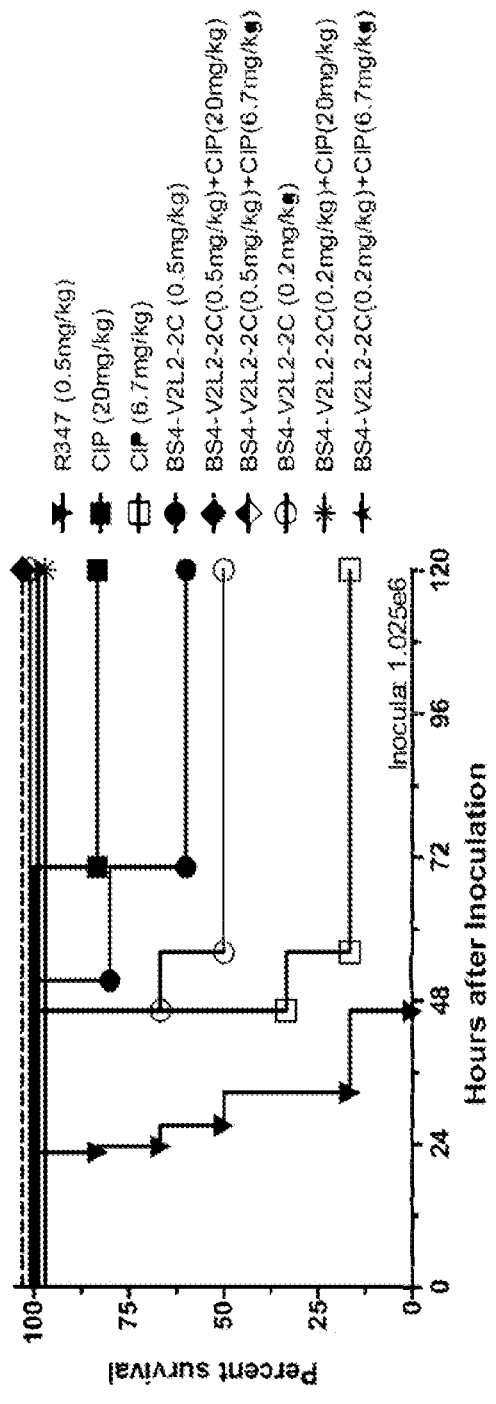
Figure 26B:
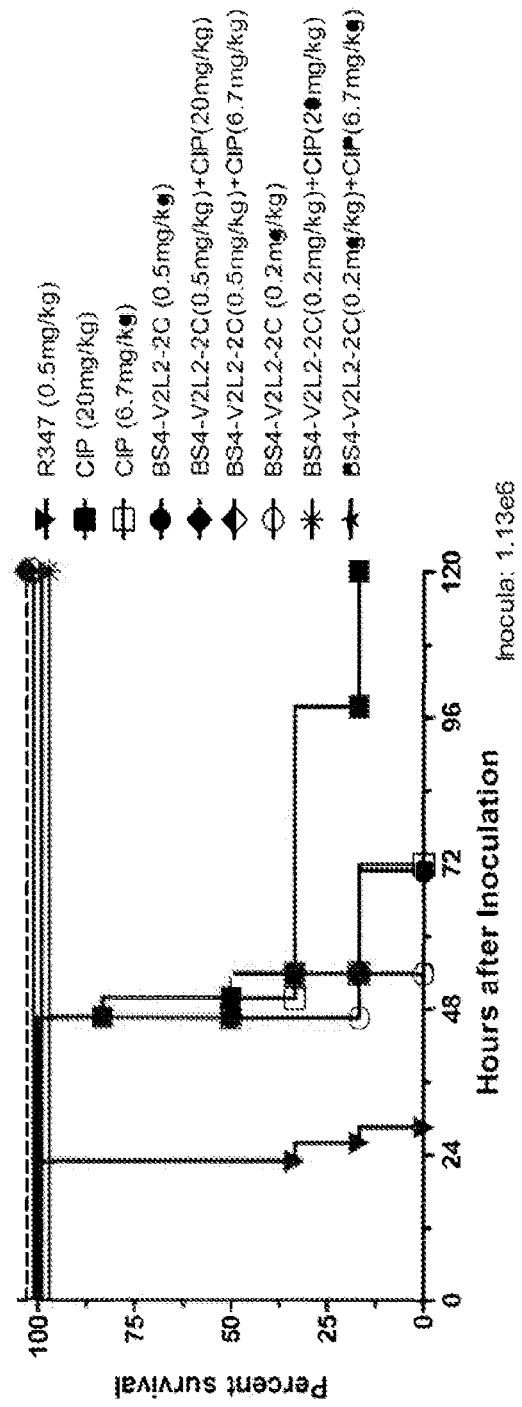
Figure 26C:
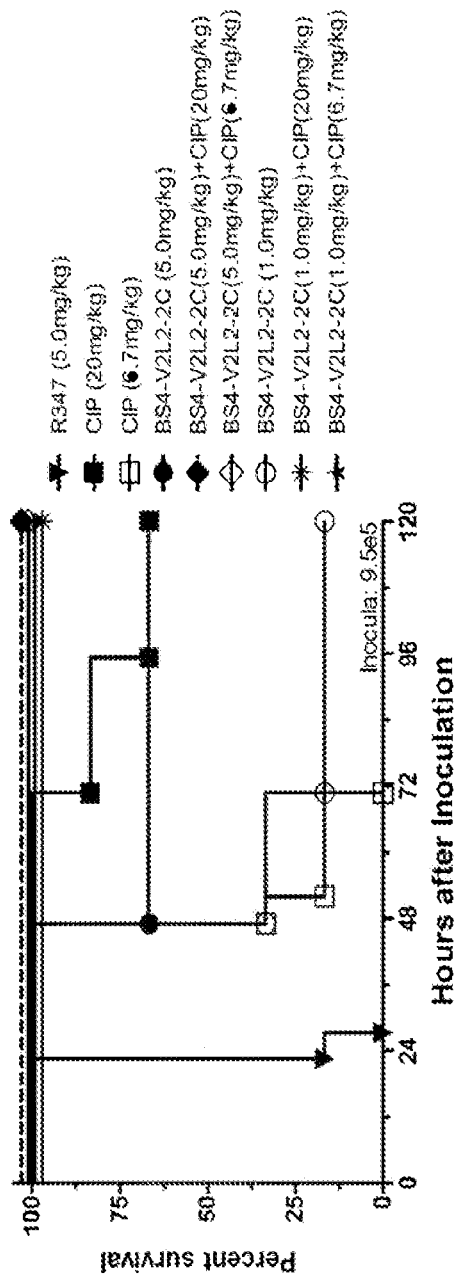
Figure 26D:
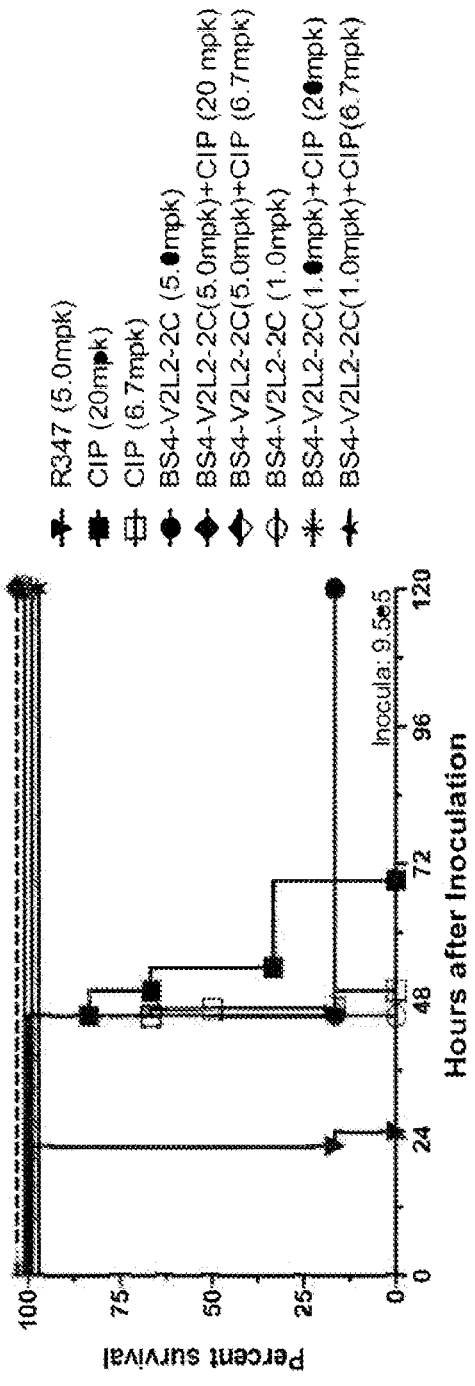
Figure 26E:
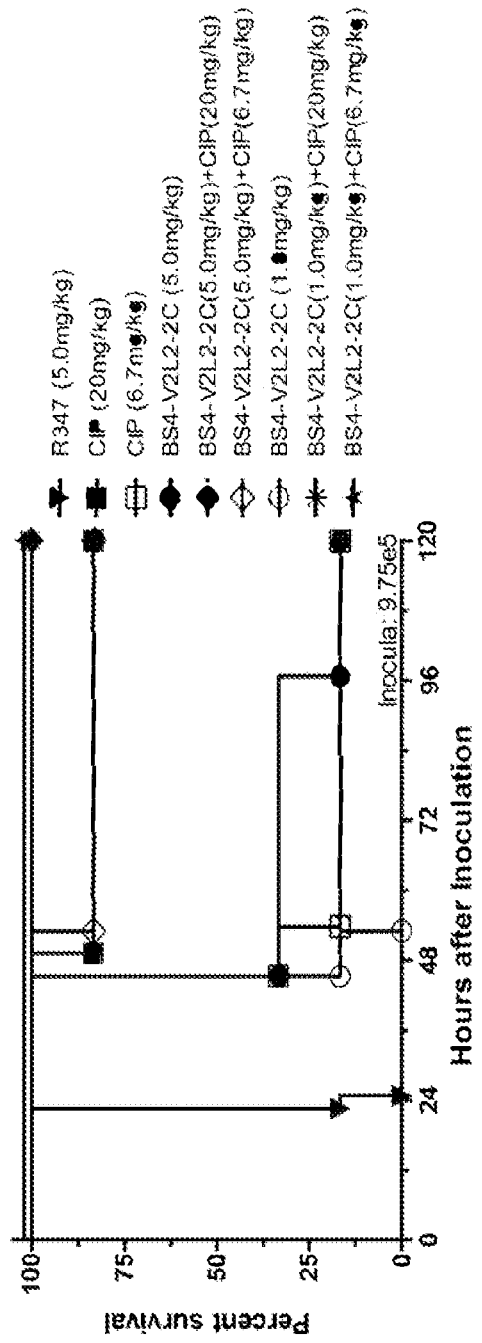
Figure 26F:
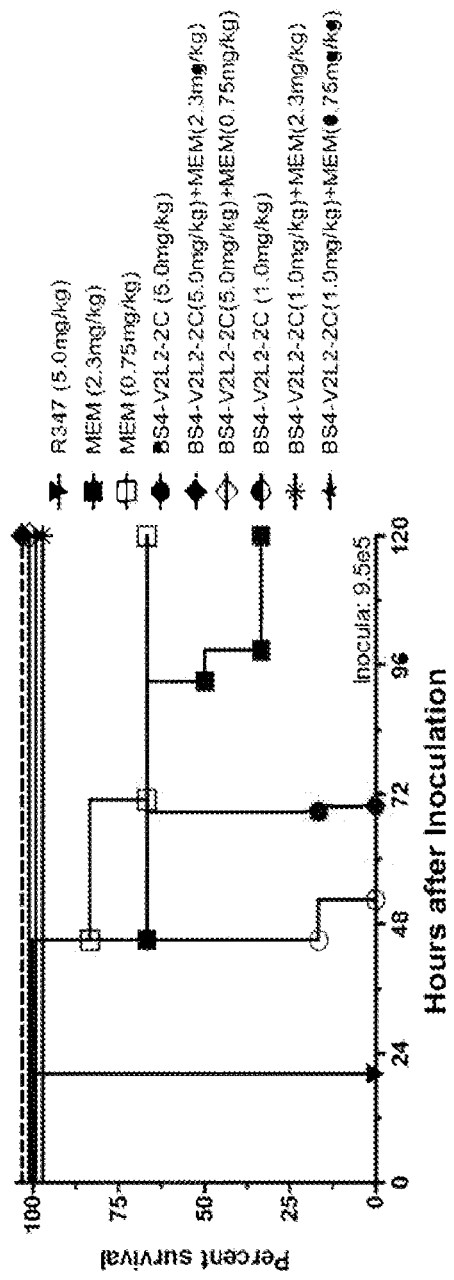
Figure 26G:
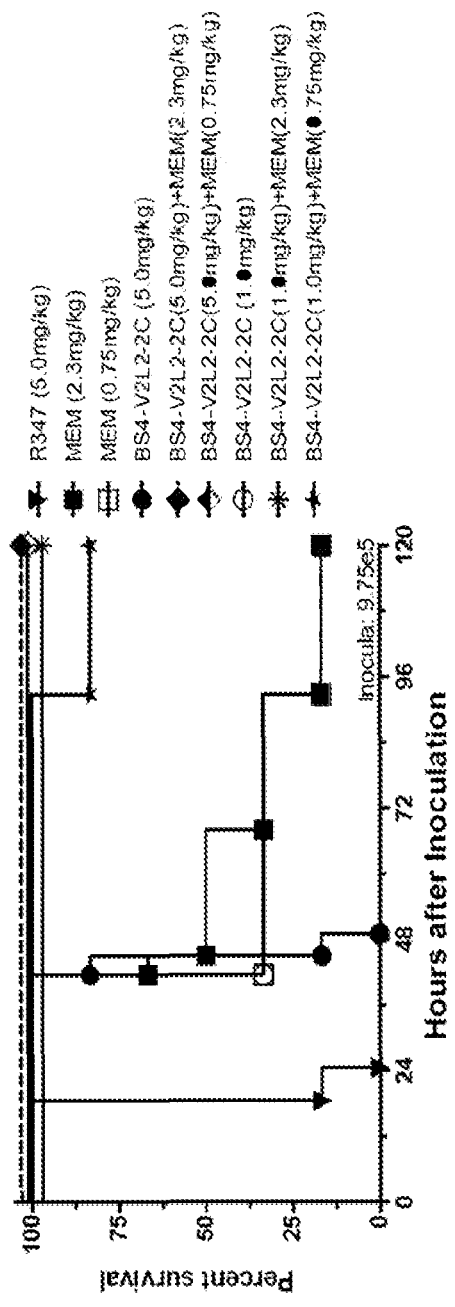
Figure 26H:
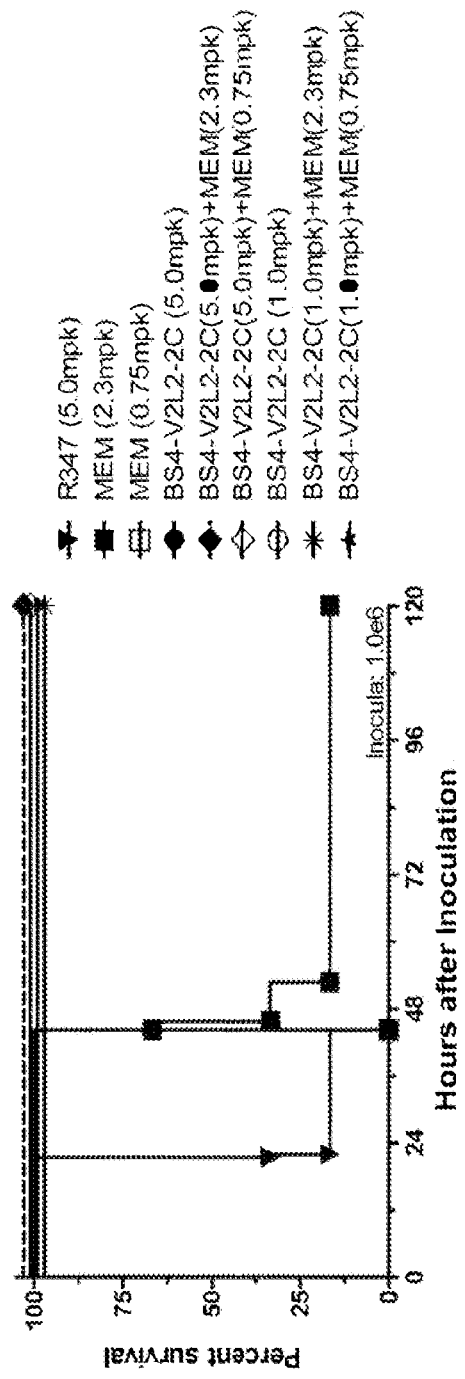
Figure 26I:
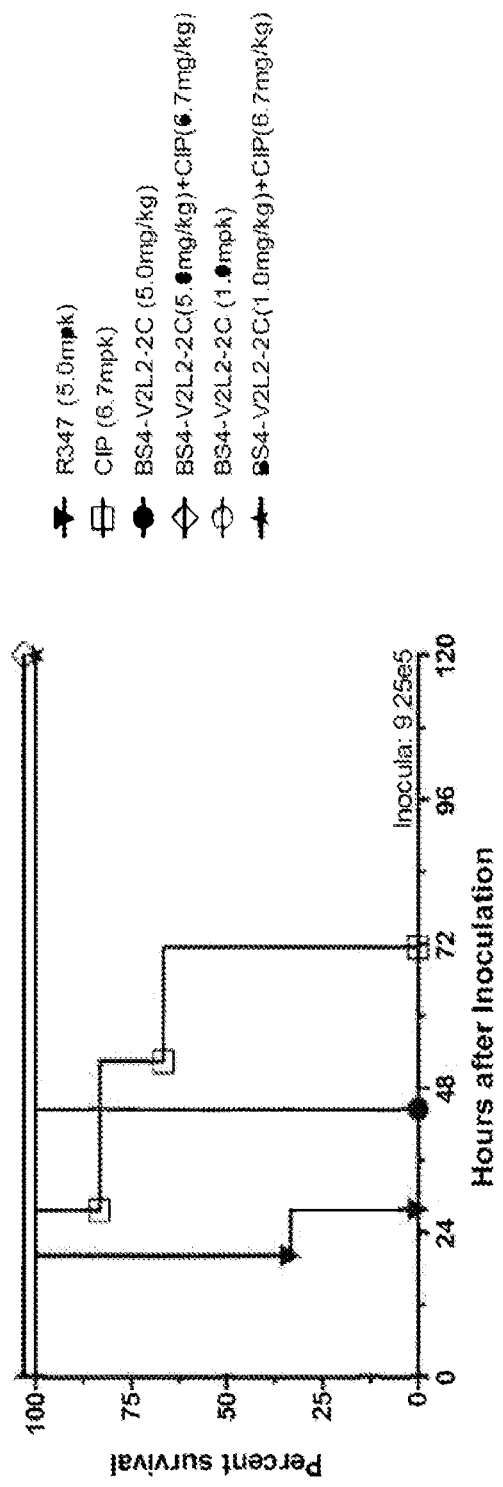
Figure 26J:
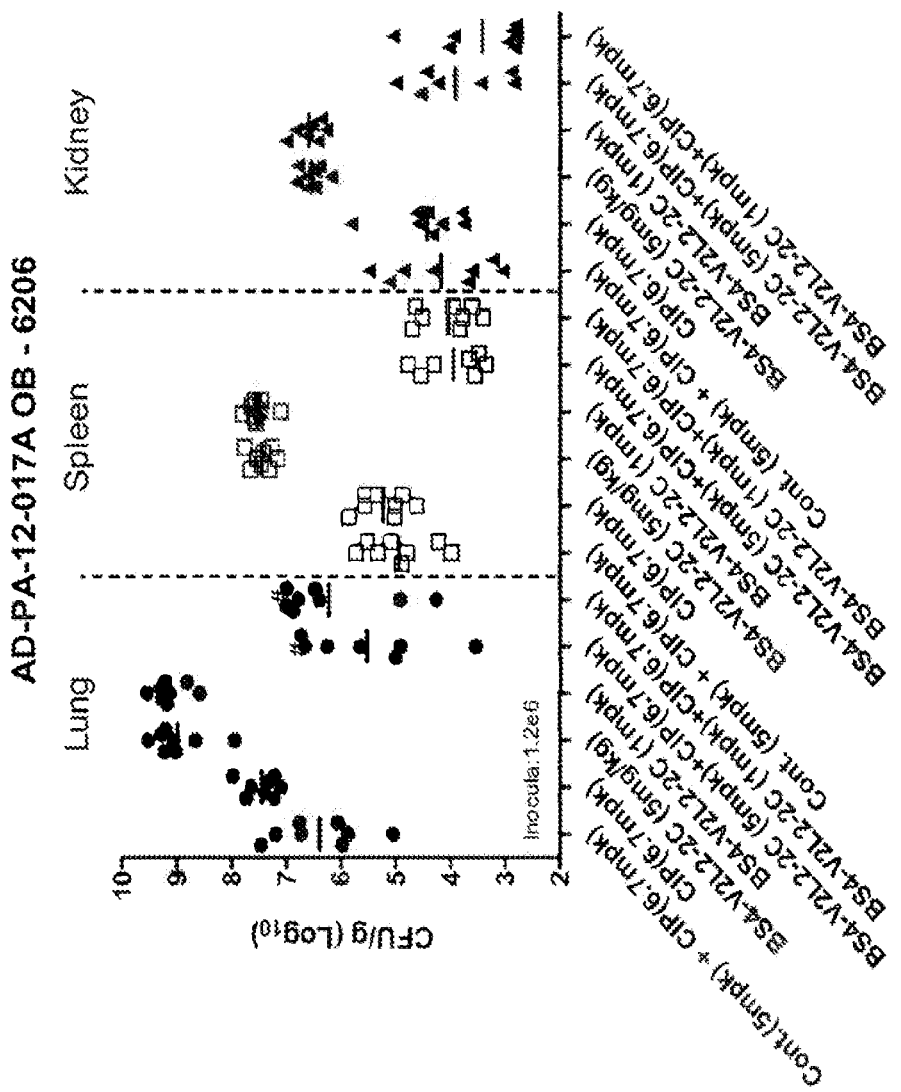

Organ burden was also assessed in bispecific antibodies treated in comparison with combination-treated animals as described above. As shown in FIGS. 25(A-C), both the BS2-V2L2 and BS3-V2L2 decreased organ burden in the lung, spleen and kidneys to a level comparable to that of the W4+V2L2 combination. In the lung, the combination significantly reduced bacterial CFUs Bs2- and Bs3-V2L2 and V2L2 using the Kruskal-Wallis with Dunn's post test. Significant differences in bacterial burden in the spleen and kidney were not observed, although a trend towards reduction was noted. An organ burden study was also performed with Bs4-GLO using 6206 in the pneumonia model. As shown in FIG. 25(D), when higher concentrations of antibody are used in prophylaxis of mice, a significant (Kruskal-Wallis with Dunn's post test) level of reduction in bacterial burden from the lung was observed. Significant reductions in bacterial dissemination to the spleen and kidneys were also observed when using higher concentrations of Bs4-GLO in this model.

These results were confirmed by histological examination of lung tissue of immunized BALB/c mice challenged with $1.33 \times 10^7$ CFU using *P. aeruginosa* strain 6294 (Table 6A), $1.7 \times 10^7$ CFU using *P. aeruginosa* strain 6294 (Table 6B) and $9.25 \times 10^5$ CFU using *P. aeruginosa* strain 6206 (Table 7).

Example 17: Therapeutic Adjunctive Therapy: Bs4-V2L2-2C+Antibiotic

Survival effect of the Bs4 bispecific antibody and antibiotic adjunctive therapy was evaluated in an acute lethal pneumonia model against *P. aeruginosa* 6206 strain as previously described in Example 6 (FIG. 26(A-J)). (A-B) Mice were treated 24 hours prior to infection with 6206 with R347 (negative control) or Bs4-V2L2-2C or Ciprofloxacin (CIP) 1 hour post infection, or a combination of the Bs4-V2L2-2C 24 hours prior to infection and Cipro 1 hour post infection. (C) Mice were treated 1 hour post infection with 6206 with R347 or CIP or Bs4-V2L2-2C, or a combination of the Bs4-V2L2-2C and CIP. (D) Mice were treated 2 hours post infection with 6206 with R347 or CIP or Bs4-V2L2-2C, or a combination of the Bs4-V2L2-2C and CIP. (E) Mice were treated 2 hours post infection with 6206 with R347 or Bs4-V2L2-2C or CIP 1 hour post infection, or a combination of the Bs4-V2L2-2C 2 hours post infection and CIP 1 hour post infection. (F) Mice were treated 1 hour post infection with 6206 with R347 or Meropenem (MEM) or Bs4-V2L2-2C, or a combination of the Bs4-V2L2-2C and MEM. (G) Mice were treated 2 hours post infection with 6206 with R347 or Bs4-V2L2-2C or MEM 1 hour post infection, or a combination of the Bs4-V2L2-2C 2 hours post infection and MEM 1 hour post infection. (H) Mice were treated 2 hours post infection with 6206 with R347 or Bs4-V2L2-2C or MEM, or a combination of the Bs4-V2L2-2C 2 and MEM. (I) Mice were treated 4 hour post infection with 6206 with R347 or Cipro or Bs4-V2L2-2C or a combination of the Bs4-V2L2-2C and Cipro. All of the control mice succumbed to infection by approximately 24 hours post-infection. As shown in FIGS. 26(A-I) Bs4 antibody combined with either CIP or MEM increases efficacy of antibiotic therapy, indicating synergistic protection when the molecules are combined. Further studies focused on the level of bacterial burden in mice treated with Bs4 or CIP alone or in combination (Bs4+CIP). As shown in FIG. 26(J), the level of bacterial burden in all organs (lung, spleen and kidneys) were similar in R347+CIP and Bs4+CIP, however only mice where Bs4 was included in the combination with CIP survive the infection (FIGS. 26(A-E, I)). Altogether, these data indicate the antibiotics are important for reducing the bacterial burden in this animal model setting, however the specific antibody is required to reduce bacterial pathogenicity, thus protecting normal host immunity.

Survival effect of the Bs4 bispecific antibody and Tobramycin antibiotic adjunctive therapy will be evaluated in an acute lethal pneumonia model against *P. aeruginosa* 6206 strain as previously described in Example 6. Mice will be treated 24 hours prior to infection with 6206 with R347 (negative control) or Bs4-V2L2-2C or Tobramycin 1 hour post infection, or a combination of the Bs4-V2L2-2C 24 hours prior to infection and Tobramycin 1 hour post infection. Mice will also be treated 1 hour post infection with 6206 with R347 or Tobramycin or Bs4-V2L2-2C, or a combination of the Bs4-V2L2-2C and Tobramycin. In addition, mice will be treated 2 hours post infection with 6206 with R347 or Tobramycin or Bs4-V2L2-2C, or a combination of the Bs4-V2L2-2C and Tobramycin. Furthermore, mice will be treated 2 hours post infection with 6206 with R347 or Bs4-V2L2-2C or Tobramycin 1 hour post infection, or a combination of the Bs4-V2L2-2C 2 hours post infection and Tobramycin 1 hour post infection. Mice will be treated 4 hour post infection with 6206 with R347 or Tobramycin or Bs4-V2L2-2C or a combination of the Bs4-V2L2-2C and Tobramycin.

Survival effect of the Bs4 bispecific antibody and Aztreonam antibiotic adjunctive therapy will be evaluated in an acute lethal pneumonia model against *P. aeruginosa* 6206 strain as previously described in Example 6. Mice will be treated 24 hours prior to infection with 6206 with R347 (negative control) or Bs4-V2L2-2C or Aztreonam 1 hour post infection, or a combination of the Bs4-V2L2-2C 24 hours prior to infection and Aztreonam 1 hour post infection. Mice will also be treated 1 hour post infection with 6206 with R347 or Aztreonam or Bs4-V2L2-2C, or a combination of the Bs4-V2L2-2C and Aztreonam. In addition, mice will be treated 2 hours post infection with 6206 with R347 or Aztreonam or Bs4-V2L2-2C, or a combination of the Bs4-V2L2-2C and Aztreonam. Furthermore, mice will be treated 2 hours post infection with 6206 with R347 or Bs4-V2L2-2C or Aztreonam 1 hour post infection, or a combination of the Bs4-V2L2-2C 2 hours post infection and Aztreonam 1 hour post infection. Mice will be treated 4 hour post infection with 6206 with R347 or Aztreonam or Bs4-V2L2-2C or a combination of the Bs4-V2L2-2C and Aztreonam.

Example 18: Construction of the BS4-GLO Bispecific Antibody

The BS4-GLO (Germlined Lead Optimized) bispecific construct was generated comprising anti-Psl scFv (Psl0096 scfv) and V2L2-MD (VH+VL) as shown in FIG. 35A. The BS4-GLO light chain comprises germilined lead optimized anti-PcrV antibody light chain variable region (i.e., V2L2-MD). The BS4-GLO heavy chain comprises the formula VH-CH1-H1-L1-S-L2-H2-CH2-CH3, wherein CHI is a heavy chain constant region domain-1, H1 is a first heavy chain hinge region fragment, L1 is a first linker, S is an anti-PcrV ScFv molecule, L2 is a second linker, H2 is a second heavy chain hinge region fragment, CH2 is a heavy chain constant region domain-2, and CH3 is a heavy chain constant region domain-3.

Bs4-GLO light chain:
(SEQ ID NO: 263)
<u>AIQMTQSPSSLSASVGDRVTITCRASQGIRNDLGWYQQKPGKAPKLLIYS</u>

<u>ASTLQSGVPSRFSGSGSGTDFTLTISSLQPEDFATYYCLQDYNYPWTFGQ</u>

<u>GTKVEIK</u>RTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
GLO (germlined lead optimized) V2L2 (i.e.,
V2L2-MD) light chain variable region is underlined Bs4-GLO heavy chain:
(SEQ ID NO: 264)
<u>EMQLLESGGGLVQPGGSLRLSCAASGFTFSSYAMNWVRQAPGEGLEWVSA</u>

<u>ITISGITAYYTDSVKGRFTISRDNSKNTLYLQMNSLRAGDTAVYYCAKEE</u>

<u>FLPGTHYYYGMDVWGQGTTVTVSS</u>[ASTKGPSVFPLAPSSKSTSGGTAAL

GCLVKDYFPEPVTVSWNSGALTSGVHTFPAVLQSSGLYSLSSVVTVPSSS

LGTQTYICNVNHKPSNTKVDKRV]<u><u>EPKSC</u></u>*QVQLQESGPGLVKPSETLSLT*

*CTVSGGSISPYYWTWIRQPPGKCLELIGYIHSSGYTDYNPSLKSRVTISG*

*DTSKKQFSLKLSSVTAADTAVYYCARADWDRLRALDIWGQGTMVTV*<u>*SSGG*</u>

<u>*GGSGGGGSGGGGSGGGGS*</u>DIQLTQSPSSLSAVGDRVTITCRASQSIRSHL

NWYQQKPGKAPKLLIYGASNLQSGVPSRFSGSGSGTDFTLTISSLQPEDF

ATYYCQQSTGAWNWFGCGTKVEIK<u>GGGGSGGGGS</u><u><u>DKTHTCPPCP</u></u>APELLG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESNGQ

PENNYKTTPPVLDSDGSFFLYSKLTVDKSRWQQGNVFSCSVMHEALHNHY

TQKSLSLSPGK
GLO (germlined-lead optimized) V2L2 (i.e.,
V2L2-MD) heavy chain variable region is
underlined; CH1 is bracketed [ ]; GLO (germlined-
lead optimized) W4-RAD (i.e., Psl0096) scFv is in
bolded italics with the G4S linkers underlined in
bolded italics; hinge regions are doubled under-
lined.

An alternative Bs4-GLO bispecific construct comprising an anti-PcrV ScFv and an anti-Psl (VH+VL) is shown in FIG. 35B, and is generated similarly.

Example 19: Evaluation of the Functional Activity and Efficacy of the Bs4-GLO Bispecific Antibody Bispecific antibodies Bs4-WT (also referred to herein as Bs4-V2L2-2C), Bs4-GL (comprising germlined anti-PcrV and anti-Psl variable regions) and Bs4-GLO produced as described in Example 18 were tested for differences in functional activity in an opsonophagocytic killing assay (FIG. 27A), as previously described in Example 2, anti-cell attachment assay (FIG. 27B), as previously described in Example 4 and a RBC lysis anti-cytotoxicity assay (FIG. 27C), as previously described in Example 12. No in vitro difference in functional activities between the antibodies was observed.

In vivo efficacy of Bs4-GLO was examined as follows. For prophylactic evaluation, mice were prophylactically treated with several concentrations of the Bs4-GLO (i.e., 0.007 mg/kg, 0.02 mg/kg, 0.07 mg/kg, 0.2 mg/kg, 0.5 mg/kg, 1 mg/kg, 3 mg/kg, 5 mg/kg, 10 mg/kg or 15 mg/kg) (FIG. 28A), 24 hours before infection with the following $P.$ $aeruginosa$ strains (6206 ($1.0 \times 10^6$), 6077 ($1.0 \times 10^6$), 6294 ($2.0 \times 10^7$) or PA103 ($1.0 \times 10^6$)). For therapeutic evaluation, mice were therapeutically treated with several concentrations of the Bs4-GLO (i.e., 0.03 mg/kg, 0.3 mg/kg, 0.5 mg/kg, 1 mg/kg, 2 mg/kg, 5 mg/kg, 10 mg/kg, 15 mg/kg, or 45 mg/kg) (FIG. 28B), at one hour after infection with the following $P.$ $aeruginosa$ strains (6206 ($1.0 \times 10^6$), 6077 ($1.0 \times 10^6$), 6294 ($2.0 \times 10^7$) or PA103 ($1.0 \times 10^6$)).

Survival effect of the Bs4-GLO bispecific antibody was evaluated in an acute lethal pneumonia model against different $P.$ $aeruginosa$ strains as previously described in Example 6. FIG. 29 shows survival rates for animals treated with the Bs4-GLO in a $P.$ $aeruginosa$ lethal bacteremia model. Aspects of the bacteremia model are disclosed in detail in U.S. Provisional Appl. No. 61/723,128, filed Nov. 6, 2012, entitled "METHODS OF TREATING S. $AUREUS$ ASSOCIATED DISEASES"), which is incorporated herein by reference in its entirety.

Animals were treated with Bs4-GLO or R347, 24 hours prior to intraperitoneal infection with (A) 6294 (06) or (B) 6206. The BS4-GLO is effective at all tested concentrations in protection against lethal pneumonia in mice challenged with $P.$ $aeruginosa$ strains (A) 6294 and (B) 6206.

Survival effect of the Bs4-GLO bispecific antibody was evaluated in a $P.$ $aeruginosa$ thermal injury model against different $P.$ $aeruginosa$ strains. FIG. 30 shows survival rates for animals prophylactically treated with the Bs4-GLO in a $P.$ $aeruginosa$ thermal injury model. Animals were treated with Bs4-GLO or R347 hours prior to induction of thermal injury and subcutaneous infection with $P.$ $aeruginosa$ strain (A) 6077 (O11-ExoU$^+$) or (B) 6206 (O11-ExoU$^+$) or (C) 6294 (06) directly under the wound. The BS4-GLO is effective at all tested concentrations in prevention in a $P.$ $aeruginosa$ thermal injury model in mice challenged with $P.$ $aeruginosa$ strains (A) 6077, (B) 6206 and (C) 6294.

FIG. 31 shows survival rates for animals therapeutically treated with bispecific antibody Bs4-GLO in a $P.$ $aeruginosa$ thermal injury model. (A) Animals were treated with Bs4-GLO or R347 (A) 4h hours or (B) 12 hours after induction of thermal injury and subcutaneous infection with $P.$ $aeruginosa$ strain 6077 (O11-ExoU$^+$) directly under the wound. The Bs4-GLO is effective at all tested concentrations in treatment in a $P.$ $aeruginosa$ thermal injury model in mice treated with Bs4-GLO (B) 4h hours or (B) 12 hours after induction of thermal injury and subcutaneous infection with $P.$ $aeruginosa$ strain 6077.

Example 20: Therapeutic Adjunctive Therapy: Bs4-GLO+Antibiotic

Survival effect of the Bs4-GLO bispecific antibody and antibiotic adjunctive therapy was evaluated in an acute lethal pneumonia model against $P.$ $aeruginosa$ 6206 strain as previously described in Example 6.

FIG. 32 shows therapeutic adjunctive therapy with ciprofloxacin (CIP). (A) Mice were treated 4 hour post infection with $P.$ $aeruginosa$ strain 6206 with R347+CIP or Bs4-WT or a combination of the Bs4-WT and CIP. (B) Mice were treated 4 hour post infection with $P.$ $aeruginosa$ strain 6206 with R347+CIP or Bs4-GLO or a combination of the Bs4-GLO and CIP. (A-B) Bs4-WT or BS4-GLO antibody combined with CIP increased efficacy of antibiotic therapy.

Figure 33A:
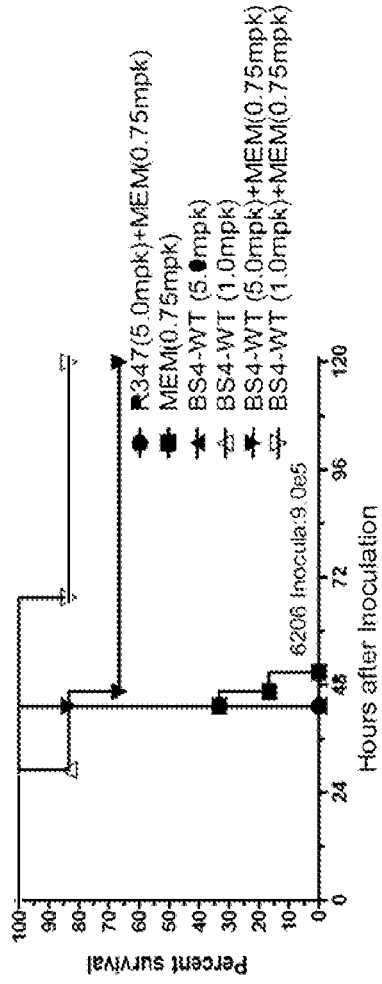
Figure 33B:
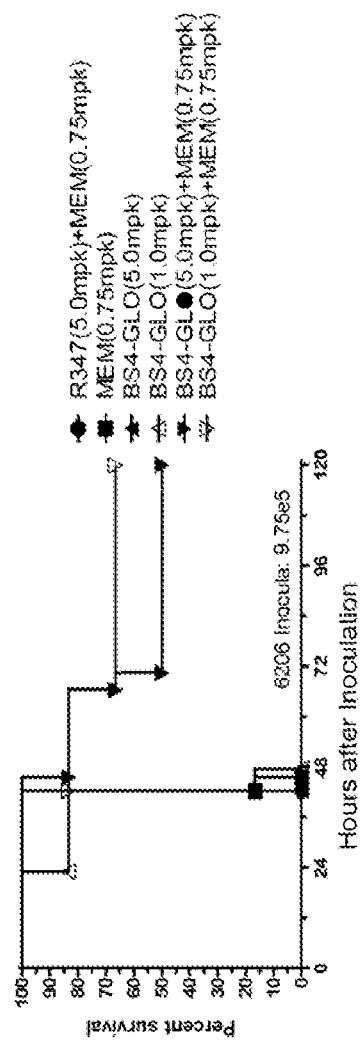

FIG. 33 shows therapeutic adjunctive therapy with meropenem (MEM): (A) Mice were treated 4 hour post infection with $P.$ $aeruginosa$ strain 6206 with R347+MEM or Bs4-WT or a combination of the BS4-WT and MEM. (B) Mice were treated 4 hour post infection with $P.$ $aeruginosa$ strain 6206 with R347+MEM or BS4 or a combination of the Bs4-GLO and MEM. (A-B) Bs4-WT or Bs4-GLO antibody combined with MEM increases efficacy of antibiotic therapy.

FIG. 34 shows therapeutic adjunctive therapy: Bs4-GLO plus antibiotic in a lethal bacteremia model. Mice were treated 24 hours prior to intraperitoneal infection with $P.$ $aeruginosa$ strain 6294 with Bs4-GLO at the indicated concentrations, which were previously determine to be sub-therapeutic protective doses in this model and R347 (negative control). One hour post infection, mice were treated subcutaneously with antibiotics at the indicated concentrations, which were previously determined to be sub-therapeutic protective doses (A) Ciprofloxacin (CIP), (B) Meropenem (MEM) or (C) Tobramycin (TOB). Animals were carefully monitored for survival up to 72 hours post-infection. Bs4-GLO antibody combined with either CIP, MEM or TOB, at sub-protective doses, increases efficacy of antibiotic therapy.

The disclosure is not to be limited in scope by the specific embodiments described which are intended as single illustrations of individual aspects of the disclosure, and any compositions or methods which are functionally equivalent are within the scope of this disclosure. Indeed, various modifications of the disclosure in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference. In addition, U.S. Provisional Application No. 61/556,645 filed Nov. 7, 2011; 61/624,651 filed Apr. 16, 2012; 61/625,299 filed Apr. 17, 2012; 61/697,585 filed Sep. 6, 2012 and International Application No: PCT/US2012/63639, filed Nov. 6, 2012 (entitled "MULTI-SPECIFIC AND MULTIVALENT BINDING PROTEINS AND USES THEREOF") are incorporated by reference in their entirety for all purposes.

TABLE 6A

| Group(n) | Treatment | Overall Impression (Involved Lung Surface Area) | Hemorrhage | Edema | Inflammatory Infiltrate | Bacteria |
|---|---|---|---|---|---|---|
| 4(3) | R347 (0.2 mg/kg) | Broncho interstitial pneumonia (57%), epithelial injury, marked congestion | 3+ Extensive | 3+ | PMN 3+ | 2+ |
| 1(3) | V2L2 (0.2 mg/kg) | Broncho interstitial pneumonia (57%), mild epithelial injury, moderate congestion | 3+ Extensive | 3+ | PMN 3+ | Neg-1+ |
| 6(3) | WapR-004 (0.2 mg/kg) | Broncho interstitial pneumonia (57%), mod epithelial injury, marked congestion | 3+ Extensive | 3+ | PMN 3+ | 2+ |
| 2(3) | BS2-V2L2 (0.2 mg/kg) | Broncho interstitial pneumonia (27%), mild epithelial injury, mild to moderate congestion | 3+ Moderate | 2+-3+ | PMN 2+ | ± |
| 3(3) | BS3-V2L2 (0.2 mg/kg) | Broncho interstitial pneumonia (20%), mild epithelial injury, mild to moderate conqestion | 3+ Mild | 2+ | PMN 1+-2+ | ± |
| 5(2) | WapR-4 + V2L2 (0.1 mg/kg ea) | Primarily Broncho pneumonia (20%) mild epithelial injury, mild congestion | 3+ Mild | 2+ | PMN 1+-2+ | Neg-± |

TABLE 6B

| Group(n) | Treatment | Overall Impression (Involved Lung Surface Area) | Hemorrhage | Edema | Inflammatory Infiltrate | Bacteria |
|---|---|---|---|---|---|---|
| 4(3) | R347 (0.2 mg/kg) | Broncho interstitial pneumonia (40%), mild epithelial injury, moderate congestion | 3+ | 3+ | PMN 2+ | 2+ |
| 1(3) | V2L2 (0.2 mg/kg) | Broncho interstitial pneumonia (30%), mild epithelial injury, mild congestion | 2+ | 3+ | PMN 2+ | Neg |
| 6(3) | WapR-004 (0.2 mg/kg) | Broncho interstitial pneumonia (40%), mod epithelial injury, moderate congestion | 3+ | 3+ | PMN 2+ | Neg-2+ |
| 2(3) | BS2-V2L2 (0.2 mg/kg) | Broncho interstitial pneumonia (20%), mild epithelial injury, mild congestion | 2+ | 2+ | PMN 1+ | Neg |
| 3(3) | BS3-V2L2 (0.2 mg/kg) | Broncho pneumonia mild epithelial injury | 1+ | ± | ± | Neg |
| 5(2) | WapR-4 + V2L2 (0.1 mg/kg ea) | Primarily Broncho pneumonia mild epithelial injury, | 1+ | ± | ± | Neg |

TABLE 7

| Group (n) | Treatment | Overall Impression (Involved Lung Surface Area) | Hemorrhage | Edema | Inflammatory Infiltrate | Bacteria |
|---|---|---|---|---|---|---|
| 4(3) | R347 (0.2 mg/kg) | Broncho interstitial pneumonia (57%), epithelial injury, marked congestion | 3+ | 3+ | PMN 3+ | 1+ |
| 1(3) | V2L2 (0.2 mg/kg) | Broncho interstitial pneumonia (40%), mild epithelial injury, moderate congestion | 3+ | 3+ | PMN 2-3+ | ± |
| 6(3) | WapR-004 (0.2 mg/kg) | Broncho interstitial pneumonia (36%), mild epithelial injury, marked congestion | 3+ | 3+ | PMN 2+ | Neg-1+ |
| 2(3) | BS2-V2L2 (0.2 mg/kg) | Broncho interstitial pneumonia (22%), mild to moderate congestion | 1+-2+ | 1+-2+ | PMN 1-2+ | Neg |
| 3(3) | BS3-V2L2 (0.2 mg/kg) | Broncho interstitial pneumonia (20%), mild to moderate congestion | 1+ | 1+ | PMN 1+ | Neg |
| 5(3) | WapR-4 + V2L2 (0.1 mg/kg ea) | Primarily Broncho pneumonia (<10%) mild congestion | 1+ | 2+ | ± | Neg |

What is claimed is:

1. An isolated antibody or antigen-binding fragment thereof that specifically binds to *Pseudomonas* PcrV, wherein the antibody or antigen-binding fragment thereof comprises:

(a) the heavy chain CDR1 comprising the amino acid sequence of SEQ ID NO:218; the heavy chain CDR2 comprising amino acids 50-66 of SEQ ID NO:264; and the heavy chain CDR3 comprising the amino acid sequence of SEQ ID NO:220; and (b) the light chain CDR1 comprising the amino acid sequence of SEQ ID NO:221; the light chain CDR2 comprising the amino acid sequence of SEQ ID NO:222; and the light chain CDR3 comprising the amino acid sequence of SEQ ID NO:223.

2. The antibody or antigen-binding fragment thereof of claim 1, comprising:

(a) the heavy chain variable region comprising amino acids 1-124 of SEQ ID NO:264; and
(b) the light chain variable region comprising amino acids 1-107 of SEQ ID NO:263.

3. The antibody or antigen-binding fragment thereof of claim 1, wherein the antibody or antigen-binding fragment thereof is a recombinant monoclonal antibody or antigen-binding fragment thereof.

4. The antibody or antigen-binding fragment thereof of claim 1, wherein the antibody or antigen-binding fragment thereof is a bispecific antibody or antigen-binding fragment thereof.

5. The antibody or antigen-binding fragment thereof of claim 2, wherein the antibody or antigen-binding fragment thereof is a recombinant monoclonal antibody or antigen-binding fragment thereof.

6. The antibody or antigen-binding fragment thereof of claim 2, wherein the antibody or antigen-binding fragment thereof is a bispecific antibody or antigen-binding fragment thereof.

7. The antibody or antigen-binding fragment thereof of claim 1, wherein the antibody or antigen-binding fragment thereof is a full-length antibody.

8. The antibody or antigen-binding fragment thereof of claim 1, wherein the antibody or antigen-binding fragment thereof is an antigen-binding fragment.

9. The antibody or antigen-binding fragment thereof of claim 8, wherein the antigen-binding fragment is selected from the group consisting of: Fab fragment, Fab' fragment, F(ab)2 fragment, and scFv fragment.

10. The antibody or antigen-binding fragment thereof of claim 4, wherein the antibody or antigen-binding fragment thereof is an IgG antibody.

11. The antibody or antigen-binding fragment thereof of claim 10, wherein the antibody or antigen-binding fragment thereof is an IgG1 antibody.

12. The antibody or antigen-binding fragment thereof of claim 6, wherein the antibody or antigen-binding fragment thereof is an IgG antibody.

13. The antibody or antigen-binding fragment thereof of claim 12, wherein the antibody or antigen-binding fragment thereof is an IgG1 antibody.

14. The antibody or antigen-binding fragment thereof of claim 4, wherein the antibody or antigen-binding fragment thereof comprises a IgGκ constant region.

15. The antibody or antigen-binding fragment thereof of claim 1, wherein the antibody or antigen-binding fragment thereof comprises a IgGλ constant region.

16. The antibody or antigen-binding fragment thereof of claim 6, wherein the antibody or antigen-binding fragment thereof comprises a IgGκ constant region.

17. The antibody or antigen-binding fragment thereof of claim 2, wherein the antibody or antigen-binding fragment thereof comprises a IgGλ constant region.

18. The antibody or antigen-binding fragment thereof of claim 1, wherein the antibody or antigen-binding fragment thereof is a humanized antibody or antigen-binding fragment thereof.

19. A pharmaceutical composition comprising the antibody or antigen-binding fragment thereof of claim 1, and a pharmaceutically acceptable carrier.

20. A pharmaceutical composition comprising the antibody or antigen-binding fragment thereof of claim 2, and a pharmaceutically acceptable carrier.

* * * * *